(12) United States Patent
Dauner et al.

(10) Patent No.: US 10,006,058 B2
(45) Date of Patent: Jun. 26, 2018

(54) RECOMBINANT HOST CELLS COMPRISING PHOSPHOKETALASE

(71) Applicant: Butamax Advanced Biofuels LLC, Wilmington, DE (US)

(72) Inventors: Michael Dauner, Claymont, DE (US); Lori Ann Maggio-Hall, Wilmington, DE (US); Jean-Francois Tomb, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days. days.

(21) Appl. No.: 15/375,858

(22) Filed: Dec. 12, 2016

(65) Prior Publication Data

US 2017/0088863 A1 Mar. 30, 2017

Related U.S. Application Data

(63) Continuation of application No. 14/335,734, filed on Jul. 18, 2014, now Pat. No. 9,550,999, which is a continuation of application No. 13/161,168, filed on Jun. 15, 2011, now Pat. No. 8,871,488.

(60) Provisional application No. 61/356,379, filed on Jun. 18, 2010.

(51) Int. Cl.

| C12P 7/16 | (2006.01) |
| C12N 1/20 | (2006.01) |
| C12N 1/00 | (2006.01) |
| C07H 21/04 | (2006.01) |
| C12N 9/88 | (2006.01) |
| C12N 9/02 | (2006.01) |
| C12N 9/10 | (2006.01) |

(52) U.S. Cl.
CPC .............. *C12P 7/16* (2013.01); *C12N 9/0004* (2013.01); *C12N 9/0008* (2013.01); *C12N 9/1029* (2013.01); *C12N 9/88* (2013.01); *C12Y 102/01003* (2013.01); *C12Y 203/01008* (2013.01); *C12Y 401/01001* (2013.01); *C12Y 401/02009* (2013.01)

(58) Field of Classification Search
None
See application file for complete search history.

(56) References Cited

U.S. PATENT DOCUMENTS

| 7,405,068 | B2 | 7/2008 | van Maris et al. |
| 7,851,188 | B2 | 12/2010 | Donaldson et al. |
| 7,910,342 | B2 | 3/2011 | Liao et al. |
| 7,932,063 | B2 | 4/2011 | Dunson et al. |
| 8,530,210 | B2 | 9/2013 | Sun et al. |
| 2005/0059136 | A1 | 3/2005 | van Maris et al. |
| 2006/0040365 | A1 | 2/2006 | Kozlov et al. |
| 2007/0031950 | A1 | 2/2007 | Winkler |
| 2007/0190629 | A1 | 8/2007 | Wahlbom et al. |
| 2007/0259410 | A1 | 11/2007 | Donaldson et al. |
| 2007/0292927 | A1 | 12/2007 | Donaldson et al. |
| 2009/0155870 | A1 | 6/2009 | Donaldson et al. |
| 2009/0163376 | A1 | 6/2009 | Li et al. |
| 2009/0171129 | A1 | 7/2009 | Evanko et al. |
| 2009/0269823 | A1 | 10/2009 | Bramucci et al. |
| 2009/0305363 | A1 | 12/2009 | Anthony |
| 2010/0081154 | A1 | 4/2010 | Flint et al. |
| 2010/0120105 | A1 | 5/2010 | Anthony et al. |
| 2010/0197519 | A1 | 8/2010 | Li et al. |
| 2011/0124060 | A1 | 5/2011 | Anthony et al. |
| 2013/0071898 | A1 | 3/2013 | Anthony et al. |
| 2013/0252296 | A1 | 9/2013 | Maggio-Hall |

FOREIGN PATENT DOCUMENTS

| WO | WO2003078643 | 9/2003 |
| WO | WO2007050671 | 5/2007 |
| WO | WO2007086608 | 8/2007 |
| WO | WO2009013159 | 1/2009 |
| WO | WO2009046370 | 4/2009 |
| WO | WO2010151832 | 12/2010 |
| WO | WO2011041415 | 4/2011 |
| WO | WO2011090753 | 7/2011 |
| WO | WO2011130378 | 10/2011 |
| WO | WO2011154503 | 12/2011 |

OTHER PUBLICATIONS

Akada et al., "PCR-mediated seamless gene deletion and marker recycling in *Saccharomyces cerevisiae*", Yeast, 2006 pp. 399-405, vol. 23.
Albert et al., "Site-specific integration of DNA into wild-type and mutant lox sites placed in the plant genome", The Plant Journal, 1995, pp. 649-659, vol. 7, No. 4.
Altschul et al., "Basic Local Alignment Search Tool", Journal of Molecular Biology, 1990, pp. 403-410, vol. 215.
Bellion et al., "Microb. Growth C1 Compd.", [Int. Symp.], 7th (1993), pp. 415-432, Editor(s): Murrell, J. Collin; Kelly, Don P. Publisher: Intercept, Andover, UK.
Bianchi et al., "The 'petite-negative' yeast kluyveromyces lactis has a single gene expressing pyruvate decarboxylase activity" Molecular Microbiology, 1996, pp. 27-36, vol. 19(1).
Boeke et al., "A positive selection for mutants lacking orotidine-5'-phosphate decarboxylase activity in yeast: 5-fluoro-orotic acid resistance", Molecular General Genetics, 1984, pp. 345-346, vol. 197.
Carlini et al., "Guerbet condensation of methanol with n-propanol to isobutyl alcohol over heterogeneous copper chromite/Mg—Al mixed oxides catalysts", J. Mol. Catal. A: Chem., 2004, pp. 215-220, vol. 220.
Chang et al., "BRENDA, AMENDA and FRENDA the enzyme information system: new content and tools in 2009", Nucleic Acids Research, 2009, pp. D588-D593, vol. 37.

(Continued)

Primary Examiner — Iqbal H Chowdhury

(57) ABSTRACT

The present invention is related to recombinant host cells comprising: (i) at least one deletion, mutation, and/or substitution in an endogenous gene encoding a polypeptide that converts pyruvate to acetaldehyde, acetyl-phosphate or acetyl-CoA; and (ii) a heterologous polynucleotide encoding a polypeptide having phosphoketolase activity. The present invention is also related to recombinant host cells further comprising (iii) a heterologous polynucleotide encoding a polypeptide having phosphotransacetylase activity.

6 Claims, 175 Drawing Sheets

(56) References Cited

OTHER PUBLICATIONS

Chinen et al., "Innovative metabolic pathway design for efficient 1-glutamate production by suppressing CO2 emission", Journal of Bioscience and Bioengineering, vol. 103, No. 3, Mar. 1, 2007, pp. 262-269.
Deshpande, "Ethanol Production from Cellulose by Coupled Saccharification/Fermentation using *Saccharomyces cerevisiae* and Cellulase Complex from Sclerotium rolfsii UV-8 Mutant", Applied Biochemistry and Biotechnology, 1992, pp. 227-234, vol. 36.
Durre, "New insights and novel developments in clostridial acetone/butanol/isopropanol fermentation", Appl. Microbiol. Biotechnol., 1998, pp. 639-648, vol. 49.
Evans et al., "Induction of xylulose-5-phosphate phosphoketolase in a variety of yeasts grown on D-xylose: the key to efficient xylose metabolism", Archives of Microbiology, 1984, pp. 48-52, vol. 139.
Finn et al., "The Pfam protein families database", Nucleic Acids Research, 2008, pp. D281-D288, vol. 36.
Flikweert et al., "Pyruvate decarboxylase: an indispensable enzyme for growth of *Saccharomyces cerevisiae* on glucose", Yeast, 1996, pp. 247-257, vol. 12.
Flikweert et al., "Growth requirements of pyruvate-decarboxylase-negative *Saccharomyces cerevisiae*", FEMS Microbiology Letters, 1999, pp. 73-79, vol. 174.
Goldberg, I. et al., "Organic acids: old metabolites, new themes", Journal of Chemical Technology and Biotechnology, 2006, pp. 1601-1611, vol. 81.
Goldberg, M. et al., "[90] Phosphoketolase", Methods in Enzymology, 1966, pp. 515-520, vol. 9.
Groot et al., "Technologies for Butanol Recovery Integrated with Fermentations", Process Chemistry, 1992, pp. 61-75, vol. 27.
Guo et al., "Pervaporation study on the dehydration of aqueous butanol solutions: a comparison of flux vs. permeance, separation factor vs. selectivity", Journal of Membrane Science, 2004, pp. 199-210, vol. 245.
Heath et al., "Pentose Fermentation by Lactobacillus Plantarum", The Journal of Biological Chemistry, 1958, pp. 1009-1029, vol. 231.
Higgins et al., "Fast and sensitive multiple sequence alignments on a microcomputer", CABIOS Communications, 1989, pp. 151-153. vol. 5, No. 2.
Higgins et al., "CLUSTAL V: improved software for multiple sequence alignment", CABIOS, 1992, vol. 8, No. 2 pp. 189-191.
Hohmann, "Characterisation of PDC2, a gene necessary for high level expression of pyruvate decarboxylase structural genes in *Saccharomyces cerevisiae*", Mol. Gen. Genet., 1993, vol. 241, pp. 657-666.
Horton et al., "Engineering hybrid genes without the use of restriction enzymes: gene splicing by overlap extension", Gene, 1989, pp. 61-68, vol. 77.
Ishida et al., "Efficient production of L-lactic acid by metabolically engineered *Saccharomyces cerevisiae* with a genome-integrated L-lactate dehydrogenase gene", Applied and Environmental Microbiology, vol. 71, No. 4, Apr. 2005, pp. 1964-1970.
Krogh et al., "Hidden Markov Models in Computational Biology", Journal of Molecular Biology, 1994, pp. 1501-1531, vol. 235.
Langley et al., "Biochemical Genetics of the a-Keto Acid Dehydrogenase Complexes of *Escherichia coli*, K12: Isolation and Biochemical Properties of Deletion Mutants", Journal of General Microbiology, 1977, pp. 263-276, vol. 99.
Li et al., "Clustering of highly homologous sequences to reduce the size of large protein databases", Bioinformatics, 2001, pp. 282-283, vol. 17, No. 3.
Ma et al., "Plasmid construction by homologous recombination in yeast", Gene, 1987, pp. 201-216, vol. 58.
Methods in Yeast Genetics, 2005, Cold Spring Harbor Laboratory Press, Cold Spring Harbor, NY, pp. 201-202.
Mnaimneh et al., "Exploration of essential gene functions via titratable promoter alleles", Cell, 2004, pp. 31-44, vol. 118.

Nakamura et al., "Codon usage tabulated from international DNA sequence databases: status for the year 2000", Nucleic Acids Research, 2000, vol. 28, No., p. 292.
Nevoigt et al., "Engineering of promoter replacement cassettes for fine-tuning of gene expression in *Saccharomyces cerevisiae*", Applied and Environmental Microbiology, Aug. 2006, vol. 72, No. 8, pp. 5266-5273.
Nystrom et al., "Reduction of organic compounds by lithium aluminum hydride", J. Am. Chem. Soc., 1947, vol. 69, p. 1198.
Panagiotou et al., "Induction of Xylulosse-5-phosphate Phosphoketolase in Aspergillus Nidulans: the Key for Efficient Production of the Acetyl-coa Precursor Molecule", Internet Citation, Apr. 2006, p. 203, XP002477270.
Pearson, Comput. Methods Genome Res., [Proc. Int. Symp.] (1994), Meeting Date 1992, 111 20. Editor(s): Suhai, Sandor. Plenum: New York, NY.
Posthuma et al., "Expression of the Xylulose 5-Phospohate Phosphoketolase Gene, xpkA, from Lactobacillus pentosus MD363 is Induced by Sugars That Are Fermented via the Phosphoketolase Pathway and Is Repressed by Glucose Mediated by CcpA and the Mannose Phosphoenolpyruvate Phosphotransferase System", Applied and Environmental Microbiology, Feb. 2002, pp. 831-837, vol. 68, No. 2.
Rado et al., "Phosphotransacetylase From Bacillus Subtilis: Purification and Physiological Studies", Biochimica et Biophysica Acta, 1973, pp. 114-125, vol. 321.
Romanos et al., "Direct selection of stabilised yeast URA3 transformants with 5-fluorouracil", Nucleic Acids Research, 1991, pp. 187, vol. 19, No. 1.
Saitou et al., "The Neighbor-joining Method: A New Method for Reconstructing Phylogenetic Trees", Molecular Biology Evolution, 1987, pp. 406-425, vol. 4, No. 4.
Sambrook, J., Fritsch, E. F. and Maniatis, T. Molecular Cloning: A Laboratory Manual, 2nd ed., Cold Spring Harbor Laboratory: Cold Spring Harbor, NY, 1989, particularly 9.50-9.51, 11.7-11.8 and Table 11.1.
Sauer, "Functional Expression of the cre-lox Site-Specific Recombination System in the Yeast *Saccharomyces cerevisiae*", Molecular and Cellular Biology, Jun. 1987, pp. 2087-2096, vol. 7, No. 6.
Schure et al., "Pyruvate decarboxylase catalyzes decarboxylation of branched-chain 2-oxo acids but is not essential for fusel alcohol production by *Saccharomyces cerevisiae*", Applied Environ Microbiol (1988) 64: 1303-1307.
Senecoff, et al., "DNA Recognition by the FLP Recominase of the Yeast 2 u Plasmid", Journal of Molecular Biology, 1938, pp. 405-421, vol. 201.
Sonderegger et al., "Metabolic Engineering of a Phosphoketolase Pathway for Pentose Catabolism in *Saccharomyces cerevisiae*", Applied and Environmental Microbiology, May 2004, pp. 2892-2897, vol. 70, No. 5.
Sulter et al., "Proliferation and metabolic significance of peroxisomes in candida boidinii during growth on D-alanine or oleic acid as the sole carbon source", Arch. Microbiol., 1990, pp. 485-489, vol. 153, No. 9.
Tamura et al., "MEGA4: Molecular Evolutionary Genetics Analysis (MEGA)" Software Version 4.0, Molecular Biology and Evolution, 2007, pp. 1596-1599, vol. 24.
Ullmann's Encyclopedia of Industrial Chemistry, 6th edition, 2003, Wiley-VCH Verlag GmbH and Co., Weinheim, Germany, vol. 5, pp. 716-719.
Thompson et al., "The CLUSTAL_X windows interface; flexible strategies for multiple sequence alignment aided by quality analysis tools", Nucleic Acids Research, 1997, pp. 4876-4882, vol. 25, No. 24.
van Maris et al., "Directed Evolution of Pyruvate Decarboxylase-Negative *Saccharomyces cerevisiae*, Yielding a C2-Independent, Glucose-Tolerant, and Pyruvate-Hyperproducing Yeast", Applied and Environmental Microbiology, Jan. 2004, pp. 159-166, vol. 70, No. 1.
van Maris et al., "Overproduction of Threonine Aldolase Circumvents the Biosynthetic Role of Pyruvate Decarboxylase in Glucose-

(56) References Cited

OTHER PUBLICATIONS

Limited Chemostat Cultures of *Saccharomyces cervisiae*", Applied and Envirnomental Microbiology, Apr. 2003, pp. 2094-2099, vol. 69, No. 4.

Voloch et al., "Fermentation Derived 2,3-Butanediol," in Comprehensive Biotechnology, Pergamon Press Ltd., England, 1986, pp. 933-947,vol. 2, Section 3.

Wach et al., "New heterologous modules for classical or PCR-based gene disruptions in *Saccharomyces cerevisiae*", Yeast, 1994, pp. 1793-1808, vol. 10.

Waterhouse et al., "Jalview Version 2—a multiple sequence alignment editor and analysis workbench", Bioinformatics, 2009, pp. 1189-1191, vol. 25, No. 9.

Yu et al., "Double-joint PCR: a PCR-based molecular tool for gene manipulations in filamentous fungi", Fungal Genetics and Biology, 2004, pp. 973-981, vol. 41.

Zelle et al., "Malic Acid Production by *Saccharomyces cerevisiae*: Engineering of Pyruvate Carboxylation, Oxaloacetate Reduction, and Malate Export", Applied and Environmental Microbiology, May 2008, pp. 2766-2777, vol. 74, No. 9.

International Search Report and Written Opinion of corresponding PCT/US2011/040608 dated Oct. 21, 2011.

pRS426::GPD-xpk1+ADH-eutD map

Table 6

```
HMMER2.0 [2.2g]
NAME XFP_XPK_exp_seqs
LENG 845
ALPH Amino
RF no
CS no
MAP yes
COM /app/public/hmmer/current/bin/hmmbuild XFP_XPK_HMM XFP_XPK_exp_seqs.aln
COM /app/public/hmmer/current/bin/hmmcalibrate --mean 800 XFP_XPK_HMM
NSEQ 8
DATE Fri Dec 4 15:29:49 2009
CKSUM 6589
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -614.573792 0.077043
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -476 | * | -1831 | | | | | | | | | | | | | | | | | | |
| 1(M) | -579 | -646 | -1823 | -1279 | -241 | -1949 | 816 | 340 | 991 | 1145 | 2778 | -1234 | 1286 | -828 | -1131 | -1025 | -537 | 205 | -1033 | -696 | 11 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -25 | -6428 | -7470 | -894 | -1115 | -701 | -1378 | -476 | * | | | | | | | | | | | | |
| 2(W) | -424 | -1143 | -649 | -112 | -1118 | -1430 | -73 | -944 | 1343 | -1091 | -364 | -285 | 1428 | 217 | 174 | -480 | -363 | 730 | 3083 | -756 | 12 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -25 | -6428 | -7470 | -894 | -1115 | -701 | -1378 | * | * | | | | | | | | | | | | |
| 3(Q) | -411 | -1812 | 202 | 1278 | -2120 | 997 | 53 | -1844 | 1011 | -1806 | -940 | 170 | -1370 | 1483 | 39 | -277 | -358 | -1435 | -1985 | -1327 | 13 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -25 | -6428 | -7470 | -894 | -1115 | -701 | -1378 | * | * | | | | | | | | | | | | |
| 4(M) | -554 | -1770 | -500 | 1294 | -2084 | -1496 | -45 | -1741 | 1490 | -1726 | 2375 | -163 | -1571 | 384 | 1179 | -467 | -467 | -1393 | -1906 | -1358 | 14 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -19 | -6836 | -7878 | -894 | -1115 | -701 | -1378 | * | * | | | | | | | | | | | | |
| 5(V) | 582 | -614 | -1167 | 546 | -657 | -1623 | 419 | 47 | -453 | 583 | 188 | -696 | -1707 | -324 | -741 | -630 | 773 | 1221 | -1069 | -649 | 15 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -19 | -6836 | -7878 | -894 | -1115 | -701 | -1378 | * | * | | | | | | | | | | | | |
| 6(M) | -388 | -632 | 233 | -716 | -648 | -1697 | 471 | 1170 | -550 | -499 | 1779 | 218 | -1768 | -407 | -821 | -698 | 1278 | 799 | -1059 | -646 | 16 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8A

Table 6

FIG. 8B

Table 6

| | | | | | | | | | | | | | | | | | | |
|---|---|---|---|---|---|---|---|---|---|---|---|---|---|---|---|---|---|---|
| 19(K) | 1232 | -7108 | -736 | -295 | -2360 | -1534 | -473 | -2014 | 2326 | -2058 | -1228 | -486 | 1165 | -74 | -221 | -634 | -677 | -1596 | -2264 | -1735 | 29 |
| | -16 | -1674 | -500 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 20(Y) | -2075 | -2643 | 1686 | -985 | -266 | -2358 | -869 | -1801 | | -2467 | -2120 | -1177 | -2732 | -1384 | -2229 | -1931 | -2114 | -2488 | 905 | 4141 | 30 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 21(W) | -2473 | -2122 | -3795 | -3534 | 136 | -3469 | -1296 | -2887 | | 1176 | -449 | -2889 | -3469 | -2568 | -2708 | -2895 | -2429 | -1317 | 5419 | 316 | 31 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 22(R) | -1335 | -1772 | -2246 | -1513 | -2127 | -2222 | 955 | -1242 | 35 | -1675 | -1197 | -1424 | -2426 | -659 | 3303 | -1507 | -1331 | 1211 | -2220 | -1868 | 32 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 23(A) | 1948 | -1167 | 891 | 1114 | -1539 | -1605 | -710 | -688 | -551 | -1278 | -608 | -703 | -1861 | -451 | -928 | -724 | -609 | 1295 | -1870 | -1386 | 33 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 24(A) | 2275 | -1339 | -993 | -558 | -2142 | -1451 | -682 | -1733 | 1352 | -1909 | -1113 | -663 | -1785 | -334 | -564 | -587 | 928 | -1336 | -2220 | -1732 | 34 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 25(N) | -1216 | -1775 | -1072 | -1034 | -1473 | -1967 | -1153 | -1429 | -1009 | 767 | -1165 | -742 | -2339 | -1043 | -1259 | -1335 | -1316 | -1331 | -1982 | -1273 | 35 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 26(Y) | -2131 | -1808 | -3471 | -3249 | 538 | -814 | 1516 | -2817 | | -864 | -742 | -2495 | -3305 | -2356 | -2649 | -2520 | -2091 | -784 | -205 | 4093 | 36 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 27(L) | -2321 | -1872 | -4652 | -4075 | -539 | -4266 | -3092 | -3803 | | 2345 | 2067 | -3915 | -3747 | -2978 | -3487 | -3494 | -2215 | -175 | -2130 | -2157 | 37 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 28(S) | -482 | -1136 | -1858 | -1915 | -3072 | -1315 | -1996 | -2905 | -2045 | -3106 | -2272 | -1475 | 1651 | -1840 | -2205 | -3487 | -873 | -2011 | -3242 | -2908 | 38 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 29(V) | 845 | -1090 | -3817 | -3373 | -1522 | 3377 | 2794 | 2147 | 3161 | -649 | 421 | -3056 | -3362 | -2955 | 3016 | -2598 | -1419 | 2690 | -2606 | -2197 | 39 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |
| 30(G) | -1283 | -2067 | 837 | 965 | 3177 | 3042 | -1462 | -3119 | -1171 | -3141 | -2429 | -1111 | -2331 | 2005 | -1448 | -1320 | -1499 | -2538 | -3099 | -2665 | 40 |
| | -16 | -149 | -500 | 43 | -381 | 399 | 106 | 210 | | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | |

FIG. 8C

Table 6

| | | | | | | | | | | | | | | | | | | | | |
|---|---|---|---|---|---|---|---|---|---|---|---|---|---|---|---|---|---|---|---|---|
| -16 | | -7108 | -8150 | -894 | -1115 | -701 | -1378 | * | | | | | | | | | | | | |
| 31(Q) | 974 | -2142 | -780 | -270 | -2589 | -1791 | -328 | -2217 | 1581 | -2142 | -1329 | -487 | -1903 | 3083 | 262 | -876 | 671 | -1860 | -2250 | -1764 | 41 |
| - | -149 | -500 | 233 | 43 | -381 | 399 | 106 | -626 | 210 | -720 | -466 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 32(L) | -1375 | -1127 | 3503 | 2949 | -697 | -3071 | -2054 | 1887 | -2629 | 2035 | 342 | -2656 | -2990 | -2251 | -2534 | -2214 | 1157 | 428 | -1759 | -1511 | 42 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 33(Y) | -1937 | -2273 | -1926 | -1563 | -232 | -2608 | -650 | -2164 | 1538 | -2035 | -1599 | -1501 | -2740 | -960 | -541 | -1929 | -1851 | -2048 | -794 | 4044 | 43 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 34(L) | -2871 | -2457 | -4231 | -4103 | -1033 | -3803 | -3165 | -541 | -3734 | -2035 | 3130 | -3935 | -3797 | -3286 | -3484 | -3713 | -2869 | -1136 | -2394 | -2220 | 44 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 35(K) | -565 | -1769 | -542 | 1150 | -2042 | 256 | -133 | -1707 | 1529 | -200 | 1362 | -220 | -1622 | 291 | 1492 | -490 | -487 | -1367 | -1948 | -1377 | 45 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 36(D) | -733 | -2199 | 2095 | 230 | -2550 | 256 | -327 | -2314 | 1307 | -31 | -1390 | -100 | -1681 | 97 | -574 | 1114 | -708 | -1861 | -2454 | -1735 | 46 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 37(N) | -1190 | -2662 | 1381 | 127 | -3153 | -1520 | -768 | -2990 | -757 | -200 | -2269 | -1390 | -1961 | -405 | -1416 | 1061 | -1253 | -2479 | -3137 | -2313 | 47 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 38(P) | -1777 | -2801 | 1868 | -561 | -3633 | -1918 | -1524 | -3634 | -1721 | -2945 | -2156 | 3138 | 3543 | -1257 | -2350 | -1648 | -1944 | -3091 | -3510 | -2972 | 48 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 39(C) | -1617 | 2940 | -3806 | -3389 | -788 | -2963 | -2369 | 4 | -2967 | 2637 | 197 | -2927 | -3094 | -2569 | -2799 | -2284 | -1672 | -278 | -1950 | -1680 | 49 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 40(M) | -1138 | -1232 | 1092 | -1546 | -625 | -2468 | -1290 | -56 | -1453 | 1974 | -3620 | -1610 | -2481 | -1228 | -1655 | -1558 | -1079 | -283 | -1540 | -1223 | 50 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 41(H) | -30 | 439 | 11 | 363 | -394 | -739 | 699 | 414 | 463 | -757 | 501 | 286 | -577 | 639 | 165 | -23 | 111 | 312 | 697 | -25 | 51 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | | | | | |
| 42(K) | 784 | -2190 | -977 | -302 | -2645 | -1847 | -256 | -2259 | 2452 | -2136 | -1309 | -504 | -1900 | 1339 | 1312 | -874 | -863 | -1897 | -2202 | -1742 | 52 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 8D

Table 6

| | | | | | | | | | | | | | | | | | | | | | | | | | | |
|---|---|---|---|---|---|---|---|---|---|---|---|---|---|---|---|---|---|---|---|---|---|---|---|---|---|---|
| 43(E) | -16 | -648 | -1915 | -516 | 1778 | -894 | -2222 | -1578 | -162 | -1378 | * | -1899 | 439 | 163 | -1023 | -238 | -1667 | 1297 | 1557 | -552 | -568 | -1536 | -2057 | -1482 | 53 | |
| | -16 | -149 | -500 | 233 | 43 | -894 | -1115 | -381 | 399 | -701 | 106 | -1378 | * | -626 | 210 | -466 | -720 | 275 | 394 | 45 | 96 | 359 | 117 | -369 | -294 | -249 |
| 44(P) | -16 | -1091 | -2157 | -710 | -354 | -894 | -2472 | -1828 | 2409 | -1378 | * | -2236 | 1296 | -2195 | -1418 | -568 | 2737 | 88 | -1007 | -1021 | -1903 | -2268 | -1751 | 54 | |
| 45(L) | -16 | -149 | -1110 | -2516 | -1945 | -894 | 1939 | -2543 | -1114 | -1378 | * | -128 | 1051 | 1953 | 309 | -1805 | -1346 | -2527 | -1480 | -1629 | -1078 | -306 | -1080 | -509 | 55 | |
| 46(T) | -16 | -695 | -1464 | -884 | -358 | -894 | -1467 | -1703 | -361 | -1378 | * | -1272 | 1547 | -1430 | -690 | -1392 | -1822 | -57 | -149 | -739 | 2166 | -1045 | -1654 | 1676 | 56 | |
| 47(R) | -16 | 1626 | -2138 | -1332 | -620 | -894 | -2693 | -1985 | -403 | -1378 | * | -2249 | 1356 | -2167 | -747 | -2067 | 11 | -1100 | -1051 | -1929 | -2243 | -1870 | 57 | | |
| 48(E) | -16 | 378 | -1941 | 703 | 1824 | -894 | -2252 | -1386 | -100 | -1378 | * | -2000 | 289 | -1956 | -1046 | -24 | -1516 | 349 | 1172 | 476 | -427 | -1561 | -2134 | -1447 | 58 | |
| 49(D) | -16 | 923 | -2559 | 2894 | 160 | -894 | -2929 | -1519 | -635 | -1378 | * | -2712 | -524 | -2688 | -1882 | -189 | -1895 | 1449 | -1131 | -904 | -1111 | -2258 | -2898 | -2120 | 59 | |
| 50(V) | -16 | 1091 | -1040 | -3230 | -3029 | -894 | -1839 | -2191 | -758 | -1378 | * | -2369 | 3094 | -2408 | 404 | -816 | -2674 | -2598 | -2801 | -1506 | -1141 | -2726 | -2349 | 60 | | |
| 51(K) | -16 | 1016 | -1925 | -1252 | -838 | -894 | -2825 | -1834 | -1948 | -1378 | * | -1367 | -2807 | -1107 | -1667 | -2126 | -380 | -14 | -1094 | -1125 | -1973 | -2524 | -2145 | 61 | | |
| 52(H) | -16 | 477 | -400 | -2258 | -1664 | -894 | 1050 | -2313 | 3152 | -1378 | * | 1043 | -1367 | -239 | -917 | 365 | -1083 | -1355 | -1008 | -417 | 915 | 715 | 1744 | 62 | | |
| 53(H) | -16 | -1023 | -1918 | -1234 | -509 | -894 | -2208 | -1943 | 947 | -1378 | * | -756 | 1315 | -1817 | -1055 | -662 | -1981 | 2592 | 1825 | -993 | -895 | -1542 | -1997 | -1584 | 63 | |
| 54(P) | -16 | 1113 | -913 | -1858 | -1496 | -894 | -1358 | -1604 | -1238 | -1378 | * | -1296 | 958 | -503 | -1306 | -1174 | 2526 | -1479 | -817 | -686 | -602 | -1858 | -1474 | 64 | | |

Table 6

| | | | | | | | | | | | | | | | | |
|---|---|---|---|---|---|---|---|---|---|---|---|---|---|---|---|---|
| 67(I) | -16 -149 -16 | -1794 -500 -7108 | -7108 233 -8150 | -8150 -894 | -1115 -381 -1115 | -701 399 -701 | -1378 106 -1378 | * -626 * | -3666 210 * | 1262 -466 | -3607 275 | -3721 394 | -3300 45 | -3605 96 | -3222 359 | -1758 117 | 1880 -369 | -2695 -294 | -2428 -249 | 77 |
| 68(Y) | -16 -149 -16 | -1692 -500 -7108 | -1354 233 -8150 | -4306 -894 | -1267 -381 -1115 | -3968 399 -701 | -3273 106 -1378 | 2808 -626 * | -3666 210 * | 1262 -466 | -3607 275 | -3721 394 | -3300 45 | -3605 96 | -3222 359 | -1758 117 | 1880 -369 | -544 -294 | 3829 -249 | 78 |
| 69(A) | -16 -149 -16 | 2378 -500 -7108 | 934 233 -8150 | -1885 -894 | -2779 -381 -1115 | 826 399 -701 | -1775 106 -1378 | -2485 -626 * | -1781 210 * | -2703 -466 | -1842 275 | -1860 394 | -1577 45 | -1989 96 | 1353 359 | 1040 117 | -1689 -369 | -2983 -294 | -2654 -249 | 79 |
| 70(H) | -16 -149 -16 | -3205 -500 -7108 | -3079 233 -8150 | -2723 -894 | -2110 -381 -1115 | -3046 399 -701 | 5295 106 -1378 | -4135 -626 * | -2617 210 * | -3813 -466 | -2886 275 | -3482 394 | -2833 45 | -2620 96 | -3291 359 | -3356 117 | -3895 -369 | -2397 -294 | -1681 -249 | 80 |
| 71(L) | -16 -149 -16 | -2379 -500 -7108 | -1915 233 -8150 | -4669 -894 | -4151 -381 -1115 | -4360 399 -701 | -3248 106 -1378 | 1934 -626 * | -3862 210 * | 553 -466 | -4017 275 | -3845 394 | -3099 45 | -3585 96 | -3641 359 | -2289 117 | -24 -369 | -2250 -294 | -2225 -249 | 81 |
| 72(N) | -16 -149 -16 | -2171 -500 -7108 | -2655 233 -8150 | -1458 -894 | -621 -381 -1115 | -3334 399 -701 | -2267 106 -1378 | -3943 -626 * | -2365 210 * | -3437 -466 | -2932 275 | -3845 394 | -2205 45 | -2608 96 | -3641 359 | -2439 117 | -3392 -369 | -3253 -294 | -2909 -249 | 82 |
| 73(R) | -16 -149 -16 | -1929 -500 -7108 | -2343 233 -8150 | -1600 -894 | -825 -381 -1115 | -2607 399 -701 | -677 106 -1378 | -2317 -626 * | 45 210 * | -1653 -466 | -1506 275 | -2681 394 | -679 45 | 3382 96 | -1922 359 | -1792 117 | -2176 -369 | -1232 -294 | 2267 -249 | 83 |
| 74(V) | -16 -149 -16 | 503 -500 -7108 | -701 233 -8150 | -3099 -894 | 1199 -381 -1115 | -2506 399 -701 | 1425 106 -1378 | 486 -626 * | -2168 210 * | 1370 -466 | -2113 275 | -2515 394 | -1800 45 | -2039 96 | -1621 359 | -848 117 | 2021 -369 | -1247 -294 | -916 -249 | 84 |
| 75(I) | -16 -149 -16 | -2091 -500 -7108 | -1746 233 -8150 | -3840 -894 | -1676 -381 -1115 | -3532 399 -701 | -3289 106 -1378 | 3684 -626 * | -3581 210 * | -693 -466 | -3562 275 | -3674 394 | -3445 45 | -3521 96 | -3194 359 | -2146 117 | 449 -369 | -2877 -294 | -2493 -249 | 85 |
| 76(K) | -16 -149 -16 | 1051 -500 -7108 | -1939 233 -8150 | -69 -894 | -2445 -381 -1115 | -1557 399 -701 | -349 106 -1378 | -2132 -626 * | 2202 210 * | -2116 -466 | 1786 275 | -1753 394 | 70 45 | -141 96 | -646 359 | -704 117 | -1719 -369 | -2284 -294 | -1701 -249 | 86 |
| 77(K) | -16 -149 -16 | -1384 -500 -7108 | -2800 233 -8150 | 1892 -894 | -3174 -381 -1115 | -1733 399 -701 | -742 106 -1378 | -2966 -626 * | -1966 210 * | -2873 -466 | -400 275 | -2087 394 | -365 45 | -775 96 | -1179 359 | -1372 117 | -2535 -369 | -2949 -294 | -2288 -249 | 87 |
| 78(Y) | -16 -149 -16 | -2118 -500 -7108 | -2084 233 -8150 | -2592 -894 | -2218 -381 -1115 | 1983 399 -701 | -3049 106 -1378 | 2937 -626 * | -1851 210 * | -1662 -466 | -1339 275 | -3049 394 | 1795 45 | -2085 96 | -2125 359 | -2036 117 | -1809 -369 | 122 -294 | 3287 -249 | 88 |

FIG. 8G

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 79(N) | -1107 | 1326 | 223 | -2992 | 1724 | -586 | -2799 | 472 | -2733 | -1910 | 2292 | -1876 | 1179 | -1098 | -894 | -2331 | -1109 | -2923 | -2116 | 89 |
| - | -149 | -500 | 43 | -381 | 399 | 106 | -626 | 210 | -466 | -720 | 275 | 394 | 45 | 96 | 359 | -369 | 117 | -294 | -249 | |
| - | -16 | -7108 | -8150 | -894 | -1115 | -701 | -1378 | * | | | | | | | | | | | | |
| 80(L) | -1690 | -1806 | -2247 | -1903 | -837 | -1536 | -464 | -1204 | 2489 | 81 | -1939 | -2835 | 1986 | -1289 | -2052 | -850 | -1642 | -1841 | -1451 | 90 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 81(D) | -1292 | -2956 | 2598 | 202 | -3213 | -1558 | -693 | -3045 | 851 | -2958 | -2170 | 2502 | -1967 | -318 | -1262 | -1043 | -2569 | -1304 | -3134 | -2291 | 91 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 82(M) | -866 | -1094 | -2548 | -2220 | -1176 | -1993 | -1696 | -374 | -1810 | -470 | 4232 | -1867 | -2385 | -1729 | -1855 | -400 | 1587 | -1260 | -1960 | -1618 | 92 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 83(F) | -1725 | -1400 | -3934 | -3394 | 2962 | -3213 | -2055 | 325 | -3076 | 1369 | 437 | -3005 | -2630 | 2505 | -2863 | -2595 | 1644 | -1653 | -1488 | -995 | 93 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 84(Y) | -2852 | -2251 | -3961 | -3935 | 2281 | -3735 | 476 | -3538 | 168 | -1379 | -1299 | -3641 | -2627 | -3134 | -2925 | -1840 | 233 | -2756 | -4154 | 94 |
| - | -149 | -500 | 233 | 43 | -381 | 399 | 106 | -626 | 210 | -466 | -720 | 275 | 394 | 45 | 96 | 359 | -369 | -294 | -249 | |
| - | -16 | -7108 | -8150 | -894 | -1115 | -701 | -1378 | * | | | | | | | | | | | | |
| 85(I) | -1759 | -1305 | -4328 | -3965 | -1743 | -4047 | -3735 | 3086 | -3833 | -588 | -522 | -3726 | -3872 | -3681 | -3903 | -3364 | -1752 | -3250 | -2813 | 95 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 86(M) | -700 | -1108 | -1144 | 2046 | -1106 | -1894 | -710 | -177 | -572 | 2421 | -857 | -1997 | -497 | -908 | -934 | 1171 | -657 | -1602 | -1155 | 96 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 87(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 97 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 88(P) | -526 | -1169 | -1848 | -1957 | -3095 | -1343 | -2052 | -2946 | -2123 | -3152 | -2333 | -1513 | 3407 | -1917 | -2261 | 1632 | -922 | -2053 | -3267 | -2938 | 98 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 89(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 99 |
| - | -149 | -500 | 233 | 43 | -381 | 399 | 106 | -626 | 210 | -466 | -720 | 275 | 394 | 45 | 96 | 359 | -369 | 117 | -294 | -249 |
| - | -16 | -7108 | -8150 | -894 | -1115 | -701 | -1378 | * | | | | | | | | | | | | |
| 90(H) | -3205 | -3079 | -2723 | -2890 | -2110 | -3046 | 5295 | -4135 | -2617 | -3813 | -3561 | -2886 | -3482 | -2833 | -2620 | -3291 | -3356 | -3895 | -2397 | -1681 | 100 |
| - | -149 | -500 | 233 | 43 | -381 | 399 | 106 | -626 | 210 | -466 | -720 | 275 | 394 | 45 | 96 | 359 | -369 | 117 | -294 | -249 |

FIG. 8H

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 91(G) | -2594 | -2690 | -3304 | -3623 | -4328 | 3747 | -3462 | -4761 | -3953 | -4671 | -3320 | -3352 | -3748 | -3779 | -2839 | -2981 | -4004 | -3668 | -4222 | 101 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 92(H) | -30 | 439 | 11 | 363 | -394 | -739 | 699 | -414 | 463 | -757 | 501 | 286 | -577 | 639 | 165 | -23 | 111 | 312 | 697 | -25 | 102 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 93(G) | 1432 | -1081 | -2340 | -2519 | -3309 | 3113 | -2408 | -3041 | -2687 | -3327 | -2482 | -1740 | -2062 | -2353 | -2689 | -702 | -903 | -2058 | -3476 | -3301 | 103 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 94(Q) | -1326 | -2187 | -825 | 789 | -2878 | -1884 | -1131 | -2784 | -3041 | -2752 | -2063 | 977 | 2646 | -1814 | -881 | -1313 | -903 | -2357 | -2787 | -2310 | 104 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 95(V) | 1470 | -815 | -2475 | -2234 | -1874 | 1135 | -1780 | -892 | -2064 | -1657 | -1016 | -1624 | -2020 | 3194 | -2121 | -717 | -687 | 2477 | -2329 | -1999 | 105 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 96(M) | -883 | -899 | -2454 | -1951 | -595 | 991 | -1285 | -31 | -1626 | 1077 | 3599 | -1754 | -2362 | -1420 | -1669 | -1376 | -878 | -131 | -1359 | -1024 | 106 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 97(V) | -1205 | -914 | -3493 | -2955 | -1023 | -3025 | -2085 | 1649 | -2672 | 917 | -32 | -2617 | -2982 | -2375 | -2606 | -2169 | 1373 | 2267 | -1903 | -1552 | 107 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 98(S) | 1719 | -1145 | -1296 | -1130 | -2738 | -1260 | -1357 | -2461 | -1234 | -2624 | -1769 | 1171 | -1844 | -1070 | -1576 | 2383 | -686 | -1744 | -2874 | -2423 | 108 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 99(N) | -809 | -2086 | -98 | 33 | -2593 | -1494 | -488 | -2361 | -147 | -2346 | -1503 | 2681 | -1787 | 1970 | -607 | 984 | -825 | 1908 | -2521 | -1851 | 109 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 100(S) | 878 | 890 | -1818 | -1458 | -1679 | -1418 | -1269 | -1166 | -1293 | 665 | 837 | -1224 | -1904 | -1156 | -1509 | 2469 | -610 | -869 | -2068 | -1669 | 110 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 101(Y) | -3588 | 2709 | -4120 | 4323 | 1034 | -3994 | -419 | -2613 | -3834 | -2031 | -2055 | -2741 | -3905 | -2826 | -3349 | -3280 | -3472 | -869 | 3673 | 4312 | 111 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 102(L) | -2496 | -2027 | -4721 | -4202 | 560 | -4432 | -3262 | -3887 | 1210 | 2852 | 611 | -4095 | -3876 | -3086 | -3587 | -3729 | -2397 | -232 | -2211 | -2201 | 112 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8I

Table 6

| | | | | | | | | | | | | | | | | | | | |
|---|---|---|---|---|---|---|---|---|---|---|---|---|---|---|---|---|---|---|---|
| | -16 | -7108 | -8150 | -894 | -1115 | -701 | -1378 | * | | | | | | | | | | | |
| 103(D) | -1791 | -3663 | 3414 | 1659 | -3853 | -1647 | -1043 | -3807 | -1343 | -3679 | -251 | -2201 | -725 | -2227 | -1438 | -1872 | -3282 | -3836 | -2831 | 113 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | * | | | | | | | | | | | |
| 104(G) | -2594 | -2690 | -3304 | -3623 | -4328 | 3747 | -3462 | -4761 | -3953 | -4671 | -3320 | -3352 | -3748 | -3779 | -2839 | -2981 | -4004 | -3668 | -4222 | 114 |
| | -149 | -500 | 233 | -894 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 105(S) | -342 | -976 | -2177 | -2128 | -2921 | -1229 | -2008 | -2606 | -2073 | -2888 | -1512 | -1936 | -1871 | -2189 | 2669 | 2327 | -1779 | -3151 | -2842 | 115 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 106(Y) | -2652 | -2206 | -3673 | -3556 | 726 | -3580 | -692 | -1359 | -3066 | 982 | -2620 | -3538 | -2500 | -2832 | -2837 | -2587 | -24 | -3276 | 4185 | 116 |
| | -149 | -500 | 233 | -894 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 107(T) | -502 | -1110 | -2201 | -2282 | -3095 | 1340 | -2204 | -2779 | -2341 | -3075 | -1660 | -2066 | -2111 | -2412 | -729 | 3346 | -1945 | -3276 | -3043 | 117 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 108(E) | -1163 | -2811 | 1893 | 2460 | -3072 | -1535 | -594 | -2884 | 1337 | -2797 | -140 | -1898 | -203 | -1072 | -933 | -1159 | -2412 | -2972 | -2157 | 118 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 109(I) | 561 | -338 | -2506 | -1896 | 1485 | -1980 | -829 | 1917 | -1557 | -155 | -1524 | -2033 | -1236 | -1465 | -1055 | 777 | 309 | -776 | 1058 | 119 |
| | -149 | -500 | 233 | -894 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 110(Y) | -3611 | -2705 | -4166 | -4409 | 2531 | -4042 | -397 | -2533 | -3989 | -1938 | -2747 | -1983 | -2851 | -3444 | -3294 | -3491 | -2684 | 345 | 4289 | 120 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 111(P) | -2931 | -2878 | -3420 | -3706 | -4181 | -2925 | -3468 | -4621 | -3859 | -4490 | -3491 | -4225 | -3781 | -3695 | -3182 | -3279 | -4087 | -3594 | -4064 | 121 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 112(E) | -785 | -2281 | -2 | 1960 | -2596 | -1496 | -297 | -2348 | 660 | -2275 | 1934 | -1399 | 1721 | -381 | -626 | -738 | -1906 | -2432 | -1737 | 122 |
| | -149 | -500 | 233 | -894 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 113(I) | -1722 | -1438 | -3424 | -3080 | 131 | -3150 | -1169 | 2917 | -2681 | -503 | -2513 | -3144 | -2305 | -2554 | -2347 | -1683 | -39 | -645 | 2880 | 123 |
| | -149 | -500 | 233 | 43 | -381 | 399 | 106 | -626 | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 114(T) | -1213 | -1674 | -2755 | -2906 | -3163 | -1922 | -2659 | -2698 | -2788 | -3105 | -2311 | -2600 | -2708 | -2753 | -1463 | 3819 | -2197 | -3286 | -3156 | 124 |
| | -149 | -500 | 233 | 43 | -381 | 399 | 106 | -626 | 210 | -466 | 275 | 394 | 45 | 96 | 359 | 117 | -369 | -294 | -249 | |

Table 6

| | | | | | | | | | | | | | | | | | |
|---|---|---|---|---|---|---|---|---|---|---|---|---|---|---|---|---|---|
| | -16 | -7108 | -8150 | -894 | -1115 | -701 | -1378 | * | | | | | | | | | |
| 127(F) | -3342 | -2776 | -4026 | -4232 | -3545 | -3545 | -1431 | -4038 | -1801 | -1900 | -3299 | -3780 | -3350 | -3645 | -3490 | -3420 | -2566 | 349 | 137 |
| | -149 | -500 | 233 | 43 | 399 | -701 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 128(S) | -897 | -1462 | -2333 | -2543 | -3185 | -1640 | -2474 | -2686 | -3497 | -2780 | -1973 | -2360 | -2483 | -2703 | -3465 | -1316 | -2413 | -3310 | 138 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 129(F) | -1908 | -1643 | -3261 | -2963 | 3263 | -3050 | -1219 | -2636 | -1197 | -851 | -2199 | -3071 | -2085 | -2476 | -2189 | 1297 | -1211 | 77 | 2811 | 139 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 130(P) | -540 | -1180 | -1850 | -1974 | -3103 | -1352 | -2072 | -2149 | -3170 | -2355 | -1527 | 3509 | -1943 | -2279 | 1382 | -938 | -2068 | -3276 | -2949 | 140 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 131(I) | 1432 | -1081 | -2340 | -2519 | -3309 | 3113 | -2408 | -2687 | -3327 | -2482 | -1740 | -2062 | -2353 | -2689 | -702 | -903 | -2058 | -3476 | -3301 | 141 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 132(G) | -2594 | -2690 | -3304 | -3623 | -4328 | 3747 | -3462 | -3953 | -4671 | -4212 | -3320 | -3352 | -3748 | -3779 | -2839 | -2981 | -4004 | -3668 | -4222 | 142 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 133(V) | -1322 | -992 | -3697 | -3181 | -1158 | -3230 | 2069 | -2914 | 914 | -126 | -2840 | -3160 | -2624 | -2849 | -2396 | 641 | 2352 | -2122 | -1765 | 143 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 134(P) | 2498 | -1088 | -2250 | -2290 | -3023 | -1338 | -2177 | -2306 | -2970 | -2190 | -1656 | 2760 | -2080 | -2382 | -710 | -882 | -1878 | -3231 | -2984 | 144 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 135(S) | -897 | -1462 | -2333 | -2543 | -3185 | -1640 | -2474 | -2686 | -3497 | -2780 | -1973 | -2360 | -2483 | -2703 | 3465 | -1316 | -2413 | -3310 | -3025 | 145 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 136(H) | -3205 | -3079 | -2723 | -2890 | -3046 | -2110 | -3046 | -2617 | -3813 | -2970 | -2886 | -3482 | -2833 | -2620 | -3291 | -3356 | -3895 | -2397 | -1681 | 146 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 137(A) | 1947 | -745 | -2823 | -2285 | 1846 | -2348 | 1572 | -1988 | -154 | 207 | -1942 | -1898 | -1677 | -1944 | -1473 | -836 | 359 | -1231 | -781 | 147 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 138(A) | 2029 | -2389 | 1954 | 92 | -2936 | -1492 | -703 | -2716 | -2715 | -1906 | 1712 | -2439 | -331 | -1237 | -881 | -1089 | -2229 | -2931 | -2168 | 148 |
| | -149 | -500 | 233 | 43 | -381 | 399 | 106 | 210 | -466 | -720 | 275 | 394 | 45 | 96 | 359 | 117 | -369 | -294 | -249 |

FIG. 8L

Table 6

| | | | | | | | | | | | | | | | | | | | |
|---|---|---|---|---|---|---|---|---|---|---|---|---|---|---|---|---|---|---|---|
| | -16 | -7108 | -8150 | -894 | -1115 | -701 | -1378 | * | | | | | | | | | | | |
| 139(P) | 1935 | -1116 | -2232 | -2301 | -3058 | -1358 | -2206 | -2705 | -2336 | 3009 | -2238 | -1674 | 3272 | -2114 | -2406 | -739 | -914 | -1913 | -3260 | -3019 | 149 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 140(E) | -1349 | -2706 | -162 | 2827 | 3109 | -1785 | -624 | -2820 | 1799 | -2704 | -1931 | -437 | -2073 | -230 | -334 | -1160 | -1298 | -2421 | -2774 | -2189 | 150 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 141(T) | -645 | -1000 | -2671 | -2474 | -1925 | -1699 | -2057 | -385 | -2200 | -1416 | -1020 | -1885 | -2274 | -2057 | -2247 | -1011 | 3256 | 1160 | -2570 | -2205 | 151 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 142(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | 3594 | -4064 | 152 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 143(H) | -30 | 439 | 11 | 363 | 394 | -739 | 699 | -414 | 463 | 757 | 501 | 286 | -577 | 639 | 165 | -23 | 111 | -312 | 697 | -25 | 153 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 144(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 154 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 145(S) | 1426 | 949 | -2380 | -2419 | 3107 | -1201 | -2226 | -2819 | -2411 | -3105 | -2246 | -1618 | -1944 | -2131 | -2456 | 3026 | -742 | -1874 | -3336 | -3080 | 155 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 146(I) | -2091 | -1746 | -3971 | -3840 | -1676 | -3532 | -3289 | 3684 | -3581 | -659 | -693 | -3562 | -3674 | -3445 | -3521 | -3194 | -2146 | 449 | -2877 | -2493 | 156 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 147(H) | -3205 | -3079 | -2723 | -2890 | -2110 | -3046 | 5295 | -4135 | -2617 | 3813 | -3561 | -3320 | -3482 | -2833 | -2620 | -3291 | -3356 | -3895 | -2397 | -1681 | 157 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 148(E) | -2641 | -3308 | -896 | 3732 | -3966 | -2458 | -2043 | -4105 | -2128 | -4016 | -3555 | -1531 | -2959 | -1842 | -2560 | -2479 | -2750 | -3722 | -3563 | -3385 | 158 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 149(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 159 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 150(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 160 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8M

Table 6

| | | | | | | | | | | | | | | | | | | | |
|---|---|---|---|---|---|---|---|---|---|---|---|---|---|---|---|---|---|---|---|
| | -16 | -7108 | -8150 | -894 | -1115 | -701 | -1378 | * | | | | | | | | | | | |
| 151(E) | 669 | -2323 | -22 | 3133 | -3044 | -1600 | -954 | -2706 | -853 | -2824 | -2095 | 473 | -2059 | -614 | -1376 | -1068 | -1279 | -2254 | -3056 | -2376 | 161 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 152(L) | -2871 | -2457 | -4231 | -4103 | -1033 | -3803 | -3165 | -541 | -3734 | 3130 | -3935 | -3797 | -3286 | -3484 | -3713 | -2869 | -1136 | -2394 | -2220 | 162 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 153(G) | -2594 | -2690 | -3304 | -3623 | -4328 | 3747 | -3462 | -4761 | -3953 | -4671 | -4212 | -3320 | -3352 | -3748 | -3779 | -2981 | -2981 | -4004 | -3668 | -4222 | 163 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 154(Y) | -3482 | -2868 | -3701 | -3919 | 238 | -3552 | -1112 | -3000 | -3638 | -2516 | -2526 | -3027 | -3772 | -3101 | -3341 | -3418 | -3527 | -3071 | -441 | 4711 | 164 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 155(S) | 2313 | 937 | -2414 | -2419 | -3070 | -1197 | -2205 | -2774 | -2385 | -3059 | -2200 | -1614 | -1936 | -2106 | -2436 | -728 | -2275 | -1846 | -3302 | -3046 | 165 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 156(L) | -2364 | -1901 | -4660 | -4144 | -630 | -4349 | -3246 | 2015 | -3856 | 2597 | 544 | -4006 | -3841 | -3101 | -3583 | -3629 | 2 | -2255 | -2227 | 166 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 157(S) | -643 | -1153 | -1942 | -2414 | -1726 | -1574 | -1553 | -1424 | -1560 | 381 | -1167 | -1475 | -2124 | -1504 | -1711 | -1260 | -911 | -1168 | -2234 | -1683 | 167 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 158(H) | -1208 | -1519 | -1818 | -1600 | 796 | -2137 | 4436 | -1042 | -1134 | -1422 | 996 | -1514 | -2459 | -2106 | -1277 | -2459 | -1442 | -1296 | -1367 | -527 | 168 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 159(G) | 1625 | -934 | -2312 | -2287 | -3120 | 2515 | -2142 | -2866 | -2304 | -3096 | -2206 | -1553 | -1910 | -2010 | -2401 | 1405 | -705 | -1884 | -3324 | -3069 | 169 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 160(Y) | 553 | 516 | -2670 | -2093 | 1648 | -2153 | -831 | 125 | -1753 | -275 | 301 | -1673 | -2204 | -1407 | -1649 | -1238 | -604 | 1878 | -648 | 2121 | 170 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 161(G) | -2594 | -2690 | -3304 | -3623 | -4328 | 3747 | -3462 | -4761 | -3953 | -4671 | -4212 | -3320 | -3352 | -3748 | -3779 | -2981 | -2981 | -4004 | -3668 | -4222 | 171 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 162(A) | 3438 | -1472 | -2846 | -3040 | -3287 | -1726 | -2735 | -2840 | -3028 | -3257 | -2662 | -2236 | -2447 | -2798 | -2944 | -1216 | -1387 | -2183 | -3405 | -3320 | 172 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8N

Table 6

| | | | | | | | | | | | | | | | | | | | | | | |
|---|---|---|---|---|---|---|---|---|---|---|---|---|---|---|---|---|---|---|---|---|---|---|
| 163(I) | -16 | -1759 | -1304 | -4329 | -3967 | -1748 | -4050 | -3739 | 3054 | -3836 | -593 | -525 | -3728 | -3874 | -3686 | -3907 | -3367 | -1751 | 2401 | -3255 | -2817 | 173 |
| | -149 | -500 | 233 | -8150 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -894 | -1115 | -701 | -1378 | * | * | | | | | | | | | | | | |
| 164(M) | -2389 | -1957 | -4609 | -4018 | 1345 | -2821 | -4211 | 78 | -3724 | 2123 | 3673 | -3822 | -3688 | -2852 | -3378 | -3418 | -2267 | -598 | -1888 | -1767 | 174 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 165(D) | -2784 | -3432 | 4016 | -1200 | -4140 | -3334 | -2466 | -2197 | -4505 | -2621 | -4365 | -3956 | -1551 | -3014 | -2039 | -3232 | -2593 | -2938 | -3710 | -3552 | 175 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 166(N) | -2171 | -2655 | -1458 | -1748 | -3334 | -2364 | -1873 | -2267 | -3943 | -2365 | -3936 | -3437 | 4205 | -2932 | -2205 | -2608 | -2224 | -2439 | -3392 | -3253 | -2909 | 176 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 167(P) | -2931 | -2878 | -3420 | -3706 | -4181 | -2925 | -3468 | -3943 | -4621 | -3859 | -4490 | -4165 | -3491 | 4225 | -3781 | -3695 | -3182 | -3279 | -4087 | -3594 | -4064 | 177 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 168(D) | -1220 | -2896 | 2608 | 1191 | -3149 | -735 | -2518 | -651 | -2978 | -602 | -2895 | -2089 | 1257 | -1925 | -269 | -1273 | 1237 | -1229 | -2498 | -3083 | -2233 | 178 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 169(L) | -1037 | -975 | -2376 | 275 | -3666 | 2083 | -3676 | -1412 | 367 | -1669 | 2017 | 219 | 94 | -1835 | -2540 | -1484 | -1766 | -1625 | -988 | -1541 | -1207 | 179 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 170(I) | -1918 | -1539 | -4076 | -3666 | 2083 | -2596 | -1867 | -2265 | 74 | -3379 | 145 | -1277 | -903 | -2107 | -3221 | -3504 | -2843 | -3198 | -2911 | -1872 | 334 | -1508 | 773 | 180 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 171(V) | 2267 | -970 | -2988 | -2782 | -1865 | -1867 | -1235 | -1739 | -2211 | -1758 | -2497 | -1687 | -2107 | -2419 | -1571 | -2332 | -1182 | -528 | 1549 | -982 | 2421 | -1545 | -2604 | -2846 | 181 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 172(A) | 2401 | -935 | -2092 | -1865 | 2083 | -2596 | -1235 | -2187 | 405 | -2700 | -983 | 575 | -2269 | -2516 | 1817 | -2419 | 1817 | -2516 | -2413 | -1946 | -2614 | -1349 | -528 | 2580 | 182 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 173(C) | 152 | 3737 | -3346 | -3008 | -1521 | -2075 | -2596 | -2187 | 1998 | -2055 | -599 | -276 | -2175 | -2880 | -1914 | -2228 | -1998 | -1157 | 2462 | -2260 | -1908 | 183 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 174(V) | -1189 | -1030 | -2667 | 1142 | -1294 | -2870 | -1904 | 1998 | -2055 | -599 | -276 | -2175 | -2880 | -1914 | -2228 | -1998 | -1157 | 2462 | -2134 | -1721 | 184 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |

FIG. 80

Table 6

| | | | | | | | | | | | | | | | | | | | |
|---|---|---|---|---|---|---|---|---|---|---|---|---|---|---|---|---|---|---|---|
| 175|V | -16 | -1753 | -1297 | -4327 | -3965 | -1769 | -4049 | -3747 | 2530 | -3837 | -621 | -3725 | -3875 | -3695 | -3913 | -3366 | -1745 | 2911 | -3274 | -2827 | 185 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 176|G | -16 | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 186 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 177|D | -16 | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 187 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 178|G | -16 | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 188 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 179|E | -16 | -2641 | -3308 | 896 | -2490 | -3966 | -2458 | -2043 | -4105 | -2128 | -4016 | -3555 | -1531 | -2959 | -1842 | -3232 | -2479 | -746 | -4046 | -3722 | -3385 | 189 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 180|A | 3124 | -934 | -2490 | -2562 | -3082 | -1203 | -2297 | -2766 | -4105 | -2535 | -4016 | -3555 | -1670 | -2959 | -1954 | -2560 | -2534 | 920 | -1844 | -3332 | -3091 | 190 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 181|E | -2641 | -3308 | 896 | -2490 | -3966 | -2458 | -2043 | -4105 | -2128 | -4016 | -3555 | -1531 | -2959 | -1842 | -2560 | -2479 | -746 | -3722 | -3563 | -3385 | 191 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 182|T | -1213 | -1674 | -2755 | -2906 | -3163 | -2659 | -2424 | -2698 | -2788 | -3105 | -2612 | -2311 | -2600 | -2708 | -2753 | -1463 | 3819 | -2197 | -3286 | -3156 | 192 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 183|G | 1080 | -1108 | -2311 | -2509 | -3336 | -3223 | -2925 | -3074 | -2706 | -3361 | -2521 | -1751 | -2082 | -2372 | -2708 | -729 | -932 | -2089 | -3493 | -3324 | 193 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 184|P | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 194 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 185|L | -1369 | -1384 | -3092 | -2737 | -825 | -2649 | -2073 | 44 | -2334 | 2571 | 187 | -2437 | -2847 | -2125 | -2306 | -1915 | 1278 | -290 | -1941 | -1678 | 195 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |
| 186|A | 2912 | -1000 | -2422 | -2157 | -1636 | -1634 | -1753 | -816 | -1876 | -1128 | 1988 | -1694 | -2169 | -1741 | -1956 | -923 | -861 | -675 | -2256 | -1899 | 196 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | | |

FIG. 8P

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 187(T) | 973 | -500 | 233 | 43 | -2484 | -2838 | -1268 | -2195 | -2209 | -2352 | -2704 | -1971 | -1675 | -1991 | -2131 | -2373 | -617 | 3427 | -1554 | -3148 | -2888 | 197 |
| | -16 | -149 | -7108 | -8150 | -894 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 188(S) | -437 | -1083 | -2006 | -2144 | -3262 | 1583 | -2197 | -3097 | -2380 | -3307 | -2434 | -1562 | -2008 | -2077 | -2485 | -2965 | -857 | -2074 | -3426 | -3160 | 198 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 189( | -4114 | -3274 | -4214 | -4453 | -1722 | -3496 | -2681 | -4109 | -4149 | -3619 | -3615 | -4044 | -3885 | -4032 | -3816 | -4355 | -4248 | -4133 | 6191 | -1329 | 199 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 190(H) | -1323 | -1832 | -1402 | -994 | 2149 | -2268 | 3183 | -1595 | -684 | -1541 | -1023 | -1062 | -2358 | -951 | -1335 | -1461 | -476 | 569 | 200 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 191(S) | 1326 | -873 | -2274 | -2002 | -2263 | -1287 | -2197 | -1644 | -1844 | -2124 | -1388 | -1463 | -1915 | -1637 | -1990 | 2623 | -646 | 880 | -2605 | -2269 | 201 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 192(N) | -573 | 1630 | 864 | 62 | -1860 | -1478 | 310 | 843 | 39 | -1634 | -837 | 2440 | -1658 | -526 | -537 | 638 | -1154 | -1980 | -1380 | 202 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 193(K) | -1324 | -1987 | -1657 | -1059 | -2437 | -2134 | -750 | -1568 | -1940 | -1374 | 286 | -2304 | -1107 | -577 | -391 | 150 | -1379 | 548 | -2320 | -1952 | 203 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 194(H) | -30 | 439 | 11 | 363 | -394 | -739 | 699 | -414 | 463 | -757 | 501 | -922 | -2674 | 639 | 165 | -23 | 111 | -312 | 697 | -25 | 204 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 195(F) | -2721 | -2160 | -3990 | -3906 | 3360 | -3716 | -572 | -1433 | -3510 | -3713 | -1275 | 744 | -240 | -2867 | -3637 | -3597 | -3108 | -2899 | -1379 | -1671 | 137 | -2722 | 205 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 196(I) | -1769 | -1321 | -4308 | -3881 | -1430 | -3998 | -3403 | -1046 | -3616 | 2941 | -3528 | -4165 | -3637 | -2186 | -3419 | -3696 | -3267 | -1740 | -2864 | -2543 | 206 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 197(N) | -1660 | -3287 | 1909 | 69 | -3610 | -1646 | -2925 | -1757 | -3086 | -3624 | -2697 | | | | | | | | | | 207 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |
| | | | | | -1115 | -701 | -1378 | * | | | | | | | | | | | | | | |
| 198(P) | -2931 | -2878 | -3420 | -3706 | -4181 | -2925 | -3468 | -4621 | -3859 | -4490 | -3491 | 3539 | -3695 | -3781 | 4225 | -3182 | -3279 | -4087 | -3594 | -4064 | 208 |
| | -16 | -149 | -500 | 233 | 43 | -381 | 399 | 106 | -626 | 210 | -466 | -720 | 275 | 394 | 45 | 96 | 359 | 117 | -369 | -294 | -249 | |

FIG. 8Q

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 199(R | 780 | -954 | -1042 | -463 | -1021 | -1681 | -388 | 1232 | 838 | -838 | -132 | -612 | -1756 | -173 | 1322 | -665 | -418 | 574 | -1339 | -893 | 209 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 200(N | -622 | -2053 | -110 | 1285 | -2366 | -1450 | -199 | -2102 | 1009 | -2062 | -1176 | 2124 | -1614 | 238 | -276 | 491 | 1247 | -1677 | -2241 | -1566 | 210 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 201(I) | -1369 | -2674 | 3374 | -58 | -3453 | -1571 | -1095 | -3380 | -1289 | -3368 | -2659 | -394 | -2124 | -784 | -2016 | 1149 | -1529 | -2785 | -3505 | -2662 | 211 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 202(G | -2594 | -2690 | -3304 | -3623 | -4328 | 3747 | -3462 | -4761 | -3953 | -3368 | -4212 | -3320 | -3352 | -3748 | -3779 | -2839 | -2981 | -4004 | -3668 | -4222 | 212 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 203(A | 2246 | -790 | -2416 | -1988 | -1270 | -1821 | -1490 | 1726 | -1755 | -905 | -386 | -1651 | -2194 | -1557 | -1854 | -1027 | 949 | 146 | -1839 | -1474 | 213 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 204(V | -1771 | -1603 | -3750 | -3689 | -2037 | -3050 | -3231 | 403 | -3479 | -1154 | -1076 | -3246 | -3399 | -3383 | -3437 | -2628 | -1917 | 3536 | -3074 | -2677 | 214 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 205(L | -2871 | -2457 | -4231 | 4103 | -1033 | -3803 | 3165 | -541 | -3734 | 3130 | -31 | -3935 | -3797 | -3286 | -3484 | -3713 | -2869 | -1136 | -2394 | -2220 | 215 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 206(P | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 216 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 207(I) | -2091 | -1746 | -3971 | -3840 | -1676 | -3532 | -3289 | 3684 | -3581 | -659 | -693 | -3562 | -3674 | -3445 | -3521 | -3194 | -2146 | 449 | -2877 | -2493 | 217 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 208(L | -2475 | -2006 | -4716 | -4195 | -570 | -4423 | -3262 | 1353 | -3887 | 2819 | 603 | -4084 | -3871 | -3089 | -3590 | -3715 | -2377 | -194 | -2218 | -2208 | 218 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 209(H | -1047 | -2367 | -130 | -12 | -2443 | -1653 | 3422 | -2425 | 11 | -2366 | -1567 | 2352 | -1902 | 1348 | -351 | -897 | -1003 | -2040 | -2389 | -1693 | 219 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 210(L | -1968 | -1597 | -4244 | -3772 | -812 | -3841 | -2955 | 582 | -3473 | 239 | 322 | -3529 | -3600 | -2960 | -3315 | -3097 | -1926 | 2070 | -2269 | -2100 | 220 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8R

Table 6

| | | | | | | | | | | | | | | | | | | |
|---|---|---|---|---|---|---|---|---|---|---|---|---|---|---|---|---|---|---|
| 211(N) | -16 | -2171 | -2655 | -1458 | -1748 | -3334 | -2364 | -2267 | -3943 | -2365 | -3936 | -3437 | 4205 | -2932 | -2205 | -2224 | -2439 | -3392 | -3253 | -2909 | 221 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 212(G) | -16 | -2594 | -2690 | -3304 | -3623 | -4328 | 3747 | -3462 | -4761 | -3953 | -4671 | -4212 | -3320 | -3352 | -3748 | -2839 | -2981 | -4004 | -3668 | -4222 | 222 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 213(F) | -16 | -3581 | -2688 | -4165 | -4401 | 3865 | -4034 | -401 | -2491 | -3981 | -1903 | -1944 | -2746 | -3921 | -2847 | -3284 | -3462 | -2647 | 341 | 3054 | 223 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 214(K) | -16 | -2620 | -2961 | -2461 | -2046 | -3743 | -2791 | -1570 | -3603 | 3784 | -3387 | -2839 | -2048 | -3039 | -1260 | -2604 | -2536 | -3331 | -3001 | -2988 | 224 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 215(I) | -16 | -2091 | -1746 | -3971 | -3840 | -1676 | -3532 | -3289 | 3684 | -3581 | -659 | -693 | -3562 | -3674 | -3445 | -3194 | -2146 | 449 | -2877 | -2493 | 225 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 216(A) | -16 | 2478 | -935 | -2423 | -2429 | -3066 | -1197 | -2208 | -2769 | -2392 | -3055 | -2196 | -1617 | -1936 | -2112 | -2440 | -728 | -1843 | -3300 | -3045 | 226 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 217(N) | -16 | -1558 | -3098 | 310 | 1592 | -3431 | -1657 | -945 | -3340 | -959 | -3271 | -2572 | 3495 | -2146 | -611 | -1578 | -1301 | -2860 | -3383 | -2547 | 227 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 218(P) | -16 | -664 | -2231 | -2030 | -1695 | -3192 | -2240 | -1444 | -3029 | -556 | -2975 | -2319 | -1668 | 3549 | -1149 | 1833 | -1745 | -1774 | -2613 | -2650 | 228 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 219(T) | -16 | -1213 | -1674 | -2755 | -2906 | -3163 | -1922 | -2659 | -2698 | -2788 | -3105 | -2612 | -2311 | -2600 | -2708 | -2753 | -1463 | -2197 | -3286 | -3156 | 229 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 220(I) | -16 | -1764 | -4294 | -3932 | -1658 | -3987 | 3644 | -3776 | -3820 | -454 | -3833 | -3684 | -3599 | -3826 | -3457 | -3303 | -1760 | -3153 | -2738 | 230 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 221(F) | -16 | -2604 | -4552 | -4135 | 2542 | -3987 | -4236 | -2203 | -115 | -3820 | 2542 | 500 | 3692 | -3785 | -2927 | -3508 | -2493 | -769 | -1337 | -643 | 231 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |
| 222(S) | -16 | 846 | -2243 | -2217 | 1905 | -3137 | 2545 | -2112 | -2888 | -2254 | -3112 | -2218 | -1528 | -1909 | -1968 | -2369 | -708 | -1899 | -3331 | -3067 | 232 |
| | -16 | -149 | -500 | 233 | 43 | -381 | 399 | -1378 | -626 | 210 | -466 | -720 | 275 | 394 | 45 | 96 | 359 | 117 | -369 | -294 | -249 |
| | | -7108 | -8150 | -894 | -1115 | -701 | * | | | | | | | | | | | | |

FIG. 8S

Table 6

| | | | | | | | | | | | | | | | | | | | | |
|---|---|---|---|---|---|---|---|---|---|---|---|---|---|---|---|---|---|---|---|---|
| -16 | -1454 | 3144 | -2763 | -2070 | -2728 | -2193 | -1414 | -2383 | -460 | -2518 | -1907 | -1827 | -2567 | -1160 | 3510 | -1626 | -1582 | -2068 | -2366 | 233 |
| -149 | -500 | 233 | -8150 | 43 | -381 | 399 | 106 | -626 | 210 | -466 | -720 | 275 | 394 | 45 | 96 | 359 | 117 | -369 | -294 | -249 |
| 223(R) | | | -7108 | -894 | -1115 | -701 | -1378 | * | | | | | | | | | | | | |
| 224(M) | -434 | -912 | 967 | 653 | -960 | -1640 | -368 | 1179 | 682 | -787 | 2592 | -569 | -1718 | -161 | -575 | -617 | 633 | -341 | -1294 | 234 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 225(S) | -1102 | -2199 | 1764 | -235 | -3206 | -1518 | -1117 | -3089 | -1203 | -3129 | -2368 | -513 | -2060 | -804 | -1816 | 2841 | -1292 | -2470 | -3271 | -2541 | 235 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 226(D) | -1724 | -3448 | 3411 | 103 | 3726 | -1642 | -1058 | -3734 | -1342 | -3628 | -2991 | 1884 | -2196 | -745 | -2191 | -1408 | -1822 | -3197 | -3743 | -2768 | 236 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 227(E) | 391 | -2060 | -303 | 2460 | -2453 | -1565 | -312 | -2145 | 213 | -2119 | -1272 | -258 | -1745 | 110 | 1394 | -657 | -720 | -1747 | -2290 | -1683 | 237 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 228(E) | -843 | -2213 | -113 | 2617 | -2562 | -1553 | -357 | -2268 | 1012 | -2237 | -1392 | -212 | -1769 | 60 | -324 | -706 | 776 | -1863 | -2412 | -1764 | 238 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 229(L) | -2324 | -1864 | -4634 | -4121 | -657 | -4319 | -3239 | 2224 | -3838 | 2493 | 517 | -3975 | -3830 | -3106 | -3578 | -3596 | -2239 | 73 | -2272 | -2231 | 239 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 230(H) | -505 | -1236 | -775 | -228 | -1373 | -1593 | 2318 | -164 | 872 | -1178 | -425 | -432 | -1693 | 14 | -290 | -578 | 1743 | 825 | -1578 | -1083 | 240 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 231(C) | -561 | 1449 | 1476 | -2294 | -1417 | -511 | 2491 | 1472 | -2003 | -1111 | -57 | -1572 | 275 | -300 | -433 | -510 | -1609 | -2194 | -1510 | 241 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 232(Y) | -2882 | -2267 | -4018 | -3995 | 2580 | -3778 | -511 | -1658 | -3593 | 923 | -1152 | -2675 | -3663 | -2654 | -3169 | -2969 | -2779 | -1865 | 205 | 3751 | 242 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 233(F) | -3342 | -2776 | -4026 | -4232 | 4354 | -3545 | -1431 | -2315 | -4038 | -1801 | -1900 | -3299 | -3780 | -3350 | -3645 | -3490 | -3420 | -2566 | -739 | 349 | 243 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |
| 234(H) | -559 | -1906 | -319 | 1741 | -2211 | -1478 | 2491 | 355 | -1899 | -1021 | -132 | -1591 | 303 | 791 | 452 | 1019 | -1527 | -2083 | -1454 | 244 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | | -7108 | -8150 | -894 | -1115 | -701 | -1378 | * | | | | | | | | | | | |

FIG. 8T

Table 6

| | | | | | | | | | | | | | | | | | | | | | | |
|---|---|---|---|---|---|---|---|---|---|---|---|---|---|---|---|---|---|---|---|---|---|---|
| -16 | -7108 | -8150 | -894 | -1115 | -701 | -1378 | * | | | | | | | | | | | | | | | |
| 235(G) | -456 | -1098 | -1993 | -2173 | -3296 | 2968 | -2244 | -3141 | -2461 | -3355 | -2485 | -1583 | -2025 | -2139 | -2549 | 1723 | -881 | -2104 | -3461 | -3203 | 245 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 236(M) | -1532 | -1301 | -3405 | -2864 | -57 | -3050 | -1438 | -56 | -2477 | 1096 | 3967 | -2484 | -2939 | -2042 | -2342 | -2169 | -1455 | -370 | -989 | 2079 | 246 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 237(G) | -1038 | -1765 | -926 | -1191 | -3372 | 3233 | -1826 | -3379 | -1926 | -3481 | -2725 | 1285 | -2271 | -1628 | -2264 | -1145 | -1377 | -2554 | -3401 | -2980 | 247 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 238( | -3553 | -2695 | -4100 | -4288 | 1022 | -428 | -2592 | -3792 | -2021 | -2038 | -2737 | -3890 | -2815 | -3323 | -3265 | -3440 | -2712 | 4944 | 3677 | 248 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 239(H) | -693 | -2112 | -279 | 1837 | -2456 | -1534 | 2434 | -2176 | 1108 | -2098 | -1217 | -167 | -1666 | 1691 | -39 | -560 | -624 | -1753 | -2235 | -1604 | 249 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 240(P) | -853 | -1252 | -2460 | -2393 | -2139 | -1784 | -2109 | -974 | -2210 | -1748 | -1364 | -1924 | 3453 | -2108 | -2271 | -1167 | -1152 | -2678 | -2307 | 250 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -812 | -6323 | -7365 | -1241 | -292 | -2448 | | | | | | | | | | | | | | | |
| 241(Y) | -906 | -1365 | -1255 | -688 | 4 | -1806 | -48 | -1150 | 314 | -1157 | -604 | -702 | -1897 | -107 | 2106 | -965 | -822 | -1011 | -491 | 2916 | 251 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -27 | -6323 | -7365 | -894 | -1115 | -701 | -1378 | * | | | | | | | | | | | | | | |
| 242(Y) | -476 | -775 | -1198 | 1077 | -755 | -1738 | -505 | 1586 | -528 | 43 | -777 | -2800 | -1822 | -410 | -817 | -751 | 649 | -143 | -1165 | 1945 | 252 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 243(F) | -1857 | -1592 | -3755 | -3460 | 3638 | -3255 | -1454 | -16 | -3144 | -206 | -1390 | -2525 | -3287 | -2604 | -2951 | -2505 | -1863 | 1480 | -1907 | 253 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 244(V) | -1203 | -1434 | -1278 | 1166 | -1756 | -2236 | -1499 | 75 | -1412 | -1192 | -819 | -1390 | -2525 | -1332 | -1696 | -1574 | -1248 | 2962 | -2384 | 254 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 245(H) | -30 | 439 | 11 | 363 | -394 | -739 | 699 | -414 | 463 | -757 | 501 | 286 | -577 | 639 | 165 | -23 | 111 | 312 | 697 | -25 | 255 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 246(E) | 1028 | -2230 | 1464 | 1545 | -2560 | -1444 | -343 | -2324 | -77 | -2285 | -1411 | -93 | -1690 | 78 | -635 | 1220 | -730 | -1876 | -2478 | -1750 | 256 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8U

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | * | | | | | | | | | | | |
| 247(G) | 802 | 892 | -1664 | -1291 | -1774 | -2148 | -1181 | -1363 | -1177 | 617 | -906 | -1109 | -1839 | -1027 | -1436 | 836 | -560 | -1000 | -2098 | -1700 | 257 |
| | -149 | -500 | -233 | 43 | -381 | -399 | 106 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 248(F) | -737 | -1710 | -1482 | -1223 | -2205 | -1628 | -301 | -1513 | -202 | -1603 | -865 | -339 | -1790 | -72 | -681 | -695 | -688 | -1259 | -1410 | -1271 | 258 |
| | -149 | -500 | -233 | 43 | -381 | -399 | 106 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 249(D) | -1662 | -3241 | -3494 | -12 | -3550 | -1708 | -991 | -3449 | -907 | -3360 | -2675 | -360 | -2197 | -658 | -1631 | -1384 | -1715 | -2975 | -3451 | -2636 | 259 |
| | -149 | -500 | -233 | 43 | -381 | -399 | 106 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 250(K) | 374 | -1824 | 783 | 927 | -2121 | -1368 | -40 | 525 | 1057 | -1830 | -920 | 824 | 249 | 411 | -141 | -290 | -342 | -1433 | -2020 | -1349 | 260 |
| | -149 | -500 | -233 | 43 | -381 | -399 | 106 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 251(E) | 424 | -2247 | 1450 | 1906 | -2557 | 209 | -314 | -2325 | -37 | -2276 | -1395 | -75 | 659 | 111 | -595 | -584 | -710 | -1874 | -2461 | -1729 | 261 |
| | -570 | -7108 | -1648 | -894 | -1115 | -701 | -1378 | * | * | | | | | | | | | | | | |
| 252(D) | -129 | -2752 | 2889 | 513 | -3030 | -1216 | -532 | -2959 | -669 | -2896 | -2188 | 2229 | -1714 | -198 | -1413 | -860 | -1196 | -2465 | -3041 | -2140 | 262 |
| | -754 | -2619 | -2035 | -2949 | -379 | -992 | -1008 | -627 | 212 | -721 | -275 | -394 | -45 | -96 | -359 | -117 | -370 | -295 | -248 | | |
| | -16 | -7108 | -8150 | -894 | -1115 | -701 | -1378 | * | * | | | | | | | | | | | | |
| 253(H) | -696 | -961 | -1261 | -873 | -178 | -1785 | 3652 | 1381 | 427 | -516 | -92 | -889 | -1934 | -521 | -602 | -945 | -673 | -203 | -756 | 22 | 273 |
| | -25 | -6457 | -7499 | -894 | -1115 | -1666 | -546 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 254(M) | -1561 | -1309 | -3310 | -2786 | -99 | -3163 | -1984 | 569 | -2364 | 1604 | 3948 | -2656 | -2936 | -1983 | -2284 | 1135 | -1493 | 116 | -1472 | -1272 | 274 |
| | -25 | -6457 | -7499 | -894 | -1115 | -777 | -1263 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 255(K) | 475 | -1891 | -137 | 1054 | -2221 | -1359 | -30 | -1946 | 1632 | -1890 | -999 | 2 | -1483 | 1488 | 30 | -2941 | 411 | -1523 | -2049 | -1403 | 275 |
| | -19 | -6850 | -7893 | -894 | -1115 | -1215 | -813 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 256(V) | -1531 | -1105 | -4020 | -3576 | -1227 | -3695 | -3034 | -2492 | -3387 | -2436 | -62 | -3320 | -3500 | -3101 | -3368 | -1152 | -1501 | 2608 | -2576 | -2243 | 276 |
| | -19 | -6850 | -7893 | -894 | -1115 | -1215 | -813 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 257(H) | -1244 | -246 | -137 | -319 | -1501 | -1694 | 4400 | -2032 | -417 | -1795 | 1396 | -153 | -2075 | -501 | -711 | -1294 | 1760 | -2140 | -1842 | -960 | 277 |
| | -19 | -6850 | -7893 | -894 | -1115 | -1215 | -813 | -626 | -210 | -466 | -720 | -275 | -394 | -45 | -96 | -359 | -117 | -369 | -294 | -249 | |
| | -16 | -7108 | -8150 | -894 | -1115 | -701 | -1378 | * | * | | | | | | | | | | | | |
| 258(R) | -675 | -1969 | -242 | 1673 | -2340 | -1479 | -164 | -2032 | 420 | -1985 | -1141 | 1471 | -153 | 261 | 1760 | -560 | -613 | -1643 | -2136 | -1550 | 278 |
| | -149 | -500 | -233 | 43 | -381 | -399 | 106 | -626 | -210 | -466 | -720 | -275 | -394 | -45 | -96 | -359 | -117 | -369 | -294 | -249 | |

FIG. 8V

Table 6

FIG. 8W

Table 6

FIG. 8X

Table 6

| | | | | | | | | | | | | | | | | | | | | |
|---|---|---|---|---|---|---|---|---|---|---|---|---|---|---|---|---|---|---|---|---|
| | -36 | -5902 | -6944 | -894 | -1115 | -2014 | -410 | * | * | -1488 | -735 | 2022 | -1167 | 9 | -450 | 17 | -79 | -791 | -1790 | -1251 | 303 |
| 283(N) | 1419 | -678 | -16 | 71 | -1606 | -696 | -281 | -1227 | -86 | -466 | -720 | 275 | 394 | 45 | 96 | 359 | 117 | -369 | -294 | -249 |
| | -149 | -500 | 233 | 43 | -381 | 399 | 106 | -626 | 210 | | | | | | | | | | | |
| | -36 | -5902 | -6944 | -894 | -1115 | -655 | -1455 | * | * | | | | | | | | | | | |
| 284(N) | -690 | -2252 | 1313 | 1338 | -2538 | -1300 | -208 | -2319 | 1491 | -2250 | -1381 | 1988 | -1564 | 211 | -512 | -509 | -660 | -1861 | -2424 | -1672 | 304 |
| | -149 | -500 | 233 | 43 | -381 | 399 | 106 | -626 | 210 | -466 | -720 | 275 | 394 | 45 | 96 | 359 | 117 | -369 | -294 | -249 |
| | -20 | -6788 | -7830 | -894 | -1115 | -421 | -1984 | * | * | | | | | | | | | | | |
| 285(D) | -1304 | -3019 | 2680 | 1285 | -3255 | -1544 | -705 | -3097 | -703 | -3006 | -2219 | 1388 | 1348 | -331 | -1399 | -1044 | -1321 | -2611 | -3195 | -2320 | 305 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 286(H) | -30 | 439 | 11 | 363 | -394 | -739 | 699 | 414 | 463 | -757 | 501 | 286 | -577 | 639 | 165 | -23 | 111 | -312 | 697 | -25 | 306 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 287(M) | 1003 | -593 | 321 | -1362 | -615 | -2007 | -849 | 1868 | -1149 | -373 | 2071 | 1988 | -2064 | -949 | -1296 | -1049 | -514 | 769 | -1128 | -747 | 307 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 288(M) | -426 | -945 | -995 | -468 | -1082 | -1580 | 1667 | -681 | -299 | -938 | 2081 | -605 | -1724 | -229 | -641 | 445 | 2054 | -498 | -1403 | -940 | 308 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 289(R) | -1619 | -2365 | 321 | -2075 | -1064 | -2835 | -469 | -2305 | 1823 | 763 | -1488 | -1073 | -2345 | -67 | 2817 | -1563 | -1402 | -2096 | -2243 | -1997 | 309 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 290(P) | -2931 | -2878 | -3420 | -3706 | -4181 | -2925 | -3468 | -4621 | -3859 | -4490 | -4165 | -3491 | -3866 | -2287 | -3695 | -3182 | -3279 | -4087 | -3594 | -4064 | 310 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 291(Q) | -802 | -740 | -2393 | -1814 | 1799 | -2272 | -1035 | 123 | -1529 | 790 | 401 | -1638 | -2287 | 2034 | -1573 | -1335 | -740 | 1456 | -1046 | -619 | 311 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 292( | 3500 | -2678 | -4063 | -4226 | 995 | -3934 | -449 | -2563 | -3717 | -2009 | -2016 | -2732 | -2798 | -3276 | -3242 | -3394 | -2681 | 5405 | 3043 | 312 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 293(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 313 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | | | | |
| 294(M) | -2406 | -2296 | -3638 | -3594 | -1525 | -3105 | -2824 | -1047 | -3121 | -596 | 5043 | -3293 | -3425 | -3046 | -2996 | -2911 | -2552 | -1398 | -2513 | -2207 | 314 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8Y

Table 6

| | | | | | | | | | | | | | | | | | | | | |
|---|---|---|---|---|---|---|---|---|---|---|---|---|---|---|---|---|---|---|---|---|
| 295(I) | -2034 | -7108 | -4395 | -3950 | -974 | -4099 | -3249 | -3388 | * | -3681 | 1202 | -3748 | -3784 | -3212 | -3556 | -3388 | -1988 | 627 | -2497 | -2285 | 315 |
| | -149 | -500 | 233 | 43 | -381 | 399 | 106 | -1378 | | 210 | -720 | 275 | 394 | 45 | 96 | 359 | 117 | -369 | -294 | -249 | |
| | -16 | -7108 | -8150 | -894 | -1115 | -701 | -626 | * | | | | | | | | | | | | | |
| 296(I) | -1757 | -1299 | -4333 | -3971 | -1766 | -4057 | -3755 | -283[ | * | -3844 | -614 | -3733 | -3880 | -3700 | -3920 | -3375 | -1749 | 2665 | -3275 | -2830 | 316 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 297(F) | -2590 | -2117 | -4458 | -4084 | 3096 | -4144 | -1957 | -191 | * | -3757 | 2203 | -3544 | -3752 | -2887 | -3401 | -3410 | -2485 | -812 | -1135 | -337 | 317 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 298(R | -2957 | -3022 | -3318 | -2735 | -3796 | -2998 | -1968 | -3912 | * | -846 | -3631 | -2611 | -3280 | -1724 | -3026 | -3026 | -2913 | -3650 | -3096 | -3185 | 318 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 299(T | 2050 | -905 | -2305 | -2099 | -3342 | -1206 | -1895 | -2371 | * | -1974 | -2648 | -1479 | -1888 | -1753 | -2118 | 1016 | 2546 | -1624 | -2968 | -2665 | 319 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 300(P | -2931 | -2878 | -3420 | -3706 | -4181 | -2925 | -3468 | -4621 | * | -3859 | -4490 | -3491 | 4225 | -3781 | -3695 | -3182 | -3279 | -4087 | -3594 | -4064 | 320 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 301(K | -2620 | -2961 | -2461 | -2046 | -3743 | -2791 | -1570 | -3603 | 3784 | 210 | -3387 | -1479 | 4225 | -1260 | -465 | -2604 | -2536 | -3331 | -3001 | -2988 | 321 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 302(G | -2594 | -2690 | -3304 | -3623 | -4328 | 3747 | -3462 | -4761 | * | -3953 | -4671 | -3320 | -3352 | -3748 | -3779 | -2839 | -2981 | -4004 | -3668 | -4222 | 322 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 303[ | -4114 | -3274 | -4214 | -4453 | -1722 | -3496 | -2681 | -4109 | * | -4149 | -3619 | -4044 | -3885 | -4032 | -3816 | -4355 | -4248 | -4133 | 6191 | -1329 | 323 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 304(T | -353 | -974 | -2215 | -2202 | -2896 | -1238 | -2053 | -2560 | * | -2141 | -2867 | -1547 | -1951 | -1940 | -2229 | 1380 | 3291 | -1759 | -3143 | -2840 | 324 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 305(C | -845 | -3279 | -3420 | -2815 | -3140 | -3342 | -2815 | -3103 | * | -3232 | -3426 | -2300 | -2379 | -2934 | -3057 | -1107 | -1278 | -2270 | -3401 | -3393 | 325 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 306(P | -2931 | -2878 | -3420 | -3706 | -4181 | -2925 | -3468 | -4621 | * | -3859 | -4490 | -3491 | 4225 | -3781 | -3695 | -3182 | -3279 | -4087 | -3594 | -4064 | 326 |
| | -149 | -500 | 233 | 43 | -381 | 399 | 106 | -626 | | 210 | -466 | 275 | 394 | 45 | 96 | 359 | 117 | -369 | -294 | -249 | |
| | -16 | -7108 | -8150 | -894 | -1115 | -701 | -1378 | * | | | | | | | | | | | | | |

FIG. 8Z

Table 6

FIG. 8AA

Table 6

| | | | | | | | | | | | | | | | |
|---|---|---|---|---|---|---|---|---|---|---|---|---|---|---|---|
| - | -16 | -7108 | -8150 | -894 | -1115 | -701 | -1378 | * | | | | | | | |
| 319(R | -1940 | -2623 | -2163 | -1317 | -2718 | -2498 | 2633 | -2821 | 557 | -2576 | -1920 | -1294 | -2549 | -305 | 3406 | -1859 | -1734 | -2575 | -2279 | -1885 | 340 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 320(A | 2865 | -932 | -2456 | -2481 | -3066 | -1198 | -2239 | -2763 | -2443 | -3058 | -2203 | -1637 | -1941 | -2156 | -2474 | 1737 | -732 | -1840 | -3307 | -3058 | 341 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 321(H | -3205 | -3079 | -2723 | -2890 | -2110 | -3046 | 5295 | -4135 | -2617 | -3813 | -3561 | -2886 | -3482 | -2833 | -2620 | -3291 | -3356 | -3895 | -2397 | -1681 | 342 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 322(Q | -2562 | -2904 | -1886 | -1971 | -3251 | -2661 | -2079 | -3690 | -1565 | -3469 | -3081 | -2107 | -3091 | 4371 | -1665 | -2585 | -2674 | -3411 | -3077 | -2821 | 343 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 323(I) | -1757 | -1300 | -4333 | -3971 | -1764 | -4057 | -3754 | 2871 | -3843 | -611 | -539 | -3733 | -3880 | -3699 | -3919 | -3375 | -1749 | 2625 | -3273 | -2829 | 344 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 324(P | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | 4064 | 345 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 325(I) | -1899 | -1466 | -4358 | 3871 | -1002 | -3993 | -3149 | 2479 | -3652 | 1948 | 170 | -3634 | -3690 | -3153 | -3516 | -3233 | -1847 | 1460 | -2466 | -2295 | 346 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 326(P | 1615 | -1136 | -2222 | -2310 | -3082 | -1373 | -2227 | -2731 | -2358 | -3036 | -2272 | -1689 | 3445 | -2139 | -2424 | -761 | -938 | -1937 | -3279 | -3042 | 347 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 327(V | 1776 | -978 | -1248 | -821 | -1609 | -1418 | -840 | -1138 | -733 | -1453 | -710 | 1478 | -1781 | -614 | -1074 | 1249 | -508 | 1777 | -1905 | -1460 | 348 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 328(D | 1973 | -1793 | 2321 | -222 | -2801 | -1401 | -864 | -2543 | -758 | -2614 | -1785 | -457 | -1858 | -510 | -1294 | 684 | -896 | -1978 | -2851 | -2198 | 349 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 329(Q | -1008 | -2231 | -986 | -310 | -2701 | -1861 | -258 | -2315 | 1642 | -2173 | -1344 | -511 | -1911 | 2494 | 1827 | 403 | -883 | -1946 | -2224 | -1767 | 350 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | |
| 330(D | -1037 | 2659 | 2253 | 1117 | -2928 | -1504 | -509 | -2731 | 1324 | -2651 | -1807 | 1958 | -1830 | -106 | -940 | -826 | -1023 | -2261 | -2827 | -2032 | 351 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8BB

Table 6

FIG. 8CC

Table 6

| | | | | | | | | | | | | | | | | |
|---|---|---|---|---|---|---|---|---|---|---|---|---|---|---|---|---|
| 343(L) | -16 | -2642 | -2168 | -4788 | -4235 | 465 | -4513 | -1115 | -701 | -1378 | * | -3878 | 2891 | 2122 | -4166 | -3888 | -3023 | -3544 | -3807 | -2521 | -607 | -2140 | -2183 | 364 |
| | | -149 | -500 | 233 | 43 | -381 | 399 | -701 | -1378 | | 210 | -466 | -720 | 275 | 394 | 45 | 96 | 359 | 117 | -369 | -294 | -249 | |
| | -16 | -7108 | -8150 | -894 | -1115 | -701 | -1378 | | * | | | | | | | | | | | | | | |
| 344(E) | -588 | -2030 | 204 | 1763 | -2360 | -1459 | -147 | 1522 | -2032 | -1135 | -1592 | 1372 | -129 | 847 | -526 | -1661 | -1529 | 365 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 345(S) | -897 | -1462 | -2333 | -2543 | -3185 | -1640 | -2474 | -2686 | -3497 | -2780 | -2360 | -2483 | -2703 | 3465 | -1316 | -3310 | -3025 | 366 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 346(Y) | 3482 | -2868 | -3701 | -3919 | 238 | -3552 | -1112 | -3638 | -2516 | -2526 | -3027 | -3772 | -3101 | -3344 | -3418 | -3527 | -441 | 4711 | 367 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 347(K) | -1779 | -2672 | -1588 | -963 | -3316 | -561 | -2329 | 3294 | -2578 | -1879 | -1030 | -2399 | 1424 | 589 | -1653 | -1579 | -2550 | -2489 | -2237 | 368 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 348(P) | -2931 | -2878 | -3420 | -3706 | -4181 | -2925 | -3468 | -3859 | -4490 | -4165 | -3491 | 4225 | -3781 | -3695 | -3182 | -3279 | 4087 | -3594 | -4064 | 369 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 349(E) | -1283 | -2980 | 2293 | 2465 | -3222 | -1551 | -680 | 846 | -2961 | -2167 | -151 | -1956 | -302 | -1278 | -1029 | -1292 | -2574 | -3140 | -2287 | 370 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 350(E) | -2641 | -3308 | -896 | 3732 | -3966 | -2458 | -2043 | -2128 | -4016 | -3555 | -1531 | -2959 | -1842 | -2560 | -2479 | -2750 | -3722 | -3563 | -3385 | 371 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 351(L) | -2871 | -2457 | -4231 | -4103 | -1033 | -3803 | -3165 | -3734 | 3130 | -31 | -3935 | -3797 | -3286 | -3484 | -3713 | -2869 | -1136 | -2394 | -2220 | 372 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 352(F) | -3342 | -2776 | -4026 | -4232 | -3966 | -3545 | -1431 | -4038 | -1801 | -1900 | -3299 | -3780 | -3350 | -3645 | -3490 | -3420 | -2566 | 739 | 349 | 373 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 353(D) | -1170 | -2662 | 2768 | 152 | -3076 | -1523 | -716 | -677 | -2851 | -2058 | 1883 | -1940 | -347 | -1326 | 973 | 1251 | -2402 | -3056 | -2245 | 374 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |
| 354(E) | 1031 | -2152 | -91 | 2416 | -2507 | -1517 | 346 | 982 | -2201 | -1350 | -188 | -1736 | 71 | -388 | -657 | -752 | -2390 | -1731 | 375 |
| | | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | |

FIG. 8DD

Table 6

| | | | | | | | | | | | | | | | | | | |
|---|---|---|---|---|---|---|---|---|---|---|---|---|---|---|---|---|---|---|
| 355(N | -1247 | -2802 | 2354 | 164 | -3217 | -1531 | -760 | -3060 | -767 | -2997 | -2213 | 2573 | -1971 | -395 | -1447 | 1055 | -1298 | -2553 | -3188 | -2339 | 376 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 356(G | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 377 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 357(H | 969 | -1896 | 1173 | 279 | -2199 | -1387 | 1573 | -1938 | 276 | -1912 | -1011 | -34 | -1518 | 1339 | -236 | 939 | 421 | -1513 | -2105 | -1426 | 378 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 358(V | -1097 | -861 | -3273 | -2702 | -715 | -2790 | -1749 | 1319 | 276 | 1604 | 246 | -2365 | 510 | -2047 | -2299 | -1909 | -1047 | 2041 | -1564 | -1253 | 379 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 359(K | -627 | -934 | -1396 | -826 | -1049 | -1906 | -680 | 1291 | -3953 | -745 | -142 | -930 | -1983 | -512 | -793 | -921 | 762 | 421 | -1475 | -1045 | 380 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 360(D | 417 | -2242 | 2268 | 951 | -2534 | -1439 | -289 | -2301 | 2 | -2249 | -1365 | -64 | 475 | 1392 | -551 | -566 | -688 | -2431 | -1702 | 381 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 361(D | -756 | -2213 | 2042 | 1784 | -2484 | -1455 | -327 | -2233 | -59 | -287 | -1351 | -90 | -1688 | 90 | -612 | 609 | -722 | -1813 | -2423 | -1705 | 382 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 362(I | -1758 | -1302 | -4331 | -3969 | -1754 | -4053 | -3745 | 3003 | -3839 | -600 | -530 | -3730 | -3876 | -3691 | -3912 | -3370 | -1751 | 2469 | -3262 | -2822 | 383 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 363(K | 489 | -1736 | -399 | 869 | -1996 | -1468 | -108 | -1679 | 1463 | 680 | -849 | -140 | -1560 | 1326 | -65 | -410 | 492 | -1326 | -1942 | -1336 | 384 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 364(E | 1607 | -1738 | -268 | 2001 | -2459 | -1405 | -567 | -2171 | -308 | -2231 | -1384 | -339 | -1737 | -179 | -802 | 1027 | -695 | -1699 | -2473 | -1839 | 385 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 365(I | -521 | -410 | -2443 | 1845 | 1682 | -2040 | 909 | 1831 | 2105 | -217 | 389 | 581 | -2091 | -1245 | -1495 | -1112 | 673 | 1143 | -913 | -551 | 386 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |
| 366(M | -1028 | -781 | 3313 | -2728 | -655 | -2725 | -1667 | 2105 | -2396 | 791 | 2636 | -2332 | -2694 | -2027 | -2260 | -1840 | 662 | 1307 | -1459 | -1146 | 387 |
| | -16 | -149 | -500 | 233 | 43 | -381 | 399 | 106 | -626 | 210 | -466 | -720 | 275 | 394 | 45 | 96 | 359 | 117 | -369 | -294 | -249 |
| | | -7108 | -8150 | -894 | -1115 | -701 | -1378 | * | | | | | | | | | | | | | |

FIG. 8EE

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 367(P | -2931 | -2878 | -3420 | -3706 | -4181 | -2925 | -3468 | -3859 | -4490 | -4165 | -3491 | 4225 | -3781 | -3695 | -3182 | -3279 | -4087 | -3594 | -4064 | 388 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 368(K | -420 | -1711 | -319 | 889 | -1985 | -1406 | -81 | -1683 | -1711 | -835 | -80 | -1506 | 351 | -148 | 802 | 593 | 66 | -1944 | -1311 | 389 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 369(G | -1210 | -2695 | 1728 | 114 | -3097 | 2436 | -713 | -2899 | -2848 | -2055 | -236 | -1965 | -340 | -1178 | -1009 | -1238 | -2429 | -3026 | -2250 | 390 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 370(D | -1173 | -2847 | 2185 | 2156 | -3091 | -1523 | 1843 | -2917 | -2832 | -2014 | 1280 | -1899 | -221 | -1180 | -937 | -1174 | -2440 | -3014 | -2176 | 391 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 371(K | -733 | -1639 | -900 | -275 | -1870 | -1727 | -272 | -1476 | 1052 | -793 | -476 | -1798 | 105 | 1100 | 1022 | -645 | -1222 | -1849 | -1373 | 392 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 372(R | -2124 | -2788 | -2710 | -1449 | -3624 | -2637 | -576 | -2974 | -2640 | -1977 | -1344 | -2596 | -161 | 3417 | -2010 | -1819 | -2745 | -2479 | -2379 | 393 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 373(M | -2186 | 1770 | 4484 | -3908 | -547 | -4083 | -2924 | -3619 | 1562 | 3822 | -3715 | -3642 | -2876 | -3343 | -3290 | -2088 | -106 | -2072 | 2052 | 394 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 374(A | 2525 | -1036 | -2401 | -2529 | 3239 | 2375 | -2366 | -2629 | -3244 | -2393 | -1719 | -2028 | -2303 | -2639 | -657 | -852 | -1993 | -3425 | -3237 | 395 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 375(M | 1980 | -959 | -1279 | -892 | -1385 | -1524 | -842 | -905 | -1211 | 2928 | 1065 | -1852 | -673 | -1053 | -675 | -559 | -683 | -1743 | -1304 | 396 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 376(N | -1426 | -2353 | -948 | 735 | -2920 | -1991 | -796 | -2769 | -2666 | -1942 | 3441 | -2268 | -432 | 1742 | -1361 | -1415 | -2383 | -2592 | -2147 | 397 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 377(P | -566 | -1202 | -1850 | -1997 | -3117 | -1371 | -2101 | -2989 | -3198 | -2391 | -1549 | 3625 | -1982 | -2305 | 1013 | -967 | -2094 | -3288 | -2963 | 398 |
| | -276 | -2582 | -8150 | -894 | -1115 | -701 | -1378 | * | | | | | | | | | | | | |
| | -16 | -7108 | -8150 | -894 | -1115 | -701 | -1378 | * | | | | | | | | | | | | |
| 378(I) | -820 | -759 | -2281 | -1810 | -939 | -2345 | -1389 | 2404 | -425 | -18 | 1689 | -2430 | -1447 | -1742 | -1465 | -804 | 1594 | -1641 | -1225 | 399 |
| | -149 | -500 | 233 | 43 | -381 | 399 | 106 | 210 | -466 | -720 | 275 | 394 | 45 | 96 | 359 | 117 | -369 | -294 | -249 | |

FIG. 8FF

Table 6

| | | | | | | | | | | | | | | | | | | | | |
|---|---|---|---|---|---|---|---|---|---|---|---|---|---|---|---|---|---|---|---|---|
| | -19 | -6850 | -7893 | -894 | -1115 | -1215 | -813 | * | | | | | | | | | | | | |
| 379(T) | 1785 | -732 | -2107 | -1994 | -2428 | -1065 | -1767 | -1811 | -1860 | -2282 | -1548 | -1351 | -1750 | -1665 | -1956 | -390 | 2954 | -1225 | -2740 | -2439 | 400 |
| | -149 | -500 | 233 | 43 | -381 | 399 | 106 | -626 | 210 | -466 | 275 | 394 | 394 | 45 | 96 | 359 | 117 | -369 | -294 | -249 | |
| | -19 | -6850 | -7893 | -894 | -1115 | -453 | -1893 | * | | | | | | | | | | | | | |
| 380(N) | -1558 | -3098 | 310 | 1592 | -3431 | -1657 | -945 | -3340 | -959 | -3271 | 3495 | -2146 | -611 | -1578 | -1301 | -1621 | -2860 | -3383 | -2547 | 401 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 381(G) | 2030 | -1051 | -2376 | -2525 | -3268 | 2820 | -2382 | -2992 | -2652 | -3227 | -1726 | -2039 | -2322 | -2659 | -672 | -869 | -2018 | -3447 | -3263 | 402 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 382(G) | -1587 | -1953 | -2017 | -2080 | -898 | 3122 | -1483 | -2565 | -2178 | -3227 | -1908 | -2727 | -2015 | -2307 | -1743 | -1817 | -2251 | -1457 | 2463 | 403 |
| | -149 | -500 | 233 | 43 | -381 | 399 | 106 | -626 | 210 | -466 | 275 | 394 | 45 | 96 | 359 | 117 | -369 | -294 | -249 | | |
| | -195 | -6931 | -3069 | -894 | -1115 | -701 | -1378 | * | | | | | | | | | | | | | |
| 383(K) | -585 | -1070 | -1140 | -510 | -1174 | -1742 | -358 | 751 | 1799 | -916 | -641 | -1802 | -103 | 873 | -754 | -507 | 1342 | -1431 | -1005 | 404 |
| | -149 | -500 | 233 | 43 | -381 | 399 | 106 | -626 | 210 | -466 | 275 | 394 | 45 | 96 | 359 | 117 | -369 | -294 | -249 | | |
| | -18 | -7973 | -894 | -1115 | -505 | -1760 | * | | | | | | | | | | | | | | |
| 384(I) | -732 | -1273 | 1962 | -516 | -1501 | -1754 | 770 | 1970 | -673 | -1163 | -718 | -1976 | -522 | -1082 | -902 | 1162 | -263 | -1908 | -1404 | 405 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 385(H) | -542 | -1652 | -558 | 18 | -1880 | -1542 | 2080 | 339 | 360 | -1605 | -241 | 1147 | 1217 | 1461 | -492 | -468 | -1229 | -1864 | -1303 | 406 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 386(K) | -682 | -1971 | -580 | 740 | -2315 | -1607 | -158 | -1989 | 2284 | 162 | 529 | -1686 | 280 | 734 | -578 | -595 | -1611 | -2087 | -1523 | 407 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 387(H) | -30 | 439 | 11 | 363 | -394 | -739 | 699 | -414 | 463 | -757 | 286 | -577 | 639 | 165 | -23 | 111 | -312 | 697 | -25 | 408 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 388(P) | 415 | -2181 | 1668 | 189 | -2543 | -1458 | -400 | -2293 | -146 | -2281 | -138 | 2240 | 1274 | -694 | -643 | -769 | -1860 | -2492 | -1780 | 409 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 389(L) | -1646 | -1694 | -2904 | -2680 | -1050 | -2701 | -2138 | -547 | -2336 | 2673 | -2479 | 1513 | -2198 | -2336 | -2107 | -1735 | 860 | -2077 | -1777 | 410 |
| | -149 | -500 | 233 | 43 | -381 | 399 | 106 | -626 | 210 | -466 | 275 | 394 | 45 | 96 | 359 | 117 | -369 | -294 | -249 | | |
| | -16 | -7108 | -8150 | -894 | -1115 | -701 | -1378 | * | | | | | | | | | | | | | |
| 390(D) | -430 | -1571 | 1536 | 153 | -1777 | -1435 | -129 | 307 | 1131 | -1533 | 889 | -1538 | 275 | -255 | -380 | -371 | 598 | -1838 | -1235 | 411 |
| | -149 | -500 | 233 | 43 | -381 | 399 | 106 | -626 | 210 | -466 | 275 | 394 | 45 | 96 | 359 | 117 | -369 | -294 | -249 | | |

FIG. 8GG

Table 6

| | | | | | | | | | | | | | | | | | |
|---|---|---|---|---|---|---|---|---|---|---|---|---|---|---|---|---|---|
| | -16 | -7108 | -8150 | -894 | -1115 | -701 | -1378 | * | * | | | | | | | | |
| 391(L | -2871 | -2457 | -4231 | -4103 | -1033 | -3803 | -3165 | -541 | -3734 | 3130 | -31 | -3935 | -3797 | -3286 | -3484 | -3713 | -2869 | -1136 | -2394 | -2220 | 412 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 392(P | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 413 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 393(D | -123 | -3021 | 2652 | 1083 | -3262 | -1545 | -715 | -3102 | -722 | -3016 | -2232 | 2288 | -1970 | -344 | -1422 | -1053 | -1333 | -2618 | -3208 | -2331 | 414 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 394( | -1183 | -940 | -3255 | -2753 | 1534 | -2632 | -772 | 1086 | -2365 | 1132 | 71 | -2086 | -2628 | -1856 | -2132 | -1737 | -1115 | -336 | 3856 | 1849 | 415 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 395(R | -1025 | -2540 | 1775 | 1142 | -2847 | -1561 | -472 | -2610 | -136 | -2532 | -1695 | -183 | -1846 | -64 | -3695 | -837 | -993 | -2170 | -2686 | -1970 | 416 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 396(D | -1284 | -2963 | 2433 | 216 | -3207 | -1549 | -693 | -3050 | -653 | -2963 | -2174 | 2058 | -1961 | 2341 | -1315 | -1034 | -1299 | -2571 | -3142 | -2286 | 417 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 397(Y | -3621 | -2707 | -4176 | -4424 | 2970 | -4050 | -394 | -2539 | -4003 | -2963 | -1987 | -2749 | -3933 | -2855 | -3451 | -3299 | -3499 | -2690 | -3142 | -2286 | 418 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 398(C | 1443 | -1117 | 1144 | -997 | -1629 | -520 | 2151 | 480 | 452 | 234 | -131 | -706 | -1773 | -348 | -779 | -656 | -418 | -324 | -1362 | -922 | 419 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 399(V | -1742 | -1294 | -4287 | -3868 | -1507 | -3983 | -3425 | -2307 | -3706 | 586 | -316 | -3621 | -3770 | -3449 | -3709 | -3254 | -1716 | 2871 | -2925 | -2571 | 420 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 400(D | -730 | -2244 | 2028 | 1115 | -2543 | -1450 | -283 | -1808 | 1800 | -2248 | -1364 | 1557 | -1665 | 147 | -498 | -571 | 502 | -1859 | -2424 | -1702 | 421 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 401(N | -410 | -1793 | -248 | 958 | -2083 | -143 | -54 | -1494 | 116 | -1797 | -898 | 1033 | -1482 | 391 | -146 | -306 | 586 | 53 | -2000 | -1340 | 422 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | * | | | | | | | | |
| 402(Q | -430 | -1511 | -419 | 58 | -1825 | 563 | -219 | -626 | 210 | -1597 | -764 | 1025 | -1570 | 1217 | -353 | 1025 | -404 | 892 | -1898 | -1308 | 423 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8HH

Table 6

FIG. 8II

Table 6

| | | | | | | | | | | | | | | | | |
|---|---|---|---|---|---|---|---|---|---|---|---|---|---|---|---|---|
| 415(M | 746 | -729 | -1725 | -1241 | -1091 | -1556 | -930 | -1043 | -922 | 3667 | -1111 | 404 | -891 | -1250 | -698 | 914 | -410 | -1509 | -1123 | 436 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 416(I) | -556 | -796 | -1468 | -861 | -813 | -1848 | -559 | 1067 | 271 | 42 | -912 | -1905 | -460 | 1342 | -865 | -488 | 747 | -1213 | -814 | 437 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 417E | 738 | -1306 | -528 | 1243 | -1448 | -1471 | -165 | 1130 | -90 | -452 | -231 | -1559 | 192 | 330 | 328 | 268 | 267 | -1616 | -1069 | 438 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 418( | -1686 | -1388 | -3865 | -3280 | -313 | -3346 | -1998 | -2910 | 2183 | 589 | -2918 | -3142 | -2351 | -2689 | -2486 | -1602 | -216 | 3506 | -1080 | 439 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 419(G | -497 | -1132 | -1973 | -2195 | -3328 | 3237 | -2289 | -2532 | -90 | -452 | -1611 | -2057 | -2201 | -2603 | 897 | -926 | -2151 | -3487 | -3237 | 440 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 420K | 632 | 1777 | 1362 | 250 | -2087 | -1381 | -86 | 1431 | -1808 | -914 | -51 | -1497 | 355 | -193 | 817 | -369 | -425 | -2019 | -1362 | 441 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 421(Y | -3621 | -2707 | -4176 | 4424 | 2953 | -4049 | -394 | -4002 | -1942 | -1987 | -2749 | -3933 | -2854 | -3451 | -3299 | -3499 | -2690 | 349 | 4093 | 442 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 422(C | -642 | 2908 | -2287 | 1063 | -2214 | -1093 | -57 | -1913 | 1497 | 494 | -1833 | -2239 | -1538 | -1745 | -1304 | 765 | 369 | -942 | -612 | 443 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 423(R | -1005 | 2443 | 1533 | 92 | -2784 | -1584 | -463 | -57 | -2471 | -1639 | 1177 | -1853 | -56 | 2770 | -836 | -972 | -2113 | -2612 | -1931 | 444 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 424(D | -1148 | -2724 | 2898 | 174 | -3006 | -1564 | -566 | 951 | -2711 | -1895 | -178 | -1903 | 1815 | -851 | -933 | -1132 | -2344 | -2872 | -2108 | 445 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 425(V | -1646 | -1230 | -4148 | -3696 | -1391 | -3782 | -3103 | -3497 | -323 | 1927 | -3416 | -3609 | -3214 | -3466 | -3018 | -1616 | 2552 | -2681 | -2340 | 446 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 426(I) | 401 | -900 | -3283 | -2756 | 1640 | -2752 | -1735 | -2451 | -121 | 132 | -2375 | -2775 | -2110 | -2360 | -1897 | -1085 | 615 | -1519 | -1079 | 447 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |

FIG. 8JJ

Table 6

| | | | | | | | | | | | | | | | | |
|---|---|---|---|---|---|---|---|---|---|---|---|---|---|---|---|---|
| -16 | -7108 | -8150 | -894 | -1115 | -701 | -1378 | * | | | | | | | | | |
| 427(K) | -834 | -1941 | -615 | 845 | -2257 | -1704 | -312 | -1778 | 2586 | -1890 | -1101 | -402 | -1823 | 95 | 65 | -764 | -756 | 788 | -2124 | -1599 | 448 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 428(N) | -857 | -1859 | -733 | -254 | -2082 | -1745 | -340 | -1726 | 1897 | 679 | -1022 | 2134 | -1861 | 45 | 77 | -813 | -778 | -1455 | -2024 | -1510 | 449 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 429(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 450 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 430(P) | -1140 | -1553 | -2272 | -2156 | -1935 | -1979 | -1912 | -1526 | -1824 | -1503 | 1339 | -1897 | 3724 | -1871 | -1917 | -1397 | -1391 | -1428 | -2485 | -2072 | 451 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 431(H) | -464 | -1881 | 1234 | 255 | -2190 | -1407 | 2368 | -1921 | 1008 | -1884 | -981 | -50 | -1513 | 375 | 482 | -349 | 1263 | -1498 | -2063 | -1403 | 452 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 432(N) | -761 | -2121 | 1175 | 150 | -2581 | -1441 | -443 | -2337 | -205 | -2327 | 1467 | 2649 | -1731 | -36 | -757 | 420 | 1163 | -1879 | -2535 | -1825 | 453 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 433(F) | -1857 | -1592 | -3755 | -3460 | 3638 | -3255 | -1454 | -16 | -3144 | -214 | -206 | -2800 | -3287 | -2604 | -2951 | -2505 | -1863 | 1480 | -853 | 99 | 454 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 434(R) | -2957 | -3022 | -3318 | -2735 | -3796 | -2998 | -1968 | -3912 | -846 | -3631 | -3157 | -2611 | -3280 | -1724 | 4056 | -3026 | -2913 | -3650 | -3096 | -3185 | 455 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 435(L) | -886 | -722 | -2913 | -2339 | -608 | 1022 | -1423 | 1356 | -2029 | 1682 | 294 | -2025 | -2497 | -1718 | -1972 | -1579 | -842 | 1130 | -1337 | -1008 | 456 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 436(F) | -3342 | -2776 | -4026 | -4232 | 4354 | -3545 | -1431 | -2315 | -4038 | -1801 | -1900 | -3299 | -3780 | -3350 | -3645 | -3490 | -3420 | -2566 | -739 | 349 | 457 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 437(G) | -468 | -1108 | -1987 | -2183 | -3307 | 3093 | -2261 | -3159 | -2489 | -3374 | -2507 | -1593 | -2035 | -2163 | -2570 | 1410 | -895 | -2119 | -3471 | -3217 | 458 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -16 | -7108 | -8150 | -894 | -1115 | -701 | -1378 | * | | | | | | | | | |
| 438(H) | -30 | 439 | 11 | 363 | 394 | -739 | 699 | -414 | 463 | -757 | 501 | 286 | -577 | 639 | 165 | -23 | 111 | 312 | 697 | -25 | 459 |
| - | -149 | -500 | 233 | 43 | -381 | 399 | 106 | -626 | 210 | -466 | -720 | 275 | 394 | 45 | 96 | 359 | 117 | -369 | -294 | -249 | |

FIG. 8KK

Table 6

| | | | | | | | | | | | | | | | | | | | |
|---|---|---|---|---|---|---|---|---|---|---|---|---|---|---|---|---|---|---|---|
| 439(P) | -16 | -7108 | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 460 |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 440(D) | -16 | -7108 | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 461 |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 441(E) | -16 | -7108 | -2641 | -3308 | 896 | 3732 | -3966 | -2458 | -2043 | -4105 | -2128 | -4016 | -3555 | -1531 | -2959 | -1842 | -2560 | -2479 | -2750 | -3722 | -3563 | -3385 | 462 |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 442(T) | -16 | -7108 | -840 | -1804 | -1403 | -1361 | -1523 | -816 | -1185 | 681 | -536 | -1214 | -173 | -1931 | -1069 | -1378 | 642 | -603 | -1788 | -1389 | 463 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 443(A) | 1657 | -1594 | 404 | 1150 | -1818 | -1465 | -154 | -1471 | 969 | -1566 | 1309 | -173 | -1572 | 248 | -202 | 422 | -412 | -1160 | -1861 | -1272 | 464 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 444(S) | -897 | -1462 | -2333 | -2543 | -3185 | -1640 | -2474 | -3294 | -2686 | -3497 | -2780 | -1973 | -2360 | -2483 | 3465 | -2703 | -1316 | -2413 | -3310 | -3025 | 465 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 445(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 466 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 446(R) | -1905 | -2715 | -2334 | -1200 | -3487 | -2506 | 485 | -2858 | 1904 | -2546 | -1846 | -1167 | -2464 | 1439 | 3148 | -1780 | -1627 | -2602 | -2423 | -2263 | 467 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 447(L) | -2639 | -2158 | 4642 | -4194 | 1586 | -4340 | -2490 | -51 | -3890 | 2827 | 573 | -3860 | -3832 | -2979 | -3524 | -3629 | 732 | -1565 | -1006 | 468 | | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 448(Q) | -549 | -1725 | -324 | 98 | -1793 | -1481 | -198 | -1668 | 163 | -1723 | 892 | 839 | -1618 | 2328 | -290 | 843 | -499 | -1331 | -1882 | 1794 | 469 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 449(A) | 2109 | -2374 | 1307 | 1077 | -2738 | 326 | -514 | -2505 | -344 | -2485 | -1647 | -151 | -1804 | -118 | -1065 | -934 | -766 | -932 | -2058 | -1950 | 470 | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |
| 450(A) | 1280 | 376 | -2219 | -1624 | 1011 | -1905 | 779 | 1073 | -1336 | -235 | 411 | -1368 | -1975 | 2328 | 1339 | 339 | 580 | 955 | -492 | 471 | | | |
| | | | -149 | -500 | 233 | 43 | -381 | 399 | 106 | -626 | 210 | -466 | -720 | 275 | 394 | 45 | 96 | 359 | 117 | -369 | -294 | -249 | |
| | | -16 | -7108 | -8150 | -894 | -1115 | -701 | -1378 | * | | | | | | | | | | | | | | |

FIG. 8LL

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 451(F) | -2619 | -2089 | -3969 | -3846 | 3011 | -3673 | -612 | -1304 | -3453 | 1530 | -788 | -2671 | -3552 | -2584 | -3066 | -2851 | -2522 | -1556 | 92 | 2879 | 472 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 452(E) | 400 | -2342 | 1163 | 2306 | -2664 | -1461 | -401 | -2438 | -168 | -2392 | -1527 | -102 | -1735 | 479 | -743 | 947 | -818 | -1984 | -2583 | -1837 | 473 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 453(H) | -424 | -834 | -1231 | -741 | -1039 | 183 | 2171 | -588 | -582 | -902 | -199 | -797 | -1793 | 1333 | -878 | -660 | 1442 | 1664 | -1404 | -972 | 474 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 454(T) | -825 | -1543 | -1050 | -931 | -2411 | -1607 | -1105 | -2069 | -661 | -2229 | -1555 | -978 | -2065 | 479 | -881 | -930 | 3234 | -1676 | -2544 | -2072 | 475 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 455(N) | -948 | -2217 | -192 | 59 | -2753 | 871 | -516 | -2480 | 1579 | -2431 | -1604 | 2747 | -1874 | -115 | -403 | -831 | -947 | -2039 | -2574 | -1954 | 476 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 456(R) | -2118 | -2789 | -2710 | -1441 | -3626 | -2635 | -569 | -2972 | 2088 | -2636 | -1971 | -1337 | -2591 | -153 | 3343 | -2003 | -1811 | -2743 | -2476 | -2375 | 477 |
| | -276 | -500 | 233 | -2582 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 457(Q) | -2077 | -2533 | -1425 | -1467 | -2808 | -2285 | -1598 | -3134 | -1059 | -2958 | -2537 | -1616 | -2694 | 4251 | -1184 | -2087 | -2168 | -2871 | -2703 | -2369 | 478 |
| | -19 | -500 | 233 | 43 | -381 | 399 | 106 | -626 | 210 | -466 | -720 | 275 | 394 | 45 | 96 | 359 | 117 | -369 | -294 | -249 | |
| | -19 | -6850 | -7893 | -894 | -1115 | -1215 | -813 | * | | | | | | | | | | | | | |
| 458(I) | -3599 | -2878 | -3805 | -3989 | -1220 | -3156 | -2211 | -3491 | -3618 | -3057 | -3027 | -3568 | -3532 | -3525 | -3338 | -3829 | -3720 | -3529 | 6135 | -830 | 479 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -19 | -6850 | -7893 | -894 | -1115 | -1215 | -813 | * | | | | | | | | | | | | | |
| 459(M) | -718 | -1070 | 1476 | -726 | -732 | -1903 | -713 | -152 | -681 | 774 | 3189 | -882 | -1991 | -541 | -1003 | -968 | -669 | -221 | -1408 | -983 | 480 |
| | -149 | -500 | -7893 | -894 | -381 | 399 | -1215 | -626 | 210 | -466 | -720 | 275 | 394 | 45 | 96 | 359 | 117 | -369 | -294 | -249 | |
| | -19 | -6850 | | | | | | * | | | | | | | | | | | | | |
| 460(E) | 598 | -1592 | -123 | 1874 | -1828 | -1337 | -104 | -1490 | 228 | -43 | -755 | 967 | -1490 | 296 | -254 | -355 | -375 | -1164 | -1876 | -1258 | 481 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -19 | -6850 | -7893 | -894 | -1115 | -1215 | -813 | * | | | | | | | | | | | | | |
| 461(P) | -556 | -1744 | 1230 | 129 | -2482 | 1292 | -454 | -2234 | -252 | -2255 | -1403 | -147 | 1758 | -66 | -790 | 781 | -633 | -1727 | -2476 | -1801 | 482 |
| | -1043 | -6850 | -983 | | | | | | | | | | | | | | | | | | |
| | -149 | -500 | 233 | 43 | -381 | 399 | 106 | -626 | 210 | -466 | -720 | 275 | 394 | 45 | 96 | 359 | 117 | -369 | -294 | -249 | |
| 462(Y) | -1345 | -1235 | -1689 | -1605 | 1266 | -1964 | 117 | -925 | -1303 | -775 | -592 | -1236 | -2169 | -1119 | -1309 | -1450 | -1367 | -939 | 590 | 3938 | 483 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8MM

Table 6

| | | | | | | | | | | | | | | | | | |
|---|---|---|---|---|---|---|---|---|---|---|---|---|---|---|---|---|---|
| 463(I) | -38 | -5845 | -6888 | -894 | -1115 | -560 | -1636 | * | -3402 | 771 | 18 | -3355 | -3517 | -3085 | -3372 | -2981 | -1545 | 1808 | -2540 | -2237 | 484 |
| | | -1578 | -1151 | -4046 | -3597 | -1151 | -3733 | -3046 | | 300 | -1988 | -1114 | 1414 | -1632 | 244 | 359 | 117 | -369 | -294 | -249 |
| | -149 | -500 | 233 | 43 | -381 | 399 | 106 | * | 210 | -466 | -720 | 275 | 394 | 45 | 96 | | | | | |
| | -19 | -6850 | -7893 | -894 | -1115 | -453 | -1893 | | | | | | | | | | | | | |
| 464(H) | -620 | -1972 | -273 | 140 | -2293 | -1493 | 2910 | 1123 | -1988 | -1114 | 1414 | -1632 | 244 | -127 | 1037 | -563 | -1615 | -2160 | -1523 | 485 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 465(E) | 290 | 1861 | 861 | 1446 | 981 | -1390 | -101 | 273 | -1861 | -968 | 953 | 303 | 339 | -239 | -355 | -411 | -1463 | -2069 | -1398 | 486 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 466(P) | -546 | -1977 | 862 | 1025 | -2262 | -1409 | -155 | 204 | -546 | -1086 | -48 | 1748 | 1636 | -313 | -420 | -495 | -1582 | -2175 | -1489 | 487 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 467( | -477 | -661 | -1479 | -920 | -458 | -1795 | -520 | -729 | -529 | 143 | 1513 | -1868 | -571 | -958 | 304 | -420 | 1257 | 2766 | 1177 | 488 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 468(D) | -2784 | -3432 | 4016 | -1200 | -4140 | -2466 | -2197 | -4505 | -2621 | -4365 | -3956 | -1551 | -3014 | -2039 | -3232 | -2938 | -4046 | -3710 | -3552 | 489 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 469(Q) | -1336 | -2814 | 130 | 2632 | -3112 | -1670 | 702 | -403 | -2921 | -2830 | -2067 | -313 | -2037 | 2655 | -853 | -1328 | -2494 | -2954 | -2238 | 490 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 470( | -1164 | -1540 | 661 | -1080 | 2483 | -2257 | 1994 | -1245 | -1304 | -742 | 745 | -2310 | 770 | -1263 | -1253 | -1097 | -1115 | 2555 | 1863 | 491 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 471(M) | -459 | -840 | -1110 | 504 | -907 | -1674 | -501 | -456 | -397 | -727 | 3234 | -715 | -1788 | -352 | -771 | 419 | 680 | -1288 | -853 | 492 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 472(H) | 1702 | -1846 | -317 | 119 | -2155 | -1480 | 1717 | 1008 | -1860 | -1009 | 1392 | -1616 | 236 | -157 | -482 | -520 | -1482 | -2080 | -1459 | 493 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 473(P) | 1735 | -849 | -2213 | -1898 | -1800 | -1446 | -1575 | -1724 | -902 | -1568 | -933 | -1474 | 2335 | -1533 | -1863 | -666 | 1535 | -2237 | -1882 | 494 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |
| 474(K) | 373 | -1864 | 703 | 990 | -2179 | -1360 | -29 | 1276 | -1928 | -1877 | -955 | 4 | -1460 | 1260 | -124 | 542 | 486 | -1483 | -2049 | -1367 | 495 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | | |

FIG. 8NN

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 475(G) | -2594 | -2690 | -3304 | -3623 | -4328 | 3747 | -3462 | 3953 | -4761 | -4671 | -4212 | -3320 | -3352 | -3748 | -3779 | -2839 | -2981 | -4004 | -3668 | -4222 | 496 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 476(R) | -1165 | -2238 | -1063 | -503 | -2794 | 820 | -418 | 526 | -2401 | -2281 | -1492 | -670 | -2047 | 2040 | 2681 | -1075 | -1064 | -2048 | -2328 | -1916 | 497 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 477(V) | -823 | -660 | -2789 | -2196 | -638 | -2422 | -1317 | -1836 | 1842 | -191 | 1866 | -1913 | -2436 | -1596 | 1039 | -1512 | -768 | -1296 | 2028 | -949 | 498 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 478(V) | -1748 | -1297 | -4301 | -3885 | -1515 | -3999 | -3451 | -3726 | 2579 | 585 | -321 | -3638 | -3782 | -3470 | -3730 | -3273 | -1722 | -2943 | -2589 | 499 | |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 479(D) | -1067 | -2475 | 2632 | 1644 | -2683 | -1544 | -584 | -469 | 1013 | -2422 | -1654 | -180 | -1882 | -209 | -1071 | -894 | -1059 | -1933 | -2725 | -1977 | 500 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -340 | -7108 | -2304 | -894 | -1115 | -701 | -1378 | * | | | | | | | | | | | |
| 480(S) | 717 | -1527 | -107 | 1500 | -2213 | 377 | -1911 | -112 | -1988 | -1149 | -164 | -1554 | 7 | -597 | 1919 | -503 | -1461 | -2242 | -1620 | 501 | |
| | -149 | -500 | 233 | 43 | -381 | 399 | -1984 | 210 | -626 | -466 | -720 | 275 | 394 | 45 | 96 | 359 | 117 | -369 | -294 | -249 | |
| | -20 | -6788 | -7830 | -894 | -1115 | -421 | -1378 | * | | | | | | | | | | | |
| 481(Q) | -790 | -1076 | -1563 | -1026 | -923 | -2037 | -834 | -669 | -178 | -369 | 1897 | -1109 | -2120 | 2919 | -906 | -1087 | 746 | 1186 | -1510 | -1104 | 502 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 482(L) | -2871 | -2457 | -4231 | 4103 | -1033 | 3803 | -3165 | -3734 | -541 | 3130 | -31 | -3935 | -3797 | -3286 | -3484 | -3713 | -2869 | -1136 | -2394 | -2220 | 503 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 483(S) | -897 | -1462 | -2333 | -2543 | -3185 | -1640 | -2474 | -2686 | -3294 | -3497 | -2780 | -1973 | -2360 | -2483 | -2703 | 3465 | -1316 | -2413 | -3310 | -3025 | 504 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 484(E) | -2641 | -3308 | -896 | 3732 | -3966 | 2110 | -2043 | -2128 | -4105 | -4016 | -3555 | -1531 | -2959 | -1842 | -2560 | -2479 | -2750 | -3722 | -3563 | -3385 | 505 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 485(H) | -3205 | -3079 | -2723 | -2890 | -2458 | -3046 | 5295 | -2617 | -4135 | -3813 | -3561 | -2886 | -3482 | -2833 | -2620 | -3291 | -3356 | -3895 | -2397 | -1681 | 506 |
| | -149 | -500 | 233 | 43 | -381 | 399 | 106 | 210 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | |
| 486(Q) | -1064 | -1426 | -1517 | -1022 | -242 | -2170 | -535 | -583 | -884 | 715 | -396 | -3561 | -2235 | 3051 | -804 | -1225 | -994 | -864 | -835 | 1693 | 507 |
| | -149 | -500 | 233 | 43 | -381 | 399 | 106 | 210 | -626 | -466 | -720 | 275 | 394 | 45 | 96 | 359 | 117 | -369 | -294 | -249 | |

FIG. 80O

Table 6

| | | | | | | | | | | | | | | | | |
|---|---|---|---|---|---|---|---|---|---|---|---|---|---|---|---|---|
| | -16 | -7108 | -8150 | -894 | -1115 | -701 | -1378 | * | | | | | | | | |
| 487(C | 1096 | 1354 | -606 | 43 | -1109 | -1571 | -566 | -613 | -497 | -939 | 1724 | -707 | -1762 | -380 | -838 | -622 | -428 | -433 | -1460 | -1015 | 508 |
| | -149 | -500 | | | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 488(E | -1401 | -2897 | 169 | 3007 | -3185 | -1677 | -753 | -3009 | -498 | -2916 | -2170 | -319 | -2069 | 1880 | -966 | -1173 | -1402 | -2580 | -3040 | -2307 | 509 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 489(H | -30 | 439 | 11 | 363 | -394 | -739 | 699 | -414 | 463 | -757 | 501 | 286 | -577 | 639 | 165 | -23 | 111 | -312 | 697 | -25 | 510 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 490(G | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 511 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 491I | -2172 | -1773 | -3771 | -3493 | 3388 | -3396 | -717 | -939 | -3099 | -528 | 2179 | -2555 | -3307 | -2387 | -2796 | -2550 | -2089 | -1165 | 3733 | 1010 | 512 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 492(L | -2620 | -2150 | -4778 | -4218 | -461 | -4493 | -3219 | 96 | -3870 | 2765 | 2758 | -4143 | -3872 | -3009 | -3534 | -3777 | -2498 | -607 | -2129 | -2177 | 513 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 493(E | -1401 | -2897 | 169 | 3007 | -3185 | -1677 | -753 | -3009 | -498 | -2916 | -2170 | -319 | -2069 | 1880 | -966 | -1173 | -1402 | -2580 | -3040 | -2307 | 514 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 494(G | 2172 | -1046 | -2384 | -2525 | -3259 | 2719 | -2377 | -2982 | -2644 | -3267 | -2417 | -1723 | -2035 | -2315 | -2652 | -666 | -864 | -2010 | -3440 | -3255 | 515 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 495(Y | -3482 | -2868 | -3701 | -3919 | 238 | -3552 | -1112 | -3000 | -3638 | -2516 | -2526 | -3027 | -3772 | -3101 | -3341 | -3418 | -3527 | -3071 | -441 | 4711 | 516 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 496(T | -971 | -915 | -2809 | -2296 | -857 | -2442 | -1626 | 433 | -1998 | 1151 | 92 | -2043 | -2569 | -1769 | -2033 | -1592 | 2524 | 1200 | -1666 | -1332 | 517 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 497(L | -2871 | -2457 | -4231 | -4103 | -1033 | -3803 | -3165 | -541 | -3734 | 3130 | -31 | -3935 | -3797 | -3286 | -3484 | -3713 | -2869 | -1136 | -2394 | -2220 | 518 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 498(T | -1213 | -1674 | -2755 | -2906 | -3163 | -1922 | -2659 | -2698 | -2788 | -3105 | -2612 | -2311 | -2600 | -2708 | -2753 | -1463 | 3819 | -2197 | -3286 | -3156 | 519 |
| | -149 | -500 | 233 | 43 | -381 | 399 | 106 | -626 | 210 | -466 | -720 | 275 | 394 | 45 | 96 | 359 | 117 | -369 | -294 | -249 | |

Table 6

| | | | | | | | | | | | | | | | | | | | | | |
|---|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | | |
| 511(V) | -929 | -722 | -3094 | -2519 | -671 | 72 | -1536 | -2197 | 1669 | 235 | -2159 | -2584 | -1873 | -2107 | -1688 | 882 | 1742 | -1406 | -1072 | 532 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 512(R) | -1152 | -2148 | -1103 | -556 | -2568 | 841 | 2681 | 448 | -2220 | -1446 | -714 | -2063 | -63 | 2686 | -1086 | -1067 | -1962 | -2250 | -1802 | 533 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 513(V) | -1261 | -1032 | -2990 | 401 | -1324 | -3032 | -2128 | 1904 | -591 | -293 | -2430 | -3023 | -2199 | -2472 | -2185 | -1232 | 2780 | -2221 | -1813 | 534 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 514(V) | -1755 | -1298 | -4332 | -3970 | -1769 | -4057 | -3755 | -3843 | -618 | -544 | -3732 | -3880 | -3701 | -3920 | -3374 | -1748 | 2759 | -3277 | -2831 | 535 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 515(D) | -1718 | 3250 | 3403 | -27 | -3066 | -1736 | 2667 | -1211 | -3381 | -2732 | -400 | -3023 | -2199 | -2472 | -2185 | -1784 | -3023 | -3204 | -2299 | 536 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 516(S) | -635 | -1657 | 1163 | -252 | -2614 | -1382 | 780 | -601 | -2421 | -1582 | -466 | -1801 | -415 | -1101 | 2397 | 1307 | -1804 | -2665 | -2044 | 537 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 517(M) | -2406 | -2296 | -3638 | -3594 | -1525 | -3105 | -2824 | -3121 | -596 | 5043 | -3293 | -3425 | -3046 | -2996 | -2911 | -2552 | -1398 | -2513 | -2207 | 538 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 518(M) | -2437 | -1975 | -4738 | -4148 | 487 | -4369 | -3139 | -3872 | 2524 | 2731 | -4019 | -3789 | 2984 | -3525 | -3603 | -2318 | -374 | -2113 | -2174 | 539 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 519(T) | -504 | -959 | -1413 | -1049 | -1473 | -1580 | -994 | -943 | -1256 | -601 | 1702 | -1931 | -837 | -1224 | -750 | 1993 | 1780 | -1865 | -1432 | 540 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 520(Q) | -2562 | -2904 | -1886 | -1971 | -3251 | -2661 | -2079 | -1565 | -3469 | -3081 | -2107 | -3091 | 4371 | -1665 | -2585 | -2674 | -3411 | -3077 | -2821 | 541 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 521(H) | -2992 | -2589 | -3064 | -3043 | 863 | -3512 | 4371 | -2584 | -2051 | -1961 | -2327 | -3545 | -2255 | -2492 | -2815 | -2919 | -2563 | 158 | 3265 | 542 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 522(F) | 1777 | -758 | -2605 | -2069 | 2426 | -2201 | -1138 | -1776 | 51 | 1943 | -1762 | -2314 | -1474 | -1762 | -1320 | -786 | -23 | -1063 | -575 | 543 |
| | -149 | -500 | 233 | 43 | -381 | 399 | 106 | 210 | -466 | -720 | 275 | 394 | 45 | 96 | 359 | 117 | -369 | -294 | -249 | |

FIG. 8RR

Table 6

| | | | | | | | | | | | | | | | | | | |
|---|---|---|---|---|---|---|---|---|---|---|---|---|---|---|---|---|---|---|
| | -16 | -7108 | -8150 | -894 | -1115 | -701 | -1378 | * | | | | | | | | | | |
| 523K | -2620 | -2961 | -2461 | -2046 | -3743 | -2791 | -1570 | -3603 | 3784 | -3387 | -2839 | -2048 | -3039 | -1260 | -465 | -2604 | -3331 | -3001 | -2988 | 544 |
| | -149 | -500 | 233 | 43 | -381 | 399 | 106 | -626 | 210 | -466 | -720 | 275 | 394 | 45 | 96 | 359 | 117 | -294 | -249 |
| | -16 | -7108 | -8150 | -894 | -1115 | -701 | -1378 | * | | | | | | | | | | |
| 524( | 3358 | -2599 | -4116 | -4259 | 2442 | -3892 | 536 | -2247 | -3821 | -1683 | -1712 | -2792 | -3835 | -2843 | -3352 | -3227 | -2441 | 5485 | 1363 | 545 |
| | -149 | -500 | 233 | 43 | -381 | 399 | 106 | -626 | 210 | -466 | -720 | 275 | 394 | 45 | 96 | 359 | 117 | -294 | -249 |
| | -16 | -7108 | -8150 | -894 | -1115 | -701 | -1378 | * | | | | | | | | | | |
| 525(L | 841 | -1175 | -3469 | -2926 | -668 | -3037 | -2058 | 1328 | -2615 | 2287 | 379 | -2642 | -2978 | -2226 | -2526 | -2188 | -1355 | 301 | -1760 | -1526 | 546 |
| | -149 | -500 | 233 | 43 | -381 | 399 | 106 | -626 | 210 | -466 | -720 | 275 | 394 | 45 | 96 | 359 | 117 | -294 | -249 |
| | -16 | -7108 | -8150 | -894 | -1115 | -701 | -1378 | * | | | | | | | | | | |
| 526(R | -837 | -2176 | -602 | 1392 | -2587 | -1688 | 216 | -2257 | 1534 | -2141 | -1281 | 1107 | -1779 | 227 | 2109 | -709 | -741 | -1854 | -2229 | -1683 | 547 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 527(M | 888 | -1677 | -357 | 850 | -1922 | -1428 | 1639 | -1611 | 1435 | -1654 | 1807 | -103 | -1521 | 338 | -129 | -358 | -369 | -1259 | -1902 | -1285 | 548 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 528(A | 2576 | 902 | -2349 | -2158 | -2756 | -1202 | -1937 | -2410 | -2031 | -2688 | -1852 | -1502 | -1892 | -1801 | -2162 | 1022 | 1811 | -1644 | -3004 | -2709 | 549 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 529K | -583 | -1746 | -490 | 34 | -1989 | -1543 | 1732 | -1666 | 1763 | -1714 | -880 | 1553 | -1641 | 238 | -31 | -516 | 875 | -513 | -1945 | -1367 | 550 |
| | -149 | -500 | 233 | 43 | -381 | 399 | 106 | -626 | 210 | -466 | -720 | 275 | 394 | 45 | 96 | 359 | 117 | -369 | -294 | -249 |
| | -1300 | -7108 | -8150 | -894 | -1115 | -701 | -1378 | * | | | | | | | | | | |
| 530(R | -915 | -1387 | -1141 | -641 | -1786 | -1421 | -246 | -1638 | 1712 | -1598 | -1052 | -657 | -1663 | 43 | 3215 | -962 | -890 | -1418 | -1542 | -1280 | 551 |
| | -38 | -5845 | -6888 | -894 | -1115 | -238 | -2716 | * | | | | | | | | | | |
| 531(E | -1710 | -3547 | 2209 | 3007 | -3749 | -1634 | -990 | -3679 | -1227 | -3559 | -2898 | -238 | -2166 | -662 | -2065 | -1376 | -1779 | -3163 | -3720 | -2744 | 552 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 532(I) | -599 | -507 | -2385 | -1791 | -457 | -2112 | -969 | 1604 | -1499 | 1009 | 366 | -1553 | -2152 | 765 | -1506 | -1178 | 1103 | -1019 | -667 | 553 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 533(P | 787 | -1572 | 724 | 108 | -1851 | -1418 | -201 | -1534 | 126 | -1626 | -789 | -169 | 1640 | 198 | -358 | 575 | -413 | -1199 | -1916 | 922 | 554 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 534( | -4114 | -3274 | -4214 | -4453 | -1722 | -3496 | -2681 | -4109 | -4149 | -3619 | -3615 | -4044 | -3885 | -4032 | -3816 | -4355 | -4248 | -4133 | 6191 | -1329 | 555 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8SS

Table 6

| | | | | | | | | | | | | | | | | | | | | | | |
|---|---|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | | | |
| 535(R | -1940 | -2623 | -2163 | -1317 | -2718 | -2498 | 2633 | -2821 | 557 | -2576 | -1920 | -1294 | -2549 | -305 | 3406 | -1859 | -1734 | -2575 | -2279 | -1885 | 556 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 536(H | -1345 | -2440 | -1207 | -576 | -2915 | -2072 | 3063 | -2527 | 2588 | -2343 | -1569 | -727 | -2129 | 1381 | 532 | -1222 | -1187 | -2200 | -2324 | -1939 | 557 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 537(D | -695 | -2182 | 1890 | 241 | -2491 | -1456 | -249 | -2246 | 1496 | -2187 | -1300 | -85 | -2835 | 1306 | -385 | -545 | -648 | -1804 | -2357 | -1656 | 558 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 538(Y | -1138 | 876 | -3345 | -2810 | -645 | -2852 | -1674 | 1928 | -2488 | -317 | 10 | -2411 | -2835 | -2166 | -2393 | -1984 | -1094 | 2117 | -1423 | 2681 | 559 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 539(P | 1031 | -974 | -2031 | 1918 | -2925 | -1207 | -1878 | -2641 | -1913 | -2865 | -2004 | -1407 | 2879 | -1695 | -2096 | 1838 | -694 | -1790 | -3123 | -2802 | 560 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 540(H | -30 | 439 | 11 | 363 | -394 | -739 | 699 | 414 | 463 | -757 | 501 | 286 | -577 | 639 | 165 | -23 | 111 | -312 | 697 | -25 | 561 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 541(S | 1737 | -944 | -2392 | -2415 | -3092 | -1199 | -2214 | -2801 | -2395 | -3086 | -2226 | -1614 | -1940 | -2116 | -2445 | -2898 | -735 | -1863 | -3322 | -3065 | 562 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 542(M | -1968 | -1576 | -4331 | -3761 | -611 | -3859 | -2765 | 1741 | -3480 | -3936 | 2227 | -3502 | -3515 | -2812 | -3229 | -3049 | -1885 | 1013 | -2038 | -1963 | 563 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 543(N | -2171 | -2655 | -1458 | -1748 | -3334 | -2364 | -2267 | -3943 | 2365 | 1333 | 2250 | 3437 | -2932 | -2205 | -2608 | -2224 | -2439 | -3392 | -3253 | -2909 | 564 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 544(I) | -1257 | -1007 | -3424 | -2868 | 1397 | -2811 | -1254 | 2188 | -2500 | 1333 | 382 | -2341 | -2749 | -1996 | -2283 | -1922 | -1186 | -115 | 815 | 2061 | 565 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 545(I) | -1831 | -1391 | -4327 | -3871 | -1200 | -3991 | -3265 | 2941 | -3675 | 1302 | -22 | -3631 | -3727 | -3275 | -3598 | -3245 | -1791 | 1578 | -2650 | -2410 | 566 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | | |
| 546(E | 999 | -1712 | 787 | 1203 | -1974 | -1412 | -152 | -1661 | 194 | -1721 | -863 | -101 | -1546 | 266 | -305 | 466 | -419 | 822 | -1983 | -1349 | 567 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8TT

Table 6

FIG. 8UU

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 547(T) | 590 | -1479 | 974 | -206 | -2293 | -1346 | -555 | -1995 | -272 | -2077 | -1218 | 407 | -1671 | -167 | 745 | 1655 | 1771 | -1514 | -2333 | -1741 | 568 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 548(S) | -897 | -1462 | -2333 | -2543 | -3185 | -1640 | -2474 | -3294 | -2686 | -3497 | -2780 | -1973 | -2360 | -2483 | -2703 | 3465 | -1316 | -2413 | -3310 | -3025 | 569 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 549(T) | -866 | -1511 | -1211 | -1054 | -1813 | -1680 | 2857 | -1969 | -793 | -2130 | -1455 | -1074 | -2117 | -914 | -1013 | -989 | 3041 | -1609 | -2119 | -1469 | 570 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 550I | -587 | -608 | -2405 | -1898 | 479 | -1928 | -993 | 42 | -1552 | -528 | 62 | -1554 | -2129 | -1332 | -1550 | 365 | -609 | 2511 | 3028 | -502 | 571 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 551I | 947 | -1346 | -3135 | -2759 | 3172 | -2759 | -620 | 882 | -2412 | 912 | 526 | -2088 | -2831 | -1938 | -2273 | -1901 | -1498 | 870 | 3648 | 929 | 572 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 552Q | -1772 | -2604 | -1870 | -1079 | -3217 | -2374 | 569 | -2777 | 660 | -2529 | -1835 | -1110 | -2420 | 3075 | 2723 | -1671 | 3041 | -2504 | -2437 | -2192 | 573 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 553Q | -2562 | -2904 | -1886 | -1971 | -3251 | -2661 | -2079 | -3690 | -1565 | -3469 | -3081 | -2107 | -3091 | 4371 | -1665 | -2585 | -2674 | -3411 | -3077 | -2821 | 574 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 554D | -1791 | -3663 | 3414 | 1659 | -3853 | -1647 | -1043 | -3807 | -1343 | -3679 | -3054 | -251 | -2201 | -725 | -2227 | -1438 | -1872 | -2504 | -3836 | -2831 | 575 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 555H | -3205 | -3079 | -2723 | -2890 | -2110 | -3046 | 5295 | -4135 | -2617 | -3813 | -3561 | -2886 | -3482 | -2833 | -2620 | -3291 | -3356 | -3895 | -3282 | -1681 | 576 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 556N | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3668 | -2909 | 577 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 557G | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3253 | -4222 | 578 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 558Y | -3620 | -2706 | -4179 | -4428 | 3303 | -4051 | -393 | -2536 | -4005 | -1939 | -1984 | -2749 | -3933 | -2855 | -3452 | -3299 | -3498 | -2688 | 350 | 3843 | 579 |
| | -149 | -500 | 233 | 43 | -381 | 399 | 106 | -626 | 210 | -466 | -720 | 275 | 394 | 45 | 96 | 359 | 117 | -369 | -294 | -249 | |

Table 6

| | | | | | | | | | | | | | | | | | | | | | |
|---|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | | |
| 559(S) | -344 | -978 | -2187 | -2155 | -2953 | -1227 | -2035 | -2643 | -2108 | -2093 | -1523 | -1940 | -1902 | -2216 | 2907 | 1859 | -1800 | -3181 | -2875 | 580 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 560(H) | -3205 | -3079 | -2723 | -2890 | -2110 | -3046 | 5295 | -4135 | -2617 | -3561 | -2886 | -3482 | -2833 | -2620 | -3291 | -3356 | -3895 | -2397 | -1681 | 581 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 561(Q) | -2562 | -2904 | -1886 | -1971 | -3251 | -2661 | -2079 | -3690 | -1565 | -3081 | -2107 | -3091 | 4371 | -1665 | -2585 | -2674 | -3411 | -3077 | -2821 | 582 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 562(D) | -1724 | -3448 | 3411 | 103 | -3726 | -1642 | -1058 | -3734 | -1342 | -3628 | 1884 | -2196 | -745 | -2191 | -1408 | -1822 | -3197 | 3743 | -2768 | 583 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 563(P) | -2931 | -2878 | -3420 | -3706 | -4181 | -2925 | -3468 | -4621 | -3859 | -4165 | -3491 | 4225 | -3781 | -3695 | -3182 | -3279 | -4087 | -3594 | -4064 | 584 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 564(G) | -468 | -1108 | -1987 | -2183 | -3307 | 3093 | -2261 | -3159 | -2489 | -2507 | -1593 | -2035 | -2163 | -2570 | 1410 | -895 | -2119 | -3471 | -3217 | 585 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 565(V) | 371 | -671 | -3209 | -2618 | 1562 | -2580 | -1515 | 1368 | -2275 | 269 | -2195 | -2574 | -1917 | -2132 | -1689 | 852 | -1337 | -1001 | 586 | |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 566(T) | -1238 | -1032 | -3270 | -2717 | 705 | -2883 | -1871 | 1700 | -2401 | 301 | -2442 | -2848 | -2072 | -2345 | -2015 | 1957 | 452 | -1675 | -1395 | 587 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 567(T) | -307 | -965 | -2051 | -1918 | -2899 | 1272 | -1866 | -2617 | -1903 | -2838 | -1975 | -1889 | -1683 | -2089 | 1577 | 2739 | -1773 | -3100 | -2780 | 588 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 568(H) | 837 | -578 | -1703 | -1139 | -579 | -1822 | 2864 | 45 | -902 | 418 | -1086 | -1915 | -740 | -1071 | -867 | -423 | 1342 | -1041 | -648 | 589 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 569(L) | -2092 | -1719 | -4323 | -3846 | -712 | -3925 | -2989 | 451 | -3531 | 2641 | -3624 | -3640 | -2952 | -3339 | -3191 | -2044 | 1542 | -2221 | -2096 | 590 |
| | -149 | -500 | 233 | 43 | -381 | -701 | 106 | -626 | 210 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 570(L) | 1056 | -648 | -2733 | -2160 | 1291 | -2277 | -874 | 5 | -1827 | 1649 | -1760 | -2303 | -1464 | -1729 | -1359 | -733 | -2 | -647 | 1605 | 591 |
| | -149 | -500 | 233 | 43 | -381 | -701 | 106 | -626 | 210 | -720 | 275 | 394 | 45 | 96 | 359 | 117 | -369 | -294 | -249 | |

FIG. 8VV

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 571(E) | -994 | -2497 | 67 | 2352 | -2818 | -1564 | -437 | -2572 | 1391 | -2487 | -1645 | 1818 | -1831 | -24 | -503 | -812 | -956 | -2133 | -2633 | -1933 | 592 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | * | | | | | | | | | | | | |
| 572(K) | -1592 | -2196 | -1883 | -1179 | -2203 | -2360 | -733 | -1718 | 3129 | 666 | -1212 | -1218 | -2435 | -383 | 258 | -1621 | -1460 | -1669 | -2199 | -1837 | 593 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -971 | -7108 | -1051 | -894 | -1115 | -701 | -1378 | * | * | | | | | | | | | | | | |
| 573(C) | -39 | ▓▓▓ | -473 | 1144 | -1043 | -1085 | -142 | -526 | 67 | -851 | -125 | -185 | -1325 | 126 | -296 | -170 | 1058 | -295 | -1316 | -837 | 594 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -360 | -6167 | -2274 | -894 | -1115 | -1874 | -459 | | | | | | | | | | | | | | |
| 574(F) | -1315 | -1110 | -2234 | -2129 | 3522 | -2099 | -247 | -203 | -1900 | 58 | 60 | -1632 | -2283 | -1510 | -1804 | -1624 | -1357 | -396 | 303 | 1334 | 595 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -38 | -5845 | -6888 | -894 | -1115 | -2039 | -402 | * | | | | | | | | | | | | | |
| 575(H) | -354 | -1360 | 326 | 436 | -1031 | -1026 | 2689 | -1410 | 436 | -1450 | -724 | 1667 | -1303 | 383 | 89 | -286 | -351 | -1096 | -1280 | -501 | 596 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -38 | -5845 | -6888 | -894 | -1115 | -238 | -2716 | * | | | | | | | | | | | | | |
| 576(K) | -1086 | -2304 | -1032 | -362 | -2797 | -1910 | -283 | -2399 | 2361 | -2235 | -1413 | 1695 | -1959 | 1479 | 1362 | -963 | -952 | -2031 | -2264 | -1826 | 597 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 577(P) | -1766 | -2832 | 2091 | -503 | -3634 | -1897 | -1480 | -3629 | -1677 | -3608 | -2962 | -830 | 3445 | -1206 | -2322 | -1624 | -1926 | -3087 | -3516 | -2951 | 598 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 578(H) | -480 | -1902 | 1434 | 926 | -2176 | -1399 | 2271 | -1893 | 300 | -1903 | -1004 | -39 | -1617 | 347 | 782 | -362 | -423 | -1511 | -2083 | 1389 | 599 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 579(Y) | 839 | 383 | -2642 | -2032 | 1206 | -2056 | -863 | 223 | -1678 | 569 | 461 | -157 | -2100 | -1333 | -1555 | -1135 | -472 | 1465 | -747 | 1987 | 600 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 580(I) | 865 | -836 | -3163 | -2646 | -1108 | -2692 | -1893 | 2677 | -2382 | -556 | -157 | -2324 | -2771 | -2135 | -2380 | -1845 | 504 | 1519 | -1868 | -1491 | 601 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 581(R) | -1066 | -2251 | -943 | -347 | -2740 | 308 | -313 | -2349 | 1342 | -2216 | -1401 | 854 | -1954 | 119 | 2761 | 953 | -949 | -1986 | -2272 | -1823 | 602 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 582(E) | -370 | -640 | -961 | 1875 | -770 | -1558 | -279 | 900 | -284 | -670 | 84 | -547 | -1598 | -160 | -606 | -577 | -301 | 965 | -907 | -668 | 603 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8WWW

Table 6

| | | | | | | | | | | | | | | | | | | | | | |
|---|---|---|---|---|---|---|---|---|---|---|---|---|---|---|---|---|---|---|---|---|---|
| | -16 | -7108 | -8150 | -894 | -1115 | -701 | | | -1378 | * | | | | | | | | | | | |
| 583(Y) | -3618 | -2707 | -4172 | 4418 | 2748 | -4047 | 395 | -2537 | 3997 | | -1940 | -1986 | -2748 | -3932 | -2853 | -3448 | -3297 | -3496 | -2688 | 348 | 4199 | 604 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 584(F) | -2597 | -2122 | 4519 | 4116 | 2769 | -4202 | -2114 | -140 | -3797 | | 2428 | 469 | -3639 | 3772 | 2912 | -3436 | -3471 | -2488 | -1265 | -783 | -532 | 605 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 585(P) | 1615 | -1136 | -2222 | 2310 | -3082 | -1373 | -2227 | -2731 | -2358 | | -3036 | -2272 | -1689 | 3445 | 2139 | -2424 | -761 | 938 | -3279 | -1937 | -3042 | 606 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 586(A) | 2397 | -935 | -2082 | -1846 | -2575 | -1236 | -1722 | -2190 | -1737 | | -2475 | -1666 | -1377 | 1554 | -1552 | -1929 | -527 | 1772 | -1532 | -2826 | -2490 | 607 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 587(D) | -2784 | 3432 | 4016 | -1200 | -4140 | -2466 | -2197 | -4505 | -2621 | | -4365 | -3956 | 3014 | -1976 | -2039 | -3232 | -2593 | -2938 | 3710 | 4046 | -3552 | 608 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 588(A) | 3098 | -930 | -2580 | -2583 | -2894 | -1243 | -2249 | -2309 | -2448 | | -2781 | -2022 | -1697 | 2932 | -2194 | -2449 | -591 | 1113 | -3196 | -3392 | -2952 | 609 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 589(N) | -2171 | -2655 | -1458 | 1748 | -3334 | -2364 | -2267 | -3943 | -2365 | | -3936 | 3437 | 4205 | -2932 | 2205 | -2608 | -2224 | -2439 | -3253 | 3710 | -2909 | 610 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 590(M) | -387 | -854 | -1643 | -1199 | -1437 | -1461 | -1020 | -962 | -1012 | | -1269 | -1075 | -1857 | 895 | -1259 | 1806 | 865 | 111 | -709 | -1810 | -1406 | 611 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 591(H) | -30 | 439 | 11 | 363 | -394 | -739 | 699 | 414 | 463 | | -757 | 501 | 286 | -577 | 639 | 165 | -23 | 111 | 312 | 697 | -25 | 612 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 592(L) | -2625 | -2145 | -4613 | 4174 | 1968 | -4304 | -2386 | -72 | -3866 | | 551 | -3801 | -3814 | -2959 | -3500 | -3585 | -2511 | -2096 | -745 | -1483 | -874 | 613 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 593(L) | -2193 | -1789 | -4457 | -3877 | -523 | -4057 | -2894 | 279 | -3584 | | 2231 | -3689 | -3624 | -2841 | -3310 | -3261 | -2096 | 1093 | -2048 | -2035 | 614 |
| | -149 | -500 | 233 | 43 | -381 | 399 | 106 | -626 | 210 | | -466 | 275 | 394 | 45 | 96 | 359 | 117 | -369 | -294 | -249 | | |
| | -16 | -7108 | -8150 | -894 | -1115 | -701 | | | -1378 | * | | | | | | | | | | | |
| 594(A) | 2970 | -925 | -2555 | -2528 | -2849 | -1243 | -2202 | -2276 | -2388 | | -2737 | -1975 | -1675 | 1968 | -2140 | -2406 | -585 | 1607 | -3151 | -2898 | 615 |
| | -149 | -500 | 233 | 43 | -381 | 399 | 106 | -626 | 210 | | -466 | 275 | 394 | 45 | 96 | 359 | 117 | -369 | -294 | -249 | | |

FIG. 8XX

Table 6

| | | | | | | | | | | | | | | | | | | |
|---|---|---|---|---|---|---|---|---|---|---|---|---|---|---|---|---|---|---|
| | -16 | -7108 | -8150 | -894 | -1115 | -701 | -1378 | * | | | | | | | | | | |
| 595(V) | 1334 | -1034 | -3629 | -3155 | -1390 | -3214 | -2516 | -2918 | -591 | -331 | -2852 | -3211 | -2701 | -2928 | -2407 | 1824 | 2364 | -2380 | -1985 | 616 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 596(M) | 998 | -406 | -1988 | -1399 | 1077 | 46 | -692 | -1142 | 733 | 1731 | -1227 | -1918 | -903 | -1209 | 286 | -359 | 167 | -855 | -487 | 617 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 597(H) | -1095 | -2732 | 1291 | 2125 | -2985 | -1512 | 3032 | -2799 | -427 | -2721 | 1256 | -1890 | -1861 | -159 | -1055 | -875 | -1088 | -2329 | -2902 | -2089 | 618 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 598(H) | -971 | -1917 | -1026 | -424 | -2119 | -1866 | 2995 | -1811 | -1852 | -1093 | -602 | -1947 | 34 | 266 | -932 | -871 | 294 | -1999 | -1507 | 619 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 599(C) | 1836 | -777 | -2905 | -2499 | -1252 | -1823 | -1705 | 1152 | -2189 | -888 | 389 | -1893 | -1876 | -2246 | -2150 | -1063 | -756 | 157 | -1855 | -1509 | 620 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 600(F) | 528 | -777 | -2899 | -2354 | 2441 | -2415 | -823 | -127 | -2008 | 1363 | 215 | -1876 | -2433 | -1604 | -1506 | -889 | -142 | 490 | 1736 | 621 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 601(K) | -1239 | -2390 | -1266 | -522 | -2934 | -2031 | -324 | 2422 | -2300 | -1501 | 1574 | 979 | -426 | -2062 | -1917 | -1116 | -1081 | -2146 | -2296 | -1915 | 622 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 602(S) | 699 | -1151 | -903 | -440 | -1699 | -1408 | -579 | -350 | -1526 | -1807 | 974 | -1694 | -269 | -750 | 2107 | -464 | -1002 | -1909 | -1408 | 623 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 603(Q) | -873 | -2060 | -736 | -198 | -2478 | -1732 | -282 | 1944 | -2635 | -2300 | -426 | -1836 | 1968 | 230 | -780 | 1853 | -1758 | -2189 | -1681 | 624 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 604(N) | -1080 | -2639 | 214 | 1668 | -2924 | -1545 | -527 | -282 | -2711 | -1807 | 2572 | -1867 | 2104 | -814 | -876 | -1062 | -2261 | -2801 | -2043 | 625 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 605(K) | 457 | 1622 | -593 | -29 | -1532 | -1520 | -184 | 1745 | -1320 | -528 | -275 | -1605 | 1259 | -206 | -467 | 609 | 916 | -1665 | 1434 | 626 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 606(I) | -1995 | -1561 | -4353 | -3926 | -1045 | -4065 | -3261 | -3652 | 924 | -3716 | -3783 | -3240 | -3554 | -3362 | -1957 | 705 | -2551 | -2295 | 627 |
| | -149 | -500 | 233 | 43 | -381 | 399 | 106 | 210 | -466 | -720 | 275 | 394 | 45 | 96 | 359 | 117 | -369 | -294 | -249 |

FIG. 8YY

Table 6

| | | | | | | | | | | | | | | | | | | |
|---|---|---|---|---|---|---|---|---|---|---|---|---|---|---|---|---|---|---|
| 607(N) | -2171 | -7108 | -1458 | -8150 | -1748 | -894 | -3334 | -1115 | -2364 | -701 | -2267 | -1378 | -3943 | -2365 | -3437 | -2932 | -2205 | -2608 | -2224 | -2439 | -3392 | -3253 | -2909 | 628 |
| | -149 | -500 | 233 | -8150 | 43 | -894 | -381 | -1115 | 399 | -701 | 106 | -1378 | -626 | 210 | -720 | 394 | 45 | 359 | 96 | 117 | -369 | -294 | -249 | |
| | -16 | -7108 | | -8150 | | -894 | | -1115 | | -701 | | -1378 | | * | | | | | | | | | | |
| 608(Y) | 1025 | -487 | -2483 | -8150 | -1892 | -894 | -336 | -1115 | -2087 | -701 | -935 | -1378 | 224 | -1576 | 403 | -2140 | -1281 | -1535 | -1165 | -537 | 999 | -908 | 2074 | 629 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 609(M) | -797 | -587 | -3073 | -8150 | -2468 | -894 | 1091 | -1115 | -2423 | -701 | -1329 | -1378 | 2169 | -2112 | 2364 | -2036 | -2429 | -1745 | -1959 | -1522 | 645 | 1209 | -1165 | -836 | 630 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 610(V) | -1573 | -1179 | -4043 | -8150 | -3576 | -894 | 867 | -1115 | -3627 | -701 | -2822 | -1378 | 2175 | -3353 | -198 | -3256 | -3486 | -3047 | -3296 | -2841 | -1540 | -2430 | -2026 | 631 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 611(A) | 2440 | -912 | -2339 | -8150 | -2201 | -894 | -2840 | -1115 | 1287 | -701 | -1997 | -1378 | -2505 | -2116 | -1935 | -1522 | -1901 | -1868 | -2234 | -517 | 1851 | -1699 | -3081 | -2799 | 632 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 612(S) | -437 | -1083 | -2006 | -8150 | -2144 | -894 | -3262 | -1115 | 1583 | -701 | -2197 | -1378 | -3097 | -2380 | -2434 | -1562 | -2008 | -2077 | -2485 | 2965 | -857 | -2074 | -3426 | -3160 | 633 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 613(K) | -2620 | -2961 | -2461 | -8150 | -2046 | -894 | -3743 | -1115 | -2791 | -701 | -1570 | -1378 | -3603 | 3784 | -2839 | -2048 | -3039 | -465 | -2604 | -2536 | -3331 | -3001 | -2988 | 634 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 614(H) | -1501 | -2478 | -747 | -8150 | -589 | -894 | -1969 | -1115 | -2033 | -701 | 3845 | -1378 | -2617 | -5 | -1816 | -796 | -2272 | 2881 | -187 | -1387 | -1442 | -2314 | -1345 | 635 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 615(P) | -2931 | -2878 | -3420 | -8150 | -3706 | -894 | -4181 | -1115 | -2925 | -701 | -3468 | -1378 | -4621 | -3859 | -4165 | -3491 | -1844 | 4225 | -3781 | -3695 | -3182 | -3279 | -4087 | -3594 | -4064 | 636 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 616(R) | 1242 | -1347 | -1254 | -8150 | -731 | -894 | -2201 | -1115 | -1510 | -701 | -719 | -1378 | -1792 | -153 | -1159 | -782 | -1844 | 375 | -529 | -656 | 1294 | -1393 | -2232 | -1788 | 637 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 617(P) | 1448 | -1164 | -798 | -8150 | -305 | -894 | -1387 | -1115 | -1533 | -701 | -406 | -1378 | -980 | -151 | -453 | -488 | 1572 | 1113 | 2580 | -448 | -759 | -1144 | 638 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |
| 618(Q) | -557 | -1175 | -1028 | -8150 | -563 | -894 | -1488 | -1115 | -1618 | -701 | -611 | -1378 | -820 | -317 | -557 | -696 | -1835 | 2724 | -638 | -698 | 1378 | 1031 | -1782 | -1308 | 639 |
| | -149 | -500 | 233 | -8150 | 43 | -894 | -381 | -1115 | 399 | -701 | 106 | -1378 | -626 | 210 | -720 | 275 | 394 | 45 | 96 | 359 | 117 | -369 | -294 | -249 | |
| | -16 | -7108 | | -8150 | | -894 | | -1115 | | -701 | | -1378 | | * | | | | | | | | | | |

Table 6

| | | | | | | | | | | | | | | | | | | | |
|---|---|---|---|---|---|---|---|---|---|---|---|---|---|---|---|---|---|---|---|
| | -16 | -7108 | -8150 | -894 | -1115 | -701 | -1378 | * | | | | | | | | | | | |
| 631(Q | 1161 | -1938 | -287 | 164 | -2274 | -1471 | -154 | 1104 | -1990 | -1956 | -1072 | 1604 | -1598 | 1906 | -101 | -461 | -513 | -1579 | -2132 | -1496 | 652 |
| | -149 | -500 | 233 | 43 | -381 | 399 | 106 | 210 | -626 | -466 | -720 | 275 | 394 | 45 | 96 | 359 | 117 | -369 | -294 | -249 | |
| 632(G | -2594 | -2690 | -3304 | -3623 | -4328 | 3747 | -3462 | -3953 | -4761 | -4671 | -4212 | -3320 | -3352 | -3748 | -3779 | -2839 | -2981 | -4004 | -3668 | -4222 | 653 |
| | -149 | -500 | 233 | 43 | -381 | 399 | 106 | 210 | -626 | -466 | -720 | 275 | 394 | 45 | 96 | 359 | 117 | -369 | -294 | -249 | |
| 633(L | 2002 | -1175 | -2785 | -2475 | -1055 | -2185 | -1898 | -2172 | -221 | 2054 | -104 | -2097 | -2542 | -1964 | -2186 | -1458 | -1162 | -325 | -1982 | -1669 | 654 |
| | -149 | -500 | 233 | 43 | -381 | 399 | 106 | 210 | -626 | -466 | -720 | 275 | 394 | 45 | 96 | 359 | 117 | -369 | -294 | -249 | |
| 634(K | 943 | -1709 | -403 | 133 | -2096 | 781 | -142 | 994 | -1801 | -1811 | -930 | -144 | -1543 | 292 | 938 | 844 | -405 | -1399 | -2023 | -1402 | 655 |
| | -149 | -500 | 233 | 43 | -381 | 399 | 106 | 210 | -626 | -466 | -720 | 275 | 394 | 45 | 96 | 359 | 117 | -369 | -294 | -249 | |
| 635(I | 525 | -452 | -2111 | 23 | -445 | -1963 | -805 | -1266 | 1776 | -283 | 345 | -1346 | -2019 | -1026 | -1323 | -1017 | -436 | 1518 | -942 | 1179 | 656 |
| | -149 | -500 | 233 | 43 | -381 | 399 | 106 | 210 | -626 | -466 | -720 | 275 | 394 | 45 | 96 | 359 | 117 | -369 | -294 | -249 | |
| 636( | -1626 | -1321 | -3570 | -3141 | 2053 | -3057 | -937 | -2760 | 2580 | -226 | -54 | -2426 | -2999 | -2185 | -2514 | -2189 | -1555 | -448 | 3586 | 581 | 657 |
| | -149 | -500 | 233 | 43 | -381 | 399 | 106 | 210 | -626 | -466 | -720 | 275 | 394 | 45 | 96 | 359 | 117 | -369 | -294 | -249 | |
| 637(D | -1498 | -3029 | 3115 | 17 | -3354 | -1691 | -852 | 1912 | -3199 | -3109 | -2371 | -341 | -2120 | -495 | -1230 | -1252 | -1519 | -2742 | -3208 | -2450 | 658 |
| | -149 | -500 | 233 | 43 | -381 | 399 | 106 | 210 | -626 | -466 | -720 | 275 | 394 | 45 | 96 | 359 | 117 | -369 | -294 | -249 | |
| 638( | -3358 | -2599 | -4116 | -4259 | 2442 | -3892 | -536 | -3821 | -2247 | -1683 | -1712 | -2792 | -3835 | -2843 | -3352 | -3227 | -3271 | -2441 | 5485 | 1363 | 659 |
| | -149 | -500 | 233 | 43 | -381 | 399 | 106 | 210 | -626 | -466 | -720 | 275 | 394 | 45 | 96 | 359 | 117 | -369 | -294 | -249 | |
| 639(C | 3004 | -3175 | -3184 | -2750 | -1300 | -2459 | -2082 | -2641 | -1933 | -2041 | -1922 | -2538 | -2722 | -657 | -796 | -1473 | -3106 | -2895 | 660 |
| | -149 | -500 | 233 | 43 | -381 | 399 | 106 | 210 | -626 | -466 | -720 | 275 | 394 | 45 | 96 | 359 | 117 | -369 | -294 | -249 | |
| 640(S) | -897 | -1462 | -2333 | -2543 | -3185 | -1640 | -2474 | -2686 | -3294 | -3497 | -2780 | -1973 | -2360 | -2483 | -2703 | -2538 | -1316 | -2413 | -3310 | -3025 | 661 |
| | -149 | -500 | 233 | 43 | -381 | 399 | 106 | 210 | -626 | -466 | -720 | 275 | 394 | 45 | 96 | 359 | 117 | -369 | -294 | -249 | |
| 641(T | -638 | -1323 | -1200 | -1263 | -2717 | -1420 | -1550 | -1436 | -2421 | -2697 | -1948 | 1009 | -2035 | -1340 | -1682 | -796 | 3384 | -1817 | -2917 | -2452 | 662 |
| | -149 | -500 | 233 | 43 | -381 | 399 | 106 | 210 | -626 | -466 | -720 | 275 | 394 | 45 | 96 | 359 | 117 | -369 | -294 | -249 | |
| 642(H | -30 | 439 | 11 | 363 | -394 | -739 | 699 | 463 | 414 | -757 | 501 | 286 | -577 | 639 | 165 | -23 | 111 | -312 | 697 | -25 | 663 |
| | -149 | -500 | 233 | 43 | -381 | 399 | 106 | 210 | -626 | -466 | -720 | 275 | 394 | 45 | 96 | 359 | 117 | -369 | -294 | -249 | |

FIG. 8BBB

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 643|D | 1256 | -1810 | 2828 | -193 | -2711 | -1421 | -825 | * | -2377 | -710 | -2507 | -1697 | -438 | -1858 | -471 | -1243 | -735 | 787 | -1875 | -2779 | -2131 | 664 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 644|K | -1038 | -2259 | -689 | -253 | -2738 | 777 | -360 | * | -2382 | 2468 | -2269 | -1451 | -481 | -1931 | 2027 | 226 | -921 | -949 | -2002 | -2343 | -1850 | 665 |
| | -535 | -1708 | -8150 | -140 | -3430 | 398 | 106 | | -626 | 210 | -466 | -721 | 276 | 395 | 45 | 96 | 360 | 118 | -369 | -294 | -249 |
| 645|G | -1044 | -1813 | -773 | -1023 | -3345 | 2987 | -1699 | * | -3331 | -1775 | -3418 | -2659 | 2131 | -2239 | -1475 | -2156 | -1127 | -1361 | -2539 | -3373 | -2907 | 667 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 646|E | -488 | -1836 | 1360 | 1439 | -2104 | -1403 | -131 | * | -1820 | 229 | 87 | -955 | -60 | -1537 | 301 | -280 | 469 | 631 | -1431 | -2061 | -1399 | 668 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 647|E | -1127 | -2366 | -800 | 2480 | -2838 | -1878 | -336 | * | -2455 | 1396 | -2301 | -1488 | -522 | -1975 | 95 | 1670 | -993 | -1007 | -2085 | -2343 | -1881 | 669 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 648|P | 955 | -915 | -2251 | -2048 | 856 | -1361 | -1790 | * | -1375 | -1894 | -1974 | -1329 | -180 | -2074 | 1731 | -1720 | -660 | -714 | 631 | -2606 | -2267 | 670 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 649|D | -1535 | -3339 | -915 | -2204 | -3535 | -1586 | -853 | * | -3417 | -967 | -3307 | -2587 | -180 | -3878 | -1711 | -2016 | -1229 | -1578 | -2919 | -3496 | -2555 | 671 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 650|V | -1754 | -4329 | -3968 | -3915 | -1770 | -4053 | -3752 | * | 2602 | -3840 | -621 | -545 | -3728 | -2074 | 1731 | -3917 | -3370 | -1746 | 2861 | -3276 | -2829 | 672 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 651|V | -1297 | -4275 | -3915 | -1733 | -3969 | -3654 | * | -3766 | 210 | -3766 | -598 | -525 | -3663 | -3828 | -3619 | -3833 | -3283 | -1733 | 3222 | -3208 | -2763 | 673 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 652|M | -2158 | -4466 | -3857 | 2098 | -3961 | 1339 | -2711 | * | -3551 | 2194 | 2215 | -3609 | -3535 | -2747 | -3220 | -3143 | -2048 | -438 | -1879 | -1836 | 674 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 653|A | 2500 | -821 | -2504 | -2171 | -1756 | -1515 | -1719 | * | -589 | -1953 | -1465 | -872 | -1633 | -2062 | -1734 | -2039 | -780 | 1073 | 1394 | -2251 | -1909 | 675 |
| | -149 | -500 | 233 | 43 | -381 | 399 | 106 | | -626 | 210 | -466 | -720 | 275 | 394 | 45 | 96 | 359 | 117 | -369 | -294 | -249 |
| | -16 | -7108 | -8150 | -894 | -1115 | -701 | -1378 | | | | | | | | | | | | | | |
| 654|A | 2412 | -931 | -2308 | -2228 | -3059 | 1309 | -2079 | * | -2797 | -2207 | -3025 | -2139 | -1529 | -1901 | -1934 | -2326 | 1722 | -691 | -1849 | -3263 | -2994 | 676 |
| | -149 | -500 | 233 | 43 | -381 | 399 | 106 | | -626 | 210 | -466 | -720 | 275 | 394 | 45 | 96 | 359 | 117 | -369 | -294 | -249 |

FIG. 8CCC

Table 6

| | | | | | | | | | | | | | | | | | | | | | | |
|---|---|---|---|---|---|---|---|---|---|---|---|---|---|---|---|---|---|---|---|---|---|---|
| 655(A | 2464 | 791 | -2155 | -1787 | -166 | -1514 | -1500 | -1408 | 1386 | -1595 | | -1309 | -672 | -1424 | -1982 | -1405 | -1732 | 688 | -624 | -473 | -1963 | -1596 | 677 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | * | * | | | | | | | | | | | | |
| 656(G | -2594 | -2690 | -3304 | -3623 | 2835 | -4328 | 3747 | -3462 | -4761 | -3953 | | -4671 | -4212 | -3320 | -3352 | -3748 | -3779 | -2839 | -2981 | -4004 | -3668 | -4222 | 678 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 657(T | -457 | -1344 | 1397 | -166 | -1749 | -1438 | 424 | -1324 | -173 | | -1546 | -757 | -384 | -1663 | -77 | -623 | 628 | 1799 | 847 | -1920 | -1372 | 679 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 658(E | -1108 | -1855 | 497 | 2835 | -2161 | -1834 | 982 | 964 | -783 | | -1744 | -1237 | -739 | -2163 | -677 | -1197 | -1164 | -1148 | 1427 | -2502 | -1927 | 680 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 659(P | -853 | -1252 | -2460 | -2393 | -1784 | -2139 | -2109 | 974 | -2210 | | -1748 | -1364 | -1924 | 3453 | -2108 | -2271 | -1167 | -1152 | 1448 | -2678 | -2307 | 681 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 660(T | -495 | -998 | -1197 | 789 | -1334 | -1567 | 751 | -851 | -618 | | -1153 | 2261 | 892 | -1849 | -564 | -910 | -695 | 2581 | -648 | -1684 | -1235 | 682 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 661(Q | -425 | -1001 | 831 | 629 | 1174 | -1595 | 316 | -637 | -152 | | 579 | -150 | -476 | -1677 | 1648 | -532 | -563 | 735 | -470 | -1354 | -875 | 683 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 662(E | -2641 | -3308 | 896 | 3732 | -3966 | -2458 | -2043 | -4105 | -2128 | | -4016 | -3555 | -1531 | -2959 | -1842 | -2560 | -2479 | -2750 | -3722 | -3563 | -3385 | 684 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 663(I) | 525 | -535 | -2111 | -1551 | -638 | -1888 | 920 | 1560 | -1309 | | -455 | 170 | -1362 | -2031 | -1084 | -1399 | 1061 | 708 | 1332 | -1134 | -763 | 685 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 664(M | -2362 | -1913 | -4673 | -4086 | -501 | 4285 | 3077 | 1692 | -3808 | | 2336 | 2939 | -3933 | -3746 | -2955 | -3477 | -3510 | -2250 | -300 | -2098 | -2139 | 686 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 665(A | 2734 | -1554 | -1235 | -966 | -2607 | -1620 | -1015 | -2163 | 1487 | | -2343 | -1601 | -988 | -2045 | -691 | -583 | -903 | -969 | -1725 | -2578 | -2168 | 687 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |
| 666(A | 3438 | -1472 | -2846 | -3040 | -3287 | -1726 | -2735 | -2840 | -3028 | | -3257 | -2662 | -2236 | -2447 | -2798 | -2944 | -1216 | -1387 | -2183 | 3405 | -3320 | 688 |
| | -149 | -500 | 233 | 43 | -381 | -1115 | 399 | 106 | -626 | 210 | * | -466 | -720 | 275 | 394 | 45 | 96 | 359 | 117 | -369 | -294 | -249 |
| | -16 | -7108 | -8150 | -894 | | -1115 | -701 | -1378 | | | | | | | | | | | | | | |

FIG. 8DDD

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1394 | * | -1378 | * | | | | | | | | | | |
| 667(I) | 1114 | -756 | -2253 | -1864 | -1305 | -1646 | 2517 | -626 | -1656 | 210 | -1054 | -466 | -461 | -720 | -1512 | 275 | -2066 | 394 | -1454 | 45 | -1761 96 | 1262 359 | -650 117 | -138 -369 | -1806 -294 | -1439 -249 | 689 |
| | -16 | -149 | -500 | 43 | -381 | -399 | -701 | | -626 | | | | | | | | | | | | | | | | | | |
| | -16 | -7108 | -8150 | -894 | -1115 | -701 | -1378 | | | | | | | | | | | | | | | | | | | | |
| 668D | 900 | -2457 | 2570 | 175 | -2815 | -1502 | -2590 | -626 | -386 | 210 | -2564 | -466 | -1737 | -720 | -168 | 275 | -1841 | 394 | 2095 | 45 | -969 96 | -821 359 | -1001 117 | -2141 -369 | -2768 -294 | -2010 -249 | 690 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 669(I) | 292 | -707 | -2167 | -1590 | -719 | -2180 | -1027 | -626 | 537 | 210 | 441 | -466 | 146 | -720 | -1486 | 275 | -2230 | 394 | -1118 | 45 | -1321 96 | -1247 359 | -668 117 | 405 -369 | -1287 -294 | -917 -249 | 691 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 670L | -2871 | -2457 | -4231 | -4103 | -1033 | -3803 | -3165 | -626 | -3734 | 210 | 3130 | -466 | -31 | -720 | -3935 | 275 | -3797 | 394 | -3286 | 45 | -3484 96 | -3713 359 | -2869 117 | -1136 -369 | -2394 -294 | -2220 -249 | 692 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 671(H) | -1177 | -2326 | -1134 | -457 | -2809 | -1977 | 3593 | -626 | 1445 | 210 | -2244 | -466 | -1443 | -720 | 844 | 275 | -2024 | 394 | 111 | 45 | 1735 96 | -1061 359 | -1033 117 | -2058 -369 | -2268 -294 | -1857 -249 | 693 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 672E | 15 | -2170 | 1563 | 1959 | -2472 | -1425 | -226 | -626 | 855 | 210 | -2177 | -466 | -1280 | -720 | -49 | 275 | -1617 | 394 | 1268 | 45 | -431 96 | -502 359 | -609 117 | -1785 -369 | -2349 -294 | -1631 -249 | 694 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 673H | -403 | -1628 | -358 | 195 | -1861 | -1414 | 1618 | -626 | 320 | 210 | -279 | -466 | 1074 | -720 | 912 | 275 | -1503 | 394 | 1197 | 45 | 1139 96 | 446 359 | -340 117 | -1203 -369 | -1863 -294 | -1247 -249 | 695 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 674C | -513 | -500 | -2600 | 2019 | 2246 | 845 | 943 | -626 | -1680 | 210 | -244 | -466 | 350 | -720 | -1605 | 275 | -2090 | 394 | -1357 | 45 | -1587 96 | -1083 359 | -488 117 | 249 -369 | -881 -294 | -474 -249 | 696 |
| | -340 | -7108 | -2304 | -894 | -381 | -399 | -701 | | | | | | | | | | | | | | | | | | | | |
| | -20 | -6788 | -7830 | -894 | -1115 | -1306 | -747 | | | | | | | | | | | | | | | | | | | | |
| 675P | -2312 | -2374 | -2796 | -3036 | -3591 | -2432 | -2883 | -626 | -3157 | 210 | -3835 | -466 | -3473 | -720 | -2848 | 275 | -3596 | 394 | -3101 | 45 | -3072 96 | -2546 359 | -2648 117 | -3391 -369 | -3143 -294 | -3459 -249 | 697 |
| | -149 | -500 | 43 | -381 | -399 | -1306 | | | | | | | | | | | | | | | | | | | | | |
| | -20 | -6788 | -7830 | -894 | -1115 | -421 | -1984 | | | | | | | | | | | | | | | | | | | | |
| 676E | -985 | -2607 | 1546 | 2542 | -2883 | -1323 | -441 | -626 | -378 | 210 | -2634 | -466 | -1828 | -720 | 58 | 275 | -1713 | 394 | -60 | 45 | -1032 96 | 869 359 | -997 117 | -2229 -369 | -2828 -294 | -1997 -249 | 698 |
| | -149 | -500 | 43 | -381 | -399 | -421 | | | | | | | | | | | | | | | | | | | | | |
| | -16 | -7108 | -8150 | -894 | -1115 | -701 | -1378 | | | | | | | | | | | | | | | | | | | | |
| 677L | -2103 | -1693 | -4449 | -3873 | -568 | -4003 | -2874 | -626 | -3596 | 210 | 2406 | -466 | 2166 | -720 | -3648 | 275 | -3596 | 394 | -2862 | 45 | -3318 96 | -3203 359 | -2010 117 | 674 -369 | -2059 -294 | -2029 -249 | 699 |
| | -16 | -149 | -500 | 43 | -381 | -399 | -701 | | | | | | | | | | | | | | | | | | | | |
| | -16 | -7108 | -8150 | -894 | -1115 | -701 | -1378 | | | | | | | | | | | | | | | | | | | | |
| 678K | -2059 | -2767 | -2575 | -1375 | -3583 | -2596 | -2947 | -626 | -558 | 106 | -2620 | -466 | -1947 | -720 | -1295 | 275 | -2560 | 394 | -141 | 45 | 2026 96 | -1942 359 | -1766 117 | -2709 -369 | -2469 -294 | -2350 -249 | 700 |
| | -149 | -500 | 43 | -381 | -399 | -701 | | | | | | | | | | | | | | | | | | | | | |

FIG. 8EEE

Table 6

FIG. 8FFF

Table 6

| | | | | | | | | | | | | | | | | | | | | |
|---|---|---|---|---|---|---|---|---|---|---|---|---|---|---|---|---|---|---|---|---|
| 691(Q | -506 | -7108 | -8150 | -894 | -1115 | -701 | -1378 | * | | -1856 | 1294 | -116 | -1554 | 1790 | 1511 | -401 | -435 | -1488 | -2030 | -1407 | 713 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 692() | -30 | 439 | 11 | 363 | -394 | -739 | 699 | -1890 | 436 | -757 | 501 | 286 | -577 | 639 | 165 | -23 | 111 | -312 | 697 | -25 | 714 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 693(N | 911 | -1243 | -1049 | -908 | -2750 | -1283 | -1224 | 414 | 463 | -2619 | -1762 | 2307 | -1836 | -911 | -1451 | 2263 | -707 | -1785 | -2854 | -2361 | 715 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 694(E | 462 | -1884 | 883 | 1229 | -2200 | -1380 | 99 | -2483 | -1070 | -1912 | -1007 | -31 | 1086 | 347 | -229 | 391 | 628 | -1510 | -2102 | -1423 | 716 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 695(K | 472 | -1945 | 816 | 942 | -2258 | 507 | 83 | -2010 | 1429 | -1957 | -1042 | -12 | -1504 | 1244 | -204 | -340 | -412 | -1564 | -2129 | -1439 | 717 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 696(K | 725 | -1680 | -306 | 1306 | 355 | -1399 | -79 | -1941 | 284 | -1633 | -1007 | -73 | -1499 | 350 | -177 | 548 | -349 | -1268 | -1917 | -1284 | 718 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -195 | -7108 | -3069 | -894 | -1115 | -701 | -1378 | * | | | | | | | | | | | | | |
| 697(H | -1103 | -2714 | 2043 | 320 | -2881 | -1429 | 2588 | -2787 | -470 | -2720 | -1925 | 2549 | -1819 | -164 | -1109 | -872 | -1112 | -2328 | -2864 | -2024 | 719 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -6931 | -7973 | -894 | -1115 | -1083 | -922 | * | | | | | | | | | | | | | |
| 698(P | -1509 | -2622 | 2222 | -258 | -3351 | -1688 | -1206 | -3299 | -1351 | -3294 | -2623 | -586 | 3242 | -916 | -1988 | -1364 | -1649 | -2782 | -3270 | -2663 | 720 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -6931 | -7973 | -894 | -1115 | -505 | -1760 | * | | | | | | | | | | | | | |
| 699(H | -601 | -1891 | -436 | 1733 | -2050 | -1535 | 2121 | -1882 | 387 | -1862 | -1003 | -192 | -1631 | 281 | 1501 | -502 | -527 | -1509 | -1978 | 1072 | 721 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 700(G | 2344 | -1041 | -2392 | -2527 | -3249 | 2572 | -2371 | -2970 | -2636 | -3255 | -2405 | -1721 | -2031 | -2309 | -2645 | -661 | -858 | -2002 | -3433 | -3246 | 722 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 701(L | -2642 | -2168 | -4788 | -4235 | 465 | -4513 | -3241 | 96 | -3878 | 2891 | 2122 | -4166 | -3888 | -3023 | -3544 | -3807 | -2521 | -607 | -2140 | -2183 | 723 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 702(S) | -532 | -1511 | -753 | -320 | -2262 | -1447 | -524 | -1930 | 1366 | -2008 | -1173 | -494 | -1732 | -137 | -413 | 1983 | 1524 | -1495 | -2248 | -1710 | 724 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |

FIG. 8GGG

Table 6

| | | | | | | | | | | | | | | | | | | | | | |
|---|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | | |
| 703(D) | -1718 | -3250 | 3403 | -27 | -3066 | -1736 | 2667 | -3486 | -1211 | -3381 | -2732 | -400 | -2240 | -752 | -1917 | -1439 | -1784 | -3023 | -3204 | -2299 | 725 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 704(E) | 1165 | -2746 | 1435 | 2588 | -3046 | -1525 | -639 | -2845 | -567 | -2796 | -1988 | -154 | -1909 | -258 | -1213 | -943 | -1174 | -2380 | -2996 | -2179 | 726 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 705(E) | 921 | -2774 | 1237 | 2767 | -3077 | -1530 | -662 | -2877 | -603 | -2830 | -2029 | 161 | -1924 | -284 | -1256 | -967 | -1205 | -2412 | -3032 | -2209 | 727 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 706(F) | -3342 | -2776 | -4026 | -4232 | 4354 | -3545 | -1431 | -2315 | -4038 | -1801 | -1900 | -3299 | -3780 | -3350 | -3645 | -3490 | -3420 | -2566 | -739 | 349 | 728 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 707(D) | 1198 | -2653 | 2928 | 116 | -3164 | -1523 | -794 | -2975 | -806 | -2952 | -2173 | 1307 | -1973 | -435 | -1474 | -1014 | -1273 | -2473 | -3161 | -2340 | 729 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 708(N) | 497 | -2045 | 1492 | 265 | -2357 | -1412 | 1608 | -2108 | 128 | -2074 | -1183 | 1928 | -1592 | 229 | -403 | 517 | -553 | -1673 | -2265 | -1565 | 730 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 709(Y) | -1550 | -1282 | -3519 | -3004 | -2 | -3093 | -1385 | 1232 | -2635 | 1579 | 299 | -2537 | -2990 | -2153 | -2464 | -2220 | -1477 | -195 | -891 | 3290 | 731 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 710(F) | -3342 | -2776 | -4026 | -4232 | 4354 | -3545 | -1431 | -2315 | -4038 | -1801 | -1900 | -3299 | -3780 | -3350 | -3645 | -3490 | -3420 | -2566 | -739 | 349 | 732 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 711(T) | -1213 | -1674 | -2755 | -2906 | -3163 | -1922 | -2659 | -2698 | -2788 | -3105 | -2612 | -2311 | -2600 | -2708 | -2753 | -1463 | 3819 | -2197 | -3286 | -3156 | 733 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 712(K) | 921 | -1810 | -280 | 1204 | -2126 | -1422 | -125 | -1835 | 1451 | -1838 | -956 | -97 | -1544 | 311 | -168 | -386 | 1295 | -1438 | -2048 | -1407 | 734 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 713(D) | -2784 | -3432 | 4016 | -1200 | -4140 | -2466 | -2197 | -4505 | -2621 | -4365 | -3956 | -1551 | -3014 | -2039 | -3232 | -2593 | -2938 | -4046 | -3710 | -3552 | 735 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | | |
| 714(K) | -1441 | -2413 | -1657 | -802 | -3025 | -2193 | 410 | -2523 | 2846 | -2335 | -1581 | -885 | -2213 | 14 | 1863 | -1343 | 790 | -2218 | -2320 | -2022 | 736 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 8HHH

Table 6

FIG. 8III

Table 6

| | | | | | | | | | | | | | | | | |
|---|---|---|---|---|---|---|---|---|---|---|---|---|---|---|---|---|
| | -16 | -7108 | -8150 | -894 | -1115 | -701 | -1378 | * | | | | | | | | |
| 727(I) | -1755 | -1312 | -4289 | -3853 | -1390 | -3961 | -3331 | -3677 | 2559 | -1378 | 1028 | -208 | -3600 | -3736 | -3367 | -3647 | -3222 | -1724 | 2382 | -2488 | 749 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 728(Q) | -1019 | -664 | 1508 | -2732 | -1794 | -307 | -2378 | 502 | -626 | * | -2248 | -1420 | -437 | -1902 | 2305 | 2189 | 887 | -914 | -1997 | -1812 | 750 |
| | -149 | -500 | 233 | 43 | -381 | 399 | 106 | 210 | | | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 729(G) | 676 | -1581 | 1006 | -319 | -2686 | 1982 | 822 | -639 | -2430 | -626 | -2491 | -1630 | -507 | -1785 | -454 | -1135 | 1417 | -738 | -1837 | -2108 | 751 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 730(L) | -2364 | -1901 | -4660 | -4144 | -630 | -4349 | -3246 | -3856 | 2015 | -626 | 2597 | 544 | -4006 | -3841 | -3101 | -3583 | -3629 | -2275 | 2 | -2227 | 752 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 731(F) | -2056 | -1668 | -4299 | -3752 | 3006 | -3840 | -2396 | -3446 | 1861 | -626 | 1502 | 554 | -3415 | -3499 | -2733 | -3168 | -3023 | -1964 | -161 | -1259 | 753 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 732(F) | -3581 | -2688 | -4165 | -4401 | 3865 | -4034 | 401 | -3981 | -2491 | -626 | -1903 | -1944 | -2746 | -3921 | -2847 | -3438 | -3284 | -3462 | -2647 | 341 | 3054 | 754 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 733(D) | -1066 | -2664 | 2593 | 230 | -2949 | 899 | -545 | 996 | -2751 | -626 | -2680 | -1846 | 1209 | -1852 | -148 | -1001 | -857 | -1060 | -2284 | -2068 | 755 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 734(R) | -2957 | -3022 | -3318 | -2735 | -3796 | -2998 | -1968 | -3912 | -846 | -626 | -3631 | -3157 | -2611 | -3280 | -1724 | 4056 | -3026 | -2913 | -3650 | -3185 | 756 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 735(H) | 673 | -1400 | -855 | -643 | -2108 | -1470 | 3344 | -596 | -1923 | -626 | -2073 | -1302 | -744 | 2404 | -583 | -931 | -699 | -761 | -1503 | -2291 | -1733 | 757 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 736(N) | -1426 | -2353 | -948 | -735 | -2920 | -1991 | -796 | 68 | -2769 | -626 | -2666 | -1942 | 3441 | -2268 | -432 | 1742 | -1361 | -1415 | -2383 | -2592 | -2147 | 758 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 737(H) | -1168 | -1729 | -1567 | -889 | -1360 | -2118 | 3917 | 284 | -1446 | -626 | 543 | 865 | -957 | -2175 | -247 | 1258 | -1239 | -1055 | -1304 | -1577 | -976 | 759 |
| | -149 | -500 | 233 | 43 | -381 | 399 | 106 | 210 | -626 | * | -466 | -720 | 275 | 394 | 45 | 96 | 359 | 117 | -369 | -294 | -249 |
| | -16 | -7108 | -8150 | -894 | -1115 | -701 | -1378 | * | | | | | | | | |
| 738(D) | -1353 | -3032 | 2615 | 202 | -3188 | -1564 | 2079 | -756 | -3118 | -626 | -3034 | -2267 | 2486 | -1998 | -383 | -1443 | -1092 | -1377 | -2642 | -3178 | -2294 | 760 |
| | -149 | -500 | 233 | 43 | -381 | 399 | 106 | 210 | -626 | * | -466 | -720 | 275 | 394 | 45 | 96 | 359 | 117 | -369 | -294 | -249 |

FIG. 8JJJ

Table 6

| | | | | | | | | | | | | | | | | | | |
|---|---|---|---|---|---|---|---|---|---|---|---|---|---|---|---|---|---|---|
| | -812 | -7108 | -1241 | -894 | -1115 | -701 | -1378 | * | | | | | | | | | | |
| 739(N) | -667 | -1675 | -384 | -20 | -2103 | -1394 | -82 | -1850 | 715 | -1813 | -1049 | 2293 | -1591 | 303 | 2121 | -603 | -621 | -1504 | -1871 | -1383 | 761 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -27 | -6323 | -7365 | -894 | -1115 | -292 | -2448 | * | * | | | | | | | | | | | | |
| 740(F) | 1835 | -719 | -3036 | -2438 | 1835 | -2475 | -1354 | 332 | -2101 | 1627 | 473 | -2059 | -2472 | -1719 | -1973 | -1574 | -844 | 1081 | -1167 | -839 | 762 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 741(H) | 501 | -1345 | -519 | 3 | -1474 | -1478 | 2277 | -1148 | 102 | -1306 | -513 | 945 | -1582 | 159 | -343 | -433 | 1418 | -890 | -1646 | 876 | 763 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 742(V) | -1752 | -1297 | -4324 | -3962 | -1768 | -4045 | -3742 | 2459 | -3833 | -621 | -545 | -3722 | -3873 | -3691 | -3909 | -3362 | -1744 | 2956 | -3271 | -2823 | 764 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 743(O) | -30 | 439 | 11 | 363 | 394 | -739 | 699 | -414 | 463 | -757 | 501 | 286 | -577 | 639 | 165 | -23 | 111 | -312 | 697 | -25 | 765 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 744(H) | -991 | -1830 | -1052 | -504 | -1930 | -1886 | 3890 | -1681 | 1542 | -1767 | -1038 | -666 | -1989 | -60 | 176 | -985 | -903 | 206 | -1921 | -1408 | 766 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 745(G) | -494 | -1130 | -1974 | -2194 | -3326 | -2287 | -3191 | -3000 | -2529 | -3407 | -2546 | -1609 | -2055 | -2198 | -2601 | -2479 | -923 | -2148 | -3486 | -3235 | 767 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 746(Y) | -3482 | -2868 | -3701 | -3919 | 1238 | -3552 | 3228 | -1112 | -3638 | -2516 | -2526 | -3027 | -3772 | -3101 | -3341 | -3418 | -3527 | -3071 | -3486 | 4711 | 768 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 747(R) | -1317 | -2448 | -1232 | 1501 | -3004 | -2062 | -362 | -2555 | 2088 | -2353 | -1567 | -710 | -2107 | 70 | 2409 | -1189 | -1156 | -2213 | -2342 | -1973 | 769 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 748(E) | -2641 | -3308 | -896 | 3722 | -3966 | -2458 | -2043 | -4105 | -2128 | -4016 | -3555 | -1531 | -2959 | -1842 | -2560 | -2479 | -2750 | -3722 | -3563 | -3385 | 770 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 749(E) | -603 | -2088 | 932 | 1740 | -2382 | -1414 | -194 | -2138 | 145 | -2093 | -1197 | 1660 | -1589 | 1157 | -389 | 462 | -556 | 226 | -2276 | -1569 | 771 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -16 | -7108 | -8150 | -894 | -1115 | -701 | -1378 | * | | | | | | | | | | | | |
| 750(G) | -2594 | -2690 | -3304 | -3623 | -4328 | 3747 | -3462 | -4761 | -3953 | -4671 | -4212 | -3320 | -3352 | -3748 | -3779 | -2839 | -2981 | -4004 | -3668 | -4222 | 772 |
| | | -149 | -500 | 233 | 43 | -381 | 399 | 106 | -626 | 210 | -466 | -720 | 275 | 394 | 45 | 96 | 359 | 117 | -369 | -294 | -249 |

FIG. 8KKK

Table 6

| | | | | | | | | | | | | | | | | | | |
|---|---|---|---|---|---|---|---|---|---|---|---|---|---|---|---|---|---|---|
| | | | | | | | | | | | | | | | | | | |
| | -16 | -7108 | -8150 | -894 | -1115 | -701 | -1378 | * | | | | | | | | | | |
| 751(D) | -1242 | -2482 | 2856 | 92 | -3324 | -1544 | -1056 | -3220 | -1180 | -3222 | -2479 | -411 | -2078 | -735 | -1856 | 2119 | -1401 | -2625 | -3370 | -2572 | 773
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 752(I) | -1125 | -1077 | -3099 | -2749 | -1383 | -2564 | -2209 | 2720 | -2446 | -620 | -388 | -2395 | -2828 | -2300 | -2481 | -1819 | 2258 | 661 | -2292 | -1909 | 774
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 753(T) | -1213 | -1674 | -2755 | -2906 | -3163 | -1922 | -2659 | -2698 | -2788 | -3105 | -2612 | -2311 | -2600 | -2708 | -2753 | -1463 | 3819 | -2197 | -3286 | -3156 | 775
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 754(T) | -1213 | -1674 | -2755 | -2906 | -3163 | -1922 | -2659 | -2698 | -2788 | -3105 | -2612 | -2311 | -2600 | -2708 | -2753 | -1463 | 3819 | -2197 | -3286 | -3156 | 776
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 755(P) | -2931 | -2878 | -3420 | -3706 | -4181 | -2925 | -3468 | -4621 | -3859 | -4490 | -4165 | -3491 | 4225 | -3781 | -3695 | -3182 | -3279 | -4087 | -3594 | -4064 | 777
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 756(F) | -3533 | -2667 | -4143 | -4362 | 4034 | -4011 | -413 | -2435 | -3947 | -1856 | -1895 | -2743 | -3904 | -2837 | -3418 | -3264 | -3419 | -2596 | -3286 | 2564 | 778
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 757(D) | -2784 | 3432 | 4016 | -1200 | -4140 | -2466 | -2197 | -4505 | -2621 | -4365 | -3956 | -1551 | -3014 | -2039 | -3232 | -2593 | -2938 | -4046 | 327 | -3552 | 779
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 758(M) | -1664 | -1479 | -3731 | -3304 | -822 | -3209 | -2514 | 381 | -2903 | 307 | 4447 | -2987 | -3235 | -2579 | -2815 | -2469 | -1688 | 1155 | -2108 | -1854 | 780
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 759(R) | -841 | -995 | -1971 | -1321 | -932 | -2129 | -856 | -136 | -533 | -467 | 2304 | -1291 | -2194 | -758 | 2401 | -1211 | -783 | 1416 | -1446 | -1079 | 781
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 760(V) | -954 | -2489 | -1863 | -806 | -2402 | -1212 | 292 | -1157 | 906 | 98 | -1725 | -2437 | -1258 | 1435 | -1506 | -901 | 2327 | -1472 | -1115 | 782
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 761(V) | -1831 | -1468 | -4142 | -3585 | -674 | -3694 | -2641 | 526 | -3292 | 1920 | 2093 | -3318 | -3425 | -2728 | -3099 | -2876 | -1760 | 2327 | -2028 | -1893 | 783
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | |
| 762(N) | -2171 | -2655 | -1458 | -1748 | -3334 | -2364 | -2267 | -3943 | -2365 | -3936 | -3437 | 4205 | -2932 | -2205 | -2608 | -2224 | -2439 | -3392 | -3253 | -2909 | 784
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8LLL

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 763(E) | -447 | -1916 | 638 | -2239 | -1385 | 1510 | -1986 | 1083 | -1928 | -1009 | -19 | -1493 | 1244 | 466 | -323 | -386 | -1540 | -2092 | -1413 | 785 |
| | -149 | -500 | 233 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 764(M) | -1749 | -1382 | -4134 | 1762 | -706 | -3632 | -2595 | -3291 | 1705 | 2738 | -3271 | -3384 | -2732 | -3086 | -2809 | -1680 | 1590 | 2012 | -1860 | 786 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 765(D) | -1369 | -2674 | 3374 | -58 | 3453 | -1571 | -1095 | -1289 | -3368 | -2659 | -394 | -2124 | -784 | -2016 | 1149 | -1529 | -2785 | -3505 | -2662 | 787 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 766(R) | -2957 | -3022 | -3318 | -2735 | -3796 | -2998 | 1968 | -3912 | 846 | -3368 | -2611 | -3280 | -1724 | 4056 | -3026 | -2913 | -3650 | -3096 | -3185 | 788 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 767(Y) | -3616 | -2704 | -4178 | 4426 | 3471 | -4049 | -394 | -2531 | -4004 | -3631 | -1934 | -2749 | -3932 | -3451 | -3298 | -3493 | -2683 | 349 | 3677 | 789 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 768(H) | 274 | -2294 | 1079 | 1119 | -2578 | -1451 | 3282 | -2348 | -50 | -2296 | -1419 | 1227 | -1687 | 101 | -610 | -606 | -736 | -1901 | -2481 | -1745 | 790 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 769(L) | -2092 | -1719 | -4323 | -3846 | -712 | -3925 | -2989 | 451 | -3531 | 2641 | 428 | -3624 | -3640 | -2952 | -3339 | -3191 | -2044 | -2221 | -2096 | 791 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 770(A) | 2058 | -944 | -1182 | -683 | -813 | -1304 | -1522 | -653 | -528 | -1127 | -414 | -754 | -897 | -2102 | -378 | -860 | -602 | 852 | 724 | -1630 | -1185 | 792 |
| | -149 | -500 | 233 | 43 | -381 | 399 | 106 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 771(K) | 1238 | -1887 | -1224 | 1094 | -2786 | -1805 | -755 | 3008 | -2384 | -2335 | -1637 | -1028 | 32 | -2539 | -48 | -228 | -1055 | -1089 | -1935 | -2512 | -2122 | 793 |
| | -149 | -500 | 233 | 43 | -381 | 399 | 106 | 210 | -466 | -720 | 275 | 394 | 45 | 96 | 359 | 117 | -369 | -294 | -249 |
| | -169 | -7108 | -3273 | -894 | -1115 | -701 | -1378 | * | | | | | | | | | | | |
| 772(A) | 1327 | -1917 | 950 | -2220 | -1330 | -74 | -1968 | -2749 | -1930 | -2405 | -2021 | -1480 | -2697 | -2272 | 547 | 411 | -1533 | -2115 | -1424 | 794 |
| | -149 | -500 | 233 | -381 | 399 | 106 | 210 | -466 | -720 | 275 | 394 | 45 | 96 | 359 | 117 | -369 | -294 | -249 |
| | -17 | -6956 | -7998 | -894 | -1115 | -1036 | -964 | | | | | | | | | | | | |
| 773(A) | 3386 | -1299 | -2601 | -2766 | -3046 | -1559 | -2499 | -2281 | -2990 | -2553 | -2749 | -2777 | -2272 | -2269 | -1037 | -1201 | -1940 | -3200 | -3073 | 795 |
| | -149 | -500 | 233 | -381 | 399 | 106 | 210 | -466 | -720 | 275 | 394 | 45 | 96 | 359 | 117 | -369 | -294 | -249 |
| | -17 | -6956 | -7998 | -894 | -1115 | -525 | -1714 | | | | | | | | | | | | |
| 774(I) | 1087 | 861 | -3107 | 161 | 882 | -2803 | 1771 | 2342 | 78 | -2300 | -2009 | 1091 | 547 | -1916 | -1039 | 1702 | -1691 | -1345 | 796 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8MMM

Table 6

| | | | | | | | | | | | | | | | | | |
|---|---|---|---|---|---|---|---|---|---|---|---|---|---|---|---|---|---|
| -16 | -7108 | -8150 | -894 | -1115 | -701 | | | -1378 | * | | | | | | | | |
| 775(Q) | 375 | -1755 | -273 | 815 | -2036 | -1376 | -39 | -1756 | 367 | -1753 | -857 | 1007 | -1469 | 1244 | 843 | -290 | 959 | 12 | -1964 | -1309 | 797 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | | * | | | | | | | | | |
| 776(M) | 1052 | -610 | -1546 | 994 | -696 | 582 | -640 | -244 | -804 | 810 | 1789 | -967 | -1833 | -639 | -1021 | 395 | -384 | -113 | -1120 | -726 | 798 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | | * | | | | | | | | | |
| 777(I) | -416 | -776 | -1113 | 474 | -802 | 469 | -424 | 1231 | -400 | 255 | 48 | -674 | -1747 | 951 | -718 | -659 | -357 | 665 | -1177 | -745 | 799 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | | * | | | | | | | | | |
| 778(D) | 1034 | -2035 | 2294 | -106 | -2869 | -1459 | -830 | -2614 | -751 | -2671 | -1863 | -387 | 2260 | -474 | -1320 | -825 | -1014 | -2092 | -2906 | -2215 | 800 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | | * | | | | | | | | | |
| 779(A) | 1299 | -1548 | -409 | 909 | -1800 | 43 | -141 | -1467 | 231 | -1558 | -718 | -156 | -1540 | 264 | 1153 | -374 | -369 | 158 | -1848 | -1253 | 801 |
| | -1040 | -7108 | -981 | -894 | -1115 | -701 | -1378 | | * | | | | | | | | | |
| 780(F) | -585 | -915 | -883 | 659 | 2573 | -1541 | -52 | -591 | -624 | -695 | -233 | 1803 | -1767 | -468 | -869 | -739 | -609 | -487 | -70 | 917 | 802 |
| | -424 | -6099 | -2060 | -894 | -1115 | -1914 | -445 | | | -466 | -720 | 275 | 394 | 45 | 96 | 359 | 117 | -369 | -294 | -249 |
| 781(N) | 313 | -1042 | 254 | 152 | -1409 | -814 | -286 | -1511 | -122 | -1692 | -1083 | 156 | -1287 | -82 | -434 | -340 | -474 | -1140 | -1574 | -976 | 803 |
| | -41 | -5717 | -6759 | -894 | -1115 | -2091 | -386 | | | -466 | -720 | 275 | 394 | 45 | 96 | 359 | 117 | -369 | -294 | -249 |
| 782(E) | -647 | 589 | 2680 | -1901 | -941 | -188 | -1630 | 4 | -1762 | -1176 | 156 | -1345 | 101 | -395 | -544 | -693 | -1348 | -1863 | -1374 | 804 |
| | -149 | -500 | 233 | 43 | -381 | 399 | 106 | -626 | 210 | -466 | -720 | 275 | 394 | 45 | 96 | 359 | 117 | -369 | -294 | -249 |
| | -41 | -5717 | -6759 | -894 | -1115 | -2091 | -386 | | | | | | | | | | | |
| 783(K) | -682 | -1365 | -434 | -118 | -1773 | -1231 | -19 | -1449 | 2744 | -1499 | -893 | -244 | -1470 | 310 | 740 | -670 | -643 | -1208 | -1538 | -1198 | 805 |
| | -41 | -5717 | -6759 | -894 | -1115 | -612 | -1532 | | | -466 | -720 | 275 | 394 | 45 | 96 | 359 | 117 | -369 | -294 | -249 |
| 784(Y) | -620 | -433 | -2763 | -2164 | -265 | -2214 | -1076 | 1484 | -1822 | 144 | 2036 | -1779 | -2223 | -1475 | -1707 | -1306 | -562 | 1635 | -935 | 2216 | 806 |
| | -149 | -500 | 233 | 43 | -381 | 399 | 106 | -626 | 210 | -466 | -720 | 275 | 394 | 45 | 96 | 359 | 117 | -369 | -294 | -249 |
| | -20 | -6788 | -7830 | -894 | -1115 | -1306 | -747 | | | | | | | | | | | |
| 785(K) | -540 | -1908 | -286 | 1554 | -2271 | 235 | -21 | -1969 | 1597 | -1892 | -1016 | -65 | -1527 | 423 | 1275 | -418 | -461 | -1559 | -2023 | -1427 | 807 |
| | -149 | -500 | 233 | 43 | -381 | 399 | 106 | -626 | 210 | -466 | -720 | 275 | 394 | 45 | 96 | 359 | 117 | -369 | -294 | -249 |
| | -20 | -6788 | -7830 | -894 | -1115 | -421 | -1984 | | | | | | | | | | | |
| 786(D) | -495 | -1834 | 1772 | 243 | -2095 | -1409 | -135 | -1811 | 226 | 93 | -952 | 959 | -1543 | 1255 | -279 | -392 | 713 | -1426 | -2056 | -1398 | 808 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8NNN

Table 6

| | | | | | | | | | | | | | | | | | | |
|---|---|---|---|---|---|---|---|---|---|---|---|---|---|---|---|---|---|---|
| -16 | -7108 | -8150 | -894 | -1115 | -701 | -1378 | * | | | | | | | | | | | |
| 787(K | -1474 | -2433 | -1703 | -833 | -3058 | -2216 | 418 | -2547 | 2890 | -2352 | -1602 | -908 | -2233 | 6 | 1874 | -1375 | 633 | -2246 | -2329 | -2042 | 809 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 788(H | -451 | -1596 | -374 | 131 | -1721 | 4 | 2032 | -1490 | 223 | -1570 | -735 | -150 | -1554 | 1294 | -242 | 993 | -394 | -1170 | -1803 | 1657 | 810 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 789(A | 2417 | -1302 | -925 | -642 | -2356 | -1358 | -885 | -2038 | -600 | -2179 | -1358 | -718 | -1792 | 1772 | -969 | 686 | -646 | -1531 | -2461 | -1952 | 811 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 790(E | 1699 | -2217 | 1896 | 1966 | -3018 | -1521 | -628 | -2814 | -547 | -2768 | -1958 | -152 | -1900 | -245 | -1190 | -928 | -1153 | -2352 | -2970 | -2159 | 812 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 791(F) | -576 | -843 | -1351 | 18 | 2111 | -1835 | -543 | -341 | 927 | 1121 | 58 | -880 | -1903 | -468 | -730 | -859 | -511 | -255 | -1145 | -680 | 813 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 792(C | -1112 | -3476 | -2950 | -1103 | -2900 | 2026 | -2659 | -523 | -2556 | -143 | -2914 | -2378 | -2583 | -2056 | 623 | 2331 | -1900 | -1524 | 814 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 793(Q | 419 | -1959 | 511 | 264 | -2287 | -1397 | -160 | -2033 | 201 | -2001 | -1102 | 892 | -1555 | 2127 | -318 | 1297 | -485 | -1597 | -2190 | -1503 | 815 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 794() | -30 | 439 | 111 | 363 | -394 | -739 | 699 | -414 | 463 | -757 | 501 | 286 | -577 | 639 | 165 | -23 | 111 | -312 | 697 | -25 | 816 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 795(E | -617 | -2049 | -177 | 2132 | -2369 | -1467 | 1606 | -2104 | 1334 | -2049 | -1159 | -104 | -1611 | 267 | -171 | 468 | -558 | -1677 | -2212 | -1550 | 817 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 796(M | -2288 | -1880 | -4481 | -3899 | 1874 | -1463 | 2287 | -4066 | -3594 | 1748 | -3656 | -3608 | -2775 | -3272 | -3259 | -2174 | -566 | -1778 | -1555 | 818 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 797(D | -194 | -2847 | 2837 | 1238 | -3100 | -1527 | -634 | -2920 | -571 | -2845 | -2036 | 1124 | -1913 | -251 | -1231 | -958 | 827 | -2447 | -3037 | -2200 | 819 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7108 | -8150 | -894 | -1115 | -701 | -1378 | * | | | | | | | | | | | |
| 798(H | -831 | -2392 | 1999 | 980 | -2678 | -1463 | 2287 | -2459 | 551 | -2391 | -1516 | 1798 | -1718 | 62 | -667 | -653 | -799 | -2000 | -2566 | -1815 | 820 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 8000

Table 6

| | | | | | | | | | | | | | | | | | | | | |
|---|---|---|---|---|---|---|---|---|---|---|---|---|---|---|---|---|---|---|---|---|
| | -16 | -7108 | -8150 | -894 | -1115 | -701 | -1378 | * | | | | | | | | | | | | |
| 799(M) | -496 | -1070 | -899 | -350 | 1464 | -1648 | -334 | 1384 | -934 | 2286 | 1246 | -1730 | -100 | -455 | -629 | -434 | -548 | -1346 | -826 | 821 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 800(I) | -1200 | -1080 | -2894 | -2252 | -618 | -2712 | -1476 | -1547 | 1701 | 361 | -2078 | -2664 | -1554 | 1445 | -1820 | -1129 | 84 | -1503 | -1217 | 822 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 801(Q) | 1195 | -1999 | 1275 | 287 | -2307 | -1399 | -132 | 888 | -2010 | -1104 | 1022 | -1544 | 1594 | -271 | -396 | -475 | -1616 | -2187 | -1494 | 823 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 802(E) | -464 | -1834 | -313 | 1601 | -2133 | -1426 | -72 | 1475 | -301 | -936 | -76 | -1522 | 1237 | -64 | -359 | 488 | -1446 | -2019 | -1377 | 824 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 803(H) | 1285 | -1168 | -1100 | -753 | -1895 | -1421 | 3671 | -616 | -1783 | -1019 | -796 | -1815 | -585 | -942 | -599 | 1325 | -1196 | -2122 | -1628 | 825 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 804(H) | -457 | -1111 | -796 | -240 | 1415 | -1595 | 1499 | -56 | -1014 | -275 | 1464 | -1677 | -16 | 1113 | -558 | -395 | 539 | -1363 | -816 | 826 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 805(Q) | 961 | -1898 | 742 | 284 | -2209 | -1388 | 1553 | 1291 | -1907 | -995 | -26 | -1499 | 1771 | -144 | -331 | -392 | -1516 | -2082 | -1407 | 827 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 806(Y) | -3616 | -2706 | -4170 | -4415 | 2670 | -4045 | -396 | -3994 | -1940 | -1985 | -2748 | -3931 | -2852 | -3447 | -3296 | -3495 | -2687 | 347 | 4234 | 828 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 807(I) | 1201 | -821 | -2746 | -2313 | -1223 | -2126 | -1705 | -2058 | -749 | -304 | -1944 | -2428 | -1844 | -2105 | -1330 | 893 | 505 | -1890 | -1524 | 829 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 808(R) | -841 | -995 | -1971 | -1321 | -932 | -2129 | -856 | -533 | -467 | 2304 | -1291 | -2194 | -758 | 2401 | -1211 | -783 | 1416 | -1446 | -1079 | 830 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 809(D) | -1157 | -2811 | 2313 | 1149 | 3071 | -1519 | -606 | -523 | -2811 | -1992 | 1715 | -1893 | -218 | -1175 | 1334 | -1159 | -2414 | -2998 | -2166 | 831 |
| | -149 | -500 | 233 | 43 | -381 | 399 | 106 | 210 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 810(N) | 377 | -1890 | -201 | 941 | -2201 | -1398 | -93 | 1328 | -1904 | -1001 | 1972 | -1518 | 353 | -173 | -356 | 594 | -1511 | -2089 | -1420 | 832 |
| | -149 | -500 | 233 | 43 | -381 | 399 | 106 | 210 | -466 | -720 | 275 | 394 | 45 | 96 | 359 | 117 | -369 | -294 | -249 | |

FIG. 8PPPP

Table 6

| | | | | | | | | | | | | | | | | | | | |
|---|---|---|---|---|---|---|---|---|---|---|---|---|---|---|---|---|---|---|---|
| 811G | -16 | -7108 | -8150 | -894 | -1501 | -2131 | -1258 | -1392 | -2600 | -1115 | -701 | -1378 | * | -1608 | -3233 | -466 | -3219 | -626 | -2576 | -1477 | -2541 | -1589 | -1850 | -1578 | -1737 | -2674 | -2756 | -2168 | 833 |
| | -149 | -500 | 233 | 43 | -894 | | | -381 | | -1115 | | | | 210 | | | | | 394 | 275 | 45 | 96 | 359 | 117 | -369 | -294 | -249 | |
| 812Y | 385 | -1523 | -449 | 96 | -1722 | -1461 | 2851 | -1378 | * | 959 | -1486 | -175 | 1557 | -186 | -399 | 1250 | -1083 | -1786 | 1631 | 834 |
| | -149 | -500 | 233 | 43 | -894 | -381 | 399 | 106 | -626 | 210 | -466 | 275 | 45 | 96 | 359 | 117 | -369 | -294 | -249 | |
| 813D | -2784 | -3432 | 4016 | -1200 | -4140 | -2466 | -2197 | -4505 | -2621 | -4365 | -1551 | -3014 | -3232 | -2593 | -2938 | -4046 | -3710 | -3552 | 835 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 814L | -587 | -625 | -1931 | -1364 | -454 | -1983 | 1655 | 818 | -1068 | 1666 | -1268 | 955 | -903 | -1182 | -1033 | -529 | 21 | -1001 | -599 | 836 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 815P | -1667 | -2676 | -329 | 1564 | -3405 | -1913 | -1351 | -3268 | -1273 | -3276 | -852 | -2612 | -1736 | -1555 | -1787 | -2810 | -3275 | -2761 | 837 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 816E | -1715 | -3562 | 2447 | 2878 | -3759 | -1632 | -991 | -3691 | -1235 | -3569 | -235 | -2910 | -2166 | -2079 | -1378 | -1784 | -3173 | -3732 | -2750 | 838 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 817V | -537 | -374 | -2717 | -2103 | 914 | -2090 | -949 | 1111 | -1742 | -147 | -1675 | -2132 | 443 | -1608 | -1398 | -663 | 1109 | 1932 | -845 | 1322 | 839 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 818T | 442 | -1699 | -325 | 943 | -1942 | -1425 | 95 | -1640 | 311 | -816 | 906 | -1525 | 330 | 784 | -363 | 1592 | -1283 | -1922 | 1369 | 840 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 819D | -1684 | -3395 | 2909 | 109 | -3677 | -1635 | -1030 | -3669 | -1283 | -3567 | 2851 | -2912 | -2178 | -713 | -1377 | -2110 | -1776 | -3137 | -3688 | -2726 | 841 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 820I | -2023 | -1815 | -3480 | -3119 | 26 | -3133 | -1280 | -780 | -2462 | -329 | -2604 | -3188 | 2687 | -2350 | -2462 | -2264 | -2001 | -1067 | 5349 | 158 | 842 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 821Q | -408 | -1655 | -342 | 851 | -1897 | -1411 | -76 | -1588 | 323 | -1635 | -87 | -770 | 785 | 1202 | 869 | -334 | 619 | 752 | -1887 | -1265 | 843 |
| | -16 | -149 | -500 | 233 | 43 | -894 | -381 | 399 | 106 | -1378 | -626 | 210 | -466 | 275 | 394 | 45 | 96 | 359 | 117 | -369 | -294 | -249 | |
| 822I | -2077 | -1892 | -3023 | -2742 | 805 | -3065 | 450 | -1653 | -2397 | -1546 | -2106 | -3118 | -1977 | -2345 | 1002 | -2038 | -1614 | 2862 | 4785 | 844 |
| | -149 | -500 | 233 | -381 | 399 | 106 | -1378 | -626 | 210 | -466 | 275 | 394 | 45 | 96 | 359 | 117 | -369 | -294 | -249 | |

Table 6

| | | | | | | | | | | | | | | | | | | | | |
|---|---|---|---|---|---|---|---|---|---|---|---|---|---|---|---|---|---|---|---|---|
| 835(A | -38 | 2597 | -5845 | -6888 | -1033 | -1004 | -894 | -1499 | -1115 | -618 | -2039 | -950 | -402 | -768 | -626 | -944 | * | -1290 | -466 | -669 | 275 | -1235 | 394 | -852 | 45 | -1081 | 96 | -19 | 359 | -107 | 117 | -412 | -369 | -1828 | -294 | -1482 | -249 | 857 |
| 836(T | 93 | -414 | -500 | -5845 | -954 | -868 | 43 | -894 | -1353 | -1115 | -741 | 399 | 106 | -402 | -616 | -626 | -701 | 210 | -1116 | -466 | -643 | 275 | -1304 | 394 | -696 | 45 | -854 | 96 | -136 | 359 | 2822 | 117 | -336 | -369 | -1700 | -294 | -1317 | -249 | 858 |
| 837(A | 2597 | -149 | -500 | -5845 | -1033 | -1004 | 43 | -894 | -1499 | -1115 | -618 | 399 | -2039 | 106 | -402 | -768 | -626 | -944 | 210 | -1290 | -466 | -669 | 275 | -1235 | 394 | -852 | 45 | -1081 | 96 | -19 | 359 | -107 | 117 | -412 | -369 | -1828 | -294 | -1482 | -249 | 859 |
| 838(A | -38 | -149 | -500 | -5845 | -1033 | -1004 | 43 | -894 | -1499 | -1115 | -618 | 399 | -2039 | 106 | -402 | -768 | -626 | -944 | 210 | -1290 | -466 | -669 | 275 | -1235 | 394 | -852 | 45 | -1081 | 96 | -19 | 359 | -107 | 117 | -412 | -369 | -1828 | -294 | -1482 | -249 | 860 |
| 839(T | 93 | -414 | -500 | -5845 | -954 | -868 | 43 | -894 | -1353 | -1115 | -741 | 399 | 106 | -402 | -616 | -626 | -701 | 210 | -1116 | -466 | -643 | 275 | -1304 | 394 | -696 | 45 | -854 | 96 | -136 | 359 | 2822 | 117 | -336 | -369 | -1700 | -294 | -1317 | -249 | 861 |
| 840(A | -38 | -149 | -500 | -5845 | -1033 | -1004 | 43 | -894 | -1499 | -1115 | -618 | 399 | -2039 | 106 | -402 | -768 | -626 | -944 | 210 | -1290 | -466 | -669 | 275 | -1235 | 394 | -852 | 45 | -1081 | 96 | -19 | 359 | -107 | 117 | -412 | -369 | -1828 | -294 | -1482 | -249 | 862 |
| 841(G | -461 | -838 | -500 | -5845 | -976 | -1119 | 43 | -894 | -2120 | -1115 | 3148 | 399 | -2039 | -1219 | 106 | -402 | -2101 | -626 | -1326 | 210 | -2273 | -466 | -986 | 275 | -1505 | 394 | -1212 | 45 | -1430 | 96 | -653 | 359 | -781 | 117 | -1558 | -369 | -1923 | -294 | -1928 | -249 | 863 |
| 842(D | -878 | -1818 | 3239 | -500 | -5845 | 428 | 43 | -894 | -2222 | -1115 | -381 | 972 | 399 | -2039 | -438 | 106 | -402 | -2180 | -626 | -575 | 210 | -2276 | -466 | -1711 | 95 | 275 | -1458 | 394 | -189 | 45 | -1148 | 96 | -733 | 359 | -456 | 117 | -979 | -1822 | -369 | -2152 | -294 | -1652 | -249 | 864 |
| 843(N | -431 | -1158 | 164 | -500 | 47 | -1545 | -381 | -1115 | 43 | -894 | -910 | 106 | -402 | -407 | 399 | -2039 | -1680 | -626 | -257 | 210 | -1848 | -466 | -1242 | -720 | 65 | 275 | -1391 | 394 | -9 | 45 | -570 | 96 | -456 | 359 | -599 | 117 | -1296 | -369 | -1696 | -294 | -1106 | -249 | 865 |
| 844(E | -771 | -1700 | 518 | -500 | 2837 | -2056 | -381 | -1115 | 43 | -894 | -1033 | 106 | -402 | -298 | 399 | -238 | -1811 | -626 | -123 | 210 | -1925 | -466 | -1338 | -720 | -1445 | 394 | -2716 | 275 | -207 | 45 | -532 | 96 | -658 | 359 | -819 | 117 | -1519 | -369 | -1994 | -294 | -1511 | -249 | 866 |
| 845() | -30 | 439 | 11 | -5845 | 363 | -394 | * | -894 | * | -1115 | -739 | * | 699 | * | -402 | -414 | * | 463 | * | 0 | -757 | 501 | * | 286 | * | 577 | * | 639 | * | 165 | * | -23 | * | 111 | * | -312 | * | 697 | * | -25 | * | 867 |

FIG. 8SSS

Table 7

TABLE 7

```
HMMER2.0 [2.3.2]
NAME XFP N
ACC PF09364.1
DESC XFP N-terminal domain
LENG 396
ALPH Amino
RF no
CS no
MAP yes
COM hmmbuild -f -F HMM fs.ann SEED.ann
COM hmmcalibrate --seed 0 HMM fs.ann
NSEQ 6
DATE Thu May 3 17:57:17 2007
CKSUM 7893
GA 15.1 15.1
TC 15.1 15.1
NC 14.6 14.6
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -10.948357 0.672333
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -93 | * | -3000 | | | | | | | | | | | | | | | | | | |
| 1(K) | -1968 | -2951 | -2155 | -1320 | -3390 | -2747 | -966 | -3007 | 2330 | -2844 | -2086 | -1422 | 2165 | -549 | 1590 | -1872 | -1791 | -2712 | -2821 | 1937 | 1 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -1193 | -9626 | | | | | | | | | | | | |
| 2(I) | -1769 | -1476 | -4090 | -3550 | -1526 | -3579 | -2618 | 2387 | -3249 | 1441 | -544 | 1396 | -3532 | -2933 | -3155 | -2723 | -1726 | 1550 | -2406 | -2063 | 2 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9624 | | | | | | | | | | | | |
| 3(S) | -1378 | -2318 | 1402 | -1145 | -3726 | -2032 | -1821 | -3503 | -1805 | -3583 | -2748 | -1309 | -2587 | -1497 | -2321 | 2452 | 2280 | -2794 | -3796 | -3178 | 3 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9622 | | | | | | | | | | | | |
| 4(D) | -2415 | -4334 | 2560 | 2263 | -4523 | -2295 | -1677 | -4467 | -1966 | -4327 | -3682 | -889 | 2279 | -1352 | -2856 | -2064 | -2494 | -3929 | -4515 | -3478 | 4 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9620 | | | | | | | | | | | | |
| 5(E) | 818 | -2294 | -768 | 2387 | -2689 | -1890 | -629 | -2403 | -181 | -2389 | -1504 | -596 | -2035 | -193 | 1173 | -879 | 979 | -1984 | -2580 | -1944 | 5 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9618 | | | | | | | | | | | | |
| 6(Y) | 868 | -2568 | -747 | 2575 | -2297 | -2202 | -1201 | -2582 | -1098 | -2680 | -1956 | -1001 | -2523 | -938 | -1573 | -1484 | -1571 | -2270 | -2610 | 2844 | 6 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9617 | | | | | | | | | | | | |

FIG. 9A

Table 7

| | | | | | | | | | | | | | | | | | | | | | | | |
|---|---|---|---|---|---|---|---|---|---|---|---|---|---|---|---|---|---|---|---|---|---|---|---|
| 7(L) | -2772 | -2280 | -5308 | -4845 | -1620 | -5006 | -4218 | 1675 | -4673 | 2505 | -404 | -4676 | -4560 | -4047 | -4494 | -4304 | -2713 | 1658 | -3269 | -3192 | 7 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9615 | | | | | | | | | | | |
| 8(H) | 899 | -2380 | -623 | 1169 | -2703 | -1834 | 2073 | 2447 | 1918 | -2389 | -1478 | 1301 | -1952 | -64 | -563 | -794 | -860 | -2005 | -2553 | -1878 | 8 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9613 | | | | | | | | | | | |
| 9(K) | -1161 | -2683 | 1251 | -212 | -2990 | 727 | -723 | -2756 | 1972 | -2690 | -1794 | 1663 | -2115 | 1586 | -911 | -1006 | -1116 | -2301 | -2857 | -2139 | 9 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9611 | | | | | | | | | | | |
| 10(M) | 2709 | -2269 | -5162 | -4623 | -1349 | -4724 | -3702 | 1512 | -4374 | 1792 | 3396 | -4390 | -4320 | -3675 | -4116 | -3951 | -2630 | 1553 | -2866 | -2812 | 10 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9609 | | | | | | | | | | | |
| 11(H) | -2820 | -4339 | 3411 | 925 | -4078 | -2615 | -4807 | -2416 | -4617 | -4088 | -3181 | -1308 | -1809 | -3221 | -2491 | -2928 | -4293 | -3302 | 11 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9607 | | | | | | | | | | | |
| 12(K) | 1531 | -2609 | -1521 | -881 | -3185 | 677 | -855 | -2809 | 2197 | -2705 | 1875 | -1069 | -2428 | -423 | 1698 | -1376 | -1380 | -2418 | -2783 | -2320 | 12 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9605 | | | | | | | | | | | |
| 13(Y) | -4639 | -3574 | -5042 | -5388 | 3053 | -4919 | -1116 | -3531 | -4943 | -2851 | -2938 | -3536 | -4775 | -3673 | -4311 | -4166 | -4491 | 3684 | 3607 | 3791 | 13 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9604 | | | | | | | | | | | |
| 14(W) | -3826 | -3700 | -3776 | -3690 | -1600 | -3954 | -2357 | -4085 | -2609 | -3642 | -3464 | -3450 | -4249 | -2584 | 2161 | -3864 | -4045 | -3853 | 14 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9602 | | | | | | | | | | | |
| 15(R) | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | 5840 | -4649 | 15 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9600 | | | | | | | | | | | |
| 16(A) | 3208 | -1704 | -3999 | -4070 | -3276 | -2242 | -3400 | -1516 | -3824 | -2767 | -2340 | -2844 | -2960 | -3485 | -3660 | -1604 | -1654 | 1301 | -3916 | -3651 | 16 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9598 | | | | | | | | | | | |
| 17(C) | 3231 | -4290 | -4524 | -4051 | -2061 | -3603 | -4177 | -3558 | -4038 | -3241 | -2842 | -2850 | -3725 | -3864 | -1443 | -1636 | -2656 | -4310 | -4227 | 17 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9596 | | | | | | | | | | | |
| 18(N) | -2093 | -3624 | 1842 | -565 | -4191 | -2225 | -1624 | -4071 | -1786 | -4008 | -3287 | 3436 | -2749 | -1290 | -2544 | -1859 | 1312 | -3511 | -3291 | 18 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9594 | | | | | | | | | | | |
| 19(Y) | -4605 | -3570 | -5021 | -5357 | 2115 | -4893 | -1140 | -3492 | -4921 | -2816 | -2906 | -3546 | -4765 | -3679 | -4305 | -4160 | -4468 | -3656 | -389 | 4545 | 19 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | | | | | | | | | | | | |

FIG. 9B

Table 7

| | | | | | | | | | | | | | | | | | | | |
|---|---|---|---|---|---|---|---|---|---|---|---|---|---|---|---|---|---|---|---|
| -11 | -7944 | -8986 | -894 | -1115 | -701 | -1378 | -9818 | -9592 | | | | | | | | | | | |
| 20(L) | -3485 | -2916 | -5860 | -5269 | -1134 | -4270 | 1416 | -5040 | 2720 | 2646 | -5288 | -4721 | -3890 | -4562 | -4907 | -3336 | -1219 | -2912 | -3094 | 20 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9591 | | | | | | | | | | | |
| 21(A) | 2093 | -1633 | -3496 | -3406 | -3943 | 1228 | -3043 | -3705 | -3256 | -3935 | -2418 | -2652 | -2942 | -3281 | 2007 | 1343 | -2649 | -4148 | -3944 | 21 |
| | -149 | -500 | 233 | 43 | -381 | 399 | 106 | -626 | 210 | -466 | 275 | 394 | 45 | 96 | 359 | 117 | -369 | -294 | -249 |
| | -11 | -7944 | -8986 | -894 | -1115 | -701 | -1378 | -9818 | -9589 | | | | | | | | | | | |
| 22(I) | 1858 | -1782 | -4736 | -4347 | -2337 | -4240 | -3903 | 2415 | -4179 | -1341 | -4002 | -4207 | -4002 | -4206 | -3513 | -2172 | 2258 | -3603 | -3167 | 22 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9587 | | | | | | | | | | | |
| 23(G) | -1257 | -1874 | -3207 | -3523 | -4341 | 3341 | -3408 | -4248 | -3853 | -4463 | -3557 | -2605 | -2866 | -3760 | 1410 | -1718 | -3031 | -4475 | -4358 | 23 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9585 | | | | | | | | | | | |
| 24(M) | -2521 | -2386 | -3846 | -3279 | -1155 | -3984 | -2657 | -686 | -2594 | 1335 | -3250 | -3784 | -3402 | -4206 | -3140 | -2428 | -1237 | -2461 | -2296 | 24 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9583 | | | | | | | | | | | |
| 25(I) | -2891 | -2390 | 5370 | -4957 | -1628 | -5096 | -4334 | 3554 | -4751 | 1008 | -437 | -4806 | -4650 | -4141 | -4574 | -4462 | -2842 | -63 | -3311 | -3180 | 25 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9581 | | | | | | | | | | | |
| 26(Y) | -4614 | -3571 | -5028 | -5366 | 3123 | -4901 | -1136 | -3497 | -4929 | -2819 | -2909 | -3545 | -3679 | -4308 | -4163 | -4474 | -3661 | -384 | 4150 | 26 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9579 | | | | | | | | | | | |
| 27(L) | -4119 | -3542 | -5389 | -5357 | -2027 | -4767 | -4358 | -1609 | -5118 | 3293 | 979 | -5230 | -4771 | -4768 | -4724 | -5069 | -4106 | -2331 | -3412 | -3400 | 27 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9577 | | | | | | | | | | | |
| 28(R) | -1752 | -2663 | -1994 | -1206 | -3071 | -2612 | -927 | -2620 | 1567 | 1194 | -1815 | -1326 | -523 | 2318 | 1048 | -1606 | -2354 | -2690 | -2328 | 28 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9576 | | | | | | | | | | | |
| 29(D) | -2163 | -3991 | 2853 | 1466 | -4198 | -2225 | -1494 | -4086 | -1627 | -3968 | -2710 | -1142 | -2410 | 971 | -2206 | -4159 | -3203 | 29 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9574 | | | | | | | | | | | |
| 30(N) | -2100 | -2812 | -1725 | -2071 | -4541 | 1400 | -2845 | -4689 | -3101 | 4717 | 3995 | 3948 | -3237 | -3854 | -2675 | -3479 | -2189 | -2459 | -3750 | -4448 | 30 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9572 | | | | | | | | | | | |
| 31(P) | -2845 | -2996 | -4029 | -4118 | -2821 | -3470 | -3585 | -2547 | -3827 | 1069 | -2145 | -3734 | -3778 | -3737 | -3186 | -3115 | -2756 | -3564 | -3278 | 31 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9570 | | | | | | | | | | | |

FIG. 9C

Table 7

| | | | | | | | | | | | | | | | | | |
|---|---|---|---|---|---|---|---|---|---|---|---|---|---|---|---|---|---|
| 32(L) | -3571 | -3027 | -4990 | -4839 | -362 | -4751 | -2053 | -1386 | -4381 | 2878 | -762 | -3969 | -4502 | -3586 | -4013 | -4093 | -3476 | -1986 | -1288 | 2490 | 32 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9568 | | | | | | | | | | |
| 33(M) | -2211 | -1924 | -4481 | -3865 | 1786 | -3872 | -2670 | -469 | -3517 | 2158 | 2560 | -3505 | -3670 | -2910 | -3263 | -3004 | -1361 | -903 | -2139 | -1963 | 33 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -464 | -894 | -1115 | -701 | -1378 | -9818 | -9566 | | | | | | | | | | |
| 34(S) | 87 | -526 | -885 | -918 | -1797 | -699 | -997 | -1679 | -970 | -1948 | -1267 | -663 | -1335 | -874 | -1147 | -2826 | -252 | -1082 | -2036 | -1577 | 34 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -34 | -6087 | -7129 | -894 | -1115 | -2832 | -701 | -1378 | -9818 | -9564 | | | | | | | | | | |
| 35(V) | -734 | -692 | -2391 | -2193 | -909 | -2005 | -1781 | 1094 | -1922 | -136 | -10 | -1902 | -2325 | -1852 | -1974 | -1413 | -858 | 2960 | -1857 | -1405 | 35 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -34 | -6087 | -7129 | -894 | -1115 | -2832 | -218 | -1378 | -9818 | -9562 | | | | | | | | | | |
| 36(T) | -84 | -586 | -1220 | -1166 | 1618 | -901 | -1090 | -915 | -1004 | -1405 | -917 | -886 | -1488 | -90 | -1134 | -317 | 3114 | -605 | -1941 | -1587 | 36 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -34 | -6087 | -7129 | -894 | -1115 | -133 | -701 | -1378 | -9818 | -9560 | | | | | | | | | | |
| 37(R) | -2583 | -3338 | -2968 | -1938 | -4226 | 2024 | -1216 | -3597 | 1648 | -3282 | -2594 | -1884 | -3156 | -798 | -2123 | -2479 | -2242 | -3324 | -3144 | -3007 | 37 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9558 | | | | | | | | | | |
| 38(E) | -1678 | -2848 | -628 | 2969 | -1726 | -3815 | 1219 | -1598 | -1552 | -3614 | -2817 | -1072 | -2634 | -1251 | -2577 | -1592 | 1327 | -3012 | -3808 | -3091 | 38 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9557 | | | | | | | | | | |
| 39(P) | -3058 | -3915 | 1871 | -3865 | -4973 | -2986 | -2783 | -3602 | -3189 | -5075 | -4546 | -2051 | 3849 | -2577 | -3857 | -2918 | -3276 | -4561 | -4629 | -4315 | 39 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9555 | | | | | | | | | | |
| 40(L) | -3389 | -2846 | -5732 | -5157 | 1795 | -5405 | -3964 | 1554 | -4913 | 2673 | 66 | -5067 | -4642 | -3819 | -4457 | -4697 | -3249 | -1211 | -2753 | -2720 | 40 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9553 | | | | | | | | | | |
| 41(K) | -1121 | -2502 | -1004 | 1296 | -2888 | -2042 | -588 | -2583 | 2027 | -2485 | -1598 | -681 | -2119 | 1586 | 1299 | -1000 | 1054 | -2164 | -2595 | -2010 | 41 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9551 | | | | | | | | | | |
| 42(P) | 784 | -2052 | -818 | 1262 | -2296 | -1869 | -546 | -1970 | -134 | -107 | -1190 | -567 | 1773 | -132 | 1208 | -813 | -814 | -1637 | -2305 | -1705 | 42 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9549 | | | | | | | | | | |
| 43(E) | -2121 | -3903 | 1652 | 3001 | -4126 | -2231 | -1448 | -3991 | 1462 | -3872 | -3127 | -825 | -2693 | -1089 | -2171 | -1828 | -2151 | -3493 | -4045 | -3137 | 43 |
| | | -149 | -500 | 233 | 43 | -381 | 399 | 106 | 210 | -466 | -466 | -720 | 275 | 394 | 45 | 96 | 359 | 117 | -369 | -294 | -249 |
| | | -11 | -1891 | -7944 | -8986 | -894 | -1115 | -701 | -1378 | -9818 | -9547 | | | | | | | | | | |
| 44(H) | -1900 | -3602 | 2493 | -392 | -3825 | -2165 | 3314 | -3680 | -1250 | -3583 | -2790 | 1715 | -2572 | 1675 | -1911 | -1645 | -1910 | -3197 | -3754 | -2893 | 44 |
| | | -149 | -500 | 233 | 43 | -381 | 399 | 106 | 210 | -466 | -466 | -720 | 275 | 394 | 45 | 96 | 359 | 117 | -369 | -294 | -249 |

FIG. 9D

Table 7

| | | | | | | | | | | | | | | | |
|---|---|---|---|---|---|---|---|---|---|---|---|---|---|---|---|
| -11 | -7944 | -8986 | -894 | -1115 | -701 | -1378 | -9818 | -9545 | | | | | | | |
| 45(I) | -2547 | -2059 | 5152 | 4751 | -2029 | -4889 | -4388 | -4626 | 1616 | -797 | -4548 | -4567 | -4264 | 4595 | -4202 | -2516 | 2260 | -3637 | -3383 | 45 |
| | -149 | -500 | 233 | 43 | -381 | 399 | 106 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9543 | | | | | | | | | | | |
| 46(K) | -4125 | -4091 | -4017 | -3615 | -5101 | -3960 | -2958 | -5182 | 3972 | -4345 | -3552 | -4249 | -2709 | -1809 | -4154 | -4044 | 4895 | -4132 | -4389 | 46 |
| | -149 | -500 | 233 | 43 | -381 | 399 | 106 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9541 | | | | | | | | | | | |
| 47(H) | 826 | -2035 | -963 | -419 | -2397 | -1898 | 3051 | -206 | -2073 | -2136 | -675 | 932 | -235 | 1162 | -866 | 1249 | -1718 | -2394 | -1810 | 47 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9539 | | | | | | | | | | | |
| 48(R) | -2700 | -3449 | -3065 | -1955 | -4296 | -3222 | -1177 | -3628 | 1592 | -3280 | 1619 | -3187 | -756 | 3400 | -2568 | -2401 | -3384 | -3125 | -3003 | 48 |
| | -149 | -500 | 233 | 43 | -381 | 399 | 106 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9537 | | | | | | | | | | | |
| 49(L) | -2172 | -1972 | -4362 | -3884 | -1289 | -3737 | -2942 | -312 | -3536 | 2565 | -217 | -3515 | 1361 | -3084 | -3377 | -2952 | 1219 | -2509 | -2319 | 49 |
| | -149 | -500 | 233 | 43 | -381 | 399 | 106 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9535 | | | | | | | | | | | |
| 50(V) | -2641 | -2155 | -5210 | -4776 | -1803 | -4918 | -4261 | 1765 | -4623 | 2179 | -584 | -4583 | -4545 | -4128 | -4515 | -2597 | 2215 | -3420 | -3258 | 50 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9533 | | | | | | | | | | | |
| 51(G) | -4088 | -3924 | -4774 | -5139 | -5615 | 3825 | -4753 | -5932 | -5453 | -6014 | -5662 | -5436 | -3187 | -4539 | -4696 | -4620 | -4352 | -5527 | -4696 | -5561 | 51 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9531 | | | | | | | | | | | |
| 52(H) | -4275 | -4356 | -4629 | -5722 | -3663 | -4242 | 5422 | -4492 | -5318 | -5298 | -4812 | -4579 | -4812 | -5232 | -4938 | -4696 | -5005 | -5648 | -3750 | -3259 | 52 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9529 | | | | | | | | | | | |
| 53(W) | -5598 | -4432 | -5385 | -5139 | -3380 | -4524 | -4140 | -5643 | -6303 | -5436 | -5427 | -4696 | -4539 | -5474 | -5106 | -5178 | -5909 | -5751 | -5890 | 6275 | -2993 | 53 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9527 | | | | | | | | | | | |
| 54(G) | -4088 | -3924 | -4774 | -5139 | -5615 | 3825 | -4753 | -5453 | -6303 | -5662 | -4812 | -4539 | -5232 | -5106 | -4370 | -4472 | -5527 | -4696 | -5561 | 54 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9526 | | | | | | | | | | | |
| 55(T) | -1093 | -1706 | -3487 | -3693 | -4074 | -1966 | -3302 | -3638 | -3842 | -4134 | -3253 | -2558 | -2748 | -3296 | -3520 | 1110 | 3646 | -2760 | -4304 | -4125 | 55 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9524 | | | | | | | | | | | |
| 56(C) | -1052 | 2901 | -3250 | -2679 | 1060 | -2526 | -1634 | 1315 | -2341 | -866 | -266 | -2229 | -2670 | -2018 | -2238 | 1521 | 1154 | 1349 | -1596 | -1246 | 56 |
| | -149 | -500 | 233 | 43 | -381 | 399 | 106 | 210 | -626 | -720 | 275 | 394 | 45 | 96 | 359 | 117 | -369 | -294 | -249 | |
| | -11 | -7944 | -8986 | -894 | -1115 | -701 | -1378 | -9818 | -9522 | | | | | | | | | | | |

FIG. 9E

Table 7

FIG. 9F

| | | | | | | | | | | | | | | | | | | | | |
|---|---|---|---|---|---|---|---|---|---|---|---|---|---|---|---|---|---|---|---|---|
| 57(P) | -1362 | -1972 | -3107 | -3390 | -4250 | -2166 | -3327 | -4213 | -3641 | -4411 | -3553 | -2613 | 3840 | -3308 | -3600 | 1256 | -1811 | -3082 | -4372 | -4198 | 57 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9520 | | | | | | | | | | | |
| 58(G) | -4088 | 3924 | 4774 | -5139 | -5615 | 3825 | 4753 | -6303 | -5453 | -6014 | -5662 | -4812 | -4539 | -5232 | -5106 | -4370 | -4472 | -5527 | -4696 | -5561 | 58 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9518 | | | | | | | | | | | |
| 59(Q) | -2629 | -2340 | -4433 | -3873 | -1140 | -4292 | -3047 | 1389 | -3342 | 2319 | -20 | -3746 | -4000 | 2559 | -3238 | -3469 | -2536 | -946 | -2531 | -2422 | 59 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9516 | | | | | | | | | | | |
| 60(S) | -1129 | -1869 | -2034 | -2027 | -3771 | -1956 | -2322 | -3546 | -2277 | -3697 | -2821 | 2528 | -2607 | -2062 | -2583 | 2544 | 1447 | -2665 | -3893 | 3470 | 60 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9514 | | | | | | | | | | | |
| 61(F) | -3253 | -2755 | -5063 | -4895 | 3979 | -2230 | -4679 | 1673 | -4579 | -697 | -843 | -4029 | -4483 | -3735 | -4216 | -4008 | -3205 | -1123 | -1463 | -453 | 61 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9512 | | | | | | | | | | | |
| 62(I) | -2667 | -2178 | -5235 | -4799 | -1779 | 4947 | -4278 | 2326 | -4646 | 2166 | -559 | -4613 | -4558 | -4130 | -4529 | -4251 | -2621 | 1716 | -3410 | -3264 | 62 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9510 | | | | | | | | | | | |
| 63(Y) | -4030 | -3324 | -4830 | -4953 | 82 | -4664 | -1400 | -2548 | -4444 | 776 | -2024 | -3603 | -4588 | -3589 | -4024 | -4010 | -3953 | -2880 | -668 | 4492 | 63 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9508 | | | | | | | | | | | |
| 64(A) | -1624 | -3741 | -3790 | -3997 | -1911 | -3253 | -3736 | -3609 | -4009 | -5436 | -5298 | -2541 | -4696 | -3231 | -3506 | 1407 | 1356 | -2665 | -4233 | -4079 | 64 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9506 | | | | | | | | | | | |
| 65(H) | -4836 | -4275 | -4356 | -4629 | -3663 | -4242 | 5422 | -5932 | -4492 | 1928 | -237 | -2799 | -3137 | -2685 | -4352 | -5005 | -5030 | -5648 | -3750 | -3259 | 65 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9504 | | | | | | | | | | | |
| 66(C) | 868 | 2955 | -3843 | -3261 | -1152 | -2129 | 1511 | -5568 | -2905 | -5460 | 4378 | -3117 | -4185 | -3865 | -2739 | -2241 | -1449 | -4 | -1921 | -1610 | 66 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9502 | | | | | | | | | | | |
| 67(N) | -3642 | -3838 | -3004 | -3356 | -4743 | -3612 | -3773 | -5643 | -4099 | -5152 | -4748 | -4156 | -4479 | -3286 | -4225 | -3744 | -3950 | -5002 | -4391 | -4381 | 67 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9500 | | | | | | | | | | | |
| 68(R) | -4488 | -4181 | -4789 | -4318 | -5193 | -4148 | -3436 | -5568 | -2393 | -5152 | -4748 | -4156 | -4479 | -3286 | -4202 | -4614 | -4467 | -5273 | -4267 | -4649 | 68 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | | -8986 | -894 | -1115 | -701 | -1378 | -9818 | -9498 | | | | | | | | | | | |
| 69(I) | 687 | -1693 | -4550 | -4054 | -1797 | -4053 | -3239 | 2451 | 3802 | 1595 | -714 | -3702 | -3939 | -3479 | -3713 | -3246 | -2027 | 1554 | -2897 | -2565 | 69 |
| | -149 | -500 | 233 | 43 | -381 | 399 | 106 | -626 | 210 | -466 | -720 | 275 | 394 | 45 | 96 | 359 | 117 | -369 | -294 | -249 | |

Table 7

| | | | | | | | | | | | | | | | | | | | | | |
|---|---|---|---|---|---|---|---|---|---|---|---|---|---|---|---|---|---|---|---|---|---|
| | -7944 | -8986 | -894 | -1115 | -701 | -1378 | -9818 | -9496 | | | | | | | | | | | | | |
| 70(I) | -3202 | -2787 | -4996 | -2836 | -4384 | -4440 | -4838 | | -1815 | -4704 | -4600 | -4683 | -4704 | -4353 | -3280 | -603 | -3938 | -3661 | 70 |
| | -149 | -500 | 43 | -381 | 399 | 106 | 210 | | -466 | 275 | 394 | 45 | 96 | 359 | 117 | -369 | -294 | -249 | |
| | -11 | -7944 | -8986 | -894 | -1115 | -701 | -1378 | | -9818 | -9494 | | | | | | | | | |
| 71(N) | 777 | -2760 | -1484 | -853 | -3260 | -2383 | 822 | 1407 | -2738 | -1911 | -2455 | -385 | 2206 | -1436 | -1435 | -2500 | -2791 | -2332 | 71 |
| | -149 | -500 | 43 | -381 | 399 | 106 | 210 | | -466 | -720 | 394 | 45 | 96 | 359 | 117 | -369 | -294 | -249 | |
| | -11 | -7944 | -8986 | -894 | -1115 | -701 | -1378 | | -9818 | -9492 | | | | | | | | | |
| 72(K) | -1654 | -2912 | 1393 | -667 | -3173 | -2287 | -1055 | -2863 | 286 | -2070 | -954 | -2512 | -658 | -811 | -1598 | -2533 | -3029 | -2434 | 72 |
| | -149 | -500 | 43 | -381 | 399 | 106 | 210 | | -466 | -720 | 275 | 45 | 96 | 359 | 117 | -369 | -294 | -249 | |
| | -11 | -7944 | -8986 | -894 | -1115 | -701 | -1378 | | -9818 | -9490 | | | | | | | | | |
| 73(Y) | -3965 | -3303 | -4553 | -4498 | 2089 | -4562 | 2685 | -3880 | -2696 | -2630 | -3283 | -4469 | -3249 | 1301 | -3756 | -3844 | -3248 | -415 | 3893 | 73 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9488 | | | | | | | | | |
| 74(D) | -2647 | -4396 | 3720 | -698 | -4634 | -2448 | -1896 | -4723 | -4559 | -3990 | -1090 | -3022 | 1848 | -3057 | -2298 | -4181 | -4595 | -3647 | 74 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9486 | | | | | | | | | |
| 75(Q) | 786 | -1836 | -2085 | -1707 | -1785 | -2491 | -1296 | -1287 | 1558 | -860 | -1741 | -2731 | 3104 | -1481 | -1664 | -1471 | -1312 | -2370 | -1975 | 75 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9484 | | | | | | | | | |
| 76(N) | -2189 | -3961 | 2351 | -476 | -4203 | -2257 | -1501 | 1323 | -4079 | -3221 | -3154 | -2736 | -1150 | -2219 | -1890 | -4120 | -3208 | 76 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9482 | | | | | | | | | |
| 77(M) | -1639 | -1552 | -3944 | 3485 | -1584 | -3112 | 2598 | -3126 | -102 | 4345 | -2996 | -3316 | -2834 | -3037 | 2326 | 1195 | 1340 | -2475 | -2167 | 77 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9480 | | | | | | | | | |
| 78(I) | -2541 | -2130 | -4989 | -4447 | 1768 | -4503 | -3473 | -4181 | 1829 | -210 | -4162 | -4181 | -3554 | -3947 | -2469 | 1402 | -2759 | -2626 | 78 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9478 | | | | | | | | | |
| 79(Y) | -4613 | -3570 | -5027 | -476 | -5365 | -4900 | -4683 | -4928 | -2818 | -2908 | -3544 | -4767 | -3678 | -4307 | -4162 | -4473 | -3660 | -383 | 4168 | 79 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9476 | | | | | | | | | |
| 80(M) | -2401 | -1938 | -4995 | -4588 | -2135 | -4683 | -4177 | -4441 | 3356 | -4340 | -4447 | -4169 | -4437 | -3971 | -2375 | 2371 | -3610 | -3272 | 80 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9474 | | | | | | | | | |
| 81(C) | -924 | 2595 | -3097 | -2552 | -1083 | 823 | -1551 | -560 | -2221 | -963 | 2359 | -2072 | -2516 | -1903 | -2136 | -963 | 739 | 2007 | -1573 | -1229 | 81 |
| | -149 | -500 | 43 | -381 | 399 | 106 | 210 | | -466 | -720 | 275 | 394 | 45 | 96 | 359 | 117 | -369 | -294 | -249 | |
| | -11 | -7944 | -8986 | -894 | -1115 | -701 | -1378 | | -9818 | -9472 | | | | | | | | | |

Table 7

| | | | | | | | | | | | | | | | | | | | | | |
|---|---|---|---|---|---|---|---|---|---|---|---|---|---|---|---|---|---|---|---|---|---|
| - | -11 | -7944 | -8986 | -894 | -1115 | -701 | -1378 | -9818 | -9445 | | | | | | | | | | | | |
| 95(Y) | -4608 | -3570 | -5023 | -5360 | 2380 | -4895 | -1138 | 3494 | -4924 | -2817 | -2907 | -3545 | -4766 | -3679 | -4306 | -4161 | -4470 | -3658 | -386 | 4475 | 95 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9443 | | | | | | | | | | | | |
| 96(L) | -3428 | -2867 | -5794 | -5267 | -1216 | -5534 | 1535 | -5028 | 2951 | -6 | -5264 | -4750 | -3972 | -4604 | -4907 | -3306 | -978 | -2993 | -3105 | 96 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9441 | | | | | | | | | | | | |
| 97(D) | -2629 | -4604 | 3026 | 2782 | -4770 | -2374 | -1828 | 4782 | -2235 | -4614 | -4052 | -973 | -2960 | -1523 | -3217 | -2241 | -2730 | -4225 | -4757 | -3689 | 97 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9439 | | | | | | | | | | | | |
| 98(G) | -2862 | -3768 | 1871 | -1615 | 5004 | 3370 | -2705 | -5181 | -3146 | -5060 | -4493 | -1931 | -3470 | -2488 | -3861 | -2740 | -3106 | -4452 | -4685 | -4318 | 98 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9437 | | | | | | | | | | | | |
| 99(T) | -1078 | 1695 | -3486 | 3659 | -4077 | -1954 | -3276 | -3853 | -3599 | -4130 | -3239 | -2539 | -2733 | -3255 | -3500 | 2681 | 2838 | -2756 | -4301 | -4124 | 99 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9435 | | | | | | | | | | | | |
| 100(Y) | -3992 | -3300 | -4836 | -4941 | 66 | -4664 | -1423 | -2456 | -4436 | 992 | -1925 | -3615 | -4579 | -3584 | -4019 | -4006 | -3913 | -2810 | -690 | 4437 | 100 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9433 | | | | | | | | | | | | |
| 101(S) | -1032 | -1663 | -3422 | -3512 | -4087 | 1390 | -3188 | -3870 | -3492 | -4107 | -3184 | -2468 | -2688 | -3124 | -3454 | 2496 | 2388 | -2740 | -4293 | -4121 | 101 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9430 | | | | | | | | | | | | |
| 102E | -1823 | -875 | 2933 | -3614 | -2362 | -1174 | -3322 | -553 | -3205 | -2407 | -1048 | 1540 | 1382 | -771 | -1665 | -1779 | -1033 | -2906 | -3277 | -2712 | 102 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9428 | | | | | | | | | | | | |
| 103(F) | 863 | -914 | -3349 | -2737 | 2502 | -2631 | -1388 | -298 | -2350 | 698 | 39 | -2234 | -2667 | -1962 | -2166 | -1719 | -1141 | -1185 | 1869 | 103 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9426 | | | | | | | | | | | | |
| 104(Y) | -4352 | -3468 | -4770 | -5008 | 2112 | -4760 | -1124 | -3396 | -4660 | -2798 | -2831 | -1505 | -4661 | -3557 | -4156 | -4005 | -4236 | -3515 | -387 | 4271 | 104 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9424 | | | | | | | | | | | | |
| 105(P) | 1085 | -2001 | -3515 | -3791 | -4319 | -2231 | -3514 | -4118 | -3884 | -4378 | -3566 | -2802 | 3892 | -3541 | -3758 | -1662 | -1872 | -3068 | -4416 | -4363 | 105 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9422 | | | | | | | | | | | | |
| 106(N) | -1628 | -3254 | 1441 | 2076 | 3527 | -2085 | -1091 | -3331 | -913 | -3246 | -2403 | 2397 | -2414 | -688 | 1516 | -1414 | -1613 | -2859 | -3417 | -2622 | 106 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9420 | | | | | | | | | | | | |

FIG. 91

Table 7

| | | | | | | | | | | | | | | | | |
|---|---|---|---|---|---|---|---|---|---|---|---|---|---|---|---|---|
| 107(I) | -1569 | 2626 | -3973 | -3416 | -1377 | -3324 | -2311 | 2751 | -3082 | -941 | -528 | -2965 | -3319 | -2753 | -2944 | -2457 | -1527 | 1473 | -2109 | 2078 | 107 |
| | -149 | -500 | 233 | 43 | 399 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9418 | | | | | | | | | | | | |
| 108(T) | 908 | -1834 | -1592 | -1168 | -2951 | -1885 | -1379 | -2651 | -1086 | -2760 | -1898 | -1245 | -2295 | 1915 | -1496 | 1739 | 2152 | -2098 | -3019 | -2494 | 108 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9416 | | | | | | | | | | | | |
| 109(M) | -879 | -2216 | -787 | 1054 | 1375 | -1857 | -485 | -2215 | 1265 | -2203 | 1871 | -512 | -1943 | 1655 | 1154 | -781 | -811 | -1824 | -2400 | -1773 | 109 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9414 | | | | | | | | | | | | |
| 110(I) | -2264 | 3415 | 3677 | -1019 | -4473 | -2407 | -2124 | -4366 | -2457 | -4415 | -3784 | -1339 | -3017 | -1850 | -3214 | -2128 | 1551 | -3724 | -4492 | -3732 | 110 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9412 | | | | | | | | | | | | |
| 111(E) | -1628 | -2756 | -1092 | 2433 | -3004 | -2358 | -986 | -2615 | 1561 | 1281 | -1850 | -1034 | -1339 | -587 | -533 | -1527 | -1543 | -2348 | -2851 | -2339 | 111 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9409 | | | | | | | | | | | | |
| 112(E) | 800 | -2932 | 1355 | 2151 | -3219 | -1985 | -890 | -3005 | -643 | -2935 | -2058 | 1450 | -2244 | 1611 | -1220 | -1179 | -1330 | -2541 | -3109 | -2350 | 112 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9407 | | | | | | | | | | | | |
| 113(G) | -4088 | -3924 | -4774 | -5139 | -5615 | 3825 | -4753 | -6303 | -5453 | -6014 | -5662 | -4812 | -4539 | -5232 | -5106 | -4370 | -4472 | 5527 | 4696 | 5561 | 113 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9405 | | | | | | | | | | | | |
| 114(M) | -3599 | -3029 | -5877 | -5316 | -1121 | -5599 | -4270 | -608 | -5016 | 2422 | 4020 | -5344 | -4752 | -3899 | -4542 | -4979 | -3452 | -1416 | -2899 | -3042 | 114 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9403 | | | | | | | | | | | | |
| 115(K) | -1165 | -2535 | -1051 | -455 | -2930 | -2079 | -612 | -2618 | 1972 | -2514 | -1633 | 1596 | -2153 | 1677 | 1320 | 873 | -1075 | -2202 | -2617 | -2045 | 115 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9401 | | | | | | | | | | | | |
| 116(K) | -2618 | -3410 | -2984 | -1883 | -4230 | -3176 | 1148 | -3580 | 2782 | -3243 | -141 | -2552 | -3140 | -725 | 2514 | -2486 | -2331 | -3326 | -3100 | -2957 | 116 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9399 | | | | | | | | | | | | |
| 117(L) | -3686 | -3083 | -5668 | -5295 | 2704 | -5391 | -3131 | -817 | -5017 | 2713 | 559 | -3345 | -3691 | -3862 | -4511 | -4763 | -3544 | -1624 | -3100 | -1439 | 117 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9397 | | | | | | | | | | | | |
| 118(F) | -2097 | 2719 | -4399 | -3936 | 3542 | -3704 | -2285 | 1698 | -3592 | -670 | -559 | -3092 | -3691 | -3092 | -3380 | -2887 | -2074 | -315 | -1780 | -1028 | 118 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9394 | | | | | | | | | | | | |
| 119(K) | -2616 | -3410 | -2980 | -1881 | -4228 | -3175 | 1148 | -3580 | 2804 | -3243 | -2552 | -2552 | -3139 | -724 | 2483 | -2484 | -2330 | -3325 | -3099 | -2957 | 119 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9394 | | | | | | | | | | | | |

FIG. 9J

Table 7

| | | | | | | | | | | | | | | | | |
|---|---|---|---|---|---|---|---|---|---|---|---|---|---|---|---|---|
| -11 | | -7944 | -8986 | -894 | | -1115 | -701 | | -1378 | -9818 | -9392 | | | | | |
| 120(Q) | -1950 | -2899 | -2068 | -1380 | | -3575 | -2688 | | -1085 | 3122 | 5 | 2965 | -2212 | -1472 | -2788 | 3499 | 1706 | -1878 | 1393 | -2788 | -2974 | -2647 | 120 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9390 | | | | | | | | | | | |
| 121(F) | -4720 | -3927 | -5139 | -5454 | | 4513 | -4504 | | -2520 | -3938 | -5326 | -3307 | -3429 | -4469 | -4782 | -4575 | -4818 | -4787 | -4810 | -4172 | -1812 | -736 | 121 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9388 | | | | | | | | | | | |
| 122(S) | -1944 | -2458 | -3696 | -4011 | | -4410 | -2644 | | -3753 | -4675 | -4191 | -4807 | -4070 | -3198 | -3384 | -3886 | -4051 | 3656 | -2393 | -3615 | -4374 | -4307 | 122 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9386 | | | | | | | | | | | |
| 123(F) | -4150 | -3318 | -4992 | -5163 | | 3777 | -4801 | | -1232 | -2695 | -4739 | 954 | -2105 | -3556 | -4637 | -3592 | -4183 | -4031 | -4023 | -3011 | -484 | 2534 | 123 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9384 | | | | | | | | | | | |
| 124(P) | -4497 | -4117 | -4899 | -5251 | | -5560 | -4139 | | -4798 | -6328 | -5454 | -5976 | -5741 | -5026 | 4302 | -5328 | -5104 | -4798 | -4844 | -5739 | -4665 | -5484 | 124 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9382 | | | | | | | | | | | |
| 125(G) | -4088 | -3924 | -4774 | -5139 | | -5615 | 3825 | | -4753 | -6303 | -5453 | -6014 | -5662 | -4812 | -4539 | -5232 | -5106 | -4370 | -4472 | -5527 | -4696 | -5561 | 125 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9379 | | | | | | | | | | | |
| 126(G) | -4088 | -3924 | -4774 | -5139 | | 5615 | 3825 | | -4753 | -6303 | -5453 | -6014 | -5662 | -4812 | -4539 | -5232 | -5106 | -4370 | -4472 | -5527 | -4696 | -5561 | 126 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9377 | | | | | | | | | | | |
| 127(I) | -2878 | -2414 | -5081 | -4778 | | 2015 | -4697 | | -2956 | 3488 | -4533 | -580 | -695 | -4245 | -4462 | -3882 | -4297 | -4026 | -2840 | -329 | -2190 | -1350 | 127 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9375 | | | | | | | | | | | |
| 128(P) | -1112 | -1752 | -3015 | -3242 | | 4210 | 2077 | | -3186 | -4033 | -3529 | -4251 | -3331 | -2415 | 3138 | -3114 | -3525 | 1101 | -1561 | -2858 | -4391 | -4208 | 128 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9373 | | | | | | | | | | | |
| 129(S) | -1944 | -2458 | -3696 | -4011 | | -4410 | -2644 | | -3753 | -4675 | -4191 | -4807 | -4070 | -3198 | -3384 | -3886 | -4051 | 3656 | -2393 | -3615 | -4374 | -4307 | 129 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9371 | | | | | | | | | | | |
| 130(H) | -4836 | 4275 | 4356 | -4629 | | -3663 | -4242 | | 5422 | -5932 | -4492 | -5436 | -5298 | -4579 | -4696 | -4620 | -4352 | -5005 | -5030 | -5648 | -3750 | -3259 | 130 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9369 | | | | | | | | | | | |
| 131(M) | 726 | 2516 | -3320 | -2699 | | 1540 | -2560 | | -1464 | -135 | -2311 | -587 | 3158 | -2207 | -2612 | -1942 | -2131 | -1653 | -952 | 1415 | -1331 | -989 | 131 |
| | -149 | -500 | 233 | 43 | | -381 | 399 | | 106 | -626 | 210 | -466 | -720 | 275 | 394 | 45 | 96 | 359 | 117 | -369 | -294 | -249 |
| | -11 | -7944 | -8986 | -894 | | -1115 | -701 | | -1378 | -9818 | -9366 | | | | | | | | | | | |

FIG. 9K

Table 7

| | | | | | | | | | | | | | | | | |
|---|---|---|---|---|---|---|---|---|---|---|---|---|---|---|---|---|
| 132(A) | 2437 | -1736 | -2547 | -2496 | -3668 | -1942 | -2557 | -3365 | -2590 | -3601 | -2745 | 1872 | -2625 | -2364 | -2796 | -1269 | 2286 | -2528 | -3861 | -3523 | 132 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | | | | | | | | | | | | |
| 133(P) | 2199 | -1920 | -3558 | -3810 | -4266 | -2163 | -3478 | -4045 | -3859 | -4314 | -3481 | -2754 | 3455 | -3500 | -3727 | -1576 | -1785 | -2985 | -4394 | -4324 | 133 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9362 | | | | | | | | | | | |
| 134(E) | -2302 | -4193 | 1609 | 3106 | -4369 | -2263 | -1582 | -4283 | -1777 | -4150 | -3462 | -851 | -2781 | 1870 | -3762 | -1969 | -2359 | -3762 | -4338 | -3341 | 134 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9360 | | | | | | | | | | | |
| 135(T) | -1509 | -1748 | -4032 | -3964 | -2803 | -2637 | -3374 | -581 | -3680 | -2093 | -1801 | -3053 | -3237 | -3460 | -3596 | -1989 | 3160 | 2274 | -3655 | -3308 | 135 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9358 | | | | | | | | | | | |
| 136(P) | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 136 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9355 | | | | | | | | | | | |
| 137(G) | -4088 | -3924 | -4774 | -5139 | -5615 | -3825 | -4753 | -6303 | -5453 | -6014 | -5662 | -4812 | -4539 | -5232 | -5106 | -4370 | -4472 | -5527 | -4696 | -5561 | 137 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9353 | | | | | | | | | | | |
| 138(S) | 1402 | -1678 | -3661 | -3893 | -4185 | -1940 | -3408 | -3979 | -3851 | -4254 | -3335 | -2598 | -4654 | -3421 | -3678 | -3267 | -1525 | -2799 | -4407 | -4277 | 138 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9351 | | | | | | | | | | | |
| 139(I) | -2917 | -2413 | -5393 | -4971 | -1597 | -5119 | -4331 | 3518 | 4766 | 1140 | -403 | -4828 | -4126 | 3267 | -4483 | -2863 | -105 | -3287 | -3176 | 139 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9349 | | | | | | | | | | | |
| 140(H) | -2691 | -3511 | -1351 | -1619 | -2597 | -2858 | 4977 | -4322 | -2002 | -4099 | -3606 | 1623 | -3363 | -2027 | -2266 | -4574 | -2835 | -3872 | -2991 | -2056 | 140 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9347 | | | | | | | | | | | |
| 141(E) | -4205 | -4417 | -2343 | 3901 | -5349 | -3698 | -3534 | -5837 | -3838 | -5561 | -5237 | -3039 | -4218 | -3453 | -4201 | -4072 | -4352 | -5409 | -4640 | -4860 | 141 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9344 | | | | | | | | | | | |
| 142(G) | -4088 | -3924 | -4774 | -5139 | -5615 | -3825 | -4753 | -6303 | -5453 | -6014 | -5662 | -4812 | -4539 | -5232 | -5106 | -4370 | -4472 | -5527 | -4696 | -5561 | 142 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9342 | | | | | | | | | | | |
| 143(G) | -4088 | -3924 | -4774 | -5139 | -5615 | -3825 | -4753 | -6303 | -5453 | -6014 | -5662 | -4812 | -4539 | -5232 | -5106 | -4370 | -4472 | -5527 | -4696 | -5561 | 143 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -11 | -7944 | -8986 | -894 | -1115 | -701 | -1378 | -9818 | -9340 | | | | | | | | | | | |
| 144(E) | -4205 | -4417 | -2343 | 3901 | -5349 | -3698 | -3534 | -5837 | -3838 | -5561 | -5237 | -3039 | -4218 | -3453 | -4201 | -4072 | -4352 | -5409 | -4640 | -4860 | 144 |
| | | -149 | -500 | 233 | 43 | -381 | 399 | 106 | -626 | 210 | -466 | -720 | 275 | 394 | 45 | 96 | 359 | 117 | -369 | -294 | -249 |

FIG. 9L

Table 7

| | | | | | | | | | | | | | | | | | | | |
|---|---|---|---|---|---|---|---|---|---|---|---|---|---|---|---|---|---|---|---|
| | -11 | -7944 | -8986 | -894 | -1115 | -701 | -1378 | -9818 | -9338 | | | | | | | | | | |
| 145(L) | -4119 | -3542 | -5389 | -5357 | -2027 | 4767 | -4358 | -1609 | -5118 | 3293 | -979 | -5230 | -4771 | -4474 | -4724 | -5069 | -4106 | -2331 | -3412 | -3400 | 145 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9335 | | | | | | | | | | |
| 146(G) | -4088 | -3924 | 4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 146 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9333 | | | | | | | | | | |
| 147(Y) | -4791 | -3935 | 4914 | -5231 | -815 | -4530 | -2178 | -4357 | -5024 | 3745 | 3807 | -4206 | -4772 | -4328 | -4584 | -4677 | -4837 | -4435 | -1477 | 4857 | 147 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9331 | | | | | | | | | | |
| 148(C) | 2078 | 2882 | -3724 | -3518 | -2695 | -2001 | -2704 | -2106 | -3218 | -2589 | -1876 | -2467 | -2661 | -2861 | -3107 | 1882 | -1336 | 1253 | -3116 | -2838 | 148 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9329 | | | | | | | | | | |
| 149(L) | -4119 | -3542 | -5389 | -5357 | -2027 | 4767 | -4358 | -1609 | -5118 | 3293 | -979 | -5230 | -4771 | -4474 | -4724 | -5069 | -4106 | -2331 | -3412 | -3400 | 149 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9326 | | | | | | | | | | |
| 150(S) | 1113 | -1682 | -3645 | -3884 | -4190 | -1942 | 3410 | -3986 | -3853 | -4261 | -3343 | -2598 | -2736 | -3423 | -3680 | 3340 | -1530 | -2804 | -4411 | -4280 | 150 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9324 | | | | | | | | | | |
| 151(H) | -2323 | -2561 | 3097 | -3086 | -1647 | -3098 | 4888 | -2143 | -2537 | -2630 | -2333 | -2801 | -3547 | -2728 | -2559 | -2581 | -2516 | 1445 | -2255 | -1333 | 151 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9322 | | | | | | | | | | |
| 152(A) | 2928 | -1667 | 3720 | -3939 | -4168 | -1934 | 3412 | -3952 | -3863 | -4230 | -3311 | -2605 | -2728 | -3429 | -3681 | 2146 | -1516 | -2782 | -4394 | -4269 | 152 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9320 | | | | | | | | | | |
| 153(Y) | -3656 | -3073 | -4655 | -4705 | 2072 | -4415 | -1160 | -2834 | -4311 | -2480 | -2370 | -3332 | -4386 | -3385 | -3897 | -3630 | 1330 | -2897 | -449 | 4200 | 153 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9317 | | | | | | | | | | |
| 154(G) | -4088 | -3924 | 4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 154 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9315 | | | | | | | | | | |
| 155(A) | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 155 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9313 | | | | | | | | | | |
| 156(I) | 1599 | -1799 | -4782 | -4398 | -2369 | -4319 | -3996 | 2490 | -4241 | -1351 | -1186 | -4067 | -4263 | -4075 | -4278 | -3599 | -2201 | 2395 | -3673 | -3229 | 156 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9311 | | | | | | | | | | |

FIG. 9M

Table 7

| 157F | -3470 | -2920 | -5747 | -5177 | 3140 | -5423 | -3794 | -632 | -4917 | 2061 | 2648 | -5046 | -4645 | -3788 | -4437 | -4711 | -3319 | -1432 | -2615 | -2450 | 157 |
|---|---|---|---|---|---|---|---|---|---|---|---|---|---|---|---|---|---|---|---|---|---|
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9308 | | | | | | | | | | | | |
| 158D | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 158 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9306 | | | | | | | | | | | | |
| 159N | -2152 | -3226 | -1659 | -1246 | 3822 | -2724 | -1126 | -3401 | -63 | -3176 | -2432 | 3327 | -2852 | 1866 | 1828 | -2010 | -2006 | -3064 | -3127 | -2771 | 159 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9304 | | | | | | | | | | | | |
| 160P | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 160 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9301 | | | | | | | | | | | | |
| 161D | -2185 | -4023 | 2971 | 1468 | -4227 | -2230 | -1509 | -4119 | -1656 | -4000 | -3274 | 1608 | -2722 | -1160 | -2448 | 972 | -2231 | -3604 | -4191 | -3227 | 161 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9299 | | | | | | | | | | | | |
| 162L | -3047 | -2911 | -3749 | -3527 | -1475 | -4117 | -2954 | -1124 | -2671 | 2926 | -473 | -3500 | -4084 | 1801 | -2645 | -3601 | -3002 | -1759 | -2782 | -2505 | 162 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9297 | | | | | | | | | | | | |
| 163I | -2388 | -1937 | -4948 | -4533 | 1635 | -4599 | -3887 | 3268 | -4365 | -905 | -1609 | -4243 | -4379 | -4047 | -4325 | -3869 | -2360 | -3319 | -2869 | -2961 | 163 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9295 | | | | | | | | | | | | |
| 164V | 1092 | -1556 | -3968 | -3774 | -2577 | -2468 | -3041 | -599 | -3503 | -2045 | -2850 | -1896 | -3046 | -3196 | -3407 | -1780 | 1216 | 3071 | -3285 | -2961 | 164 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9292 | | | | | | | | | | | | |
| 165F | 1547 | -939 | -2765 | -2207 | 1594 | -2286 | -1398 | -514 | -1927 | -906 | -256 | 1121 | -4599 | -1657 | -1937 | -1398 | 1348 | 1100 | -1513 | -1155 | 165 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9290 | | | | | | | | | | | | |
| 166C | 1272 | 5052 | -4189 | -4423 | -4093 | 1091 | -3532 | -3812 | -4117 | -4134 | -3233 | -2716 | -2738 | -3626 | -3808 | -1304 | -1508 | -2711 | -4345 | -4265 | 166 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9288 | | | | | | | | | | | | |
| 167V | -2483 | -1992 | -5115 | -4742 | -2252 | -4880 | -4534 | 1808 | -4643 | 723 | -1005 | -4536 | -4599 | -4405 | -4684 | -4208 | -2462 | 3131 | -3865 | -3512 | 167 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9285 | | | | | | | | | | | | |
| 168V | 699 | -1835 | -4861 | -4496 | -2442 | -4434 | -4193 | 1822 | -4360 | -1374 | -1231 | -4183 | -4356 | -4220 | -4421 | -3732 | -2257 | 3136 | -3831 | -3371 | 168 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | -9283 | | | | | | | | | | | | |
| 169G | -4088 | -3924 | -4774 | -5139 | 3825 | -4753 | -6303 | -5453 | -6014 | -1374 | -5662 | -4812 | -4539 | -5232 | -5106 | -4370 | -4472 | -5527 | -4696 | -5561 | 169 |
| | -149 | -500 | 233 | 43 | -381 | -701 | 106 | -626 | 210 | -466 | -720 | 275 | 394 | 45 | 96 | 359 | 117 | -369 | -294 | -249 | |
| | -11 | -7944 | -8986 | -894 | -1115 | | -1378 | -9818 | | | | | | | | | | | | | |

FIG. 9N

Table 7

| | | | | | | | | | | | | | | | | | | |
|---|---|---|---|---|---|---|---|---|---|---|---|---|---|---|---|---|---|---|
| | -11 | -7944 | -8986 | -894 | -1115 | -701 | -1378 | -9818 | -9281 | | | | | | | | | |
| 170(D) | -4232 | -4465 | 4158 | -2649 | -5412 | -3676 | -3575 | -6036 | -4125 | -5722 | 5419 | -2993 | -4216 | -3512 | -4617 | -4077 | -4401 | -5553 | -4696 | -4914 | 170 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9278 | | | | | | | | | |
| 171(G) | -4088 | -3924 | -4774 | -5139 | -5615 | 3825 | -4753 | -6303 | -5453 | -6014 | 5662 | -4812 | -4539 | -5232 | -5106 | -4370 | -4472 | -5527 | -4696 | -5561 | 171 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9276 | | | | | | | | | |
| 172(E) | -4205 | -4417 | -2343 | 3901 | -5349 | -3698 | -3534 | -5837 | -3838 | -5561 | 5237 | -3039 | -4218 | -3453 | -4201 | -4072 | -4352 | -5409 | -4640 | -4860 | 172 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9274 | | | | | | | | | |
| 173(A) | 3289 | -1671 | -3729 | -3971 | -4173 | -1939 | -3433 | -3954 | -3901 | -4239 | 3324 | -2617 | -2734 | -3460 | -3704 | 1119 | -1523 | -2786 | -4402 | -4279 | 173 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9271 | | | | | | | | | |
| 174(E) | -4205 | -4417 | -2343 | 3901 | -5349 | -3698 | -3534 | -5837 | -3838 | -5561 | 5237 | -3039 | -4218 | -3453 | -4201 | -4072 | -4352 | -5409 | -4640 | -4860 | 174 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9269 | | | | | | | | | |
| 175(T) | -2430 | -2823 | -4179 | -4462 | -4591 | -3027 | -4037 | -4454 | -4406 | -4707 | 4191 | -3664 | -3724 | -4237 | -4215 | -2689 | 4010 | -3747 | -4431 | -4588 | 175 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9267 | | | | | | | | | |
| 176(G) | -4088 | -3924 | -4774 | -5139 | -5615 | 3825 | -4753 | -6303 | -5453 | -6014 | 5662 | -4812 | -4539 | -5232 | -5106 | -4370 | -4472 | -5527 | -4696 | -5561 | 176 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9264 | | | | | | | | | |
| 177(P) | -4497 | -4899 | -5251 | -4462 | -5560 | -4139 | -4798 | -6328 | -5454 | -5976 | 5741 | -5026 | 4302 | -5328 | -5104 | -4798 | -4844 | -5739 | -4665 | -5484 | 177 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9262 | | | | | | | | | |
| 178(L) | -2381 | -2370 | -4412 | -4172 | -1521 | -3608 | -3357 | -845 | -3741 | -437 | 2871 | -3695 | -3832 | -3365 | -3575 | -2971 | 4844 | -1264 | -2889 | -2744 | 178 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9260 | | | | | | | | | |
| 179(A) | 3191 | -1777 | -3712 | -3682 | -2796 | -2273 | -3050 | -2040 | -3349 | -2216 | 2634 | -2731 | -2945 | -3125 | -3255 | -1630 | -1688 | -1822 | -3467 | -3179 | 179 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9257 | | | | | | | | | |
| 180(T) | 1105 | -1691 | -3751 | -3950 | -4036 | -1980 | -3391 | -3579 | -3788 | -4004 | -3179 | -2639 | -2764 | -3418 | -3611 | -1351 | 3649 | -2631 | -4299 | -4165 | 180 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9255 | | | | | | | | | |
| 181(S) | 1115 | -1654 | -3622 | -3791 | -4192 | 1188 | -3347 | -3991 | -3762 | -4236 | -3295 | -2550 | -2702 | -3327 | -3634 | 3032 | -1489 | -2786 | -4402 | -4277 | 181 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9253 | | | | | | | | | |

FIG. 9O

Table 7

| | | | | | | | | | | | | | | | | | |
|---|---|---|---|---|---|---|---|---|---|---|---|---|---|---|---|---|---|
| 182( | -5598 | -4432 | -5385 | -5722 | -3380 | -4524 | -4140 | -5941 | -5643 | -5318 | -5354 | -5427 | -4938 | -5474 | -5178 | -5909 | -5751 | -5890 | 6275 | -2993 | 182 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9250 | | | | | | | | | | | |
| 183(H) | -2817 | 3584 | -1743 | -1758 | -2728 | -3054 | 4625 | -4009 | -1063 | -3728 | -3189 | -1926 | -3378 | 2752 | -1170 | -2680 | -2782 | -3708 | -2912 | -2121 | 183 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9248 | | | | | | | | | | | |
| 184(S) | 2113 | -1671 | -3691 | -3909 | -4175 | -1935 | -3404 | -3963 | -3845 | -4238 | -3318 | -2599 | -2728 | -3415 | -3673 | 2974 | -1518 | -2788 | 4398 | -4270 | 184 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9246 | | | | | | | | | | | |
| 185(N) | -1667 | -2295 | -1303 | -1206 | -1708 | -2454 | 2688 | 1228 | -1127 | -2276 | -1659 | 3307 | -2730 | -1191 | -1399 | -1726 | -1677 | -1853 | -2144 | -1341 | 185 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9243 | | | | | | | | | | | |
| 186(K) | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 186 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9241 | | | | | | | | | | | |
| 187(F) | -3793 | -3163 | -5295 | -5191 | 4063 | -5003 | -2160 | -1329 | 4845 | 1075 | -704 | -4205 | -4663 | -3781 | -4356 | -4376 | -3689 | -1985 | -1339 | -323 | 187 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9238 | | | | | | | | | | | |
| 188(I) | -2691 | -2201 | -5254 | -4813 | -1747 | -4966 | -4275 | 2399 | -4658 | 2193 | -527 | -4632 | -4563 | -4118 | -4528 | -4270 | -2643 | 1553 | -3385 | 3255 | 188 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9236 | | | | | | | | | | | |
| 189(N) | -2608 | 4312 | 1902 | -698 | -4665 | -2423 | -1924 | -4776 | -2319 | -4628 | -4060 | 3855 | -3013 | -1633 | -3242 | -2275 | -2738 | -4189 | -4662 | -3683 | 189 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9234 | | | | | | | | | | | |
| 190(P) | -4497 | 4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 190 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9231 | | | | | | | | | | | |
| 191(A) | 1597 | -1385 | -1621 | -1030 | -1453 | -2189 | 892 | 994 | 1158 | -1265 | -571 | -1153 | -2261 | -699 | 1188 | -1186 | -908 | 900 | -1781 | -1350 | 191 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9229 | | | | | | | | | | | |
| 192(R) | -1138 | 2535 | 738 | 1346 | -2893 | -1985 | -675 | -2612 | -163 | -2551 | -1669 | 1495 | -2128 | -235 | 2008 | -1012 | 1851 | -2189 | -2703 | -2067 | 192 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9226 | | | | | | | | | | | |
| 193(D) | -2243 | -3522 | 3665 | -856 | -4525 | -2330 | -2015 | -4560 | -2391 | -4501 | -3857 | -1194 | -2947 | -1733 | -3224 | -3224 | -2461 | -3845 | -4571 | -3690 | 193 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | -9818 | -9224 | | | | | | | | | | | |
| 194(G) | -4088 | -3924 | -4774 | -5139 | -5615 | 3825 | -4753 | -6303 | -5453 | -6014 | -5662 | -4812 | 4539 | -5232 | -5106 | -4370 | -4472 | -5527 | -4696 | -5561 | 194 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | | -7944 | -8986 | -1115 | -701 | -1378 | | | | | | | | | | | | | |

FIG. 9P

Table 7

| | | | | | | | | | | | | | | | | |
|---|---|---|---|---|---|---|---|---|---|---|---|---|---|---|---|---|
| | -11 | -7944 | -8986 | -894 | -1115 | -701 | -1378 | -9818 | -9222 | | | | | | | |
| 195(A) | 3150 | -1781 | -3954 | -3897 | -2697 | 2590 | -3290 | 1498 | -3639 | -1978 | -1734 | -3003 | -3197 | -3386 | -3549 | -1945 | -1810 | -689 | -3544 | -3207 | 195
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9219 |
| 196(V) | 2448 | -1959 | -5109 | -4794 | -2563 | -4877 | -4851 | 1886 | -4730 | -1341 | -1284 | -4579 | -4666 | -4653 | -4865 | -4248 | -2447 | 3388 | -4252 | -3753 | 196
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9217 |
| 197(L) | -3405 | -2846 | -5779 | -5255 | -1228 | -5518 | -4333 | 1719 | -5019 | 2902 | -18 | -5245 | -4745 | -3976 | -4603 | -4888 | -3285 | -936 | -3002 | -3110 | 197
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9214 |
| 198(P) | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 198
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9212 |
| 199(I) | -2459 | -1963 | -5126 | -4808 | -2568 | -4914 | -4889 | 3247 | -4751 | -1338 | -1283 | -4603 | -4685 | -4676 | -4891 | -4286 | -2455 | 2426 | -4274 | -3777 | 199
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9209 |
| 200(L) | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 200
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9207 |
| 201(H) | -2395 | 4306 | 1759 | 1612 | -4428 | -2292 | 4419 | -4404 | -1894 | -4265 | -3611 | -881 | -2831 | -1320 | -2741 | -2046 | -2464 | -3880 | -4428 | -3405 | 201
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9205 |
| 202(L) | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -4391 | -3400 | 202
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9202 |
| 203(N) | -3642 | -3838 | -3004 | -3356 | -4743 | -3612 | -3773 | -5643 | -4099 | -5460 | -5060 | 4378 | -4185 | -3865 | -4225 | -3744 | -3950 | -5002 | -4391 | -4381 | 203
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9200 |
| 204(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 204
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9197 |
| 205(Y) | -4606 | -3570 | -5022 | -5359 | 2254 | -4894 | -3493 | -1139 | -4923 | -2816 | -2906 | -3546 | -4765 | -3679 | -4305 | -4161 | -4469 | -3657 | -387 | 4510 | 205
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9195 |
| 206(K) | -4125 | -4091 | -4017 | 3615 | -5101 | -3960 | -2958 | -5182 | 3972 | -4825 | -4345 | -3552 | -4249 | -2709 | -1809 | -4154 | -4044 | -4895 | -4132 | -4389 | 206
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9192 |

FIG. 9Q

Table 7

| | | | | | | | | | | | | | | | |
|---|---|---|---|---|---|---|---|---|---|---|---|---|---|---|---|
| 207(I) | -3202 | -2787 | -5004 | -4996 | -2836 | -4384 | -4440 | 3937 | -4838 | -1815 | -1871 | -4704 | -4600 | -4683 | -4704 | -4353 | -3280 | -603 | -3938 | -3661 | 207 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9190 | | | | | | | | | | | |
| 208(S) | 1943 | -1773 | -2482 | -2503 | -3907 | -1935 | -2647 | -3686 | -2717 | -3870 | -2975 | 1555 | -2640 | -2445 | -2934 | 2632 | -1475 | -2699 | -4064 | -3728 | 208 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9187 | | | | | | | | | | | |
| 209(N) | -2546 | -4182 | -358 | 1608 | -4553 | -2427 | -1858 | -4587 | -2065 | -4451 | -3846 | 3842 | -2989 | -1553 | -2799 | -2233 | -2653 | -4040 | -4492 | -3586 | 209 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9185 | | | | | | | | | | | |
| 210(P) | -3075 | -3411 | -3652 | -3377 | -4713 | -3421 | -2871 | -4754 | -1885 | -4551 | -3970 | -3201 | 3874 | -2637 | 1884 | -3201 | -3246 | -4233 | -4063 | -4155 | 210 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9182 | | | | | | | | | | | |
| 211(T) | -1093 | -1706 | -3487 | -3693 | -4074 | -1966 | -3302 | -3842 | -3638 | -4134 | -3253 | -2558 | -2748 | -3296 | -3520 | 1110 | 3646 | -2760 | -4304 | -4125 | 211 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9180 | | | | | | | | | | | |
| 212(I) | -2500 | -2007 | -5132 | -4756 | -2220 | -4898 | -4538 | 2959 | -4657 | 869 | -973 | -4554 | -4605 | -4399 | -4689 | -4227 | -2477 | 2250 | -3844 | -3510 | 212 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9177 | | | | | | | | | | | |
| 213(Y) | -3774 | -3094 | -5016 | -5007 | 2147 | -4760 | -1471 | -1948 | 4610 | 2513 | -1319 | -3670 | -4532 | -3545 | -4108 | -3980 | -3652 | -2427 | -717 | 2621 | 213 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9175 | | | | | | | | | | | |
| 214(A) | 2561 | -1647 | -3667 | -3813 | -4167 | 1400 | -3339 | -3961 | -3748 | -4207 | -2554 | -3256 | -2698 | -3319 | -3621 | 1972 | -1482 | -2770 | -4380 | -4254 | 214 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9172 | | | | | | | | | | | |
| 215(R) | -2761 | 3372 | -4411 | -3701 | -4318 | -3291 | -2762 | -4186 | -1690 | -4160 | -3592 | -3256 | -3742 | -2538 | 3812 | -2949 | -2961 | -3734 | -3870 | -3866 | 215 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9170 | | | | | | | | | | | |
| 216(I) | -1976 | -1690 | -4334 | -3831 | -1599 | -3763 | -2958 | 3100 | -3513 | -670 | 2664 | -3459 | -3733 | -3184 | -3413 | -2951 | 1215 | 192 | -2661 | -2363 | 216 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9167 | | | | | | | | | | | |
| 217(S) | -1740 | -2857 | 1787 | 890 | -4083 | -2148 | -1822 | -3944 | -1950 | -3947 | -3166 | -1164 | 2282 | -1503 | -2599 | 2462 | -1955 | -3236 | -4123 | -3368 | 217 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9165 | | | | | | | | | | | |
| 218(D) | -1796 | -3465 | 2956 | 1278 | -3721 | -2140 | 2354 | -3541 | 1157 | -3446 | -2631 | -742 | -2513 | -824 | -1706 | -1558 | -1793 | -3064 | -3617 | -2792 | 218 |
| | -149 | -500 | 233 | 43 | -381 | 399 | 106 | -626 | 210 | -466 | -720 | 275 | 394 | 45 | 96 | 359 | 117 | -369 | -294 | -249 |
| | -11 | -7944 | -8986 | -894 | -1115 | -701 | -1378 | -9818 | -9162 | | | | | | | | | | | |
| 219(D) | -1468 | -2962 | 2158 | 2010 | -3256 | -2035 | -1014 | -3010 | -825 | -2993 | -2150 | -673 | -2334 | -612 | -1413 | 1100 | -1455 | 908 | -3204 | -2451 | 219 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 9R

Table 7

| | | | | | | | | | | | | | | | | | |
|---|---|---|---|---|---|---|---|---|---|---|---|---|---|---|---|---|---|
| 220(E) | -11 | -2636 | -4572 | 1783 | 3438 | -4760 | -2391 | -1842 | 4773 | -2236 | -4607 | -4040 | -996 | -2973 | -1538 | -3199 | -2254 | -2736 | -4219 | -4732 | -3692 | 220 |
| | | -149 | -500 | 233 | | -381 | 399 | 106 | -626 | 210 | -466 | -720 | 275 | 394 | 45 | 96 | 359 | 117 | -369 | -294 | -249 | |
| | -11 | -7944 | -8986 | -894 | | -1115 | -701 | -1378 | -9818 | -9160 | | | | | | | | | | | | |
| 221(L) | -3421 | -2860 | -5790 | -5264 | -1219 | -5529 | 4333 | 1589 | -5025 | | 2937 | 9 | -5258 | 4748 | -3973 | 4603 | -4902 | -3300 | -965 | -2995 | -3106 | 221 |
| | -149 | -500 | 233 | | -381 | 399 | 106 | -626 | -9818 | -9157 | -466 | -720 | 275 | 394 | 45 | 96 | 359 | 117 | -369 | -294 | -249 | |
| | -11 | -7944 | -8986 | -894 | -1115 | -701 | -1378 | -9818 | -9155 | | | | | | | | | | | | | |
| 222(H) | -1434 | -2670 | -1420 | 1033 | -3099 | -2316 | 2338 | -2728 | 1395 | 511 | -1776 | 966 | -2367 | -301 | 2245 | -1323 | -1317 | -2360 | -2690 | -2208 | 222 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9152 | | | | | | | | | | | | |
| 223(K) | 1469 | -2443 | 1279 | 267 | -2862 | -1879 | -707 | -2612 | 1960 | -2574 | -1677 | -575 | -2071 | -271 | -856 | 1040 | -1018 | -2154 | -2755 | -2069 | 223 |
| | -149 | -500 | 43 | | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9150 | | | | | | | | | | | | |
| 224(F) | -3694 | -3088 | -5579 | -5263 | 3299 | -5296 | -2867 | -919 | -4969 | 2350 | -235 | -4680 | 4707 | -3837 | -4468 | -4661 | -3559 | -1683 | -1918 | -1128 | 224 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9147 | | | | | | | | | | | | |
| 225(F) | -4720 | -3927 | -5139 | -5454 | 4513 | -4504 | -2520 | -3938 | -5326 | -3307 | -3429 | -4469 | -4782 | -4575 | -4818 | -4787 | -4810 | -4172 | -1812 | -736 | 225 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9145 | | | | | | | | | | | | |
| 226(E) | 688 | -2344 | -716 | 2314 | -2761 | -1878 | -641 | -2492 | -210 | -2459 | -1564 | -580 | -2036 | -201 | 1256 | 1020 | -948 | -2051 | -2637 | -1982 | 226 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9142 | | | | | | | | | | | | |
| 227(G) | -4088 | -3924 | -4774 | -5139 | -5615 | 3825 | -4753 | -5453 | -6014 | -5662 | -4812 | -4539 | -5232 | -5106 | -4370 | -4472 | -5527 | -4696 | -5561 | 227 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9140 | | | | | | | | | | | | |
| 228(Y) | -1597 | -1396 | -3573 | -3051 | 2007 | -3040 | -1283 | 840 | -2686 | 801 | 2421 | 1263 | -3058 | -2245 | -2516 | -2133 | -1532 | -823 | 882 | 2863 | 228 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9137 | | | | | | | | | | | | |
| 229(G) | -4088 | -3924 | -4774 | -5139 | -5615 | 3825 | -4753 | -5453 | -6014 | -5662 | -4812 | -4539 | -5232 | -5106 | -4370 | -4472 | -5527 | -4696 | -5561 | 229 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9134 | | | | | | | | | | | | |
| 230(Y) | -4620 | -3593 | -5015 | -5337 | 280 | -4863 | -1187 | -3570 | -4864 | -2899 | -2980 | -3577 | -4762 | -3702 | -4279 | -4188 | -4490 | -3719 | 3436 | 4551 | 230 |
| | -149 | -500 | 43 | | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9132 | | | | | | | | | | | | |
| 231(H) | -862 | -2311 | -632 | 1878 | -2629 | -1803 | 2148 | -2371 | 1173 | -2322 | -1409 | -442 | -1911 | -24 | -537 | 854 | 933 | -1933 | -2493 | -1820 | 231 |
| | -149 | -500 | 43 | | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9129 | | | | | | | | | | | | |

FIG. 9S

Table 7

| 232(P | -1820 | -2216 | -3792 | -3938 | -3452 | -2669 | -3505 | -2107 | -3787 | -3057 | -2729 | -3136 | 3804 | -3614 | -3691 | -2143 | -2196 | 1506 | -3938 | -3681 | 232 |
|---|---|---|---|---|---|---|---|---|---|---|---|---|---|---|---|---|---|---|---|---|---|
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9127 | | | | | | | | | | | | |
| 233(Y | 996 | -1294 | -2366 | -1763 | -954 | -2474 | -1131 | -841 | -1179 | 533 | -479 | -1680 | -2552 | -1243 | 1281 | -1538 | -1120 | -749 | -1438 | 3229 | 233 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9124 | | | | | | | | | | | | |
| 234(F | -1969 | -1770 | -3543 | 966 | 3139 | -3305 | -1223 | 1499 | -2815 | -1359 | -912 | -2576 | -3319 | -2375 | -2708 | -2407 | -1903 | -1180 | -760 | 2316 | 234 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9122 | | | | | | | | | | | | |
| 235(V | -2342 | -1893 | -4914 | -4505 | 1622 | 4568 | -3913 | 1826 | -4342 | -1030 | -963 | -4213 | -4369 | -4072 | -4326 | -3838 | -2317 | 3076 | -3397 | -2930 | 235 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9119 | | | | | | | | | | | | |
| 236(E | 722 | -2323 | -653 | 2387 | -2684 | -1948 | -848 | -2315 | -559 | -2434 | -1603 | 1662 | -2171 | -449 | -1065 | -1048 | -1111 | 813 | -2716 | 2073 | 236 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8986 | -894 | -1115 | -701 | -1378 | -9818 | -9116 | | | | | | | | | | | | |
| 237(G | 917 | -3198 | 1792 | -603 | -3972 | 2355 | -1545 | -3811 | -1605 | -3767 | -2983 | 1737 | -2642 | -194 | -2291 | -1663 | -1944 | -3223 | -3965 | 3136 | 237 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1266 | -7944 | -790 | -894 | -1115 | -701 | -1378 | -9818 | -9114 | | | | | | | | | | | | |
| 238(D | -1223 | -2437 | 2763 | 82 | -3208 | 2150 | -912 | -3128 | -1082 | -3109 | -2410 | -254 | -1932 | -608 | -1769 | -1060 | -1365 | -2572 | -3146 | -2456 | 238 |
| | -149 | -500 | 233 | 43 | -376 | 399 | 106 | -626 | 210 | -466 | -720 | 275 | 394 | 45 | 96 | 359 | 117 | -369 | -294 | -249 | |
| | -649 | -1491 | -7744 | -157 | -3277 | -2587 | -263 | -9818 | -9111 | | | | | | | | | | | | |
| 239(D | -2102 | -2902 | 3872 | -571 | -3494 | -1911 | -1556 | -3716 | -1893 | -3662 | -3195 | -920 | -2449 | -1361 | -2516 | -1915 | -2242 | -3285 | -3201 | -2890 | 240 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -23 | -6702 | -7744 | -894 | -1115 | -2587 | | -9818 | -9109 | | | | | | | | | | | | |
| 240(N | -694 | -999 | -1141 | -940 | -1064 | -1767 | -919 | 2282 | -849 | -787 | -349 | 2352 | -2038 | -817 | -1093 | -1000 | -743 | 143 | -1624 | -1073 | 241 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -23 | -6702 | -7744 | -894 | -1115 | -562 | -1632 | -9818 | -9106 | | | | | | | | | | | | |
| 241(H | -1431 | -2871 | -230 | 2243 | -3163 | -1925 | 3560 | -3017 | -719 | -2971 | -2155 | -593 | -2261 | -564 | -1242 | 1041 | -1433 | -2572 | -3114 | -2362 | 242 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7670 | -8713 | -894 | -1115 | -1555 | -600 | -9818 | -9103 | | | | | | | | | | | | |
| 242(D | -2381 | -4329 | 3618 | 1594 | -4505 | -2138 | -1588 | -4512 | -1982 | -4352 | -3784 | -740 | -2721 | -1283 | -2949 | -1999 | -2481 | -3960 | -4490 | -3437 | 243 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7670 | -8713 | -894 | -1115 | -345 | -2232 | -9818 | -9101 | | | | | | | | | | | | |
| 243(P | -1293 | -1824 | -1648 | -1248 | -1123 | -2332 | 2376 | -1662 | -1068 | -1836 | -1165 | -1350 | 2605 | -1031 | -1373 | -1420 | 1364 | -1468 | -1606 | 2015 | 244 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9098 | | | | | | | | | | | | |
| 244(M | 683 | -1426 | -1284 | 1643 | -1482 | -2033 | -782 | -1054 | -631 | 424 | 2181 | -936 | 1207 | -541 | -1010 | -1010 | -810 | -892 | -1806 | -1337 | 245 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9T

Table 7

| | | | | | | | | | | | | | | | | | | | | |
|---|---|---|---|---|---|---|---|---|---|---|---|---|---|---|---|---|---|---|---|---|
| | -11 | -7944 | -8987 | -894 | -1115 | -701 | -1378 | -9818 | -9095 | | | | | | | | | | | |
| 245(S) | 861 | -1834 | 1340 | -516 | -2191 | -1877 | -758 | -1838 | 462 | 203 | -1169 | -752 | -2056 | -387 | -921 | 1571 | 1006 | -1523 | -2319 | -1756 | 246 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9093 | | | | | | | | | | | | |
| 246(M) | -1263 | -1161 | -3038 | -2448 | -745 | -2739 | -1453 | 1314 | -2054 | -532 | -2170 | 1690 | -2762 | -2026 | -1815 | -1199 | 464 | -1382 | 1937 | 247 |
| | -149 | -500 | 233 | 43 | -381 | 399 | 106 | -626 | 210 | -466 | 275 | 394 | 45 | 96 | 359 | 117 | -369 | -294 | -249 | |
| | -11 | -7944 | -8987 | -894 | -1115 | -701 | -1378 | -9818 | -9090 | | | | | | | | | | | |
| 247(H) | -2671 | -3516 | -1308 | -1575 | -2624 | -2837 | 4896 | -4310 | -1982 | -4092 | -3590 | 1952 | -3342 | -1994 | -2257 | -2551 | -2812 | -3859 | -3012 | -2078 | 248 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9087 | | | | | | | | | | | |
| 248(R) | -2804 | -3490 | -3516 | -2098 | -4381 | -3320 | -1175 | -3662 | 2379 | -3289 | -2620 | -1979 | -3242 | 2620 | 2657 | -2671 | -2465 | -3437 | -3117 | -3033 | 249 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9085 | | | | | | | | | | | |
| 249(R) | 732 | -1128 | -2794 | -2187 | -1101 | -2570 | -1459 | 356 | -1683 | 1417 | 262 | -1988 | -2651 | 1613 | 1995 | -1657 | -1104 | 1378 | -1647 | -1297 | 250 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9082 | | | | | | | | | | | |
| 250(M) | 923 | -1665 | -3899 | -3427 | 1737 | -3128 | -2177 | -660 | -3081 | -421 | -2915 | -3268 | -2649 | -2926 | -2316 | -1774 | -849 | -1851 | -1321 | 251 |
| | -149 | -500 | 233 | 43 | -381 | 399 | 106 | -626 | 210 | -466 | 275 | 394 | 45 | 96 | 359 | 117 | -369 | -294 | -249 | |
| | -11 | -7944 | -8987 | -894 | -1115 | -701 | -1378 | -9818 | -9079 | | | | | | | | | | | |
| 251(A) | 3609 | -2508 | -4184 | -4493 | -4592 | -2737 | -3989 | -4421 | -4496 | 4324 | -4051 | -3440 | -3474 | -4171 | -4253 | -2294 | -2487 | -3536 | -4484 | -4643 | 252 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9077 | | | | | | | | | | | |
| 252(E) | 1863 | -2261 | -1000 | 2576 | -3283 | -2007 | -1447 | -2956 | -1252 | -3072 | -2244 | -1127 | -2442 | -1087 | -4253 | -1727 | -1275 | 1155 | -2422 | -3329 | -2724 | 253 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9074 | | | | | | | | | | | |
| 253(T) | -1822 | -1611 | -4151 | -3676 | -1688 | -3491 | -2844 | 186 | -3366 | 815 | -670 | -3264 | -3577 | -3075 | -3294 | -2693 | 2637 | 2187 | -2655 | -2324 | 254 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9071 | | | | | | | | | | | |
| 254(M) | -3494 | -2937 | -5788 | -5208 | 2737 | -5472 | -3898 | -624 | -4954 | 2288 | 2851 | -5116 | -4665 | -3807 | -4446 | -4768 | -3340 | -1435 | -2676 | -2586 | 255 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9069 | | | | | | | | | | | |
| 255(D) | -2671 | -4634 | 3718 | 1448 | -4812 | -2395 | -1863 | -4839 | -2290 | -4667 | -4121 | -999 | -2987 | -1563 | -3285 | -2280 | -2777 | -4278 | -4793 | -3731 | 256 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9066 | | | | | | | | | | | |
| 256( | -807 | -1865 | 984 | -295 | -2038 | -1850 | 2023 | 698 | 1219 | -1817 | -996 | -567 | -1940 | -139 | -647 | -780 | 1016 | -1409 | 2991 | -1556 | 257 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9063 | | | | | | | | | | | |

FIG. 9U

Table 7

| | | | | | | | | | | | | | | | | | | |
|---|---|---|---|---|---|---|---|---|---|---|---|---|---|---|---|---|---|---|
| 257(C | 2301 | 2673 | -4116 | -3625 | -1761 | -3338 | -2704 | 1666 | -3330 | -1177 | -798 | -3141 | -3451 | -3036 | -3235 | -2529 | -1663 | 1516 | -2564 | -2191 | 258 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9061 | | | | | | | | | | | | |
| 258(F) | -1716 | -1417 | -4136 | -3595 | 2444 | -3534 | -2588 | 1707 | -3287 | -928 | -598 | -3178 | -3504 | -2965 | -3167 | -2682 | 1032 | 2265 | -2368 | -1993 | 259 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9058 | | | | | | | | | | | | |
| 259(E | -2313 | -4187 | 2435 | 2792 | -4402 | -2263 | -1610 | -4323 | -1844 | -4194 | -3514 | -860 | -2792 | -1276 | -2693 | 882 | -2382 | -3790 | -4388 | -3377 | 260 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9055 | | | | | | | | | | | | |
| 260(E | -1939 | -3595 | 1643 | 2581 | -3872 | -2212 | -1304 | -3690 | -1146 | -3580 | -2792 | -818 | -2607 | -925 | 2340 | -1689 | -1941 | -3216 | -3731 | -2921 | 261 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9053 | | | | | | | | | | | | |
| 261(I) | -3202 | -2787 | -5004 | -4996 | -2836 | -4384 | -4440 | 3937 | -4838 | -1815 | -1871 | -4704 | -4600 | -4683 | -4704 | -4353 | -3280 | -603 | -3938 | -3661 | 262 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9050 | | | | | | | | | | | | |
| 262(H | -1017 | 2728 | -2493 | -1992 | -1270 | -2240 | 3922 | -987 | -1659 | 529 | -639 | -1791 | -2500 | -1540 | -1774 | 784 | -1071 | 839 | -1737 | -1261 | 263 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9047 | | | | | | | | | | | | |
| 263(Q | 1741 | -3277 | 2434 | -357 | -3577 | -2095 | -1155 | -3386 | -1029 | -3313 | -2481 | 1522 | -2449 | 2598 | -1654 | -1458 | -1671 | -2910 | -3496 | -2688 | 264 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9044 | | | | | | | | | | | | |
| 264(D | -3202 | -2787 | -5004 | -4996 | -2836 | -4384 | -4440 | 3937 | -4838 | -1815 | -1871 | -4704 | -4600 | -4683 | -4704 | -4353 | -3280 | -603 | -3938 | -3661 | 265 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9042 | | | | | | | | | | | | |
| 265(Q | -2715 | -3506 | -2454 | -1838 | -4264 | -3140 | -1326 | -3747 | 2319 | -3422 | -2758 | -1861 | -3215 | 3713 | -73 | -2577 | -2482 | -3480 | -3261 | -3082 | 266 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9039 | | | | | | | | | | | | |
| 266(H | 1766 | -2665 | -1250 | -679 | -3083 | -2257 | 3314 | -2738 | 2115 | -2633 | -1790 | -913 | -2340 | 1628 | -214 | -1286 | -1299 | -2357 | -2720 | -2207 | 267 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7944 | -8987 | -894 | -1115 | -701 | -1378 | -9818 | -9036 | | | | | | | | | | | | |
| 267(A | 1483 | -2544 | 1329 | 1148 | -2853 | -1866 | -632 | -2614 | -278 | -2555 | -1651 | 1353 | -2033 | -189 | 1407 | -900 | -994 | -2162 | -2727 | -2019 | 268 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7945 | -8987 | -894 | -1115 | -701 | -1378 | -9818 | -9033 | | | | | | | | | | | | |
| 268(A | 3609 | -2508 | -4184 | -4493 | 4592 | 2737 | -3989 | -4421 | -4496 | -4701 | -4051 | -3440 | -3474 | -4171 | -4253 | -2294 | -2487 | -3536 | -4484 | -4643 | 269 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -11 | -7945 | -8987 | -894 | -1115 | -701 | -1378 | -9818 | -9031 | | | | | | | | | | | | |
| 269(R | -2965 | -3547 | -3408 | -2282 | -4379 | -3379 | -1388 | -3839 | 12 | -3467 | -2835 | -2157 | -3384 | 1874 | 3734 | -2857 | -2671 | -3611 | -3250 | -3161 | 270 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9V

Table 7

| | | | | | | | | | | | | | | | | | | |
|---|---|---|---|---|---|---|---|---|---|---|---|---|---|---|---|---|---|---|
| 270(N | -1308 | -7945 | -761 | -894 | -1115 | -701 | -1378 | -9818 | -9028 | | | | | | | | | 271 |
| | -1039 | -2562 | 586 | 2367 | -2858 | -1300 | -470 | -2699 | -385 | -2652 | -1895 | 2515 | -1724 | -111 | -973 | -813 | -1067 | -2247 | -2807 | -2007 |
| | -149 | -500 | 235 | 43 | -381 | 399 | 106 | -626 | 210 | -466 | -720 | 275 | 394 | 45 | 96 | 359 | 117 | -369 | -294 | -249 |
| | -714 | -1382 | -1703 | -151 | -3331 | -2609 | -258 | -9818 | -9025 | | | | | | | | | |
| 271(N | -622 | -1477 | -200 | -357 | -2707 | 2061 | -999 | -2606 | 952 | -2696 | -1925 | 2838 | -1767 | -722 | -1374 | -664 | -868 | -1957 | -2760 | -2210 |
| | -149 | -500 | 233 | 43 | -381 | 399 | 106 | -626 | 210 | -466 | -720 | 275 | 394 | 45 | 96 | 359 | 117 | -369 | -294 | -249 |
| | -24 | -6661 | -7703 | -894 | -1115 | -156 | -3286 | -9818 | -9022 | | | | | | | | | |
| 272(S) | -828 | -2001 | -805 | 1032 | -2258 | -1836 | -533 | -1931 | -149 | -2007 | -1158 | 547 | -1941 | -119 | 1234 | 1440 | 1026 | 880 | -2282 | -1677 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9020 | | | | | | | | | |
| 273(N | -1190 | -2573 | 1355 | -283 | -2861 | 654 | -809 | -2615 | -530 | -2616 | -1754 | 2375 | -2165 | -395 | -1071 | -1062 | 1012 | -2205 | -2829 | 1781 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9017 | | | | | | | | | |
| 274(Q | 645 | -2328 | 1160 | -107 | -2646 | 495 | -476 | -2397 | -72 | -2344 | -1425 | 1283 | -1901 | 1657 | 1361 | -730 | -798 | -1950 | -2514 | -1827 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9014 | | | | | | | | | |
| 275(M | -816 | -2072 | 1026 | 1269 | -2307 | -1806 | 491 | 649 | -121 | -2050 | 1968 | 1387 | -1908 | -67 | -614 | -740 | 927 | -1644 | -2309 | -1678 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9011 | | | | | | | | | |
| 276(C | 897 | 2636 | -1616 | 1312 | -2623 | 1770 | -1334 | -2281 | -1102 | -2451 | -1631 | -1244 | -2278 | -1004 | -1507 | -1024 | 1250 | -1839 | -2782 | -2281 |
| | -149 | -500 | 233 | 43 | -381 | 399 | 106 | -626 | 210 | -466 | -720 | 275 | 394 | 45 | 96 | 359 | 117 | -369 | -294 | -249 |
| | -242 | -7945 | -2754 | -894 | -1115 | -701 | -1378 | -9818 | -9008 | | | | | | | | | |
| 277(S) | -911 | -1183 | -1682 | 1126 | -1300 | -2191 | -1054 | 1565 | -1062 | -1045 | -424 | -1278 | -2298 | -937 | -1360 | 1632 | -874 | 1229 | -1746 | -1317 |
| | -149 | -500 | 233 | 43 | -381 | 399 | 106 | -626 | 210 | -466 | -720 | 275 | 394 | 45 | 96 | 359 | 117 | -369 | -294 | -249 |
| | -13 | -7716 | -8758 | -894 | -1115 | -374 | -2130 | -9818 | -9006 | | | | | | | | | |
| 278(R | -2689 | -3297 | 3482 | -2098 | -4001 | -3278 | -1187 | 1210 | 1825 | -3091 | -2443 | -1979 | -3214 | -777 | 3313 | -2610 | -2385 | -3099 | -3035 | -2916 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9003 | | | | | | | | | |
| 279(P | -4497 | 4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -9000 | | | | | | | | | |
| 280(R | 778 | -2256 | -849 | 1049 | 1188 | -1910 | -526 | 1217 | -1062 | -2239 | -1363 | -569 | -1997 | -87 | 2088 | -847 | -872 | -1870 | -2431 | -1819 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8997 | | | | | | | | | |
| 281( | -4593 | -3601 | -4995 | -5296 | 213 | -4817 | -1247 | -3585 | -4805 | -2925 | -3000 | -3610 | -4749 | -3723 | -4255 | -4202 | -4477 | -3731 | 5803 | 2567 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8994 | | | | | | | | | |

FIG. 9W

Table 7

| 282(P | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 284 |
|---|---|---|---|---|---|---|---|---|---|---|---|---|---|---|---|---|---|---|---|---|---|
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8992 | | | | | | | | | | | | |
| 283(M | -2922 | -2503 | -5243 | -4802 | -1395 | -4799 | -3922 | 1630 | -4451 | -67 | 4721 | -4580 | -4460 | -3821 | -4212 | -4136 | -2877 | -524 | -2992 | -2887 | 285 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8989 | | | | | | | | | | | | |
| 284(I) | -2495 | -2001 | -5129 | -4756 | -2240 | -4897 | -4552 | 2929 | -4659 | 812 | -991 | -4553 | -4608 | -4412 | -4697 | -4228 | -2473 | 2322 | -3865 | -3522 | 286 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8986 | | | | | | | | | | | | |
| 285(I) | -2456 | -1959 | -5125 | -4808 | -2579 | -4919 | -4900 | 3028 | -4754 | -1349 | -1292 | -4605 | -4688 | -4684 | -4898 | -4291 | -2452 | 2714 | -4288 | -3786 | 287 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8983 | | | | | | | | | | | | |
| 286(M | 848 | -1916 | -4474 | -3859 | 1726 | -3859 | -2665 | -466 | -3512 | 2254 | 2464 | -3496 | -3662 | -2906 | -3258 | -2991 | -2116 | -895 | -2138 | -1962 | 288 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8980 | | | | | | | | | | | | |
| 287(R | -4488 | -4181 | -4789 | -4318 | -5193 | -4148 | -3436 | -5568 | -2393 | -5152 | -4748 | -4156 | -4479 | -3286 | -4202 | -4614 | -4467 | -5273 | -4267 | -4649 | 289 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8977 | | | | | | | | | | | | |
| 288(T | -1068 | -1511 | -3017 | -2766 | -2440 | -2076 | -2321 | -1926 | -2515 | 691 | -1630 | -2213 | -2655 | -2340 | 4202 | -2580 | 984 | -1612 | -2890 | -2538 | 290 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8974 | | | | | | | | | | | | |
| 289(P | -4497 | -4117 | -4899 | -5251 | -5560 | -4139 | -4798 | -6328 | -5454 | -5976 | -5744 | -5026 | 4302 | -5328 | -5104 | -4798 | -4844 | -5739 | -4665 | -5484 | 291 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8972 | | | | | | | | | | | | |
| 290(K | -4125 | -4091 | -4017 | -3615 | -5251 | -4139 | -3960 | -5182 | 3972 | -4825 | -4345 | -3552 | -4249 | -2709 | -5104 | -4154 | -4044 | -4895 | -4132 | -4389 | 292 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8969 | | | | | | | | | | | | |
| 291(G | -4088 | -3924 | -4774 | -5139 | -5615 | 3825 | -4753 | -6303 | -5453 | -6014 | -5662 | -4812 | -4539 | -2403 | -5106 | -4370 | -4472 | -5527 | -4696 | -5561 | 293 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8966 | | | | | | | | | | | | |
| 292( | -3761 | -4018 | -3442 | -2596 | -3886 | 2277 | -2358 | -4281 | 1706 | -3948 | -3562 | -3262 | -4095 | -3472 | -1546 | -3781 | -3651 | -4139 | 5825 | 2093 | 294 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8963 | | | | | | | | | | | | |
| 293(T | -1328 | -1922 | -3470 | 3733 | -4307 | 3097 | -3460 | -4117 | -3841 | -4377 | -3512 | -2726 | -2930 | -3445 | -3723 | -1571 | 3260 | -3014 | -4415 | -4352 | 295 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8960 | | | | | | | | | | | | |
| 294(C | -1973 | 4291 | -4548 | -4851 | 4702 | 3097 | -4084 | -4671 | -4689 | -4886 | -4115 | -3509 | -3445 | -4310 | -4354 | -2238 | -2433 | -3616 | -4524 | -4782 | 296 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9X

Table 7

| | | | | | | | | | | | | | | | | | | | |
|---|---|---|---|---|---|---|---|---|---|---|---|---|---|---|---|---|---|---|---|
| | -12 | -7945 | -8987 | -894 | -1115 | -701 | -1378 | -9818 | -8957 | | | | | | | | | | |
| 295(P | -4497 | 4117 | 4899 | -5251 | 5560 | 4798 | -6328 | 5454 | | -5976 | -5741 | -5026 | 4302 | -5328 | -5104 | -4798 | -4844 | -5739 | -4665 | -5484 | 297 |
| | -149 | -500 | 233 | 43 | -381 | 106 | -626 | 210 | | -466 | -720 | 275 | 394 | 45 | 96 | 359 | 117 | -369 | -294 | -249 |
| | -12 | -7945 | -8987 | -894 | -1115 | -701 | -1378 | -9818 | -8954 | | | | | | | | | | |
| 296(K | -2049 | -3206 | 1214 | -1125 | 3777 | -2660 | -1057 | -3338 | 3118 | -3117 | -2350 | -1305 | -2771 | -635 | 1683 | -1896 | -1900 | -2990 | -3089 | -2711 | 298 |
| | -149 | -500 | 233 | 43 | -381 | 106 | -626 | 210 | | -466 | -720 | 275 | 394 | 45 | 96 | 359 | 117 | -369 | -294 | -249 |
| | -12 | -7945 | -8987 | -894 | -1115 | -701 | -1378 | -9818 | -8951 | | | | | | | | | | |
| 297(Y | -3980 | -3319 | -4251 | 999 | 2912 | -4528 | -1135 | -3159 | -4198 | -2674 | -2627 | -3261 | -4474 | -3325 | -3891 | -3769 | -3878 | -3246 | -434 | 3896 | 299 |
| | -1892 | -7945 | -465 | -894 | -1115 | -701 | -1378 | -9818 | -8948 | -466 | -720 | 275 | 394 | 45 | 96 | 359 | 117 | -369 | -294 | -249 |
| 298(N | -682 | -1389 | -43 | -192 | -1821 | -1114 | -672 | -2026 | -553 | -2169 | -1573 | 3502 | -1613 | -485 | -863 | -706 | -866 | -1616 | -1943 | -1374 | 300 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8945 | | | | | | | | | | |
| 299(D | -1183 | -2113 | 3476 | 202 | -2559 | -1197 | -709 | -2583 | -900 | -2640 | -2095 | -138 | -1700 | -471 | -1494 | -1021 | -1294 | -2203 | -2437 | -1969 | 301 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8943 | | | | | | | | | | |
| 300( | -2006 | -1640 | -2485 | -2452 | 132 | -2122 | -859 | -1689 | -1966 | -1425 | -1294 | -2093 | -2439 | -1935 | -1852 | -2230 | -2075 | -1731 | 5734 | 501 | 302 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8940 | | | | | | | | | | |
| 301(S | 87 | 526 | -885 | -918 | -1797 | -699 | 997 | -1679 | -970 | -1948 | -1267 | -663 | -1335 | -874 | -1147 | 2826 | -252 | -1082 | -2036 | -1577 | 303 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8937 | | | | | | | | | | |
| 302(G | -822 | -1159 | -1384 | -1565 | 2531 | 3361 | -1634 | -2586 | -1803 | -2721 | -2161 | -1396 | -1832 | -1670 | -1866 | -1023 | -1160 | -1997 | -2255 | -2352 | 304 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8934 | | | | | | | | | | |
| 303(P | -1003 | -1278 | -1425 | -1532 | -2259 | -1370 | -1531 | -2247 | -1572 | -2349 | -1911 | -1434 | 3795 | -1555 | -1648 | -1199 | -1287 | -1861 | -2108 | -2096 | 305 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -218 | -9818 | -8931 | | | | | | | | | | |
| 304(K | -1075 | -1727 | -849 | 488 | -2222 | -1560 | -298 | -1928 | 3141 | -1906 | -1299 | -589 | -1788 | 39 | 576 | -1050 | -1018 | -1673 | -1848 | -1572 | 306 |
| | -149 | -500 | 233 | 43 | -381 | 399 | 106 | -626 | 210 | -466 | -720 | 275 | 394 | 45 | 96 | 359 | 117 | -369 | -294 | -249 |
| | -35 | -6088 | -7130 | -894 | -1115 | -2832 | -3510 | -9818 | -8928 | | | | | | | | | | |
| 305(V | -2351 | -1948 | -4836 | -4325 | 1729 | -4359 | -3437 | 1662 | -4074 | 1144 | -429 | -4011 | -4122 | -3586 | -3910 | -3565 | -2297 | 2576 | -2861 | -2632 | 307 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8925 | | | | | | | | | | |
| 306(D | -2623 | -4424 | 3671 | -647 | -4716 | -2401 | -1896 | -4807 | -2315 | -4650 | -4093 | 1964 | -2996 | -1602 | -3278 | -2267 | -2747 | -4224 | -4722 | -3696 | 308 |
| | -12 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8922 | | | | | | | | | | |

FIG. 9Y

Table 7

| | | | | | | | | | | | | | | | | | | | | |
|---|---|---|---|---|---|---|---|---|---|---|---|---|---|---|---|---|---|---|---|---|
| 307(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 309 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1892 | -7945 | -465 | -894 | -1115 | -701 | -1378 | -9818 | -8919 | | | | | | | | | | | | |
| 308(K) | -1075 | -1727 | -849 | -488 | -2222 | -1560 | -298 | -1928 | 3141 | -1906 | -1299 | -589 | -1788 | 39 | 576 | -1050 | -1018 | -1673 | -1848 | -1572 | 310 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -35 | -6088 | -7130 | -894 | -1115 | -2832 | -218 | -9818 | -8916 | | | | | | | | | | | | |
| 309(G) | -822 | -1159 | -1384 | -1565 | -2531 | 3361 | -1634 | -2586 | -1803 | -2721 | -2161 | -1396 | -1832 | -1670 | -1866 | -1023 | -1160 | -1997 | -2255 | -2352 | 311 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -35 | -6088 | -7130 | -894 | -1115 | -133 | -3510 | -9818 | -8913 | | | | | | | | | | | | |
| 310(M) | -972 | -1126 | -2062 | -1461 | -1092 | -2307 | 2087 | -624 | 1939 | 525 | 2294 | -1457 | -2364 | -1036 | -1244 | -1332 | -906 | -1529 | -1141 | 312 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8910 | | | | | | | | | | | | |
| 311(K) | -1820 | -2479 | -2019 | -1558 | 1878 | -2659 | -1288 | -2471 | 2648 | -2477 | -1862 | -1639 | 2280 | -1101 | -838 | -1862 | -1798 | -2256 | -2259 | -1515 | 313 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8907 | | | | | | | | | | | | |
| 312(T) | -1151 | -994 | -3207 | -2614 | 1014 | -2726 | -1631 | 1486 | -2292 | 872 | -195 | 1131 | -2765 | -1990 | -2222 | -1813 | 1899 | 1286 | -1587 | -1232 | 314 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8904 | | | | | | | | | | | | |
| 313(E) | 4205 | -4417 | -2343 | 3901 | 5349 | -3698 | -3534 | -5837 | -3838 | -5561 | 5237 | 3039 | -4218 | 3453 | 4201 | -4072 | -4352 | -5409 | -4640 | -4860 | 315 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8901 | | | | | | | | | | | | |
| 314(G) | -2817 | -3261 | -2719 | -3002 | -3965 | 3464 | 2847 | -5005 | -3386 | -4897 | -4328 | -2988 | -3770 | -3306 | -3516 | -2944 | -3148 | -4263 | -3982 | -3566 | 316 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8898 | | | | | | | | | | | | |
| 315(F) | -106 | -1561 | -3154 | -2946 | 2579 | -2093 | -2290 | -2229 | -2773 | -2503 | -1842 | -2289 | -2698 | -2501 | -2812 | 2488 | 1579 | -1836 | -2597 | -1956 | 317 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8895 | | | | | | | | | | | | |
| 316( | -4550 | -3570 | -5043 | -5348 | 3560 | -4834 | -1253 | -3407 | -4915 | -2729 | -2820 | -3625 | -4750 | -3739 | -4322 | -4199 | -4435 | -3608 | 4998 | 679 | 318 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8892 | | | | | | | | | | | | |
| 317(R) | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 319 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8889 | | | | | | | | | | | | |
| 318(A) | 3015 | -1667 | -3723 | -3946 | -4169 | -1935 | -3415 | -3952 | -3869 | -4231 | -3312 | -2607 | -2729 | -3434 | -3685 | 1976 | -1516 | -2782 | -4395 | -4270 | 320 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8886 | | | | | | | | | | | | |
| 319(H) | -4836 | -4275 | -4356 | -4629 | -3663 | -4242 | 5422 | -5932 | -4492 | -5436 | -5298 | -4579 | -4696 | -4620 | -4352 | -5005 | -5030 | -5648 | -3750 | -3259 | 321 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9Z

Table 7

| | | | | | | | | | | | | | | | | | | | | | | |
|---|---|---|---|---|---|---|---|---|---|---|---|---|---|---|---|---|---|---|---|---|---|---|
| 320(Q | -12 | -7945 | -8987 | -894 | -1115 | -701 | -1378 | -9818 | -8883 | | | | | | | | | | | | | |
| | -4207 | 4117 | -3531 | -3731 | -4752 | -3930 | -3721 | -3395 | | -5179 | -4897 | -3823 | -4399 | 4556 | -3405 | -4301 | -4380 | -5208 | -4301 | -4384 | 322 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8880 | | | | | | | | | | | | |
| 321(V | -2838 | -2616 | -4834 | -4880 | -3213 | -3955 | -4416 | -4757 | | -2310 | -2253 | -4383 | -4345 | -4643 | -4642 | -3732 | -3007 | 3763 | -4157 | -3886 | 323 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8877 | | | | | | | | | | | | |
| 322(P | 4497 | -4117 | -4899 | -5251 | -5560 | -4139 | -4798 | -5454 | | -5976 | -5741 | -5026 | 4302 | -5328 | -5104 | -4798 | -4844 | -5739 | -4665 | -5484 | 324 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8873 | | | | | | | | | | | | |
| 323(L | -3647 | -3060 | -5937 | -5371 | -1118 | -5682 | -4332 | -5087 | | 2996 | 2562 | -5429 | -4784 | -3924 | -4592 | -5073 | -3493 | -1434 | -2915 | -3081 | 325 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8870 | | | | | | | | | | | | |
| 324(A | 1628 | -2000 | -1147 | -671 | -2849 | 708 | -956 | 1413 | | -2602 | -1707 | -874 | 1246 | -539 | -1044 | 862 | -977 | -2054 | -2809 | -2207 | 326 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8867 | | | | | | | | | | | | |
| 325(G | -994 | -1140 | -2933 | -2481 | -1432 | 1651 | -1741 | -2217 | | -844 | -640 | -2068 | -2570 | -1955 | -2226 | -1096 | 1103 | -889 | -1926 | -1575 | 327 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8864 | | | | | | | | | | | | |
| 326(M | 1630 | -1391 | 944 | -805 | -1486 | -2021 | -819 | -1063 | | 342 | 2038 | 972 | -2298 | -594 | -1070 | 829 | -812 | -889 | -1808 | -1343 | 328 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8861 | | | | | | | | | | | | |
| 327(R | 741 | -2275 | -1345 | -792 | -2855 | -2120 | 2241 | -225 | | -2528 | -1693 | -987 | -2298 | 476 | 2769 | 943 | -1193 | -2130 | -2695 | -2176 | 329 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8858 | | | | | | | | | | | | |
| 328(E | -921 | -2389 | 1203 | 1772 | -2695 | -1817 | -532 | 1276 | | -2398 | -1488 | -451 | -1950 | -84 | -661 | -792 | 1210 | -2005 | -2575 | 1454 | 330 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8855 | | | | | | | | | | | | |
| 329(N | -1665 | -3235 | 1720 | -369 | -3518 | -2098 | 2328 | -1031 | | -3275 | -2450 | 2949 | -2451 | -767 | -1649 | -1460 | 1173 | -2871 | -3460 | -2660 | 331 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8852 | | | | | | | | | | | | |
| 330(M | -984 | -1840 | -1021 | 1102 | -2105 | -1976 | -854 | -582 | | -1892 | 2223 | -850 | 1910 | -518 | -1007 | -1020 | 1988 | -1453 | -2293 | -1758 | 332 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8849 | | | | | | | | | | | | |
| 331(A | 2196 | -2790 | -511 | 1218 | -3438 | 973 | -1226 | -1068 | | -3198 | -2356 | 1800 | -2422 | -839 | -1642 | -1356 | -1536 | -2702 | -3401 | -2670 | 333 |
| | -149 | -500 | 233 | 43 | -381 | 399 | 106 | 210 | | -466 | -720 | 275 | 394 | 45 | 96 | 359 | 117 | -369 | -294 | -249 | |
| | -12 | -7945 | -8987 | -894 | -1115 | -701 | -1378 | -9818 | -8845 | | | | | | | | | | | | |

FIG. 9AA

Table 7

| | | | | | | | | | | | | | | | | | | | |
|---|---|---|---|---|---|---|---|---|---|---|---|---|---|---|---|---|---|---|---|
| 332(H) | -1254 | -2578 | 716 | 424 | -2897 | -2040 | 3715 | -2651 | 343 | -2622 | -1770 | 1388 | -2228 | 1875 | 752 | -1137 | 1164 | 2249 | 2782 | -2139 | 334 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8842 | | | | | | | | | | | | |
| 333(L) | -2624 | -2340 | -4474 | -3875 | 1811 | -4126 | -2401 | -789 | -3050 | 2542 | -178 | -3525 | -3908 | -2863 | 1521 | -3305 | -2528 | -1300 | -1886 | -1260 | 335 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8839 | | | | | | | | | | | | |
| 334(N) | -994 | -2499 | 1168 | 1208 | -2810 | -1843 | -590 | -2571 | 1159 | -2510 | -1599 | 1604 | 1101 | 1558 | -751 | -854 | -943 | -2117 | -2678 | -1972 | 336 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8836 | | | | | | | | | | | | |
| 335(Q) | -1074 | -1608 | -1378 | 1055 | -1583 | -2212 | -948 | -1034 | -735 | 1334 | -653 | -1095 | -2304 | 2285 | -1076 | -1227 | -1014 | 962 | -1974 | -1519 | 337 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8833 | | | | | | | | | | | | |
| 336(L) | -3687 | -3085 | -5735 | -5323 | 1918 | -5462 | -3361 | -783 | -5056 | 2956 | -82 | -4983 | -4746 | -3886 | -4547 | -4848 | -3542 | -1585 | -2287 | -1717 | 338 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8830 | | | | | | | | | | | | |
| 337(E) | -1470 | -2699 | -964 | 2371 | -3064 | -2232 | -901 | -2597 | 2215 | -2668 | -1868 | -905 | -2396 | -486 | -559 | -1359 | -1400 | 909 | -2856 | -2297 | 339 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8827 | | | | | | | | | | | | |
| 338(E) | 690 | -2696 | 1523 | 1869 | -2999 | 734 | -738 | -2770 | 1285 | -2707 | -1812 | -539 | -2120 | -303 | -973 | -1012 | -1128 | -2313 | -2880 | -2153 | 340 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8823 | | | | | | | | | | | | |
| 339( | -5598 | -4432 | -5385 | -5722 | -3380 | -4524 | -4140 | -5941 | -5643 | -5318 | -5354 | -5427 | -4938 | -5474 | -5178 | -5909 | -5751 | -5890 | 6275 | -2993 | 341 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8820 | | | | | | | | | | | | |
| 340(M) | -3596 | -3028 | -5873 | -5313 | -1121 | -5593 | -4267 | -607 | -5011 | 2392 | 4057 | -5338 | -4750 | -3897 | -4538 | -4973 | -3450 | -1415 | -2899 | -3039 | 342 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8817 | | | | | | | | | | | | |
| 341(K) | -991 | -2413 | -818 | 1144 | -2767 | -1924 | -530 | -2487 | 1895 | -2410 | -1508 | 1562 | -2015 | -77 | 1221 | -869 | 1088 | -2056 | -2547 | -1918 | 343 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8814 | | | | | | | | | | | | |
| 342(S) | -1944 | -2458 | -3696 | -4011 | -4410 | -2644 | -3753 | -4675 | -4191 | -4807 | -4070 | -3198 | -3384 | -3886 | -4051 | 3656 | -2393 | -3615 | -4374 | -4307 | 344 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8811 | | | | | | | | | | | | |
| 343(Y) | -4791 | -3935 | -4914 | -5231 | -815 | -4530 | -4357 | -5024 | 1895 | -3745 | -3807 | -4206 | -4772 | -4328 | -4584 | -4677 | -4837 | -4435 | -1477 | 4857 | 345 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8807 | | | | | | | | | | | | |
| 344(K) | -2113 | -3150 | -2249 | -1388 | -3797 | -2829 | -992 | -3281 | 2710 | -3026 | -2265 | 1725 | -2831 | 1860 | 1625 | -1985 | -1911 | -2964 | -2962 | -2675 | 346 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9BB

Table 7

| | | | | | | | | | | | | | | | | | | | |
|---|---|---|---|---|---|---|---|---|---|---|---|---|---|---|---|---|---|---|---|
| -12 | -7945 | -8987 | -894 | -1115 | -701 | -1378 | -9818 | -8804 | | | | | | | | | | | |
| 345P | -2272 | 3432 | -4625 | -4892 | -4644 | -2928 | -4139 | -4609 | -4669 | -4819 | -4180 | -3725 | 3909 | -4404 | -4368 | -2543 | -2718 | -3748 | -4454 | -4686 | 347 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8801 | | | | | | | | | | | |
| 346E | -2460 | -4036 | -460 | 3371 | -4348 | -2457 | -1702 | -4275 | -1584 | -4118 | -3462 | -1104 | -2946 | 2051 | -2090 | -2167 | -2503 | -3804 | -4163 | -3385 | 348 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8798 | | | | | | | | | | | |
| 347E | -2181 | -3963 | 1851 | 3002 | 4213 | -2236 | -1529 | -4092 | -1674 | -3990 | -3269 | -843 | -2732 | -1182 | -2455 | -1882 | 1292 | -3581 | -4185 | -3235 | 349 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8794 | | | | | | | | | | | |
| 348L | -3686 | -3084 | -5725 | -5318 | 2066 | -5451 | -3323 | -791 | -5050 | 2922 | -90 | -4961 | -4743 | -3882 | -4541 | -4834 | -3541 | -1590 | -2260 | -1671 | 350 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8791 | | | | | | | | | | | |
| 349(F) | -3772 | -3147 | -5332 | -5198 | 4004 | -5042 | -2246 | -1256 | -4859 | 1259 | -621 | -4264 | -4667 | -3786 | -4369 | -4411 | -3663 | -1931 | -1412 | -419 | 351 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8788 | | | | | | | | | | | |
| 350(D | -2611 | -4416 | 3402 | -640 | -4705 | -2395 | -1885 | -4789 | -2297 | -4633 | -4071 | 2681 | -2988 | -1589 | -3255 | -2256 | -2733 | -4207 | -4711 | -3684 | 352 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8785 | | | | | | | | | | | |
| 351(E | 2436 | -2868 | -924 | 2744 | -4080 | -2309 | -2015 | -3815 | -2053 | -3929 | -3209 | -1413 | -2875 | -1718 | -2576 | -1853 | -2106 | -3206 | -4090 | -3471 | 353 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8781 | | | | | | | | | | | |
| 352H | 692 | -2743 | 2175 | -223 | -3038 | -1936 | 2515 | -2810 | 480 | -2751 | -1863 | 1409 | -2154 | 1594 | -1031 | -1057 | -1179 | -2357 | -2927 | -2196 | 354 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8778 | | | | | | | | | | | |
| 353G | -2929 | -3168 | -3518 | -3782 | -1975 | 3489 | -2803 | -4394 | -4019 | -4184 | -3856 | -3400 | -3940 | -3733 | -3967 | -3094 | -3258 | -3950 | -2519 | 2220 | 355 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8775 | | | | | | | | | | | |
| 354(S) | 743 | -1505 | -1390 | -843 | -1747 | -1981 | -884 | -1345 | -674 | 588 | -830 | -999 | -2148 | -615 | 1093 | 1645 | 1025 | -1123 | -2016 | -1540 | 356 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8771 | | | | | | | | | | | |
| 355P | -2511 | -2204 | -4688 | -4170 | -1213 | -4215 | -3207 | 1516 | -3824 | 2221 | 98 | 3895 | 2348 | -3271 | -3624 | 3424 | -2456 | -677 | -2586 | -2462 | 357 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8768 | | | | | | | | | | | |
| 356K | -1302 | -1414 | -2419 | -1840 | -1577 | -2693 | -1530 | 1325 | 2435 | -1189 | -660 | -1855 | -2761 | -1446 | -1616 | -1749 | 1313 | 1240 | -2101 | -1697 | 358 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8765 | | | | | | | | | | | |

FIG. 9CC

Table 7

| | | | | | | | | | | | | | | | | | | | |
|---|---|---|---|---|---|---|---|---|---|---|---|---|---|---|---|---|---|---|---|
| 357(E | 687 | -2542 | -623 | 1957 | -2905 | -1944 | -710 | -2641 | 1433 | -2592 | -1707 | -604 | 1914 | -274 | -748 | -998 | -1082 | -2205 | -2761 | -2094 | 359 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8762 | | | | | | | | | | | |
| 358(E | -2040 | -3771 | 1647 | 2163 | -4056 | 1964 | -1435 | -3921 | -1508 | -3821 | -3060 | -809 | -2658 | -1075 | -2248 | 864 | -2081 | -3410 | -4011 | -3098 | 360 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8758 | | | | | | | | | | | |
| 359(I) | -2526 | -2113 | -4983 | -4447 | 1598 | -4503 | -3494 | 2404 | -4186 | 1749 | -242 | -4162 | -4188 | -3576 | -3962 | -3711 | -2456 | 1420 | -2790 | -2649 | 361 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8755 | | | | | | | | | | | |
| 360(R | -1519 | -2765 | -1433 | 1043 | -3230 | -2362 | -786 | -2853 | 1407 | -2712 | -1878 | -1010 | -2424 | -346 | 2271 | -1399 | 2090 | -2477 | -2766 | -2295 | 362 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8752 | | | | | | | | | | | |
| 361(A | 2266 | -3817 | 1712 | 2253 | -4133 | -2221 | -1507 | -3996 | -1626 | -3174 | -845 | -3910 | -2706 | -1158 | -2386 | -1834 | -2166 | -3485 | -4107 | -3184 | 363 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8748 | | | | | | | | | | | |
| 362(F) | -885 | -3196 | 2253 | -2582 | 2439 | -2571 | 2436 | 1238 | -2213 | 706 | 10 | -2148 | -2609 | -1856 | -2072 | -1653 | 1024 | -245 | -1243 | -832 | 364 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8745 | | | | | | | | | | | |
| 363(M | -1042 | -1084 | -3069 | -2501 | -1009 | -2553 | -1611 | 411 | -2186 | 950 | 2374 | -2167 | -2680 | -1891 | -2150 | -1666 | 1057 | -397 | -1620 | -1292 | 365 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8741 | | | | | | | | | | | |
| 364(P | -4497 | 2115 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 366 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8738 | | | | | | | | | | | |
| 365(K | -1362 | -2752 | -891 | 1110 | -3142 | -2149 | -769 | -2837 | 2560 | -2727 | -1865 | -782 | 1373 | 1618 | 441 | -1221 | -1281 | -2420 | -2829 | -2241 | 367 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8735 | | | | | | | | | | | |
| 366(G | 1022 | -1909 | -2732 | -2555 | -3858 | 2953 | -2403 | -3572 | -1903 | -3702 | -2863 | -2142 | -2736 | -2152 | 1711 | -1431 | -1592 | -2728 | -3841 | -3572 | 368 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8731 | | | | | | | | | | | |
| 367(E | -1926 | -3649 | 1536 | 2753 | -3890 | -2165 | -1327 | -3735 | -1325 | -3640 | -2851 | 1567 | -2586 | -953 | -2024 | -1665 | 1092 | -3244 | -3826 | -2947 | 369 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8728 | | | | | | | | | | | |
| 368(K | -2153 | -2373 | -3052 | -2232 | 1767 | 3262 | -1649 | 1215 | 3030 | 859 | 2514 | -2219 | -3217 | -1370 | 831 | -2425 | -2024 | -1487 | -2493 | -2241 | 370 |
| | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8725 | | | | | | | | | | | |
| 369(R | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 371 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 9DD

Table 7

| | | | | | | | | | | | | | | | | | | | |
|---|---|---|---|---|---|---|---|---|---|---|---|---|---|---|---|---|---|---|---|
| 370(M) | -12 | -7945 | -8987 | -894 | -1115 | -701 | -1378 | -9818 | -8721 | | | | | | | | | | |
| | | -3269 | -2747 | -5652 | -5079 | -1177 | -5325 | -4102 | 1525 | -4829 | 1255 | 4460 | 5012 | -4616 | -3829 | -4428 | -4616 | -3145 | -974 | -2895 | -3004 | 372 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8718 | | | | | | | | | | |
| 371(G) | 2030 | -1651 | -3665 | -3855 | -4195 | -5325 | -3377 | -3993 | -3822 | -4242 | -3302 | -2568 | -2705 | -3371 | -3670 | 1117 | -1491 | -2786 | -4410 | -4294 | 373 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8714 | | | | | | | | | | |
| 372(A) | 2364 | -1861 | -1953 | -1763 | -3466 | -1952 | -1976 | -3199 | -1760 | -3331 | -2471 | -1666 | -2522 | 1987 | -2080 | 1936 | -1374 | -2468 | -3555 | -3102 | 374 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8711 | | | | | | | | | | |
| 373(N) | -1618 | -2562 | -1583 | -1250 | -3475 | -2356 | -1296 | -3134 | -474 | -3082 | -2296 | 3378 | -2657 | -908 | 1726 | -1605 | 1129 | -2676 | -3159 | -2725 | 375 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8707 | | | | | | | | | | |
| 374(P) | -1913 | -2274 | -2279 | -2086 | -1517 | -2783 | 2782 | -2081 | -1589 | 560 | -1612 | -2058 | 3317 | -1785 | -1716 | -2097 | -1976 | -2000 | -2063 | -1260 | 376 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8704 | | | | | | | | | | |
| 375(H) | -929 | 2010 | -791 | 1272 | 2044 | -1913 | 2963 | -1853 | -298 | -1959 | -1145 | 1363 | -2029 | -239 | -766 | -888 | -872 | 799 | -2186 | 1512 | 377 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8700 | | | | | | | | | | |
| 376(A) | 2877 | -1669 | -3800 | 3976 | -4022 | -1962 | -3382 | -3596 | -3795 | -3999 | -3156 | -2631 | -2746 | -3409 | -3616 | -1328 | 2512 | -2627 | -4284 | -4151 | 378 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8697 | | | | | | | | | | |
| 377(N) | -3122 | -3352 | -2228 | -2577 | -596 | -3446 | -1619 | -3701 | -2981 | -3309 | -3133 | 3888 | -3831 | -2693 | -3130 | -3026 | -3247 | -3561 | -4184 | -2585 | 379 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8693 | | | | | | | | | | |
| 378(G) | -2018 | -2692 | -1922 | -2271 | -4544 | 3363 | -2969 | -4678 | -3249 | -4731 | -3990 | 1984 | -3232 | -2825 | -3564 | -2140 | -2400 | -3690 | -4460 | -4184 | 380 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8690 | | | | | | | | | | |
| 379(G) | -1257 | -1874 | -3207 | -3523 | -4341 | 3341 | -3408 | -4248 | -3853 | -4463 | -3557 | -2605 | -2866 | 3402 | -3760 | 1410 | -1823 | -3031 | -4475 | -4358 | 381 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8687 | | | | | | | | | | |
| 380(Y) | -1236 | -3220 | 1254 | -2594 | -757 | -2737 | -1473 | -388 | -2061 | 1865 | -99 | -2233 | -2760 | -1870 | 1132 | -1823 | 1244 | -1376 | 2076 | 382 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8683 | | | | | | | | | | |
| 381(L) | -2379 | -2141 | -1100 | -3407 | -1292 | -3975 | -2923 | 1518 | -3405 | 2543 | -203 | -3359 | -3842 | -2943 | -3392 | -3194 | -2319 | -538 | -2579 | -2378 | 383 |
| | | -149 | -500 | 233 | 43 | -381 | 399 | 106 | -626 | 210 | -466 | -720 | 275 | 394 | 45 | 96 | 359 | 117 | -369 | -294 | -249 |
| | -12 | -7945 | -8987 | -894 | -1115 | -701 | -1378 | -9818 | -8679 | | | | | | | | | | |

FIG. 9EE

Table 7

| | | | | | | | | | | | | | | | | | | | | |
|---|---|---|---|---|---|---|---|---|---|---|---|---|---|---|---|---|---|---|---|---|
| 382(R | -1224 | -1996 | -1644 | -1058 | 2408 | -2207 | -1005 | 2022 | -378 | 315 | -1393 | -1189 | 1416 | -662 | 2668 | 937 | -1215 | -1747 | -2459 | -2006 | 384 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -288 | -7945 | -2519 | -894 | -1115 | -701 | -1378 | -9818 | -8676 | | | | | | | | | | | | |
| 383(R | -1347 | 2594 | 872 | 1389 | -3097 | -2078 | 754 | -2768 | 37 | -2671 | -1846 | -784 | -2259 | 333 | 2876 | 1137 | -1287 | -2364 | -2765 | -2230 | 385 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7671 | -8713 | -894 | -1115 | -1555 | -600 | -9818 | -8672 | | | | | | | | | | | | |
| 384(N | -1422 | -3052 | 1734 | 1461 | -3326 | 980 | -901 | -3136 | -759 | -3056 | -2213 | 1864 | -2210 | -500 | -1385 | 1028 | -1413 | -2660 | 3236 | -2429 | 386 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7671 | -8714 | -894 | -1115 | -345 | -2232 | -9818 | -8669 | | | | | | | | | | | | |
| 385(L | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 387 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8665 | | | | | | | | | | | | |
| 386(K | -1622 | -2790 | -1624 | 1030 | -3260 | -2461 | -828 | -2846 | 2708 | -2716 | -1905 | -1116 | -2506 | -393 | 1496 | -1511 | -1487 | 892 | -2768 | -2339 | 388 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8662 | | | | | | | | | | | | |
| 387(M | -1888 | -1623 | -4198 | -3600 | -1092 | -3572 | -2482 | -158 | -3255 | 2140 | 2397 | -3210 | -3470 | -2776 | -3059 | -2699 | 1034 | 1479 | -2114 | -1890 | 389 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8658 | | | | | | | | | | | | |
| 388(P | -4497 | 4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 390 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8655 | | | | | | | | | | | | |
| 389(D | -2522 | -4504 | 3422 | 1446 | -4683 | 938 | -1750 | -4661 | -2127 | -4504 | -3910 | -909 | -2894 | -1438 | -3092 | -2147 | -2619 | 4102 | -4695 | -3603 | 391 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8651 | | | | | | | | | | | | |
| 390( | -3715 | -3061 | -5054 | -5000 | 2784 | -4779 | -1574 | -1778 | -4602 | 1668 | -1132 | -3738 | -4524 | -3553 | -4110 | -4005 | -3593 | -2304 | 4571 | 289 | 392 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8647 | | | | | | | | | | | | |
| 391(H | -1137 | -2529 | 1169 | -405 | -2911 | -2042 | 2148 | -2611 | 1514 | -2512 | -1626 | -678 | -2128 | 1722 | 2034 | -1013 | -1053 | -2189 | -2623 | -2031 | 393 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8644 | | | | | | | | | | | | |
| 392(Q | -1523 | -3117 | 2166 | 1365 | -3403 | -2057 | -1004 | -3194 | 1438 | -3110 | -2253 | -667 | -2351 | 2526 | -1325 | -1325 | -1499 | -2728 | -3276 | -2509 | 394 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8987 | -894 | -1115 | -701 | -1378 | -9818 | -8640 | | | | | | | | | | | | |
| 393(Y | -4598 | -3559 | -5006 | -5329 | 2257 | -4898 | 2594 | -3515 | -4887 | -2848 | -2926 | -3523 | -4759 | -3654 | -4280 | -4143 | -4453 | -3662 | -366 | 4237 | 395 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8988 | -894 | -1115 | -701 | -1378 | -9818 | -8637 | | | | | | | | | | | | |
| 394(A | 2380 | -2381 | -1061 | 1282 | -3846 | 2045 | -1941 | -3614 | -1958 | -3704 | -2890 | -1385 | -2665 | -1636 | -2457 | -1509 | -1729 | -2895 | -3915 | -3319 | 396 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 9FF

Table 7

| | | | | | | | | | | | | | | | | | | | | | |
|---|---|---|---|---|---|---|---|---|---|---|---|---|---|---|---|---|---|---|---|---|---|
| - | -12 | -7945 | -8988 | -894 | -1115 | -701 | -1378 | -9818 | -8633 | | | | | | | | | | | | |
| 395(V) | -2097 | -1741 | -4406 | -4026 | -2222 | -4103 | -3555 | 2399 | -3840 | -1319 | -1108 | 1444 | -4071 | -3681 | -3882 | -3349 | -2094 | 2762 | -3366 | -2920 | 397 |
| - | -149 | -500 | 233 | 43 | -381 | 399 | 106 | -626 | 210 | -466 | -720 | 275 | 394 | 45 | 96 | 359 | 117 | -369 | -294 | -249 | |
| - | -12 | -7945 | -8988 | -894 | -1115 | -701 | -1378 | -9818 | -8629 | | | | | | | | | | | | |
| 396(D) | -928 | -2371 | 1886 | -165 | -2715 | -1822 | -563 | -2464 | 1387 | -2421 | -1512 | -478 | 1080 | -116 | -692 | 750 | 1043 | -2018 | -2599 | -1913 | 398 |
| - | * | * | * | * | * | * | * | * | * | * | * | * | * | * | * | * | * | * | * | * | |
| - | * | * | * | * | * | * | * | -9818 | 0 | | | | | | | | | | | | |
| - | * | * | * | * | * | * | * | * | | | | | | | | | | | | | |

FIG. 9GG

Table 8

TABLE 8

```
HMMER2.0 [2.3.2]
NAME XFP
ACC PF03894.6
DESC D-xylulose 5-phosphate/D-fructose 6-phosphate phosphoketolase
LENG 187
ALPH Amino
RF no
CS no
MAP yes
COM hmmbuild -f -F HMM fs.ann SEED.ann
COM hmmcalibrate --seed 0 HMM fs.ann
NSEQ 6
DATE Sun Apr 29 15:58:33 2007
CKSUM 8559
GA 15.5 15.5
TC 18.2 15.7
NC 13.6 14.2
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -10.339054 0.664450
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -222 | * | -2807 | | | | | | | | | | | | | | | | | | |
| 1(M) | -919 | -1308 | -2565 | -2222 | -1930 | -1975 | -1841 | -1394 | -1946 | -1641 | 3218 | -1876 | 1316 | -1826 | -2064 | -1219 | 2730 | -1183 | -2403 | -2047 | 1 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -1222 | -8539 | | | | | | | | | | | | |
| 2(R) | 691 | -1720 | -837 | -294 | -1975 | -1756 | -501 | 673 | -144 | -1751 | -937 | 1196 | -1878 | -121 | 1881 | 951 | -681 | -1325 | -2078 | -1516 | 2 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -8762 | -8535 | | | | | | | | | | | | |
| 3(V) | -885 | -1621 | -999 | 990 | -1982 | -1862 | -915 | -1514 | 733 | -1796 | -1048 | -873 | 1044 | -622 | -1147 | 858 | -916 | 2279 | -2227 | 1717 | 3 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -8762 | -8531 | | | | | | | | | | | | |
| 4(L) | -2842 | -2379 | -5209 | -4634 | 994 | -4802 | -3633 | -174 | -4364 | 2574 | 2538 | -4478 | -4252 | -3491 | -4019 | -4045 | -2735 | 1455 | -2614 | -2661 | 4 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -8762 | -8527 | | | | | | | | | | | | |
| 5(G) | -1046 | -1667 | -2864 | 3162 | 4077 | 3372 | -3114 | -3979 | 3511 | -4193 | -3299 | -2337 | -2643 | 3089 | 3461 | 1104 | -1501 | -2797 | 4216 | 4066 | 5 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -8762 | -8524 | | | | | | | | | | | | |
| 6(K) | 696 | -1959 | -661 | -115 | -2242 | -1707 | -387 | -1932 | 1754 | -1971 | -1104 | -400 | -1809 | 1727 | -429 | 726 | -657 | 544 | -2214 | -1595 | 6 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7717 | -8760 | -894 | -1115 | -701 | -1378 | -8762 | -8520 | | | | | | | | | | | | |

FIG. 10A

Table 8

| | | | | | | | | | | | | | | | | | | | | |
|---|---|---|---|---|---|---|---|---|---|---|---|---|---|---|---|---|---|---|---|---|
| 7(Y) | -4363 | -3343 | -4802 | -5127 | 2939 | -4674 | -927 | -3251 | -4692 | -2586 | -2669 | -3329 | -4545 | -3458 | -4081 | -3935 | -4227 | -3413 | -177 | 4223 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7717 | -8760 | -894 | -1115 | -701 | -1378 | -8762 | -8516 | | | | | | | | | | | 7 |
| 8(C) | -1627 | 2687 | -3970 | -3367 | 1521 | -3283 | -2148 | -37 | -3007 | 2149 | 118 | -2930 | -3201 | -2520 | -2790 | -2405 | -1562 | 1206 | -1785 | -1498 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8512 | | | | | | | | | | | 8 |
| 9(R) | 737 | -2550 | 1594 | -497 | -3149 | -1980 | -968 | -2870 | -526 | -2846 | -2019 | -774 | -2281 | -570 | 3052 | -1221 | -1340 | -2417 | -3004 | -2383 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8508 | | | | | | | | | | | 9 |
| 10(D) | -2399 | -4358 | 3324 | 2308 | -4527 | -2166 | -1608 | -4527 | -1994 | -4367 | -3790 | -765 | -2746 | -1301 | -2956 | -2018 | -2496 | -3976 | -4515 | -3456 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8504 | | | | | | | | | | | 10 |
| 11(V) | -2284 | -1804 | -4895 | -4504 | -1990 | -4629 | -4189 | 2412 | -4382 | 1011 | -761 | -4283 | -4358 | -4111 | -4394 | -3938 | -2259 | 2686 | -3549 | 3219 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8500 | | | | | | | | | | | 11 |
| 12(M) | -2278 | -1867 | -4746 | -4224 | -1303 | -4284 | -3343 | 1656 | -3973 | 1240 | 3304 | -3939 | -3999 | -3423 | -3784 | -3494 | -2217 | 2073 | 2691 | -2538 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8496 | | | | | | | | | | | 12 |
| 13(K) | 693 | -2202 | -1423 | -749 | -2553 | -2182 | -674 | -2107 | 2480 | -2170 | -1388 | -928 | -2252 | -275 | 1432 | -1210 | -1146 | 1012 | -2378 | -1932 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8492 | | | | | | | | | | | 13 |
| 14(N) | -1049 | -1434 | -1773 | -1500 | -1636 | -2109 | -1397 | -1127 | -1366 | 1815 | -824 | 2287 | -2427 | -1298 | -1590 | -1307 | 1405 | -1004 | -2112 | -1674 |
| | -149 | -500 | 233 | 43 | -381 | 399 | 106 | -626 | 210 | -466 | -720 | 275 | 394 | 45 | 96 | 359 | 117 | -369 | -294 | -249 |
| | -14 | -7718 | -8760 | -894 | -1115 | -701 | -1378 | -8762 | -8488 | | | | | | | | | | | 14 |
| 15(N) | -3232 | -3514 | -2565 | -2905 | -4358 | -3267 | -3364 | -5192 | -3627 | -5059 | -4632 | 4348 | -3843 | -3410 | -3792 | -3319 | -3533 | -4568 | -4087 | -3976 |
| | -149 | -500 | 233 | 43 | -381 | 399 | 106 | -626 | 210 | -466 | -720 | 275 | 394 | 45 | 96 | 359 | 117 | -369 | -294 | -249 |
| | -867 | -7718 | -1171 | -894 | -1115 | -701 | -1378 | -8762 | -8484 | | | | | | | | | | | 15 |
| 16(E) | -1220 | -2441 | 99 | 2757 | -2966 | -1568 | -808 | -2774 | -675 | -2772 | -2036 | -363 | 2075 | -466 | -1190 | -1070 | -1278 | -2337 | -2879 | -2244 |
| | -149 | -500 | 233 | 43 | -381 | 399 | 106 | -626 | 210 | -466 | -720 | 275 | 394 | 45 | 96 | 359 | 117 | -369 | -294 | -249 |
| | -22 | -6873 | -7915 | -894 | -1115 | -2169 | -363 | -8762 | -8480 | | | | | | | | | | | 16 |
| 17(D) | -1004 | -1749 | 2891 | -305 | -2104 | -1632 | -964 | -886 | -981 | -1762 | -1266 | -575 | -2040 | -692 | -1495 | -1057 | -1089 | 1706 | -2499 | -1874 |
| | -149 | -500 | 233 | 43 | -381 | 399 | 106 | -626 | 210 | -466 | -720 | 275 | 394 | 45 | 96 | 359 | 117 | -369 | -294 | -249 |
| | -460 | -6873 | -1933 | -894 | -1115 | -216 | -2846 | -8762 | -8476 | | | | | | | | | | | 17 |
| 18(M) | 823 | -1578 | 1383 | -173 | -1837 | -1620 | -411 | -1480 | -107 | -1624 | 2041 | -425 | 938 | -38 | -569 | -595 | 1047 | -1187 | -1968 | -1402 |
| | -149 | -500 | 233 | 43 | -381 | 399 | 106 | -626 | 210 | -466 | -720 | 275 | 394 | 45 | 96 | 359 | 117 | -369 | -294 | -249 |
| | -16 | -7493 | -8536 | -894 | -1115 | -1355 | -715 | -8762 | -8472 | | | | | | | | | | | 18 |
| 19(T) | -897 | -2121 | -888 | -291 | -2541 | -1825 | -413 | -2206 | 1465 | -2164 | -1310 | -532 | -1923 | 20 | 1428 | 1124 | 1894 | -1823 | -2313 | -1770 |
| | -149 | -500 | 233 | 43 | -381 | 399 | 106 | -626 | 210 | -466 | -720 | 275 | 394 | 45 | 96 | 359 | 117 | -369 | -294 | -249 |
| | | | | | | | | | | | | | | | | | | | | 19 |

FIG. 10B

Table 8

| | | | | | | | | | | | | | | | | | | |
|---|---|---|---|---|---|---|---|---|---|---|---|---|---|---|---|---|---|---|
| | -16 | -7493 | -8536 | -894 | -1115 | -404 | -2032 | -8762 | -8468 | | | | | | | | | |
| 20(N) | -867 | -2024 | -881 | 423 | -2654 | -1782 | 693 | -230 | | -2371 | -1499 | 2664 | -2000 | -273 | 1178 | 870 | 1294 | -1909 | -2569 | -1974 | 20 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8464 | | | | | | | | | | | | |
| 21(F) | -3465 | -2876 | -5057 | -4893 | 3938 | -4762 | -2035 | -4547 | | 1305 | -409 | -4001 | -4411 | -3532 | -4090 | -4106 | -3362 | -1663 | -1215 | -228 | 21 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8459 | | | | | | | | | | | | |
| 22(R) | -4070 | -3868 | -4406 | -3890 | -4820 | -3837 | -3026 | -1946 | | -4739 | -4314 | -3733 | -4155 | -2844 | 4177 | -4178 | -4041 | -4836 | -3949 | -4248 | 22 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8455 | | | | | | | | | | | | |
| 23(I) | -2379 | -1901 | -4955 | -4531 | -1728 | -4662 | -4059 | -4381 | 2900 | -4321 | -512 | -3497 | -4336 | -3965 | -4313 | -3959 | -2342 | 1650 | -3306 | -3087 | 23 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8451 | | | | | | | | | | | | |
| 24(F) | -2676 | -2354 | -4538 | -4394 | 3992 | -3956 | -1878 | -4074 | | -869 | -929 | -3497 | -4006 | -3383 | -3780 | -3277 | -2708 | 1235 | -1189 | -154 | 24 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8447 | | | | | | | | | | | | |
| 25(G) | -1031 | -1653 | -2874 | 3165 | -4069 | 3287 | -3106 | -3500 | | -4180 | -3282 | -2329 | -2632 | -3078 | -3451 | 1430 | -1486 | -2782 | -4212 | -4060 | 25 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8443 | | | | | | | | | | | | |
| 26(P) | -4077 | -3791 | -4518 | -4858 | -2236 | -3818 | -4460 | -5053 | | -5602 | -5343 | -4628 | 4289 | -4938 | -4749 | -4364 | -4429 | -5313 | -4385 | -5119 | 26 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8439 | | | | | | | | | | | | |
| 27(D) | -3832 | -4189 | 4132 | -4132 | -5073 | -3341 | -3194 | -3716 | | -5365 | -5035 | -2584 | -3886 | -3102 | -4252 | -3662 | -4000 | -5151 | -4434 | -4544 | 27 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8435 | | | | | | | | | | | | |
| 28(E) | -3777 | -4125 | -1925 | 3871 | -4984 | -3355 | -3125 | -5379 | | -5156 | -4796 | -2611 | -3875 | -3007 | -3762 | -3630 | -3916 | -4960 | -4357 | -4463 | 28 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8430 | | | | | | | | | | | | |
| 29(T) | -1009 | -1466 | -1761 | -1492 | -1840 | -2028 | -1429 | -1350 | | 766 | -1045 | 1393 | -2396 | -1299 | -1587 | -1239 | 2910 | -1154 | -2256 | -1801 | 29 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8426 | | | | | | | | | | | | |
| 30(M) | 1499 | -1643 | -917 | 1243 | -1962 | -1786 | -691 | -425 | | -1763 | 2853 | -693 | -1975 | -349 | -862 | 779 | -773 | -1304 | -2139 | -1601 | 30 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8422 | | | | | | | | | | | | |
| 31(S) | -1644 | -2173 | -3321 | -3615 | -4077 | -2357 | -3411 | -3792 | | -4459 | -3725 | -2859 | -3095 | -3512 | -3692 | 3619 | -2088 | -3285 | -4091 | -3959 | 31 |
| | -149 | -500 | 233 | 43 | -381 | 399 | 106 | 210 | | -466 | -720 | 275 | 394 | 45 | 96 | 359 | 117 | -369 | -294 | -249 | |
| | -14 | -7718 | -8760 | -894 | -1115 | -701 | -1378 | -8762 | -8418 | | | | | | | | | | | | |

FIG. 10C

Table 8

FIG. 10D

Table 8

| | | | | | | | | | | | | | | | | | | | | |
|---|---|---|---|---|---|---|---|---|---|---|---|---|---|---|---|---|---|---|---|---|
| | -17 | -7443 | -8485 | -894 | -1115 | -1459 | -652 | -8762 | -8362 | | | | | | | | | | | |
| 45(W) | -4735 | -3754 | -4703 | -4993 | -2377 | -3915 | -3273 | -4870 | -4782 | -4319 | -4338 | -4620 | -4317 | -4639 | -4390 | -4998 | -4881 | -4870 | 6237 | -1984 | 45 |
| | | -149 | -500 | 43 | -381 | 399 | 106 | -626 | 210 | -466 | -720 | 275 | 394 | 45 | 96 | 359 | 117 | -369 | -294 | -249 | |
| | -17 | -7443 | -8486 | -894 | -1115 | -372 | -2136 | -8762 | -8358 | | | | | | | | | | | |
| 46(M) | -914 | -874 | 871 | -1922 | -783 | -2384 | -1220 | 1249 | -1670 | 662 | 3001 | -1756 | -2427 | -1420 | -1731 | -1438 | 1257 | -98 | -1343 | -990 | 46 |
| | | -149 | -500 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8353 | | | | | | | | | | | |
| 47(M) | 641 | -2071 | -521 | 1084 | -2362 | -1649 | 321 | -2091 | 82 | -2076 | 2071 | 1285 | -1749 | 1468 | -420 | 684 | -616 | -1678 | -2276 | -1612 | 47 |
| | | -149 | -500 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8349 | | | | | | | | | | | |
| 48(Q) | -757 | -2178 | -529 | 1705 | -2487 | 519 | 368 | -2219 | 1195 | -2182 | -1278 | -340 | -1806 | 1749 | -411 | -642 | -696 | 453 | -2362 | -1699 | 48 |
| | | -149 | -500 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8344 | | | | | | | | | | | |
| 49(Y) | -1288 | -1144 | -3267 | -2757 | -710 | -2784 | -1561 | 2546 | -2393 | -763 | -315 | -2345 | -2866 | -505 | -2314 | -1913 | 1335 | -38 | -1365 | 2756 | 49 |
| | | -149 | -500 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8340 | | | | | | | | | | | |
| 50(K) | -1352 | -2460 | 1542 | -473 | -2590 | -2065 | -876 | -2234 | 1932 | 1737 | -1566 | -761 | -2285 | -481 | 815 | -1266 | -1304 | -1990 | -2658 | -2071 | 50 |
| | | -149 | -500 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8335 | | | | | | | | | | | |
| 51(P) | -1299 | -2774 | -236 | 1949 | -3178 | -1870 | -886 | -2961 | -678 | -2912 | -2058 | 1447 | 2218 | -481 | -1251 | 890 | -1302 | -2487 | -3099 | -2347 | 51 |
| | | -149 | -500 | 43 | -381 | 399 | 106 | -626 | 210 | -466 | -720 | 275 | 394 | 45 | 96 | 359 | 117 | -369 | -294 | -249 | |
| | -291 | -7718 | -2514 | -894 | -1115 | -701 | -1378 | -8762 | -8331 | | | | | | | | | | | |
| 52(P) | 1084 | -2190 | -341 | 2185 | -2933 | -1688 | -929 | -2655 | -732 | -2706 | -1884 | -590 | 2271 | -556 | -1245 | -978 | -1128 | -2169 | -2938 | -2278 | 52 |
| | | -149 | -500 | 43 | -381 | 399 | 106 | -626 | 210 | -466 | -720 | 275 | 394 | 45 | 96 | 359 | 117 | -369 | -294 | -249 | |
| | -17 | -7443 | -8486 | -894 | -1115 | -1459 | -652 | -8762 | -8326 | | | | | | | | | | | |
| 53(N) | -1418 | -2809 | 2479 | -106 | -2949 | -1799 | -926 | -2766 | -883 | 578 | -2068 | 2542 | -2188 | 576 | -1502 | -1234 | -1435 | -2399 | -3048 | -2264 | 53 |
| | | -149 | -500 | 43 | -381 | 399 | 106 | -626 | 210 | -466 | -720 | 275 | 394 | 45 | 96 | 359 | 117 | -369 | -294 | -249 | |
| | -283 | -7443 | -2563 | -894 | -1115 | -1459 | -652 | -8762 | -8322 | | | | | | | | | | | |
| 54(D) | -888 | -2124 | 2400 | 66 | -2357 | -1565 | -509 | -1956 | -285 | -2113 | -1336 | -255 | -1834 | 1955 | -808 | -781 | -871 | 1155 | -2428 | -1753 | 54 |
| | | -149 | -500 | 43 | -381 | 399 | 106 | -626 | 210 | -466 | -720 | 275 | 394 | 45 | 96 | 359 | 117 | -369 | -294 | -249 | |
| | -19 | -7180 | -8222 | -894 | -1115 | -1865 | -463 | -8762 | -8317 | | | | | | | | | | | |
| 55(D) | -1805 | -3680 | 2903 | 2554 | -3868 | -1689 | -1066 | -3813 | -1341 | -3684 | -3041 | -289 | -2233 | -743 | -2210 | -1458 | -1880 | -3289 | -3847 | -2846 | 55 |
| | | -149 | -500 | 43 | -381 | 399 | 106 | -626 | 210 | -466 | -720 | 275 | 394 | 45 | 96 | 359 | 117 | -369 | -294 | -249 | |
| | -1334 | -7180 | -753 | -894 | -1115 | -1865 | -463 | -8762 | -8313 | | | | | | | | | | | |
| 56(G) | 515 | 887 | -1038 | -1187 | -2183 | 3187 | -1282 | -2175 | -1398 | -2342 | -1770 | -1048 | -1555 | -1281 | -1496 | -708 | -838 | -1625 | -1974 | -1993 | 56 |
| | | -149 | 233 | 43 | -381 | 399 | 106 | -626 | 210 | -466 | -720 | 275 | 394 | 45 | 96 | 359 | 117 | -369 | -294 | -249 | |
| | -41 | -5887 | -6930 | -894 | -1115 | -2652 | -250 | -8762 | -8308 | | | | | | | | | | | |

FIG. 10E

Table 8

| | | | | | | | | | | | | | | | | | | | | | |
|---|---|---|---|---|---|---|---|---|---|---|---|---|---|---|---|---|---|---|---|---|---|
| 57(G) | -515 | 887 | -1038 | -1187 | -2183 | 3187 | -1282 | -2175 | -1398 | -2342 | -1770 | -1048 | -1555 | -1281 | -1496 | -708 | -838 | -1625 | -1974 | -1993 | 57 |
| | | -149 | 233 | 43 | -381 | 399 | 106 | -626 | 210 | -466 | -720 | 275 | 394 | 45 | 96 | 359 | 117 | -369 | -294 | -249 | |
| | -41 | | -5887 | -6930 | -894 | -1115 | -151 | -3329 | -8762 | -8304 | | | | | | | | | | | |
| 58(E) | -1346 | -1562 | -1816 | 2436 | 2337 | -2525 | -1279 | -603 | -1533 | -1038 | -631 | -1602 | -2663 | -1361 | -1800 | -1658 | -1319 | -1614 | -909 | | 58 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8299 | | | | | | | | | | | | |
| 59(H) | -933 | -961 | -2242 | -1707 | -764 | -2320 | 2094 | 1132 | -1393 | 1839 | -65 | 1195 | -2382 | -1248 | -1495 | -1381 | -874 | -1292 | -847 | | 59 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8295 | | | | | | | | | | | | |
| 60(M) | -1293 | -1342 | -2996 | -2500 | -1038 | -2617 | -1796 | -510 | -2162 | 890 | 3410 | -2240 | -2790 | -1938 | -1495 | 2186 | -1323 | -1840 | -1502 | | 60 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8290 | | | | | | | | | | | | |
| 61(P) | 2028 | -1663 | -1726 | -1624 | -3398 | 998 | -1915 | -3145 | -1828 | -3283 | -2409 | 1487 | 2266 | -1625 | -2185 | -1038 | -1207 | -3511 | -3060 | | 61 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8285 | | | | | | | | | | | | |
| 62(D) | -752 | -2203 | 1771 | 1070 | -2520 | -1688 | -359 | -2261 | 1383 | -2210 | -1298 | -324 | -1796 | 94 | 1124 | -630 | -691 | 543 | -2379 | -1707 | 62 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -231 | -7718 | -2838 | -894 | -1115 | -701 | -1378 | -8762 | -8281 | | | | | | | | | | | | |
| 63(R) | -796 | -2105 | -516 | 1238 | -2496 | 1498 | -421 | -2206 | 49 | -2188 | -1314 | -382 | -1834 | 11 | 1567 | -698 | 1155 | -1794 | -2375 | -1748 | 63 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7504 | -8546 | -894 | -1115 | -701 | -2011 | -8762 | -8276 | | | | | | | | | | | | |
| 64(G) | -2419 | -2885 | -3067 | -2886 | -4406 | 3143 | -2559 | -4353 | -1679 | -4234 | -3572 | -2708 | -3407 | -2316 | 2444 | -2556 | -2650 | -3716 | -3837 | -3878 | 64 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8271 | | | | | | | | | | | | |
| 65(R) | -1920 | -2516 | -2433 | -1527 | -2802 | -2746 | -961 | 1879 | 176 | -2261 | -1647 | -1532 | -2759 | 1746 | 2935 | -1945 | -1744 | -2067 | -2537 | -2247 | 65 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8267 | | | | | | | | | | | | |
| 66(V) | -2252 | -1773 | -4891 | -4567 | -2335 | -4633 | -4538 | 1812 | -4482 | -1132 | -1073 | -4339 | -4440 | -4385 | -4597 | -3992 | -2250 | -3973 | -3489 | | 66 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8262 | | | | | | | | | | | | |
| 67(M) | -849 | -923 | 1670 | -1529 | -893 | -2248 | -1067 | -233 | -1327 | 600 | 2147 | -1485 | -2308 | -1135 | -1498 | -1282 | 1243 | -1394 | -1015 | | 67 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8257 | | | | | | | | | | | | |
| 68(E) | -1776 | -3015 | -373 | 3097 | -3872 | -2071 | -1546 | -3755 | -1570 | -3731 | -2992 | -934 | -2595 | -1219 | -2164 | 1764 | -1926 | -3163 | -3855 | -3091 | 68 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8253 | | | | | | | | | | | | |
| 69(M) | -1335 | -1165 | -3272 | -2688 | -1002 | -2941 | -1834 | 1451 | -2360 | -376 | 3121 | -2427 | -2930 | 2286 | -2331 | -2034 | -1279 | -1766 | -1445 | | 69 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 10F

Table 8

| | | | | | | | | | | | | | | | | | | | | | | |
|---|---|---|---|---|---|---|---|---|---|---|---|---|---|---|---|---|---|---|---|---|---|---|
| | -15 | -7718 | -8760 | -894 | -1115 | -701 | -1378 | -8762 | -8248 | | | | | | | | | | | | | |
| 70(L) | -3777 | -3243 | -5089 | -5032 | -1735 | -4514 | 4040 | -1299 | -4754 | 3261 | -696 | -4891 | -4508 | -4152 | -4395 | -4705 | -3767 | -1993 | -3125 | -3069 | 70 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8243 | | | | | | | | | | | | |
| 71(S) | -1644 | -2173 | -3321 | -3615 | -4077 | -2357 | -3411 | -4307 | -3792 | -4459 | -3725 | -2859 | -3095 | -3512 | -3692 | 3619 | -2088 | 3285 | 4091 | -3959 | 71 |
| | -149 | -500 | 233 | -894 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8238 | | | | | | | | | | | | |
| 72(E) | -3777 | -4125 | -1925 | 3871 | -4984 | -3355 | -3125 | -5379 | -3371 | -5156 | -4796 | -2611 | -3875 | -3007 | -3762 | -3630 | -3916 | -4960 | -4357 | -4463 | 72 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8234 | | | | | | | | | | | | |
| 73(H) | -4406 | -3961 | -3921 | -4171 | -3231 | -3926 | 5401 | -5468 | -3992 | -5013 | -4849 | -4130 | -4378 | -4151 | -3893 | -4548 | -4592 | -5195 | -3383 | -2818 | 73 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8229 | | | | | | | | | | | | |
| 74(Q) | -1172 | -1561 | -1803 | -1343 | -1477 | -2292 | -1190 | -991 | -908 | 1463 | 565 | -1415 | -2454 | 2378 | -1119 | -1403 | 1904 | -979 | -1998 | -1592 | 74 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8760 | -894 | -1115 | -701 | -1378 | -8762 | -8224 | | | | | | | | | | | | |
| 75(C) | 943 | 4854 | -3669 | -3391 | -1886 | -2164 | -2449 | -922 | -3000 | 676 | -1025 | -2492 | -2705 | -2686 | -2861 | -1458 | -1303 | -805 | -2559 | -2242 | 75 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8219 | | | | | | | | | | | | |
| 76(E) | -2096 | -3637 | -282 | 2979 | -3947 | -2215 | -1377 | -3824 | -1173 | -3688 | -2987 | -859 | -2659 | 2792 | -1646 | -1832 | -2117 | -3370 | -3761 | -3011 | 76 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8214 | | | | | | | | | | | | |
| 77(G) | -3681 | -3593 | -4389 | -4747 | -5281 | 3812 | -4419 | -5908 | -5071 | -5671 | -5288 | -4417 | -4223 | -4850 | -4766 | -3952 | -4069 | -5125 | -4424 | -5214 | 77 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8209 | | | | | | | | | | | | |
| 78(W) | -4254 | -3318 | -4804 | -5081 | 3098 | -4588 | -1050 | -3111 | -4645 | -2453 | -2534 | -3403 | -4509 | -3506 | -4073 | -3950 | -4146 | -3314 | 5352 | 877 | 78 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8205 | | | | | | | | | | | | |
| 79(L) | -3375 | -2814 | -5645 | -5079 | -928 | -5372 | -4042 | -409 | -4777 | 2894 | 2856 | -5098 | -4540 | -3683 | -4317 | -4734 | -3229 | -1208 | -2698 | -2837 | 79 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8200 | | | | | | | | | | | | |
| 80(E) | -2150 | -3708 | -263 | 3290 | -4011 | -2224 | -1421 | -3906 | -1260 | -3766 | -3081 | -868 | -2687 | 2032 | -1753 | -1875 | -2180 | -3447 | -3837 | -3070 | 80 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8195 | | | | | | | | | | | | |
| 81(G) | 2022 | -1618 | -3291 | -3557 | -4069 | 3053 | -3239 | -3867 | -3682 | -4133 | -3245 | -2462 | -2643 | -3254 | -3542 | -1260 | -1474 | -2727 | -4214 | -4140 | 81 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7718 | -8761 | -894 | -1115 | -701 | -1378 | -8762 | -8190 | | | | | | | | | | | | |

FIG. 10G

Table 8

| | | | | | | | | | | | | | | | | | |
|---|---|---|---|---|---|---|---|---|---|---|---|---|---|---|---|---|---|
| 82(Y) | -4444 | -3646 | -4593 | -4892 | -509 | -4268 | -1873 | -3993 | -4663 | -3407 | -3460 | -3884 | -4503 | -3998 | -4255 | -4336 | -4491 | -4072 | -1177 | 4829 | 82 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8185 | | | | | | | | | | | | |
| 83(L) | -1931 | -1973 | -3870 | -3595 | -1374 | -3144 | -2842 | -646 | -3171 | 2519 | -338 | -3150 | -3415 | -2899 | -3072 | -2469 | 2215 | -950 | -2583 | -2364 | 83 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8180 | | | | | | | | | | | | |
| 84(L) | -3777 | -3243 | -5089 | -5032 | -1735 | -4514 | -4040 | -1299 | -4754 | 3261 | -696 | -4891 | -4508 | -4152 | -4395 | -4705 | -3767 | -1993 | -3125 | -3069 | 84 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8175 | | | | | | | | | | | | |
| 85(T) | -2081 | -2497 | -3792 | -4048 | -4206 | -2712 | -3671 | -3972 | -3974 | -4274 | -3765 | -3291 | -3408 | -3829 | -3824 | -2338 | 3976 | -3321 | -4129 | -4203 | 85 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8170 | | | | | | | | | | | | |
| 86(G) | -3681 | -3593 | -4389 | -4747 | -5281 | 3812 | -4419 | -5908 | -5071 | -5671 | -5288 | -4417 | -4223 | -4850 | -4766 | -3952 | -4069 | -5125 | -4424 | -5214 | 86 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8165 | | | | | | | | | | | | |
| 87(R) | -4070 | -3868 | -4406 | -3890 | -4820 | -3837 | -3026 | -5122 | -3130 | -4739 | -4314 | -3731 | -4155 | -4850 | 4177 | -4178 | -4041 | -4836 | -3949 | -4248 | 87 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8160 | | | | | | | | | | | | |
| 88(H) | -1602 | -2202 | -2033 | -2051 | -2524 | -2310 | 4500 | -3130 | -1754 | -3221 | -2593 | -1952 | -2860 | -2844 | -1889 | -1744 | -4041 | -2641 | -2857 | -2142 | 88 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8155 | | | | | | | | | | | | |
| 89(G) | 1424 | -1648 | 3257 | -3538 | -4097 | 3299 | -3253 | -3902 | -3697 | -3283 | -3283 | -2476 | -2666 | -3269 | -3560 | -1290 | -1506 | -2760 | -4228 | -4161 | 89 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8150 | | | | | | | | | | | | |
| 90(F) | 653 | -1307 | -3869 | -3274 | 2383 | -3222 | 2101 | 2307 | -2923 | -2457 | 54 | -2851 | -3158 | -2477 | -2735 | -2341 | -1496 | -62 | -1785 | -1478 | 90 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8145 | | | | | | | | | | | | |
| 91(F) | -4268 | -3318 | -4807 | 5092 | 4134 | -4606 | -1026 | 3118 | -4656 | -3713 | -2538 | -3389 | -4515 | -3495 | -4075 | -3946 | -4154 | -3320 | 3520 | 904 | 91 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8140 | | | | | | | | | | | | |
| 92(A) | 2436 | -1450 | -3080 | -3062 | -3722 | -1707 | -2801 | -3478 | -3005 | -3713 | -2813 | -2174 | 1760 | -2697 | -3044 | 2014 | -1242 | -2447 | -3930 | -3709 | 92 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8134 | | | | | | | | | | | | |
| 93(S) | -797 | 2971 | -3664 | -3672 | -3546 | -1712 | -2998 | -3220 | -3388 | -2685 | -2538 | -2356 | -2477 | -3023 | -3254 | 2975 | 1394 | -2305 | -3830 | -3649 | 93 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | -8129 | | | | | | | | | | | | |
| 94(Y) | -4444 | -3646 | -4593 | -4892 | -509 | -4268 | -1873 | -3993 | -4663 | -3407 | -3460 | -3884 | -4503 | -3998 | -4255 | -4336 | -4491 | -4072 | -1177 | 4829 | 94 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | | -7719 | -894 | -1115 | -701 | -1378 | -8762 | | | | | | | | | | | | | |

FIG. 10H

Table 8

| | | | | | | | | | | | | | | | | |
|---|---|---|---|---|---|---|---|---|---|---|---|---|---|---|---|---|
| | -15 | -7719 | -8761 | -894 | -1115 | -701 | -1378 | -8762 | -8124 | | | | | | | |
| 95(E) | -3777 | -4125 | -1925 | 3871 | -4984 | -3355 | -3125 | -5379 | -3371 | -5156 | -4796 | -2611 | -3875 | -3007 | -3762 | -3630 | -3916 | -4960 | -4357 | -4463 | 95 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7719 | -8761 | -894 | -1115 | -701 | -1378 | -8762 | -8119 | | | | | | | | | | | | |
| 96(A) | 2588 | -1457 | -3368 | -3530 | -3881 | -1722 | -3095 | -3647 | -3472 | -3926 | -3021 | -2338 | -2505 | -3081 | -3355 | -2536 | -1295 | -2531 | -4108 | -3950 | 96 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7719 | -8761 | -894 | -1115 | -701 | -1378 | -8762 | -8114 | | | | | | | | | | | | |
| 97(F) | -4350 | -3618 | -4843 | -5137 | 4483 | -4245 | -2206 | -3493 | -4990 | -2887 | -3007 | -4147 | -4512 | -4243 | -4506 | -4433 | -4439 | -3737 | -1500 | -417 | 97 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7719 | -8761 | -894 | -1115 | -701 | -1378 | -8762 | -8109 | | | | | | | | | | | | |
| 98(M) | 706 | -1201 | -3821 | -3231 | -1007 | -3165 | -2103 | 1510 | -2884 | 1469 | 2600 | -2801 | -3121 | -2481 | -2711 | -2285 | -1405 | 1421 | -1846 | -1550 | 98 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7719 | -8761 | -894 | -1115 | -701 | -1378 | -8762 | -8103 | | | | | | | | | | | | |
| 99(H) | -1732 | -2580 | -1961 | -1265 | -3039 | -2507 | 3869 | -2740 | 117 | -2656 | -1919 | -1338 | -2617 | -548 | 2281 | -1696 | 1373 | -2439 | -2662 | -2280 | 99 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8098 | | | | | | | | | | | | |
| 100(I) | -2262 | -1772 | -4916 | -4590 | -2360 | -4692 | -4608 | 2948 | -4520 | -1146 | -1086 | -4377 | -4472 | -4432 | -4647 | -4052 | -2257 | -4024 | -3536 | 100 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8093 | | | | | | | | | | | | |
| 101(V) | -2259 | -1770 | -4911 | -4585 | -2361 | -4682 | -4599 | 2472 | -4513 | -1151 | -1088 | -4370 | -4467 | -4427 | -4640 | -4043 | -2254 | 3105 | -4021 | -3531 | 101 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8087 | | | | | | | | | | | | |
| 102(D) | -1281 | -2033 | 3087 | -908 | -2698 | -2028 | -1475 | -1596 | -1454 | -1758 | -1118 | -2459 | -1191 | -1938 | -1365 | 1158 | 1286 | -3025 | -2452 | 102 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8082 | | | | | | | | | | | | |
| 103(S) | -1644 | -2173 | -3321 | -3615 | -4077 | -2357 | -3411 | -4307 | -3792 | -4459 | -3725 | -2859 | -3095 | -3512 | -3692 | -3938 | -2088 | -3285 | -4091 | -3959 | 103 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8077 | | | | | | | | | | | | |
| 104(M) | -3457 | -3250 | -4578 | -4682 | -2595 | -3839 | -3833 | -2264 | -4294 | -1708 | 5248 | -4331 | -4225 | -4184 | -4072 | 3619 | -3655 | -2653 | -3435 | -3236 | 104 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8071 | | | | | | | | | | | | |
| 105(L) | -2433 | -2031 | -4839 | -4270 | 1637 | -4331 | -3217 | 1476 | -3985 | 2288 | -3990 | -3978 | -4225 | -3290 | -3710 | -3525 | -2348 | 1287 | -2465 | -2367 | 105 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8066 | | | | | | | | | | | | |
| 106(N) | -952 | -1482 | -1959 | -1737 | -2360 | -1930 | -1748 | -1480 | -1701 | -2148 | -1486 | 2935 | -2420 | -1580 | -1960 | -1182 | 2024 | 1339 | -2731 | -2304 | 106 |
| | -16 | -500 | 233 | 43 | -381 | 399 | 106 | -626 | 210 | -466 | -720 | 275 | 394 | 45 | 96 | 359 | 117 | -369 | -294 | -249 | |
| | -16 | -7719 | -8761 | -894 | -1115 | -701 | -1378 | -8762 | -8061 | | | | | | | | | | | | |

FIG. 10I

Table 8

| | | | | | | | | | | | | | | | | | | | | | | |
|---|---|---|---|---|---|---|---|---|---|---|---|---|---|---|---|---|---|---|---|---|---|---|
| 107(Q) | -3758 | -3792 | -3072 | -3245 | -4342 | -3586 | -3274 | -5053 | -2880 | -4719 | -4410 | -3349 | -4049 | 4526 | -2916 | -3829 | -3917 | -4726 | -3973 | -3953 | 107 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8055 | | | | | | | | | | | | |
| 108(H) | -3941 | -3303 | -3939 | -4079 | 336 | -4266 | -3317 | -3580 | | -2730 | -2734 | -3097 | -4295 | -3109 | -3362 | -3363 | -3868 | -3403 | 373 | 2757 | 108 |
| | -149 | -500 | 233 | 43 | -381 | 399 | 106 | 210 | | -466 | -720 | 275 | 394 | 45 | 96 | 359 | 117 | -369 | -294 | -249 | |
| | -16 | | -7719 | -8761 | -894 | -701 | -1378 | -8050 | | | | | | | | | | | | | |
| 109(A) | 238 | -1319 | -2661 | -2353 | 1521 | 924 | -2061 | -2216 | | -2443 | -1684 | -1875 | -2365 | -1993 | -2375 | 1314 | -1085 | -1685 | -2841 | -2472 | 109 |
| | -149 | -500 | 233 | 43 | -381 | 399 | 106 | 210 | | -466 | -720 | 275 | 394 | 45 | 96 | 359 | 117 | -369 | -294 | -249 | |
| | -16 | | -7719 | -8761 | -894 | -701 | -1378 | -8044 | | | | | | | | | | | | | |
| 110(K) | -3709 | -3782 | -3592 | -3179 | -4734 | -3639 | -2561 | 4748 | 3938 | -4426 | -3926 | -3130 | -3916 | -2292 | -1410 | -3723 | -3624 | -4465 | -3818 | -3998 | 110 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8039 | | | | | | | | | | | | |
| 111( ) | -4239 | -3322 | 4800 | -5070 | 2397 | -4565 | -1086 | 3101 | | -2445 | -2527 | -3425 | -4503 | -3523 | -4074 | -3959 | -4140 | -3310 | 5693 | 837 | 111 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8033 | | | | | | | | | | | | |
| 112(L) | -3174 | -2633 | -5520 | -4994 | -1029 | -5242 | -4053 | 1453 | | -2932 | 174 | -4959 | -4514 | -3738 | -4340 | -4596 | -3057 | -761 | -2778 | -2863 | 112 |
| | -149 | -500 | 233 | 43 | -381 | 399 | 106 | 210 | | -466 | -720 | 275 | 394 | 45 | 96 | 359 | 117 | -369 | -294 | -249 | |
| | -16 | | -7719 | -8761 | -894 | -701 | -1378 | -8028 | | | | | | | | | | | | | |
| 113(K) | -1073 | -2547 | 1983 | 1205 | -2885 | -1851 | -580 | -2624 | 2040 | -2541 | -1656 | 477 | -2021 | -141 | 1183 | -924 | -1014 | -2183 | -2682 | -2014 | 113 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8022 | | | | | | | | | | | | |
| 114(M) | 1488 | -784 | -2685 | -2089 | -758 | -2378 | -1239 | 1284 | -1794 | -540 | 2454 | -1834 | -2427 | 1221 | -1791 | -1444 | -817 | 1168 | -1289 | 933 | 114 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8017 | | | | | | | | | | | | |
| 115(C) | 1116 | 3924 | -3654 | -3615 | -3360 | 1383 | -2916 | -3025 | -3341 | -3335 | -2502 | -2336 | -2465 | -2960 | -3214 | -1051 | 2263 | -2200 | -3668 | 3472 | 115 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1842 | | -7719 | 489 | -894 | -701 | -1378 | -8762 | -8011 | | | | | | | | | | | | |
| 116(V) | -588 | -579 | -2160 | -1946 | 759 | -1834 | -1555 | 1143 | -1670 | 9 | 123 | -1684 | -2156 | -1608 | -1741 | -1222 | -711 | 2811 | -1682 | -1223 | 116 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -42 | | -5919 | -6961 | -894 | -152 | -3320 | -8762 | -8006 | | | | | | | | | | | | |
| 117(R) | 740 | -1533 | -1479 | -915 | -1874 | -1953 | -873 | -1460 | -464 | 601 | -933 | -1028 | -2151 | -588 | 2555 | 747 | 902 | -1223 | -2081 | -1631 | 117 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -8762 | -8000 | | | | | | | | | | | | |
| 118(E) | -1519 | -3167 | 1458 | 2619 | -3424 | -1929 | 2323 | -3240 | -838 | -3155 | -2323 | -534 | -2279 | 1614 | -1462 | -1295 | -1511 | -2766 | -3331 | -2516 | 118 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | | -7719 | -8761 | -894 | -701 | -1378 | -7994 | | | | | | | | | | | | | |
| 119(I) | -1108 | -1022 | -2831 | -2246 | -840 | -2607 | -1460 | 2037 | -1908 | 1407 | 36 | -2034 | -2633 | 1279 | -1920 | -1682 | 1280 | -126 | -1499 | -1169 | 119 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 10J

Table 8

| | | | | | | | | | | | | | | | | | | | | |
|---|---|---|---|---|---|---|---|---|---|---|---|---|---|---|---|---|---|---|---|---|
| | -16 | -7719 | -8761 | -894 | -1115 | -701 | -1378 | -8762 | -7989 | | | | | | | | | | | |
| 120P | -1226 | -2486 | -581 | -427 | -3101 | 1037 | -2834 | 1189 | -2796 | -1949 | 1466 | 2619 | -497 | -899 | -1126 | -1246 | -2362 | -2960 | -2322 | 120 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7983 | | | | | | | | | | | |
| 121I | -5218 | -4132 | -5085 | -5404 | -2925 | -4252 | -3753 | -5268 | -4877 | -4907 | -5071 | -4661 | -5108 | -4833 | -5506 | -5369 | -5443 | 6261 | -2535 | 121 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7977 | | | | | | | | | | | |
| 122R | -2786 | -3324 | -3159 | -2158 | -3444 | -3203 | 2835 | 19 | -3307 | -2690 | -2048 | -3245 | -942 | 3648 | -2697 | -2534 | -3415 | -2888 | -2551 | 122 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7972 | | | | | | | | | | | |
| 123H | 661 | -2311 | -894 | 302 | -2686 | 811 | 2065 | 1951 | -2300 | -1425 | 565 | -1991 | -22 | 1309 | -873 | -899 | -1971 | -2431 | -1856 | 123 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7966 | | | | | | | | | | | |
| 124D | -1783 | -3362 | 2774 | -330 | -3711 | -2050 | -1197 | 1468 | -3445 | -2669 | -689 | 2225 | 827 | -1652 | -1548 | -1805 | -3056 | 3598 | -2798 | 124 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7960 | | | | | | | | | | | |
| 125I | -2784 | -2321 | -4408 | -4214 | 2256 | -4011 | -1193 | 3098 | -1290 | -1179 | -3131 | -3919 | -3037 | -3465 | -3182 | -2704 | -1420 | -513 | 2319 | 125 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7954 | | | | | | | | | | | |
| 126S | 1918 | -1460 | -2882 | -2748 | -3664 | 1367 | -2596 | -2688 | -3630 | -2719 | -2048 | 1372 | -2426 | -2827 | 1999 | -1206 | -2419 | -3840 | -3573 | 126 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7948 | | | | | | | | | | | |
| 127S | -1644 | -2173 | -3321 | -3615 | -4077 | -2357 | -3411 | -3792 | -4459 | -3725 | -2859 | -3095 | -3512 | -3692 | 3619 | -2088 | -3285 | -4091 | -3959 | 127 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7943 | | | | | | | | | | | |
| 128L | -2843 | -2399 | -5187 | -4720 | -1139 | -4765 | -3832 | -4437 | 2876 | 38 | -4542 | -4330 | -3660 | -4145 | -4094 | -2781 | 1324 | -2793 | -2769 | 128 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7937 | | | | | | | | | | | |
| 129N | -3232 | -3514 | -2565 | -2905 | -4358 | 3267 | -3364 | -3627 | -5059 | -4632 | 4348 | -3843 | -3410 | -3792 | -3319 | -3533 | -4568 | -4087 | -3976 | 129 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8761 | -894 | -1115 | -701 | -1378 | -8762 | -7931 | | | | | | | | | | | |
| 130Y | -1616 | -1344 | -3951 | -3366 | -912 | -3313 | -2164 | -3018 | 1578 | -20 | -2936 | -3238 | -2574 | -2829 | -2438 | -1554 | 1298 | -1825 | 2867 | 130 |
| | -149 | -500 | 233 | 43 | -381 | 399 | -626 | 210 | -466 | 275 | | 394 | 45 | 96 | 359 | 117 | -369 | -294 | -249 | |
| | -16 | -7719 | -8762 | -894 | -1115 | -701 | -1378 | -8762 | -7925 | | | | | | | | | | | |
| 131I | -2438 | -1963 | -4986 | -4538 | -1573 | -4670 | -3957 | 2309 | 2112 | -365 | -4331 | -4311 | -3863 | -4246 | -3955 | -2391 | 1749 | -3152 | -2992 | 131 |
| | -149 | -500 | 233 | 43 | -381 | 399 | -626 | 210 | -466 | 275 | | 394 | 45 | 96 | 359 | 117 | -369 | -294 | -249 | |
| | -16 | -7720 | -8762 | -894 | -1115 | -701 | -1378 | -8762 | -7919 | | | | | | | | | | | |

FIG. 10K

Table 8

| | | | | | | | | | | | | | | | | | | | | | |
|---|---|---|---|---|---|---|---|---|---|---|---|---|---|---|---|---|---|---|---|---|---|
| 132(M) | 694 | -667 | -2636 | -2033 | -642 | -2235 | -1106 | -145 | -1725 | 645 | 2178 | -1733 | -2301 | -1435 | -1691 | 561 | 1254 | 1172 | -1134 | -779 | 132 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7913 | | | | | | | | | | | | |
| 133(T) | -866 | -1487 | -3132 | -3246 | -3768 | -1744 | -2940 | -3519 | -3190 | -3799 | -2925 | -2263 | -2509 | -2888 | -3152 | 2652 | 2778 | -2491 | -3995 | -3782 | 133 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7907 | | | | | | | | | | | | |
| 134(S) | 1644 | -2173 | -3321 | -3615 | -4077 | -2357 | -3411 | -4307 | -3792 | -4459 | -3725 | -2859 | -3095 | -3512 | -3692 | 3619 | -2088 | -3285 | -4091 | -3959 | 134 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7901 | | | | | | | | | | | | |
| 135(H) | -1254 | -2216 | 843 | -755 | -2687 | -1970 | 3314 | -2636 | 839 | -2710 | -1932 | 1437 | -2343 | -837 | -1206 | 3288 | 2636 | -2214 | -2810 | -2158 | 135 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7895 | | | | | | | | | | | | |
| 136I | -2217 | -1998 | -4211 | -3930 | -1050 | -3517 | -2291 | -446 | -3456 | -4410 | -1150 | -3322 | -3697 | -3202 | -3309 | -2906 | -2265 | -1244 | -4091 | -961 | 136 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7889 | | | | | | | | | | | | |
| 137I | 1105 | -2160 | -3956 | -3730 | 1959 | -3434 | -1130 | -1795 | -3348 | -1692 | -1411 | -2810 | -3571 | -2764 | -3122 | -2642 | -2381 | -1804 | 5259 | 566 | 137 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7883 | | | | | | | | | | | | |
| 138(R) | -2269 | -3123 | 2497 | -1540 | -3728 | -2880 | 2414 | 3259 | 347 | -2971 | -2265 | -1547 | -2868 | 2539 | 3022 | -2145 | -2019 | -2993 | -2838 | -2604 | 138 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7877 | | | | | | | | | | | | |
| 139(Q) | -3758 | -3792 | -3072 | -3245 | -4342 | -3586 | -3274 | -5053 | -2880 | -4719 | -4410 | -3349 | -4049 | 4526 | -2916 | -3829 | -3917 | -4726 | -3973 | -3953 | 139 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7870 | | | | | | | | | | | | |
| 140(D) | -2399 | -4357 | 3309 | 2333 | -4526 | -2166 | -1607 | -4526 | -1993 | -4365 | -3789 | 765 | -2745 | -1300 | -2954 | -2017 | -2495 | -3974 | -4514 | -3455 | 140 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7864 | | | | | | | | | | | | |
| 141(H) | -4406 | -3961 | -3921 | -4171 | 3231 | -3926 | 5401 | -5468 | -3992 | -5013 | -4849 | -4130 | -4378 | -4151 | -3893 | -4548 | -4592 | -5195 | -3383 | -2818 | 141 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7858 | | | | | | | | | | | | |
| 142(N) | -3232 | -3514 | -2565 | -2905 | -4358 | -3267 | -3364 | -5192 | -3627 | -5059 | -4632 | 4348 | -3843 | -4850 | -3792 | -4766 | -3533 | -4568 | -4087 | -3976 | 142 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7852 | | | | | | | | | | | | |
| 143(G) | -3681 | -3593 | -4389 | -4747 | -5281 | 3812 | -4419 | -5908 | -5071 | -5671 | -5288 | -4417 | -4223 | -3410 | -3319 | -3952 | -4069 | -5125 | -4424 | -5214 | 143 |
| | | -149 | -500 | 233 | -381 | 399 | 106 | -626 | 210 | -466 | -720 | 275 | 394 | 45 | 96 | 359 | 117 | -369 | -294 | -249 | |
| | | -16 | -7720 | -8762 | -1115 | -701 | -1378 | -8762 | -7845 | | | | | | | | | | | | |
| 144(F) | 4352 | -3337 | -4799 | -5121 | 3888 | -4670 | -928 | -3235 | -4686 | -2571 | -2654 | -3328 | -4541 | -3456 | -4078 | -3931 | -4217 | -3400 | -178 | 3260 | 144 |
| | | -149 | -500 | 233 | -381 | 399 | 106 | -626 | 210 | -466 | -720 | 275 | 394 | 45 | 96 | 359 | 117 | -369 | -294 | -249 | |
| | | -17 | -7720 | -8762 | -1115 | -701 | -1378 | -8762 | | | | | | | | | | | | | |

FIG. 10L

Table 8

| | | | | | | | | | | | | | | | | | | | |
|---|---|---|---|---|---|---|---|---|---|---|---|---|---|---|---|---|---|---|---|
| | -17 | -7720 | -8762 | -894 | -1115 | -701 | -1378 | -8762 | -7839 | | | | | | | | | | |
| 145(T | -866 | -1487 | -3132 | -3246 | -3768 | -1744 | -2940 | -3519 | -3190 | -3799 | -2925 | -2263 | -2509 | -2888 | -3152 | 2652 | 2778 | -2491 | -3995 | -3782 | 145 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7833 | | | | | | | | | | |
| 146(H | -4406 | -3961 | -3921 | -4171 | -3231 | -3926 | 5401 | -5468 | -3992 | -5013 | -4849 | -4130 | -4378 | -4151 | -3893 | -4548 | -4592 | -5195 | -3383 | -2818 | 146 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7827 | | | | | | | | | | |
| 147(Q | -3758 | -3792 | -3072 | -3245 | -4342 | -3586 | -3274 | -5053 | -2880 | -4719 | -4410 | -3349 | -4049 | 4526 | -2916 | -3829 | -3917 | -4726 | -3973 | -3953 | 147 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7820 | | | | | | | | | | |
| 148(D | -2001 | -3292 | 3601 | -626 | -4238 | -2111 | -1759 | -4246 | -2092 | -4199 | -3539 | -963 | -2715 | -1470 | -2900 | 1255 | -2206 | -3561 | -4288 | -3412 | 148 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7814 | | | | | | | | | | |
| 149(P | -4077 | -3791 | -4518 | -4858 | -5206 | -3818 | -4460 | -5898 | -5053 | -5602 | -5343 | -4628 | 4289 | -4938 | -4749 | -4364 | -4429 | -5313 | -4385 | -5119 | 149 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7807 | | | | | | | | | | |
| 150(G | -2415 | -2868 | 3074 | -2972 | -4434 | 3359 | -2704 | -4428 | -1915 | -4330 | -3670 | -2780 | -3430 | -2492 | 1875 | -2564 | -2676 | 3754 | -3904 | -3964 | 150 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7801 | | | | | | | | | | |
| 151(F) | -2339 | -1986 | -4665 | -4064 | 3176 | -4095 | -2859 | 229 | -3739 | 1224 | 2452 | -3737 | -3789 | -3040 | -3446 | -3256 | -2245 | 1216 | 2175 | -2011 | 151 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7794 | | | | | | | | | | |
| 152(I) | -2056 | -1731 | -4386 | -3851 | -1203 | -3873 | -2916 | 2292 | -3540 | 2065 | -105 | -3529 | -3714 | -3075 | -3381 | -3054 | 1098 | 51 | -2437 | -2237 | 152 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7788 | | | | | | | | | | |
| 153(D | -1118 | -2211 | 2195 | 621 | -3243 | 803 | -1223 | -3009 | -1065 | -3036 | -2177 | -857 | -2246 | -848 | -1597 | 985 | 2152 | -2413 | -3246 | -2588 | 153 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7781 | | | | | | | | | | |
| 154(H | -1003 | -1199 | -2356 | -1954 | -1388 | -2206 | -636 | -1619 | 229 | -1264 | -667 | -1770 | -2496 | -1555 | -1734 | -1385 | 1395 | 2407 | -1879 | -1430 | 154 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7775 | | | | | | | | | | |
| 155(M | 695 | -1534 | -4131 | -3535 | -944 | -3528 | -2430 | 2154 | -3199 | 1674 | 2687 | -3161 | -3396 | -2699 | -2998 | -2660 | -1749 | -182 | -2022 | -1814 | 155 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7768 | | | | | | | | | | |
| 156(L | 682 | -1592 | -4101 | -3606 | -1242 | -3407 | -2684 | 95 | -3291 | 2495 | -186 | -3196 | -3443 | -2879 | -3157 | -2606 | -1799 | 1329 | -2351 | -2114 | 156 |
| | -149 | -500 | 233 | 43 | -381 | 399 | 106 | -626 | 210 | -466 | -720 | 275 | 394 | 45 | 96 | 359 | 117 | -369 | -294 | -249 |
| | -17 | -7720 | -8762 | -894 | -1115 | -701 | -1378 | -8762 | -7762 | | | | | | | | | | |

FIG. 10M

Table 8

| | | | | | | | | | | | | | | | | |
|---|---|---|---|---|---|---|---|---|---|---|---|---|---|---|---|---|
| 157(N) | -1782 | -3518 | 1546 | 1312 | -3758 | -1994 | -1175 | -3610 | -1194 | -3512 | 2730 | 2977 | -2426 | -804 | -1905 | 1148 | -1804 | 3115 | -3698 | -2808 | 157 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7720 | -8762 | -894 | -1115 | -701 | -1378 | -8762 | -7755 | | | | | | | | | | | | |
| 158(K) | -2459 | -2938 | -2880 | -2055 | -2893 | -3094 | -1378 | -2442 | 3407 | 840 | -1882 | -2005 | -3159 | -1028 | -200 | -2490 | -2293 | -2474 | -2837 | -2553 | 158 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7720 | -8762 | -894 | -1115 | -701 | -1378 | -8762 | -7748 | | | | | | | | | | | | |
| 159(K) | -1148 | -2117 | -1407 | -950 | 3066 | 1999 | -1021 | -2720 | 2980 | -2713 | -1884 | -1076 | -2295 | -623 | -548 | 886 | 1179 | -2234 | -2851 | -2379 | 159 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7720 | -8762 | -894 | -1115 | -701 | -1378 | -8762 | -7741 | | | | | | | | | | | | |
| 160(P) | 1034 | -1295 | -2486 | -2150 | 1616 | -1809 | -1863 | -1877 | -2017 | -2165 | -1435 | -1781 | 2897 | -1813 | -2195 | 966 | -1055 | -1493 | -2567 | -2152 | 160 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7720 | -8762 | -894 | -1115 | -701 | -1378 | -8762 | -7735 | | | | | | | | | | | | |
| 161(D) | -2104 | -3998 | 2881 | 1352 | -4180 | 1216 | -1393 | -4095 | -1610 | -3965 | -3275 | 1701 | -2586 | -1055 | -2452 | -1771 | -2164 | -3570 | -4160 | -3154 | 161 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1843 | -7720 | -490 | | | | | | | | | | | | | | | | | | |
| 162(N) | -498 | -1221 | 110 | -15 | -1620 | -964 | 477 | -1773 | -335 | -1934 | -1330 | 3292 | -1450 | -280 | -647 | -522 | -670 | -1383 | -1763 | -1178 | 162 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -43 | -5920 | -6962 | -894 | -1115 | -2643 | -252 | -8762 | -7721 | | | | | | | | | | | | |
| 163(D) | -961 | -1901 | 3312 | 369 | -2315 | -1032 | -511 | -2292 | -663 | -2377 | -1817 | 34 | -1523 | -264 | -1242 | -811 | -1065 | -1927 | -2232 | -1739 | 163 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -43 | -5920 | -6962 | -894 | -1115 | -2643 | -252 | -8762 | -7714 | | | | | | | | | | | | |
| 164(H) | -997 | -1393 | -635 | -583 | -386 | -1411 | 4407 | -1664 | -259 | -1594 | -1144 | -676 | -1756 | -466 | -415 | -1034 | -1055 | -1464 | -790 | 42 | 164 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -43 | -5920 | -6962 | -894 | -1115 | -152 | -3320 | -8762 | -7707 | | | | | | | | | | | | |
| 165(V) | -2121 | -1684 | -4679 | -4254 | 1449 | -4310 | -3633 | 2372 | 4076 | 839 | 756 | -3954 | -4126 | -3800 | -4049 | -3566 | -2094 | 2791 | -3155 | -2717 | 165 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7720 | -8763 | -894 | -1115 | -701 | -1378 | -8762 | -7700 | | | | | | | | | | | | |
| 166(V) | -1172 | -1063 | -3285 | -2755 | -1280 | -2703 | -1906 | -3657 | -2465 | -907 | 407 | -2383 | -2845 | -997 | -2434 | 949 | 1115 | -3316 | -3168 | -2942 | 166 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7693 | | | | | | | | | | | | |
| 167(R) | -2428 | -3127 | -2310 | -1828 | -3921 | -2880 | -1372 | -3657 | -155 | -3392 | -2732 | 1602 | -3079 | 3685 | -2367 | -1977 | -2329 | 2471 | -1913 | -1547 | 167 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7687 | | | | | | | | | | | | |
| 168(I) | 673 | -1102 | -3159 | -2611 | -1247 | -2870 | -1866 | 2195 | -2325 | -820 | -354 | -2364 | -2914 | 1287 | -2345 | -1977 | -1221 | 2181 | -1906 | -1534 | 168 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | | | | | | | | | | | | | | | | | | | | |
| 169(Y) | 4444 | -3646 | -4593 | -4892 | -509 | -4268 | -1873 | -3993 | -4663 | -3407 | -3460 | -3884 | 4503 | -3998 | 4255 | 4336 | -4491 | 4072 | -1177 | 4829 | 169 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 10N

Table 8

| | | | | | | | | | | | | | | | | | | | | |
|---|---|---|---|---|---|---|---|---|---|---|---|---|---|---|---|---|---|---|---|---|
| -17 | | -7721 | -8763 | -894 | -1115 | -701 | -1378 | -8762 | -7672 | | | | | | | | | | | |
| 170(F) | -3400 | -2827 | -5361 | -4990 | -2846 | -5067 | -2816 | -651 | -4697 | 2592 | 25 | -4506 | -4471 | -3608 | -4224 | -4409 | -3268 | -1403 | -1851 | -1138 | 170 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7665 | | | | | | | | | | | | |
| 171(P) | 1191 | -1755 | -3163 | -3402 | -3998 | -1985 | -3182 | -3756 | -3492 | -4031 | -3233 | -2502 | 3818 | -3181 | -3412 | -1407 | -1613 | -2766 | -4124 | -4023 | 171 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7658 | | | | | | | | | | | | |
| 172(P) | 1902 | -1437 | -3147 | -3131 | -3577 | -1724 | -2798 | -3245 | -3019 | -3540 | -2684 | -2204 | 3083 | -2726 | -3028 | -1065 | 1432 | -2336 | -3823 | -3602 | 172 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7651 | | | | | | | | | | | | |
| 173(D) | -3832 | -4189 | 4132 | -2236 | -5073 | -3341 | -3194 | -5633 | -3716 | -5365 | -5035 | -2584 | -3886 | -3102 | -4252 | -3662 | -4000 | -5151 | -4434 | -4544 | 173 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7721 | -8763 | -894 | -1115 | -701 | -1378 | -8762 | -7644 | | | | | | | | | | | | |
| 174(A) | 2913 | -1375 | -3389 | -3354 | -3146 | 1014 | -2798 | -2432 | -3176 | -3025 | -2284 | -2297 | -2499 | -2833 | -3104 | -1111 | -1235 | -4568 | -3514 | -3272 | 174 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7722 | -8764 | -894 | -1115 | -701 | -1378 | -8762 | -7638 | | | | | | | | | | | | |
| 175(N) | 3232 | -3514 | -2565 | -2905 | 4358 | -3267 | 3364 | 5192 | -3627 | -5059 | -4632 | 4348 | -3843 | -3410 | -3792 | -3319 | -3533 | -4568 | -4087 | -3976 | 175 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7629 | | | | | | | | | | | | |
| 176(C) | -775 | 3036 | -2850 | -2408 | 1588 | -1919 | -1731 | -1110 | -2133 | -1469 | 2376 | -1909 | -2363 | -1881 | -2164 | 925 | 2536 | -890 | -2035 | -1692 | 176 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7622 | | | | | | | | | | | | |
| 177(L) | -3406 | -2832 | -5440 | -5026 | 2063 | -5151 | -3069 | -587 | -4746 | 2880 | 97 | -4659 | -4495 | -3638 | -4269 | -4506 | -3269 | -1359 | -2041 | -1444 | 177 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7615 | | | | | | | | | | | | |
| 178(L) | -3777 | -5089 | -5032 | -1735 | -4514 | -4040 | -1299 | -4754 | 3261 | -696 | -4891 | -4508 | -4152 | -4395 | -4705 | -3767 | -1993 | -3125 | -3069 | | 178 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7607 | | | | | | | | | | | | |
| 179(C) | 2942 | -3243 | -3827 | -3914 | -3641 | -1706 | -3124 | -3330 | -3613 | -3649 | -2779 | -2414 | -2485 | -3185 | -3403 | 1168 | -1242 | -2356 | -3925 | -3779 | 179 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7600 | | | | | | | | | | | | |
| 180(V) | -2004 | 2982 | -4544 | -4142 | -2135 | -4125 | -3700 | 1840 | -3967 | -1140 | -967 | -3830 | -4052 | -3798 | -4000 | -3390 | 1338 | 2999 | -3399 | -2963 | 180 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7592 | | | | | | | | | | | | |
| 181(F) | 1588 | -1608 | -2996 | -2447 | 2261 | -2299 | -1475 | -182 | -2129 | -756 | -166 | -2019 | -2485 | -1821 | -2060 | -1435 | 1085 | 1429 | -1479 | -1117 | 181 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7585 | | | | | | | | | | | | |

FIG. 10O

Table 8

| | | | | | | | | | | | | | | | | | | | | | |
|---|---|---|---|---|---|---|---|---|---|---|---|---|---|---|---|---|---|---|---|---|---|
| 182D | 1088 | -3814 | 3226 | 1427 | -4086 | -2058 | -1384 | -3970 | -1570 | -3872 | -3169 | -670 | -2570 | -1045 | -2378 | -1733 | -2102 | -3453 | -4073 | -3107 | 182 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7577 | | | | | | | | | | | | |
| 183H | -2540 | -3259 | -3155 | -1838 | -4078 | -3083 | 3373 | -3420 | 2334 | -3069 | -2392 | -1745 | -3017 | -555 | 2597 | -2412 | -2222 | -3187 | -2907 | -2791 | 183 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7570 | | | | | | | | | | | | |
| 184C | 998 | 4910 | -3920 | -3803 | -2550 | -2066 | -2898 | 917 | -3459 | -2125 | -1635 | -2602 | -2717 | -3092 | -3274 | -1392 | -1333 | 1279 | -3175 | -2885 | 184 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7562 | | | | | | | | | | | | |
| 185M | -3195 | -2670 | -5480 | -4897 | 2597 | -5129 | -3599 | -426 | -4630 | 2310 | 2844 | -4767 | -4399 | -3550 | -4175 | -4399 | -3050 | -1206 | -2449 | -2343 | 185 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7555 | | | | | | | | | | | | |
| 186Q | -1978 | -3010 | -1873 | -1184 | -3573 | -2640 | 2315 | -3132 | 2388 | -2890 | -2142 | -1292 | -2679 | 3064 | 193 | -1845 | -1787 | -2819 | -2820 | -2501 | 186 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -18 | -7721 | -8763 | -894 | -1115 | -701 | -1378 | -8762 | -7547 | | | | | | | | | | | | |
| 187S | -1150 | -2122 | 1356 | -858 | -3376 | -1832 | -1484 | -3135 | -1404 | -3212 | -2374 | -1042 | -2342 | -1143 | -1916 | 2458 | 2054 | -2488 | -3434 | -2812 | 187 |
| | * | * | * | * | * | * | * | * | * | * | * | * | * | * | * | * | * | * | * | * | |
| | * | * | * | * | * | * | * | * | -8762 | 0 | | | | | | | | | | | |

FIG. 10P

Table 9

```
HMMER2.0 [2.3.2]
NAME XFP_C
ACC PF09363.1
DESC XFP C-terminal domain
LENG 212
ALPH Amino
RF no
CS no
MAP yes
COM hmmbuild -f -F HMM_fs.ann SEED.ann
COM hmmcalibrate --seed 0 HMM_fs.ann
NSEQ 6
DATE Thu May 3 17:57:57:02 2007
CKSUM 5491
GA 25.0 25.0
TC 47.0 29.4
NC 15.7 15.7
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -10.483098 0.640397
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -193 | * | -2999 | | | | | | | | | | | | | | | | | | |
| 1(K) | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 1 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -1193 | -8721 | | | | | | | | | | | | |
| 2(Q) | -1392 | -2802 | -618 | -424 | -3105 | -2084 | 2223 | -2893 | 446 | -2828 | -1977 | 1616 | 1057 | 3114 | -866 | -1245 | -1350 | -2468 | -2957 | -2283 | 2 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8718 | | | | | | | | | | | | |
| 3(P) | 1097 | -2000 | -3515 | -3791 | -4319 | -2230 | -3513 | -4117 | -3884 | -4378 | -3565 | -2801 | 3889 | -3540 | -3757 | -1661 | -1871 | -3066 | -4416 | -4363 | 3 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8714 | | | | | | | | | | | | |
| 4(H) | 829 | -2314 | -845 | -285 | -2656 | -1910 | 2103 | -2366 | 0 | -2324 | -1434 | -569 | -2003 | 1714 | 2028 | 709 | -889 | -1956 | -2490 | -1870 | 4 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8711 | | | | | | | | | | | | |
| 5(W) | 872 | -1301 | -1524 | -969 | -1324 | -2103 | -863 | -924 | -771 | 407 | -486 | -1096 | 1119 | 2314 | -1087 | -1098 | -833 | -778 | 2741 | -1233 | 5 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8707 | | | | | | | | | | | | |
| 6(Q) | 1139 | -1910 | -1850 | -1613 | -3267 | -2003 | -1790 | -2923 | -1462 | -3080 | -2266 | -1578 | -2518 | 3569 | -1755 | -1258 | 1437 | -2329 | -3351 | -2895 | 6 |
| | -149 | -500 | 233 | 43 | -381 | 399 | 106 | 210 | 210 | -466 | -720 | 275 | 394 | 45 | 96 | 359 | 117 | -369 | -294 | -249 | |
| | -12 | -7945 | -8987 | -894 | -1115 | -701 | -1378 | -8914 | -8704 | | | | | | | | | | | | |

FIG. 11A

Table 9

FIG. 11B

Table 9

| | | | | | | | | | | | | | | | | | | | |
|---|---|---|---|---|---|---|---|---|---|---|---|---|---|---|---|---|---|---|---|
| 20(G) | -12 | -7945 | -4088 | -3924 | -4774 | -5139 | -5615 | 3825 | -4753 | -1378 | -8914 | -8658 | -6014 | -5662 | -4812 | -4539 | -5232 | -5106 | -4370 | -4472 | -5527 | -4696 | -5561 | 20 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | | -8655 | | | | | | | | | | | | |
| 21(I) | 1832 | | -1779 | -4707 | -4321 | | -2320 | -4169 | -3857 | 2857 | | -4145 | -1329 | -1156 | -3958 | -4165 | -3960 | -4165 | -3443 | -2157 | 1658 | -3571 | -3143 | 21 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | -8914 | -8651 | | | | | | | | | | | | |
| 22(A) | 1979 | | -2132 | 1358 | -1230 | | -3624 | 895 | -1764 | -3399 | | -1659 | -3464 | -2589 | -1343 | -2501 | -1420 | -2138 | 1914 | -1456 | -2656 | -3665 | -3086 | 22 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | -8914 | -8647 | | | | | | | | | | | | |
| 23(I) | -1613 | | -1432 | -3370 | 991 | | -1684 | -3301 | -2327 | 2219 | | -2660 | -1128 | -723 | -2715 | -3318 | -2464 | -2756 | -2418 | 1220 | 2185 | -2433 | -2038 | 23 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | -8914 | -8644 | | | | | | | | | | | | |
| 24(W) | -3333 | | -2943 | -4821 | -4705 | | -865 | -4258 | -2319 | 1550 | | -4105 | -1483 | -1550 | -3928 | -4360 | -3731 | -3856 | -3853 | -3350 | -1751 | 5765 | -662 | 24 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | -8914 | -8640 | | | | | | | | | | | | |
| 25(D) | -2155 | | -3941 | 2895 | 1331 | | -4165 | -2244 | -1467 | 2266 | | -3906 | -723 | -3170 | -838 | -2712 | -1110 | -2170 | -1857 | -2186 | -3532 | -4076 | -3168 | 25 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8987 | -894 | -1115 | -701 | | | -8914 | -8637 | | | | | | | | | | | | |
| 26(W) | -4535 | | -3580 | -5043 | -5339 | | 2264 | -4800 | -1315 | -3404 | | -4909 | -2727 | -2820 | -3667 | -4744 | -3774 | -4331 | -4221 | -4434 | -3613 | 5781 | 611 | 26 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8633 | | | | | | | | | | | | |
| 27(A) | 3609 | | -2508 | -4184 | -4493 | | -4592 | -2737 | -3989 | -4421 | | -4496 | -4701 | -4051 | -3440 | -3474 | -4171 | -4253 | -2294 | -2487 | -3536 | -4484 | -4643 | 27 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8629 | | | | | | | | | | | | |
| 28(S) | -1944 | | -2458 | -3696 | -4011 | | -4410 | -2644 | -3753 | -4675 | | -4191 | -4807 | -4070 | -3198 | -3384 | -3886 | -4051 | 3656 | -2393 | -3615 | -4374 | -4307 | 28 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8626 | | | | | | | | | | | | |
| 29(N) | -1462 | | -2164 | -1894 | -2122 | | -3935 | -2171 | -2578 | -3801 | | -2603 | -4009 | -3230 | 3172 | -2856 | -2392 | -2846 | -1616 | 2907 | -2960 | -4077 | -3633 | 29 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8622 | | | | | | | | | | | | |
| 30(D) | 2036 | | -3092 | 3356 | -1144 | | -4437 | -2344 | -2201 | -4300 | | -2537 | -4380 | -3702 | -1420 | -2974 | -1935 | -3248 | -2004 | -2335 | -3577 | -4473 | -3774 | 30 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8618 | | | | | | | | | | | | |
| 31(K) | 719 | | -2804 | 1286 | -282 | | -3133 | -1980 | -846 | -2900 | | 2557 | -2836 | -1958 | 1613 | -2216 | -421 | -1059 | -1135 | -1263 | -2444 | -3007 | -2283 | 31 |
| | | | -149 | -500 | 233 | 43 | -381 | 399 | 106 | -626 | 210 | | -466 | -720 | 275 | 394 | 45 | 96 | 359 | 117 | -369 | -294 | -249 | |
| | | | -12 | -7945 | -8988 | -894 | -1115 | -701 | | | -8914 | -8615 | | | | | | | | | | | | |

FIG. 11C

Table 9

| | | | | | | | | | | | | | | | | | | | | |
|---|---|---|---|---|---|---|---|---|---|---|---|---|---|---|---|---|---|---|---|---|
| 32(G) | -1795 | -2851 | 1703 | -1000 | -4330 | 2898 | -2022 | -4220 | -2294 | -4229 | -3471 | -1259 | -2791 | -1732 | -2991 | 1182 | -2066 | -3405 | -4399 | -3633 | 32 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1206 | -7945 | -837 | -894 | -1115 | -701 | -1378 | -8611 | | | | | | | | | | | | | |
| 33(N) | -713 | -1555 | -300 | -476 | -2841 | 2208 | -1131 | -2756 | -1105 | -2843 | -2074 | 2836 | -1863 | -861 | -1525 | 760 | -971 | -2081 | -2888 | -2349 | 33 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -24 | -6764 | -7806 | -894 | -1115 | -162 | -3231 | -8607 | | | | | | | | | | | | | |
| 34(E) | 652 | -2550 | 1383 | 2004 | -2857 | -1868 | -643 | -2618 | -298 | -2563 | -1660 | -497 | -2040 | 1542 | -832 | -908 | 985 | -2168 | -2738 | -2028 | 34 |
| | -149 | -500 | 233 | 43 | -381 | 399 | 106 | -626 | 210 | -466 | -720 | 275 | 394 | 45 | 96 | 359 | 117 | -369 | -294 | -249 | |
| | | -7945 | -8988 | -894 | -1115 | -701 | -1378 | -8604 | | | | | | | | | | | | | |
| 35(E) | 978 | -3351 | -336 | 2983 | -3871 | -2170 | -1425 | -3692 | -1401 | -3640 | -2859 | 1765 | -2619 | -1063 | -2043 | -1667 | -1932 | -3175 | -3830 | -3006 | 35 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8988 | -894 | -1115 | -701 | -1378 | -8600 | | | | | | | | | | | | | |
| 36(P) | -1823 | -2153 | -3843 | -3947 | -3271 | -2734 | -3495 | -1581 | -3785 | -2766 | -2465 | -3169 | 3446 | -3607 | -3696 | -2195 | -2168 | 2328 | -3859 | -3579 | 36 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8988 | -894 | -1115 | -701 | -1378 | -8596 | | | | | | | | | | | | | |
| 37(D) | -2642 | -4390 | 3693 | -696 | -4628 | -2447 | -1891 | -4714 | -2203 | -4552 | -3980 | -1088 | -3019 | 1971 | -3045 | -2293 | -2745 | -4173 | -4588 | -3642 | 37 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8988 | -894 | -1115 | -701 | -1378 | -8592 | | | | | | | | | | | | | |
| 38(V) | -2557 | -2122 | -5071 | -4711 | -1962 | -4673 | 4220 | 320 | -4512 | 984 | -791 | -4445 | -4483 | -4165 | -4454 | -4020 | -2550 | 3348 | -3513 | -3210 | 38 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7945 | -8988 | -894 | -1115 | -701 | -1378 | -8589 | | | | | | | | | | | | | |
| 39(V) | -2838 | -2616 | 4834 | -4880 | 3213 | -3955 | -4416 | -610 | -4757 | -2310 | -2253 | -4383 | -4345 | -4643 | -4642 | -3732 | -3007 | 3763 | -4157 | -3886 | 39 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -12 | -7946 | -8988 | -894 | -1115 | -701 | -1378 | -8585 | | | | | | | | | | | | | |
| 40(M) | -3038 | -2583 | -5400 | 4796 | 1866 | -4936 | -3671 | 2288 | -4513 | 1389 | 3379 | -4610 | -4379 | -3590 | -4127 | -4157 | -2917 | -1104 | -2668 | -2694 | 40 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8581 | | | | | | | | | | | | | |
| 41(A) | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 41 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8577 | | | | | | | | | | | | | |
| 42(C) | 2065 | 2925 | -3988 | -4043 | -3973 | -2206 | -3331 | -3726 | -3772 | -3993 | -3088 | -2601 | -2687 | -3352 | -3601 | 2060 | -1451 | -2653 | -4224 | -4091 | 42 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8574 | | | | | | | | | | | | | |
| 43(A) | 2866 | 2846 | -4109 | -4001 | -2791 | -2206 | -3077 | -1268 | -3662 | 2419 | -1888 | -2761 | -2871 | -3275 | -3465 | -1533 | -1500 | 1398 | -3377 | -3097 | 43 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8570 | | | | | | | | | | | | | |
| 44(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 44 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 11D

Table 9

| | | | | | | | | | | | | | | | | | | | | | |
|---|---|---|---|---|---|---|---|---|---|---|---|---|---|---|---|---|---|---|---|---|---|
| -13 | -7946 | -8988 | -894 | -1115 | -701 | -1378 | -8914 | -8566 | | | | | | | | | | | | | |
| 45(D) | 1008 | -3741 | 3309 | -578 | -4350 | -2242 | 1698 | -4254 | -1941 | -3484 | 1820 | -2795 | -1375 | -2757 | -1930 | -2306 | -3665 | -4371 | -3418 | 45 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8362 | | | | | | | | | | | |
| 46(V) | -1488 | -1444 | -2805 | 1912 | -1672 | -3036 | -1995 | 1499 | -2149 | -719 | -2290 | -3083 | -1996 | -2352 | -2120 | 998 | 2130 | -2347 | -1936 | 46 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8558 | | | | | | | | | | | |
| 47(P) | -2288 | -2497 | -3856 | -3931 | -2960 | -3134 | 3483 | 1588 | -3705 | -2229 | -3416 | 3829 | -3629 | -3645 | -2690 | -2575 | -1605 | -3649 | -3323 | 47 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8555 | | | | | | | | | | | |
| 48(T) | -1494 | -1874 | -3613 | -3499 | -2448 | -2472 | -2890 | -1675 | -3034 | 2674 | -2770 | -3069 | -2947 | -2983 | -1828 | 3524 | -1602 | -3212 | -2888 | 48 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8551 | | | | | | | | | | | |
| 49(F) | -1077 | -1060 | -2607 | -2006 | 1617 | -2517 | -1308 | 1338 | 853 | -74 | -1856 | -2554 | 1561 | -1724 | -1568 | -1013 | -416 | -1457 | -1095 | 49 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8547 | | | | | | | | | | | |
| 50(E) | -4205 | -4417 | -2343 | 3901 | -5349 | -3698 | -3534 | -5837 | -3838 | -5237 | -3039 | -4218 | -3453 | -4201 | -4072 | -4352 | -5409 | -4640 | -4860 | 50 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8543 | | | | | | | | | | | |
| 51(T) | 1578 | -1365 | -3818 | -3310 | -1660 | -3164 | 2456 | 1709 | -3026 | 726 | -2898 | -3288 | -2750 | -2975 | -2334 | 2031 | 1609 | -2396 | -2024 | 51 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8539 | | | | | | | | | | | |
| 52(M) | -3164 | -2670 | -5546 | -4970 | -1172 | 5167 | 3972 | 395 | -4712 | 2735 | -4857 | -4533 | -3759 | -4329 | -4434 | -3047 | 1340 | -2847 | -2936 | 52 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8535 | | | | | | | | | | | |
| 53(A) | 3164 | -2290 | -2449 | -2301 | -3900 | -2380 | -2191 | -3516 | 1483 | -2906 | -2112 | -3288 | -1904 | -1531 | -1776 | -1904 | -2880 | -3730 | -3462 | 53 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8531 | | | | | | | | | | | |
| 54(A) | 3609 | -2508 | -4184 | -4493 | -4592 | -2737 | -3989 | -4421 | -4496 | -4051 | -3440 | -3474 | -4171 | -4253 | -2294 | -2487 | -3536 | -4484 | -4643 | 54 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8527 | | | | | | | | | | | |
| 55(V) | 950 | -941 | -2811 | -2248 | -1031 | -2327 | -1422 | 440 | -1962 | 740 | -1933 | -2494 | -1690 | -1964 | 896 | 1079 | 1807 | -1521 | -1165 | 55 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8524 | | | | | | | | | | | |
| 56(H) | 659 | -2340 | 1265 | 1241 | -2654 | -1788 | 2240 | -2406 | -89 | -2353 | -421 | -1907 | 1509 | -604 | -738 | 910 | -1959 | -2525 | -1836 | 56 |
| - | -149 | -500 | 233 | 43 | -381 | 399 | 106 | -626 | 210 | -720 | 275 | 394 | 45 | 96 | 359 | 117 | -369 | -294 | -249 | |
| - | -13 | -7946 | -8988 | -894 | -1115 | -701 | -1378 | -8914 | -8520 | | | | | | | | | | | |

FIG. 11E

Table 9

| | | | | | | | | | | | | | | | | | | | | |
|---|---|---|---|---|---|---|---|---|---|---|---|---|---|---|---|---|---|---|---|---|
| 57(M) | 905 | -1698 | -4314 | -3724 | -1143 | -3706 | -2623 | 2145 | -3388 | 1126 | 3388 | -3345 | -3578 | -2895 | -3189 | -2841 | -1918 | -295 | -2218 | -2005 | 57 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8516 | | | | | | | | | | | | |
| 58(L) | -3094 | -2629 | -5472 | -5009 | -1335 | -5054 | -266 | -4744 | -148 | -4850 | -4577 | -3917 | -4430 | -4403 | -3029 | 1404 | -3024 | -3024 | 58 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8512 | | | | | | | | | | | | |
| 59(N) | -1718 | -2924 | -1536 | -943 | -3401 | -2491 | 2272 | -3022 | 67 | -2851 | -2042 | 2480 | -2560 | 1853 | 2240 | -1589 | -1584 | -2659 | -2864 | -2426 | 59 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8508 | | | | | | | | | | | | |
| 60(Q) | -1303 | -2782 | -604 | 1957 | -3121 | -2037 | -786 | -2861 | 11397 | -2771 | -1895 | 1587 | -2225 | 2403 | -741 | -1147 | -1246 | -2420 | -2908 | -2240 | 60 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8504 | | | | | | | | | | | | |
| 61(M) | -836 | -1314 | 1097 | -815 | 1234 | -2045 | 2007 | -937 | -682 | -1198 | 2233 | -976 | -2124 | 1369 | -1042 | -1018 | -776 | 996 | -1675 | -1208 | 61 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8500 | | | | | | | | | | | | |
| 62(F) | -1264 | -1055 | -3592 | -2980 | 2448 | 801 | -1770 | 1523 | -2606 | 732 | 96 | -2510 | -2888 | 4287 | -2426 | -1975 | -1207 | 1242 | -1588 | -1251 | 62 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -267 | -7946 | -2622 | -894 | -1115 | -701 | -1378 | -8914 | -8496 | | | | | | | | | | | | |
| 63(P) | -4031 | -3755 | -4476 | -4814 | -5166 | -3783 | 4422 | -5849 | -5008 | -5560 | -5299 | -4583 | -4583 | 4894 | -4709 | -4316 | -4383 | -5266 | -4354 | -5078 | 63 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7693 | -8735 | -894 | -1115 | -1509 | -624 | -8914 | -8492 | | | | | | | | | | | | |
| 64(E) | -1699 | 3425 | 1700 | 2340 | 3660 | -1960 | -1101 | -3504 | -1077 | -3405 | -2608 | 1773 | -3858 | 2059 | -1764 | -1441 | -1711 | -3013 | -3587 | -2715 | 64 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7693 | -8735 | -894 | -1115 | -358 | -2187 | -8914 | -8488 | | | | | | | | | | | | |
| 65(L) | 891 | -2044 | -4713 | -4184 | -1318 | -4146 | -3223 | 1658 | -3880 | 2504 | -198 | -3858 | -3970 | -3332 | -3681 | -3346 | -2320 | -337 | -2643 | -2499 | 65 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8484 | | | | | | | | | | | | |
| 66(R) | -3030 | -3584 | -3982 | -2344 | -4551 | -3458 | -1269 | -3800 | 2924 | -3397 | -2757 | -2153 | -3376 | 852 | 3034 | -2903 | -2656 | -3598 | -3188 | -3160 | 66 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8480 | | | | | | | | | | | | |
| 67(F) | -2326 | 1891 | -4869 | -4440 | 2685 | 4485 | -3701 | 2340 | -4251 | -921 | -863 | -4124 | -4292 | -3991 | -4198 | -3737 | -2296 | 2290 | -3181 | -2708 | 67 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8476 | | | | | | | | | | | | |
| 68(R) | -3054 | -3592 | -3980 | -2373 | -4560 | -3469 | -1297 | -3823 | 1781 | -3421 | -2785 | -2179 | -3395 | -881 | 3702 | -2930 | -2684 | -3621 | -3206 | -3181 | 68 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8472 | | | | | | | | | | | | |
| 69(F) | -3145 | -2644 | -4628 | -4516 | 2787 | -4252 | -1269 | -1824 | -4116 | -1928 | -1754 | -3303 | -4186 | -3281 | -3729 | -3432 | -3069 | 2671 | -580 | 2537 | 69 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 11F

Table 9

FIG. 11G

Table 9

| | | | | | | | | | | | | | | | | | | | | |
|---|---|---|---|---|---|---|---|---|---|---|---|---|---|---|---|---|---|---|---|---|
| 82(H) | -956 | -2424 | -615 | 1087 | -2749 | -1853 | 2292 | -2494 | 2040 | -2432 | -1522 | 1288 | -1978 | -92 | -585 | 753 | -897 | -2050 | -2592 | -1916 | 82 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -1873 | -7946 | 474 | -894 | -1115 | -701 | -1378 | -8914 | -8414 | | | | | | | | | | | |
| 83(G) | -853 | -1186 | -1419 | -1603 | -2565 | 3376 | -1668 | -2627 | -1844 | -2759 | -2200 | -1431 | -1859 | -1709 | -1902 | -1054 | -1192 | -2034 | -2282 | -2387 | 83 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -36 | -6109 | -7151 | -894 | -1115 | -2826 | -219 | -8914 | -8409 | | | | | | | | | | | |
| 84(A) | 2862 | -488 | -1346 | -1349 | -1807 | -785 | -1257 | -1298 | -1627 | -1088 | -934 | -1428 | -1183 | -1403 | -201 | -309 | -714 | -2107 | -1798 | 84 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -36 | -6109 | -7151 | -894 | -1115 | -2826 | -219 | -8914 | -8405 | | | | | | | | | | | |
| 85(L) | -1446 | -1261 | -2639 | -2396 | -166 | -2529 | -1687 | 443 | -1969 | 2652 | 716 | -2264 | -2607 | -1810 | -1925 | -1403 | -1460 | 71 | -1338 | -963 | 85 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -36 | -6109 | -7151 | -894 | -1115 | -431 | -1952 | -8914 | -8401 | | | | | | | | | | | |
| 86(E) | -1620 | -3077 | -205 | 2781 | -2713 | -2016 | -1027 | -3107 | -935 | -3054 | -2295 | 1905 | -2376 | -703 | -1502 | -2083 | -1618 | -2704 | -2909 | 1972 | 86 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -15 | -7696 | -8738 | -894 | -1115 | -1502 | -628 | -8914 | -8397 | | | | | | | | | | | |
| 87(H) | -1687 | -3020 | -524 | -508 | -3027 | -2149 | 4043 | -3137 | 478 | -3027 | -2263 | 1907 | -2446 | 2055 | 794 | -1416 | -1649 | -2742 | -2951 | -2237 | 87 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -15 | -7696 | -8738 | -894 | -1115 | -360 | -2179 | -8914 | -8392 | | | | | | | | | | | |
| 88(P) | -2450 | -4345 | 1816 | 1516 | -4562 | -2311 | -1714 | -4514 | -2022 | -3745 | -914 | 3318 | -1394 | -755 | -1508 | -2536 | -2951 | -4556 | -3521 | 88 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8388 | | | | | | | | | | | |
| 89(H) | -3297 | -1451 | 1311 | -3729 | -2695 | 4349 | -3419 | -165 | -3210 | -2472 | -1349 | -2852 | -1683 | -2920 | -2098 | -2038 | -3149 | -2733 | 89 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8384 | | | | | | | | | | | |
| 90(G) | 1135 | -2508 | -960 | 1390 | -3988 | 2880 | -1982 | -3774 | -2052 | -3851 | -3054 | -1368 | -2715 | -3909 | -2580 | 1705 | -1591 | -1835 | -3036 | -3424 | 90 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8379 | | | | | | | | | | | |
| 91(M) | -3620 | -3042 | -5906 | -5341 | -1118 | -5639 | -4298 | -608 | -5051 | 2656 | 3645 | -5383 | -4766 | -3909 | -4566 | -5021 | -3469 | -1425 | -2906 | -3062 | 91 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8375 | | | | | | | | | | | |
| 92(S) | -1385 | -2104 | -1840 | -2115 | -4039 | -2094 | -2642 | -4072 | -2802 | -4207 | -3375 | 1808 | -2809 | -2466 | -3073 | 3255 | -1780 | -3055 | -4205 | -3726 | 92 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8371 | | | | | | | | | | | |
| 93(D) | -2954 | -4081 | 3777 | -1338 | -4930 | -2812 | -2481 | -5106 | -2896 | -4959 | -4423 | -1697 | 1695 | -2236 | -3689 | -2728 | -3134 | -4489 | -4667 | -4137 | 93 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -13 | -7946 | -8988 | -894 | -1115 | -701 | -1378 | -8914 | -8366 | | | | | | | | | | | |
| 94(R) | 847 | -2632 | -1132 | 2003 | -3046 | -2175 | -695 | -2716 | 1321 | -2604 | -1741 | -819 | -2258 | -250 | 2101 | -1179 | -1206 | -2313 | -2696 | -2152 | 94 |
| | | -149 | -500 | 233 | 43 | -381 | 399 | 106 | -626 | 210 | -466 | -720 | 275 | 394 | 45 | 96 | 359 | 117 | -369 | -294 | -249 |

FIG. 11H

Table 9

| | | | | | | | | | | | | | | | | | | | | | |
|---|---|---|---|---|---|---|---|---|---|---|---|---|---|---|---|---|---|---|---|---|---|
| 95(D) | -13 | -2629 | -4604 | 3009 | 2799 | -4770 | -2374 | -1828 | -4782 | -2234 | -4614 | -4051 | -973 | -2960 | -1523 | -3216 | -2241 | -2730 | -4224 | -4757 | -3689 | 95 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8362 | | | | | | | | | | | | |
| 96(F) | -4587 | -3562 | -5019 | -5350 | 4191 | -4887 | -1144 | -3464 | -4916 | -2789 | -2878 | -3547 | -4760 | -3678 | -4301 | -4156 | -4453 | -3634 | -393 | 2478 | 96 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8353 | | | | | | | | | | | | |
| 97(D) | 988 | 3875 | 2907 | 1483 | -4100 | -2208 | -1447 | -3972 | -1539 | -3865 | -3114 | 1567 | -2675 | -1089 | -2294 | -1800 | -2126 | -3467 | -4055 | -3126 | 97 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8349 | | | | | | | | | | | | |
| 98(S) | 1458 | -2457 | 1399 | -292 | -2897 | -1890 | -750 | -2648 | 1311 | -2615 | -1722 | -599 | -2098 | -317 | -922 | 1668 | -1053 | -2187 | -2800 | -2113 | 98 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8344 | | | | | | | | | | | | |
| 99(L) | -3562 | -3022 | -4998 | -4839 | 384 | -4758 | -2089 | -1358 | -4382 | 2908 | 731 | -3989 | -4502 | -3590 | -4015 | -4103 | -3467 | -1964 | -1321 | 2369 | 99 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8340 | | | | | | | | | | | | |
| 100(F) | -4720 | -3927 | -5139 | -5454 | -3748 | -4504 | -2520 | -3938 | -5326 | -3307 | -3429 | -4469 | -4782 | -4575 | -4818 | -4787 | -4810 | -4172 | -1812 | -736 | 100 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8335 | | | | | | | | | | | | |
| 101(T) | -1345 | -1936 | -3485 | -4998 | -4307 | 1297 | -3469 | -4115 | -3845 | -3519 | -2741 | -1119 | -2943 | -3484 | -3725 | -1588 | 3638 | -3022 | -4411 | -4351 | 101 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8331 | | | | | | | | | | | | |
| 102(P) | 1040 | -1933 | -1444 | -985 | -2825 | -1942 | -1172 | -2498 | 1349 | -2593 | -1749 | 2171 | -2951 | -794 | -1131 | -1051 | 1955 | -2025 | -2847 | -2320 | 102 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8326 | | | | | | | | | | | | |
| 103(D) | -2253 | -3538 | 3694 | -855 | -4532 | -2334 | -2017 | -4570 | -2397 | -4510 | -3869 | -1194 | -1859 | -1736 | -3233 | -1902 | 1140 | -2471 | -4578 | -3695 | 103 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -1873 | -7946 | -8988 | -894 | -1115 | -701 | -1378 | -8914 | -8322 | | | | | | | | | | | | |
| 104(G) | -853 | -1186 | -1419 | -1603 | -1871 | -2565 | 3376 | -1668 | -2627 | -2759 | -2200 | -1431 | -2951 | -1709 | -1902 | -1054 | -1192 | -2034 | -2282 | -2387 | 104 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -36 | -6109 | -7151 | -894 | -1115 | -133 | -3504 | -8914 | -8317 | | | | | | | | | | | | |
| 105(K) | -2513 | -3301 | -3024 | -1871 | -4114 | -3126 | -1139 | -3484 | 3142 | -3184 | -2485 | -1825 | -3101 | -717 | 1860 | -2405 | 1288 | -3220 | -3066 | -2911 | 105 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -3504 | -8914 | -8313 | | | | | | | | | | | | |
| 106(P) | -3125 | -3472 | -2885 | -3107 | -3559 | -3370 | 2901 | -4916 | -3129 | -4732 | -4256 | -3117 | 3925 | -3250 | -3218 | -3230 | -3395 | -4360 | -3686 | -3131 | 106 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -13 | -7946 | -8988 | -894 | -1115 | -701 | -1378 | -8914 | -8308 | | | | | | | | | | | | |

FIG. 111

Table 9

| | | | | | | | | | | | | | | | | |
|---|---|---|---|---|---|---|---|---|---|---|---|---|---|---|---|---|
| 107(V) | -2449 | -1961 | -5107 | -4792 | -2559 | -4869 | -4842 | 1787 | -4726 | -1338 | -1282 | -4575 | -4662 | -4648 | -4859 | -4241 | -2447 | 3416 | -4245 | -3747 | 107 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8304 | | | | | | | | | | | | |
| 108(I) | -2038 | -1784 | -4073 | -3538 | -1026 | -3659 | 2506 | 3064 | 3042 | -254 | 1092 | -3185 | -3570 | -2750 | -2918 | -2809 | -1976 | -421 | -2001 | -1514 | 108 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8299 | | | | | | | | | | | | |
| 109(F) | -4720 | -3927 | -5139 | -5454 | 4513 | -4504 | -2520 | -3938 | -5326 | -3429 | -3307 | -4469 | -4782 | -4575 | -4818 | -4787 | -4810 | -4172 | -1812 | -736 | 109 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8295 | | | | | | | | | | | | |
| 110(N) | 2479 | -1867 | -2193 | -2351 | -4027 | 1237 | -2680 | -3819 | -2833 | -3118 | -4000 | 2632 | -2690 | -2487 | -3076 | -1354 | -1567 | -2811 | -4182 | -3832 | 110 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8290 | | | | | | | | | | | | |
| 111(Y) | -4612 | -3570 | -5027 | -5365 | 3457 | -4900 | -1135 | -3495 | -4928 | -2906 | -2816 | -3544 | -4767 | -3678 | -4307 | -4162 | -4473 | -3659 | -383 | 3895 | 111 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8285 | | | | | | | | | | | | |
| 112(H) | -4836 | -4275 | -4356 | -4629 | -3663 | -4242 | 5422 | -5932 | -4492 | -5298 | -5436 | -4579 | -4696 | -4620 | -4352 | -5005 | -5030 | -5648 | -3750 | -3259 | 112 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8281 | | | | | | | | | | | | |
| 113(G) | 1132 | -1656 | -3630 | -3843 | 4215 | 3045 | -3388 | -4017 | -3845 | -3324 | -4265 | -2567 | -2709 | -3385 | -3688 | 1328 | -1497 | -2799 | -4429 | -4315 | 113 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8988 | -894 | -1115 | -701 | -1378 | -8914 | -8276 | | | | | | | | | | | | |
| 114(Y) | -4604 | -3569 | -5020 | -5357 | 2093 | -4892 | -1140 | -3492 | -4921 | -2905 | -2815 | -3546 | -4764 | -3679 | -4305 | -4160 | -4468 | -3656 | -389 | 4550 | 114 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | -8271 | | | | | | | | | | | | |
| 115(P) | 1686 | -1775 | -1257 | 1192 | -2259 | -1996 | -1137 | -1747 | -939 | -1306 | -2059 | -1082 | 2013 | -833 | -1354 | -1109 | -1078 | 1053 | -2490 | -1979 | 115 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | -8267 | | | | | | | | | | | | |
| 116( | -911 | -1979 | 1204 | -354 | -1971 | -1917 | 2044 | -1821 | -260 | -1361 | -1921 | -627 | -2020 | 1682 | -714 | -875 | -851 | -1531 | 3682 | -1476 | 116 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | -8262 | | | | | | | | | | | | |
| 117(D) | -1595 | -2205 | 2386 | -1132 | -2251 | -2360 | -1616 | -1668 | -1672 | 1961 | -2059 | -1358 | -2717 | -1399 | -2106 | -1703 | 1087 | -1603 | -2785 | -2280 | 117 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | -8257 | | | | | | | | | | | | |
| 118(I) | -2533 | -2040 | -5154 | -4770 | -2133 | -4913 | -4501 | 3201 | -4662 | 891 | 936 | -4572 | -4602 | -4354 | -4667 | -4240 | -2507 | 1754 | -3764 | -3470 | 118 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | -8253 | | | | | | | | | | | | |
| 119(H) | -1221 | -2591 | -1040 | 1217 | -2989 | -2108 | 3064 | -2676 | 1463 | -1690 | -2566 | 1307 | -2192 | -200 | 1508 | -1095 | -1130 | -2261 | -2664 | -2094 | 119 |
| | -149 | -500 | 233 | 43 | -381 | 399 | 106 | -626 | 210 | -720 | -466 | 275 | 394 | 45 | 96 | 359 | 117 | -369 | -294 | -249 | |
| | -13 | -7946 | -8989 | -894 | -1115 | -701 | -1378 | -8914 | | | | | | | | | | | | | |

FIG. 11J

Table 9

| | | | | | | | | | | | | | | | | |
|---|---|---|---|---|---|---|---|---|---|---|---|---|---|---|---|---|
| | -13 | -7946 | -8989 | -894 | -1115 | -701 | -1378 | -8914 | -8248 | | | | | | | |
| 120(R) | 862 | -2187 | 859 | 332 | -2662 | 770 | -616 | -2382 | 160 | -2365 | -1469 | -604 | -1998 | 1525 | 1934 | 922 | -871 | -1941 | -2551 | -1920 | 120 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7948 | -8990 | -894 | -1115 | -701 | -1378 | -8914 | -8244 | | | | | | | | | | | | |
| 121(L) | -3417 | -2857 | -5787 | -5262 | -1221 | -5526 | -4333 | 1616 | 5024 | 2930 | -11 | -5255 | -4747 | -3973 | -4603 | -4899 | -3296 | -959 | -2997 | -3107 | 121 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8238 | | | | | | | | | | | | |
| 122(T) | -1746 | -1500 | -4034 | -3432 | 1750 | -3391 | -2252 | 1561 | -3078 | 1096 | 52 | -3017 | -3319 | -2616 | -2884 | -2508 | 2450 | -353 | -1923 | -1630 | 122 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8234 | | | | | | | | | | | | |
| 123(Y) | -4607 | -3570 | -5022 | -5359 | 2289 | -4894 | -1139 | -3493 | -4923 | -2816 | -2907 | -3546 | -4765 | -3679 | -4305 | -4161 | -4470 | -3658 | 387 | 4501 | 123 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8229 | | | | | | | | | | | | |
| 124(D) | -1348 | -2787 | 2242 | 415 | -3129 | -2090 | 2199 | -2863 | -263 | -2769 | -1903 | -717 | -2264 | 1787 | 2067 | -1197 | -1284 | -2435 | -2889 | -2250 | 124 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8224 | | | | | | | | | | | | |
| 125(R) | -4488 | -4181 | -4789 | -4318 | -5193 | -4148 | -3436 | -5568 | -2393 | -5152 | -4748 | -4156 | -4479 | -3286 | -4202 | -4614 | -4467 | -5273 | -4267 | -4649 | 125 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8219 | | | | | | | | | | | | |
| 126(T) | -900 | -1750 | -1012 | 977 | -4318 | -1985 | 754 | 1034 | -516 | -1791 | -1012 | -790 | 1172 | -435 | -956 | -941 | 1779 | -1338 | -2179 | -1644 | 126 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -510 | -7947 | -1783 | -894 | -1115 | -701 | -1378 | -8914 | -8214 | | | | | | | | | | | | |
| 127(N) | -1735 | -2957 | -337 | -503 | -3341 | -2022 | -1191 | -3403 | -833 | -3305 | -2603 | 3506 | -2459 | 2336 | -1181 | -1571 | -1796 | -2939 | -3255 | -2559 | 127 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -17 | -7453 | -8496 | -894 | -1115 | -258 | -2612 | -8914 | -8209 | | | | | | | | | | | | |
| 128(H) | -1956 | -3025 | -776 | -1013 | -3561 | 1155 | 4532 | -3890 | -1721 | -3852 | -3139 | 1561 | -2848 | -1522 | 1178 | -1872 | -2130 | -3302 | -3700 | -2914 | 128 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8205 | | | | | | | | | | | | |
| 129(D) | -1326 | -2680 | 2762 | -433 | -3190 | 751 | -1003 | -2946 | -718 | -2918 | -2057 | -743 | -2295 | -594 | 1178 | -1205 | 1254 | -2474 | -3108 | -2410 | 129 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8200 | | | | | | | | | | | | |
| 130(N) | -803 | -1319 | -1257 | -3841 | 1092 | -1554 | -3580 | -862 | -3494 | -2719 | 3434 | -2788 | -1187 | 1621 | -1770 | -1905 | -3037 | -3520 | -3054 | 130 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8195 | | | | | | | | | | | | |
| 131(L) | -2659 | -2243 | -5081 | -4521 | 1845 | 4592 | -3494 | 1459 | -4246 | 2227 | -106 | -4254 | -4217 | -3540 | -3970 | -3797 | -2575 | 1425 | -2707 | -2618 | 131 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8190 | | | | | | | | | | | | |

FIG. 11K

Table 9

| | | | | | | | | | | | | | | | | | | | | |
|---|---|---|---|---|---|---|---|---|---|---|---|---|---|---|---|---|---|---|---|---|
| 132(H) | -1265 | -2433 | -2035 | -1445 | -2449 | 3775 | 1372 | -1614 | -839 | -1394 | -1901 | -2701 | -1628 | -1732 | -1623 | 2191 | -807 | -1952 | -1432 | 132 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8185 | | | | | | | | | | | |
| 133(V) | -2378 | -2013 | -4879 | -4522 | -2020 | -4336 | -3971 | 321 | 4271 | -861 | 2587 | 4174 | -4288 | -3996 | -4221 | -3659 | -2396 | 3447 | -3110 | 133 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8180 | | | | | | | | | | | |
| 134(H) | -1298 | -2431 | -1191 | 1210 | -2723 | -2201 | 3201 | -52 | -2373 | -2378 | -1563 | -884 | -2290 | -333 | 2092 | -1222 | -1207 | 912 | -2555 | -2032 | 134 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8175 | | | | | | | | | | | |
| 135(G) | -4088 | -3924 | -4774 | -5139 | -5615 | 3825 | -4753 | -5453 | -6303 | -6014 | -5662 | -4812 | -4539 | -5232 | -5106 | -4370 | -4472 | -5527 | -4696 | -5561 | 135 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8170 | | | | | | | | | | | |
| 136(Y) | -4791 | 3935 | -4914 | -5231 | -815 | -4530 | -2178 | -4357 | -5024 | -3745 | -3807 | -4206 | -4772 | -4328 | -4584 | -4677 | -4837 | -4435 | 1477 | 4857 | 136 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8165 | | | | | | | | | | | |
| 137(R) | -2010 | -3025 | -2206 | -1337 | -3603 | -2773 | -965 | -3110 | 2304 | -2910 | 2165 | 1370 | -3039 | -2777 | -536 | 2519 | -1900 | -1822 | -2804 | -2890 | -2581 | 137 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8160 | | | | | | | | | | | |
| 138(E) | -4205 | -4417 | -2343 | 3901 | -5349 | -3698 | -3534 | -5837 | -3838 | -5561 | -5237 | -3039 | -4218 | -3453 | -4201 | -4072 | -4352 | -5409 | -4640 | -4860 | 138 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8155 | | | | | | | | | | | |
| 139(E) | -1541 | 3143 | 1571 | 2510 | -5139 | -3425 | -1020 | -3219 | 1175 | -3136 | -2281 | -669 | -2361 | 1840 | -1368 | -1340 | -1518 | -2751 | -3304 | -2529 | 139 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8150 | | | | | | | | | | | |
| 140(G) | -4088 | -3924 | -4774 | -5139 | -5615 | 3825 | -4753 | -5453 | -6303 | -6014 | -5662 | -4812 | -4539 | -5232 | -5106 | -4370 | -4472 | -5527 | -4696 | -5561 | 140 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8145 | | | | | | | | | | | |
| 141(T) | -1448 | 2786 | 1566 | -494 | -3406 | -2031 | -1186 | -3187 | -1023 | -3164 | -2316 | 1513 | -3407 | 794 | -1603 | 1061 | 2567 | -2675 | -3364 | -2628 | 141 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8140 | | | | | | | | | | | |
| 142(I) | -1880 | -1845 | -4196 | -3993 | -2337 | -3273 | 3434 | 2845 | -3687 | -1437 | -1287 | -3407 | -3652 | -3527 | -3649 | -2612 | 2766 | 19 | -3410 | -3029 | 142 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8134 | | | | | | | | | | | |
| 143(T) | -1427 | -2097 | -2121 | -2355 | -3933 | -2165 | -2713 | -3790 | -2759 | -4026 | -3246 | 1603 | -2869 | -2560 | -2943 | -1604 | 3622 | -2931 | -4094 | -3692 | 143 |
| | -149 | -500 | 233 | 43 | -381 | 399 | 106 | 210 | -626 | -466 | -720 | 275 | 394 | 45 | 96 | 359 | 117 | -369 | -294 | -249 |
| | -14 | -7947 | -8989 | -894 | -1115 | -701 | -1378 | -8914 | -8129 | | | | | | | | | | | |
| 144(T) | -2430 | -2823 | -4179 | -4462 | -4591 | -3027 | -4037 | -4454 | -4406 | -4707 | -4191 | -3664 | -3724 | -4237 | -4215 | -2689 | 4010 | -3747 | -4431 | -4588 | 144 |
| | -149 | -500 | 233 | 43 | -381 | 399 | 106 | 210 | -626 | -466 | -720 | 275 | 394 | 45 | 96 | 359 | 117 | -369 | -294 | -249 |

FIG. 11L

Table 9

| | | | | | | | | | | | | | | | | |
|---|---|---|---|---|---|---|---|---|---|---|---|---|---|---|---|---|
| | -14 | -7947 | -8989 | .894 | -1115 | -701 | -1378 | -8914 | -8124 | | | | | | | |
| 145(P | -1505 | -2080 | -3392 | -3633 | -4254 | -2301 | -3425 | -4043 | -3658 | -4296 | -3530 | -2794 | 3850 | -3427 | -3585 | -1744 | 1558 | -3083 | -4340 | -4254 | 145 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8119 | | | | | | | | | | | | |
| 146(F) | -3994 | 3227 | 4915 | -5043 | 3832 | -4698 | -1205 | -2713 | -4616 | -2132 | 2459 | -3492 | -4563 | -3530 | -4094 | -3916 | -3878 | -2950 | -467 | 2613 | 146 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8114 | | | | | | | | | | | | |
| 147(D | -2625 | -4424 | 3697 | -649 | -4717 | -2403 | -1898 | -4810 | -2318 | -4653 | -4097 | 1859 | -2997 | -1605 | -3282 | -2269 | -2750 | -4226 | -4723 | -3698 | 147 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8109 | | | | | | | | | | | | |
| 148(M | -3455 | -2954 | -5636 | 5138 | -1157 | -5278 | 4061 | -621 | -4736 | 1276 | 4790 | -5054 | -4653 | 3832 | -4350 | -4674 | -3346 | -1354 | -2859 | -2873 | 148 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8103 | | | | | | | | | | | | |
| 149(M | 737 | -1039 | -2128 | -1551 | -1071 | -2251 | -1108 | -553 | -1284 | -925 | 2340 | -1505 | -2347 | -1148 | 1957 | -1292 | 992 | 1190 | -1511 | -1125 | 149 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8098 | | | | | | | | | | | | |
| 150(V | -1589 | -1340 | -3842 | -3261 | -1369 | 3310 | -2277 | 1533 | -2856 | -783 | 2491 | -2892 | 3292 | -2604 | 1266 | -2434 | -1540 | 2552 | -2138 | -1796 | 150 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8093 | | | | | | | | | | | | |
| 151(C | -948 | 2699 | -2923 | -2314 | -734 | -2453 | -1287 | -272 | -1969 | 629 | -6 | -1970 | -2503 | 2182 | -1898 | -1524 | -890 | 1281 | -1253 | 1875 | 151 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8087 | | | | | | | | | | | | |
| 152(N | -1513 | -2274 | -1534 | -1835 | 4051 | -2147 | -2506 | -4137 | -2664 | -4241 | -3442 | 3900 | -2843 | -2309 | -3007 | 1223 | -1886 | -3166 | -4207 | -3653 | 152 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8082 | | | | | | | | | | | | |
| 153(Q | -1078 | -2597 | 1398 | 1298 | -2904 | 570 | -660 | -2670 | 1137 | -2607 | -1702 | 1544 | -2056 | 1583 | -856 | -929 | -1031 | -2214 | -2776 | -2059 | 153 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8077 | | | | | | | | | | | | |
| 154(M | -2272 | -1957 | -4590 | -3986 | -1077 | -4004 | -2865 | 1417 | -3652 | 2191 | 2665 | -3646 | -3782 | -3053 | -3407 | -3149 | 1251 | -644 | -2313 | -2179 | 154 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8071 | | | | | | | | | | | | |
| 155(D | -2253 | 3537 | 3692 | -855 | -4532 | -2333 | -2017 | -4569 | -2396 | -4510 | -3868 | -1194 | -2951 | -1735 | -3232 | 1151 | -2470 | -3856 | -4577 | -3695 | 155 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8066 | | | | | | | | | | | | |
| 156(R | -4488 | -4181 | -4789 | 4318 | -5193 | -4148 | -3436 | -5568 | -2393 | -5152 | -4748 | -4156 | -4479 | -3286 | 4202 | -4614 | -4467 | -5273 | -4267 | -4649 | 156 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8061 | | | | | | | | | | | | |

FIG. 11M

Table 9

| | | | | | | | | | | | | | | | | | | | | |
|---|---|---|---|---|---|---|---|---|---|---|---|---|---|---|---|---|---|---|---|---|
| 157(F) | -4608 | -3568 | -5026 | -5363 | 3806 | -4898 | 1136 | -3489 | -4926 | 2811 | -2901 | -3545 | -4766 | -3678 | -4306 | -4161 | -4469 | -3654 | -384 | 3465 | 157 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8055 | | | | | | | | | | | | |
| 158(H) | 1044 | -2139 | -1080 | -861 | -3017 | -1958 | 3956 | -2774 | -984 | -2841 | -1992 | 1421 | -2333 | -887 | -1434 | 909 | -1252 | -2260 | -3059 | -2457 | 158 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8050 | | | | | | | | | | | | |
| 159(L) | -1995 | 1713 | -4228 | -3647 | -1208 | -3730 | -2645 | 1439 | -3309 | -2122 | -164 | -3321 | -3602 | 1641 | -3161 | -2864 | -1930 | 1443 | -2284 | -2058 | 159 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8044 | | | | | | | | | | | | |
| 160(A) | 2383 | 1556 | -2401 | -2072 | -2208 | -2210 | -1881 | -1266 | -1832 | -1939 | -1334 | -1898 | -2639 | 1793 | -2020 | -1435 | -1318 | 1882 | -2638 | -2245 | 160 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8039 | | | | | | | | | | | | |
| 161(I) | 855 | -2283 | -1296 | -661 | -2565 | -2186 | -701 | 1827 | 1284 | -2220 | -1411 | -884 | -2249 | 1555 | -1169 | -1126 | -1886 | -2436 | -1937 | | 161 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8033 | | | | | | | | | | | | |
| 162(D) | -1082 | -2449 | 2531 | -267 | -2754 | -1915 | -698 | -2479 | 1332 | -2474 | 2209 | -579 | -2090 | -271 | -827 | 743 | -1039 | -2075 | -2684 | -2016 | 162 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8028 | | | | | | | | | | | | |
| 163(V) | 2572 | -1717 | -4125 | 4110 | -2971 | -2517 | -3473 | -716 | -3875 | -2280 | -1954 | -3032 | -4398 | 3569 | -3746 | -1871 | -1754 | 2604 | -3798 | -3481 | 163 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8022 | | | | | | | | | | | | |
| 164(M) | -2861 | -2402 | -5299 | -4748 | -1283 | -4880 | -3804 | 1499 | -4501 | 2317 | 2674 | -4552 | -3712 | 2820 | -4200 | -4119 | -2770 | -3727 | -2863 | -2864 | 164 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8017 | | | | | | | | | | | | |
| 165(Q) | -2277 | -4157 | 2369 | 2212 | -4337 | -2257 | -1565 | -4246 | -1745 | -4116 | -3418 | -845 | -2768 | -882 | -2553 | -1949 | -2331 | -3727 | -4303 | -3315 | 165 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8011 | | | | | | | | | | | | |
| 166( | -895 | -1130 | -1817 | -1235 | -1105 | -2196 | 2271 | -700 | -958 | 627 | -314 | 1121 | -2263 | -882 | -1030 | -1203 | -832 | 1095 | 2753 | -1082 | 166 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8989 | -894 | -1115 | -701 | -1378 | -8914 | -8006 | | | | | | | | | | | | |
| 167(L) | 894 | -1665 | -4454 | -3932 | -1615 | -3916 | -3023 | 1762 | -3653 | 2037 | -555 | -3565 | -3811 | 2573 | -3532 | -3090 | -1967 | 1475 | -2679 | -2377 | 167 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8990 | -894 | -1115 | -701 | -1378 | -8914 | -8000 | | | | | | | | | | | | |
| 168(P) | -1358 | -1915 | 1378 | -983 | -1290 | -2313 | -1059 | -1560 | -1164 | 599 | -1093 | -1181 | -2047 | -988 | -1557 | -1458 | -1325 | -1413 | -1772 | 2001 | 168 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -14 | -7947 | -8990 | -894 | -1115 | -701 | -1378 | -8914 | -7994 | | | | | | | | | | | | |
| 169(H) | 835 | -2044 | -983 | -412 | -2272 | -1961 | 2288 | -1925 | -107 | -2006 | -1181 | -671 | 2276 | -988 | 1159 | -910 | -883 | 818 | -2280 | -1718 | 169 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 11N

Table 9

| | | | | | | | | | | | | | | | | | | |
|---|---|---|---|---|---|---|---|---|---|---|---|---|---|---|---|---|---|---|
| | | -7947 | -8990 | -894 | | -1115 | -701 | | -1378 | -8914 | -7989 | | | | | | | |
| 170(N | -2018 | -3288 | 1710 | -611 | -3318 | -2277 | 1866 | -2576 | 2651 | -2730 | -1220 | -2271 | -1839 | -2066 | -2863 | -3553 | -2765 | 170 |
| | -149 | -500 | 233 | 43 | -381 | 399 | -720 | 275 | 394 | 45 | 96 | 359 | 117 | -369 | -294 | -249 | | |
| | -14 | -7947 | -8990 | -894 | -1115 | -701 | -1378 | -8914 | -7983 | | | | | | | | | |
| 171(R | -1939 | -2994 | -2042 | -1272 | 3636 | 697 | -2958 | -2181 | -1388 | 1383 | -551 | 2420 | -1831 | -1784 | -2823 | -2935 | -2603 | 171 |
| | -149 | -500 | 233 | 43 | -381 | 399 | -466 | -720 | 275 | 394 | 45 | 96 | 359 | 117 | -369 | -294 | -249 | |
| | -14 | -7947 | -8990 | -894 | 982 | -1115 | -701 | -1378 | -8914 | -7977 | | | | | | | | |
| 172(Y | -813 | -1780 | -908 | -364 | -1941 | 446 | -1731 | 928 | 1199 | -1968 | -200 | -701 | -813 | 1109 | 664 | 2082 | 1675 | 172 |
| | -149 | -500 | 233 | 43 | -381 | 399 | -466 | -720 | 275 | 394 | 45 | 96 | 359 | 117 | -369 | -294 | -249 | |
| | -14 | -7947 | -8990 | -894 | -1115 | -701 | -1378 | -8914 | -7972 | | | | | | | | | |
| 173(V | 1834 | -1515 | -2997 | -2525 | -2124 | -2365 | -1816 | -1242 | -2181 | -2772 | -1966 | 1207 | -1599 | -1390 | 2598 | -2580 | -2228 | 173 |
| | -1214 | -7948 | -834 | -894 | -1115 | -701 | -466 | -720 | 275 | 394 | 45 | 96 | 359 | 117 | -369 | -294 | -249 | |
| | | | | | | | | | -7966 | | | | | | | | | |
| 174(N | 2098 | -1102 | -662 | -657 | -2411 | -1122 | -2331 | -1548 | 2678 | -1684 | -766 | -1264 | -457 | -604 | -1513 | -2576 | -2066 | 174 |
| | -149 | -500 | 233 | 43 | -381 | 399 | -466 | -720 | 275 | 394 | 45 | 96 | 359 | 117 | -369 | -294 | -249 | |
| | -26 | -6760 | -7802 | -894 | -1115 | -2557 | -8914 | -7960 | | | | | | | | | | |
| 175(Q | -711 | -1121 | -1177 | -831 | -1223 | -1760 | -238 | -384 | -912 | -1989 | 2576 | -639 | -946 | -736 | -1698 | -1211 | 175 | |
| | -149 | -500 | 233 | 43 | -381 | 399 | -466 | -720 | 275 | 394 | 45 | 96 | 359 | 117 | -369 | -294 | -249 | |
| | -26 | -6760 | -7802 | -894 | -1115 | -2557 | -8914 | -7954 | | | | | | | | | | |
| 176(N | -707 | -1550 | -295 | -469 | -2833 | 2212 | -1097 | -2065 | 2825 | -1857 | -854 | -1516 | -754 | -965 | -2881 | -2341 | 176 | |
| | -149 | -500 | 233 | 43 | -381 | 399 | -466 | -720 | 275 | 394 | 45 | 96 | 359 | 117 | -369 | -294 | -249 | |
| | -686 | -6760 | -1453 | -894 | -1115 | -2557 | -8914 | -7948 | | | | | | | | | | |
| 177(L | -1446 | -1261 | -2639 | -2396 | -166 | -2529 | 443 | 716 | -2264 | -2607 | -1810 | -1925 | -2083 | -1460 | 71 | -1338 | -963 | 177 |
| | -149 | -500 | 233 | 43 | -381 | 399 | -466 | -720 | 275 | 394 | 45 | 96 | 359 | 117 | -369 | -294 | -249 | |
| | -37 | -6111 | -7153 | -894 | -1115 | -435 | -1941 | -8914 | -7943 | | | | | | | | | |
| 178(C | 1406 | 3275 | -2556 | -2171 | -2790 | 2067 | -2675 | -1880 | -1777 | -2338 | -1781 | 1478 | -1008 | -1091 | -1870 | -3029 | -2681 | 178 |
| | -149 | -500 | 233 | 43 | -381 | 399 | -466 | -720 | 275 | 394 | 45 | 96 | 359 | 117 | -369 | -294 | -249 | |
| | -16 | -7695 | -8737 | -894 | -1115 | -1509 | -624 | -8914 | -7937 | | | | | | | | | |
| 179(N | 1616 | -1783 | -884 | -388 | -2121 | -1793 | -1882 | -1075 | 1636 | -1951 | -220 | -618 | -795 | -775 | 841 | -1651 | 179 | |
| | -149 | -500 | 233 | 43 | -381 | 399 | -466 | -720 | 275 | 394 | 45 | 96 | 359 | 117 | -369 | -294 | -249 | |
| | -16 | -7695 | -8737 | -894 | -1115 | -358 | -2187 | -8914 | -7931 | | | | | | | | | |
| 180(H | 826 | -2030 | 1249 | -286 | -2281 | -1850 | -2046 | 2137 | -570 | -1980 | -190 | -741 | 713 | -829 | -1630 | -2333 | -1721 | 180 |
| | -149 | -500 | 233 | 43 | -381 | 399 | -466 | -720 | 275 | 394 | 45 | 96 | 359 | 117 | -369 | -294 | -249 | |
| | -15 | -7948 | -8990 | -894 | -1115 | -701 | -1378 | -8914 | -7925 | | | | | | | | | |
| 181(L | -1888 | -1658 | -4011 | -3398 | 1778 | -3497 | 1355 | 19 | -3057 | -3387 | -2573 | -2834 | -2608 | -1812 | -657 | -1938 | -1655 | 181 |
| | -149 | -500 | 233 | 43 | -381 | 399 | -466 | -720 | 275 | 394 | 45 | 96 | 359 | 117 | -369 | -294 | -249 | |
| | -15 | -7948 | -8990 | -894 | -1115 | -701 | -1378 | -8914 | -7919 | | | | | | | | | |

FIG. 11O

Table 9

| | | | | | | | | | | | | | | | | | |
|---|---|---|---|---|---|---|---|---|---|---|---|---|---|---|---|---|---|
| 182C | -1582 | 2847 | 3677 | -3112 | -1572 | -3286 | -2308 | 2397 | 1781 | -1057 | -639 | -2820 | -3303 | -2550 | -2691 | -2415 | 1459 | -2297 | -1922 | 182 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7913 | | | | | | | | | | | |
| 183Q | 889 | -2895 | 1501 | 1223 | 3185 | -1975 | -867 | -2968 | 610 | -2899 | 2019 | 1640 | -2225 | 2395 | -1182 | -1154 | -1298 | -2505 | -3073 | -2320 | 183 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7907 | | | | | | | | | | | |
| 184M | 624 | -2075 | -807 | 1189 | -2318 | -1853 | 499 | -2000 | 1304 | 56 | 1892 | -530 | -1940 | -75 | 1281 | -778 | -1655 | -783 | -2297 | -1689 | 184 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7901 | | | | | | | | | | | |
| 185M | -2863 | -2466 | -4981 | -4452 | -787 | -4528 | -2772 | -688 | -4077 | 1881 | 3969 | -4038 | -4163 | -3323 | -3759 | -3712 | -1286 | -2008 | 2156 | 185 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7895 | | | | | | | | | | | |
| 186N | 889 | -2816 | 1294 | -278 | -3142 | -1979 | -855 | -2912 | 2030 | -2849 | -1972 | 2349 | -2220 | -1946 | -1093 | -1140 | -1272 | -2455 | -3022 | -2293 | 186 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7889 | | | | | | | | | | | |
| 187 | -912 | -2365 | 1857 | 1258 | -2669 | -1819 | -525 | -2416 | -128 | -2373 | -1466 | 456 | -2361 | -894 | 718 | -1304 | -855 | -1981 | 2923 | -1868 | 187 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7883 | | | | | | | | | | | |
| 188K | -1038 | -1343 | -1852 | -1266 | 1554 | -2283 | -1007 | -874 | -152 | -1087 | 2145 | -1514 | -1336 | -77 | 1280 | -1097 | 773 | -1243 | 188 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7877 | | | | | | | | | | | |
| 189L | -2298 | -2730 | -2950 | -2003 | -2607 | -3127 | -1308 | -2182 | 1083 | 2394 | 512 | -362 | -1650 | -1955 | 1691 | 1757 | -1608 | -2379 | -2109 | -2248 | -2425 | 189 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7870 | | | | | | | | | | | |
| 190V | -1079 | -1178 | -2219 | 953 | -1217 | -2479 | -1279 | 1243 | -152 | -2038 | -362 | -2531 | -2244 | -460 | -1608 | -1507 | -1021 | -2689 | -1318 | 190 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7864 | | | | | | | | | | | |
| 191E | -1354 | -2910 | 1356 | 2455 | -3203 | -1991 | -882 | -2982 | 1322 | -2913 | -2008 | -1650 | -608 | -2003 | -1787 | -1170 | -1178 | 1230 | -2523 | -3086 | -2339 | 191 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7858 | | | | | | | | | | | |
| 192H | 995 | 2611 | -2882 | -2350 | -1156 | -2330 | 3755 | 1388 | -1028 | 400 | -2003 | -2551 | -1787 | -115 | -1469 | -1023 | 451 | -1652 | -1275 | 192 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7852 | | | | | | | | | | | |
| 193F | -873 | -2098 | -751 | 1196 | 2231 | -1853 | -534 | -2026 | -137 | -2078 | -1223 | 1242 | -1958 | 2528 | 1091 | 800 | 953 | -1680 | -2329 | -1708 | 193 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |
| | -15 | -7948 | -8990 | -894 | | | -1378 | | | -7845 | | | | | | | | | | | |
| 194Q | 684 | -2845 | -419 | 1349 | -3160 | -1991 | -875 | -2930 | -582 | -2870 | -1997 | 2370 | -2238 | -115 | -1121 | -1166 | -1300 | -2477 | -3045 | -2315 | 194 |
| | -149 | -500 | 233 | 43 | -381 | -1115 | 106 | -626 | -8914 | 210 | -466 | -720 | 275 | 394 | 45 | 96 | 359 | 117 | -369 | -294 | -249 |

FIG. 11P

Table 9

| | | | | | | | | | | | | | | | | |
|---|---|---|---|---|---|---|---|---|---|---|---|---|---|---|---|---|
| 195(Y | -3797 | -4834 | -4924 | 2259 | -4579 | -1182 | -2596 | -4505 | -2328 | -2267 | -3426 | -4481 | -3479 | -4016 | -3789 | -3700 | 1231 | -456 | 4130 | 195 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7833 |
| 196(I | 1842 | -3746 | -3421 | -2131 | -2613 | -2685 | 2759 | -3142 | -1622 | -1194 | -2759 | -3062 | -2873 | -3093 | -1882 | 1362 | -243 | -2830 | -2485 | 196 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7827 |
| 197(C | -917 | 2447 | -2927 | -2307 | -2421 | -1266 | -267 | -1915 | -627 | 2390 | -1950 | -2475 | -1643 | 1928 | -1495 | -858 | 1278 | -1243 | 1688 | 197 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7820 |
| 198(E | -2062 | -3846 | 1749 | 2650 | -4068 | -2200 | -1423 | -1496 | -3829 | -3070 | 1774 | -2658 | -1061 | -2241 | 835 | -2093 | -3434 | -4016 | -3094 | 198 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7814 |
| 199(H | -1285 | -2612 | -523 | 1316 | -2833 | -2011 | 3126 | -558 | -2606 | -1772 | 2447 | -2236 | -462 | -1057 | -1160 | -1248 | 676 | -2824 | -2144 | 199 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7807 |
| 200(G | -2654 | -3212 | -2507 | -2588 | -4732 | -2707 | -4668 | 1545 | -4548 | -3892 | -3567 | -2604 | -2456 | -2072 | -2733 | -2883 | -4011 | -4170 | -4141 | 200 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7801 |
| 201(Y | -818 | 1165 | 976 | -1948 | -1871 | -567 | 748 | -261 | -1738 | -935 | -608 | -1966 | 1445 | -722 | -813 | -758 | 820 | -2091 | 1672 | 201 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7794 |
| 202(D | -4232 | -4465 | 4158 | -2649 | -3676 | -3575 | -6036 | -4125 | -5722 | -5419 | -2993 | -4216 | -3512 | -4617 | -4077 | -4401 | -5553 | -4696 | -4914 | 202 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7788 |
| 203(M | -2141 | -1848 | -4423 | -3825 | -3850 | -2726 | 2359 | -3484 | 1059 | 3290 | -3479 | 1362 | -2946 | -3270 | -2988 | -2066 | -538 | -2251 | -2080 | 203 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7781 |
| 204(P | -4497 | -4899 | -5251 | -1086 | -4139 | -4798 | -6328 | -5454 | -5976 | -5741 | -5026 | 4302 | -5328 | -5104 | -4798 | -4844 | -5739 | -4665 | -5484 | 204 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7775 |
| 205(E | -4572 | -4117 | 3431 | -5560 | -2390 | -1841 | -4772 | -2235 | -4607 | -4040 | -995 | -2973 | -1537 | -3199 | -2253 | -2735 | -4218 | -4733 | -3691 | 205 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7768 |
| 206(I | -2636 | -2476 | 1810 | -4760 | -4680 | -2731 | 3180 | -4519 | -584 | -703 | -4172 | -4449 | -3817 | -4249 | -3998 | -2901 | -494 | -1967 | -1074 | 206 |
| | -149 | 233 | -381 | 399 | 106 | -626 | 210 | -466 | -720 | 275 | 394 | 45 | 96 | 359 | 117 | -369 | -294 | -249 |
| | -15 | -7948 | -8990 | -894 | -1115 | -701 | -1378 | -8914 | -7762 |
| 206(I | -2944 | -5069 | -4784 | 2837 | -4680 | -2731 | 3180 | -4519 | -584 | -703 | -4172 | -4449 | -3817 | -4249 | -3998 | -2901 | -494 | -1967 | -1074 | |
| | -149 | 233 | -381 | 399 | 106 | -626 | 210 | -466 | -720 | 275 | 394 | 45 | 96 | 359 | 117 | -369 | -294 | -249 |
| | -15 | -8991 | -894 | -1115 | -701 | -1378 | -8914 | -7762 |

FIG. 11Q

Table 9

| 207(T | -1149 | -1001 | -3245 | -2651 | -830 | -2680 | -1537 | -200 | -2295 | 678 | -115 | -2252 | -2729 | -1967 | -2187 | -1772 | 2521 | 1202 | -1425 | 1941 | 207 |
|---|---|---|---|---|---|---|---|---|---|---|---|---|---|---|---|---|---|---|---|---|---|
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8991 | -894 | -1115 | -701 | -1378 | -8914 | -7755 | | | | | | | | | | | | |
| 208(N | 968 | -3781 | 2422 | 1475 | -4014 | -2190 | -1399 | -3875 | -1453 | -3773 | -3006 | 2431 | -2639 | -1035 | -2184 | -1745 | -2052 | -3376 | -3962 | -3054 | 208 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8991 | -894 | -1115 | -701 | -1378 | -8914 | -7748 | | | | | | | | | | | | |
| 209( | 1214 | -2627 | -4165 | -4274 | -2248 | -2999 | -2977 | -3589 | -3845 | -3575 | -3208 | -3402 | -3626 | -3726 | -3688 | -2549 | -2659 | -3197 | 5855 | -1919 | 209 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -15 | -7948 | -8991 | -894 | -1115 | -701 | -1378 | -8914 | -7741 | | | | | | | | | | | | |
| 210(V | -1358 | -2495 | -1397 | -737 | -2853 | -2276 | -735 | -1399 | 1340 | -2436 | -1616 | 951 | 1242 | 1587 | 1414 | -1276 | -1250 | 1808 | -2580 | -2097 | 210 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7949 | -8991 | -894 | -1115 | -701 | -1378 | -8914 | -7735 | | | | | | | | | | | | |
| 211( | -3498 | -2927 | -4676 | -4658 | 236 | -4377 | -1183 | -2501 | -4186 | -2296 | -2147 | -3324 | -4322 | -3336 | -3785 | -3580 | -3418 | 1241 | 5352 | 2614 | 211 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -16 | -7949 | -8991 | -894 | -1115 | -701 | -1378 | -8914 | -7728 | | | | | | | | | | | | |
| 212(H | -955 | -1646 | -1373 | -926 | 1547 | 635 | 2162 | -1632 | -859 | -1839 | -1087 | -1075 | 2103 | -763 | -1254 | 967 | -989 | -1372 | -2122 | -1543 | 212 |
| | * | * | * | * | * | * | * | * | * | * | * | * | * | * | * | * | * | * | * | * | |
| | * | * | * | * | * | * | * | -8914 | 0 | | | | | | | | | | | | |

FIG. 11R

TABLE 14

```
HMMER2.0 [2.2g]
NAME PTA_PTB_exp_seqs
LENG 355
ALPH Amino
RF no
CS no
MAP yes
COM /app/public/hmmer/current/bin/hmmbuild PTA_exp_hmm PTA_PTB_exp_seqs.aln
COM /app/public/hmmer/current/bin/hmmcalibrate PTA_exp_hmm
NSEQ 10
DATE Mon Nov 30 18:53:24 2009
CKSUM 2317
XT -8455 -4 -1000 -1000 -8455 -4 -8455 -4
NULT -4 -8455
NULE 595 -1558 85 338 -294 453 -1158 197 249 902 -1085 -142 -21 -313 45 531 201 384 -1998 -644
EVD -321.869965 0.133020
```

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | -438 | * | -1933 | | | | | | | | | | | | | | | | | | |
| 1(M) | -1511 | -1258 | -3275 | -2807 | 2269 | -2995 | -1346 | 266 | -2474 | 800 | 3792 | -2446 | -2858 | -1968 | -2335 | -2172 | -1449 | -138 | -793 | -87 | 26 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -23 | | -6577 | -7619 | -894 | -701 | -1378 | -438 | * | | | | | | | | | | | | |
| 2(M) | 426 | -1446 | -3780 | -3363 | -1521 | -2856 | -2514 | -90 | -3024 | -729 | 4481 | -2828 | -3133 | -2721 | -2939 | -2091 | -1564 | 1100 | -2424 | -2124 | 27 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -10 | | -7762 | -8804 | -894 | -701 | -1378 | * | * | | | | | | | | | | | | |
| 3(D) | -898 | -2223 | 2613 | -202 | -2512 | -1832 | -557 | -2225 | 779 | -2241 | 1722 | -504 | -1962 | -125 | -678 | 389 | 566 | -1836 | -2468 | -1816 | 28 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | | -7942 | -8984 | -894 | -701 | -1378 | * | * | | | | | | | | | | | | |
| 4(L) | -3343 | -2811 | -5687 | -5115 | 2061 | -5345 | -3911 | 1769 | -4867 | 2527 | 56 | -5003 | -4615 | -3800 | -4424 | -4629 | -3207 | -1173 | -2733 | -2675 | 29 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | | -7942 | -8984 | -894 | -701 | -1378 | * | * | | | | | | | | | | | | |
| 5(F) | -3039 | -2583 | -5400 | -4800 | 2731 | -4939 | -3665 | 2351 | -4517 | 1482 | 1999 | -4610 | -4383 | -3595 | -4132 | -4161 | -2919 | -1092 | -2663 | -2673 | 30 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | | -7942 | -8984 | -894 | -701 | -1378 | * | * | | | | | | | | | | | | |
| 6(E) | -1913 | -3483 | -329 | 3240 | -3847 | -2201 | -1343 | -3669 | -1205 | -3580 | -2799 | -844 | -2614 | 1375 | -1770 | 328 | -1937 | -3187 | -3742 | -2936 | 31 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | | -7942 | -8984 | -894 | -701 | -1378 | * | * | | | | | | | | | | | | |

FIG. 12A

Table 14

| | | | | | | | | | | | | | | | | | | |
|---|---|---|---|---|---|---|---|---|---|---|---|---|---|---|---|---|---|---|
| 7(K) | -892 | -2327 | -754 | -192 | -2667 | -1850 | -472 | -2397 | 1835 | -2332 | -1421 | 831 | -1938 | 1186 | 1037 | 1297 | 497 | -1961 | -2483 | -1835 | 32 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 8(I) | 514 | 1727 | -4577 | -4078 | -1745 | -4080 | -3252 | 2588 | -3824 | 1712 | -655 | -3731 | -3953 | -3476 | -3724 | -3273 | -2060 | 1203 | -2879 | -2568 | 33 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 9(W) | 681 | -1696 | -954 | -400 | 531 | -1888 | -578 | 324 | 1375 | -1628 | -839 | -651 | -1974 | 1030 | 909 | 344 | -741 | -1214 | 2014 | -1462 | 34 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 10(E) | -1665 | -3313 | 1727 | 2676 | -3578 | 225 | -1130 | -3392 | -1004 | -3309 | -2472 | -694 | -2435 | 928 | -1638 | 306 | -1659 | -2915 | -3488 | -2672 | 35 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 11(K) | -1580 | 1884 | -1764 | -1020 | -2907 | -2481 | -2479 | 845 | 1956 | 772 | -1679 | -1179 | -2514 | 1923 | 1777 | -1525 | -1447 | -2203 | -2604 | -2197 | 36 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 12(A) | 2315 | -1624 | -4424 | -3936 | -1894 | -3936 | -3165 | 1771 | -3688 | 61 | -834 | -3585 | -3870 | -3418 | -3634 | -3127 | -1946 | 1865 | -2913 | -2538 | 37 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 13(K) | 240 | -2148 | -1205 | -600 | -2451 | -2088 | -695 | -2066 | 2741 | -2143 | -1331 | -829 | -2179 | -293 | 688 | -1066 | 326 | 519 | -2394 | -1872 | 38 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 14(Q) | 251 | -2245 | 585 | -74 | -2564 | 1048 | -408 | -2314 | 875 | -2260 | -1335 | -384 | 515 | 1120 | 955 | 394 | -715 | -1866 | -2429 | -1747 | 39 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 15(D) | 511 | -2241 | 1741 | -132 | -2549 | -1792 | 445 | -2281 | 1286 | 455 | -1337 | -435 | -1886 | 971 | 685 | -711 | -760 | -1857 | -2426 | -1765 | 40 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 16(K) | -884 | -2341 | 1633 | -125 | -2653 | 223 | -507 | -2400 | 1752 | -2356 | -1445 | 919 | 707 | -57 | -629 | -761 | -829 | 80 | -2535 | -1850 | 41 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 17(K) | 535 | -1741 | -1193 | -620 | -1889 | -2043 | -709 | 327 | 2612 | -1654 | -903 | -840 | -2126 | 854 | -679 | -1007 | -888 | 295 | -2069 | -1566 | 42 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 18(K) | -2416 | -3238 | -2867 | -1785 | -4015 | -3059 | -1120 | -3414 | 2580 | -3139 | -2429 | -1764 | -3047 | -698 | 2089 | -2312 | 2234 | -3140 | -3041 | -2859 | 43 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 19(I) | -2521 | -2024 | -5153 | -4783 | -2223 | -4929 | -4595 | 3447 | -4687 | 294 | -972 | -4589 | -4629 | -4430 | -4724 | -4267 | -2498 | 1528 | -3873 | -3540 | 44 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |

FIG. 12B

Table 14

| | | | | | | | | | | | | | | | | | | | | |
|---|---|---|---|---|---|---|---|---|---|---|---|---|---|---|---|---|---|---|---|---|
| | -9 | -7942 | -8984 | -894 | -1115 | -701 | -1378 | * | | | | | | | | | | | | |
| 20(V) | 213 | -1847 | -4873 | -4520 | -2465 | -4420 | -4247 | 1419 | -4388 | -1381 | -1247 | -4198 | -4362 | -4252 | -3727 | -2270 | 3336 | -3880 | -3419 | 45 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 21(F) | -3693 | -3087 | -5586 | -5265 | 3261 | -5304 | -2888 | -912 | -4973 | 2381 | -226 | -4694 | -4708 | -3838 | -4472 | -4669 | -3558 | -1678 | -1934 | -1153 | 46 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 22(P) | 1357 | -1977 | -3526 | -3796 | -4305 | -2211 | -3504 | -4098 | -3878 | -4361 | -3542 | -2788 | 3823 | -3529 | -3749 | -1636 | -1847 | -3043 | -4411 | -4353 | 47 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 23(E) | -2645 | -4564 | 1495 | 3508 | -4762 | -2401 | -1853 | -4778 | -2245 | -4613 | -4046 | -1009 | -2982 | -1550 | -3202 | -2265 | -2745 | -4225 | -4728 | -3699 | 48 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 24(G) | 828 | -1562 | -2312 | -1921 | -2620 | 2562 | -1856 | -641 | -1813 | -2508 | -1731 | -1730 | -2452 | -1660 | -2098 | 554 | 782 | -1818 | -2902 | 1503 | 49 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 25(E) | -1027 | -2214 | -837 | 2256 | -2461 | -1966 | -2263 | -2117 | 974 | 634 | -1343 | -652 | -2082 | -229 | -588 | -955 | 1152 | -1790 | -2438 | -1847 | 50 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 26(W) | -150 | 757 | 49 | 299 | -277 | -651 | 839 | -485 | 392 | -910 | 599 | 300 | -401 | 623 | 162 | -99 | 38 | -448 | 1107 | 126 | 51 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 27(D) | -2650 | -4626 | 3535 | 2005 | -4794 | -2383 | -1844 | -4814 | -2264 | -4643 | -4090 | -983 | -2972 | -1542 | -3255 | -2259 | -2754 | -4254 | -4780 | -3711 | 52 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 28(E) | 884 | -1962 | -861 | 2360 | -2149 | -1901 | -576 | 272 | -2393 | -268 | -1086 | -611 | 909 | -182 | -632 | -849 | -822 | -1489 | -2226 | -1648 | 53 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 29(R) | -4488 | -4181 | -4789 | -4318 | -5193 | -4148 | -3436 | -5568 | -2933 | -5152 | -4748 | -4156 | -4479 | -3286 | 4202 | -4614 | -4467 | -5273 | 4267 | -4649 | 54 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 30(V) | -1615 | -1406 | -3692 | -3190 | -1680 | -2149 | -2460 | 2105 | -2933 | -1136 | 1527 | -3366 | 1527 | -2700 | -2939 | -2463 | 576 | 2489 | -2439 | -2054 | 55 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 31(L) | -2893 | -2389 | -5409 | -4931 | -1519 | -5116 | -4253 | 2238 | -4753 | 2516 | -300 | -4794 | -4601 | -4030 | -4524 | -4423 | -2823 | 819 | -3207 | -3187 | 56 |
| | -149 | -500 | 233 | 43 | -381 | 399 | 106 | -626 | 210 | -466 | -720 | 275 | 394 | 45 | 96 | 359 | 117 | -369 | -294 | -249 |

FIG. 12C

Table 14

| | | | | | | | | | | | | | | | | | | | | |
|---|---|---|---|---|---|---|---|---|---|---|---|---|---|---|---|---|---|---|---|---|
| 32(K) | -810 | -2256 | -666 | 736 | -2577 | 491 | 428 | 19 | 1965 | -2266 | -1348 | -419 | -1872 | 1176 | 702 | 323 | 747 | -1879 | -2434 | -1767 | 57 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 33(A) | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 58 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 34(A) | 2937 | -1528 | -3502 | -3308 | -3125 | -1952 | -2769 | -2630 | -3081 | -3039 | -2271 | -2390 | -2643 | -2779 | -3078 | 549 | 1011 | 493 | -3475 | -3206 | 59 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 35(H) | 804 | -2234 | 624 | 1374 | -2527 | -1779 | 1863 | -180 | -65 | -2239 | -1335 | -424 | -1886 | -14 | -572 | 1383 | -764 | -1842 | -2435 | -1765 | 60 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 36(K) | -927 | -1951 | -1003 | 613 | -2143 | -1960 | -589 | 446 | 1801 | -1893 | -680 | -2039 | -201 | 1687 | -903 | -856 | -1504 | -2198 | 1303 | 61 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 37(I) | -3179 | -2647 | -5611 | -5124 | -1356 | -5341 | -4317 | 2901 | -4907 | 2264 | -148 | -5052 | -4698 | -4019 | -4582 | -4697 | -3088 | -546 | -3099 | -3137 | 62 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 38(I) | 1305 | -916 | -2346 | -1758 | -894 | -2325 | -1140 | 1372 | 98 | 911 | -104 | -1638 | -2383 | 1135 | -1607 | -1364 | -839 | 747 | -1366 | -994 | 63 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 39(K) | 103 | -2280 | -655 | 781 | -2607 | -33 | -431 | -2352 | 2090 | -2292 | -1371 | 817 | -1875 | 1393 | 703 | -697 | -754 | -1906 | -2454 | -1782 | 64 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 40(D) | -876 | -2355 | 1990 | 1398 | -2673 | -1797 | 489 | -2425 | 861 | -2368 | -1450 | 862 | -1916 | -35 | 739 | -749 | -818 | -1976 | -2535 | 1245 | 65 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 41(G) | -1910 | -3521 | 1036 | 459 | -3833 | 2939 | -1305 | -3641 | 669 | -3546 | -2760 | -819 | -2598 | 922 | -1710 | -1672 | -1918 | -3170 | -3710 | -2907 | 66 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 42(L) | -2752 | -2316 | -5181 | -4626 | 1316 | -4723 | -3629 | 2215 | -4364 | 2228 | -104 | -4388 | -4302 | -3622 | -4077 | -3942 | -2665 | 822 | -2775 | -2716 | 67 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 43(A) | 2595 | -1592 | -4065 | -3655 | -1874 | -3190 | -2875 | 69 | -3364 | 237 | -870 | -3140 | -3438 | -3084 | -3305 | -2430 | -1771 | 2003 | -2788 | -2442 | 68 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 44(K) | -781 | -2248 | 1290 | 1182 | -2566 | -1751 | 412 | -18 | 1303 | -2262 | -1338 | 836 | -1846 | 47 | 956 | -662 | 674 | -1869 | 2432 | -1751 | 69 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |

FIG. 12D

Table 14

| | | | | | | | | | | | | | | | | | | | | |
|---|---|---|---|---|---|---|---|---|---|---|---|---|---|---|---|---|---|---|---|---|
| 45(P) | -9 | -1999 | -1685 | -4334 | -3818 | -1612 | -3852 | -2976 | 1828 | -3535 | 394 | -557 | -3486 | 3050 | -3199 | -3450 | -3026 | -1964 | 1176 | 2676 | -2369 | 70 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 46(V) | -2452 | -1958 | -5119 | -4802 | -2578 | -4903 | -4884 | 2288 | -4745 | -1352 | -1293 | -4595 | -4680 | -4675 | -4887 | -4275 | -2449 | 3237 | -4279 | -3776 | 71 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 47(L) | -2998 | -2538 | -5403 | -4947 | -1395 | -4989 | -4115 | -173 | -4693 | -209 | -4769 | -4551 | -3928 | -4414 | -4328 | -2940 | 1827 | -3062 | -3033 | 72 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 48(V) | -2510 | -2021 | -5126 | -4737 | -2130 | -4872 | -4437 | 1947 | -4622 | 1286 | -893 | -4529 | -4574 | -4319 | -4624 | -4190 | -2483 | 2866 | -3732 | -3431 | 73 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 49(G) | 931 | -1908 | -3564 | -3879 | -4400 | 3463 | -3561 | -4237 | -4052 | -4490 | -3601 | -2764 | -4551 | -3928 | -3877 | -1557 | -1777 | -3055 | -4501 | -4478 | 74 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 50(N) | 91 | -2861 | 975 | -587 | -3637 | -2069 | -1361 | -3439 | -1272 | -3412 | -2579 | 2972 | -2496 | -985 | -1877 | 1896 | -1654 | -2876 | -2851 | 75 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 51(E) | -1387 | -2840 | -463 | 2722 | -3195 | -2028 | -944 | -2952 | -645 | -2907 | -2050 | -684 | -2927 | -3600 | -1162 | -1231 | 313 | -2508 | -3091 | -2377 | 76 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 52(N) | 1378 | -2248 | 457 | 624 | 806 | -1762 | -434 | -2299 | 865 | -2258 | -1342 | 1494 | -1863 | 20 | 534 | 341 | -740 | -1863 | -2438 | -1760 | 77 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 53(E) | 975 | -2349 | 734 | 2085 | -2655 | -1807 | -516 | -2399 | 1272 | -2359 | -1451 | 445 | -1934 | 67 | -640 | -772 | -840 | 10 | -2541 | -1856 | 78 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 54(I) | -2526 | -2030 | -5153 | -4776 | -2181 | -4921 | -4549 | 3338 | -4675 | 616 | -934 | -4580 | -4616 | -4394 | -4697 | -4253 | -2501 | 1644 | -3821 | -3507 | 79 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 55(K) | 398 | -2606 | -1173 | 479 | -3022 | -2165 | -660 | -2692 | 2540 | -2573 | -1705 | -805 | -2232 | 1750 | 1236 | -1146 | -2286 | -2659 | -2117 | 80 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 56(E) | 1257 | -2318 | -622 | 1753 | -2641 | -1799 | 475 | -2386 | 1275 | -2333 | -1417 | -437 | -1908 | 1398 | -542 | 391 | -801 | -1943 | -2501 | -1824 | 81 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |

FIG. 12E

Table 14

| | | | | | | | | | | | | | | | | | |
|---|---|---|---|---|---|---|---|---|---|---|---|---|---|---|---|---|---|
| 57(F) | 471 -149 -9 | -982 -500 -7942 | -1994 233 -8984 | -1417 43 -894 | 1160 -381 -1115 | -2213 399 -701 | -1003 106 -1378 | -523 -626 * | 1101 210 * | 784 -466 | -172 -720 | 584 275 | -2279 394 | -1043 45 | -1416 96 | -1230 359 | 532 117 | 1019 -369 | -1408 -294 | -1017 -249 | 82 |
| 58(A) | 3609 -149 -9 | -2508 -500 -7942 | -4184 233 -8984 | -4493 43 -894 | -4592 -381 -1115 | -2737 399 -701 | -3989 106 -1378 | -4421 -626 * | -4496 210 * | -4701 -466 | -4051 -720 | -3440 275 | -3474 394 | -4171 45 | -4253 96 | -2294 359 | -2487 117 | -3536 -369 | -4484 -294 | -4643 -249 | 83 |
| 59(K) | 252 -149 -9 | -2225 -500 -7942 | 594 233 -8984 | -101 43 -894 | -2531 -381 -1115 | 1206 399 -701 | -438 106 -1378 | -2270 -626 * | 1451 210 * | -150 -466 | -1326 -720 | 673 275 | -1865 394 | -536 45 | 14 96 | 340 359 | -739 117 | -1841 -369 | -2425 -294 | -1752 -249 | 84 |
| 60(E) | 1167 -149 -11 | -2286 -500 -7654 | 732 233 -8696 | 1831 43 -894 | -2598 -381 -1115 | -1667 399 -1585 | -407 106 -585 | -2354 -626 * | 951 210 * | -2301 -466 | -1391 -720 | -300 275 | -1816 394 | -560 40 45 | -783 96 | 359 | -749 117 | -1906 -369 | -2475 -294 | -1775 -249 | 85 |
| 61(H) | -815 -149 -11 | -727 -500 -7654 | -2621 233 -8696 | -2031 43 -894 | 1145 -381 -1115 | -2289 399 -337 | 2094 106 -2262 | -200 -626 * | -1722 210 * | 1681 -466 | 107 -720 | 494 275 | -2340 394 | -1435 45 | 1047 96 | -1354 359 | -755 117 | 1054 -369 | -1030 -294 | -564 -249 | 86 |
| 62(N) | -1704 -149 -9 | -3281 -500 -7942 | 1777 233 -8984 | -397 43 -894 | -3622 -381 -1115 | 1646 399 -701 | -1188 106 -1378 | -3429 -626 * | -1036 210 * | -3352 -466 | -2526 -720 | 2598 275 | -2480 394 | -796 45 | -2615 96 | -1495 359 | -1710 117 | -2949 -369 | -3526 -294 | -2731 -249 | 87 |
| 63(M) | 20 -149 -9 | -1214 -500 -7942 | -3805 233 -8984 | -3190 43 -894 | 774 -381 -1115 | -3078 399 -701 | -1973 106 -1378 | 1042 -626 * | -2815 210 * | 1458 -466 | 2157 -720 | -2723 275 | -3056 394 | -2395 45 | -1157 96 | -2183 359 | -1382 117 | 1944 -369 | -1731 -294 | -1436 -249 | 88 |
| 64(D) | 605 -149 -9 | -2467 -500 -7942 | 2563 233 -8984 | -401 43 -894 | -3040 -381 -1115 | -1918 399 -701 | 912 106 -1378 | -2798 -626 * | -624 210 * | -2777 -466 | -1892 -720 | 929 275 | -2187 394 | -492 45 | 1186 96 | 553 117 | -2307 -369 | -2970 -294 | -2279 -249 | 89 |
| 65(L) | -3447 -149 -9 | -2885 -500 -7942 | -5829 233 -8984 | -5243 43 -894 | -1145 -381 -1115 | -4253 399 -701 | -4253 106 -1378 | 1795 -626 * | -5014 210 * | 2666 -466 | 2377 -720 | -5248 275 | -4707 394 | -3887 45 | -4549 96 | -4864 359 | -3303 117 | -1162 -369 | -2916 -294 | -3088 -249 | 90 |
| 66(D) | 250 -149 -9 | -2410 -500 -7942 | 1559 233 -8984 | 1458 43 -894 | -2748 -381 -1115 | 39 399 -701 | 576 106 -1378 | -2502 -626 * | -207 210 * | -2454 -466 | -1544 -720 | 475 275 | -1976 394 | -130 45 | -729 96 | 1014 359 | 986 117 | -2052 -369 | -2631 -294 | -1936 -249 | 91 |
| 67(G) | -2653 -149 -9 | -3216 -500 -7942 | -2503 233 -8984 | -2570 43 -894 | -4722 -381 -1115 | 3367 399 -701 | -2672 106 -1378 | -4647 -626 * | 1672 210 * | -4521 -466 | -3864 -720 | -2587 275 | -3560 394 | -2414 45 | -2013 96 | -2728 359 | -2874 117 | -3999 -369 | -4152 -294 | -4117 -249 | 92 |
| 68(V) | 1628 -149 -9 | -1694 -500 -7942 | -4600 233 -8984 | -4141 43 -894 | -2065 -381 -1115 | -4161 399 -701 | -3476 106 -1378 | 2051 -626 * | -3925 210 * | 24 -466 | -959 -720 | -3809 275 | -4058 394 | -3687 45 | -3896 96 | -3377 359 | -2060 117 | 2431 -369 | -3181 -294 | -2784 -249 | 93 |
| 69(Q) | -1107 -149 -9 | -2491 -500 -7942 | -869 233 -8984 | 2104 43 -894 | -2843 -381 -1115 | -2005 399 -701 | -610 106 -1378 | -2548 -626 * | 1501 210 * | -2474 -466 | 1449 -720 | -645 275 | -2106 394 | 2280 45 | -390 96 | -986 359 | -1031 117 | -2135 -369 | -2613 -294 | -2004 -249 | 94 |

FIG. 12F

Table 14

| | | | | | | | | | | | | | | | | | | | |
|---|---|---|---|---|---|---|---|---|---|---|---|---|---|---|---|---|---|---|---|
| | -9 | -7942 | -8984 | -894 | | -1115 | -701 | -1378 | * | | | | | | | | | | |
| 70(I) | -2462 | -1971 | -5120 | -4803 | -2532 | -4890 | -4848 | 3484 | -4737 | -1301 | -1256 | -4591 | -4671 | -4645 | -4865 | -4262 | -2459 | 1950 | -4227 | -3745 | 95 |
| | -149 | -500 | 233 | 43 | -381 | -701 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 71(V) | -1021 | -845 | -3291 | 115 | -783 | -2586 | -1463 | 1772 | -2289 | 1731 | -2204 | -2623 | -1926 | -2122 | -1672 | -963 | 1810 | -1336 | 1149 | 96 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 72(D) | -4232 | -4465 | 4158 | -2649 | 5412 | -3676 | -3575 | -6036 | -4125 | -5722 | 5419 | -2993 | -4216 | -3512 | -4617 | -4077 | -4401 | -5553 | -4696 | -4914 | 97 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 73(P) | -1143 | -1675 | -3005 | -2989 | 3065 | -2064 | -2700 | 565 | -2869 | -2950 | -2300 | -2338 | 3698 | -2683 | -2908 | 587 | -1504 | -2001 | -3467 | -3104 | 98 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 74(H) | 1253 | -2202 | -717 | 1654 | -2478 | -1838 | 2550 | -2187 | 868 | -372 | -1310 | -496 | -1938 | -63 | -532 | -776 | -809 | -1802 | -2405 | -1767 | 99 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 75(T) | -1143 | -1868 | -2054 | -2081 | -3765 | -1965 | -2374 | -3533 | -2354 | -3699 | -2834 | 2518 | -2626 | -2132 | -2643 | 882 | 2968 | -2663 | -3905 | -3493 | 100 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 76(Y) | -1148 | -1566 | -1831 | -1449 | -1231 | -2241 | -1207 | -1418 | -1361 | -1676 | -1002 | 1156 | -2489 | -1227 | -1649 | 1580 | -1191 | 429 | -1711 | 3317 | 101 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 77(W) | -150 | 757 | 49 | 299 | -277 | -651 | 839 | -485 | 392 | -910 | 599 | 300 | -401 | 623 | 162 | -99 | 38 | -448 | 1107 | 126 | 102 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 78(E) | -1130 | -2548 | 993 | 1837 | -2823 | -1914 | -731 | -2562 | -425 | 645 | -1679 | -557 | 1649 | -306 | -961 | 330 | -1088 | -2151 | -2765 | -2070 | 103 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 79(K) | 705 | -2293 | -914 | -357 | -2734 | 819 | -598 | -2445 | 2189 | -2399 | -1507 | -628 | -2037 | -153 | 975 | 617 | -923 | -2013 | -2558 | -1945 | 104 |
| | -149 | -500 | 233 | 43 | -381 | 399 | 106 | -626 | 210 | -466 | -720 | 275 | 394 | 45 | 96 | 359 | 117 | -369 | -294 | -249 |
| | -1567 | -7942 | -603 | -894 | -1115 | -701 | -1378 | * | | | | | | | | | | | | |
| 80(E) | -1455 | -2350 | 50 | 3362 | -2809 | -1547 | -927 | -2700 | -845 | -2735 | -2178 | -487 | -2000 | -660 | -1278 | -1311 | -1525 | -2365 | -2625 | -2220 | 105 |
| | -149 | -500 | 233 | 43 | -381 | 399 | 106 | -626 | 210 | -466 | -720 | 275 | 394 | 45 | 96 | 359 | 117 | -369 | -294 | -249 |
| | -26 | -6400 | -7442 | -894 | -1115 | -1808 | -483 | | | | | | | | | | | | | |
| 81(M) | -551 | -928 | 1713 | -589 | -942 | -1741 | -615 | 5 | -559 | -521 | 2643 | -741 | -1867 | -429 | -905 | -804 | -519 | 1266 | -1450 | -997 | 106 |
| | -149 | -500 | 233 | 43 | -381 | 399 | 106 | -626 | 210 | -466 | -720 | 275 | 394 | 45 | 96 | 359 | 117 | -369 | -294 | -249 |
| | -19 | -6823 | -7865 | -894 | -1115 | -167 | -3194 | | | | | | | | | | | | | |

FIG. 12G

Table 14

FIG. 12H

Table 14

| | | | | | | | | | | | | | | | | | | | | |
|---|---|---|---|---|---|---|---|---|---|---|---|---|---|---|---|---|---|---|---|---|
| 95(H) | -9 | -7942 | -8984 | -894 | -1115 | -701 | -1378 | * | * | -2417 | -1504 | 868 | -1955 | -84 | -643 | 392 | -872 | -2026 | -2586 | -1897 | 120 |
| | -928 | -2405 | -563 | 997 | -2720 | 1543 | 2401 | -2472 | 959 | -466 | 275 | 394 | 45 | 96 | 359 | 117 | -369 | -294 | -249 | |
| | -149 | -500 | 233 | 43 | -381 | 399 | 106 | -626 | 210 | | | | | | | | | | | |
| | -9 | -7942 | -8984 | -894 | -1115 | -701 | -1378 | * | * | | | | | | | | | | | |
| 96(K) | -4125 | -4091 | -4017 | -3615 | -5101 | -3960 | -2958 | -5182 | 3972 | -4825 | -3552 | -4249 | -2709 | -1809 | -4154 | -4044 | -4895 | -4132 | -4389 | 121 |
| | -149 | -500 | 233 | 43 | -381 | 399 | 106 | -626 | 210 | -466 | 275 | 394 | 45 | 96 | 359 | 117 | -369 | -294 | -249 | |
| | -809 | -7942 | -1234 | -894 | -1115 | -1115 | -1378 | * | * | | | | | | | | | | | |
| 97(G) | -2666 | -2751 | -3377 | 3700 | -4393 | 3753 | -3528 | -4841 | -4031 | -4741 | -4286 | -3411 | -3824 | -3848 | -2912 | -3053 | -4080 | -3719 | -4290 | 122 |
| | -149 | -500 | 233 | 43 | -381 | 399 | 106 | -626 | 210 | -466 | 275 | 394 | 45 | 96 | 359 | 117 | -369 | -294 | -249 | |
| | -15 | -7148 | -8190 | -894 | -1115 | -541 | -1677 | * | * | | | | | | | | | | | |
| 98(M) | 412 | -754 | -2560 | -1966 | -741 | -2291 | -1150 | 981 | -1684 | -598 | 3179 | 1245 | -2352 | -1421 | -1700 | 649 | 877 | -1235 | -874 | 123 |
| | -149 | -500 | 233 | 43 | -381 | 399 | 106 | -626 | 210 | -466 | 275 | 394 | 45 | 96 | 359 | 117 | -369 | -294 | -249 | |
| | -10 | -7762 | -8804 | -894 | -1115 | -413 | -2007 | * | * | | | | | | | | | | | |
| 99(T) | -2430 | -2823 | -4179 | -4462 | -4591 | -3027 | -4037 | -4454 | -4406 | -4707 | -4191 | -3664 | -3724 | -4237 | -4215 | -2689 | 4010 | -3747 | -4431 | -4588 | 124 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |
| 100(P) | 270 | -1065 | -2103 | 243 | -1059 | -2317 | -1151 | 1403 | -1372 | 790 | -240 | -1539 | 2257 | -1198 | -1557 | -1358 | -904 | -375 | -1531 | -1145 | 125 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |
| 101(E) | -2392 | -4275 | 1163 | 3312 | -4486 | -2295 | -1667 | -4423 | -1934 | -4288 | -3633 | -894 | 1125 | -1341 | -2802 | -2468 | -3888 | -4470 | -3454 | 126 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -1115 | -1378 | * | * | | | | | | | | | | | |
| 102(Q) | 297 | 2471 | 1012 | -160 | -2788 | -1849 | 577 | -2543 | 1870 | -2482 | -1573 | -1994 | 2462 | -693 | -848 | -930 | -2093 | -2649 | -1955 | 127 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |
| 103(A) | 3227 | -1594 | -3807 | -3849 | -3646 | -1945 | -3198 | -3067 | -3621 | -3576 | -2572 | -2704 | -3241 | -3481 | 576 | -1455 | 241 | -3977 | 3779 | 128 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |
| 104(D) | 1261 | -2267 | 1791 | 738 | -2557 | -1813 | -517 | -2280 | -130 | -2273 | -1380 | -1934 | -76 | 1383 | -771 | -825 | 386 | -2479 | -1813 | 129 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |
| 105(K) | 415 | -2546 | -735 | 1917 | -2896 | -1973 | -635 | -2621 | 2122 | -2543 | -1653 | -2101 | 1705 | -517 | -981 | -1047 | -2189 | -2683 | -2042 | 130 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -1115 | -1378 | * | * | | | | | | | | | | | |
| 106(M) | 308 | 827 | -2563 | -1964 | -795 | -2335 | -1167 | 1419 | 607 | -677 | 2765 | -1747 | -2393 | -1425 | -1700 | 1409 | 241 | -1388 | -912 | 131 |
| | -149 | -500 | 233 | 43 | -381 | 399 | 106 | -626 | 210 | -466 | 275 | 394 | 45 | 96 | 359 | 117 | -369 | -294 | -249 | |
| | -9 | -7942 | -8984 | -894 | -1115 | -701 | -1378 | * | * | | | | | | | | | | | |

FIG. 12I

Table 14

| | | | | | | | | | | | | | | | |
|---|---|---|---|---|---|---|---|---|---|---|---|---|---|---|---|
| 107(M | -2838 | -2385 | -5273 | -4720 | -1280 | -4846 | 3769 | 1119 | -4469 | 2241 | 2938 | -4517 | -4377 | -3690 | -4172 | 4080 | -2748 | 1487 | -2847 | -2840 | 132 |
| | -149 | -500 | 233 | 43 | -381 | 399 | 106 | * | 210 | -466 | -720 | 275 | 394 | 45 | 96 | 359 | 117 | -369 | -294 | -249 |
| | -9 | -7942 | -8984 | -894 | -1115 | -701 | -1378 | | | | | | | | | | | | | |
| 108(K | -1031 | -2407 | -918 | 1080 | -2761 | -1972 | -2464 | 1949 | 434 | -1505 | -616 | -2053 | -100 | 1475 | 1180 | -952 | -2050 | -2533 | -1929 | 133 |
| | -149 | -500 | 233 | 43 | -381 | 400 | 106 | 210 | -466 | -720 | 275 | 394 | 45 | 96 | 359 | 117 | -369 | -294 | -249 |
| | -169 | -3204 | -8984 | -206 | -2913 | -701 | -1378 | * | | | | | | | | | | | | |
| 109(D | -4232 | 4465 | 4158 | -2649 | -5412 | -3676 | -6036 | -4125 | -5722 | -5419 | -2993 | -4216 | -3512 | -4617 | -4077 | -4401 | -5553 | 4696 | -4914 | 135 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 110(P | -893 | 2081 | -1781 | 940 | -1121 | -2183 | -978 | 444 | -1070 | -334 | -1295 | 2567 | -933 | -1326 | -1202 | -842 | -568 | -1538 | 1138 | 136 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 111(N | -1006 | -916 | -2854 | -2266 | -891 | -2503 | -1385 | -1966 | 1747 | -97 | -2563 | 1859 | -1688 | -1947 | -70 | -954 | 854 | -1419 | -1063 | 137 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 112(Y | -4083 | -3282 | -4926 | -5082 | 1832 | -4728 | -1188 | -2828 | -4652 | 2245 | -3495 | -4595 | -3549 | -4122 | -3951 | -3965 | -3052 | -449 | 4351 | 138 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 113(F) | -4576 | 3559 | -5015 | -5343 | 4263 | -4881 | -1152 | -3449 | -4910 | -2776 | -3550 | -4757 | -3679 | -4300 | -4154 | -4444 | -3622 | -401 | 2124 | 139 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 114(G | 2612 | -1827 | -3654 | -3943 | -4336 | 2661 | -3533 | -4149 | -4027 | -4411 | -3508 | -2727 | -2864 | -3570 | -3838 | -1474 | -2967 | -4475 | -4432 | 140 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 115(T | 1598 | -1522 | -3726 | -3555 | -2787 | -2149 | -2868 | -3288 | -2470 | -1892 | -2585 | -2799 | -2974 | -3213 | -1463 | 2927 | 1522 | -3313 | -3022 | 141 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 116(M | 845 | -1514 | -3507 | -3305 | -2427 | -2152 | -2615 | -1675 | -2968 | 4655 | -2481 | -2760 | -2728 | -2908 | -1457 | 695 | -1444 | -2989 | -2699 | 142 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 117(M | 103 | -2295 | -4810 | -4261 | -1123 | -4222 | -3233 | -505 | -3905 | 1982 | 4088 | -3963 | -4004 | -3656 | -3428 | -2527 | -1018 | -2542 | -2485 | 143 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 118(V | 249 | -1764 | -4559 | -4171 | -2124 | -3892 | -3557 | 400 | -3936 | 216 | -1010 | -3749 | -3970 | -3700 | -3157 | -2087 | 3302 | -3297 | -2917 | 144 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 119(Y | -1748 | -2787 | -1867 | -1117 | -3134 | -2580 | -896 | -2823 | 2430 | -2708 | -1928 | -1262 | -2616 | -482 | 1298 | 588 | -1603 | -2513 | -2720 | 2852 | 145 |
| | -149 | -500 | 233 | 43 | -381 | 399 | 106 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |

FIG. 12J

Table 14

FIG. 12K

Table 14

| | | | | | | | | | | | | | | | | | | | | | | |
|---|---|---|---|---|---|---|---|---|---|---|---|---|---|---|---|---|---|---|---|---|---|---|
| 132(V) | 1970 | -1618 | -4439 | -3946 | -1865 | -3942 | -3147 | 1777 | -3693 | 528 | 807 | -3588 | -3866 | -3412 | -3626 | -3130 | -1942 | 2096 | -2880 | -2511 | 158 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 133(H) | | -1102 | -1738 | -1466 | -2663 | -2010 | 4358 | -2506 | -1383 | -2678 | -1892 | 969 | -2465 | -1337 | -1706 | 783 | -1293 | -2046 | -2891 | -2346 | 159 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 134(S) | 419 | -1643 | -3250 | -3104 | -3814 | -1905 | -2857 | -3555 | -2981 | -3781 | -2885 | 2298 | -2311 | -2716 | -3080 | 2397 | 1614 | -2583 | -4014 | -3764 | 160 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 135(T) | | -1714 | -3480 | -3700 | 4076 | -1973 | 3311 | -3843 | -3648 | | -4140 | -3265 | -2565 | -2755 | -3310 | -3525 | 656 | 3729 | -2765 | -4307 | -4127 | 161 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 136(G) | 2443 | -1650 | -3680 | -3879 | -4195 | 2494 | -3389 | -3992 | -3844 | -4243 | -3304 | -2574 | -2707 | -3388 | -3682 | 672 | -1492 | -2786 | -4412 | -4299 | 162 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 137(D) | -2610 | -4414 | 3375 | -640 | -4704 | -2395 | -1885 | -4787 | -2296 | -4632 | -4069 | -2988 | -4479 | -1589 | -3253 | -2255 | -2733 | -4206 | -4710 | -3683 | 163 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 138(T) | -1802 | -1610 | -4107 | -3628 | -4886 | -1625 | -3434 | -2777 | -3310 | 979 | -612 | -3213 | -3529 | -3008 | -3231 | -2634 | 2771 | -2850 | -2588 | -2269 | 164 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 139(L) | -2900 | -2445 | -5330 | -4886 | -1470 | -4921 | -4106 | -73 | -4643 | 2578 | -286 | -4689 | -4527 | -3948 | -4403 | -4253 | -4467 | -3114 | -3047 | 165 | |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 140(R) | -4488 | -4181 | -4789 | -4318 | -5193 | -4148 | -3436 | -5568 | -2393 | -5152 | -4748 | -4156 | -4479 | -3286 | -4614 | -4467 | -5273 | -4267 | -4649 | 166 | |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 141(P) | 1695 | -1951 | -3539 | -3802 | -4288 | -2189 | -3492 | -4075 | -3870 | -4341 | -3515 | -2772 | 3709 | -3517 | -3739 | -1609 | -1819 | -3017 | -4404 | -4341 | 167 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 142(A) | 2997 | -1820 | -3672 | -3957 | -4327 | 2092 | -3531 | -4137 | -4026 | -4400 | -3498 | -2726 | -2859 | -3569 | -3834 | -1467 | -1684 | -2957 | -4469 | -4425 | 168 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 143(L) | -3221 | -2748 | -5558 | -5092 | -1274 | -5134 | -4164 | -386 | -4812 | 3030 | -86 | -4956 | -4613 | -3913 | -4456 | -4503 | -3148 | -2987 | 3018 | 169 | |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |
| 144(Q) | -2871 | -3512 | -2899 | -2161 | -4235 | -3278 | -1502 | -3869 | -191 | -3535 | -2901 | -2118 | -3368 | 4099 | 1519 | -2774 | -2657 | -3608 | -3317 | -3159 | 170 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | | |

FIG. 12L

Table 14

| | | | | | | | | | | | | | | | | | | | | |
|---|---|---|---|---|---|---|---|---|---|---|---|---|---|---|---|---|---|---|---|---|
| 145(I) | -9 | -7942 | -1967 | -4804 | -2546 | -4899 | -701 | -1378 | * | 3420 | -4742 | -1315 | -4595 | -4676 | -4657 | -4875 | -4271 | -2457 | 2106 | -4245 | -3757 | 171 |
| | | -149 | -500 | 43 | -381 | 399 | | 106 | | -626 | 210 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 146(I) | -9 | -2482 | -1984 | -5127 | -4768 | -2335 | -4912 | -4643 | 3097 | -4684 | -1266 | -4568 | -4633 | -4487 | -4753 | -4252 | 2463 | 2302 | -3978 | -3593 | 172 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 147(K) | -9 | -2698 | -3306 | -2555 | -2385 | 4613 | 1689 | -2226 | -4379 | 3466 | -4176 | -3510 | -2406 | -3487 | -1898 | -1272 | -2718 | -2789 | -3870 | -3879 | -3804 | 173 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 148(T) | -9 | -1775 | -2078 | -3737 | -3648 | -2269 | -2758 | -3026 | -1461 | -3198 | 577 | -1417 | -3004 | -3304 | -3108 | -3140 | -2144 | 3610 | -2789 | -3171 | -2809 | 174 |
| | | -149 | -500 | 233 | 43 | -381 | 399 | 106 | -626 | 210 | -720 | -466 | 275 | 394 | 45 | 96 | 359 | 117 | -1504 | -369 | -294 | -249 |
| | | -9 | -7942 | -8984 | -894 | -1115 | -701 | -1378 | * | | | | | | | | | | | | | |
| 149(K) | 1442 | -2243 | -1132 | -565 | -2592 | -2073 | -704 | -2218 | 2425 | 860 | -2266 | -1439 | -805 | -2179 | 1424 | 419 | -1063 | 139 | -2490 | -1948 | 175 |
| | | -149 | -500 | 233 | 43 | -381 | 399 | 106 | -626 | 210 | -720 | -466 | 275 | 394 | 45 | 96 | 359 | 117 | -1056 | -369 | -294 | -249 |
| | | -9 | -7942 | -8984 | -894 | -1115 | -701 | -1378 | * | | | | | | | | | | | | | |
| 150(P) | -2229 | -3531 | -751 | 745 | -248 | -4074 | -2482 | -1471 | -3788 | -5453 | -3650 | -1174 | -4812 | 3599 | -1104 | -1174 | -2025 | -2220 | -3370 | -3701 | -3125 | 176 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 151(G) | -4088 | -3924 | -4774 | -5139 | -5615 | 3825 | -4753 | -6303 | -5453 | -6014 | -4812 | -4539 | -5232 | -5106 | -4370 | -4472 | -5527 | -4696 | -5561 | 177 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 152(C) | 1031 | 2336 | -3000 | -751 | -248 | -2410 | -2361 | -1377 | 341 | -2075 | 407 | 99 | -2001 | -2486 | -1756 | -1986 | -500 | 688 | 649 | 1750 | -1361 | -1013 | 178 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 153(K) | 299 | -2345 | -751 | -248 | -2698 | -1882 | 2125 | -2424 | 2532 | -2376 | -1479 | 830 | -1590 | -2372 | -1223 | -500 | -1350 | -894 | -1997 | -2541 | -1898 | 179 |
| | | -149 | -500 | 233 | 43 | -381 | 399 | 106 | -626 | 210 | -720 | -466 | 275 | 394 | 45 | 96 | 359 | 117 | 327 | -369 | -294 | -249 |
| | | -9 | -7942 | -8984 | -894 | -1115 | -701 | -1378 | * | | | | | | | | | | | | | |
| 154(T) | -908 | -953 | -2280 | -1684 | -935 | -2313 | -1108 | 722 | 344 | 1215 | -140 | 830 | -3234 | -3048 | -1223 | 1008 | -1350 | 1552 | 668 | -1392 | -1018 | 180 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 155(V) | 248 | -1426 | -4165 | -3634 | -1671 | -3597 | -2693 | 2073 | -3341 | 492 | -700 | -3234 | -3564 | -3243 | -2750 | 488 | 2467 | -2499 | -2124 | 181 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |
| 156(S) | -1944 | -2458 | -3696 | -4011 | -4410 | -2644 | -3753 | -4675 | -4191 | -4807 | -4070 | -3198 | -3384 | -3886 | -4051 | 3656 | -2393 | -3615 | -4374 | -4307 | 182 |
| | | -149 | -500 | 233 | 43 | -381 | 399 | 106 | -626 | 210 | -720 | -466 | 275 | 394 | 45 | 96 | 359 | 117 | | -369 | -294 | -249 |
| | | -9 | -7942 | -8984 | -894 | -1115 | -701 | -1378 | * | | | | | | | | | | | | | |

FIG. 12M

Table 14

| | | | | | | | | | | | | | | | | | | | |
|---|---|---|---|---|---|---|---|---|---|---|---|---|---|---|---|---|---|---|---|
| 157(G) | 693 | -1658 | -3600 | -3793 | -4209 | 2495 | -3362 | -4011 | -3794 | -4256 | -2553 | -2706 | -3347 | -3658 | 2479 | -1495 | -2797 | -4419 | -4298 | 183 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 158(F) | 757 | -848 | -3195 | -2588 | 2258 | -2533 | -1456 | 1163 | -2229 | -678 | -69 | -2151 | -2599 | -1889 | -2097 | 1006 | -949 | -1371 | -1020 | 184 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 159(F) | -3561 | -3044 | -5093 | -4992 | 4144 | -4702 | -2042 | -1417 | -4612 | -651 | 2173 | -3997 | -4516 | -3679 | -4183 | -4055 | -3507 | -1990 | -1263 | -230 | 185 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 160(I) | -2399 | -1985 | -4894 | -4389 | 1240 | -4436 | -3536 | 2456 | -4148 | 1300 | -435 | -4090 | -4179 | -3651 | -3986 | -3652 | -2345 | 2073 | -2927 | -2716 | 186 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 161(M) | -2968 | -2569 | -5237 | -4809 | -1359 | -4763 | -3886 | 1091 | -4419 | 34 | 4848 | -4576 | -4450 | -3792 | -4170 | -4116 | -2930 | -673 | -2953 | -2839 | 187 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 162(Q) | 309 | -798 | -2699 | -2096 | 1118 | -2361 | -1203 | 789 | -1796 | 499 | 6 | -1823 | -2416 | 1904 | -1779 | 902 | -818 | -1249 | -892 | 188 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 163(V) | -884 | -1453 | -1331 | -759 | -1529 | -2054 | -754 | 426 | 1538 | -1352 | -623 | -938 | 708 | -503 | -1024 | 716 | -1438 | -1814 | -1348 | 189 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 164(P) | -1205 | -2096 | -1371 | -1294 | -3530 | 1986 | -1732 | -3286 | -1522 | -3357 | -2495 | -1382 | 2600 | 1480 | -1930 | 689 | -2587 | -3557 | -3013 | 190 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 165(D) | -1308 | -2864 | 2377 | 1708 | -3151 | -1969 | -847 | -2932 | 908 | -2865 | -1984 | 1026 | -2212 | -1617 | 1132 | -1139 | -1136 | -1274 | -3039 | 1438 | 191 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 166(C) | 544 | 3117 | -563 | 1527 | -2011 | -1598 | -229 | -1884 | 984 | -1975 | -920 | -317 | -1617 | 1132 | -431 | -599 | -614 | -1347 | -1372 | 192 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 167(E) | -1135 | -2652 | 805 | 2212 | -2960 | 449 | 701 | -2724 | -352 | -2658 | -534 | -1760 | -2098 | 1133 | 1725 | -983 | -1089 | -2270 | -2825 | -2111 | 193 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |
| 168(Y) | -3596 | -3426 | -4011 | -4236 | 756 | -3926 | -2017 | -3923 | -4119 | -3489 | -3396 | -3558 | 1274 | -3712 | -3935 | -3783 | -3834 | -1423 | 4617 | 194 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -809 | -7942 | -1234 | -894 | -1115 | -701 | -1378 | * | | | | | | | | | | | |
| 169(G) | -2666 | -2751 | -3377 | -3700 | -4393 | 3753 | -3528 | -4841 | -4031 | -4741 | -3394 | -4286 | -3411 | -3824 | -3848 | -2912 | -3053 | -4080 | -3719 | -4290 | 195 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | -7942 | -8984 | -894 | -1115 | -701 | -1378 | * | | | | | | | | | | | |

FIG. 12N

Table 14

| | | | | | | | | | | | | | | | | | | | |
|---|---|---|---|---|---|---|---|---|---|---|---|---|---|---|---|---|---|---|---|
| 170(H) | -909 | -2472 | 1648 | 1963 | -2749 | -1496 | 2279 | -207 | -2473 | -1609 | -112 | -1774 | -16 | -789 | 911 | -884 | -2079 | -2655 | -1892 | 196 |
| | -149 | -500 | 233 | 43 | -381 | 399 | 106 | 210 | -466 | -720 | 275 | 394 | 45 | 96 | 359 | 117 | -369 | -294 | -249 | |
| | -15 | -7148 | -8190 | -894 | -1115 | -2275 | -334 | * | | | | | | | | | | | | |
| 171(I) | -1659 | -3544 | 3062 | 1534 | -3720 | -1620 | -946 | -1158 | -3508 | -2820 | 1807 | -2140 | -608 | -1992 | -1327 | -1718 | -3114 | -3702 | -2701 | 197 |
| | -149 | -500 | 233 | 43 | -381 | 399 | 106 | 210 | -466 | -720 | 275 | 394 | 45 | 96 | 359 | 117 | -369 | -294 | -249 | |
| | -15 | -7148 | -8190 | -894 | -1115 | -2275 | -334 | * | | | | | | | | | | | | |
| 172(G) | -2666 | -2751 | -3377 | -3700 | -4393 | 3753 | -3528 | -4031 | -4741 | -4286 | -3394 | -3411 | -3824 | -3848 | -2912 | -3053 | -4080 | -3719 | -4290 | 198 |
| | -149 | -500 | 233 | 43 | -381 | 399 | 106 | 210 | -466 | -720 | 275 | 394 | 45 | 96 | 359 | 117 | -369 | -294 | -249 | |
| | -15 | -7148 | -8190 | -894 | -1115 | -1358 | -713 | * | | | | | | | | | | | | |
| 173(M) | 896 | 558 | -2670 | -2060 | 1251 | -2185 | -1048 | -1731 | 665 | 2262 | -1717 | -2232 | -1411 | -1654 | -1259 | 1662 | 83 | -1007 | -665 | 199 |
| | -149 | -500 | 233 | 43 | -381 | 399 | 106 | 210 | -466 | -720 | 275 | 394 | 45 | 96 | 359 | 117 | -369 | -294 | -249 | |
| | -13 | -7414 | -8456 | -894 | -1115 | -1982 | -421 | * | | | | | | | | | | | | |
| 174(L) | -3012 | -2483 | -4991 | -4588 | 2563 | -4681 | -2567 | -365 | -4286 | 286 | -4144 | -4140 | -3283 | -3862 | -3990 | -2889 | -1078 | -1633 | -952 | 200 |
| | -149 | -500 | 233 | 43 | -381 | 399 | 106 | 210 | -466 | -720 | 275 | 394 | 45 | 96 | 359 | 117 | -369 | -294 | -249 | |
| | -13 | -7414 | -8456 | -894 | -1115 | -249 | -2660 | * | | | | | | | | | | | | |
| 175(V) | -1666 | -1535 | -3931 | -3496 | -1547 | 517 | -2575 | -46 | 1766 | -593 | -3023 | -2232 | -2859 | -3069 | -2394 | -1705 | -2418 | -2089 | 201 | |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 176(F) | -4576 | -3559 | -5015 | -5343 | 4263 | -4881 | -1152 | -3449 | -2776 | -2865 | -3550 | -4757 | -3679 | -4300 | -4154 | -4444 | -3622 | -4405 | 2124 | 202 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 177(A) | 3345 | -1674 | -3727 | -3977 | -4175 | -1941 | -3439 | -3955 | -4243 | -3329 | -2621 | -2737 | -3468 | -3709 | 825 | -1527 | -2788 | -4405 | -4282 | 203 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 178( | -150 | 757 | 49 | 299 | -277 | -651 | 839 | 392 | -910 | 599 | 300 | -401 | 623 | 162 | -99 | 38 | -448 | 1107 | 126 | 204 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 179(I) | -4232 | 4465 | 4158 | -2649 | -5412 | -3676 | -3575 | -4125 | -5722 | -5419 | -2993 | -4216 | -3512 | -4617 | -4077 | -4401 | -5553 | -4696 | -4914 | 205 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 180(C) | -1236 | 5496 | -4197 | -4463 | -4068 | -2103 | -3603 | -3911 | -4251 | -3414 | -2867 | -2893 | -3739 | -3846 | 647 | -1702 | -2864 | -4296 | -4138 | 206 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |
| 181(A) | 2681 | -1648 | -3686 | -3867 | -4184 | 2067 | -3375 | -3979 | -4229 | -3291 | -2570 | -2704 | -3369 | -3665 | 954 | -1488 | -2779 | -4401 | -4284 | 207 |
| | -149 | -500 | 233 | 43 | -381 | 399 | 106 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | |

FIG. 12O

Table 14

| | | | | | | | | | | | | | | | | | | | | |
|---|---|---|---|---|---|---|---|---|---|---|---|---|---|---|---|---|---|---|---|---|
| 182(V) | -2422 | -1967 | -4993 | -4556 | -1946 | -4647 | -4007 | 2482 | -4386 | 447 | 1863 | -4301 | -4388 | -4024 | -4325 | -3914 | -2387 | 2602 | -3399 | -3128 | 208 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 183(N) | -1642 | -1630 | -3011 | -2702 | -1675 | -3027 | -2261 | -141 | -2480 | 399 | -827 | 3044 | -3220 | -2357 | -2577 | -2236 | -1678 | 2152 | -2448 | -1987 | 209 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 184(I) | -1310 | -1421 | -2217 | 1185 | -1569 | -2673 | -1609 | 2204 | -1689 | -1167 | -660 | -1843 | 2154 | -1552 | -1934 | -1762 | -1280 | 885 | -2135 | -1720 | 210 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 185(N) | 257 | 1558 | 440 | 612 | -2481 | -1765 | -435 | -2211 | 31 | -2194 | 1330 | 2360 | -1863 | 1379 | -534 | -683 | -729 | -1796 | -2393 | -1727 | 211 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 186(P) | -2875 | -3093 | -3978 | -4134 | -3333 | -3398 | -3665 | -3255 | -3879 | -167 | -2945 | -3727 | 4087 | -3894 | -3795 | -3160 | -3199 | -3243 | -3784 | -3483 | 212 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 187(T) | -1617 | -2991 | 2432 | -518 | 3614 | -2086 | -1314 | -3413 | -1230 | -3383 | -2559 | 996 | -2497 | -937 | -1848 | 429 | 2498 | -2889 | -3583 | -2811 | 213 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 188(A) | 2241 | -1737 | -1506 | 513 | -2489 | -1943 | -1317 | -2071 | -1119 | -2312 | -1526 | -1230 | -2307 | -1010 | -1520 | 1714 | -1101 | 416 | -2692 | -2195 | 214 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 189(E) | 525 | -2429 | 1776 | 1822 | -2741 | -1821 | -551 | -2497 | -176 | -2443 | -1530 | -453 | 124 | 1127 | -700 | -809 | 481 | -2048 | -2615 | -1917 | 215 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 190(Q) | -1567 | -3175 | 1704 | 1474 | -3449 | -2060 | -1054 | -3249 | 877 | -3174 | -2325 | -671 | -2377 | -1481 | -700 | -1362 | 1084 | -2781 | -3353 | -2563 | 216 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 191(L) | -3337 | -2808 | -5707 | -5127 | -1152 | -5377 | -4133 | -460 | -4878 | 2928 | 1801 | -5079 | -4636 | -3831 | -4452 | -4675 | -3207 | 697 | -2886 | -3022 | 217 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 192(A) | 3213 | -1669 | -3729 | -3963 | -4171 | -1937 | -3427 | -3953 | -3889 | -4236 | -3319 | -2614 | -2732 | -3450 | -3697 | 1430 | -1520 | -2784 | -4399 | -4276 | 218 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 193(E) | -2200 | -4049 | 2514 | 2580 | -4247 | -2234 | -1519 | -4143 | -1674 | -4022 | -3301 | 1158 | -2729 | -1171 | -2473 | 318 | -2248 | 3627 | -4213 | -3243 | 219 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 194(I) | -2474 | -2002 | -5104 | -4792 | -2432 | -4811 | -4734 | 3681 | -4697 | -1199 | -1182 | -4556 | -4627 | -4560 | -4788 | -4186 | -2477 | 1241 | -4098 | -3650 | 220 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |

FIG. 12P

Table 14

| | | | | | | | | | | | | | | | | | | |
|---|---|---|---|---|---|---|---|---|---|---|---|---|---|---|---|---|---|---|
| | -9 | -7942 | -8984 | -894 | | | -1115 | -701 | -1378 | * | | | | | | | | |
| 195(A | 3609 | -2508 | -4184 | -4493 | -4592 | -2737 | -3989 | -4421 | -4496 | -4701 | -4051 | -3440 | -3474 | -4171 | -4253 | -2294 | -2487 | -3536 | -4484 | -4643 | 221 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 196(I) | -1091 | -1076 | -2583 | 413 | -1145 | -2551 | -1453 | 2635 | -1815 | -911 | -317 | -1908 | -2625 | -1603 | -1923 | -64 | 352 | 1441 | -1667 | -1289 | 222 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 197(Q | 518 | -2071 | -706 | 1236 | -2329 | -1787 | -464 | 158 | -79 | -2066 | -1190 | -460 | -1883 | 1523 | -571 | 1071 | 1153 | -1661 | -2309 | -1673 | 223 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 198(S) | 690 | -1632 | -3665 | -3707 | -4013 | -1911 | -3224 | -3755 | -3549 | -4023 | -3114 | -2519 | -2683 | -3185 | -3470 | 2818 | 2263 | -2676 | -4240 | -4079 | 224 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 199(A | 2957 | -1575 | -3607 | -3525 | -3508 | 456 | -2992 | -3142 | -3331 | -3468 | -2642 | -2460 | -2661 | -2989 | -3286 | 646 | -1410 | 731 | -3811 | -3585 | 225 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 200(E | 56 | -2745 | 1143 | 2154 | -3045 | -1930 | -765 | -2818 | 1875 | -2752 | -1859 | 945 | -2144 | -332 | -1009 | -1045 | -1166 | -2359 | -2923 | -2190 | 226 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 201(T | -1256 | -2015 | -1982 | -1726 | -3420 | -2098 | -1785 | -3082 | 927 | -3191 | -2379 | -1663 | -2604 | -1463 | -1433 | 524 | 3369 | -2475 | -3390 | -2984 | 227 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 202( | 2769 | -2207 | -4068 | -3807 | 2256 | -3458 | -1352 | -1888 | -3438 | -1847 | -1513 | -2925 | -3632 | -2881 | -3227 | -2665 | -2291 | -1867 | 3112 | 296 | 228 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 203(R | -2470 | -3357 | -2623 | 1389 | -4114 | -3061 | -3509 | 2409 | -3196 | 119 | -2485 | -1713 | -3049 | -686 | 2844 | -2333 | -2214 | -3234 | -3079 | -2887 | 229 |
| | -540 | -7942 | -7942 | -894 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 204(M | 816 | -1388 | -782 | -226 | -1511 | -1668 | -358 | -1120 | 1679 | 2429 | 1761 | 1028 | -1755 | -26 | -458 | -619 | -511 | -896 | -1709 | -1189 | 230 |
| | -13 | -7414 | -8456 | -894 | -381 | 399 | -249 | -2660 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 205(L | -2837 | -2376 | -5287 | -4745 | -1320 | -4877 | -3831 | 1365 | -4505 | 1943 | -305 | -4548 | -4406 | -3738 | -4219 | -4120 | -2750 | 1537 | -2900 | -2889 | 231 |
| | -149 | -500 | 233 | 43 | -381 | 399 | -701 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 206(C | -1191 | 2897 | -3560 | -2991 | 2519 | -2720 | -1807 | -69 | -2623 | -837 | -305 | -2465 | -2840 | -2267 | -2460 | -1855 | 899 | 2022 | -1675 | -1297 | 232 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |

FIG. 12Q

Table 14

| | | | | | | | | | | | | | | | | | | |
|---|---|---|---|---|---|---|---|---|---|---|---|---|---|---|---|---|---|---|
| 207(G) | -1539 | -3140 | 2028 | -312 | -3421 | 2111 | -1027 | -3216 | 685 | -3138 | -2285 | 998 | -2361 | 1202 | -1409 | -1339 | -1520 | -2749 | -3312 | -2532 | 233 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 208(I) | 334 | -1130 | 401 | 620 | -1157 | -2255 | -1040 | 2289 | -1141 | -979 | 1812 | -1358 | -2323 | -992 | -1401 | -1264 | -866 | 644 | -1591 | -1181 | 234 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 209(E) | 425 | -2447 | 1685 | 2151 | -2749 | -1843 | -586 | -2497 | 831 | -2456 | -1553 | -477 | -2323 | -142 | -743 | -847 | -928 | 108 | -2639 | -1943 | 235 |
| | -149 | -500 | 235 | 43 | -381 | 399 | 106 | -626 | 210 | -466 | -720 | 275 | 394 | 45 | 96 | 359 | 117 | -369 | -294 | -249 |
| | -169 | -3204 | -8984 | -206 | -2913 | -701 | -1378 | * | | | | | | | | | | | | |
| 210(P) | -4497 | -4117 | -4899 | -5251 | -5560 | -4139 | -4798 | -6328 | -5454 | -5976 | -5741 | -5026 | -4302 | -5328 | -5104 | -4798 | -4844 | -5739 | -4665 | -5484 | 237 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 211(R) | -2896 | -3530 | -3730 | -2192 | -4456 | -3379 | -1195 | -3707 | 2481 | -3319 | -2662 | -2040 | -3291 | 1300 | 3145 | -2762 | -2535 | -3495 | -3134 | -3075 | 238 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 212(V) | -2838 | -2616 | -4834 | -4880 | -3213 | -3955 | -4416 | -610 | -4757 | -2310 | -2253 | -4383 | -4345 | -4643 | -4642 | -3732 | -3007 | -4157 | -3886 | 239 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 213(A) | 3345 | -1674 | -3727 | -3977 | -4175 | -1941 | -3439 | -3955 | -3910 | -4243 | -3329 | -2621 | -2737 | -3468 | -3709 | 825 | -1527 | -2788 | -4405 | -4282 | 240 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 214(M) | -3386 | -2926 | -5503 | -5047 | -1187 | -3953 | -644 | -626 | 4586 | 916 | 4893 | 4906 | 4599 | -3801 | -4244 | -4517 | -3301 | -1338 | -2841 | -2779 | 241 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 215(L) | -4119 | -3542 | -5389 | -5357 | -2027 | -4767 | -4359 | -1609 | -5118 | 3293 | -979 | -5230 | -4771 | -3801 | -4474 | -4724 | -5069 | 3656 | -2331 | -3412 | -3400 | 242 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 216(S) | -1944 | -2458 | -3696 | -4011 | -4410 | -2644 | -3753 | -4675 | -4191 | -4807 | -4070 | -3198 | -3384 | -3886 | -4051 | -4158 | -2393 | -3615 | -4374 | -4307 | 243 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 217(F) | -4596 | -3564 | -5022 | -5356 | 4100 | -4892 | -1140 | -3474 | -4920 | -2799 | -2888 | -3546 | -4763 | -3678 | -4303 | 3656 | -4459 | -3642 | -389 | 2808 | 244 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 218(S) | -1944 | -2458 | -3696 | -4011 | -4410 | -2644 | -3753 | -4675 | -4191 | -4807 | -4070 | -3198 | -3384 | -3886 | -4051 | 3656 | -2393 | -3615 | -4374 | -4307 | 245 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 219(T) | -1086 | -1700 | -3489 | -3680 | -4071 | -1960 | -3290 | -3842 | -3622 | -4127 | -3243 | -2550 | -2741 | -3278 | -3511 | 1633 | 3501 | -2755 | 4299 | -4122 | 246 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |

FIG. 12R

Table 14

| | | | | | | | | | | | | | | | | | | | |
|---|---|---|---|---|---|---|---|---|---|---|---|---|---|---|---|---|---|---|---|
| 220(K) | -9 | -1211 | -7942 | -2188 | -8984 | -1252 | 894 | -684 | -1115 | -2201 | -701 | -2183 | -1378 | -2041 | * | 2458 | -2110 | 2342 | 1770 | -2264 | -372 | -433 | -1182 | -1128 | 117 | -1772 | -369 | -2263 | -294 | 1110 | -249 | 247 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 221(G) | -9 | -4088 | -7942 | -3924 | -8984 | -4774 | 894 | -5139 | -1115 | -5615 | -701 | 3825 | -1378 | -4753 | * | -5453 | -6014 | -5662 | -4812 | -4539 | -5232 | -5106 | -4370 | -4472 | 117 | -5527 | -369 | -4696 | -294 | -5561 | -249 | 248 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 222(S) | -9 | -1944 | -7942 | -2458 | -8984 | -3696 | 894 | -4011 | -1115 | -4410 | -701 | -2644 | -1378 | -3753 | * | -4191 | -4807 | -4070 | -3198 | -3384 | -3886 | -4051 | 3656 | -2393 | 117 | -3615 | -369 | -4374 | -294 | -4307 | -249 | 249 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 223(A) | -9 | 3609 | -7942 | -2508 | -8984 | -4184 | 894 | -4493 | -1115 | -4592 | -701 | -2737 | -1378 | -3989 | * | -4496 | -4701 | -4051 | -3440 | -3474 | -4171 | -4253 | -2294 | -2487 | 117 | -3536 | -369 | -4484 | -294 | -4643 | -249 | 250 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 224(K) | -9 | -2345 | -7942 | -3215 | -8984 | -2680 | 894 | -1702 | -1115 | -4004 | -701 | -2994 | -1378 | -1114 | * | 3145 | -3150 | -2429 | -1707 | -3005 | -690 | 1537 | 1210 | -2130 | 117 | -3134 | -369 | -3052 | -294 | -2847 | -249 | 251 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 225(H) | -9 | -1041 | -7942 | -1842 | -8984 | -1795 | 894 | -1535 | -1115 | -3225 | -701 | 1554 | -1378 | 2940 | * | -1555 | -3088 | -2233 | -1512 | -2445 | -1442 | -1925 | 2143 | 928 | 117 | -2312 | -369 | -3333 | -294 | -2843 | -249 | 252 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 226(P) | -9 | -1812 | -7942 | -3493 | -8984 | 1638 | 894 | 2272 | -1115 | -3746 | -701 | -2139 | -1378 | -1234 | * | 714 | -3480 | -2668 | -741 | -2261 | -848 | -1793 | -1570 | -1815 | 117 | -3091 | -369 | -3658 | -294 | -2819 | -249 | 253 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 227(M) | -9 | -1063 | -7942 | -1672 | -8984 | -1185 | 894 | 1731 | -1115 | -1647 | -701 | -2144 | -1378 | -910 | * | -725 | 1142 | 2726 | 1099 | -2261 | -651 | -1101 | -1179 | -1008 | 117 | -1100 | -369 | -2011 | -294 | -1532 | -249 | 254 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 228( | -9 | -150 | -7942 | 49 | -8984 | 299 | 894 | 757 | -1115 | -277 | -701 | -651 | -1378 | 839 | * | 392 | -910 | 599 | 300 | -401 | 623 | 162 | -99 | 38 | 117 | 448 | -369 | 1107 | -294 | 126 | -249 | 255 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 229(V) | -9 | -1683 | -7942 | -1779 | -8984 | -4225 | 894 | -4114 | -1115 | -2704 | -701 | -2952 | -1378 | -3573 | * | -3855 | -1868 | -1633 | -3296 | -3474 | -3653 | -3791 | -2302 | 2073 | 117 | 3159 | -369 | -3712 | -294 | -3334 | -249 | 256 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 230(E) | -9 | 576 | -7942 | -3124 | -8984 | 2215 | 894 | 2294 | -1115 | -3448 | -701 | -2061 | -1378 | -1092 | * | -936 | -3183 | -2340 | -696 | -2393 | -692 | -1547 | -1375 | 1093 | 117 | -2772 | -369 | -3374 | -294 | -2589 | -249 | 257 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |
| 231(K) | -9 | 315 | -7942 | -2794 | -8984 | -1360 | 894 | -1079 | -1115 | -3606 | -701 | -2397 | -1378 | -1201 | * | 3269 | -3135 | -2344 | 1290 | -2657 | -798 | -553 | -1655 | -1723 | 117 | -2800 | -369 | -3186 | -294 | -2733 | -249 | 258 |
| | -149 | -500 | -8984 | 233 | -894 | 43 | -1115 | -381 | 399 | -701 | 106 | -1378 | * | 210 | -466 | -720 | 275 | 394 | 45 | 96 | 359 | | | | | | | | | | | |

Table 14

| | | | | | | | | | | | | | | | | | | | |
|---|---|---|---|---|---|---|---|---|---|---|---|---|---|---|---|---|---|---|---|
| 245(D) | 206 | -2972 | 2710 | 1351 | -3255 | -2000 | 1755 | -3042 | -683 | -2972 | -2100 | -614 | -2269 | 1462 | -1262 | -1213 | -2579 | -3148 | -2386 | 272 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 246(L) | -3414 | -2874 | 5769 | 5161 | 1383 | -5422 | -4072 | 994 | 4912 | 2728 | 2007 | -5118 | -4630 | -3791 | -4438 | -4708 | -3264 | -2810 | -2947 | 273 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 247(A) | 1831 | -2029 | 575 | -204 | -2274 | -1806 | -494 | -1962 | 927 | -82 | -1160 | 494 | 270 | -72 | -607 | -735 | 508 | 1613 | -2285 | -1663 | 274 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 248(I) | -2431 | -2000 | 4947 | 4466 | 1231 | -4532 | -3688 | 3189 | -4249 | 517 | -529 | -4183 | -4266 | -3781 | -4114 | -3766 | -2383 | 1363 | -3060 | -2816 | 275 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 249(D) | 4232 | 4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 276 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 250(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 277 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 251(E) | 4205 | 4417 | -2343 | 3901 | -3731 | -3698 | -3534 | -5837 | -3838 | -5561 | -5237 | -3039 | -4218 | -3453 | -4201 | -4072 | -4352 | -5409 | -4640 | -4860 | 278 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 252(L) | -3602 | -3015 | -5919 | -5328 | 1158 | -5654 | -4138 | 616 | -5093 | 2938 | 2013 | -5330 | -4744 | -3877 | -4575 | -4984 | -3438 | -1455 | -2794 | -2838 | 279 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 253(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 280 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 254(F) | -2863 | -2433 | -5172 | -4640 | 3169 | -4702 | -3234 | -392 | -4348 | 1785 | -84 | -4307 | -4290 | -3544 | -4021 | -3916 | -2769 | 1504 | -2393 | -2005 | 281 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 255(D) | 4232 | 4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 282 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 256(A) | 3609 | -2508 | 4184 | 4493 | 4592 | -2737 | -3989 | -4421 | -4496 | -4701 | -4051 | -3440 | -3474 | -4171 | -4253 | -2294 | -2487 | -3536 | -4484 | -4643 | 283 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |

FIG. 12U

Table 14

| | | | | | | | | | | | | | | | | |
|---|---|---|---|---|---|---|---|---|---|---|---|---|---|---|---|---|
| 257(A) | 3186 | -1669 | -3728 | -3961 | -4171 | -1936 | -3425 | -3953 | 3886 | -4235 | -3318 | -2613 | -2731 | 3447 | -3695 | 1524 | -2783 | -1520 | 4398 | -4275 | 284 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 258(F) | -3002 | -2525 | -5316 | -4818 | 3177 | -4924 | -3350 | 2613 | -4551 | 818 | -147 | 4496 | -4441 | 3703 | -4215 | -4169 | -2905 | -737 | -2444 | -1989 | 285 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 259(V) | -2294 | -2438 | 724 | -2485 | -3071 | -3156 | -3064 | -720 | -3372 | -2390 | -2164 | -2598 | -3629 | 2975 | -3716 | -2757 | -2460 | 3538 | -3861 | -3370 | 286 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 260(P) | -1594 | -2934 | -619 | 588 | -3418 | -2163 | -1118 | -3148 | 755 | -3092 | -2272 | -870 | 3320 | -720 | -1108 | 321 | -1590 | -2706 | -3251 | -2595 | 287 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 261(E) | 232 | -2432 | -633 | 1887 | -2799 | -1880 | -622 | -2541 | 1768 | -2491 | -1591 | -543 | -2032 | -178 | -679 | 1460 | -962 | -2096 | -2660 | -1989 | 288 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 262(V) | -2838 | -2616 | -4834 | -4880 | -3213 | -3955 | -4416 | -610 | -4757 | -2310 | -2253 | -4383 | -4345 | -4643 | -3716 | -3732 | -3007 | 3763 | -4157 | -3886 | 289 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 263(A) | -1827 | -3692 | -3978 | -4328 | -3541 | -3541 | -4137 | -4037 | -4403 | -3503 | -2739 | -2867 | -3583 | -3840 | -1477 | -1693 | -2962 | -4468 | -4428 | 290 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 264(E) | 1471 | 669 | 1713 | -2799 | -1806 | -509 | -622 | 1384 | -680 | -1440 | -444 | -1930 | -60 | -624 | -766 | -833 | -1955 | -2531 | -1848 | 291 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 265(Q) | 236 | -2063 | -853 | -302 | -2314 | -1882 | -542 | -1988 | 1473 | 779 | -1199 | -578 | -1977 | 1845 | -534 | 1012 | -820 | -1652 | -2307 | -1712 | 292 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 266(K) | -4125 | -4091 | -3615 | -3960 | -2958 | -5182 | 3972 | -4825 | -4345 | -3552 | -4249 | -2709 | -1809 | -4154 | -4044 | -4895 | -4132 | -4389 | 293 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 267(A) | 3348 | -2109 | -3336 | -3412 | -1764 | -2509 | -2437 | -2956 | -3286 | -3118 | -2630 | -2708 | -3150 | -3050 | -3249 | -1903 | -2016 | -2533 | -2364 | 1487 | 294 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 268(P) | -1528 | -2315 | -1720 | -1687 | -3833 | -2233 | -1895 | -3559 | 797 | -3582 | -2793 | -1690 | 3653 | -1574 | -1445 | 406 | -1768 | -2881 | -3673 | -3270 | 295 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |
| 269(G) | -1935 | -3089 | 2442 | 885 | 4418 | 2762 | -1974 | -4330 | -2285 | -4310 | -3586 | -1182 | -2821 | -1681 | -3048 | 394 | -2183 | -3549 | -4481 | -3646 | 296 |
| | | -149 | -500 | 233 | 43 | -381 | 399 | -701 | -626 | 210 | -466 | -720 | 275 | 394 | 45 | 96 | 359 | 117 | -369 | -294 | -249 |
| | | -9 | -7942 | -8984 | -894 | -1115 | | -1378 | | * | | | | | | | | | | | |

FIG. 12V

Table 14

| | | | | | | | | | | | | | | | | | | | | |
|---|---|---|---|---|---|---|---|---|---|---|---|---|---|---|---|---|---|---|---|---|
| | -9 | -7942 | -8984 | 894 | -1115 | -701 | -1378 | * | | | | | | | | | | | | |
| 270(S) | -1944 | -2458 | -3696 | 4011 | -4410 | -2644 | -3753 | -4675 | -4191 | 4807 | 4070 | -3198 | -3384 | -3886 | -4051 | 3656 | -2393 | -3615 | -4374 | -4307 | 297 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 271(K) | -986 | -2487 | 579 | 781 | -2798 | -1840 | -584 | -2559 | 1709 | -2499 | -1588 | 1699 | 1485 | -137 | -743 | 394 | -935 | -2105 | -2668 | -1964 | 298 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 272(V) | -2488 | -1997 | -5115 | -4741 | -2236 | -4876 | -4521 | 1399 | -4638 | 586 | -992 | -4534 | -4596 | -4394 | -4675 | -4204 | -2466 | 3282 | -3849 | -3500 | 299 |
| | -149 | -500 | 233 | 43 | -381 | 399 | 106 | -626 | 210 | -466 | 275 | 394 | 45 | 96 | 359 | 117 | -369 | -294 | -249 | | |
| | -9 | -7942 | -8984 | -894 | -1115 | -701 | -1378 | * | | | | | | | | | | | | | |
| 273(A) | 2860 | -2613 | -1445 | -1105 | -3345 | -2365 | -1181 | -2968 | 911 | -2930 | -2150 | -1269 | -2615 | 1502 | -562 | -1587 | -1627 | -2570 | -3048 | -2602 | 300 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 274(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 301 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 275(H) | -1098 | -2519 | 644 | -333 | -2880 | -1987 | 2767 | -2597 | 2281 | -2509 | -1617 | 857 | -2093 | -153 | 1114 | -970 | -1024 | -2167 | -2636 | -2015 | 302 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 276(A) | -2508 | -4184 | -4493 | -4592 | -2737 | -3989 | 4421 | -4496 | -4701 | -4051 | -3440 | -3474 | -4171 | -4253 | -2294 | -2487 | -3536 | -4484 | -4643 | 303 | |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 277(N) | -1586 | -2305 | -1738 | -2020 | -4028 | -2232 | -2587 | -3973 | -2635 | -4158 | -3406 | 4054 | -2920 | -2402 | -2900 | -1720 | 681 | -3116 | -4157 | -3676 | 304 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 278(V) | -2446 | -1963 | -5100 | -4786 | -2548 | -4847 | -4816 | 1583 | -4714 | -1330 | -1276 | -4562 | -4651 | -4631 | -4841 | -4218 | -2447 | 3468 | -4224 | -3729 | 305 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 279( | -150 | 757 | 49 | 299 | -277 | -651 | 839 | -485 | 392 | -910 | 599 | 300 | -401 | 623 | 162 | -99 | 38 | -448 | 1107 | 126 | 306 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 280(F) | -3486 | -2932 | -5765 | -5195 | 3114 | -5447 | -3820 | -632 | -4937 | 2173 | 2384 | -5073 | -4656 | -3798 | -4452 | -4740 | -3334 | -1436 | -2628 | -2474 | 307 |
| | -149 | -500 | 233 | 43 | -381 | 399 | 106 | -626 | 210 | -466 | -720 | 275 | 394 | 45 | 96 | 359 | 117 | -369 | -294 | -249 | |
| | -9 | -7942 | -8984 | -894 | -1115 | -701 | -1378 | * | | | | | | | | | | | | | |
| 281(I) | -2458 | -1961 | -5125 | -4807 | -2569 | -4914 | -4890 | 3219 | -4751 | -1339 | -1284 | -4603 | -4685 | -4676 | -4892 | -4286 | -2453 | 2471 | -4276 | -3778 | 308 |
| | -149 | -500 | 233 | 43 | -381 | 399 | 106 | -626 | 210 | -466 | -720 | 275 | 394 | 45 | 96 | 359 | 117 | -369 | -294 | -249 | |

FIG. 12W

Table 14

| | | | | | | | | | | | | | | | | |
|---|---|---|---|---|---|---|---|---|---|---|---|---|---|---|---|---|
| 282(F) | -4720 | -3927 | -5139 | -5454 | 4513 | -4504 | -2520 | -3938 | -5326 | -3307 | -3429 | -4469 | -4782 | -4575 | -4818 | -4787 | -4810 | -4172 | -1812 | -736 | 309 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 283P | -4497 | 4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 310 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 284D | -2322 | -4185 | 3035 | 1469 | -4418 | -2266 | -1625 | -4341 | -1869 | -4214 | -3539 | -867 | -2800 | -1293 | -2724 | 1786 | -2396 | -3805 | -4409 | -3395 | 311 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 285L | -3492 | -2925 | -5831 | -5302 | -1190 | -5571 | -4334 | 974 | -5050 | 3059 | 17 | -5312 | -4763 | -3965 | -4606 | -4957 | -3364 | -1095 | -2972 | -3089 | 312 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 286Q | -2004 | -3769 | 1173 | 2079 | -3991 | -2187 | -1375 | -3849 | -1403 | -3743 | -2969 | 1136 | -2626 | 3177 | -2117 | -1727 | -2027 | -3552 | -3926 | -3026 | 313 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 287A | 2861 | 2401 | -3941 | -3933 | -3713 | -1915 | -3209 | -3405 | -3647 | -3703 | -2846 | -2573 | -2679 | -3249 | -3498 | 1246 | 795 | -2497 | -4004 | -3830 | 314 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 288G | 804 | -1917 | -3555 | -3872 | 4406 | 3488 | -3564 | -4245 | -4053 | -4497 | -3611 | -2768 | -2934 | -3603 | -3880 | -1567 | -1787 | -3064 | -4502 | -4481 | 315 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 289N | -3642 | -3838 | -3004 | -3356 | -4743 | -3612 | -3773 | -5643 | -4099 | -5460 | -5060 | 4378 | -4185 | -3865 | -4225 | -3744 | -3950 | -5002 | -4391 | -4381 | 316 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 290I | -3202 | -2787 | -5004 | -4996 | -2836 | -4384 | -4440 | 3937 | -4838 | -1815 | -3807 | -4704 | -4600 | -4683 | -4704 | -4353 | -3280 | -603 | -3938 | -3661 | 317 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 291G | 1452 | -1874 | -3596 | -3903 | -4376 | 3335 | -3550 | -4203 | -4044 | -4459 | -3565 | -2747 | -2900 | -3588 | -3862 | -1522 | -1740 | -3018 | -4492 | -4461 | 318 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 292Y | -4791 | -3935 | -4914 | -5231 | -815 | -4530 | -2178 | -4357 | -5024 | -3745 | -3807 | -4206 | -4772 | -4328 | -4584 | -4677 | -4837 | -4435 | -1477 | 4857 | 319 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 293K | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 320 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |
| 294I | -3130 | -2603 | -5572 | -5096 | -1392 | -5301 | -4317 | 3061 | -4881 | 2084 | -185 | -5010 | -4688 | -4034 | -4578 | -4656 | -3046 | -463 | -3127 | -3143 | 321 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | | | |

FIG. 12X

Table 14

FIG. 12Y

| | | | | | | | | | | | | | | | | | | |
|---|---|---|---|---|---|---|---|---|---|---|---|---|---|---|---|---|---|---|
| | -9 | -7942 | -8984 | -894 | -1115 | -701 | -1378 | * | | | | | | | | | | |
| 295(A) | 2675 | -1535 | -3836 | -3683 | -2774 | -2214 | -2959 | -1215 | -3410 | -2393 | -1857 | -2670 | -2859 | -3085 | -3310 | -1533 | 792 | 2057 | -3350 | -3057 | 322 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 296(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 323 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 297(R) | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 324 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 298(F) | -3500 | -2941 | -5773 | -5206 | 3166 | -5461 | -3812 | -635 | -4949 | 2227 | -5083 | -4665 | -3805 | -3382 | -4462 | -4757 | -3346 | -1441 | -2619 | -2449 | 325 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 299(G) | 2279 | -1650 | -3675 | -3870 | -4196 | 2606 | -3385 | -3993 | -3836 | -4243 | -3303 | -2572 | -2706 | -3678 | 828 | -1491 | -2786 | -4412 | -4298 | 326 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 300(K) | -1571 | -2888 | -927 | -655 | -3321 | 2063 | 1468 | -3019 | 2355 | -2910 | -2082 | 920 | -2447 | -523 | -551 | -1431 | -1504 | -2612 | -2998 | -2431 | 327 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 301(F) | 2448 | -2615 | -4303 | -4172 | 2956 | -3922 | -1214 | -2324 | -3828 | -2183 | -1926 | -3107 | -3996 | -3105 | -3543 | -3119 | -2926 | -2325 | -560 | 2239 | 328 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 302(E) | -1402 | -2920 | 1061 | 2832 | -3242 | -2054 | 879 | -2998 | 774 | -2910 | -2042 | -672 | -2284 | -454 | 1073 | -1230 | -1357 | -2549 | -3055 | -2355 | 329 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 303(A) | 3609 | -2508 | -4184 | -4493 | -4592 | -2737 | -3989 | -4421 | -4496 | -4701 | -4051 | -3440 | -3474 | -4171 | -4253 | -2294 | -2487 | 3536 | -4484 | -4643 | 330 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 304(I) | -1878 | -1552 | -4312 | -3775 | -1491 | -3734 | -2739 | -4753 | -3471 | 521 | -3367 | -3656 | -3110 | -3335 | -2889 | -4370 | -1832 | 2126 | -2430 | 2171 | 331 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 305(G) | -4088 | -3924 | -4774 | -5139 | -5615 | 3825 | -4753 | -6303 | -5453 | -6014 | -5662 | -4812 | -4539 | -5232 | -5106 | -4472 | -5527 | -4696 | -5561 | 332 |
| | -149 | -500 | 233 | 43 | -381 | 399 | 106 | -626 | 210 | -466 | -720 | 275 | 394 | 45 | 96 | 359 | 117 | -369 | -294 | -249 |
| | -9 | -7942 | -8984 | -894 | -1115 | -701 | -1378 | * | | | | | | | | | | |
| 306(P) | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 333 |
| | -149 | -500 | 233 | 43 | -381 | 399 | 106 | -626 | 210 | -466 | -720 | 275 | 394 | 45 | 96 | 359 | 117 | -369 | -294 | -249 |

Table 14

| | | | | | | | | | | | | | | | | | | | |
|---|---|---|---|---|---|---|---|---|---|---|---|---|---|---|---|---|---|---|---|
| 307(I) | -2574 | -2082 | -5179 | -4778 | -2009 | -4923 | -4424 | 3104 | -4656 | 1327 | 776 | -4584 | -4587 | -4278 | -4620 | -4242 | -2542 | 1595 | -3640 | -3399 | 334 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 308(C) | -1490 | 2918 | -3842 | -3258 | -1170 | -3142 | -2133 | 1934 | -2902 | 1595 | -258 | -2806 | -3152 | -2528 | -2741 | -2266 | 1394 | 65 | -1929 | -1611 | 335 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 309(Q) | -4207 | -4117 | -3531 | -3731 | -4752 | -3930 | -3721 | -5554 | -3395 | -5179 | -4897 | -3823 | -4399 | 4556 | -3405 | -4301 | -4380 | -5208 | -4301 | -4384 | 336 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 310(G) | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 337 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 311(L) | -3686 | -3084 | -5727 | -5319 | 2036 | -5453 | -3331 | -789 | -5052 | 2929 | -88 | -4966 | -4743 | -3883 | -4542 | -4837 | -3542 | -1589 | -2266 | -1680 | 338 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 312(A) | 2898 | -1987 | -2240 | -2485 | -1052 | -2085 | -2826 | -872 | -3004 | -4117 | -3288 | 2707 | -2813 | -2683 | -3186 | 1142 | -1726 | -2917 | -4217 | -3861 | 339 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 313(K) | 1066 | -2626 | -1795 | -1052 | -3050 | -2498 | -2618 | 2866 | -5454 | -2563 | 1526 | -1206 | -2543 | -458 | -3186 | -1506 | -1494 | -2321 | -2682 | -2281 | 340 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 314(P) | -4497 | -4117 | -4899 | -5251 | -5560 | -4139 | -4798 | -6328 | -5454 | -5976 | -5741 | -5026 | -4539 | -5328 | -5104 | -4798 | -4844 | -5739 | -4665 | -5484 | 341 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 315(V) | -2475 | -1980 | 5117 | -4752 | -2317 | -4893 | -4598 | 2349 | -4663 | 557 | -1062 | -4548 | -4617 | -4458 | -4725 | -4228 | -2455 | 2932 | -3943 | -3564 | 342 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 316(H) | 173 | -2262 | 944 | -767 | 3091 | 1973 | 2974 | -2865 | 947 | -2905 | -2052 | 2949 | -2338 | -840 | -1414 | 1020 | -1292 | -2346 | -3104 | -2474 | 343 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 317(D) | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 344 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 318(L) | -4119 | -3542 | -5389 | -5357 | -2027 | -4767 | -4359 | -1609 | -5118 | 3293 | -979 | -5230 | -4771 | -4474 | -4724 | -5069 | -4106 | -2331 | -3412 | -3400 | 345 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |
| 319(S) | -1944 | -2458 | -3696 | -4011 | -2410 | -2644 | -3753 | -4675 | -4191 | -4807 | -4070 | -3198 | -3384 | -3886 | -4051 | 3656 | -2393 | -3615 | -4374 | -4307 | 346 |
| | | -149 | -500 | 233 | 43 | -381 | 399 | 106 | -626 | 210 | -466 | -720 | 275 | 394 | 45 | 96 | 359 | 117 | -369 | -294 | -249 |
| | | -9 | | -7942 | -8984 | -894 | -1115 | -701 | -1378 | * | | | | | | | | | | | |

FIG. 12Z

Table 14

| | | | | | | | | | | | | | | | | | | | | | |
|---|---|---|---|---|---|---|---|---|---|---|---|---|---|---|---|---|---|---|---|---|---|
| | -9 | -4488 | -4181 | -7942 | -4318 | -5193 | -4148 | -3436 | -5568 | -2393 | -5152 | -4748 | -4479 | -3286 | 4202 | -4614 | -4467 | -5273 | -4267 | -4649 | 347 |
| 320(R) | | | | | | | | | | | | | | | | | | | | | |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 321(G) | -4088 | -3924 | -4774 | -5139 | -5615 | 3825 | -4753 | -6303 | -5453 | -6014 | -5662 | -4539 | -5232 | -5106 | -4370 | -4472 | -5527 | -4696 | -5561 | 348 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 322(C) | -1383 | 5545 | -4327 | -4558 | -4019 | -2243 | 3671 | -3414 | -4157 | -3975 | -3301 | -3016 | -3818 | -1656 | 540 | -2675 | -4269 | -4170 | 349 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 323(S) | -1998 | -3389 | 920 | -646 | -4194 | -2202 | -1688 | -4095 | -1857 | -4037 | -3301 | 1873 | -2745 | -1360 | -2596 | 2972 | -2145 | -3473 | -4215 | -3333 | 350 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 324(A) | 1796 | -2218 | 759 | 1121 | -2509 | -1874 | -667 | -1688 | -343 | -2259 | -1405 | -2039 | -578 | -254 | -849 | 333 | -937 | 1127 | -2521 | -1880 | 351 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 325(E) | -2264 | -4130 | 1161 | 3061 | -4316 | -2257 | -1556 | -4221 | -1720 | -4092 | -3390 | -2763 | -846 | 2340 | -2512 | -1940 | -2316 | -3705 | -4277 | -3299 | 352 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 326(D) | -33 | -4335 | 3607 | 1205 | -4570 | -2294 | -1708 | -4511 | -2035 | -4382 | -3756 | -2858 | -897 | -1390 | -2952 | -2084 | -2528 | -3963 | -4583 | -3525 | 353 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 327(I) | -2456 | -1959 | -5125 | -4808 | -2580 | -4919 | -4900 | 3012 | -4754 | -1350 | -1292 | -4605 | -4688 | -4898 | -4291 | -2452 | 2731 | -4288 | -3786 | 354 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 328(Y) | -2065 | -1703 | 4458 | -4000 | -1497 | -3978 | -2824 | 1512 | -3720 | -1096 | -877 | -3567 | -3404 | -3627 | -3169 | -2033 | 2744 | -2424 | 2949 | 355 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 329(K) | -1420 | -3005 | 1129 | 1097 | -3290 | -1087 | -935 | -3080 | 2093 | -3005 | -2135 | -2283 | -401 | -517 | -1280 | -1233 | -1393 | -2613 | -3178 | -2412 | 356 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 330( ) | -150 | 757 | 49 | 299 | -277 | -651 | 839 | -485 | 392 | -910 | 599 | 300 | 1724 | 623 | 162 | -99 | 38 | -448 | 1107 | 126 | 357 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |
| 331(V) | 242 | -1739 | -4505 | -4069 | -1901 | -3865 | -3328 | 339 | -3811 | 1145 | -812 | -3892 | -3662 | -3515 | -3741 | -3100 | -2045 | 3053 | -3031 | -2693 | 358 |
| | -149 | -500 | 233 | -894 | -381 | -1115 | -701 | -1378 | -626 | 210 | -466 | -720 | 394 | 45 | 96 | 359 | 117 | -369 | -294 | -249 | |
| | -9 | | | -7942 | -8984 | | | | * | * | | | | | | | | | | | |

FIG. 12AA

Table 14

FIG. 12BB

Table 14

| | | | | | | | | | | | | | | | | | | |
|---|---|---|---|---|---|---|---|---|---|---|---|---|---|---|---|---|---|---|
| 345(R) | -1110 | -6951 | -919 | -894 | -1115 | -2432 | -296 | * | -1640 | -1095 | -694 | -1696 | 14 | 3253 | -1003 | -929 | -1464 | -1574 | -1319 | 372 |
|  | -956 | -1423 | -1186 | -681 | -1830 | -1454 | -276 | 690 | -1967 | -1380 | -1471 | 394 | 45 | 96 | 359 | 117 | -369 | -294 | -249 |
|  | -149 | -500 | 233 | 43 | -381 | 399 | 106 | 210 | -466 | -720 |  |  |  |  |  |  |  |  |  |
|  | -37 | -5878 | -6920 | -894 | -1115 | -2888 | -209 | * |  |  |  |  |  |  |  |  |  |  |  |
| 346(E) | -804 | -1735 | 497 | 2874 | -2096 | -1058 | -327 | -157 | -1967 | -1380 | -1471 | -39 | -568 | -688 | -853 | -1562 | -2027 | -1547 | 373 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 347(R) | -956 | -1423 | -1186 | -681 | -1830 | -1454 | -276 | 690 | -1640 | -1095 | -694 | -1696 | 14 | 3253 | -1003 | -929 | -1464 | -1574 | -1319 | 374 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 348(S) | 227 | -390 | -660 | -668 | -1564 | -565 | -762 | -705 | -1690 | -1020 | -460 | -1182 | -625 | -900 | 2604 | -94 | -861 | -1818 | -1338 | 375 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 349(L) | -1162 | -1035 | -2273 | -2015 | -35 | -2243 | -1374 | -1587 | 2466 | 801 | -1903 | -2350 | -1486 | -1587 | -1745 | -1181 | 283 | -1141 | -718 | 376 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 350(H) | -948 | -1353 | -590 | -533 | -353 | -1374 | 4354 | -210 | -1544 | -1090 | -628 | -1716 | -415 | -369 | -985 | -1004 | -1409 | -758 | 74 | 377 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 351(T) | 71 | -435 | -987 | -905 | -1386 | -761 | -851 | -738 | -1152 | -667 | -673 | -1327 | -733 | -889 | -159 | 2865 | -370 | -1730 | -1351 | 378 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 352(L) | -1162 | -1035 | -2273 | -2015 | -35 | -2243 | -1374 | -1587 | 2466 | 801 | -1903 | -2350 | -1486 | -1587 | -1745 | -1181 | 283 | -1141 | -718 | 379 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 353(V) | -558 | -557 | -2112 | -1895 | -730 | -1799 | -1509 | -1619 | 15 | 149 | -1639 | -2121 | -1558 | -1693 | -1183 | -681 | 2778 | -1647 | -1187 | 380 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 354(E) | -804 | -1735 | 497 | 2874 | -2096 | -1058 | -327 | -157 | -1967 | -1380 | -1471 | -39 | -568 | -688 | -853 | -1562 | -2027 | -1547 | 381 |
|  | -149 | -500 | 233 | 43 | -381 | 399 | 106 | 210 | -466 | -720 | 394 | 45 | 96 | 359 | 117 | -369 | -294 | -249 |
|  | -37 | -5878 | -6920 | -894 | -1115 | -2888 | -209 | * |  |  |  |  |  |  |  |  |  |  |  |
| 355() | -150 | 757 | 49 | 299 | 277 | -651 | 839 | -3565 | -910 | 599 | -401 | 623 | 162 | -99 | 38 | -448 | 1107 | 126 | 382 |
|  | * | * | * | * | * | * | * | 485 | * | 300 | * | * | * | * | * | * | * | * |
|  | * | * | * | * | * | * | * | 392 |  |  |  |  |  |  |  |  |  |  |  |
|  | * | * | * | * | * | * | * | 0 |  |  |  |  |  |  |  |  |  |  |  |

FIG. 12CC

RECOMBINANT HOST CELLS COMPRISING PHOSPHOKETALASE

CROSS-REFERENCE TO RELATED APPLICATIONS

This application is a continuation of U.S. patent application Ser. No. 14/335,734, filed on Jul. 18, 2014 which is a continuation of U.S. patent application Ser. No. 13/161,168, filed on Jun. 15, 2011, now U.S. Pat. No. 8,871,488, which is related to and claims the benefit of priority of U.S. Provisional Patent Application No. 61/356,379, filed on Jun. 18, 2010, the entirety of each is herein incorporated by reference.

FIELD OF THE INVENTION

The invention relates generally to the field of industrial microbiology. The invention relates to recombinant host cells comprising (i) a modification in an endogenous gene encoding a polypeptide that converts pyruvate to acetyl-CoA, acetaldehyde or acetyl-phosphate and (ii) a heterologous polynucleotide encoding a polypeptide having phosphoketolase activity. The invention also relates to recombinant host cells comprising (i) a modification in an endogenous gene encoding a polypeptide having pyruvate decarboxylase (PDC) activity, or a modification in an endogenous polypeptide having PDC activity, and (ii) a heterologous polynucleotide encoding a polypeptide having phosphoketolase activity. The invention also relates to recombinant host cells further comprising (iii) a heterologous polynucleotide encoding a polypeptide having phosphotransacetylase activity. Additionally, the invention relates to methods of making and using such recombinant host cells including, for example, methods of increasing cell growth, methods of reducing or eliminating the requirement of an exogenous carbon substrate for cell growth, methods of increasing glucose consumption and methods of increasing the production of a product of a pyruvate-utilizing pathway.

BACKGROUND OF THE INVENTION

Global demand for liquid transportation fuel is projected to strain the ability to meet certain environmentally driven goals, for example, the conservation of oil reserves and limitation of greenhouse gas emissions. Such demand has driven the development of technology which allows utilization of renewable resources to mitigate the depletion of oil reserves and to minimize greenhouse gas emissions.

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A: Chem.* 220:215-220, 2004). These processes use starting materials derived from petrochemicals, are generally expensive, and are not environmentally friendly. The production of isobutanol from plant-derived raw materials would minimize greenhouse gas emissions and would represent an advance in the art.

2-Butanone, also referred to as methyl ethyl ketone (MEK), is a widely used solvent and is the most important commercially produced ketone, after acetone. It is used as a solvent for paints, resins, and adhesives, as well as a selective extractant, activator of oxidative reactions, and it can be chemically converted to 2-butanol by reacting with hydrogen in the presence of a catalyst (Nystrom, R. F. and Brown, W. G. (*J. Am. Chem. Soc.* (1947) 69:1198). 2,3-butanediol can be used in the chemical synthesis of butene and butadiene, important industrial chemicals currently obtained from cracked petroleum, and esters of 2,3-butanediol may be used as plasticizers (Voloch et al., "Fermentation Derived 2,3-Butanediol," in Comprehensive Biotechnology, Pergamon Press Ltd., England Vol. 2, Section 3:933-947 (1986)).

Microorganisms can be engineered for the expression of biosynthetic pathways that initiate with cellular pyruvate to produce, for example, 2,3-butanediol, 2-butanone, 2-butanol and isobutanol. U.S. Pat. No. 7,851,188 discloses the engineering of recombinant microorganisms for production of isobutanol. U.S. Patent Application Publication Nos. US 20070259410 A1 and US 20070292927 A1 disclose the engineering of recombinant microorganisms for production of 2-butanone or 2-butanol. Multiple pathways are disclosed for biosynthesis of isobutanol and 2-butanol, all of which initiate with cellular pyruvate. Butanediol is an intermediate in the 2-butanol pathway disclosed in U.S. Patent Application Publication No. US 20070292927 A1.

The disruption of the enzyme pyruvate decarboxylase (PDC) in recombinant host cells engineered to express a pyruvate-utilizing biosynthetic pathway has been used to increase the availability of pyruvate for product formation via the biosynthetic pathway. For example, U.S. Application Publication No. US 20070031950 A1 discloses a yeast strain with a disruption of one or more pyruvate decarboxylase genes (a PDC knock-out or PDC-KO) and expression of a D-lactate dehydrogenase gene, which is used for production of D-lactic acid. U.S. Application Publication No. US 20050059136 A1 discloses glucose tolerant two-carbon source-independent (GCSI) yeast strains with no PDC activity, which may have an exogenous lactate dehydrogenase gene. Nevoigt and Stahl (*Yeast* 12:1331-1337 (1996)) describe the impact of reduced PDC and increased NAD-dependent glycerol-3-phosphate dehydrogenase in *Saccharomyces cerevisiae* on glycerol yield. U.S. Application Publication No. 20090305363 A1 discloses increased conversion of pyruvate to acetolactate by engineering yeast for expression of a cytosol-localized acetolactate synthase and substantial elimination of PDC activity.

While PDC-KO recombinant host cells can be used to produce the products of pyruvate-utilizing biosynthetic pathways, PDC-KO recombinant host cells require exogenous carbon substrate supplementation (e.g., ethanol or acetate) for their growth (Flikweert et al. 1999. FEMS Microbiol. Lett. 174(1):73-79 "Growth requirements of pyruvate-decarboxylase-negative *Saccharomyces cerevisiae*"). A similar auxotrophy is observed in *Escherichia coli* strains carrying a mutation of one or more genes encoding pyruvate dehydrogenase (Langley and Guest, 1977, J. Gen. Microbiol. 99:263-276).

In commercial applications, addition of exogenous carbon substrate in addition to the substrate converted to a desired product can lead to increased costs. There remains a need in the art for recombinant host cells with reduced or eliminated need for exogenous carbon substrate supplementation.

BRIEF SUMMARY OF THE INVENTION

One aspect of the invention relates to a recombinant host cell comprising (i) at least one deletion, mutation, and/or substitution in an endogenous gene encoding a polypeptide that converts pyruvate to acetaldehyde, acetyl-phosphate, or acetyl-CoA; and ii) a heterologous polynucleotide encoding a polypeptide having phosphoketolase activity. Another aspect of the invention relates to such a recombinant host cell further comprising (iii) a heterologous polynucleotide encoding a polypeptide having phosphotransacetylase activity. In embodiments, the polypeptide that converts pyruvate to acetaldehyde, acetyl-phosphate, or acetyl-CoA is pyruvate decarboxylase, pyruvate-formate lyase, pyruvate dehydrogenase, pyruvate oxidase, or pyruvate:ferredoxin oxidoreductase.

One aspect of the invention relates to a recombinant host cell comprising (i) a modification in an endogenous gene encoding a polypeptide having pyruvate decarboxylase activity or in an endogenous polypeptide having pyruvate decarboxylase activity; and (ii) a heterologous polynucleotide encoding a polypeptide having phosphoketolase activity. Another aspect of the invention relates to such a recombinant host cell further comprising (iii) a heterologous polynucleotide encoding a polypeptide having phosphotransacetylase activity.

One aspect of the invention relates to a recombinant host cell comprising (i) at least one deletion, mutation, and/or substitution in an endogenous gene encoding a polypeptide having pyruvate decarboxylase activity; and (ii) a heterologous polynucleotide encoding a polypeptide having phosphoketolase activity. Another aspect of the invention relates to a recombinant host cell further comprising: (iii) a heterologous polynucleotide encoding a polypeptide having phosphotransacetylase activity. Another aspect of invention relates to a reduced or eliminated requirement of such cells for an exogenous two-carbon substrate for its growth in culture compared to a recombinant eukaryotic host cell comprising (i) and not (ii) or (iii). Another aspect of the invention relates to the growth of such host cells in culture media that is not supplemented with an exogenous two-carbon substrate, for example, at a growth rate substantially equivalent to, or greater than, the growth rate of a host cell comprising (i) and not (ii) or (iii) in culture media supplemented with an exogenous two-carbon substrate.

In one aspect of the invention, the recombinant host cell is a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula,* or *Saccharomyces*. In another aspect of the invention, the recombinant host cell is *S. cerevisiae*

In another aspect of the invention, the recombinant host cell expresses a pyruvate-utilizing biosynthetic pathway including, for example, a biosynthetic pathway for a product such as 2,3-butanediol, isobutanol, 2-butanol, 2-butanone, valine, leucine, alanine, lactic acid, malic acid, fumaric acid, succinic acid, or isoamyl alcohol. Another aspect of the invention relates to expression of an isobutanol biosynthetic pathway in the recombinant host cell comprising at least one DNA molecule encoding a polypeptide that catalyzes a substrate to product conversion selected from the group consisting of (i) pyruvate to acetolactate; (ii) acetolactate to 2,3-dihydroxyisovalerate; (iii) 2,3-dihydroxyisovalerate to 2-ketoisovalerate; (iv) 2-ketoisovalerate to isobutyraldehyde; and (v) isobutyraldehyde to isobutanol. Another aspect of the invention relates to expression of a 2-butanone biosynthetic pathway in the recombinant host cell comprising at least one DNA molecule encoding a polypeptide that catalyzes a substrate to product conversion selected from the group consisting of (i) pyruvate to acetolactate; (ii) acetolactate to acetoin; (iii) acetoin to 2,3-butanediol; and (iv) 2,3-butanediol to 2-butanone.

Another aspect of the invention relates to expression of a 2-butanol biosynthetic pathway in the recombinant host cell comprising at least one DNA molecule encoding a polypeptide that catalyzes a substrate to product conversion selected from the group consisting of (i) pyruvate to acetolactate; (ii) acetolactate to acetoin; (iii) acetoin to 2,3-butanediol; (iv) 2,3-butanediol to 2-butanone; and (v) 2-butanone to 2-butanol.

One aspect of the invention relates to methods for the production of a product selected from the group consisting of 2,3-butanediol, isobutanol, 2-butanol, 2-butanone, valine, leucine, alanine, lactic acid, malic acid, fumaric acid, succinic acid and isoamyl alcohol comprising growing the recombinant host cells described herein under conditions wherein the product is produced and optionally recovering the product. Another aspect of the invention relates to methods of producing a recombinant host cell comprising transforming a host cell comprising at least one deletion, mutation, and/or substitution in an endogenous gene encoding a polypeptide having pyruvate decarboxylase activity with (i) a heterologous polynucleotide encoding a polypeptide having phosphoketolase activity; and optionally (ii) a heterologous polynucleotide encoding a polypeptide having phosphotransacetylase activity.

Another aspect of the invention relates to methods of improving the growth of a recombinant host cell comprising at least one deletion, mutation or substitution in an endogenous gene encoding a polypeptide having pyruvate decarboxylase activity, comprising (i) transforming the recombinant host cell with a heterologous polynucleotide encoding a polypeptide having phosphoketolase activity; and optionally (ii) transforming the recombinant host cell with a heterologous polynucleotide encoding a polypeptide having phosphotransacetylase activity. In embodiments, the methods further comprise growing the recombinant host cell in media containing limited carbon substrate.

Another aspect of the invention relates to methods of reducing the requirement for an exogenous two-carbon substrate for the growth of a recombinant host cell comprising at least one deletion, mutation or substitution in an endogenous gene encoding a polypeptide having pyruvate decarboxylase activity, comprising (i) transforming the host cell with a heterologous polynucleotide encoding a polypeptide having phosphoketolase activity; and optionally (ii) transforming the host cell with a heterologous polynucleotide encoding a polypeptide having phosphotransacetylase activity.

Another aspect of the invention relates to methods of eliminating the requirement for an exogenous two-carbon substrate for the growth of a recombinant host cell comprising at least one deletion, mutation or substitution in an endogenous gene encoding a polypeptide having pyruvate decarboxylase activity, comprising (i) transforming the host cell with a heterologous polynucleotide encoding a polypeptide having phosphoketolase activity; and optionally (ii) transforming the host cell with a heterologous polynucleotide encoding a polypeptide having phosphotransacetylase activity.

Still another aspect of the invention relates to methods for increasing the activity of the phosphoketolase pathway in a recombinant host cell comprising (i) providing a recombinant host cell of the invention; and (ii) growing the recombinant host cell under conditions whereby the activity of the phosphoketolase pathway in the recombinant host cell is increased.

In another aspect, the recombinant host cells comprise a phosphoketolase that matches the Profile HMM given in Table 6 with an E value of less than 7.5E-242. In another aspect, the phosphoketolase has at least about 40% identity to at least one of SEQ ID NO: 355, 379, 381, 388, 481, 486, 468, or 504. In another aspect, the phosphoketolase has at least about 90% identity to at least one of SEQ ID NO: 355, 379, 381, 388, 481, 486, 468, or 504. In another aspect, the phosphoketolase matches the Profile HMMs given in Tables 6, 7, 8, and 9 with E values of less than 7.5E-242, 1.1E-124, 2.1E-49, 7.8E-37, respectively. In another aspect, the recombinant host cells further comprise a phosphotransacetylase which matches the Profile HMM given in Table 14 with an E value of less than 5E-34. In another aspect, the phosphotransacetylase has at least about 40% identity to SEQ ID NO: 1475, 1472, 1453, 1422, 1277, 1275, 1206, 1200, 1159, or 1129. In another aspect, the phosphotransacetylase has at least about 90% identity to SEQ ID NO: 1475, 1472, 1453, 1422, 1277, 1275, 1206, 1200, 1159, or 1129.

BRIEF DESCRIPTION OF THE DRAWINGS/FIGURES AND INCORPORATION OF SEQUENCE LISTING AND TABLES

The various embodiments of the invention can be more fully understood from the detailed description, the figures, and the accompanying sequence descriptions, which form a part of this application.

Figure 4:
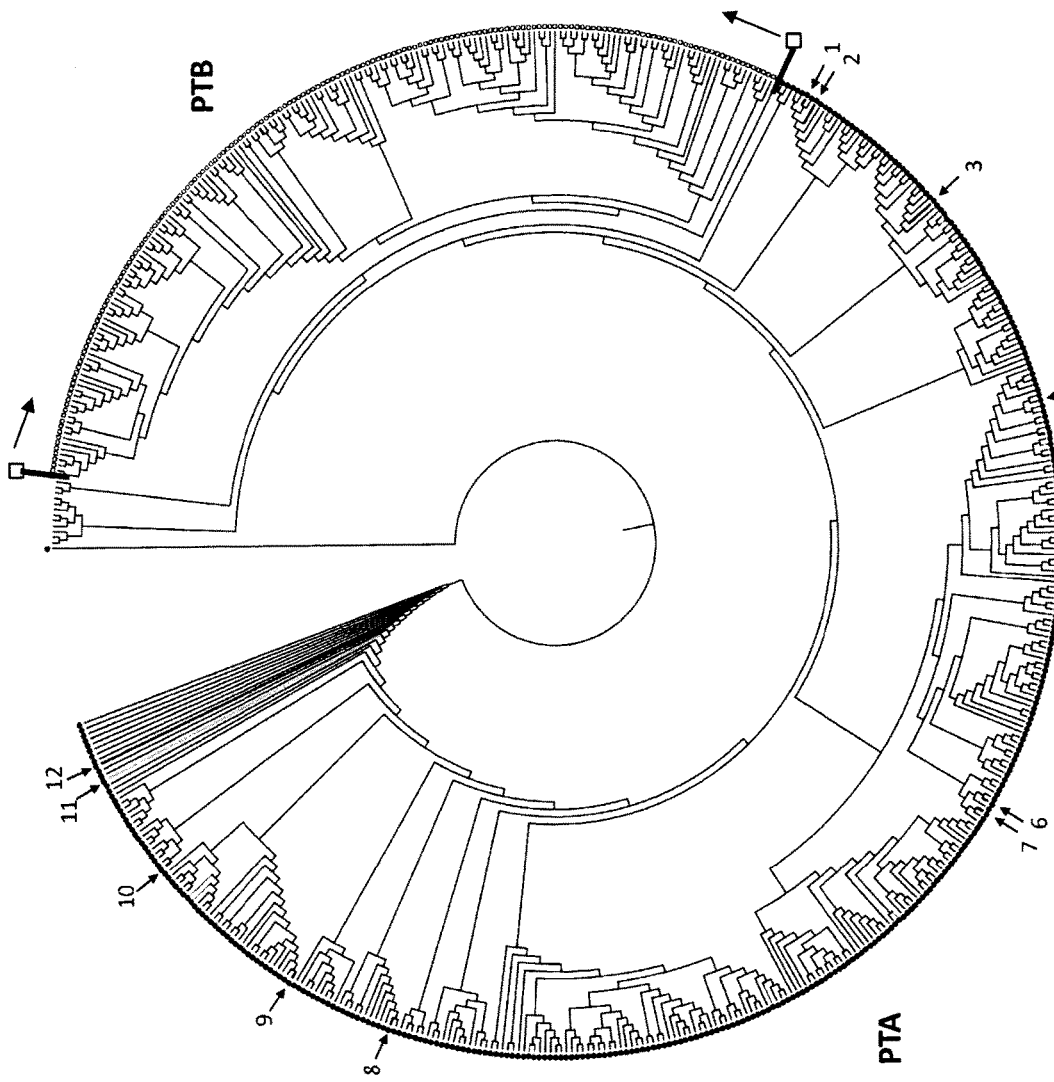
Figure 5:
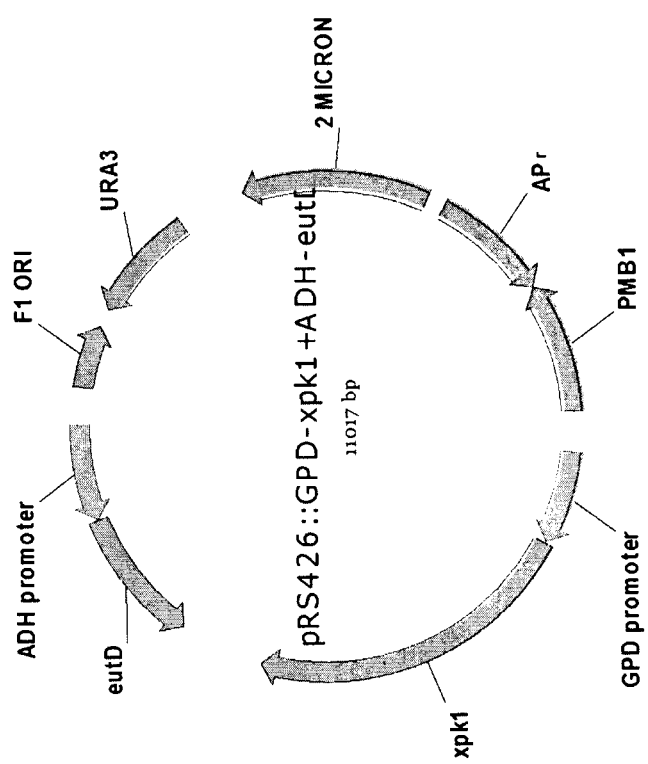

FIG. 4 depicts a phylogenetic tree of phosphate acetyltransferase (PTA) and phosphate butyryltransferase (PTB) sequences. Multiple sequence alignment was performed with Clustal X using default parameters. Phylogenetic tree was deduced using neighbor-joining method and drawn with Mega 4 software. Marked sequences are as follows: (#, Species, GI#) 1, *S. enterica*, 56412650; 2, *E. coli* K12, 88192043; 3, *V. parvula*, 227371784; 4, *C. kluyveri*, 153954015; 5, *C. Acetobutylicum*, 15895019; 6, *C. thermocellum*, 196254011; 7, *M. thermophila*, 88192043; 8, *S. pyogenes*, 48425286; 9, *B. subtilis*, 58176784; 10, *L. fermentum*, 227514417; 11, *L. plantarum*, 28377658; 12, *L. sanfranciscensis*, 11862872;

FIG. 5 is a plasmid map of pRS426::GPD-xpk1+ADH-eutD map which is described herein.

Figure 6:
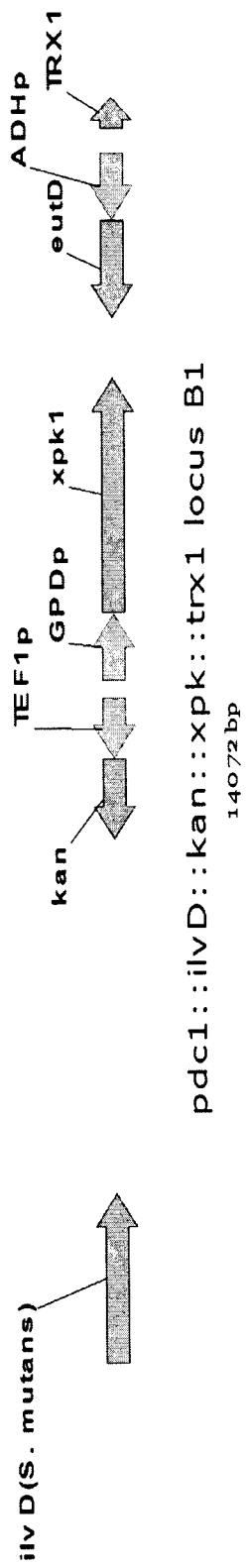

FIG. 6 depicts the Δpdc1::ilvD(Sm) locus of BP913 after integration of a phosphoketolase pathway vector (described herein).

Figure 7A:
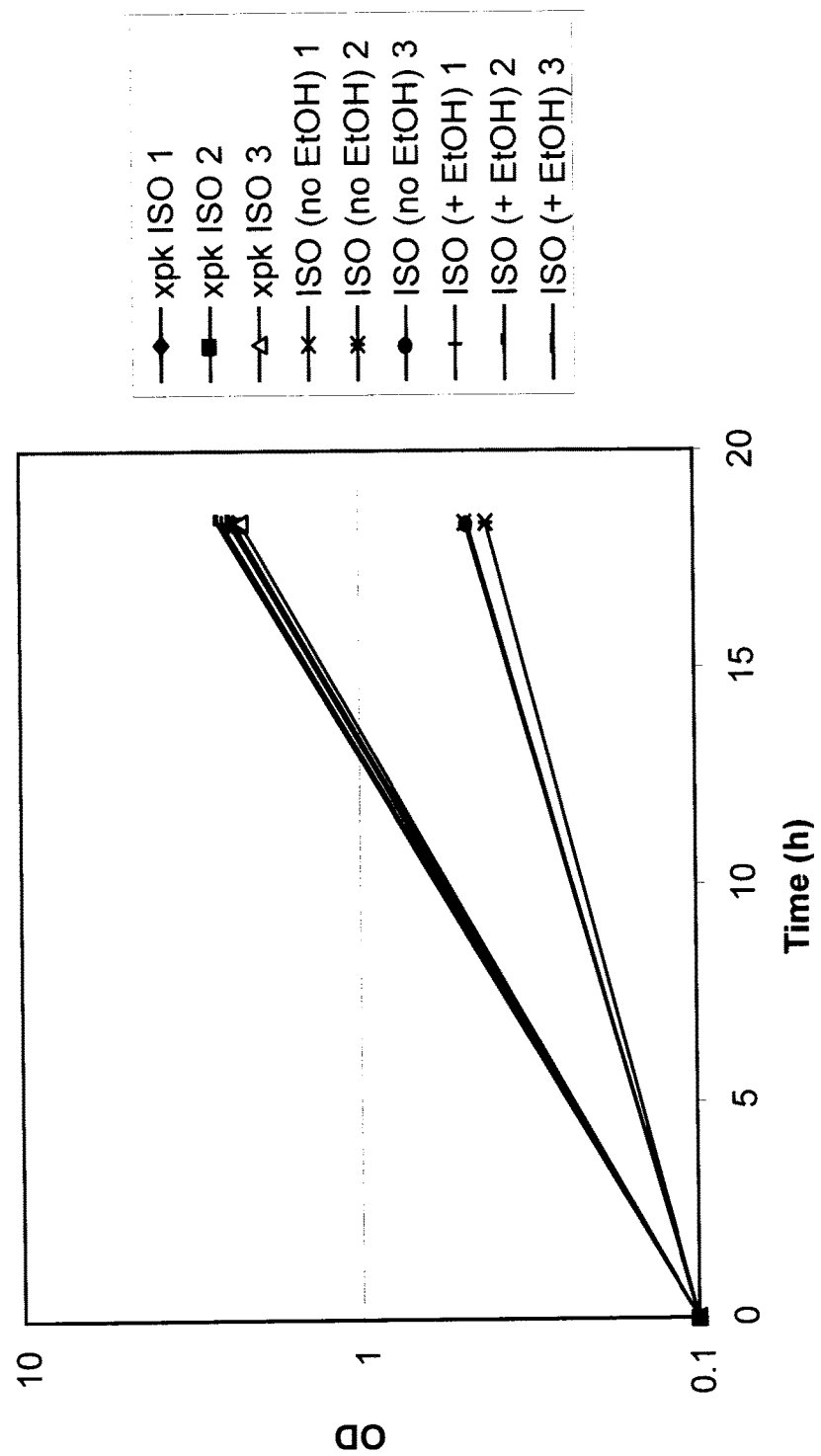

FIG. 7A shows the growth of an isobutanol-producing strain in the absence (no ETOH) and presence (+ETOH) of EtOH and the absence and presence of the phosphoketolase pathway (xpk). ISO1, ISO2 and ISO3 refer to replicates.

Figure 7B:
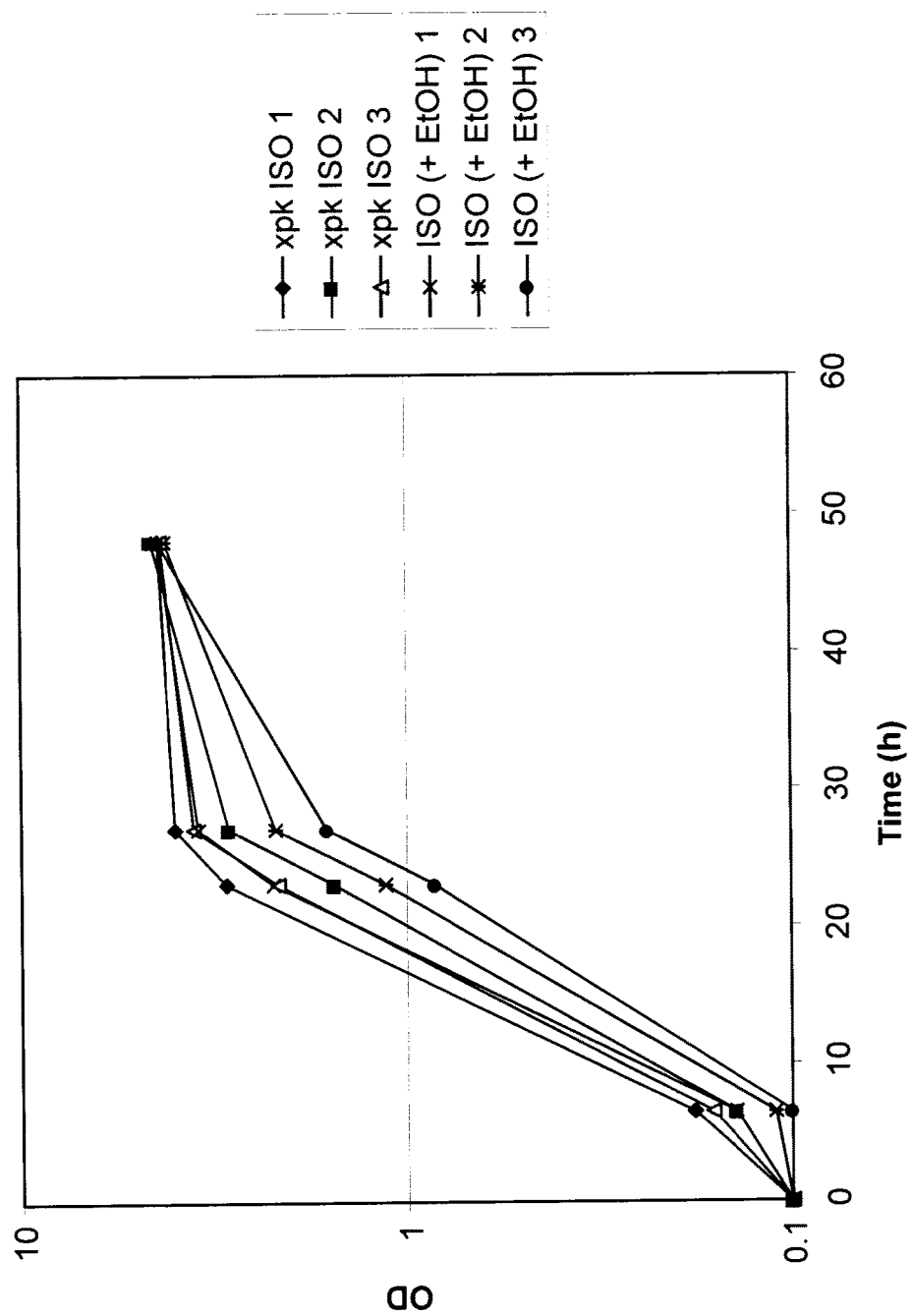

FIG. 7B shows the growth of a second subculture of strains from FIG. 7A.

Figure 8B:
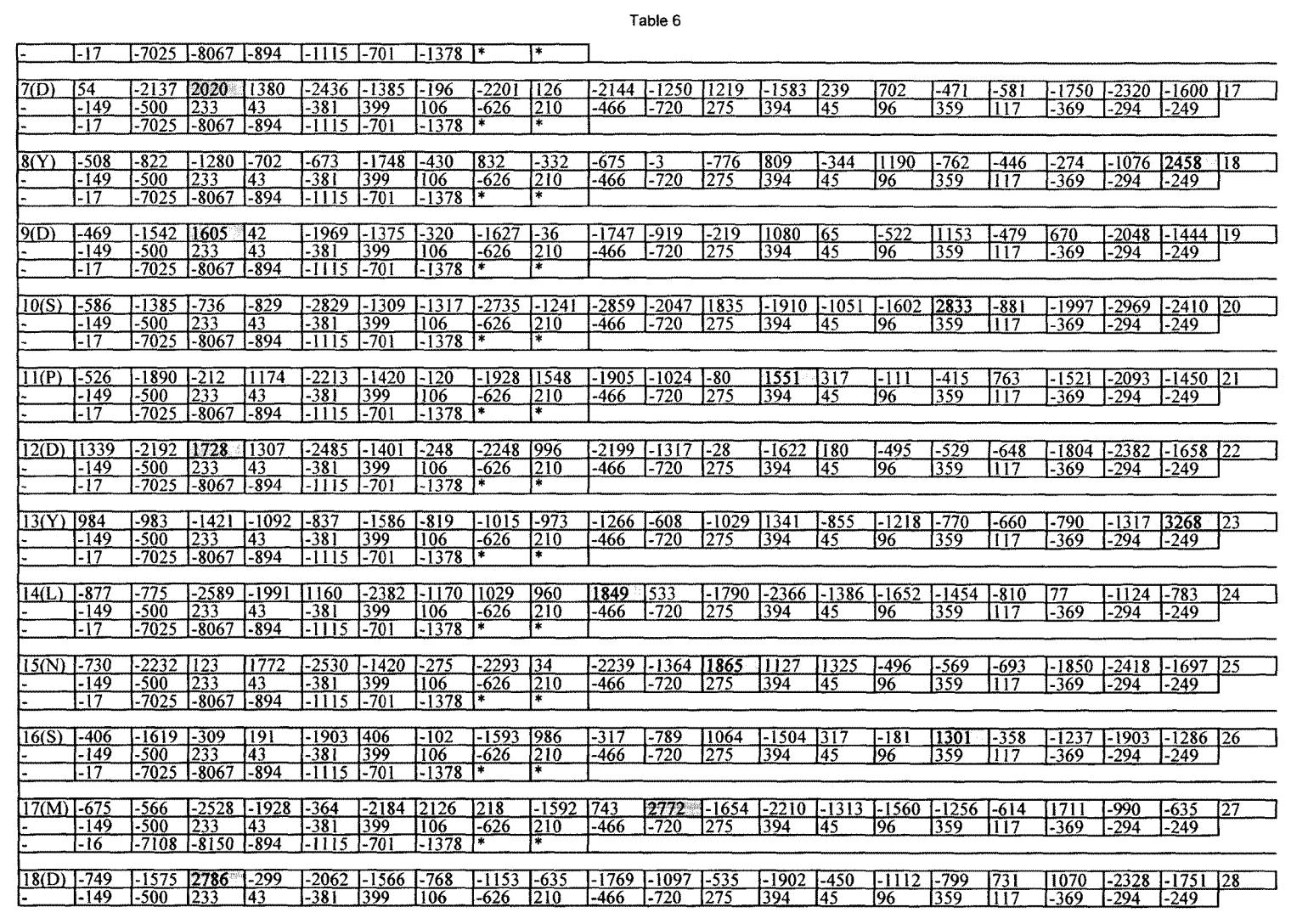
Figure 8F:
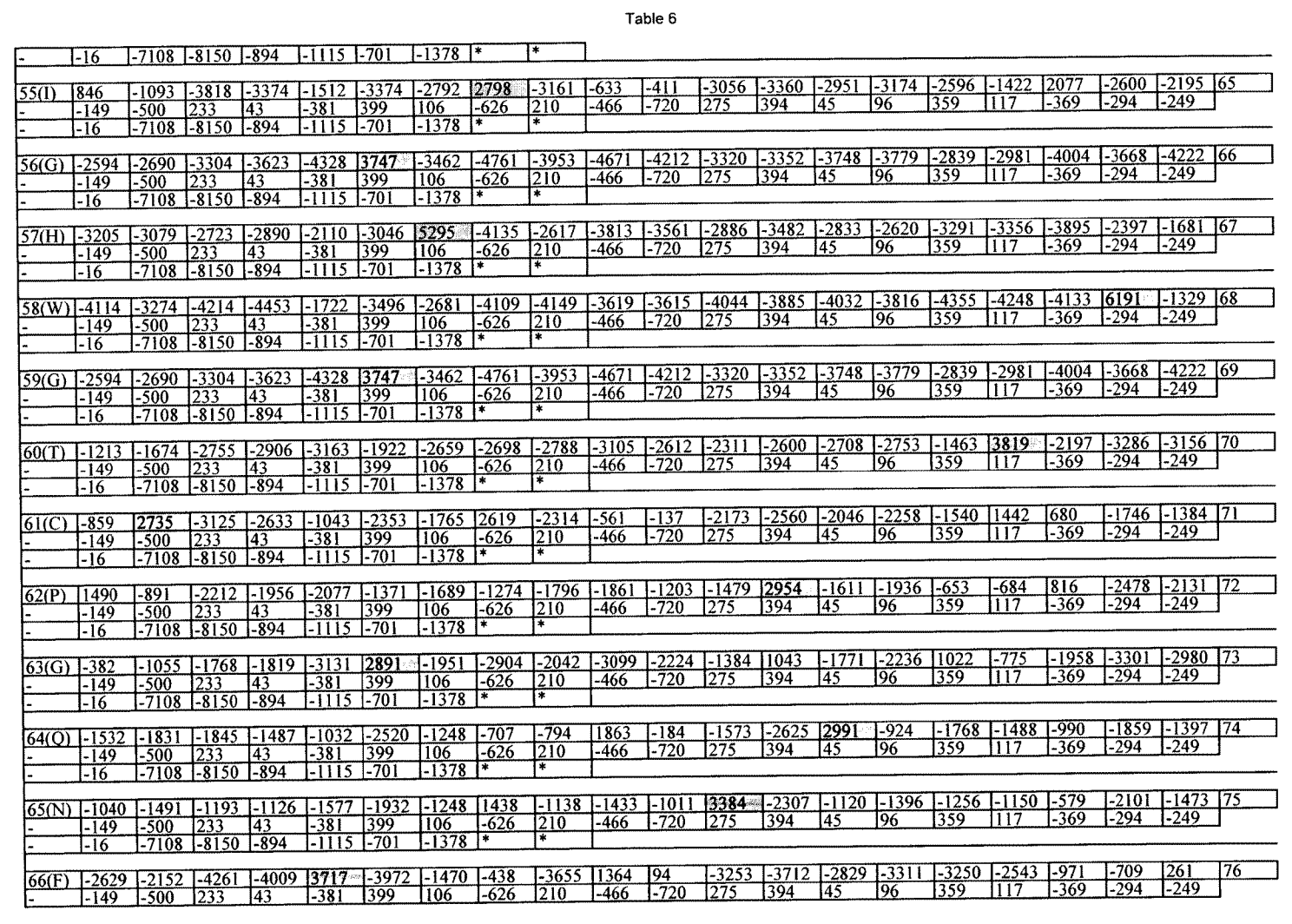
Figure 8K:
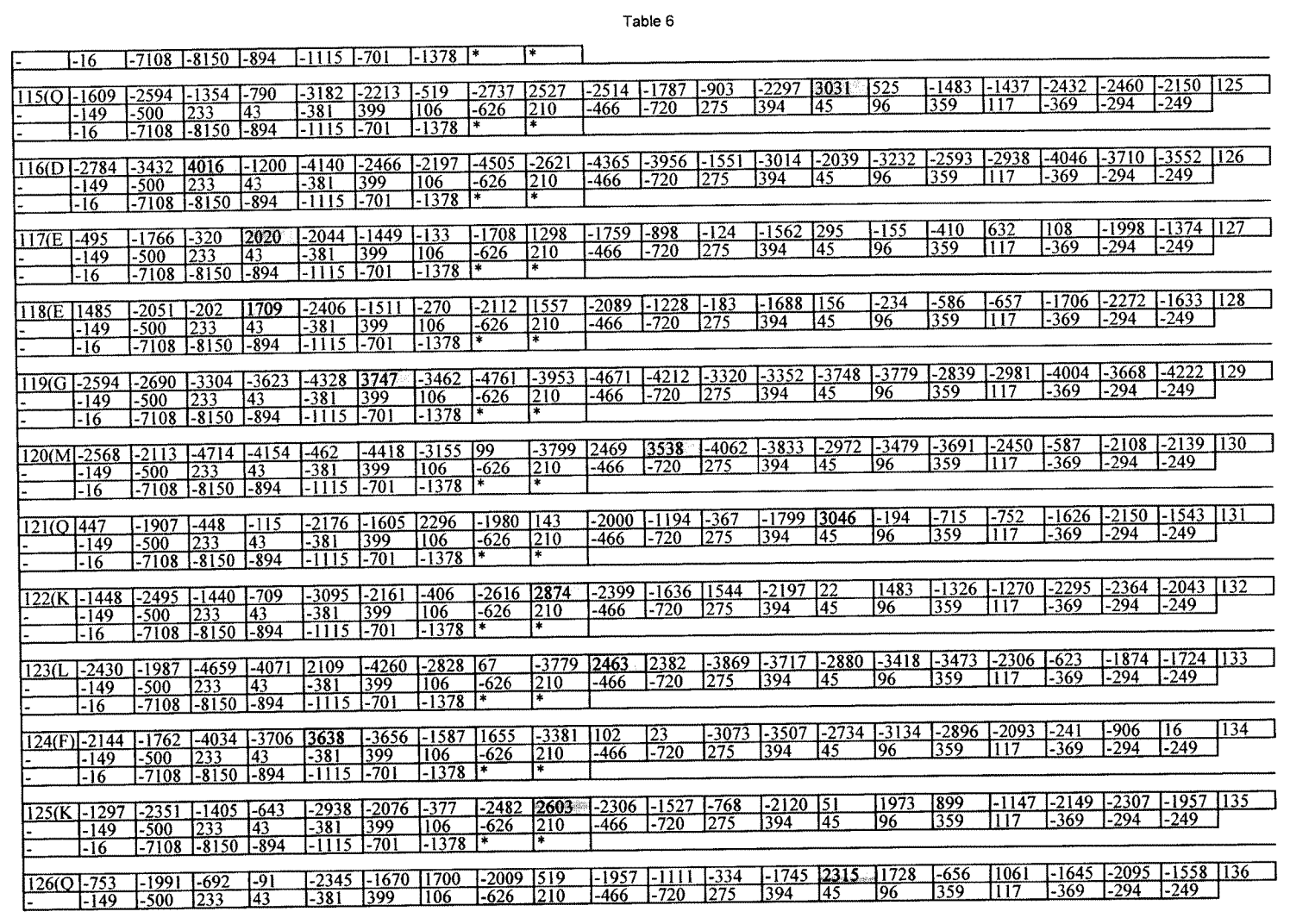
Figure 8W:
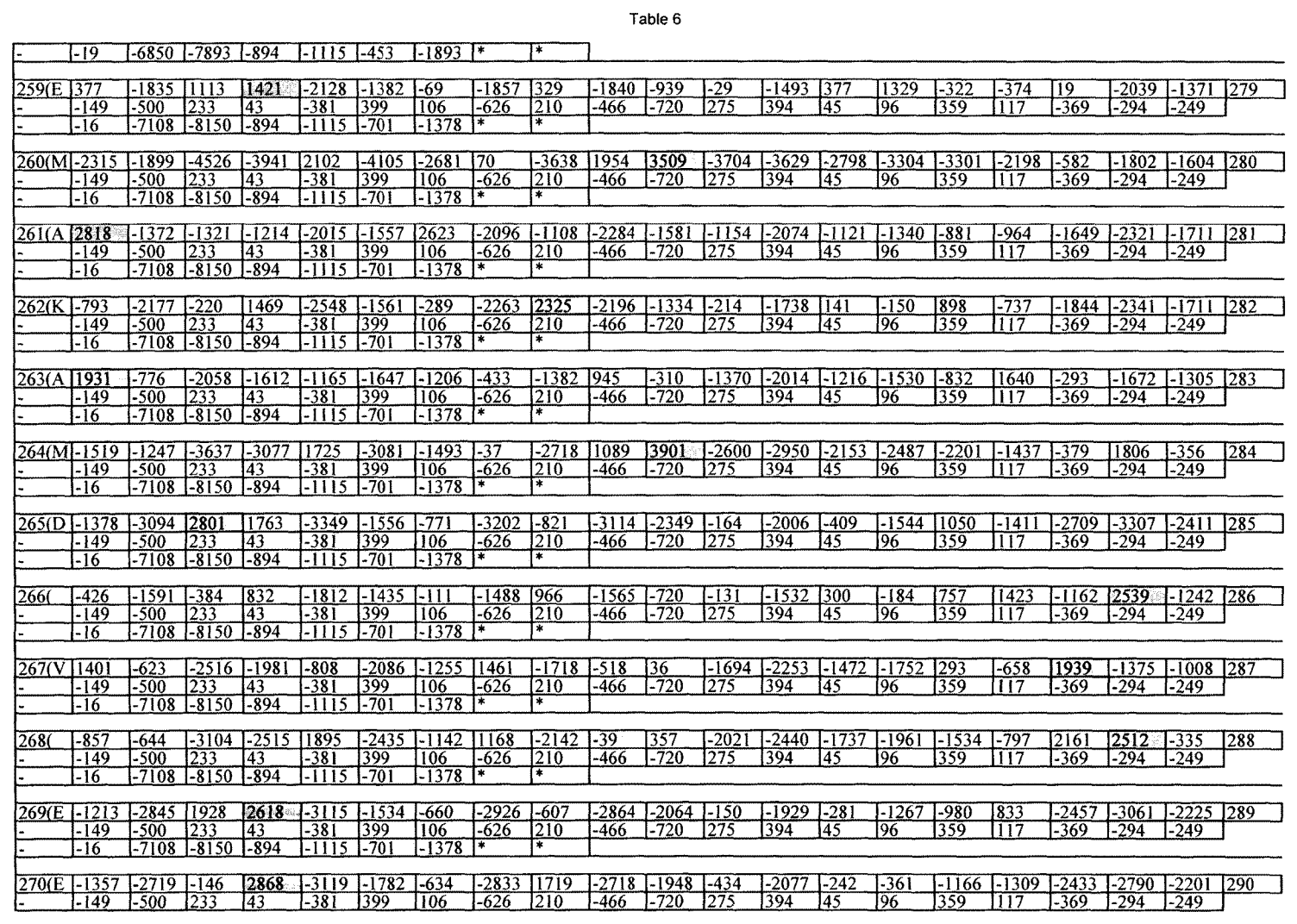
Figure 8X:
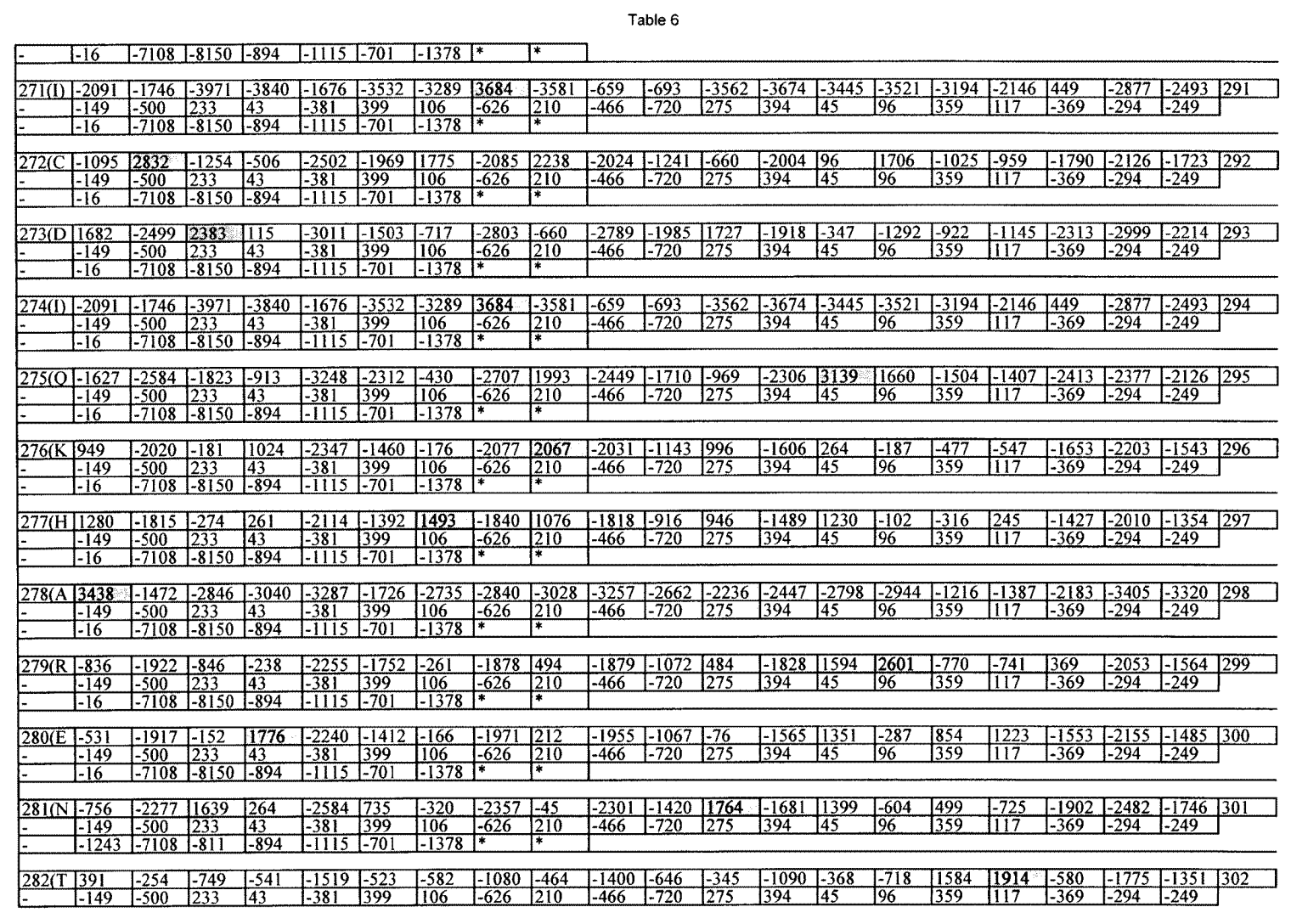
Figure 8:
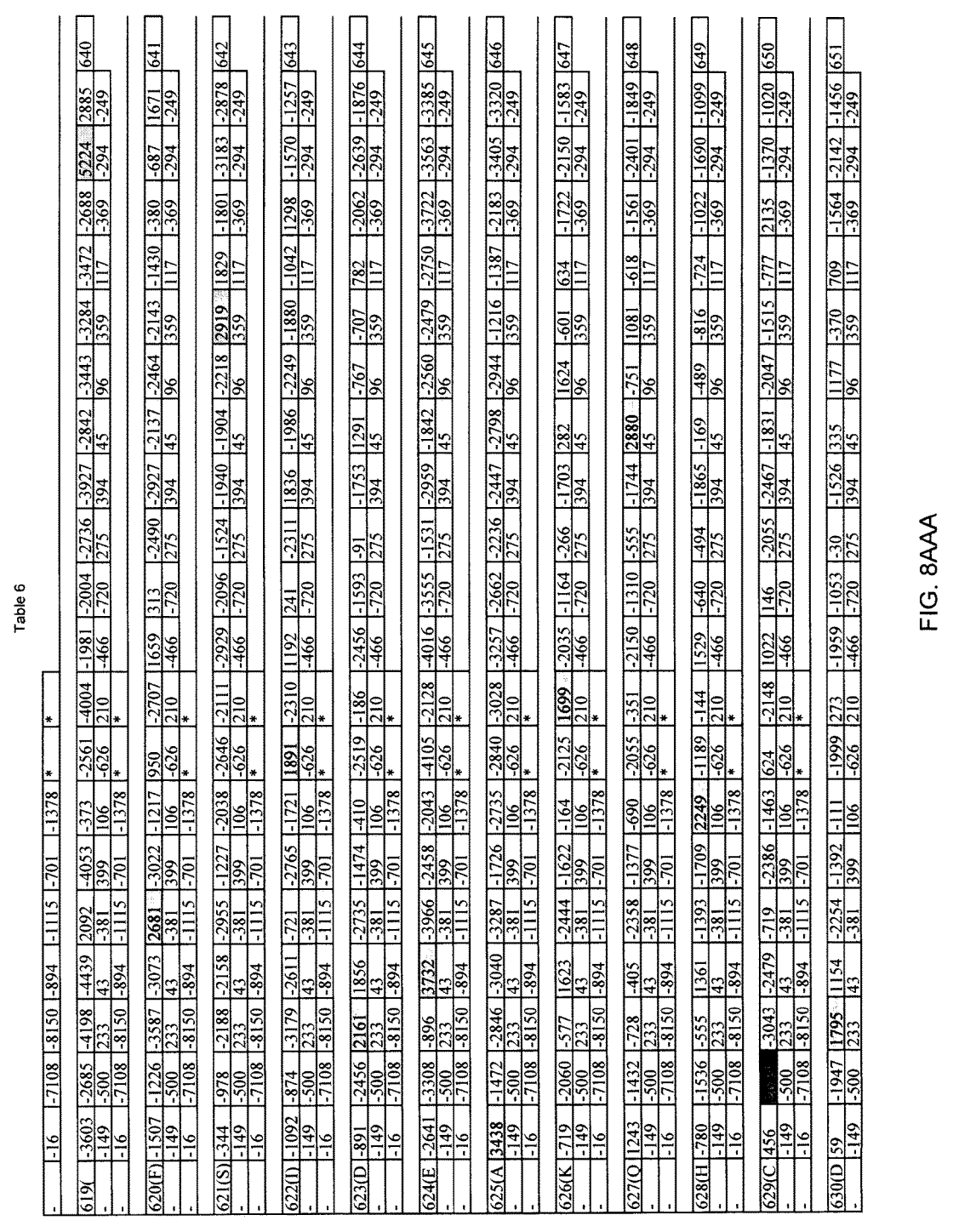
Figure 8:
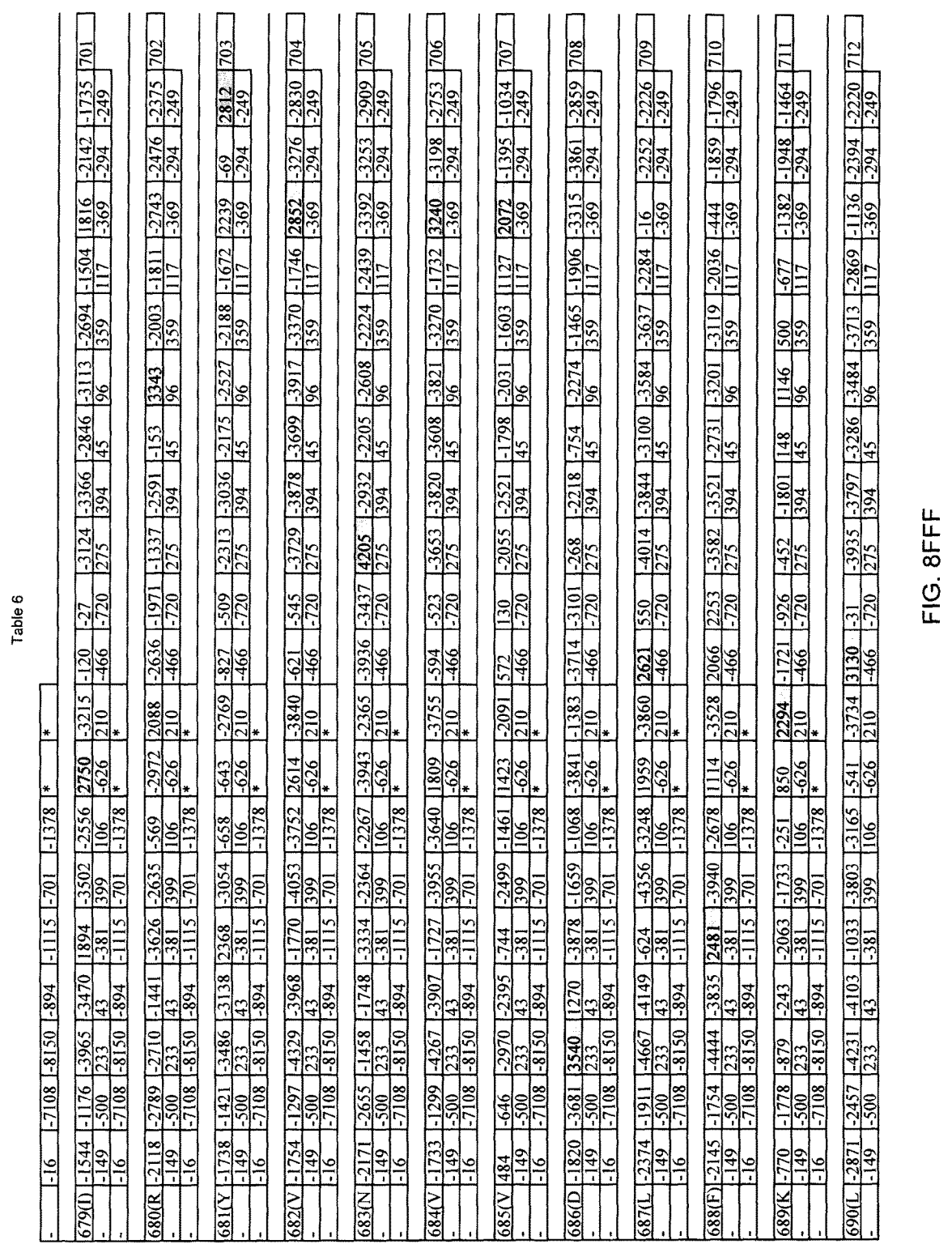
Figure 8:
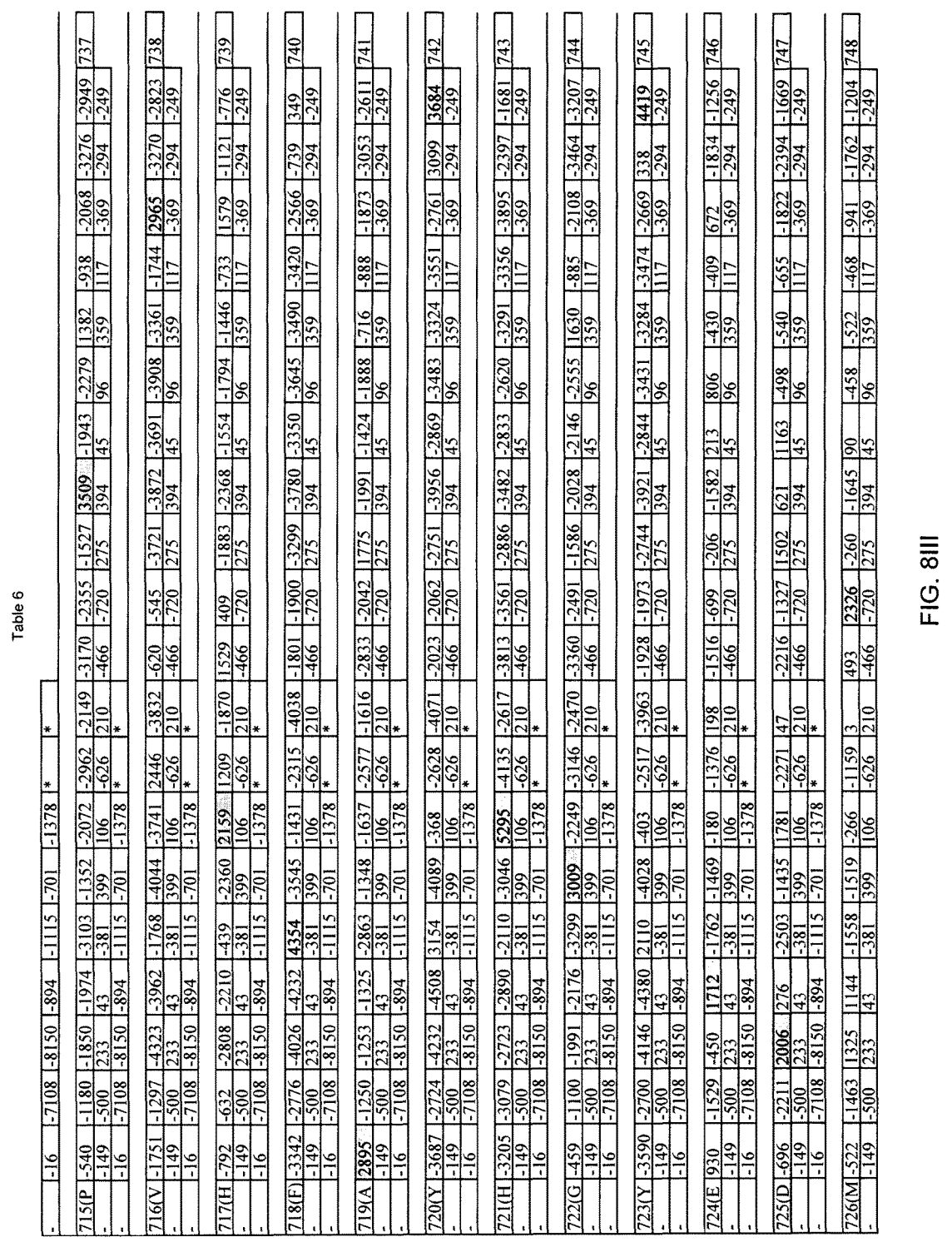
Figure 8:
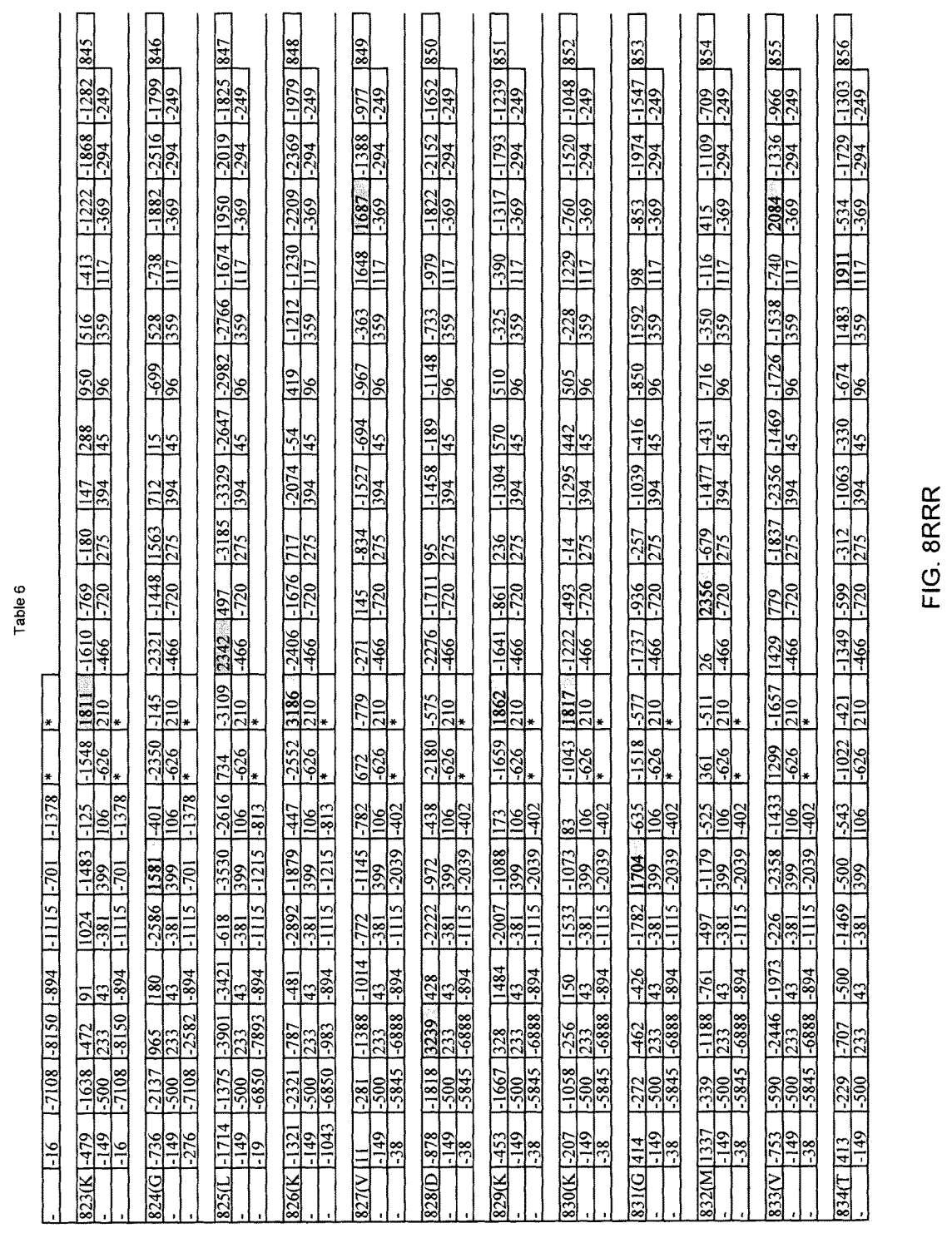

FIG. 8A to FIG. 8SSS depicts Table 6. Table 6 is a table of the Profile Hidden Markov Model (HMM) for phosphoketolases.

Figure 9H:
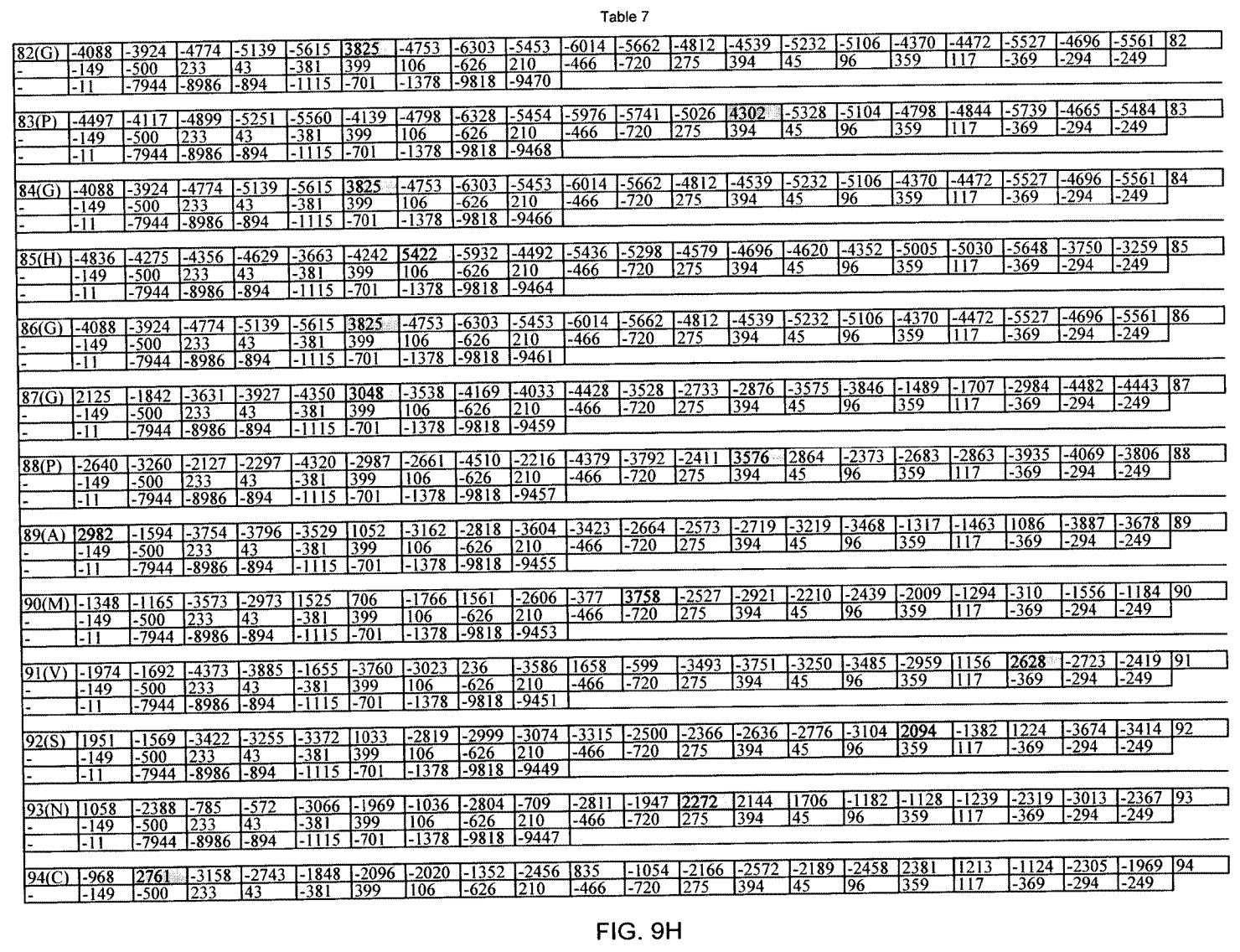

FIG. 9A to FIG. 9GG depicts Table 7. Table 7 is a table of the Profile HMM for phosphoketolase domain XFP_N.

Figure 10D:
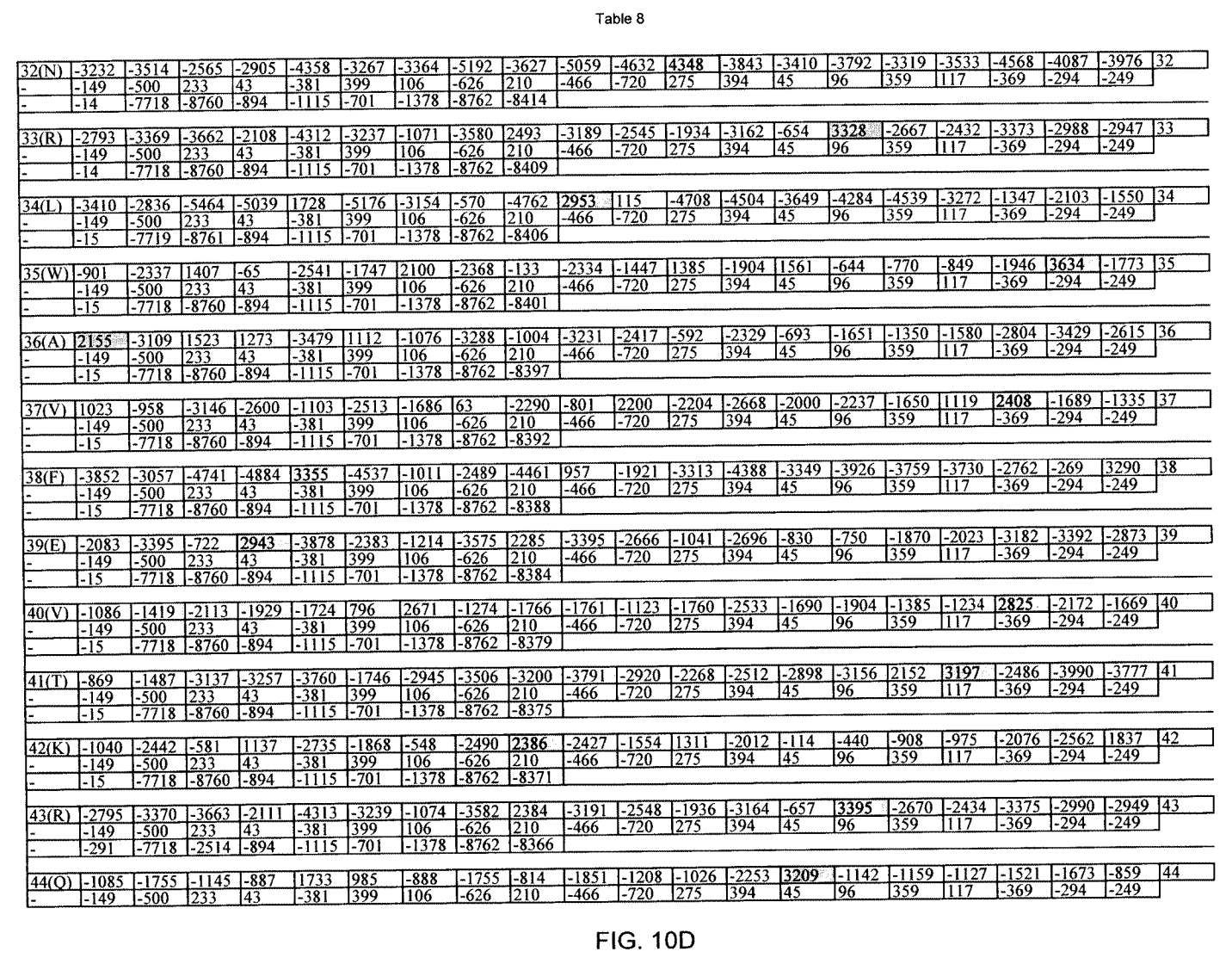

FIG. 10A to FIG. 10P depicts Table 8. Table 8 is a table of the Profile HMM for phosphoketolase domain XFP.

Figure 11B:
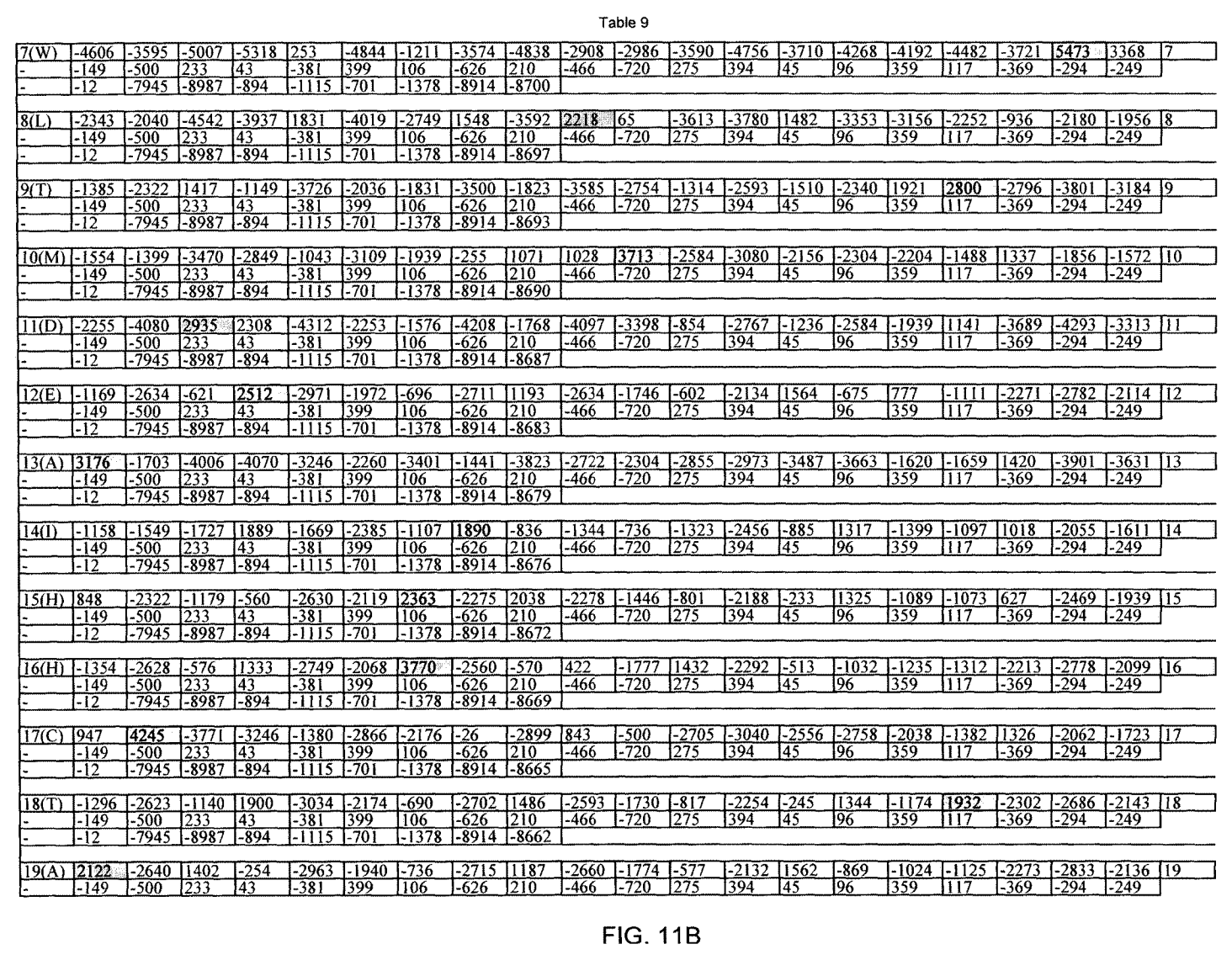
Figure 11G:
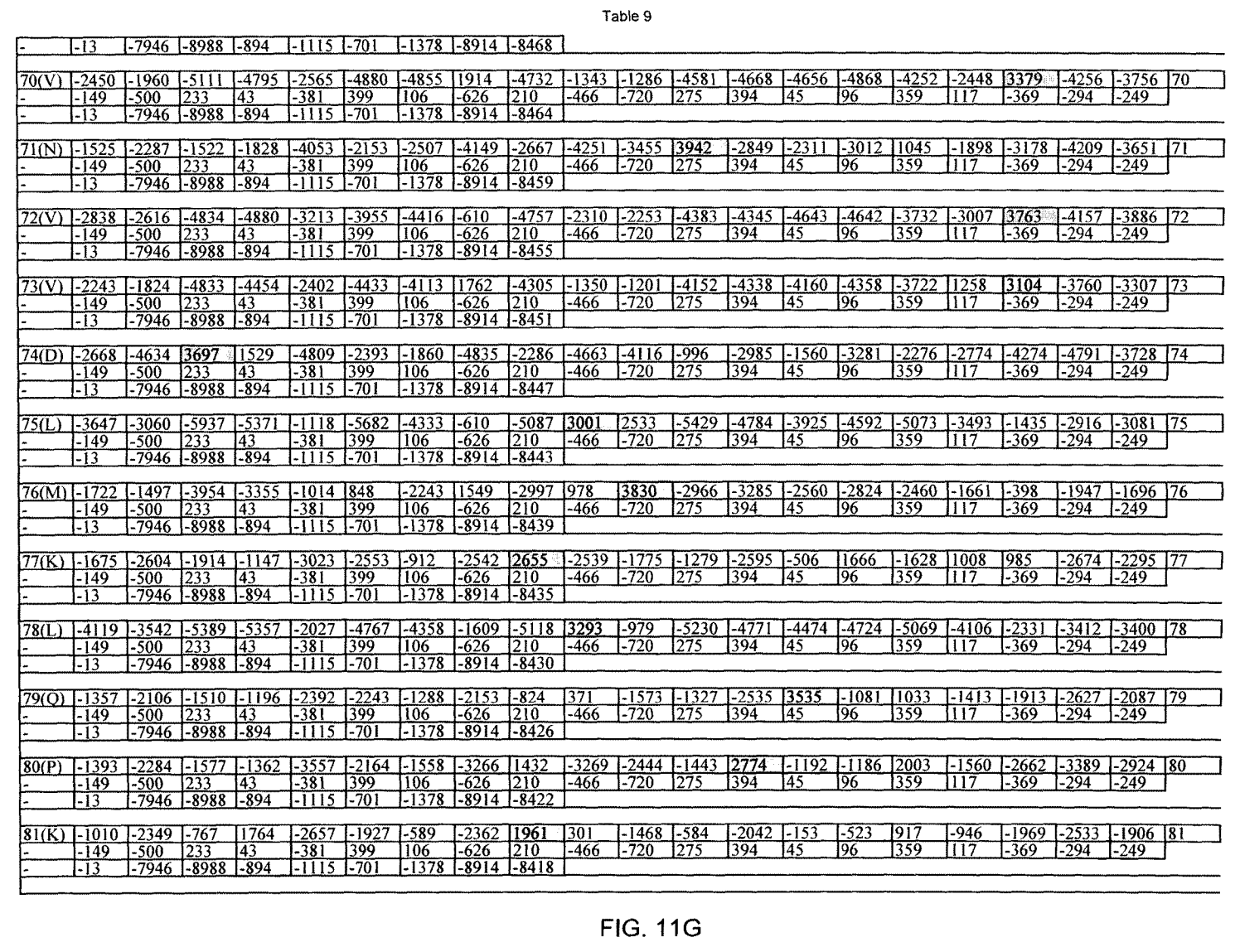

FIG. 11A to FIG. 11R depicts Table 9. Table 9 is a table of the Profile HMM for phosphoketolase domain XFP_C.

Figure 12H:
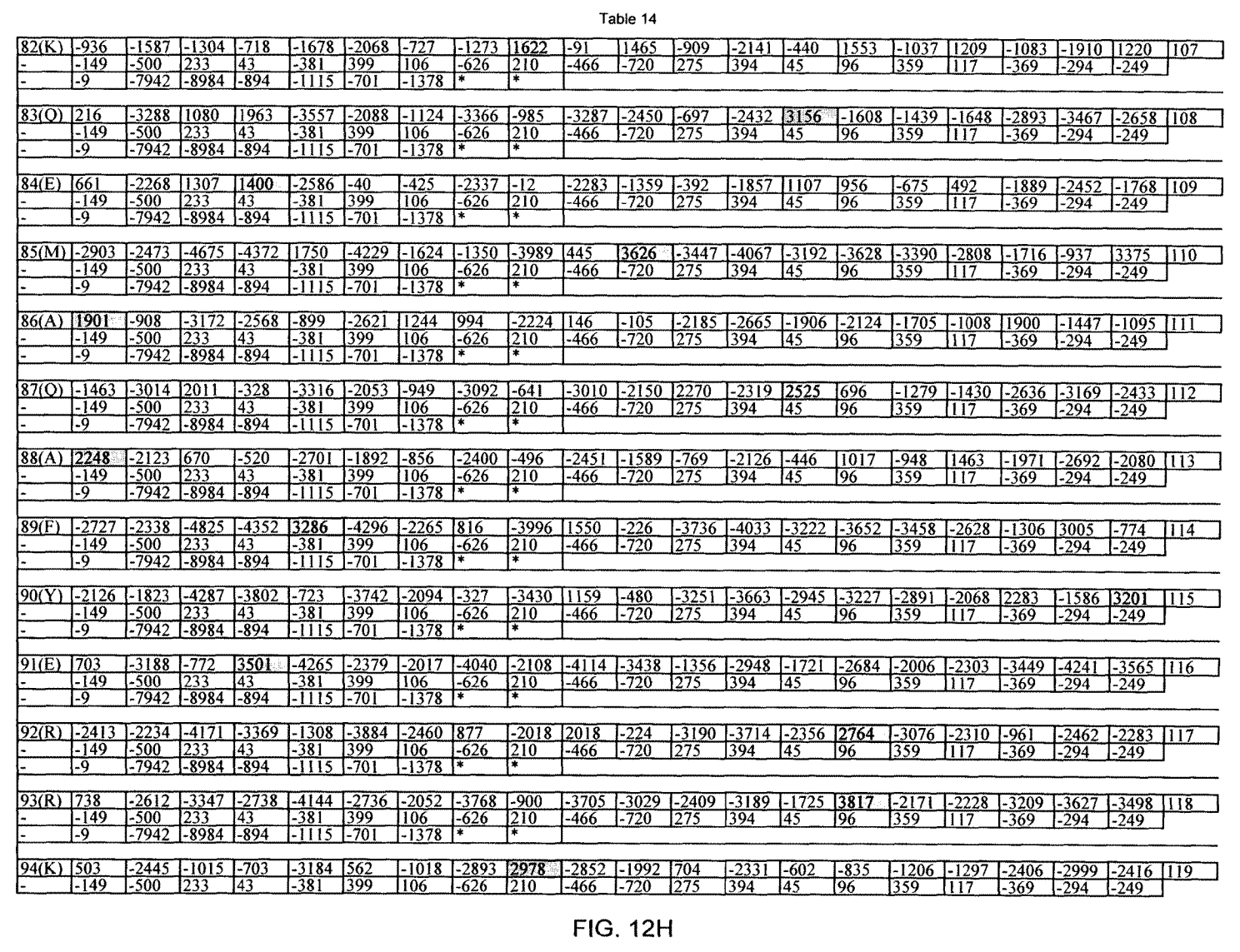
Figure 12K:
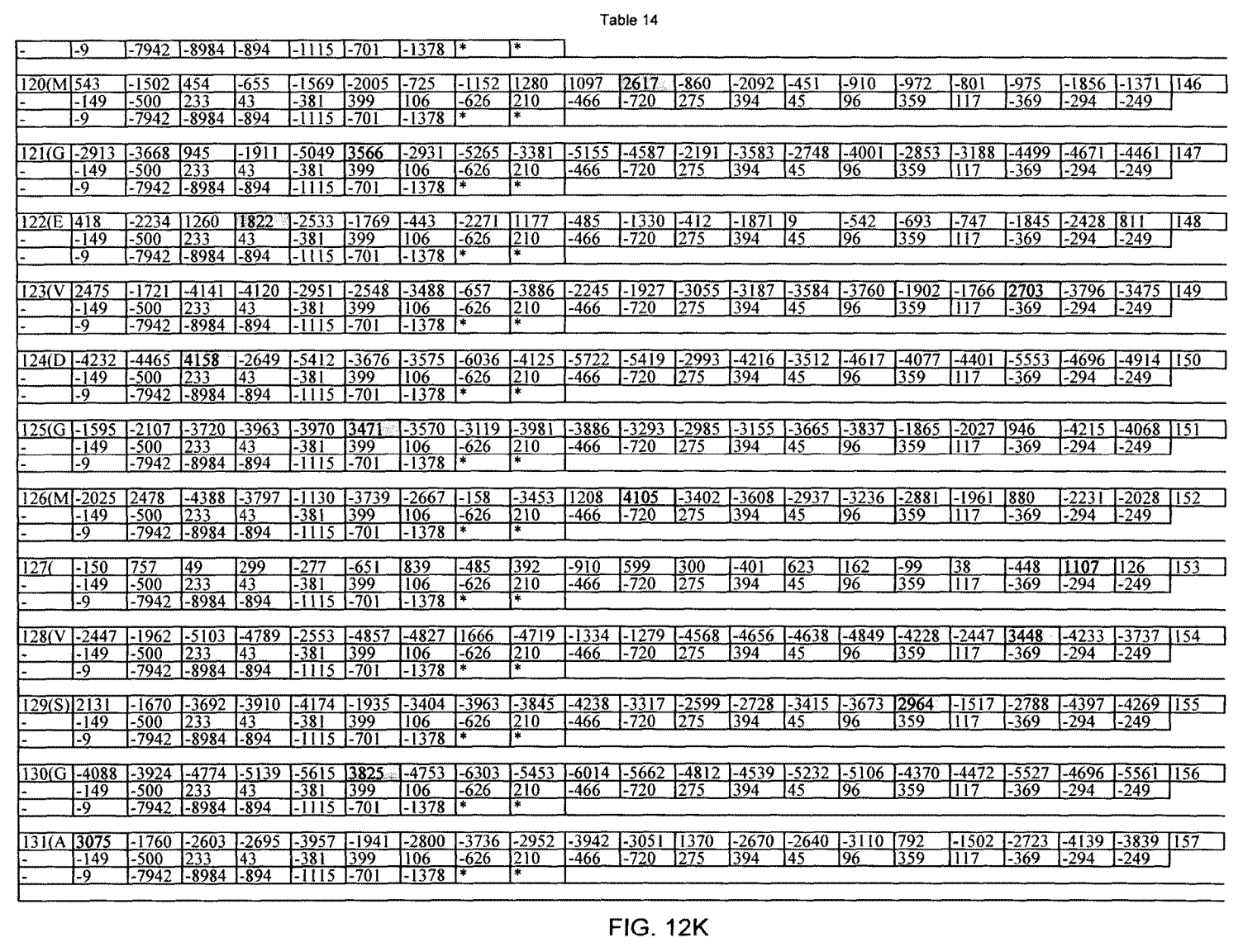
Figure 12T:
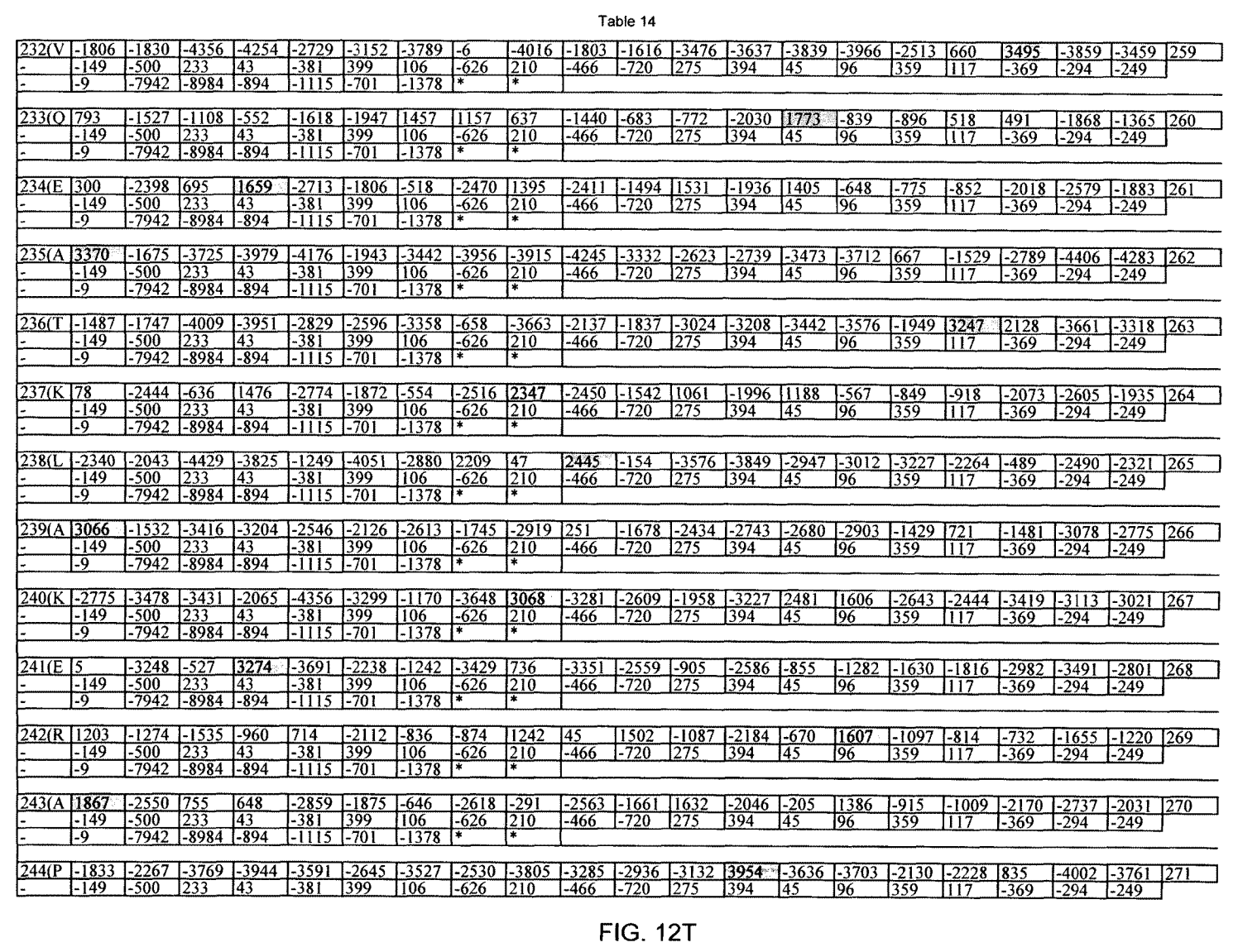

FIG. 12A to FIG. 12CC depicts Table 14. Table 14 is a table of the Profile HMM for phosphotransacetylases.

The invention can be more fully understood from the following detailed description and the accompanying sequence descriptions which form a part of this application.

The sequence listing provided herewith is herein incorporated by reference and conforms with 37 C.F.R. 1.821-1.825 ("Requirements for Patent Applications Containing Nucleotide Sequences and/or Amino Acid Sequence Disclosures—the Sequence Rules") and is consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. § 1.822. The content of the electronically submitted sequence listing Name: 20110615_CL4871USNA_SeqList.txt; Size: 6.67 MB; and Date of Creation/Modification: Jun. 9, 2011/Jun. 15, 2011 is incorporated herein by reference in its entirety.

SEQ ID NOs: 1-20 are sequences of PDC target gene coding regions and proteins.

SEQ ID NOs: 21-638 are phosphoketolase target gene coding regions and proteins.

SEQ ID NOs: 762-1885 are phosphotransacetylase target gene coding regions and proteins.

SEQ ID NOs: 1893-1897 are hybrid promoter sequences.

SEQ ID NOs: 639-642, 644-654, 656-660, 662-701-714, 725-726, 729-740, 742-748, and 750-761 are primers.

SEQ ID NO: 643 is the vector pRS426::GPD-xpk1+ADH1-eutD.

SEQ ID NO: 655 is the TEF1p-kan-TEF1t gene.

SEQ ID NO: 661 is vector pLA54.

SEQ ID NO: 715 is vector pRS423::pGAL1-cre.

SEQ ID NO: 716 is the vector pLH468-sadB.

SEQ ID NOs: 717 and 718 are the amino acid and nucleic acid sequences for sadB from *Achromobacter xylosoxidans*.

SEQ ID NO: 719 is the kivD coding region from *L. lactis*.

SEQ ID NO: 720 is the plasmid pRS425::GPM-sadB.

SEQ ID NO: 721 is the GPM promoter.

SEQ ID NO: 722 is the ADH1 terminator.

SEQ ID NO: 723 is the GPM-sadB-ADHt segment.

SEQ ID NO: 724 is the pUC19-URA3 plasmid.

SEQ ID NO: 741 is the ilvD-FBA1t segment.

SEQ ID NO: 749 is URA3r2 template DNA.

SEQ ID NO: 1886 is the ilvD coding region from *S. mutans*.

SEQ ID NO: 1888 is vector pLH468.

SEQ ID NO: 1898 is pUC19-URA3::pdc1::GPD-xpk1+ADH1-eutD.

SEQ ID NOs: 1899-1906 are the sequences of modified *S. cerevisiae* loci.

SEQ ID NO: 1907 is the sequence of pLH702.

SEQ ID NO: 1908 is the sequence of pYZ067DkivDDhADH

SEQ ID NO: 1909 is the amino acid sequence of ALD6.

SEQ ID NO: 1910 is the amino acid sequence of K9D3.
SEQ ID NO: 1911 is the amino acid sequence of K9G9.
SEQ ID NO: 1912 is the amino acid sequence of YMR226c.
SEQ ID NOs: 1913 and 1914 are the nucleic acid and amino acid sequences of AFT1.
SEQ ID NOs: 1915 and 1916 are the nucleic acid and amino acid sequences of AFT2.
SEQ ID NOs: 1917 and 1918 are the nucleic acid and amino acid sequences of FRA2.
SEQ ID NOs: 1919 and 1920 are the nucleic acid and amino acid sequences of GRX3.
SEQ ID NOs: 1921 and 1922 are the nucleic acid and amino acid sequences of CCC1.
SEQ ID NO: 1923 is the amino acid sequence of an alcohol dehydrogenase from *Beijerinckia indica*.

DETAILED DESCRIPTION OF THE INVENTION

Applicants have solved the stated problem by reducing or eliminating the need for providing two substrates, one of which is converted to a desired product, the other fully or partly into acetyl-CoA by recombinant host cells requiring such supplementation for growth comprising the expression of enzymes of the phosphoketolase pathway in such cells. One such enzyme, phosphoketolase (Enzyme Commission Number EC 4.1.2.9), catalyzes the conversion of xylulose 5-phosphate into glyceraldehyde 3-phosphate and acetyl-phosphate (Heath et al., *J. Biol. Chem.* 231: 1009-29; 1958). Another such enzyme is phosphotransacetylase (Enzyme Commission Number EC 2.3.1.8) which converts acetyl-phosphate into acetyl-CoA.

Applicants have provided PDC-KO recombinant host cells comprising a heterologous polynucleotide encoding a polypeptide having phosphoketolase activity, and optionally a heterologous polynucleotide encoding a polypeptide having phosphotransacetylase activity. Such cells exhibit a reduced or eliminated requirement for exogenous two-carbon substrate supplementation for their growth compared to PDC-KO cells. Applicants have also provided methods of making and using such recombinant host cells including, for example, methods of increasing cell growth, methods of reducing or eliminating the requirement of an exogenous two-carbon substrate for cell growth, methods of increasing glucose consumption and methods of increasing the production of a product of a pyruvate-utilizing pathway.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 2-butanol, 1-butanol, isobutanol, or mixtures thereof.

The term "pyruvate-utilizing biosynthetic pathway" refers to an enzyme pathway to produce a biosynthetic product from pyruvate.

The term "isobutanol biosynthetic pathway" refers to an enzyme pathway to produce isobutanol from pyruvate.

The term "2-butanol biosynthetic pathway" refers to an enzyme pathway to produce 2-butanol from pyruvate.

The term "2-butanone biosynthetic pathway" refers to an enzyme pathway to produce 2-butanone from pyruvate.

The terms "pdc-," "PDC knock-out," or "PDC-KO" as used herein refer to a cell that has a genetic modification to inactivate or reduce expression of at least one gene encoding pyruvate decarboxylase (PDC) so that the cell substantially or completely lacks pyruvate decarboxylase enzyme activity. If the cell has more than one expressed (active) PDC gene, then each of the active PDC genes may be inactivated or have minimal expression thereby producing a pdc-cell.

The term "carbon substrate" refers to a carbon source capable of being metabolized by the recombinant host cells disclosed herein. Non-limiting examples of carbon substrates are provided herein and include, but are not limited to, monosaccharides, oligosaccharides, polysaccharides, ethanol, lactate, succinate, glycerol, carbon dioxide, methanol, glucose, fructose, sucrose, xylose, arabinose, dextrose, or mixtures thereof.

The term "exogenous two-carbon substrate" refers to the carbon source provided to be metabolized into acetyl-CoA by a host cell that lacks the ability to convert pyruvic acid into acetyl-CoA. The term is used to distinguish from the carbon substrate which is converted into a pyruvate-derived product by a pyruvate-utilizing biosynthetic pathway, herein also referred to as the "pathway substrate" which includes, for example, glucose.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment having dihydroxy-acid dehydratase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA or synthetic DNA.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Endogenous gene" refers to a native gene in its natural location in the genome of an organism. A "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Foreign genes can comprise native genes inserted into a non-native organism, or chimeric genes.

As used herein the term "coding region" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the term "variant" refers to a polypeptide differing from a specifically recited polypeptide of the invention by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

Alternatively, recombinant polynucleotide variants encoding these same or similar polypeptides may be synthesized or selected by making use of the "redundancy" in the genetic code. Various codon substitutions, such as silent changes which produce various restriction sites, may be introduced to optimize cloning into a plasmid or viral vector for expression. Mutations in the polynucleotide sequence may be reflected in the polypeptide or domains of other peptides added to the polypeptide to modify the properties of any part of the polypeptide.

Amino acid "substitutions" may be the result of replacing one amino acid with another amino acid having similar structural and/or chemical properties, i.e., conservative amino acid replacements, or they may be the result of replacing one amino acid with an amino acid having different structural and/or chemical properties, i.e., non-conservative amino acid replacements. "Conservative" amino acid substitutions may be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions may be made by selecting the differences in polarity, charge, solubility, hydrophobicity, hydrophilicity, or the amphipathic nature of any of these amino acids. "Insertions" or "deletions" may be within the range of variation as structurally or functionally tolerated by the recombinant proteins. The variation allowed may be experimentally determined by systematically making insertions, deletions, or substitutions of amino acids in a polypeptide molecule using recombinant DNA techniques and assaying the resulting recombinant variants for activity.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths may have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

The term "overexpression," as used herein, refers to expression that is higher than endogenous expression of the same or related gene. A heterologous gene is overexpressed if its expression is higher than that of a comparable endogenous gene.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe(F)<br>TTC "<br>TTA Leu (L)<br>TTG " | TCT Ser (S)<br>TCC "<br>TCA "<br>TCG " | TAT Tyr (Y)<br>TAC "<br>TAA Stop<br>TAG Stop | TGT Cys(C)<br>TGC "<br>TGA Stop<br>TGG Trp(W) |
| C | CTT Leu(L)<br>CTC "<br>CTA "<br>CTG " | CCT Pro (P)<br>CCC "<br>CCA "<br>CCG " | CAT His(H)<br>CAC "<br>CAA Gln(Q)<br>CAG " | CGT Arg(R)<br>CGC "<br>CGA "<br>CGG " |
| A | ATT Ile(I)<br>ATC "<br>ATA "<br>ATG Met (M) | ACT Thr(T)<br>ACC "<br>ACA "<br>ACG " | ATT Asn(N)<br>AAC "<br>AAA Lys(K)<br>AAG " | AGT Ser(S)<br>AGC "<br>AGA Arg(R)<br>AGG " |
| G | GTT Val(V)<br>GTC "<br>GTA "<br>GTG " | GCT ALA(A)<br>GCC "<br>GCA "<br>GCG " | GAT Asp(D)<br>GAC "<br>GAA Glu(E)<br>GAG " | GGT Gly(G)<br>GGC "<br>GGA "<br>GGG " |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/(visited Mar. 20, 2008), and these tables can be adapted in a number of ways. See Nakamura, Y., et al. *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. Table 2 has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |

TABLE 2-continued

Codon Usage Table for *Saccharomyces cerevisiae* Genes

| Amino Acid | Codon | Number | Frequency per thousand |
|---|---|---|---|
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, e.g., the "backtranslation" function (Entelechon GmbH, Regensburg, Germany) and the "backtranseq" function (NRC Saskatoon Bioinformatics, Saskatoon, Saskatchewan, Canada). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (University of Maryland, Baltimore, Md.).

A polynucleotide or nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art.

The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, such as from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning. A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in Methods in Enzymology, Volume 194, *Guide to Yeast Genetics and Molecular and Cell Biology* (Part A, 2004, Christine Guthrie and Gerald R. Fink (Eds.), Elsevier Academic Press, San Diego, Calif.). Other molecular tools and techniques are known in the art and include splicing by overlapping extension polymerase chain reaction (PCR) (Yu, et al. (2004) Fungal Genet. Biol. 41:973-981), positive selection for mutations at the URA3 locus of *Saccharomyces cerevisiae* (Boeke, J. D. et al. (1984) Mol. Gen. Genet. 197, 345-346; M A Romanos, et al. Nucleic Acids Res. 1991 Jan. 11; 19(1): 187), the cre-lox site-specific recombination system as well as mutant lox sites and FLP substrate mutations (Sauer, B. (1987) Mol Cell Biol 7: 2087-2096; Senecoff, et al. (1988) Journal of Molecular Biology, Volume 201, Issue 2, Pages 405-421; Albert, et al. (1995) The Plant Journal. Volume 7, Issue 4, pages 649-659), "seamless" gene deletion (Akada, et al. (2006) Yeast; 23(5):399-405), and gap repair methodology (Ma et al., *Genetics* 58:201-216; 1981). Applicants have discovered that activation of the phosphoketolase pathway in a recombinant host cell comprising a modification in an endogenous gene encoding a polypeptide having pyruvate decarboxylase activity or a modification in an endogenous polypeptide having pyruvate decarboxylase activity, reduces or eliminates the need for an exogenous carbon substrate for the growth of such a cell. In embodiments, the recombinant host cells comprise (i) at least one deletion, mutation and/or substitution in an endogenous gene encoding a polypeptide having pyruvate decarboxylase activity); (ii) a heterologous polynucleotide encoding a polypeptide having phosphoketolase activity; and optionally (iii) a heterologous polynucleotide encoding a polypeptide having phosphotransacetylase activity.

The genetic manipulations of the host cells described herein can be performed using standard genetic techniques and screening and can be made in any host cell that is suitable to genetic manipulation (*Methods in Yeast Genetics*, 2005, Cold Spring Harbor Laboratory Press, Cold Spring Harbor, N.Y., pp. 201-202). In embodiments, the recombinant host cells disclosed herein can be any bacteria, yeast or fungi host useful for genetic modification and recombinant gene expression. In other embodiments, a recombinant host cell can be a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia,* or *Saccharomyces*. In other embodiments, the host cell can be *Saccharomyces cerevisiae, Schizosaccharomyces pombe, Kluyveromyces lactis, Kluyveromyces thermotolerans, Kluyveromyces marxianus, Candida glabrata, Candida albicans, Pichia stipitis, Yarrowia lipolytica, E. coli,* or *L. plantarum*. In still other embodiments, the host cell is a yeast host cell. In some embodiments, the host cell is a member of the genera *Saccharomyces*. In some embodiments, the host cell is *Kluyveromyces lactis, Candida glabrata* or *Schizosaccharomyces pombe*. In some embodiments, the host cell is *Saccharomyces cerevisiae*. *S. cerevisiae* yeast are known in the art and are available from a variety of sources, including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

Sources of Acetyl-CoA

Acetyl-CoA is a major cellular building block, required for the synthesis of fatty acids, sterols, and lysine. Pyruvate is often a major contributor to the acetyl-CoA pool. Pyruvate dehydrogenase catalyzes the direct conversion of pyruvate to acetyl-CoA (E.C. 1.2.4.1, E.C. 1.2.1.51) or acetate (E.C. 1.2.2.2) and is almost ubiquitous in nature. Other enzymes involved in conversion of pyruvate to acetyl-CoA, acetyl-phosphate or acetate include pyruvate-formate lyase (E.C. 2.3.1.54), pyruvate oxidase (E.C. 1.2.3.3, E.C. 1.2.3.6), pyruvate-ferredoxin oxidoreductase (E.C. 1.2.7.1), and pyruvate decarboxylase (E.C. 4.1.1.1). Genetic modifications made to a host cell to conserve the pyruvate pool for a product of interest may include those that restrict conversion to acetyl-CoA, leading to decreased growth in the absence of an exogenously supplied two-carbon substrate, a carbon substrate that can be readily converted to acetyl-CoA independent of pyruvate (e.g. ethanol or acetate). An example is the documented auxotrophy observed in pyruvate decarboxylase deficient *Saccharomyces cerevisiae* (Flikweert et al. 1999, supra). Another example is the documented auxotrophy observed in pyruvate dehydrogenase deficient *Escherichia coli* when grown aerobically on glucose (Langley and Guest, 1977, J. Gen. Microbiol. 99:2630276).

Modification of Pyruvate Decarboxylase

In embodiments, the recombinant host cells disclosed herein comprise a modification in an endogenous polynucleotide encoding a polypeptide having pyruvate decarboxylase (PDC) or a modification in an endogenous polypeptide having PDC activity. In embodiments, the recombinant host cells disclosed herein can have a modification or disruption of one or more polynucleotides, genes or polypeptides encoding PDC. In embodiments, the recombinant host cell comprises at least one deletion, mutation, and/or substitution in one or more endogenous polynucleotides or genes encoding a polypeptide having PDC activity, or in one or more endogenous polypeptides having PDC activity. Such modifications, disruptions, deletions, mutations, and/or substitu- Hohmann (*Mol. Gen. Genet.* (1993) 241:657-666). *Saccharomyces* strains having no pyruvate decarboxylase activity are available from the ATCC with Accession #200027 and #200028.

Examples of PDC polynucleotides, genes and polypeptides that can be targeted for modification or inactivation in the recombinant host cells disclosed herein include, but are not limited to, those of the following table.

TABLE 3

SEQ ID NOs of pyruvate decarboxylase (PDC) target gene coding regions and proteins.

| Description | SEQ ID NO: Nucleic acid | SEQ ID NO: Amino acid |
| --- | --- | --- |
| PDC1 pyruvate decarboxylase from *Saccharomyces cerevisiae* | 1 | 2 |
| PDC5 pyruvate decarboxylase from *Saccharomyces cerevisiae* | 3 | 4 |
| PDC6 pyruvate decarboxylase from *Saccharomyces cerevisiae* | 5 | 6 |
| pyruvate decarboxylase from *Candida glabrata* | 7 | 8 |
| PDC1 pyruvate decarboxylase from *Pichia stipitis* | 9 | 10 |
| PDC2 pyruvate decarboxylase from *Pichia stipitis* | 11 | 12 |
| pyruvate decarboxylase from *Kluyveromyces lactis* | 13 | 14 |
| pyruvate decarboxylase from *Yarrowia lipolytica* | 15 | 16 |
| pyruvate decarboxylase from *Schizosaccharomyces pombe* | 17 | 18 |
| pyruvate decarboxylase from *Zygosaccharomyces rouxii* | 18 | 20 | tions can result in PDC activity that is reduced or eliminated, resulting in a PDC knock-out (PDC-KO) phenotype.

In embodiments, the endogenous pyruvate decarboxylase activity of the recombinant host cells disclosed herein converts pyruvate to acetaldehyde, which can then be converted to ethanol or to acetyl-CoA via acetate.

In embodiments, the recombinant host cell is *Kluyveromyces lactis* containing one gene encoding pyruvate decarboxylase, *Candida glabrata* containing one gene encoding pyruvate decarboxylase, or *Schizosaccharomyces pombe* containing one gene encoding pyruvate decarboxylase.

In other embodiments, the recombinant host cell is *Saccharomyces cerevisiae* containing three isozymes of pyruvate decarboxylase encoded by the pdc1, pdc5, and pdc6 genes, as well as a pyruvate decarboxylase regulatory gene, pdc2. In a non-limiting example in *S. cerevisiae*, the pdc1 and pdc5 genes, or all three genes, are disrupted. In another non-limiting example in *S. cerevisiae*, pyruvate decarboxylase activity may be reduced by disrupting the pdc2 regulatory gene. In another non-limiting example in *S. cerevisiae*, polynucleotides or genes encoding pyruvate decarboxylase proteins such as those having about 70% to about 75%, about 75% to about 80%, about 80% to about 85%, about 85% to about 90%, about 90% to about 95%, about 96%, about 97%, about 98%, or about 99% sequence identity to pdc1 or pdc5 can be disrupted.

In embodiments, the polypeptide having PDC activity or the polynucleotide or gene encoding a polypeptide having PDC activity is associated with Enzyme Commission Number EC 4.1.1.1. In other embodiments, a PDC gene of the recombinant host cells disclosed herein is not active under the fermentation conditions used, and therefore such a gene would not need to be modified or inactivated.

Examples of recombinant host cells with reduced pyruvate decarboxylase activity due to disruption of pyruvate decarboxylase encoding genes have been reported, such as for *Saccharomyces* in Flikweert et al. (*Yeast* (1996) 12:247-257), for *Kluyveromyces* in Bianchi et al. (*Mol. Microbiol.* (1996) 19(1):27-36), and disruption of the regulatory gene in Other examples of PDC polynucleotides, genes and polypeptides that can be targeted for modification or inactivation in the recombinant host cells disclosed herein include, but are not limited to, PDC polynucleotides, genes and/or polypeptides having at least about 70% to about 75%, about 75% to about 80%, about 80% to about 85%, about 85% to about 90%, about 90% to about 95%, about 96%, about 97%, about 98%, or about 99% sequence identity to any one of the sequences of Table 3.

In embodiments, the sequences of other PDC polynucleotides, genes and/or polypeptides can be identified in the literature and in bioinformatics databases well known to the skilled person using sequences disclosed herein and available in the art. For example, such sequences can be identified through BLAST (as described above) searching of publicly available databases with known PDC encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, the PDC polynucleotide or polypeptide sequences described herein or known the art can be used to identify other PDC homologs in nature. For example, each of the PDC encoding nucleic acid fragments described herein can be used to isolate genes encoding homologous proteins. Isolation of homologous genes using sequence-dependent protocols is well known in the art. Examples of sequence-dependent protocols include, but are not limited to (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker et al., *Proc. Natl. Acad. Sci. U.S.A.,* 89:392 (1992)]; and (3) methods of library construction and screening by complementation.

In embodiments, PDC polynucleotides, genes and/or polypeptides related to the recombinant host cells described herein can be modified or disrupted. Many methods for genetic modification and disruption of target genes to reduce or eliminate expression are known to one of ordinary skill in the art and can be used to create the recombinant host cells described herein. Modifications that can be used include, but are not limited to, deletion of the entire gene or a portion of the gene encoding a PDC protein, inserting a DNA fragment into the encoding gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less active protein is expressed. In other embodiments, expression of a target gene can be blocked by expression of an antisense RNA or an interfering RNA, and constructs can be introduced that result in cosuppression. In other embodiments, the synthesis or stability of the transcript can be lessened by mutation. In embodiments, the efficiency by which a protein is translated from mRNA can be modulated by mutation. All of these methods can be readily practiced by one skilled in the art making use of the known or identified sequences encoding target proteins.

In other embodiments, DNA sequences surrounding a target PDC coding sequence are also useful in some modification procedures and are available, for example, for yeasts such as *Saccharomyces cerevisiae* in the complete genome sequence coordinated by Genome Project ID9518 of Genome Projects coordinated by NCBI (National Center for Biotechnology Information) with identifying GOPID #13838. An additional non-limiting example of yeast genomic sequences is that of *Candida albicans*, which is included in GPID #10771, #10701 and #16373. Other yeast genomic sequences can be readily found by one of skill in the art in publicly available databases.

In other embodiments, DNA sequences surrounding a target PDC coding sequence can be useful for modification methods using homologous recombination. In a non-limiting example of this method, PDC gene flanking sequences can be placed bounding a selectable marker gene to mediate homologous recombination whereby the marker gene replaces the PDC gene. In another non-limiting example, partial PDC gene sequences and PDC gene flanking sequences bounding a selectable marker gene can be used to mediate homologous recombination whereby the marker gene replaces a portion of the target PDC gene. In embodiments, the selectable marker can be bounded by site-specific recombination sites, so that following expression of the corresponding site-specific recombinase, the resistance gene is excised from the PDC gene without reactivating the latter. In embodiments, the site-specific recombination leaves behind a recombination site which disrupts expression of the PDC protein. In other embodiments, the homologous recombination vector can be constructed to also leave a deletion in the PDC gene following excision of the selectable marker, as is well known to one skilled in the art.

In other embodiments, deletions can be made to a PDC target gene using mitotic recombination as described in Wach et al. (*Yeast*, 10:1793-1808; 1994). Such a method can involve preparing a DNA fragment that contains a selectable marker between genomic regions that can be as short as 20 bp, and which bound a target DNA sequence. In other embodiments, this DNA fragment can be prepared by PCR amplification of the selectable marker gene using as primers oligonucleotides that hybridize to the ends of the marker gene and that include the genomic regions that can recombine with the yeast genome. In embodiments, the linear DNA fragment can be efficiently transformed into yeast and recombined into the genome resulting in gene replacement including with deletion of the target DNA sequence ((as described, for example, in *Methods in Enzymology*, Volume 194, Guide to Yeast Genetics and Molecular and Cell Biology (Part A, 2004, Christine Guthrie and Gerald R. Fink (Eds.), Elsevier Academic Press, San Diego, Calif.)).

Moreover, promoter replacement methods can be used to exchange the endogenous transcriptional control elements allowing another means to modulate expression such as described in Mnaimneh et al. ((2004) *Cell* 118(1):31-44).

In other embodiments, the PDC target gene encoded activity can be disrupted using random mutagenesis, which can then be followed by screening to identify strains with dependency on carbon substrates for growth. In this type of method, the DNA sequence of the target gene encoding region, or any other region of the genome affecting carbon substrate dependency for growth, need not be known. In embodiments, a screen for cells with reduced PDC activity and/or two-carbon substrate dependency, or other mutants having reduced PDC activity and a reduced or eliminated dependency for exogenous two-carbon substrate for growth, can be useful as recombinant host cells of the invention.

Methods for creating genetic mutations are common and well known in the art and can be applied to the exercise of creating mutants. Commonly used random genetic modification methods (reviewed in *Methods in Yeast Genetics*, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of host cells can involve, but is not limited to, treatment with one of the following DNA mutagens: ethyl methanesulfonate (EMS), nitrous acid, diethyl sulfate, or N-methyl-N'-nitro-N-nitroso-guanidine (MNNG). Such methods of mutagenesis have been reviewed in Spencer et al. (Mutagenesis in Yeast, 1996, *Yeast Protocols: Methods in Cell and Molecular Biology*. Humana Press, Totowa, N.J.). In embodiments, chemical mutagenesis with EMS can be performed as described in *Methods in Yeast Genetics*, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al. (Mutagenesis in Yeast, 1996, *Yeast Protocols: Methods in Cell and Molecular Biology*. Humana Press, Totowa, N.J.). In embodiments, the introduction of a mutator phenotype can also be used to generate random chromosomal mutations in host cells. In embodiments, common mutator phenotypes can be obtained through disruption of one or more of the following genes: PMS1, MAG1, RAD18 or RAD51. In other embodiments, restoration of the non-mutator phenotype can be obtained by insertion of the wildtype allele. In other embodiments, collections of modified cells produced from any of these or other known random mutagenesis processes may be screened for reduced or eliminated PDC activity.

Genomes have been completely sequenced and annotated and are publicly available for the following yeast strains: *Ashbya gossypii* ATCC 10895, *Candida glabrata* CBS 138, *Kluyveromyces lactis* NRRL Y-1140, *Pichia stipitis* CBS 6054, *Saccharomyces cerevisiae* S288c, *Schizosaccharomyces pombe* 972h-, and *Yarrowia lipolytica* CLIB122. Typically BLAST (described above) searching of publicly available databases with known PDC polynucleotide or polypeptide sequences, such as those provided herein, is used to identify PDC-encoding sequences of other host cells, such as yeast cells.

Accordingly, it is within the scope of the invention to provide pyruvate decarboxylase polynucleotides and polypeptides having at least about 70% to about 75%, about 75% to about 80%, about 80% to about 85%, about 85% to about 90%, about 90% to about 95%, about 96%, about 97%, about 98%, or about 99% sequence identity to any of the PDC polypeptides or polypeptides disclosed herein (SEQ ID NOs: 1-20). Identities are based on the Clustal W method of alignment using the default parameters of GAP PENALTY=10, GAP LENGTH PENALTY=0.1, and Gonnet 250 series of protein weight matrix.

The modification of PDC in the host cells disclosed herein to reduce or eliminate PDC activity can be confirmed using methods known in the art. For example, PCR methods well known in the art can be used to confirm deletion of PDC. Other suitable methods will be known to those of skill in the art and include, but are not limited to, lack of growth on yeast extract peptone-dextrose medium (YPD).

Introduction of the Phosphoketolase Pathway

Applicants have found that expression of enzymes associated with the phosphoketolase pathway (e.g., phosphoketolase and/or phosphotransacetylase) results in a reduced or eliminated requirement for exogenous two-carbon substrate supplementation for growth of PDC-KO cells. Phosphoketolases and/or phosphotransacetylases identified as described herein, can be expressed in such cells using methods described herein.

Figure 1:
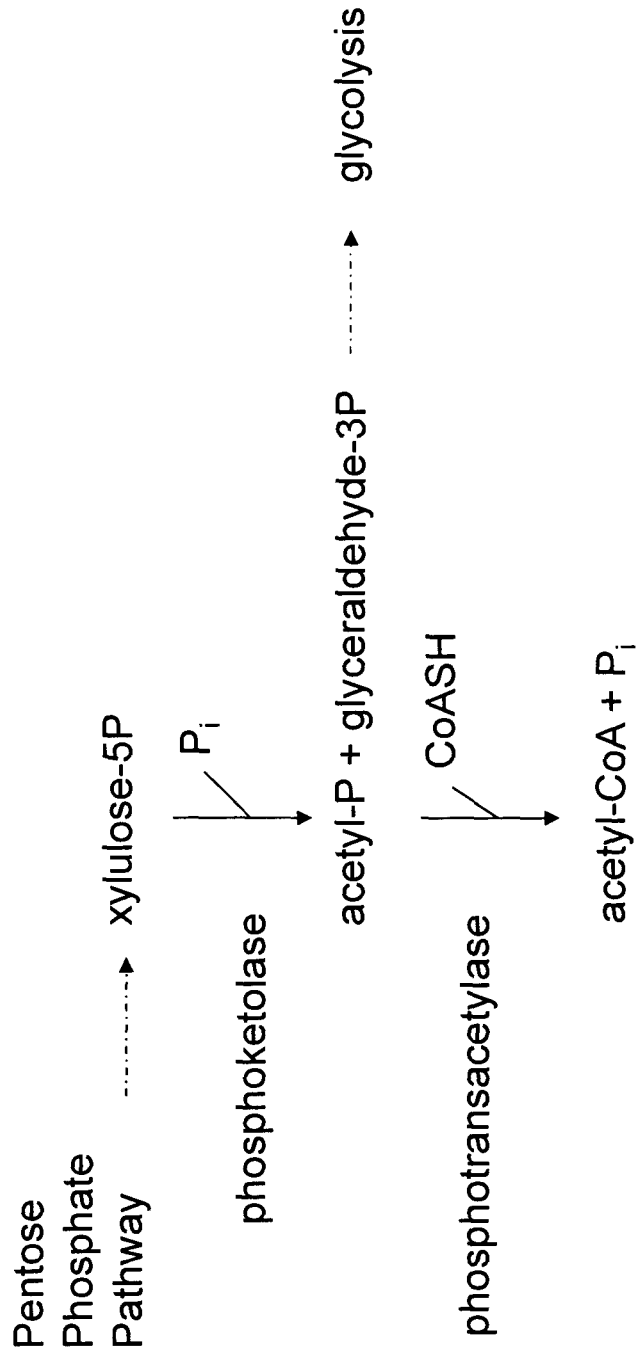
FIG. 1 depicts a schematic representation of the phosphoketolase pathway, including the phosphoketolase and phosphotransacetylase enzymes.

Enzymes of the phosphoketolase pathway include phosphoketolase and phosphotransacetylase (FIG. 1). Phosphoketolase (Enzyme Commission Number EC 4.1.2.9) catalyzes the conversion of xylulose 5-phosphate into glyceraldehyde 3-phosphate and acetyl-phosphate (Heath et al., *J. Biol. Chem.* 231: 1009-29; 1958). Phosphoketolase activity has been identified in several yeast strains growing with xylose as the sole carbon source but not in yeast strains grown with glucose (Evans and Ratledge, *Arch. Microbiol.* 139: 48-52; 1984). Inhibitors of phosphoketolase include, but are not limited to, erythrose 4-phosphate and glyceraldehyde 3-phosphate. Phosphotransacetylase (Enzyme Commission Number EC 2.3.1.8) converts acetyl-phosphate into acetyl-CoA.

In embodiments, the phosphoketolase pathway is activated in the recombinant host cells disclosed herein by engineering the cells to express polynucleotides and/or polypeptides encoding phosphoketolase and, optionally, phosphotransacetylase. In embodiments, the recombinant host cells disclosed herein comprise a heterologous polynucleotide encoding a polypeptide having phosphoketolase activity. In other embodiments, the recombinant host cells disclosed herein comprise a heterologous polynucleotide encoding a polypeptide having phosphoketolase activity and a heterologous polynucleotide encoding a polypeptide having phosphotransacetylase activity. In other embodiments, the heterologous polynucleotide encoding a polypeptide having phosphoketolase activity is overexpressed, or expressed at a level that is higher than endogenous expression of the same or related endogenous gene, if any. In still other embodiments, the heterologous polynucleotide encoding a polypeptide having phosphotransacetylase activity is overexpressed, or expressed at a level that is higher than endogenous expression of the same or related endogenous gene, if any.

In embodiments, a polypeptide having phosphoketolase activity catalyzes the conversion of xylulose 5-phosphate into glyceraldehyde-3-phosphate and acetyl-phosphate and/or the conversion of fructose-6-phosphate into erythrose-4-phosphate and acetyl-phosphate. In embodiments, the activity of a polypeptide having phosphoketolase activity is inhibited by erythrose 4-phosphate and/or glyceraldehyde 3-phosphate. In other embodiments, a polypeptide having phosphotransacetylase activity catalyzes the conversion of acetyl-phosphate into acetyl-CoA.

Numerous examples of polynucleotides, genes and polypeptides encoding phosphoketolase activity are known in the art and can be used in the recombinant host cells disclosed herein. In embodiments, such a polynucleotide, gene and/or polypeptide can be the xylulose 5-phosphateketolase (XpkA) of *Lactobacillus pentosus* MD363 (Posthuma et al., *Appl. Environ. Microbiol.* 68: 831-7; 2002). XpkA is the central enzyme of the phosphoketolase pathway (PKP) in lactic acid bacteria, and exhibits a specific activity of 4.455 µmol/min/mg (Posthuma et al., *Appl. Environ. Microbiol.* 68: 831-7; 2002). In other embodiments, such a polynucleotide, gene and/or polypeptide can be the phosphoketolase of *Leuconostoc mesenteroides* which exhibits a specific activity of 9.9 µmol/min/mg and is stable at pH above 4.5 (Goldberg et al., *Methods Enzymol.* 9: 515-520; 1966). This phosphoketolase exhibits a Km of 4.7 mM for D-xylulose 5-phosphate and a Km of 29 mM for fructose 6-phosphate (Goldberg et al., *Methods Enzymol.* 9: 515-520; 1966). In other embodiments, such a polynucleotide, gene and/or polypeptide can be the D-xylulose 5-phosphate/D-fructose 6-phosphate phosphoketolase gene xfp from *B. lactis*, as described, for example, in a pentose-metabolizing *S. cerevisiae* strain by Sonderegger et al. (*Appl. Environ. Microbiol.* 70: 2892-7; 2004).

In embodiments, a polynucleotide, gene and/or polypeptide encoding phosphoketolase corresponds to the Enzyme Commission Number EC 4.1.2.9.

In embodiments, host cells comprise a polypeptide having at least about 80%, at least about 85%, at least about 90%, or 100% identity to a polypeptide of Table 4 or an active fragment thereof or a polynucleotide encoding such a polypeptide. In other embodiments, a polynucleotide, gene and/or or polypeptide encoding phosphoketolase can include, but is not limited to, a sequence provided in the following tables 4 or 5.

TABLE 4

SEQ ID NOs of phosphoketolase target gene coding regions and proteins

| Description | SEQ ID NO: Nucleic acid | SEQ ID NO: Amino acid | Amino Acid sequence |
|---|---|---|---|
| Xpk1 phosphoketolase from *Lactobacillus plantarum* | 172 | 481 | MTTDYSSPAYLQKVDKYWRAANYLSVGQLYLKDNPLLQRPL KASDVKVHPIGHWGTIAGQ NFIYAHLNRVINKYGLKMFYVEGPGHGGQVMVSNSYLDGTY TDIYPEITQDVEGMQKLFK QFSFPGGVASHAAPETPGSIHEGGELGYSISHGVGAILDNP DEIAAVVVGDGESETGPLA TSWQSTKFINPINDGAVLPILNLNGFKISNPTIFGRTSDAK IKEYFESMNWEPIFVEGDD PEKVHPALAKAMDEAVEKIKAIQKHARENNDATLPVWPMIV FRAPKGWTGPKSWDGDKIE GSFRAHQIPIPVDQNDMEHADALVDWLESYQPKELFNEDGS LKDDIKEIIPTGDSRMAAN PITNGGVDPKALNLPNFRDYAVDTSKEGANVKQDMIVWSDY LRDVIKKNPDNFRLFGPDE TMSNRLYGVFETTNRQWMEDIHPDSDQYEAPAGRVLDAQLS EHQAEGWLEGYVLTGRHGL FASYEAFLRVVDSMLTQHFKWLRKANELDWRKKYPSLNIIA ASTVFQQDHNGYTHQDPGA LTHLAEKKPEYIREYLPADANTLLAVGDVIFRSQEKINYVV TSKHPRQQWFSIEEAKQLV DNGLGIIDWASTDQGSEPDIVFAAAGTEPTLETLAAIQLLH DSFPEMKIRFVNVVDILKL RSPEKDPRGLSDAEFDHYFTKDKPVVFAFHGYEDLVRDIFF DRHNHNLYVHGYRENGDIT TPFDVRVMNQMDRFDLAKSAIAAQPAMENTGAAFVQSMDNM LAKHNAYIRDAGTDLPEVN DWQWKGLK |
| XpkA phosphoketolase from *Lactobacillus pentosus* MD363 | 1890 | 1889 | MSTDYSSPAYLQKVDKYWRAANYLSVGQLYLKDNPLLQRPL KASDVKVHPIGHWGTIAGQ NFIYAHLNRVINKYGLKMFYVEGPGHGGQVMVSNSYLDGTY TDIYPEITQDVEGMQKLFK QFSFPGGVASHAAPETPGSIHEGGELGYSISHGVGAILDNP DEIAAVVVGDGESETGPLA TSWQSTKFINPINDGAVLPILNLNGFKISNPTIFGRTSDEK IKQYFESMNWEPIFVEGDD PEKVHPALAKAMDEAVEKIKAIQKNARENDDATLPVWPMIV FRAPKGWTGPKSWDGDKIE GSFRAHQIP1PVDQTDMEHADALVDWLESYQPKELFNEDGS LKDDIKEIIPTGDARMAAN PITNGGVDPKALNLPNFRDYAVDTSKHGANVKQDMIVWSDY LRDVIKKNPDNFRLFGPDE TMSNRLYGVFETTNRQWMEDIHPDSDQYEAPAGRVLDAQLS EHQAEGWLEGYVLTGRHGL FASYEAFLRVVDSMLTQHFKWLRKANELDWRKKYPSLNIIA ASTVFQQDHNGYTHQDPGA LTHLAEKKPEYIREYLPADANSLLAVGDVIFRSQEKINYVV TSKHPRQQWFSIEEAKQLV DNGLGIIDWASTDQGSEPDIVFAAAGTEPTLETLAAIQLLH DSFPDMKIRFVNVVDILKL RSPEKDPRGLSDAEFDHYFTKDKPVVFAFHGYEDLVRDIFF DRHNHNLHVHGYRENGDIT TPFDVRVMNQMDRFDLAKSAIAAQPAMENTGAAFVQDMDNM LAKHNAYIRDAGTDLPEVN DWQWKGLK |
| Xpf D-xylulose 5-phosphate/D-fructose 6-phosphate phosphoketolase from *B. lactis* | 79 | 388 | MTNPVIGTPWQKLDRPVSEEAIEGMDKYWRVANYMSIGQIY LRSNPLMKEPFTRDDVKHR LVGHWGTTPGLNFLLAHINRLIADHQQNTVFIMGPGHGGPA GTAQSYIDGTYTEYYPNIT KDEAGLQKFFRQFSYPGGIPSHFAPETPGSIHEGGELGYAL SHAYGAIMDNPSLFVPCII GDGEAETGPLATGWQSNKLVNPRTDGIVLPILHLNGYKIAN PTILARISDEELHDFFRGM GYHPYEFVAGFDNEDHLSIHRRFAELFETIFDEICDIKAAA QTDDMTRPFYPMLIFRTPK GWTCPKFIDGKKTEGSWRAHQVPLASARDTEAHFEVLKGWM ESYKPEELFNADGSIKEDV TAFMPKGELRIGANPNANGGRIREDLKLPELDQYEITGVKE YGHGWGQVEAPRSLGAYCR DIIKNNPDSFRVFGPDETASNRLNATYEVTKKQWDNGYLSA LVDENMAVTGQVVEQLSEH QCEGFLEAYLLTGRHGIWSSYESFVHVIDSMLNQHAKWLEA |

TABLE 4-continued

SEQ ID NOs of phosphoketolase target gene coding regions and proteins

| Description | SEQ ID NO: Nucleic acid | SEQ ID NO: Amino acid | Amino Acid sequence |
|---|---|---|---|
| | | | TVREIPWRKPISSVNLLVS SHVWRQDHNGFSHQDPGVTSVLLNKTFNNDHVTNIYFATDA NMLLAIAEKCFKSTNKINA IFAGKQPAATWITLDEARAELEAGAAEWKWASNAKSNDEVQ VVLAAAGDVPTQEIMAASD ALNKMGIKFKVVNVVDLIKLQSSKENDEAMSDEDFADLFTA DKPVLFAYHSYAQDVRGLI YDRPNHDNFTVVGYKEQGSTTTPFDMVRVNDMDRYALQAKA LELIDADKYADKINELNEF RKTAFQFAVDNGYDIPEFTDWVYPDVKVDETSMLSATAATA GDNE |

In other embodiments, a polynucleotide, gene and/or polypeptide encoding phosphoketolase can have at least about 70% to about 75%, about 75% to about 80%, about 80% to about 85%, about 85% to about 90%, about 90% to about 95%, about 96%, about 97%, about 98%, or about 99% sequence identity to that of any one of the sequences of Table 4, wherein the polynucleotide, gene and/or polypeptide encodes a polypeptide having phosphoketolase activity.

In other embodiments, a polynucleotide, gene and/or polypeptide encoding phosphoketolase can be used to identify other phosphoketolase polynucleotide, gene and/or polypeptide sequences or to identify phosphoketolase homologs in other cells, as described above for PDC. Such phosphoketolase encoding sequences can be identified, for example, in the literature and/or in bioinformatics databases well known to the skilled person. For example, the identification of phosphoketolase encoding sequences in other cell types using bioinformatics can be accomplished through BLAST (as described above) searching of publicly available databases with known phosphoketolase encoding DNA and polypeptide sequences, such as those provided herein. Identities are based on the Clustal W method of alignment using the default parameters of GAP PENALTY=10, GAP LENGTH PENALTY=0.1, and Gonnet 250 series of protein weight matrix.

Additional phosphoketolase target gene coding regions were identified using diversity search, clustering, experimentally verified xylulose-5-phosphate/fructose-6-phosphate phosphoketolases and domain architecture. Briefly, a BLAST search with the experimentally verified sequences with an Evalue cut-off of 0.01 resulted in 595 sequence matches. Clustering with the CD-HIT program at 95% sequence identity and 90% length overlap reduced the number to 436. CD-HIT is a program for clustering large protein database at high sequence identity threshold. The program removes redundant sequences and generates a database of only the representatives. (Clustering of highly homologous sequences to reduce the size of large protein database, Weizhong Li, Lukasz Jaroszewski & Adam Godzik Bioinformatics, (2001) 17:282-283)

Xylulose-5-phosphate/fructose-6-phosphate phosphoketolases have three Pfam domains: XFP_N; XFP; XFP_C. Although each of these domains may be present in several domain architectures, e.g. XFP_N is found in eight architectures. The architecture of interest was determined to be XFP_N; XFP; XFP_C. The cumulative length of the three domains is 760 amino acids.

A structure/function characterization of the phosphoketolases was performed using the HMMER software package. The following information based on the HMMER software user guide gives some description of the way that the hmmbuild program prepares a Profile HMM. A Profile HMM is capable of modeling gapped alignments, e.g. including insertions and deletions, which lets the software describe a complete conserved domain (rather than just a small ungapped motif). Insertions and deletions are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a "node". These states are interconnected with arrows called state transition probabilities. M and I states are emitters, while D states are silent. The transitions are arranged so that at each node, either the M state is used (and a residue is aligned and scored) or the D state is used (and no residue is aligned, resulting in a deletion-gap character, '-'). Insertions occur between nodes, and I states have a self-transition, allowing one or more inserted residues to occur between consensus columns.

The scores of residues in a match state (i.e. match state emission scores), or in an insert state (i.e. insert state emission scores) are proportional to $\text{Log}\_2\ (p\_x)/(null\_x)$. Where p_x is the probability of an amino acid residue, at a particular position in the alignment, according to the Profile HMM and null_x is the probability according to the Null model. The Null model is a simple one state probabilistic model with pre-calculated set of emission probabilities for each of the 20 amino acids derived from the distribution of amino acids in the SWISSPROT release 24. State transition scores are also calculated as log odds parameters and are proportional to $\text{Log}\_2\ (t\_x)$. Where t_x is the probability of transiting to an emitter or non-emitter state.

Using a multiple sequence alignment of experimentally verified sequences containing the architecture of interest XFP_N; XFP; XFP_C, a profile Hidden Markov Model (HMM) was created for representing members of the xylulose-5-phosphate/fructose-6-phosphate phosphoketolases (XPK-XFP). As stated in the user guide, Profile HMMs are statistical models of multiple sequence alignments. They capture position-specific information about how conserved each column of the alignment is, and which amino acid residues are most likely to occur at each position. Thus HMMs have a formal probabilistic basis. Profile HMMs for a large number of protein families are publicly available in the PFAM database (Janelia Farm Research Campus, Ashburn, Va.

Eight xylulose-5-phosphate/fructose-6-phosphate phosphoketolases sequences with experimentally verified function were identified in the BRENDA database:

1. CBF76492.1 from *Aspergillus nidulans* FGSC A4 (SEQ ID NO: 355)
2. AAR98787.1 from *Bifidobacterium longum* (SEQ ID NO: 379)
3. ZP_03646196.1 from *Bifidobacterium bifidum* NCIMB 41171 (SEQ ID NO: 381)
4. ZP_02962870.1 from *Bifidobacterium animalis* subsp. *lactis* HN019 (SEQ ID NO: 388)
5. NP_786060.1 from *Lactobacillus plantarum* WCFS1 (SEQ ID NO: 481)
6. ZP_03940142.1 from *Lactobacillus brevis* subsp. *gravesensis* ATCC 27305 (SEQ ID NO: 486)
7. ZP_03073172.1 from *Lactobacillus reuteri* 100-23 (SEQ ID NO 468)
8. YP_818922.1 from *Leuconostoc mesenteroides* subsp. *mesenteroides* ATCC 8293 (SEQ ID NO: 504)

The BRENDA database is a freely available information system containing biochemical and molecular information on all classified enzymes as well as software tools for querying the database and calculating molecular properties. The database covers information on classification and nomenclature, reaction and specificity, functional parameters, occurrence, enzyme structure and stability, mutants and enzyme engineering, preparation and isolation, the application of enzymes, and ligand-related data. (BRENDA, AMENDA and FRENDA the enzyme information system: new content and tools in 2009. Nucleic Acids Res. 2009 January; 37 (Database issue):D588-92. Epub 2008 Nov. 4. Chang A, Scheer M, Grote A, Schomburg I, Schomburg D.) The eight sequences were used to build a profile HMM which is provided herein as Table 6.

To further identify the proteins of interest, the 436 sequences were searched with four profile HMMs: the generated XPK_XFP_HMM profile HMM provided in Table 6 as well as the three published profiles for the three domains XFP_N; XFP; XFP_C (PFAM DATABASE) described in Tables 7, 8, and 9, respectively. 309 protein sequences which lengths were between 650 amino acids and 900 amino acids, and contained the three domains were retained.

All 309 sequences are at least 40% identical to an experimentally verified phosphoketolase, with exception of 12 sequences that are within 35% identity distance. However, all 309 sequences have a highly significant match to all 4 profile HMMs. The least significant matches have Evalues of 7.5E-242, 1.1E-124, 2.1E-49, 7.8E-37 to XFP_XPK HMM, XFP_N, XFP, and XFP_C profile HMMs respectively. The 309 sequences are provided in Table 5, however, it is understood that any xylulose-5-phosphate/fructose-6-phosphate phosphoketolase identifiable by the method described may be expressed in host cells as described herein. Where accession information is given as "complement (NN_NNNNN.N:X ... Y)", it should be understood to mean the reverse complement of nucleotides X to Y of the sequence with Accession number NN_NNNNN.N. Where accession information is given as "join (NNNNNN.N: X ... Y, NNNNNN.N:Z ... Q)", it should be understood to mean the sequence resulting from joining nucleotides X to Y of NNNNNN.N to nucleotides Z to Q of NNNNNN.N.

TABLE 5

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 162147402 | complement(NC_010125.1: 1624982 ... 1627414) | 21 | YP_001601863.1 | 330 | *Gluconacetobacter diazotrophicus* PAl5 |
| 127512024 | complement(NC_009092.1: 1256548 ... 1258914) | 22 | YP_001093221.1 | 331 | *Shewanella loihica* PV-4 |
| 119774052 | complement(NC_008700.1: 1105589 ... 1107955) | 23 | YP_926792.1 | 332 | *Shewanella amazonensis* SB2B |
| 113971300 | NC_008321.1: 3541276 ... 3543642 | 24 | YP_735093.1 | 333 | *Shewanella* sp. MR-4 |
| 126173290 | complement(NC_009052.1: 1204351 ... 1206717) | 25 | YP_001049439.1 | 334 | *Shewanella baltica* OS155 |
| 163750647 | complement(NZ_ABIC01000018.1: 47875 ... 50253) | 26 | ZP_02157884.1 | 335 | *Shewanella benthica* KT99 |
| 157374325 | complement(NC_009831.1: 1410491 ... 1412857) | 27 | YP_001472925.1 | 336 | *Shewanella sediminis* HAW-EB3 |
| 170725643 | complement(NC_010506.1: 1624098 ... 1626464) | 28 | YP_001759669.1 | 337 | *Shewanella woodyi* ATCC 51908 |
| 167623058 | complement(NC_010334.1: 1364332 ... 1366698) | 29 | YP_001673352.1 | 338 | *Shewanella halifaxensis* HAW-EB4 |
| 91794082 | NC_007954.1: 3270590 ... 3272956 | 30 | YP_563733.1 | 339 | *Shewanella denitrificans* OS217 |
| 254498997 | NZ_ACUL01000224.1: 8243 ... 10492 | 31 | ZP_05111697.1 | 340 | *Legionella drancourtii* LLAP12 |
| 239607320 | join(EQ999973.1: 7995808 ... 7995885, EQ999973.1: 7996059 ... 7996116, EQ999973.1: 7996178 ... 7996412, EQ999973.1: 7996486 ... 7996638, EQ999973.1: 7996791 ... 7997016, | 32 | EEQ84307.1 | 341 | *Ajellomyces dermatitidis* ER-3 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| | EQ999973.1: 7997082 . . . 7997548, EQ999973.1: 7997603 . . . 7997705, EQ999973.1: 7997779 . . . 7998604, EQ999973.1: 7998677 . . . 7998717) | | | | |
| 261200667 | XM_002626688.1: 1 . . . 2034 | 33 | XP_002626734.1 | 342 | *Ajellomyces dermatitidis* SLH14081 |
| 154276328 | XM_001538959.1: 1 . . . 2421 | 34 | XP_001539009.1 | 343 | *Ajellomyces capsulatus* NAm1 |
| 225555843 | join(GG663374.1: 72330 . . . 72492, GG663374.1: 72695 . . . 72929, GG663374.1: 73005 . . . 73157, GG663374.1: 73216 . . . 74203, GG663374.1: 74274 . . . 75146) | 35 | EEH04133.1 | 344 | *Ajellomyces capsulatus* G186AR |
| 225681974 | join(DS544805.1: 2187102 . . . 2187264, DS544805.1: 2187353 . . . 2187427, DS544805.1: 2187521 . . . 2187755, DS544805.1: 2187839 . . . 2187991, DS544805.1: 2188086 . . . 2188395, DS544805.1: 2188462 . . . 2189082, DS544805.1: 2189147 . . . 2189263, DS544805.1: 2189358 . . . 2189973, DS544805.1: 2190044 . . . 2190084) | 36 | EEH20258.1 | 345 | *Paracoccidioides brasiliensis* Pb03 |
| 226289140 | join(DS572750.1: 3105630 . . . 3105792, DS572750.1: 3106049 . . . 3106283, DS572750.1: 3106367 . . . 3106519, DS572750.1: 3106614 . . . 3106923, DS572750.1: 3107023 . . . 3107610, DS572750.1: 3107675 . . . 3108500, DS572750.1: 3108572 . . . 3108612) | 37 | EEH44652.1 | 346 | *Paracoccidioides brasiliensis* Pb18 |
| 258564014 | XM_002582706.1: 1 . . . 2421 | 38 | XP_002582752.1 | 347 | *Uncinocarpus reesii* 1704 |
| 240108203 | join(ACFW01000030.1: 1281918 . . . 1282080, ACFW01000030.1: 1282133 . . . 1282207, ACFW01000030.1: 1282266 . . . 1282500, ACFW01000030.1: 1282551 . . . 1282703, ACFW01000030.1: 1282757 . . . 1283066, ACFW01000030.1: 1283132 . . . 1283752, ACFW01000030.1: 1283828 . . . 1284653, ACFW01000030.1: 1284726 . . . 1284763) | 39 | EER26377.1 | 348 | *Coccidioides posadasii* C735 delta SOWgp |
| 238838423 | join(DS995701.1: 2675053 . . . 2675215, DS995701.1: 2675278 . . . 2675352, DS995701.1: 2675424 . . . 2675658, DS995701.1: 2675745 . . . 2675897, DS995701.1: 2675972 . . . 2676281, DS995701.1: 2676341 . . . 2676961, DS995701.1: 2677062 . . . 2677836, DS995701.1: 2677864 . . . 2677933, DS995701.1: 2677998 . . . 2678013) | 40 | EEQ28085.1 | 349 | *Microsporum canis* CBS 113480 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 169770631 | XM_001819733.1: 1 . . . 2457 | 41 | XP_001819785.1 | 350 | *Aspergillus oryzae* RIB40 |
| 145232813 | XM_001399743.1: 1 . . . 2421 | 42 | XP_001399780.1 | 351 | *Aspergillus niger* |
| 119491775 | XM_001263381.1: 1 . . . 2421 | 43 | XP_001263382.1 | 352 | *Neosartorya fischeri* NRRL 181 |
| 121705634 | XM_001271079.1: 1 . . . 2421 | 44 | XP_001271080.1 | 353 | *Aspergillus clavatus* NRRL 1 |
| 115396290 | XM_001213784.1: 1 . . . 2400 | 45 | XP_001213784.1 | 354 | *Aspergillus terreus* NIH2624 |
| 259482219 | join(BN001303.1: 576345 . . . 576507, BN001303.1: 576696 . . . 576930, BN001303.1: 576981 . . . 577133, BN001303.1: 577185 . . . 577494, BN001303.1: 577544 . . . 578161, BN001303.1: 578210 . . . 579035, BN001303.1: 579091 . . . 579128) | 46 | CBF76492.1 | 355 | *Aspergillus nidulans* FGSC A4 |
| 255942289 | XM_002561867.1: 1 . . . 2469 | 47 | XP_002561913.1 | 356 | *Penicillium chrysogenum* Wisconsin 54-1255 |
| 242784458 | XM_002480346.1: 69 . . . 2489 | 48 | XP_002480391.1 | 357 | *Talaromyces stipitatus* ATCC 10500 |
| 212527714 | XM_002143978.1: 139 . . . 2559 | 49 | XP_002144014.1 | 358 | *Penicillium marneffei* ATCC 18224 |
| 70999652 | XM_749450.1: 1 . . . 2145 | 50 | XP_754543.1 | 359 | *Aspergillus fumigatus* Af293 |
| 154314622 | XM_001556585.1: 1 . . . 2061 | 51 | XP_001556635.1 | 360 | *Botryotinia fuckeliana* B05.10 |
| 156053245 | XM_001592499.1: 1 . . . 2430 | 52 | XP_001592549.1 | 361 | *Sclerotinia sclerotiorum* 1980 |
| 46124351 | XM_386729.1: 1 . . . 2418 | 53 | XP_386729.1 | 362 | *Gibberella zeae* PH-1 |
| 256733824 | complement(join(GG698897.1: 220636 . . . 220670, GG698897.1: 220723 . . . 221650, GG698897.1: 221704 . . . 222510, GG698897.1: 222576 . . . 222732, GG698897.1: 222783 . . . 223020, GG698897.1: 223072 . . . 223146, GG698897.1: 223199 . . . 223361)) | 54 | EEU47171.1 | 363 | *Nectria haematococca* mpVI 77-13-4 |
| 261354209 | join(DS985216.1: 747889 . . . 748126, DS985216.1: 748174 . . . 748564, DS985216.1: 748620 . . . 748929, DS985216.1: 748985 . . . 749555, DS985216.1: 749607 . . . 749833, DS985216.1: 749946 . . . 750572) | 55 | EEY16637.1 | 364 | *Verticillium albo-atrum* VaMs.102 |
| 85081035 | XM_951556.2: 215 . . . 2662 | 56 | XP_956649.1 | 365 | *Neurospora crassa* OR74A |
| 145609083 | XM_364271.2: 1 . . . 2442 | 57 | XP_364271.2 | 366 | *Magnaporthe grisea* 70-15 |
| 171679277 | XM_001904550.1: 1 . . . 2316 | 58 | XP_001904585.1 | 367 | *Podospora anserine* |
| 169859036 | XM_001836107.1: 1 . . . 2418 | 59 | XP_001836159.1 | 368 | *Coprinopsis cinerea* okayama7#130 |
| 19112755 | NM_001021872.1: 1 . . . 2478 | 60 | NP_595963.1 | 369 | *Schizosaccharomyces pombe* |
| 213405339 | XM_002173405.1: 1 . . . 2469 | 61 | XP_002173441.1 | 370 | *Schizosaccharomyces japonicus* yFS275 |
| 58267408 | XM_570860.1: 39 . . . 2594 | 62 | XP_570860.1 | 371 | *Cryptococcus neoformans* var. *neoformans* JEC21 |
| 71018661 | XM_754468.1: 1 . . . 2682 | 63 | XP_759561.1 | 372 | *Ustilago maydis* 521 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 254413307 | NZ_DS989851.1: 81897 . . . 84338 | 64 | ZP_05027078.1 | 373 | *Microcoleus chthonoplastes* PCC 7420 |
| 256377454 | NC_013093.1: 3941285 . . . 3943633 | 65 | YP_003101114.1 | 374 | *Actinosynnema mirum* DSM 43827 |
| 221195188 | NZ_ACFE01000002.1: 241103 . . . 243577 | 66 | ZP_03568244.1 | 375 | *Atopobium rimae* ATCC 49626 |
| 257785020 | complement(NC_013203.1: 1365893 . . . 1368364) | 67 | YP_003180237.1 | 376 | *Atopobium parvulum* DSM 20469 |
| 227516879 | complement(NZ_ACGK01000053.1: 213016 . . . 215490) | 68 | ZP_03946928.1 | 377 | *Atopobium vaginae* DSM 15829 |
| 210630184 | NZ_ABXJ01000012.1: 49466 . . . 51985 | 69 | ZP_03296299.1 | 378 | *Collinsella stercoris* DSM 13279 |
| 41056825 | AY518215.1: 989 . . . 3466 | 70 | AAR98787.1 | 379 | *Bifidobacterium longum* |
| 223467373 | NZ_ACCG01000015.1: 9765 . . . 12350 | 71 | ZP_03618909.1 | 380 | *Bifidobacterium breve* DSM 20213 |
| 224282874 | NZ_ABQP01000009.1: 218668 . . . 221073 | 72 | ZP_03646196.1 | 381 | *Bifidobacterium bifidum* NCIMB 41171 |
| 229817819 | complement(NZ_ABYS02000004.1: 901411 . . . 903888) | 73 | ZP_04448101.1 | 382 | *Bifidobacterium angulatum* DSM 20098 |
| 212716076 | complement(NZ_ABXY01000011.1: 578312 . . . 580789) | 74 | ZP_03324204.1 | 383 | *Bifidobacterium catenulatum* DSM 16992 |
| 41056831 | AY518218.1: 1430 . . . 3907 | 75 | AAR98790.1 | 384 | *Bifidobacterium* sp. CFAR 172 |
| 41056829 | AY518217.1: 951 . . . 3428 | 76 | AAR98789.1 | 385 | *Bifidobacterium pullorum* |
| 227507561 | NZ_ACGF01000124.1: 41655 . . . 44132 | 77 | ZP_03937610.1 | 386 | *Gardnerella vaginalis* ATCC 14019 |
| 261337317 | NZ_ABXB03000001.1: 154886 . . . 157366 | 78 | ZP_05965201.1 | 387 | *Bifidobacterium gallicum* DSM 20093 |
| 183601500 | complement(NZ_ABOT01000001.1: 194894 . . . 197371) | 79 | ZP_02962870.1 | 388 | *Bifidobacterium animalis* subsp. *lactis* HN019 |
| 41056827 | AY518216.1:988 . . . 3465 | 80 | AAR98788.1 | 389 | *Bifidobacterium pseudolongum* subsp. *Globosum* |
| 227516469 | complement(NZ_ACGK01000047.1: 28634 . . . 31102) | 81 | ZP_03946518.1 | 390 | *Atopobium vaginae* DSM 15829 |
| 76556241 | AJ509177.1: 1 . . . 2625 | 82 | YP_001511171.1 | 391 | *Frankia* sp. EAN1pec |
| 158318663 | NC_009921.1: 8441355 . . . 8443790 | 83 | YP_713678.1 | 392 | *Frankia alni* ACN14a |
| 111222884 | complement(NC_008278.1: 3758441 . . . 3760909) | 84 | YP_002778395.1 | 393 | *Rhodococcus opacus* B4 |
| 226360617 | complement(NC_012522.1: 1273076 . . . 1275478) | 85 | YP_701466.1 | 394 | *Rhodococcus jostii* RHA1 |
| 111018494 | complement(NC_008268.1: 1575800 . . . 1578352) | 86 | ZP_04383880.1 | 395 | *Rhodococcus erythropolis* SK121 |
| 229490027 | NZ_ACNO01000014.1: 107516 . . . 109885 | 87 | YP_947598.1 | 396 | *Arthrobacter aurescens* TC1 |
| 119962524 | NC_008711.1: 2018415 . . . 2020796 | 88 | CAD48946.1 | 397 | *Propionibacterium freudenreichii* subsp. *Shermanii* |
| 28868876 | NC_004578.1: 1837381 . . . 1839888 | 89 | NP_791495.1 | 398 | *Pseudomonas syringae* pv. tomato str. DC3000 |
| 256425339 | NC_013132.1: 8027760 . . . 8030123 | 90 | YP_003125992.1 | 399 | *Chitinophaga pinensis* DSM 2588 |
| 161075783 | EU223897.1: 1 . . . 2430 | 91 | ABX56639.1 | 400 | *Verrucomicrobiae bacterium* V4 |
| 218246512 | complement(NC_011726.1: 1758431 . . . 1760839) | 92 | YP_002371883.1 | 401 | *Cyanothece* sp. PCC 8801 |
| 172055269 | NC_010547.1: 390265 . . . 392673 | 93 | YP_001806596.1 | 402 | *Cyanothece* sp. ATCC 51142 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 126659520 | complement(NZ_AAXW01000034.1: 5415 . . . 7823) | 94 | ZP_01730652.1 | 403 | Cyanothece sp. CCY0110 |
| 258380665 | complement(AM990467.1: 2704 . . . 5112) | 95 | CAQ48286.1 | 404 | Planktothrix rubescens NIVA-CYA 98 |
| 209527806 | NZ_ABYK01000067.1: 8063 . . . 10480 | 96 | ZP_03276298.1 | 405 | Arthrospira maxima CS-328 |
| 196258744 | NZ_ABVE01000007.1: 72906 . . . 75314 | 97 | ZP_03157277.1 | 406 | Cyanothece sp. PCC 7822 |
| 218440702 | complement(NC_011729.1: 4207741 . . . 4210149) | 98 | YP_002379031.1 | 407 | Cyanothece sp. PCC 7424 |
| 166366228 | complement(NC_010296.1: 3156762 . . . 3159182) | 99 | YP_001658501.1 | 408 | Microcystis aeruginosa NIES-843 |
| 119488765 | NZ_AAVU01000020.1: 110903 . . . 113317 | 100 | ZP_01621774.1 | 409 | Lyngbya sp. PCC 8106 |
| 17228976 | complement(NC_003272.1: 1746056 . . . 1748482) | 101 | NP_485524.1 | 410 | Nostoc sp. PCC 7120 |
| 254422632 | NZ_DS989904.1: 4613864 . . . 4616290 | 102 | ZP_05036350.1 | 411 | Synechococcus sp. PCC 7335 |
| 158333641 | NC_009925.1: 422232 . . . 424652 | 103 | YP_001514813.1 | 412 | Acaryochloris marina MBIC11017 |
| 254425820 | complement(NZ_DS989905.1: 71540 . . . 74017) | 104 | ZP_05039537.1 | 413 | Synechococcus sp. PCC 7335 |
| 170695087 | complement(NZ_ABLD01000020.1: 33972 . . . 36368) | 105 | ZP_02886235.1 | 414 | Burkholderia graminis C4D1M |
| 209515639 | complement(NZ_ABYL01000006.1: 33232 . . . 35628) | 106 | ZP_03264503.1 | 415 | Burkholderia sp. H160 |
| 87303015 | NZ_AANO01000008.1: 122233 . . . 124656 | 107 | ZP_01085819.1 | 416 | Synechococcus sp. WH 5701 |
| 254431900 | complement(NZ_DS990556.1: 2146872 . . . 2149313) | 108 | ZP_05045603.1 | 417 | Cyanobium sp. PCC 7001 |
| 88808134 | NZ_AAOK01000002.1: 342081 . . . 344516 | 109 | ZP_01123645.1 | 418 | Synechococcus sp. WH 7805 |
| 148238545 | complement(NC_009481.1: 226771 . . . 229206) | 110 | YP_001223932.1 | 419 | Synechococcus sp. WH 7803 |
| 87123187 | NZ_AANP01000001.1: 180603 . . . 183032 | 111 | ZP_01079038.1 | 420 | Synechococcus sp. RS9917 |
| 187919971 | complement(NC_010676.1: 1450148 . . . 1452541) | 112 | YP_001889002.1 | 421 | Burkholderia phytofirmans PsJN |
| 91778759 | complement(NC_007952.1: 1882080 . . . 1884473) | 113 | YP_553967.1 | 422 | Burkholderia xenovorans LB400 |
| 170690542 | NZ_ABLD01000001.1: 565487 . . . 567880 | 114 | ZP_02881709.1 | 423 | Burkholderia graminis C4D1M |
| 209521856 | NZ_ABYL01000194.1: 6778 . . . 9171 | 115 | ZP_03270532.1 | 424 | Burkholderia sp. H160 |
| 186474278 | complement(NC_010623.1: 2647064 . . . 2649448) | 116 | YP_001861620.1 | 425 | Burkholderia phymatum STM815 |
| 225873826 | complement(NC_012483.1: 2598033 . . . 2600420) | 117 | YP_002755285.1 | 426 | Acidobacterium capsulatum ATCC 51196 |
| 206602403 | DS995260.1: 236338 . . . 238704 | 118 | EDZ38884.1 | 427 | Leptospirillum sp. Group II '5-way CG' |
| 251772639 | complement(GG693868.1: 86578 . . . 88956) | 119 | EES53204.1 | 428 | Leptospirillum ferrodiazotrophum |
| 56752022 | complement(NC_006576.1: 2156604 . . . 2158994) | 120 | YP_172723.1 | 429 | Synechococcus elongatus PCC 6301 |
| 22298729 | complement(NC_004113.1: 1224195 . . . 1226633) | 121 | NP_681976.1 | 430 | Thermosynechococcus elongatus BP-1 |
| 53804073 | NC_002977.6: 1693459 . . . 1695894 | 122 | YP_114037.1 | 431 | Methylococcus capsulatus str. Bath |
| 220907266 | NC_011884.1: 1725657 . . . 1728098 | 123 | YP_002482577.1 | 432 | Cyanothece sp. PCC 7425 |
| 16332268 | NC_000911.1: 3500713 . . . 3503178 | 124 | NP_442996.1 | 433 | Synechocystis sp. PCC 6803 |
| 220907424 | complement(NC_011884.1: 1898702 . . . 1901167) | 125 | YP_002482735.1 | 434 | Cyanothece sp. PCC 7425 |
| 241777601 | complement(NZ_ACQQ01000020.1: 30393 . . . 32762) | 126 | ZP_04774866.1 | 435 | Allochromatium vinosum DSM 180 |
| 114778289 | NZ_AATS01000014.1: 23435 . . . 25801 | 127 | ZP_01453148.1 | 436 | Mariprofundus ferrooxydans PV-1 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 251827471 | complement(NZ_ACSD01000006.1: 39617 . . . 41986) | 128 | ZP_04830548.1 | 437 | *Gallionella ferruginea* ES-2 |
| 121712503 | XM_001273862.1: 1 . . . 2436 | 129 | XP_001273863.1 | 438 | *Aspergillus clavatus* NRRL 1 |
| 119473535 | XM_001258642.1: 1 . . . 2439 | 130 | XP_001258643.1 | 439 | *Neosartorya fischeri* NRRL 181 |
| 169763560 | XM_001727628.1: 1 . . . 2433 | 131 | XP_001727680.1 | 440 | *Aspergillus oryzae* RIB40 |
| 145248115 | XM_001396269.1: 1 . . . 2448 | 132 | XP_001396306.1 | 441 | *Aspergillus niger* |
| 115400974 | XM_001216075.1: 1 . . . 2457 | 133 | XP_001216075.1 | 442 | *Aspergillus terreus* NIH2624 |
| 255952755 | XM_002567084.1: 1 . . . 2433 | 134 | XP_002567130.1 | 443 | *Penicillium chrysogenum* Wisconsin 54-1255 |
| 212527388 | XM_002143815.1: 98 . . . 2551 | 135 | XP_002143851.1 | 444 | *Penicillium marneffei* ATCC 18224 |
| 242783584 | XM_002480171.1: 1 . . . 2448 | 136 | XP_002480216.1 | 445 | *Talaromyces stipitatus* ATCC 10500 |
| 154321267 | XM_001559899.1: 1 . . . 2466 | 137 | XP_001559949.1 | 446 | *Botryotinia fuckeliana* B05.10 |
| 156054348 | XM_001593050.1: 1 . . . 2499 | 138 | XP_001593100.1 | 447 | *Sclerotinia sclerotiorum* 1980 |
| 189191706 | XM_001932157.1: 1 . . . 2469 | 139 | XP_001932192.1 | 448 | *Pyrenophora tritici-repentis* Pt-1C-BFP |
| 169600613 | XM_001793677.1: 1 . . . 2466 | 140 | XP_001793729.1 | 449 | *Phaeosphaeria nodorum* SN15 |
| 58260732 | XM_567776.1: 41 . . . 2545 | 141 | XP_567776.1 | 450 | *Cryptococcus neoformans* var. neoformans JEC21 |
| 46123901 | XM_386504.1: 1 . . . 2460 | 142 | XP_386504.1 | 451 | *Gibberella zeae* PH-1 |
| 256732917 | complement(join(GG698898.1: 321524 . . . 322233, GG698898.1: 322285 . . . 322489, GG698898.1: 322540 . . . 324081)) | 143 | EEU46265.1 | 452 | *Nectria haematococca* mpVI 77-13-4 |
| 225729111 | FJ790496.1: 215 . . . 2677 | 144 | ACO24516.1 | 453 | *Metarhizium anisopliae* |
| 85094948 | XM_954892.2: 155 . . . 2638 | 145 | XP_959985.1 | 454 | *Neurospora crassa* OR74A |
| 171679479 | XM_001904651.1: 1 . . . 2517 | 146 | XP_001904686.1 | 455 | *Podospora anserine* |
| 198283820 | NC_011206.1: 1682860 . . . 1685307 | 147 | YP_002220141.1 | 456 | *Acidithiobacillus ferrooxidans* ATCC 53993 |
| 148243889 | NC_009468.1: 90683 . . . 93145 | 148 | YP_001220128.1 | 457 | *Acidiphilium cryptum* JF-5 |
| 157364435 | NC_009828.1: 1658895 . . . 1661258 | 149 | YP_001471202.1 | 458 | *Thermotoga lettingae* TMO |
| 217966781 | NC_011661.1: 369050 . . . 371428 | 150 | YP_002352287.1 | 459 | *Dictyoglomus turgidum* DSM 6724 |
| 92109503 | complement(NC_007960.1: 14429 . . . 16810) | 151 | YP_571790.1 | 460 | *Nitrobacter hamburgensis* X14 |
| 87310270 | complement(NZ_AANZ01000017.1: 80191 . . . 82560) | 152 | ZP_01092401.1 | 461 | *Blastopirellula marina* DSM 3645 |
| 152995974 | NC_009654.1: 2214232 . . . 2216625 | 153 | YP_001340809.1 | 462 | *Marinomonas* sp. MWYL1 |
| 32473390 | NC_005027.1: 2520925 . . . 2523306 | 154 | NP_866384.1 | 463 | *Rhodopirellula baltica* SH 1 |
| 254495580 | complement(NZ_ACUL01000002.1: 21176 . . . 23557) | 155 | ZP_05108502.1 | 464 | *Legionella drancourtii* LLAP12 |
| 254380451 | NZ_DS570384.1: 88623 . . . 90992 | 156 | ZP_04995817.1 | 465 | *Streptomyces* sp. Mg1 |
| 227974767 | NZ_ACGW01000133.1: 1172 . . . 3235 | 157 | ZP_04023055.1 | 466 | *Lactobacillus reuteri* SD2112 |
| 227530011 | NZ_ACGV01000134.1: 2320 . . . 4794 | 158 | ZP_03960060.1 | 467 | *Lactobacillus vaginalis* ATCC 49540 |
| 194467185 | complement(NZ_AAPZ02000001.1: 905298 . . . 907709) | 159 | ZP_03073172.1 | 468 | *Lactobacillus reuteri* 100-23 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 256847586 | NZ_GG698803.1: 21616 . . . 24015 | 160 | ZP_05553031.1 | 469 | *Lactobacillus coleohominis* 101-4-CHN |
| 260662452 | complement(NZ_GG704700.1: 145244 . . . 147643) | 161 | ZP_05863347.1 | 470 | *Lactobacillus fermentum* 28-3-CHN |
| 227903484 | NZ_ACHN01000046.1: 59035 . . . 61452 | 162 | ZP_04021289.1 | 471 | *Lactobacillus acidophilus* ATCC 4796 |
| 227877116 | NZ_ACKR01000020.1: 11753 . . . 14191 | 163 | ZP_03995194.1 | 472 | *Lactobacillus crispatus* JV-V01 |
| 227893117 | NZ_ACGU01000035.1: 36787 . . . 39186 | 164 | ZP_04010922.1 | 473 | *Lactobacillus ultunensis* DSM 16047 |
| 256844475 | NZ_GG698762.1: 280846 . . . 283242 | 165 | ZP_05549961.1 | 474 | *Lactobacillus crispatus* 125-2-CHN |
| 227521312 | complement(NZ_ACGO01000008.1: 37191 . . . 39647) | 166 | ZP_03951361.1 | 475 | *Lactobacillus gasseri* JV-V03 |
| 259501613 | complement(NZ_ACLN01000019.1: 10173 . . . 12569) | 167 | ZP_05744515.1 | 476 | *Lactobacillus iners* DSM 13335 |
| 104773655 | NC_008054.1: 449229 . . . 451631 | 168 | YP_618635.1 | 477 | *Lactobacillus delbrueckii* subsp. *bulgaricus* ATCC 11842 |
| 227525868 | NZ_ACGQ01000037.1: 36941 . . . 39310 | 169 | ZP_03955917.1 | 478 | *Lactobacillus jensenii* JV-V16 |
| 227512366 | NZ_ACGH01000107.1: 31655 . . . 34045 | 170 | ZP_03942415.1 | 479 | *Lactobacillus buchneri* ATCC 11577 |
| 118587374 | complement(NZ_AAUV01000059.1: 59008 . . . 61416) | 171 | ZP_01544800.1 | 480 | *Oenococcus oeni* ATCC BAA-1163 |
| 28379168 | complement(NC_004567.1: 2362936 . . . 2365302) | 172 | NP_786060.1 | 481 | *Lactobacillus plantarum* WCFS1 |
| 21363093 | AJ309011.1: 181 . . . 2547 | 173 | Q937F6 | 482 | XPKA_LACPE |
| 81427904 | NC_007576.1: 286496 . . . 288859 | 174 | YP_394903.1 | 483 | *Lactobacillus sakei* subsp. *sakei* 23K |
| 116492156 | NC_008525.1: 398927 . . . 401290 | 175 | YP_803891.1 | 484 | *Pediococcus pentosaceus* ATCC 25745 |
| 259648565 | AP011548.1: 211570 . . . 213957 | 176 | BAI40727.1 | 485 | *Lactobacillus rhamnosus* GG |
| 227510093 | complement(NZ_ACGG01000115.1: 64541 . . . 66952) | 177 | ZP_03940142.1 | 486 | *Lactobacillus brevis* subsp. *gravesensis* ATCC 27305 |
| 227891468 | complement(NZ_ACGT01000007.1: 44265 . . . 46625) | 178 | ZP_04009273.1 | 487 | *Lactobacillus salivarius* ATCC 11741 |
| 227528594 | NZ_ACGS01000122.1: 352 . . . 2721 | 179 | ZP_03958643.1 | 488 | *Lactobacillus ruminis* ATCC 25644 |
| 229542373 | complement(NZ_AAWV02000001.1: 1384102 . . . 1386486) | 180 | ZP_04431433.1 | 489 | *Bacillus coagulans* 36D1 |
| 238021480 | complement(NZ_ACJW02000002.1: 913355 . . . 915730) | 181 | ZP_04601906.1 | 490 | *Kingella oralis* ATCC 51147 |
| 259046526 | NZ_ACKZ01000008.1: 36586 . . . 38955 | 182 | ZP_05736927.1 | 491 | *Granulicatella adiacens* ATCC 49175 |
| 157150221 | NC_009785.1: 333239 . . . 335623 | 183 | YP_001449631.1 | 492 | *Streptococcus gordonii* str. *Challis* substr. CH1 |
| 25011879 | complement(NC_004368.1: 1900754 . . . 1903132) | 184 | NP_736274.1 | 493 | *Streptococcus agalactiae* NEM316 |
| 229555065 | complement(NZ_ACCR01000006.1: 74043 . . . 76418) | 185 | ZP_04442854.1 | 494 | *Listeria grayi* DSM 20601 |
| 257866707 | NZ_GG670386.1: 478278 . . . 480644 | 186 | ZP_05646360.1 | 495 | *Enterococcus casseliflavus* EC30 |
| 257870669 | NZ_GG670289.1: 233512 . . . 235875 | 187 | ZP_05650322.1 | 496 | *Enterococcus gallinarum* EG2 |
| 257895654 | NZ_GG670306.1: 612981 . . . 615353 | 188 | ZP_05675307.1 | 497 | *Enterococcus faecium* Com12 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 238810139 | AP009608.1: 744956 . . . 747334 | 189 | BAH69929.1 | 498 | *Mycoplasma fermentans* PG18 |
| 193216764 | NC_011025.1: 384420 . . . 386801 | 190 | YP_002000006.1 | 499 | *Mycoplasma arthritidis* 158L3-1 |
| 148377390 | NC_009497.1: 136795 . . . 139182 | 191 | YP_001256266.1 | 500 | *Mycoplasma agalactiae* PG2 |
| 191639669 | NC_010999.1: 2885324 . . . 2887711 | 192 | YP_001988835.1 | 501 | *Lactobacillus casei* BL23 |
| 28379861 | NC_004567.1: 3169067 . . . 3171478 | 193 | NP_786753.1 | 502 | *Lactobacillus plantarum* WCFS1 |
| 227892171 | complement(NZ_ACGT01000037.1: 21330 . . . 23759) | 194 | ZP_04009976.1 | 503 | *Lactobacillus salivarius* ATCC 11741 |
| 116618551 | NC_008531.1: 1449343 . . . 1451709 | 195 | YP_818922.1 | 504 | *Leuconostoc mesenteroides* subsp. *mesenteroides* ATCC 8293 |
| 116333142 | NC_008497.1: 507704 . . . 510163 | 196 | YP_794669.1 | 505 | *Lactobacillus brevis* ATCC 367 |
| 241895257 | complement(NZ_ACKU01000007.1: 101374 . . . 103833) | 197 | ZP_04782553.1 | 506 | *Weissella paramesenteroides* ATCC 33313 |
| 170016535 | NC_010471.1: 181964 . . . 184417 | 198 | YP_001727454.1 | 507 | *Leuconostoc citreum* KM20 |
| 116619034 | complement(NC_008531.1: 1934181 . . . 1936622) | 199 | YP_819405.1 | 508 | *Leuconostoc mesenteroides* subsp. *mesenteroides* ATCC 8293 |
| 161702316 | EU255918.1: 18411 . . . 20879 | 200 | ABX75772.1 | 509 | *Lactococcus lactis* subsp. *Lactis* |
| 116491770 | complement(NC_008528.1: 1731509 . . . 1733962) | 201 | YP_811314.1 | 510 | *Oenococcus oeni* PSU-1 |
| 182419955 | complement(NZ_ABDT01000107.2: 13616 . . . 15991) | 202 | ZP_02951191.1 | 511 | *Clostridium butyricum* 5521 |
| 255523324 | complement(NZ_ACVI01000003.1: 55354 . . . 57747) | 203 | ZP_05390294.1 | 512 | *Clostridium carboxidivorans* P7 |
| 15894622 | NC_003030.1: 1482782 . . . 1485172 | 204 | NP_347971.1 | 513 | *Clostridium acetobutylicum* ATCC 824 |
| 226324778 | complement(NZ_ABVR01000041.1: 500857 . . . 503232) | 205 | ZP_03800296.1 | 514 | *Coprococcus comes* ATCC 27758 |
| 253580358 | NZ_GG696051.1: 158015 . . . 160390 | 206 | ZP_04857624.1 | 515 | *Ruminococcus* sp. 5_1_39B_FAA |
| 257413435 | NZ_ABYJ02000055.1: 10320 . . . 12779 | 207 | ZP_04743029.2 | 516 | *Roseburia intestinalis* L1-82 |
| 154500233 | complement(NZ_AAXG02000041.1: 34174 . . . 36609) | 208 | ZP_02038271.1 | 517 | *Bacteroides capillosus* ATCC 29799 |
| 219119570 | XM_002180506.1: 1 . . . 2508 | 209 | XP_002180542.1 | 518 | *Phaeodactylum tricornutum* CCAP 1055/1 |
| 91975971 | NC_007958.1: 1660408 . . . 1662762 | 210 | YP_568630.1 | 519 | *Rhodopseudomonas palustris* BisB5 |
| 86750966 | complement(NC_007778.1: 4411322 . . . 4413676) | 211 | YP_487462.1 | 520 | *Rhodopseudomonas palustris* HaA2 |
| 39934743 | NC_005296.1: 1858439 . . . 1860790 | 212 | NP_947019.1 | 521 | *Rhodopseudomonas palustris* CGA009 |
| 90425290 | complement(NC_007925.1: 4235875 . . . 4238229) | 213 | YP_533660.1 | 522 | *Rhodopseudomonas palustris* BisB18 |
| 121583071 | NC_008758.1: 65532 . . . 67904 | 214 | YP_973512.1 | 523 | *Polaromonas naphthalenivorans* CJ2 |
| 115376972 | complement(NZ_AAMD01000095.1: 4173 . . . 6533) | 215 | ZP_01464191.1 | 524 | *Stigmatella aurantiaca* DW4/3-1 |
| 148547676 | complement(NC_009512.1: 2807645 . . . 2810020) | 216 | YP_001267778.1 | 525 | *Pseudomonas putida* F1 |
| 116668711 | NC_008541.1: 145493 . . . 147928 | 217 | YP_829644.1 | 526 | *Arthrobacter* sp. FB24 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 220911083 | NC_011886.1: 321712 . . . 324174 | 218 | YP_002486392.1 | 527 | *Arthrobacter chlorophenolicus* A6 |
| 260517200 | complement(NZ_ABUN01000002.1: 92936 . . . 95461) | 219 | ZP_05816651.1 | 528 | *Sanguibacter keddieii* DSM 10542 |
| 229821527 | NC_012669.1: 3398743 . . . 3401217 | 220 | YP_002883053.1 | 529 | *Beutenbergia cavernae* DSM 12333 |
| 256832813 | NC_013174.1: 1712156 . . . 1714588 | 221 | YP_003161540.1 | 530 | *Jonesia denitrificans* DSM 20603 |
| 227428425 | complement(NZ_ABVC01000008.1: 152502 . . . 154988) | 222 | ZP_03911482.1 | 531 | *Xylanimonas cellulosilytica* DSM 15894 |
| 165929357 | AM182260.1: 1 . . . 2481 | 223 | CAJ57850.1 | 532 | *Cellulomonas flavigena* |
| 145223927 | NC_009338.1: 3525804 . . . 3528275 | 224 | YP_001134605.1 | 533 | *Mycobacterium gilvum* PYR-GCK |
| 120404048 | NC_008726.1: 3236585 . . . 3239083 | 225 | YP_953877.1 | 534 | *Mycobacterium vanbaalenii* PYR-1 |
| 257069356 | NC_013172.1: 2493744 . . . 2496215 | 226 | YP_003155611.1 | 535 | *Brachybacterium faecium* DSM 4810 |
| 256824167 | NC_013169.1: 273585 . . . 276047 | 227 | YP_003148127.1 | 536 | *Kytococcus sedentarius* DSM 20547 |
| 148271607 | NC_009480.1: 506602 . . . 509040 | 228 | YP_001221168.1 | 537 | *Clavibacter michiganensis* subsp. *michiganensis* NCPPB 382 |
| 145594129 | complement(NC_009380.1: 1798516 . . . 1800918) | 229 | YP_001158426.1 | 538 | *Salinispora tropica* CNB-440 |
| 159037167 | complement(NC_009953.1: 1767167 . . . 1769569) | 230 | YP_001536420.1 | 539 | *Salinispora arenicola* CNS-205 |
| 238063593 | complement(NZ_GG657738.1: 5405062 . . . 5407251) | 231 | ZP_04608302.1 | 540 | *Micromonospora* sp. ATCC 39149 |
| 118469963 | NC_008596.1: 3674267 . . . 3676639 | 232 | YP_887914.1 | 541 | *Mycobacterium smegmatis* str. MC2 155 |
| 108799759 | NC_008146.1: 2939527 . . . 2941947 | 233 | YP_639956.1 | 542 | *Mycobacterium* sp. MCS |
| 240170498 | complement(NZ_ACBV01000039.1: 21 . . . 2423) | 234 | ZP_04749157.1 | 543 | *Mycobacterium kansasii* ATCC 12478 |
| 183982748 | complement(NC_010612.1: 3341817 . . . 3344219) | 235 | YP_001851039.1 | 544 | *Mycobacterium marinum* M |
| 41407671 | complement(NC_002944.2: 1726717 . . . 1729131) | 236 | NP_960507.1 | 545 | *Mycobacterium avium* subsp. *paratuberculosis* K-10 |
| 254819329 | NZ_ABIN01000047.1: 36474 . . . 38837 | 237 | ZP_05224330.1 | 546 | *Mycobacterium intracellulare* ATCC 13950 |
| 169629591 | complement(NC_010397.1: 2559451 . . . 2561871) | 238 | YP_001703240.1 | 547 | *Mycobacterium abscessus* |
| 84496279 | complement(NZ_AAMN01000002.1: 433314 . . . 435707) | 239 | ZP_00995133.1 | 548 | *Janibacter* sp. HTCC2649 |
| 72163369 | NC_007333.1: 3478272 . . . 3480650 | 240 | YP_291026.1 | 549 | *Thermobifida fusca* YX |
| 227984600 | complement(NZ_ABUZ01000013.1: 70531 . . . 72909) | 241 | ZP_04031845.1 | 550 | *Thermomonospora curvata* DSM 43183 |
| 229855558 | complement(NZ_ABUU01000106.1: 1385 . . . 3700) | 242 | ZP_04475514.1 | 551 | *Streptosporangium roseum* DSM 43021 |
| 229209207 | NZ_ABUI01000028.1: 55841 . . . 58189 | 243 | ZP_04335641.1 | 552 | *Nocardiopsis dassonvillei* subsp. *dassonvillei* DSM 43111 |
| 229862587 | NZ_ABUS01000001.1: 1911934 . . . 1914330 | 244 | ZP_04482201.1 | 553 | *Stackebrandtia nassauensis* DSM 44728 |
| 256376052 | NC_013093.1: 2125566 . . . 2127935 | 245 | YP_003099712.1 | 554 | *Actinosynnema mirum* DSM 43827 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 32141117 | complement(NC_003888.3: 656319 . . . 658772) | 246 | NP_733508.1 | 555 | *Streptomyces coelicolor* A3(2) |
| 117164830 | complement(AM238664.1: 846551 . . . 849055) | 247 | CAJ88379.1 | 556 | *Streptomyces ambofaciens* ATCC 23877 |
| 256811868 | complement(NZ_ACFA01000015.1: 3377 . . . 5761) | 248 | ZP_05536883.1 | 557 | *Streptomyces griseoflavus* Tu4000 |
| 254405496 | complement(NZ_DS570938.1: 43288 . . . 45726) | 249 | ZP_05020421.1 | 558 | *Streptomyces sviceus* ATCC 29083 |
| 260644540 | complement(FN554889.1: 480316 . . . 482694) | 250 | CBG67625.1 | 559 | *Streptomyces scabiei* 87.22 |
| 29827814 | complement(NC_003155.4: 1579336 . . . 1581717) | 251 | NP_822448.1 | 560 | *Streptomyces avermitilis* MA-4680 |
| 239932594 | NZ_ABYA01000503.1: 5217 . . . 7595 | 252 | ZP_04689547.1 | 561 | *Streptomyces ghanaensis* ATCC 14672 |
| 256800397 | complement(NZ_ACEZ01000048.1: 24916 . . . 27303) | 253 | ZP_05530021.1 | 562 | *Streptomyces viridochromogenes* DSM 40736 |
| 256774038 | complement(NZ_ACEX01000074.1: 46221 . . . 48614) | 254 | ZP_05512501.1 | 563 | *Streptomyces hygroscopicus* ATCC 53653 |
| 260452518 | NZ_ACZH01000001.1: 321972 . . . 324359 | 255 | ZP_05800927.1 | 564 | *Streptomyces flavogriseus* ATCC 33331 |
| 182440556 | NC_010572.1: 8084439 . . . 8086826 | 256 | YP_001828275.1 | 565 | *Streptomyces griseus* subsp. *griseus* NBRC 13350 |
| 239982969 | NZ_ABYC01000425.1: 13265 . . . 15646 | 257 | ZP_04705493.1 | 566 | *Streptomyces albus* J1074 |
| 254381599 | NZ_DS570386.1: 118817 . . . 121204 | 258 | ZP_04996963.1 | 567 | *Streptomyces* sp. Mg1 |
| 256674998 | NZ_ACEU01000020.1: 1507 . . . 3900 | 259 | ZP_05485309.1 | 568 | *Streptomyces* sp. SPB78 |
| 227377421 | NZ_ABUC01000002.1: 229225 . . . 231603 | 260 | ZP_03860882.1 | 569 | *Kribbella flavida* DSM 17836 |
| 54023297 | complement(NC_006361.1: 1487629 . . . 1490097) | 261 | YP_117539.1 | 570 | *Nocardia farcinica* IFM 10152 |
| 158313048 | NC_009921.1: 1426213 . . . 1428621 | 262 | YP_001505556.1 | 571 | *Frankia* sp. EAN1pec |
| 86742227 | complement(NC_007777.1: 4238578 . . . 4240986) | 263 | YP_482627.1 | 572 | *Frankia* sp. CcI3 |
| 256395329 | NC_013131.1: 7133131 . . . 7135533 | 264 | YP_003116893.1 | 573 | *Catenulispora acidiphila* DSM 44928 |
| 117927729 | NC_008578.1: 555555 . . . 557948 | 265 | YP_872280.1 | 574 | *Acidothermus cellulolyticus* 11B |
| 119717842 | complement(NC_008699.1: 3839565 . . . 3841961) | 266 | YP_924807.1 | 575 | *Nocardioides* sp. JS614 |
| 134098496 | NC_009142.1: 2098116 . . . 2100512 | 267 | YP_001104157.1 | 576 | *Saccharopolyspora erythraea* NRRL 2338 |
| 209550756 | NC_011369.1: 3264963 . . . 3267347 | 268 | YP_002282673.1 | 577 | *Rhizobium leguminosarum* bv. *trifolii* WSM2304 |
| 241206160 | NC_012850.1: 3503904 . . . 3506288 | 269 | YP_002977256.1 | 578 | *Rhizobium leguminosarum* bv. *trifolii* WSM1325 |
| 190893254 | NC_010994.1: 3714233 . . . 3716620 | 270 | YP_001979796.1 | 579 | *Rhizobium etli* CIAT 652 |
| 86359034 | NC_007761.1: 3623921 . . . 3626308 | 271 | YP_470926.1 | 580 | *Rhizobium etli* CFN 42 |
| 222081270 | complement(NC_011983.1: 490969 . . . 493383) | 272 | YP_002540633.1 | 581 | *Agrobacterium radiobacter* K84 |
| 254720555 | NZ_ACBQ01000064.1: 129340 . . . 131718 | 273 | ZP_05182366.1 | 582 | *Brucella* sp. 83/13 |
| 239835057 | complement(NZ_ACQA01000003.1: 10528 . . . 13017) | 274 | ZP_04683384.1 | 583 | *Ochrobactrum intermedium* LMG 3301 |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 153012043 | NC_009671.1: 16319 . . . 18706 | 275 | YP_001373254.1 | 584 | *Ochrobactrum anthropi* ATCC 49188 |
| 146339061 | complement(NC_009445.1: 2141749 . . . 2144226) | 276 | YP_001204109.1 | 585 | *Bradyrhizobium* sp. ORS278 |
| 148253833 | complement(NC_009485.1: 2424642 . . . 2427059) | 277 | YP_001238418.1 | 586 | *Bradyrhizobium* sp. BTAi1 |
| 27377629 | complement(NC_004463.1: 2749734 . . . 2752139) | 278 | NP_769158.1 | 587 | *Bradyrhizobium japonicum* USDA 110 |
| 92117435 | complement(NC_007964.1: 2109162 . . . 2111570) | 279 | YP_577164.1 | 588 | *Nitrobacter hamburgensis* X14 |
| 240137143 | NC_012808.1: 407982 . . . 410417 | 280 | YP_002961612.1 | 589 | *Methylobacterium extorquens* AM1 |
| 110634584 | complement(NC_008254.1: 2388345 . . . 2390747) | 281 | YP_674792.1 | 590 | *Mesorhizobium* sp. BNC1 |
| 260467447 | NZ_ACZA01000051.1: 15952 . . . 18360 | 282 | ZP_05813617.1 | 591 | *Mesorhizobium opportunistum* WSM2075 |
| 75676138 | NC_007406.1: 2135469 . . . 2137856 | 283 | YP_318559.1 | 592 | *Nitrobacter winogradskyi* Nb-255 |
| 170749020 | complement(NC_010505.1: 2769888 . . . 2772470) | 284 | YP_001755280.1 | 593 | *Methylobacterium radiotolerans* JCM 2831 |
| 170746859 | complement(NC_010505.1: 465997 . . . 468552) | 285 | YP_001753119.1 | 594 | *Methylobacterium radiotolerans* JCM 2831 |
| 254558916 | NC_012988.1: 271224 . . . 273809 | 286 | YP_003066011.1 | 595 | *Methylobacterium extorquens* DM4 |
| 240140298 | NC_012808.1: 3931130 . . . 3933676 | 287 | YP_002964777.1 | 596 | *Methylobacterium extorquens* AM1 |
| 220925990 | NC_011894.1: 6291823 . . . 6294321 | 288 | YP_002501292.1 | 597 | *Methylobacterium nodulans* ORS 2060 |
| 220919962 | complement(NC_011892.1: 451339 . . . 453840) | 289 | YP_002495265.1 | 598 | *Methylobacterium nodulans* ORS 2060 |
| 170741732 | NC_010511.1: 3988668 . . . 3991166 | 290 | YP_001770387.1 | 599 | *Methylobacterium* sp. 4-46 |
| 239815802 | complement(NC_012791.1: 2971257 . . . 2973608) | 291 | YP_002944712.1 | 600 | *Variovorax paradoxus* S110 |
| 89069402 | NZ_AAOT01000017.1: 31124 . . . 33460 | 292 | ZP_01156757.1 | 601 | *Oceanicola granulosus* HTCC2516 |
| 119509641 | complement(NZ_AAVW01000007.1: 15878 . . . 18259) | 293 | ZP_01628787.1 | 602 | *Nodularia spumigena* CCY9414 |
| 186682350 | NC_010628.1: 2389837 . . . 2392218 | 294 | YP_001865546.1 | 603 | *Nostoc punctiforme* PCC 73102 |
| 75906719 | complement(NC_007413.1: 617971 . . . 620352) | 295 | YP_321015.1 | 604 | *Anabaena variabilis* ATCC 29413 |
| 225522346 | NZ_ACIR01000182.1: 624 . . . 2756 | 296 | ZP_03769140.1 | 605 | *Nostoc azollae'* 0708 |
| 37520566 | NC_005125.1: 1065716 . . . 1068097 | 297 | NP_923943.1 | 606 | *Gloeobacter violaceus* PCC 7421 |
| 86608623 | NC_007776.1: 1182311 . . . 1184686 | 298 | YP_477385.1 | 607 | *Synechococcus* sp. JA-2-3B'a(2-13) |
| 150398192 | complement(NC_009636.1: 3144485 . . . 3146857) | 299 | YP_001328659.1 | 608 | *Sinorhizobium medicae* WSM419 |
| 116249832 | complement(NC_008380.1: 82152 . . . 84617) | 300 | YP_765670.1 | 609 | *Rhizobium leguminosarum* bv. *viciae* 3841 |
| 195970218 | complement(NC_003047.1: 123688 . . . 126141) | 301 | NP_384212.2 | 610 | *Sinorhizobium meliloti* 1021 |
| 171912985 | NZ_ABIZ01000001.1: 4370841 . . . 4373354 | 302 | ZP_02928455.1 | 611 | *Verrucomicrobium spinosum* DSM 4136 |
| 163849496 | complement(NC_010172.1: 46285 . . . 48720) | 303 | YP_001637539.1 | 612 | *Methylobacterium extorquens* PA1 |
| 85714839 | NZ_AAMY01000005.1: 72844 . . . 75210 | 304 | ZP_01045825.1 | 613 | *Nitrobacter* sp. Nb-311A |

TABLE 5-continued

SEQ ID NOs of xylulose-5-phosphate/fructose-6-phosphate phosphoketolase target gene coding regions and proteins.

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 168704325 | complement(NZ_ABGO01000323.1: 57 . . . 2462) | 305 | ZP_02736602.1 | 614 | *Gemmata obscuriglobus* UQM 2246 |
| 256829143 | complement(NC_013173.1: 1530488 . . . 1532881) | 306 | YP_003157871.1 | 615 | *Desulfomicrobium baculatum* DSM 4028 |
| 223939426 | complement(NZ_ABOX02000044.1: 41392 . . . 43863) | 307 | ZP_03631304.1 | 616 | *bacterium* Ellin514 |
| 237747078 | complement(NZ_GG658151.1: 2005797 . . . 2008190) | 308 | ZP_04577558.1 | 617 | *Oxalobacter formigenes* HOxBLS |
| 237749232 | complement(NZ_GG658170.1: 2042015 . . . 2044411) | 309 | ZP_04579712.1 | 618 | *Oxalobacter formigenes* OXCC13 |
| 116624013 | NC_008536.1: 6218168 . . . 6220537 | 310 | YP_826169.1 | 619 | *Solibacter usitatus* Ellin6076 |
| 194336959 | complement(NC_011060.1: 2004498 . . . 2006885) | 311 | YP_002018753.1 | 620 | *Pelodictyon phaeoclathratiforme* BU-1 |
| 194334425 | complement(NC_011059.1: 1762093 . . . 1764489) | 312 | YP_002016285.1 | 621 | *Prosthecochloris aestuarii* DSM 271 |
| 189346840 | complement(NC_010803.1: 1427679 . . . 1430054) | 313 | YP_001943369.1 | 622 | *Chlorobium limicola* DSM 245 |
| 21674344 | complement(NC_002932.3: 1423776 . . . 1426289) | 314 | NP_662409.1 | 623 | *Chlorobium tepidum* TLS |
| 110597897 | complement(NZ_AASE01000009.1: 37756 . . . 40179) | 315 | ZP_01386179.1 | 624 | *Chlorobium ferrooxidans* DSM 13031 |
| 78187379 | complement(NC_007512.1: 1709621 . . . 1712050) | 316 | YP_375422.1 | 625 | *Chlorobium luteolum* DSM 273 |
| 71907690 | complement(NC_007298.1: 2220090 . . . 2222456) | 317 | YP_285277.1 | 626 | *Dechloromonas aromatica* RCB |
| 74316849 | NC_007404.1: 876540 . . . 878978 | 318 | YP_314589.1 | 627 | *Thiobacillus denitrificans* ATCC 25259 |
| 91775246 | complement(NC_007947.1: 935825 . . . 938200) | 319 | YP_545002.1 | 628 | *Methylobacillus flagellatus* KT |
| 30250069 | NC_004757.1: 2318109 . . . 2320481 | 320 | NP_842139.1 | 629 | *Nitrosomonas europaea* ATCC 19718 |
| 114332052 | NC_008344.1: 2209596 . . . 2211971 | 321 | YP_748274.1 | 630 | *Nitrosomonas eutropha* C91 |
| 82702122 | NC_007614.1: 1152112 . . . 1154535 | 322 | YP_411688.1 | 631 | *Nitrosospira multiformis* ATCC 25196 |
| 77166175 | NC_007484.1: 3082455 . . . 3084869 | 323 | YP_344700.1 | 632 | *Nitrosococcus oceani* ATCC 19707 |
| 46445639 | complement(NC_005861.1: 5907 . . . 8303) | 324 | YP_007004.1 | 633 | *Candidatus Protochlamydia amoebophila* UWE25 |
| 16263040 | complement(NC_003037.1: 591065 . . . 593440) | 325 | NP_435833.1 | 634 | *Sinorhizobium meliloti* 1021 |
| 229532493 | NZ_ABUV01000006.1: 47234 . . . 49585 | 326 | ZP_04421874.1 | 635 | *Sulfurospirillum deleyianum* DSM 6946 |
| 13475490 | NC_002678.2: 5384229 . . . 5386652 | 327 | NP_107054.1 | 636 | *Mesorhizobium loti* MAFF303099 |
| 209885940 | complement(NC_011386.1: 2786353 . . . 2788746) | 328 | YP_002289797.1 | 637 | *Oligotropha carboxidovorans* OM5 |
| 182679166 | NC_010581.1: 2524033 . . . 2526420 | 329 | YP_001833312.1 | 638 | *Beijerinckia indica* subsp. *indica* ATCC 9039 |

Numerous examples of polynucleotides, genes and/or polypeptides encoding phosphotransacetylase are known in the art and can be used in relation to the recombinant host cells disclosed herein. In embodiments, the phosphotransacetylase can be EutD from *Lactobacillus plantarum*. In embodiments, the phosphotransacetylase can be the phosphotransacetylase from *Bacillus subtilis*. This phosphotransacetylase has a specific activity of 1371 μmol/min/mg and a Km 0.06 mM for acetyl-CoA (Rado and Hoch, *Biochim. Biophys. Acta.* 321: 114-25; 1973). In addition, the equilibrium constant (Keq) of this reaction was found to be 154±14 in favor of the formation of acetyl-CoA according to the following formula:

$$\frac{[acetyl\text{-}CoA][Pi]}{[CoA][acetyl\text{-}P]} = Keq$$

In embodiments, host cells comprise a polypeptide having at least about 80%, at least about 85%, at least about 90%, or at least about 99% identity to a polypeptide of Table 10 or an active fragment thereof or a polynucleotide encoding such a polypeptide. In embodiments, the phosphotransacetylase can be a polypeptide having at least about 80%, at least about 85%, at least about 90%, at least about 95%, or at least about 99% identity to SEQ ID NO: 1472 or an active fragment thereof. In other embodiments, a polynucleotide, gene and/or polypeptide encoding phosphotransacetylase can include, but is not limited to, a sequence provided in the following tables 10 or 12.

in the following organisms: *S. enterica, E. coli* K12, *V. Parvula, C. Kluyveri, C. Acetobutylicum, C. Thermocellum, M. thermophila, S. pyogenes, B. subtilis, L. fermentum, L. plantarum, L. sanfranciscensis, B. subtilis, L. fermentum, L. plantarum, L. sanfranciscensis, R. palustris, E. coli*.

Experimentally verified phosphate acetyltransferases (EC 2.3.1.8) belong to the PTA_PTB pfam family. However, the PTA_PTB domain is present in 13 distinct architectures (http://pfam.janelia.org/family/PF01515, Pfam database version 24). The motivation for investigating the domain architecture is to determine which of the proteins, that were identified by BLAST search, are likely to be phosphate acetyltransferases. Experimentally verified sequences extracted from the BRENDA database as well as sequences retained after the CD-HIT clustering and clean-up, were searched against the Pfam database to determine their domain architecture. Pfam is a collection of multiple sequence alignments and profile hidden Markov models (HMMs). Each Pfam HMM represents a protein family or domain. By searching a protein sequence against the Pfam library of HMMs, it is possible to determine which domains it carries i.e. its domain architecture. (*The Pfam protein families database*: R. D. Finn, J. Tate, J. Mistry, P. C. Coggill, J. S. Sammut, H. R. Hotz, G. Ceric, K. Forslund, S. R. Eddy, E. L. Sonnhammer and A. Bateman Nucleic Acids Research (2008) Database Issue 36:D281-D288)

Twelve of the experimentally verified proteins only contained the PTA_PTB domain. Two sequences, from *R. palustris* and *E. coli*, contained two domains PTA_PTB and DRTGG, a domain of unknown function. Therefore, from

TABLE 10

SEQ ID NOs of phosphotransacetylase target gene coding regions and proteins.

| Description | SEQ ID NO: Nucleic acid | SEQ ID NO: Amino acid | Amino acid sequence |
| --- | --- | --- | --- |
| EutD phosphotransacetylase from *Lactobacillus plantarum* | 1111 | 1472 | MDLFESLAQKITGKDQTIVFPEGTEPRIVGAAARLAADGLVKPIVLGATDKVQAVANDLN ADLTGVQVLDPATYPAEDKQAMLDALVERRKGKNTPEQAAKMLEDENYFGTMLVYMGKAD GMVSGAIHPTGDTVRPALQIIKTKPGSHRISGAFIMQKGEERYVFADCAINIDPDADTLA EIATQSAATAKVFDIDPKVAMLSFSTKGSAKGEMVTKVQEATAKAQAAEPELAIDGELQF DAAFVEKVGLQKAPGSKVAGHANVFVFPELQSGNIGYKIAQRFGHFEAVGPVLQGLNKPV SDLSRGCSEEDVYKVAIITAAQGLA |
| Phosphotransacetylase from *Bacillus subtilis* | 1061 | 1422 | MADLFSTVQEKVAGKDVKIVFPEGLDERILEAVSKLAGNKVLNPIVIGNENEIQAKAKEL NLTLGGVKIYDPHTYEGMEDLVQAFVERRKGKATEEQARKALLDENYFGTMLVYKGLADG LVSGAAHSTADTVRPALQIIKTKEGVKKTSGVFIMARGEEQYVFADCAINIAPDSQDLAE IAIESANTAKMFDIEPRVAMLSFSTKGSAKSDETEKVADAVKIAKEKAPELTLDGEFQFD AAFVPSVAEKKAPDSEIKGDANVFVFPSLEAGNIGYKIAQRLGNFEAVGPILQGLNMPVN DISRGCNAEDVYNLALITAAQAL |

Additional suitable phosphotransacetylase target gene coding regions and proteins were identified by diversity searching and clustering. A blast search of the non redundant GenBank protein database (NR) was performed with the *L. plantarum* EutD protein as a query sequence. A blast cut-off (Evalue) of 0.01 was applied. This search resulted in 2124 sequence matches. Redundancy reduction was achieved by clustering proteins with the CD-HIT program with parameters set at 95% sequence identity and 90% length overlap. The longest seed sequence, representative of each cluster, is retained for further analysis. Clustering reduced the number of protein sequences to 1336. Further clean-up of the sequences by removing sequences<280 amino acids and sequences>795 amino acids resulted in 1231 seqs.

The Brenda database was queried for experimentally verified phosphate acetyltransferases. Thirteen were found the CD-HIT clustering results, proteins that contained either the PTA_PTB domain only (Group 1: 549 sequences) or a combination of PTA_PTB+DRTGG domains (Group 2: 201 sequences) were chosen.

Furthermore, the PTA_PTB domain, as the name indicates, is actually not specific to phosphate acetyltransferases. The domain is also a signature for phosphate butyryltransferases (EC 2.3.1.19). Two methods to distinguish between the two subfamilies: acetyltransferases and butyryltransferases were employed and are as follows:

To further characterize the relationship among the sequences, multiple sequence alignment MSA), phylogenetic analysis, profile HMMs and GroupSim analysis were performed. For this set of analyses, the phosphate acetyltransferases are split in two groups. Group 1 contains phosphate acetyltransferases with the PTA_PTB domain only, while Group 2 contains phosphate acetyltransferases with PTA_PTB+DRTGG. The motivation here is to generate groups with similar lengths.

Clustal X, version 2.0 was used for sequence alignments with default parameters. (Thompson J D, et al. The CLUSTAL_X windows interface: flexible strategies for multiple sequence alignment aided by quality analysis tools. *Nucleic Acids Res.* (1997) 25:4876-4882.)

Alignment results were utilized to compute % sequence identities to a reference sequence. If the sequence from *L. plantarum* is taken as a reference, % IDs range from as low as 10.5% to 75.6% for the closest sequence. Alignment results also provided the basis for re-constructing phylogenetic trees. The Neighbor Joining method, available in the Jalview package version 2.3, was used to produce the trees, and computed trees were visualized in MEGA 4 (Tamura, Dudley, Nei, and Kumar 2007). The Neighbor Joining method is a method for re-constructing phylogenetic trees, and computing the lengths of the branches of this tree. In each stage, the two nearest nodes of the tree (the term "nearest nodes" will be defined in the following paragraphs) are chosen and defined as neighbors in our tree. This is done recursively until all of the nodes are paired together. "The neighbor-joining method: a new method for reconstructing phylogenetic trees. Mol Biol Evol. 1987 July; 4(4):406-25. Saitou N, Nei M." Jalview Version 2 is a system for interactive editing, analysis and annotation of multiple sequence alignments (Waterhouse, A. M., Procter, J. B., Martin, D. M. A, Clamp, M. and Barton, G. J. (2009) "Jalview Version 2—a multiple sequence alignment editor and analysis workbench" *Bioinformatics* 25 (9) 1189-1191). The MEGA software provides tools for exploring, discovering, and analyzing DNA and protein sequences from an evolutionary perspective. MEGA4 enables the integration of sequence acquisition with evolutionary analysis. It contains an array of input data and multiple results explorers for visual representation; the handling and editing of sequence data, sequence alignments, inferred phylogenetic trees; and estimated evolutionary distances. The results explorers allow users to browse, edit, summarize, export, and generate publication-quality captions for their results. MEGA 4 also includes distance matrix and phylogeny explorers as well as advanced graphical modules for the visual representation of input data and output results (Tamura K, Dudley J, Nei M & Kumar S (2007) MEGA4: Molecular Evolutionary Genetics Analysis (MEGA) software version 4.0. Molecular Biology and Evolution 24:1596-1599).

Taken together, % IDs and the generated tree (FIG. 4) indicated that potential phosphate acetyltransferases (PTA_PTB domain only) are divided in two major subfamilies. Subfamily 1 from 10.5% ID to ~20% ID (176 sequences) and Subfamily 2 from ~20% ID to 75.6% ID (361 sequences). The third Subfamily, of 12 sequences, has % ID ranging from 17% ID to 25% ID with respect to the *L. plantarum* sequence.

Based on experimentally verified sequences contained within each of the Subfamilies, Subfamily 1 and Subfamily 2 were determined to represent phosphate butyryltransferases (PTB) and phosphate acetyltransferases (PTA) respectively.

Discrimination between Subfamily 1 members and Subfamily 2 members was also performed by GroupSim analysis (Capra and Singh (2008) Bioinformatics 24: 1473-1480). The GroupSim method identifies amino acid residues that determine a protein's functional specificity. In a multiple sequence alignment (MSA) of a protein family whose sequences are divided into multiple Subfamilies, amino acid residues that distinguish between the functional Subfamilies of sequences can be identified. The method takes a multiple sequence alignment (MSA) and known specificity groupings as input, and assigns a score to each amino acid position in the MSA. Higher scores indicate a greater likelihood that an amino acid position is a specificity determining position (SDP).

GroupSim analysis performed on the MSA of 537 sequences (divided into Subfamily 1 and Subfamily 2 by the phylogenetic analysis above) identified highly discriminating positions. Listed in Table 11 are positions (Pos) having scores greater than to 0.7, where a perfect score of 1.0 would indicate that all proteins within the Subfamily have the listed amino acid in the specified position and between Subfamilies the amino acid would always be different. The "Pattern" columns give the amino acid(s) in single letter code. Numbers between parentheses indicate frequency of occurrence of each amino acid at the particular position. The amino acid position number in column 1 is for the PTA protein sequence from *Lactobacillus plantarum*, the representative protein of group 2 with a GI#28377658 (SEQ ID NO: 1472).

TABLE 11

Highly discriminating amino acid positions for Subfamily 1 (PTB) and Subfamily 2 (PTA) from GroupSim analysis.

| Pos | Score | Pattern PTB | Pattern PTA |
|---|---|---|---|
| 212 | 0.980314 | Group 1: E(173), D(2), L(1) | Group 2: S(360), N(1) |
| 305 | 0.87236 | Group 1: L(152), V(11), M(5), I(5), F(3) | Group 2: D(360), Q(1) |
| 242 | 0.831201 | Group 1: A(142), D(15), S(13), G(4), T(2) | Group 2: Q(361) |
| 208 | 0.776954 | Group 1: L(130), I(35), V(11) | Group 2: S(355), A(6) |
| 125 | 0.705868 | Group 1: K(175), R(1) | Group 2: S(215), A(85), G(41), C(14), N(4), T(2) |

An alternative structure/function characterization of the PTA and PTB subfamilies of enzymes was performed using the HMMER software package (the theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., 1994; J. Mol. Biol. 235:1501-1531), following the user guide which is available from HMMER (Janelia Farm Research Campus, Ashburn, Va.).

Using a multiple sequence alignment of the experimentally verified sequences (containing the PTA_PTB domain only) in Subfamily 2, a profile Hidden Markov Model (HMM) was created for representing Subfamily 2 members. The sequences were:
  1. BAB19267.1 from *Lactobacillus sanfranciscensis* (SEQ ID NO: 1475)
  2. NP_784550.1 from *Lactobacillus plantarum* WCFS1 (SEQ ID NO: 1472)
  3. ZP_03944466.1 from *Lactobacillus fermentum* ATCC 14931 (SEQ ID NO: 1453)
  4. NP_391646.1 from *Bacillus subtilis* subsp. *subtilis* str. 168 (SEQ ID NO: 1422)
  5. AAA72041.1 from *Methanosarcina thermophila* (SEQ ID NO: 1277)
  6. ZP_03152606.1 from *Clostridium thermocellum* DSM 4150 (SEQ ID NO: 1275)
  7. NP_348368.1 from *Clostridium acetobutylicum* ATCC 824 (SEQ ID NO: 1206)

8. YP_001394780.1 from *Clostridium kluyveri* DSM 555 (SEQ ID NO: 1200)
9. ZP_03855267.1 from *Veillonella parvula* DSM 2008 (SEQ ID NO: 1159)
10. YP_149725.1 from *Salmonella enterica* subsp. *enterica* serovar Paratyphi A str. ATCC 9150 (SEQ ID NO: 1129).

The Profile HMM was built as follows: The 10 seed sequences (sequences representing experimentally verified function) that are in Subfamily 2 were aligned using Clustal X (interface to Clustal W) with default parameters. The hmmbuild program was run on each set of the aligned sequences using default parameters. hmmbuild reads the multiple sequence alignment file, builds a new Profile HMM, and saves the Profile HMM to file. Using this program an un-calibrated profile was generated from the multiple alignment for each set of subunit sequences described above.

The Profile HMM was read using hmmcalibrate which scores a large number of synthesized random sequences with the Profile (the default number of synthetic sequences used is 5,000), fits an extreme value distribution (EVD) to the histogram of those scores, and re-saves the HMM file now including the EVD parameters. These EVD parameters ($\mu$ and $\lambda$) are used to calculate the E-values of bit scores when the profile is searched against a protein sequence database. hmmcalibrate writes two parameters into the HMM file on a line labeled "EVD": these parameters are the $\mu$ (location) and $\lambda$ (scale) parameters of an extreme value distribution (EVD) that best fits a histogram of scores calculated on randomly generated sequences of about the same length and residue composition as SWISS-PROT. This calibration was done once for the Profile HMM.

The calibrated profile HMM for the Subfamily 2 set is provided as Table 14. The Profile HMM table gives the probability of each amino acid occurring at each position in the amino acid sequence. The amino acids are represented by the one letter code. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E. Table 14 shows that in the Subfamily 2 profile HMM, methionine has a 3792 ans 4481 probability of being in the first two positions.

The Subfamily 2 profile HMM was evaluated using hmmsearch, with the Z parameter set to one billion, for the ability to discriminate Subfamily 1 members from those of Subfamily 2. The hmmsearch program takes the hmm file for the Subfamily 2 profile HMM and all the sequences from both Subfamilies and assigns an E-value score to each sequence. This E-value score is a measure of fit to the Profile HMM, with a lower score being a better fit. The Profile HMM distinguished Subfamily 2 members from Subfamily 1 members and there was a large margin of E-value difference between the worst scoring Subfamily 2 member (5e-34) and the best scoring Subfamily 1 member (4.3e-07). This analysis shows that the Profile HMM prepared for Subfamily 2 phosphate acetyltransferases (PTA) distinguishes PTA sequences from phosphate butyryltransferase PTB protein sequences.

Based on these analyses, 361 phosphate acetyltransferase sequences (PTA_PTB domain only) were identified and are provided in Table 12a.

TABLE 12a

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 255994631 | complement (NZ_ACON01000003.1: 407639 . . . 408607) | 762 | ZP_05427766.1 | 1123 | *Eubacterium saphenum* ATCC 49989 |
| 223935781 | NZ_ABOX02000007.1: 10458 . . . 11600 | 763 | ZP_03627696.1 | 1124 | bacterium Ellin514 |
| 196232920 | NZ_ABVL01000018.1: 134406 . . . 135449 | 764 | ZP_03131770.1 | 1125 | *Chthoniobacter flavus* Ellin428 |
| 187735919 | NC_010655.1: 1714393 . . . 1715484 | 765 | YP_001878031.1 | 1126 | *Akkermansia muciniphila* ATCC BAA-835 |
| 237732443 | complement (NZ_GG657366.1: 2437071 . . . 2438087 | 766 | ZP_04562924.1 | 1127 | *Citrobacter* sp. 30_2 |
| 157144617 | NC_009792.1: 326993 . . .328009 | 767 | YP_001451936.1 | 1128 | *Citrobacter koseri* ATCC BAA-895 |
| 56412650 | NC_006511.1 473496 . . . 474512 | 768 | YP_149725.1 | 1129 | *Salmonella enterica* subsp. *enterica* serovar Paratyphi A str. ATCC 9150 |
| 161502384 | NC_010067.1: 425125 . . . 426141 | 769 | YP_001569496.1 | 1130 | *Salmonella enterica* subsp. *arizonae* serovar 62:z4, z23:-- |
| 16130383 | complement (NC_000913.2: 2570511 . . . 2571527) | 770 | NP_416953.1 | 1131 | *Escherichia coli* str. K-12 substr. MG1655 |
| 238895918 | complement (NC_012731.1: 3863205 . . . 3864221) | 771 | YP_002920654.1 | 1132 | *Klebsiella pneumoniae* NTUH-K2044 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 238794182 | complement (NZ_AALF02000025.1: 17041 . . . 18039) | 772 | ZP_04637797.1 | 1133 | *Yersinia intermedia* ATCC 29909 |
| 90414632 | complement (NZ_AAPH01000046.1: 12550 . . . 13527) | 773 | ZP_01222604.1 | 1134 | *Photobacterium profundum* 3TCK |
| 163749608 | complement (NZ_ABIC01000008.1: 73942 . . . 74913) | 774 | ZP_02156855.1 | 1135 | *Shewanella benthica* KT99 |
| 120554157 | NC_008740.1: 1389827 . . . 1390810 | 775 | YP_958508.1 | 1136 | *Marinobacter aquaeolei* VT8 |
| 51246887 | complement (NC_006138.1: 3433697 . . . 3434677) | 776 | YP_066771.1 | 1137 | *Desulfotalea psychrophila* LSv54 |
| 226362753 | complement (NC_012522.1: 3613049 . . . 3614074) | 777 | YP_002780531.1 | 1138 | *Rhodococcus opacus* B4 |
| 111020534 | complement (NC_008268.1: 3751557 . . . 3752585) | 778 | YP_703506.1 | 1139 | *Rhodococcus jostii* RHA1 |
| 256669010 | NZ_ACEV01000044.1: 80096 . . . 81085 | 779 | ZP_05479963.1 | 1140 | *Streptomyces* sp. AA4 |
| 226227292 | complement (NC_012489.1: 2203452 . . . 2204474) | 780 | YP_002761398.1 | 1141 | *Gemmatimonas aurantiaca* T-27 |
| 239627158 | complement (NZ_DS990260.1: 924717 . . . 925736) | 781 | ZP_04670189.1 | 1142 | *Clostridiales bacterium* 1_7_47FAA |
| 256753163 | complement (NZ_ACXX01000001.1: 167634 . . . 168635) | 782 | ZP_05493958.1 | 1143 | *Clostridium papyrosolvens* DSM 2782 |
| 257063834 | NC_013165.1: 1278820 . . 1279818 | 783 | YP_003143506.1 | 1144 | *Slackia heliotrinireducens* DSM 20476 |
| 254477436 | NZ_DS999054.1: 3384063 . . . 3384914 | 784 | ZP_05090822.1 | 1145 | *Ruegeria* sp. R11 |
| 126732220 | complement (NZ_AAYA01000016.1: 68052 . . . 68996) | 785 | ZP_01748021.1 | 1146 | *Sagittula stellata* E-37 |
| 19704507 | complement (NC_003454.1: 1833702 . . . 1834715) | 786 | NP_604069.1 | 1147 | *Fusobacterium nucleatum* subsp. *nucleatum* ATCC 25586 |
| 260494604 | NZ_GG704456.1: 222376 . . . 223389 | 787 | ZP_05814734.1 | 1148 | *Fusobacterium* sp. 3_1_33 |
| 262067001 | complement (NZ_ACJY01000064.1: 9865 . . . 10869) | 788 | ZP_06026613.1 | 1149 | *Fusobacterium periodonticum* ATCC 33693 |
| 257452333 | complement (NZ_ACDD01000037.1: 1250 . . . 2263) | 789 | ZP_05617632.1 | 1150 | *Fusobacterium* sp. 3_1_5R |
| 257463639 | NZ_ACDG01000104.1: 17109 . . . 18122 | 790 | ZP_05628030.1 | 1151 | *Fusobacterium* sp. D12 |
| 253583748 | complement (NZ_GG696122.1: 645905 . . . 646912) | 791 | ZP_04860946.1 | 1152 | *Fusobacterium varium* ATCC 27725 |
| 237736963 | NZ_GG657909.1: 489336 . . . 490343 | 792 | ZP_04567444.1 | 1153 | *Fusobacterium mortiferum* ATCC 9817 |
| 157736754 | complement (NC_009850.1: 500921 . . . 501916) | 793 | YP_001489437.1 | 1154 | *Arcobacter butzleri* RM4018 |
| 257125122 | NC_013192.1: 327731 . . . 328735 | 794 | YP_003163236.1 | 1155 | *Leptotrichia buccalis* C-1013-b |
| 260891157 | NZ_ACVB02000026.1: 170989 . . . 171993 | 795 | ZP_05902420.1 | 1156 | *Leptotrichia hofstadii* F0254 |
| 262037878 | complement (NZ_ADAD01000064.1: 9188 . . . 10195) | 796 | ZP_06011308.1 | 1157 | *Leptotrichia goodfellowii* F0264 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 229859891 | NZ_ABUT01000004.1: 63190 . . . 64215 | 797 | ZP_04479548.1 | 1158 | *Streptobacillus moniliformis* DSM 12112 |
| 227371784 | NZ_ABVB01000002.1: 260421 . . . 261419 | 798 | ZP_03855267.1 | 1159 | *Veillonella parvula* DSM 2008 |
| 227498373 | complement (NZ_ACGB01000001.1: 109630 . . . 110643) | 799 | ZP_03928523.1 | 1160 | *Acidaminococcus* sp. D21 |
| 42525561 | NC_002967.9: 48816 . . . 49823 | 800 | NP_970659.1 | 1161 | *Treponema denticola* ATCC 35405 |
| 257456313 | NZ_ACYH01000011.1: 210840 . . . 211847 | 801 | ZP_05621510.1 | 1162 | *Treponema vincentii* ATCC 35580 |
| 15639088 | NC_000919.1: 102879 . . . 103889 | 802 | NP_218534.1 | 1163 | *Treponema pallidum* subsp. *pallidum* str. Nichols |
| 228000316 | complement (NZ_ABTG01000001.1: 1179041 . . . 1180048) | 803 | ZP_04047318.1 | 1164 | *Brachyspira murdochii* DSM 12563 |
| 225619252 | NC_012225.1: 340269 . . . 341276 | 804 | YP_002720478.1 | 1165 | *Brachyspira hyodysenteriae* WA1 |
| 218960931 | complement (NS_000195.1: 716420. . . 717424) | 805 | YP_001740706.1 | 1166 | *Candidatus Cloacamonas acidaminovorans* |
| 239878221 | complement (join(GG681098.1: 49679 . . . 49966, GG681098.1: 50017 . . . 50325, GG681098.1: 50380 . . . 50442, GG681098.1: 50494 . . . 50605, GG681098.1: 50656 . . . 50780, GG681098.1: 50826 . . . 50908, GG681098.1: 50958 . . . 51039)) | 806 | EER05013.1 | 1167 | *Perkinsus marinus* ATCC 50983 |
| 119953373 | NC_008710.1: 614125 . . . 615171 | 807 | YP_945582.1 | 1168 | *Borrelia turicatae* 91E135 |
| 187918450 | NC_010673.1: 616784 . . . 617842 | 808 | YP_001884013.1 | 1169 | *Borrelia hermsii* DAH |
| 203284493 | NC_011229.1: 622676 . . . 623746 | 809 | YP_002222233.1 | 1170 | *Borrelia duttonii* Ly |
| 224534734 | complement (NZ_ABKB02000009.1: 27640 . . . 28677) | 810 | ZP_03675306.1 | 1171 | *Borrelia spielmanii* A14S |
| 216263399 | NZ_ABCU02000001.1: 172066 . . . 173103 | 811 | ZP_03435394.1 | 1172 | *Borrelia afzelii* ACA-1 |
| 219685198 | NZ_ABPZ02000001.1: 172004 . . . 173041 | 812 | ZP_03540018.1 | 1173 | *Borrelia garinii* Far04 |
| 224532296 | NZ_ABCY02000001.1: 609419 . . . 610456 | 813 | ZP_03672928.1 | 1174 | *Borrelia valaisiana* VS116 |
| 15594934 | NC_001318.1: 608020 . . . 609078 | 814 | NP_212723.1 | 1175 | *Borrelia burgdorferi* B31 |
| 189485346 | NS_000191.1: 518918 . . . 519919 | 815 | YP_001956287.1 | 1176 | uncultured Termite group 1 bacterium phylotype Rs-D17 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 42560817 | NC_005364.2: 308545 . . . 309513 | 816 | NP_975268.1 | 1177 | *Mycoplasma mycoides* subsp. *mycoides* SC str. PG1 |
| 83319483 | NC_007633.1: 277239 . . . 278207 | 817 | YP_424216.1 | 1178 | *Mycoplasma capricolum* subsp. *capricolum* ATCC 27343 |
| 50364858 | NC_006055.1: 58892 . . . 59860 | 818 | YP_053283.1 | 1179 | *Mesoplasma florum* L1 |
| 110005214 | complement (AM285317.1: 14153 . . . 15130) | 819 | CAK99540.1 | 1180 | *Spiroplasma citri* |
| 12045155 | complement (NC_000908.2: 368733 . . . 369695) | 820 | NP_072966.1 | 1181 | *Mycoplasma genitalium* G37 |
| 13508167 | complement (NC_000912.1: 515605 . . . 516567) | 821 | NP_110116.1 | 1182 | *Mycoplasma pneumoniae* M129 |
| 31544825 | complement (NC_004829.1: 851083 . . . 852075) | 822 | NP_853403.1 | 1183 | *Mycoplasma gallisepticum* R |
| 26553955 | complement (NC_004432.1: 640803 . . . 641777) | 823 | NP_757889.1 | 1184 | *Mycoplasma penetrans* HF-2 |
| 54020554 | complement (NC_006360.1: 638554 . . . 639507) | 824 | YP_116016.1 | 1185 | *Mycoplasma hyopneumoniae* 232 |
| 240047219 | NC_012806.1: 88435 . . . 89406 | 825 | YP_002960607.1 | 1186 | *Mycoplasma conjunctivae* |
| 148377406 | NC_009497.1: 159649 . . . 160605 | 826 | YP_001256282.1 | 1187 | *Mycoplasma agalactiae* PG2 |
| 238809713 | complement (AP009608.1: 242111 . . . 243064) | 827 | BAH69503.1 | 1188 | *Mycoplasma fermentans* PG18 |
| 71894663 | complement (NC_007294.1: 757812 . . . 758771) | 828 | YP_278771.1 | 1189 | *Mycoplasma synoviae* 53 |
| 15828708 | NC_002771.1: 274992 . . . 275948 | 829 | NP_326068.1 | 1190 | *Mycoplasma pulmonis* UAB CTIP |
| 47459003 | NC_006908.1: 230100 . . . 231068 | 830 | YP_015865.1 | 1191 | *Mycoplasma mobile* 163K |
| 148377754 | NC_009497.1: 572993 . . . 573967 | 831 | YP_001256630.1 | 1192 | *Mycoplasma agalactiae* PG2 |
| 116515056 | NC_008513.1: 131608 . . . 132594 | 832 | YP_802685.1 | 1193 | *Buchnera aphidicola* str. Cc (*Cinara cedri*) |
| 187934490 | NC_010674.1: 1263289 . . . 1264287 | 833 | YP_001885432.1 | 1194 | *Clostridium botulinum* B str. Eklund 17B |
| 150016048 | NC_009617.1: 1384403 . . . 1385404 | 834 | YP_001308302.1 | 1195 | *Clostridium beijerinckii* NCIMB 8052 |
| 254519224 | complement (NZ_EQ999773.1: 2015491 . . . 2016492) | 835 | ZP_05131280.1 | 1196 | *Clostridium* sp. 7_2_43FAA |
| 182417251 | NZ_ABDT01000035.2: 9769 . . . 10770 | 836 | ZP_02948604.1 | 1197 | *Clostridium butyricum* 5521 |
| 18310707 | complement (NC_003366.1: 2001712 . . . 2002719) | 837 | NP_562641.1 | 1198 | *Clostridium perfringens* str. 13 |
| 255524273 | complement (NZ_ACVI01000014.1: 63543 . . . 64547) | 838 | ZP_05391232.1 | 1199 | *Clostridium carboxidivorans* P7 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 153954015 | NC_009706.1: 1428554 . . . 1429555 | 839 | YP_001394780.1 | 1200 | *Clostridium kluyveri* DSM 555 |
| 187778946 | NZ_ABKW02000004.1: 733017 . . . 734015 | 840 | ZP_02995419.1 | 1201 | *Clostridium sporogenes* ATCC 15579 |
| 28210926 | NC_004557.1: 1326340 . . . 1327359 | 841 | NP_781870.1 | 1202 | *Clostridium tetani* E88 |
| 253681395 | NZ_ACSJ01000007.1: 344343 . . . 345338 | 842 | ZP_04862192.1 | 1203 | *Clostridium botulinum* D str. 1873 |
| 118444574 | complement (NC_008593.1: 1416375 . . . 1417373) | 843 | YP_878298.1 | 1204 | *Clostridium novyi* NT |
| 242260238 | NZ_ACPD01000011.1: 83320 . . . 84318 | 844 | ZP_04804960.1 | 1205 | *Clostridium cellulovorans* 743B |
| 15895019 | NC_003030.1: 1890289 . . . 1891290 | 845 | NP_348368.1 | 1206 | *Clostridium acetobutylicum* ATCC 824 |
| 169247670 | EU313773.1: 40 . . . 1026 | 846 | ACA51668.1 | 1207 | *Thermoanaerobacterium saccharolyticum* |
| 255257449 | NZ_ACVG01000034.1: 8635 . . . 9621 | 847 | ZP_05336886.1 | 1208 | *Thermoanaerobacterium thermosaccharolyticum* DSM 571 |
| 20807926 | complement (NC_003869.1: 1451520 . . . 1452515) | 848 | NP_623097.1 | 1209 | *Thermoanaerobacter tengcongensis* MB4 |
| 167040369 | complement (NC_010320.1: 1738259 . . . 1739257) | 849 | YP_001663354.1 | 1210 | *Thermoanaerobacter* sp. X514 |
| 220931863 | NC_011899.1: 1110901 . . . 1111899 | 850 | YP_002508771.1 | 1211 | *Halothermothrix orenii* H 168 |
| 258514457 | complement (NC_013216.1: 1194895 . . . 1195899) | 851 | YP_003190679.1 | 1212 | *Desulfotomaculum acetoxidans* DSM 771 |
| 188586231 | complement (NC_010718.1: 1692944 . . . 1693942) | 852 | YP_001917776.1 | 1213 | *Natranaerobius thermophilus* JW/NM-WN-LF |
| 78044760 | complement (NC_007503.1: 1302969 . . . 1303973) | 853 | YP_360288.1 | 1214 | *Carboxydothermus hydrogenoformans* Z-2901 |
| 262295620 | complement (GG705150.1: 648642 . . . 649655) | 854 | EEY83551.1 | 1215 | *Bacteroides* sp. 2_1_33B |
| 154494088 | complement (NZ_AAXE02000107.1: 241237 . . . 242250) | 855 | ZP_02033408.1 | 1216 | *Parabacteroides merdae* ATCC 43184 |
| 34540818 | complement (NC_002950.2: 1149763 . . . 1150773) | 856 | NP_905297.1 | 1217 | *Porphyromonas gingivalis* W83 |
| 228471187 | complement (NZ_ACLR01000214.1: 23231 . . . 24238) | 857 | ZP_04056000.1 | 1218 | *Porphyromonas uenonis* 60-3 |
| 229496164 | NZ_ACNN01000020.1: 205218 . . . 206225 | 858 | ZP_04389884.1 | 1219 | *Porphyromonas endodontalis* ATCC 35406 |
| 160887812 | complement (NZ_AAY1302000031.1: 6367 . . . 7386) | 859 | ZP_02068815.1 | 1220 | *Bacteroides uniformis* ATCC 8492 |
| 218131945 | NZ_ABVO01000052.1: 25694 . . . 26710 | 860 | ZP_03460749.1 | 1221 | *Bacteroides eggerthii* DSM 20697 |
| 224536405 | complement (NZ_ACCH01000118.1: 1796 . . . 2812) | 861 | ZP_03676944.1 | 1222 | *Bacteroides cellulosilyticus* DSM 14838 |
| 53711769 | NC_006347.1: 557297 . . . 558316 | 862 | YP_097761.1 | 1223 | *Bacteroides fragilis* YCH46 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 237715344 | complement (NZ_EQ973249.1: 217217 . . . 218236) | 863 | ZP_04545825.1 | 1224 | Bacteroides sp. D1 |
| 224025178 | NZ_ACBW01000140.1: 3350 . . . 4369 | 864 | ZP_03643544.1 | 1225 | Bacteroides coprophilus DSM 18228 |
| 198274546 | NZ_ABQC02000011.1: 44269 . . . 45279 | 865 | ZP_03207078.1 | 1226 | Bacteroides plebeius DSM 17135 |
| 150003111 | NC_009614.1: 740818 . . . 741831 | 866 | YP_001297855.1 | 1227 | Bacteroides vulgatus ATCC 8482 |
| 258649233 | complement (NZ_ACIJ02000031.1: 14596 . . . 15612) | 867 | ZP_05736702.1 | 1228 | Prevotella tannerae ATCC 51259 |
| 261881160 | NZ_ACKS01000109.1: 4227 . . . 5276 | 868 | ZP_06007587.1 | 1229 | Prevotella bergensis DSM 17361 |
| 260593477 | NZ_ACVA01000073.1: 31053 . . . 32099 | 869 | ZP_05858935.1 | 1230 | Prevotella veroralis F0319 |
| 260910323 | complement (NZ_ACZS01000043.1: 34220 . . . 35257) | 870 | ZP_05916997.1 | 1231 | Prevotella sp. oral taxon 472 str. F0295 |
| 212550465 | complement (NC_011565.1: 126538 . . . 127539) | 871 | YP_002308782.1 | 1232 | Candidatus Azobacteroides pseudotrichonymphae genomovar. CFP2 |
| 114566305 | NC_008346.1: 872558 . . . 873550 | 872 | YP_753459.1 | 1233 | Syntrophomonas wolfei subsp. wolfei str. Goettingen |
| 139437229 | NZ_AAVN02000001.1: 368246 . . . 369226 | 873 | ZP_01771389.1 | 1234 | Collinsella aerofaciens ATCC 25986 |
| 210631306 | complement (NZ_ABXJ01000041.1: 3328 . . . 4308) | 874 | ZP_03296849.1 | 1235 | Collinsella stercoris DSM 13279 |
| 229814970 | complement (NZ_ABXH02000002.1: 65772 . . . 66770) | 875 | ZP_04445308.1 | 1236 | Collinsella intestinalis DSM 13280 |
| 221194458 | complement (NZ_ACFE01000001.1: 86128 . . . 87273) | 876 | ZP_03567515.1 | 1237 | Atopobium rimae ATCC 49626 |
| 257784450 | complement (NC_013203.1: 723329 . . . 724309) | 877 | YP_003179667.1 | 1238 | Atopobium parvulum DSM 20469 |
| 227516084 | complement (NZ_ACGK01000007.1: 63717 . . . 64691) | 878 | ZP_03946133.1 | 1239 | Atopobium vaginae DSM 15829 |
| 227872296 | NZ_ACKX01000061.1: 10209 . . . 11261 | 879 | ZP_03990654.1 | 1240 | Oribacterium sinus F0268 |
| 229824780 | NZ_ACIN02000002.1: 126870 . . . 127931 | 880 | ZP_04450849.1 | 1241 | Abiotrophia defectiva ATCC 49176 |
| 260443831 | NZ_ACIQ01000073.1: 32192 . . . 33196 | 881 | ZP_05797601.1 | 1242 | Oribacterium sp. oral taxon 078 str. F0262 |
| 225176688 | complement (NZ_ACFX01000006.1: 113088 . . . 114089) | 882 | ZP_03730247.1 | 1243 | Clostridium sp. M62/1 |
| 253578981 | complement (NZ_GG696046.1: 364564 . . . 365595) | 883 | ZP_04856252.1 | 1244 | Ruminococcus sp. 5_1_39BFAA |
| 153813664 | NZ_AAVO02000036.1: 4823 . . . 5992 | 884 | ZP_01966332.1 | 1245 | Ruminococcus obeum ATCC 29174 |
| 255281061 | complement (NZ_ACCL02000005.1: 162813 . . . 163811) | 885 | ZP_05345616.1 | 1246 | Bryantella formatexigens DSM 14469 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 225571965 | NZ_ACBZ01000008.1: 1408 . . . 2442 | 886 | ZP_03780829.1 | 1247 | *Blautia hydrogenotrophica* DSM 10507 |
| 210612569 | NZ_ABWO01000095.2: 3132 . . . 4127 | 887 | ZP_03289360.1 | 1248 | *Clostridium nexile* DSM 1787 |
| 154505354 | complement (NZ_AAYG02000022.1: 50151 . . . 51146) | 888 | ZP_02042092.1 | 1249 | *Ruminococcus gnavus* ATCC 29149 |
| 197303064 | NZ_ABOU02000039.1: 71843 . . . 72838 | 889 | ZP_03168112.1 | 1250 | *Ruminococcus lactaris* ATCC 29176 |
| 153816169 | complement (NZ_AAVP02000015.1: 36559 . . . 37554) | 890 | ZP_01968837.1 | 1251 | *Ruminococcus torques* ATCC 27756 |
| 167758299 | complement (NZ_ABFY02000009.1: 238358 . . . 239380) | 891 | ZP_02430426.1 | 1252 | *Clostridium scindens* ATCC 35704 |
| 225570721 | NZ_ABYI02000032.1: 3477 . . . 4499 | 892 | ZP_03779744.1 | 1253 | *Clostridium hylemonae* DSM 15053 |
| 166031766 | NZ_AAXA02000013.1: 54410 . . . 55414 | 893 | ZP_02234595.1 | 1254 | *Dorea formicigenerans* ATCC 27755 |
| 153853264 | complement (NZ_AAXB02000002.1: 216862 . . . 217857) | 894 | ZP_01994673.1 | 1255 | *Dorea longicatena* DSM 13814 |
| 160879474 | NC_010001.1: 1657582 . . . 1658577 | 895 | YP_01558442.1 | 1256 | *Clostridium phytofermentans* ISDg |
| 239624054 | complement (NZ_DS990263.1: 658578 . . . 659573) | 896 | ZP_04667085.1 | 1257 | *Clostridiales bacterium* 1_7_47FAA |
| 160938034 | complement (NZ_ABCC02000027.1: 52316 . . . 53311) | 897 | ZP_02085391.1 | 1258 | *Clostridium bolteae* ATCC BAA-613 |
| 260437037 | complement (NZ_ABWN01000017.1: 33488 . . . 34483) | 898 | ZP_05790853.1 | 1259 | *Butyrivibrio crossotus* DSM 2876 |
| 154483586 | complement (NZ_AAVL02000033.1: 74910 . . . 75941) | 899 | ZP_02026034.1 | 1260 | *Eubacterium ventriosum* ATCC 27560 |
| 238916996 | complement (NC_012778.1: 1076225 . . . 1077220) | 900 | YP_002930513.1 | 1261 | *Eubacterium eligens* ATCC 27750 |
| 242309058 | NZ_DS990446.1: 108718 . . . 109737 | 901 | ZP_04808213.1 | 1262 | *Helicobacter pullorum* MIT 98-5489 |
| 224418114 | complement (NZ_ABQS01000024.1: 18744 . . . 19745) | 902 | ZP_03656120.1 | 1263 | *Helicobacter canadensis* MIT 98-5491 |
| 237752737 | NZ_GG661974.1: 463241 . . . 464236 | 903 | ZP_04583217.1 | 1264 | *Helicobacter winghamensis* ATCC BAA-430 |
| 32266808 | complement (NC_004917.1: 1266998 . . . 1267993) | 904 | NP_860840.1 | 1265 | *Helicobacter hepaticus* ATCC 51449 |
| 224436915 | complement (NZ_ABQT01000013.1: 10506 . . . 11522) | 905 | ZP_03657896.1 | 1266 | *Helicobacter cinaedi* CCUG 18818 |
| 167745652 | complement (NZ_ABAX03000002.1: 101957 . . . 102961) | 906 | ZP_02417779.1 | 1267 | *Anaerostipes caccae* DSM 14662 |
| 167765558 | complement (NZ_ABGC03000004.1: 50807 . . . 51820) | 907 | ZP_02437622.1 | 1268 | *Clostridium* sp. SS2/1 |
| 163814038 | NZ_ABEY02000003.1: 15727 . . . 16794 | 908 | ZP_02205430.1 | 1269 | *Coprococcus eutactus* ATCC 27759 |
| 168334441 | complement (NZ_ABEQ01000029.2: 21420 . . . 22418) | 909 | ZP_02692616.1 | 1270 | *Epulopiscium* sp. 'N.t. morphotype B' |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 257791476 | NC_013204.1: 2035882 . . . 2036880 | 910 | YP_003182082.1 | 1271 | Eggerthella lenta DSM 2243 |
| 256827068 | complement (NC_013170.1: 735166 . . . 736167) | 911 | YP_003151027.1 | 1272 | Cryptobacterium curtum DSM 15641 |
| 257063929 | complement (NC_013165.1: 1407526 . . . 1408521) | 912 | YP_003143601.1 | 1273 | Slackia heliotrinireducens DSM 20476 |
| 256757417 | complement (NZ_ACXX01000078.1: 7706 . . . 8701) | 913 | ZP_05498135.1 | 1274 | Clostridium papyrosolvens DSM 2782 |
| 196254011 | NZ_ABVG01000076.1: 9016 . . . 10092 | 914 | ZP_03152606.1 | 1275 | Clostridium thermocellum JW20 |
| 146297046 | complement (NC_009437.1: 2185773 . . . 2186804) | 915 | YP_001180817.1 | 1276 | Caldicellulosiruptor saccharolyticus DSM 8903 |
| 349833 | L23147.1: 207 . . . 1208 | 916 | AAA72041.1 | 1277 | Methanosarcina thermophila |
| 20092407 | complement (NC_003552.1: 4448053 . . . 4449054) | 917 | NP_618482.1 | 1278 | Methanosarcina acetivorans C2A |
| 73669327 | complement (NC_007355.1: 2275987 . . . 2276988) | 918 | YP_305342.1 | 1279 | Methanosarcina barkeri str. Fusaro |
| 163734840 | NZ_ABIG01000010.1: 132890 . . . 133867 | 919 | ZP_02142278.1 | 1280 | Roseobacter litoralis Och 149 |
| 110678177 | complement (NC_008209.1: 803709 . . . 804707) | 920 | YP_681184.1 | 1281 | Roseobacter denitrificans OCh 114 |
| 159044374 | complement (NC_009952.1: 1904769 . . . 1905794) | 921 | YP_001533168.1 | 1282 | Dinoroseobacter shibae DFL 12 |
| 254512869 | NZ_DS999532.1: 435221 . . . 436255 | 922 | ZP_05124935.1 | 1283 | Rhodobacteraceae bacterium KLH11 |
| 260432366 | complement (NZ_GG704596.1: 1443685 . . . 1444707) | 923 | ZP_05786337.1 | 1284 | Silicibacter lacuscaerulensis ITI-1157 |
| 150376990 | NC_009620.1: 1371590 . . . 1372624 | 924 | YP_001313586.1 | 1285 | Sinorhizobium medicae WSM419 |
| 16264720 | NC_003078.1: 1058537 . . . 1059529 | 925 | NP_437512.1 | 1286 | Sinorhizobium meliloti 1021 |
| 239833801 | complement (NZ_ACQA01000002.1: 595918 . . . 596886) | 926 | ZP_04682129.1 | 1287 | Ochrobactrum intermedium LMG 3301 |
| 153010822 | complement (NC_00968.1: 862920 . . . 863897) | 927 | YP_001372036.1 | 1288 | Ochrobactrum anthropi ATCC 49188 |
| 187919084 | complement (NC_010676.1: 423371 . . . 424405) | 928 | YP_001888115.1 | 1289 | Burkholderia phytofirmans PsJN |
| 91779405 | NC_007952.1: 2605754 . . . 2606791 | 929 | YP_554613.1 | 1290 | Burkholderia xenovorans LB400 |
| 186470979 | NC_010625.1: 763673 . . . 764704 | 930 | YP_001862297.1 | 1291 | Burkholderia phymatum STM815 |
| 73537607 | complement (NC_007348.1: 372720 . . . 373757) | 931 | YP_297974.1 | 1292 | Ralstonia eutropha JMP134 |
| 194292312 | NC_010530.1: 1692071 . . . 1693105 | 932 | YP_002008219.1 | 1293 | Cupriavidus taiwanensis |
| 161521061 | NC_010086.1: 1600765 . . . 1601856 | 933 | YP_001584488.1 | 1294 | Burkholderia multivorans ATCC 17616 |
| 206563034 | complement (NC_011001.1: 1288493 . . . 1289527) | 934 | YP_002233797.1 | 1295 | Burkholderia cenocepacia J2315 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 90412230 | complement (NZ_AAPH01000013.1: 616 . . . 1653) | 935 | ZP_01220235.1 | 1296 | Photobacterium profundum 3TCK |
| 224825256 | complement (NZ_ACIS01000005.1: 7593 . . . 8612) | 936 | ZP_03698361.1 | 1297 | Lutiella nitroferrum 2002 |
| 148973982 | complement (NZ_AAZW01000001.1: 115872 . . . 116945) | 937 | ZP_01811515.1 | 1298 | Vibrionales bacterium SWAT-3 |
| 84385317 | complement (NZ_AAMR01000001.1: 227808 . . . 228881) | 938 | ZP_00988349.1 | 1299 | Vibrio splendidus 12B01 |
| 149187938 | NZ_ABCH01000003.1: 163877 . . . 164926 | 939 | ZP_01866234.1 | 1300 | Vibrio shilonii AK1 |
| 260776268 | complement (NZ_ACZN01000015.1: 316917 . . . 317966) | 940 | ZP_05885163.1 | 1301 | Vibrio coralliilyticus ATCC BAA-450 |
| 45862014 | AY498613.1: 8897 . . . 9853 | 941 | AAS78789.1 | 1302 | Paracoccus denitrificans |
| 77404622 | NC_007488.1: 38175 . . . 39173 | 942 | YP_345196.1 | 1303 | Rhodobacter sphaeroides 2.4.1 |
| 23630309 | AY134843.1: 2180 . . . 3148 | 943 | AAN08490.1 | 1304 | Castellaniella defragrans |
| 83952615 | NZ_AALY01000004.1: 6833 . . . 7819 | 944 | ZP_00961345.1 | 1305 | Roseovarius nubinhibens ISM |
| 56698382 | complement (NC_003911.11: 3772593 . . . 3773606) | 945 | YP_168755.1 | 1306 | Ruegeria pomeroyi DSS-3 |
| 149912659 | NZ_ABCR01000001.1: 262172 . . . 263161 | 946 | ZP_01901193.1 | 1307 | Roseobacter sp. AzwK-3b |
| 126736835 | complement (NZ_AAYC01000001.1: 23010 . . . 24029) | 947 | ZP_01752570.1 | 1308 | Roseobacter sp. SK209-2-6 |
| 163732628 | complement (NZ_ABIG01000003.1: 152433 . . . 153374) | 948 | ZP_02140073.1 | 1309 | Roseobacter litoralis Och 149 |
| 89055338 | NC_007802.1: 2864232 . . . 2865239 | 949 | YP_510789.1 | 1310 | Jannaschia sp. CCS1 |
| 254459737 | NZ_DS995276.1: 713420 . . . 714472 | 950 | ZP_05073153.1 | 1311 | Rhodobacterales bacterium HTCC2083 |
| 116620211 | NC_008536.1: 1336713 . . . 1337708 | 951 | YP_822367.1 | 1312 | Candidatus Solibacter usitatus Ellin6076 |
| 95930364 | NZ_AAEW02000012.1: 74280 . . . 75281 | 952 | ZP_01313101.1 | 1313 | Desulfuromonas acetoxidans DSM 684 |
| 77920135 | NC_007498.2: 2984046 . . . 2985047 | 953 | YP_357950.1 | 1314 | Pelobacter carbinolicus DSM 2380 |
| 222054722 | complement (NC_011979.1: 1793784 . . . 1794785) | 954 | YP_002537084.1 | 1315 | Geobacter sp. FRC-32 |
| 148265418 | NC_009483.1: 3992460 . . . 2993461 | 955 | YP_001232124.1 | 1316 | Geobacter uraniireducens Rf4 |
| 39997800 | NC_002939.4: 2984470 . . . 2985471 | 956 | NP_953751.1 | 1317 | Geobacter sulfurreducens PCA |
| 78222253 | complement (NC_007517.1: 1150703 . . . 1151704) | 957 | YP_384000.1 | 1318 | Geobacter metallireducens GS-15 |
| 118579718 | complement (NC_008609.1: 1359173 . . . 1360177) | 958 | YP_900968.1 | 1319 | Pelobacter propionicus DSM 2379 |
| 189424275 | complement (NC_010814.1: 1256052 . . . 1257053) | 959 | YP_001951452.1 | 1320 | Geobacter lovleyi SZ |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 255059775 | NZ_ACPJ01000030.1: 50425 . . . 51426 | 960 | ZP_05311922.1 | 1321 | *Geobacter* sp. M18 |
| 253700569 | complement (NC_012918.1: 2257017 . . . 2258018) | 961 | YP_003021758.1 | 1322 | *Geobacter* sp. M21 |
| 77920440 | complement (NC_007498.2: 3332135 . . . 3333136) | 962 | YP_358255.1 | 1323 | *Pelobacter carbinolicus* DSM 2380 |
| 227423754 | NZ_ABTN01000011.1: 41883 . . . 42872 | 963 | ZP_03906856.1 | 1324 | *Denitrovibrio acetiphilus* DSM 12809 |
| 193215894 | NC_011026.1: 2629909 . . . 2630916 | 964 | YP_001997093.1 | 1325 | *Chloroherpeton thalassium* ATCC 35110 |
| 150386298 | complement (NZ_ABDE01000122.1: 6609 . . . 7619) | 965 | ZP_01924858.1 | 1326 | *Victivallis vadensis* ATCC BAA-548 |
| 217034411 | NZ_ABSX01000018.1: 29972 . . . 31570 | 966 | ZP_03439825.1 | 1327 | *Helicobacter pylori* 98-10 |
| 254779508 | complement (NC_012973.1: 876982 . . . 878538) | 967 | YP_003057614.1 | 1328 | *Helicobacter pylori* B38 |
| 188527730 | complement (NC_010698.2: 936737 . . . 938293) | 968 | YP_001910417.1 | 1329 | *Helicobacter pylori* Shi470 |
| 15611908 | complement (NC_000921.1: 920263 . . . 921822) | 969 | NP_223559.1 | 1330 | *Helicobacter pylori* J99 |
| 109947805 | complement (NC_008229.1: 1105678 . . . 1107201) | 970 | YP_665033.1 | 1331 | *Helicobacter acinonychis* str. Sheeba |
| 148926656 | NZ_AASY01000008.1: 52243 . . . 53778 | 971 | ZP_01810337.1 | 1332 | *Campylobacter jejuni* subsp. *jejuni* CG8486 |
| 57167700 | complement (NZ_AAFL01000001.1: 232544 . . . 234046) | 972 | ZP_00366840.1 | 1333 | *Campylobacter coli* RM2228 |
| 57242590 | complement (NZ_AAFJ01000004.1: 6136 . . . 7638) | 973 | ZP_00370527.1 | 1334 | *Campylobacter upsaliensis* RM3195 |
| 222823645 | NC_012039.1: 612447 . . . 613916 | 974 | YP_002575219.1 | 1335 | *Campylobacter lari* RM2100 |
| 154148075 | complement (NC_009714.1: 1098161 . . . 1099597) | 975 | YP_001406718.1 | 1336 | *Campylobacter hominis* ATCC BAA-381 |
| 257459711 | NZ_ACYG01000019.1: 245785 . . . 247383 | 976 | ZP_05624820.1 | 1337 | *Campylobacter gracilis* RM3268 |
| 118475502 | complement (NC_008599.1: 824533 . . . 825927) | 977 | YP_891988.1 | 1338 | *Campylobacter fetus* subsp. *fetus* 82-40 |
| 157164211 | NC_009802.1: 1056736 . . . 1058103 | 978 | YP_001466901.1 | 1339 | *Campylobacter concisus* 13826 |
| 154173700 | complement (NC_009715.1: 947742 . . . 949112) | 979 | YP_001408221.1 | 1340 | *Campylobacter curvus* 525.92 |
| 255322202 | NZ_ACVQ01000017.1: 43696 . . . 45081 | 980 | ZP_05363348.1 | 1341 | *Campylobacter showae* RM3277 |
| 225351910 | NZ_ABXX02000003.1: 117844 . . . 119514 | 981 | ZP_03742933.1 | 1342 | *Bifidobacterium pseudocatenulatum* DSM 20438 |
| 171743080 | complement (NZ_ABIX02000002.1: 2348529 . . . 2350229) | 982 | ZP_02918887.1 | 1343 | *Bifidobacterium dentium* ATCC 27678 |
| 154487476 | complement (NZ_AAX1302000028.1: 209751 . . . 211442) | 983 | ZP_02028883.1 | 1344 | *Bifidobacterium adolescentis* L2-32 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 229817818 | complement (NZ_ABYS02000004.1: 899528 . . . 901234) | 984 | ZP_04448100.1 | 1345 | *Bifidobacterium angulatum* DSM 20098 |
| 223467350 | complement (NZ_ACCG01000014.1: 93417 . . . 95159) | 985 | ZP_03618886.1 | 1346 | *Bifidobacterium breve* DSM 20213 |
| 227546035 | NZ_ACHI01000009.1: 13043 . . . 14755 | 986 | ZP_03976084.1 | 1347 | *Bifidobacterium longum* subsp. *infantis* ATCC 55813 |
| 213692597 | NC_011593.1: 1898224 . . . 1899936 | 987 | YP_002323183.1 | 1348 | *Bifidobacterium longum* subsp. *infantis* ATCC 15697 |
| 224282865 | complement (NZ_ABQP01000009.1: 208984 . . . 210654) | 988 | ZP_03646187.1 | 1349 | *Bifidobacterium bifidum* NCIMB 41171 |
| 227507562 | NZ_ACGF01000124.1: 44384 . . . 46048 | 989 | ZP_03937611.1 | 1350 | *Gardnerella vaginalis* ATCC 14019 |
| 183601499 | complement (NZ_ABOT01000001.1: 192971 . . . 194653) | 990 | ZP_02962869.1 | 1351 | *Bifidobacterium animalis* subsp. *lactis* HN019 |
| 261337301 | complement (NZ_ABXB03000001.1: 137782 . . . 139455) | 991 | ZP_05965185.1 | 1352 | *Bifidobacterium gallicum* DSM 20093 |
| 154507766 | NZ_AAYI02000004.1: 231567 . . . 233045 | 992 | ZP_02043408.1 | 1353 | *Actinomyces odontolyticus* ATCC 17982 |
| 227494860 | complement (NZ_ACFG01000030.1: 86700 . . . 88295) | 993 | ZP_03925176.1 | 1354 | *Actinomyces coleocanis* DSM 15436 |
| 19553946 | complement (NC_003450.3: 2936506 . . . 2937891) | 994 | NP_601948.1 | 1355 | *Corynebacterium glutamicum* ATCC 13032 |
| 25029147 | complement (NC_004369.1: 2758982 . . . 2760496) | 995 | NP_739201.1 | 1356 | *Corynebacterium efficiens* YS-314 |
| 38234612 | complement (NC_002935.2: 2103677 . . . 2105128) | 996 | NP_940379.1 | 1357 | *Corynebacterium diphtheriae* NCTC 13129 |
| 252124104 | complement (NZ_ACSH01000003.1: 61905 . . . 63305) | 997 | ZP_04835255.1 | 1358 | *Corynebacterium matruchotii* ATCC 14266 |
| 227489285 | NZ_ABYP01000094.1: 61648 . . . 63048 | 998 | ZP_03919601.1 | 1359 | *Corynebacterium glucuronolyticum* ATCC 51867 |
| 258561950 | NZ_ACLJ01000070.1: 13162 . . . 14523 | 999 | ZP_05708623.1 | 1360 | *Corynebacterium genitalium* ATCC 33030 |
| 227547861 | NZ_ACHJ01000017.1: 9541 . . . 10899 | 1000 | ZP_03977910.1 | 1361 | *Corynebacterium lipophiloflavum* DSM 44291 |
| 227502015 | NZ_ACGD01000004.1: 82938 . . . 84305 | 1001 | ZP_03932064.1 | 1362 | *Corynebacterium accolens* ATCC 49725 |
| 255325798 | NZ_ACVP01000037.1: 5746 . . . 7107 | 1002 | ZP_05366890.1 | 1363 | *Corynebacterium tuberculostearicum* SK141 |
| 227505901 | NZ_ACGE01000122.1: 37468 . . . 38826 | 1003 | ZP_03935950.1 | 1364 | *Corynebacterium striatum* ATCC 6940 |
| 227834110 | complement (NC_012590.1: 2492850 . . . 2494214) | 1004 | YP_002835817.1 | 1365 | *Corynebacterum aurimucosum* ATCC 700975 |
| 68535315 | NC_007164.1: 307337 . . . 308848 | 1005 | YP_250020.1 | 1366 | *Corynebacterium jeikeium* K411 |
| 172041418 | complement (NC_010545.1: 2018026 . . . 2019369) | 1006 | YP_001801132.1 | 1367 | *Corynebacterium urealyticum* DSM 7109 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 237786249 | complement (NC_012704.1: 1975731 . . . 1977287) | 1007 | YP_002906954.1 | 1368 | *Corynebacterium kroppenstedtii* DSM 44385 |
| 213965099 | complement (NZ_ABZU01000003.1: 128017 . . . 129543) | 1008 | ZP_03393297.1 | 1369 | *Corynebacterium amycolatum* SK46 |
| 225075788 | complement (NZ_ACEN01000020.1: 5387 . . . 6889) | 1009 | ZP_03718987.1 | 1370 | *Neisseria flavescens* NRL30031/H210 |
| 255067101 | NZ_ACKO02000012.1: 64851 . . . 66353 | 1010 | ZP_05318956.1 | 1371 | *Neisseria sicca* ATCC 29256 |
| 161869564 | complement (NC_010120.1: 603202 . . . 604836) | 1011 | YP_001598731.1 | 1372 | *Neisseria meningitidis* 053442 |
| 238022551 | NZ_ACJW02000003.1: 751672 . . . 753150 | 1012 | ZP_04602977.1 | 1373 | *Kingella oralis* ATCC 51147 |
| 83592714 | complement (NC_007643.1: 1625036 . . . 1626802) | 1013 | YP_426466.1 | 1374 | *Rhodospirillum rubrum* ATCC 11170 |
| 32490929 | complement (NC_004344.2: 212680 . . . 214818) | 1014 | NP_871183.1 | 1375 | *Wigglesworthia glossinidia* endosymbiont of *Glossina brevipalpis* |
| 27904667 | NC_004545.1: 186377 . . . 188524 | 1015 | NP_777793.1 | 1376 | *Buchnera aphidicola* str. Bp (*Baizongia pistaciae*) |
| 261415723 | complement (NC_013410.1: 1639393 . . . 1640796) | 1016 | YP_003249406.1 | 1377 | *Fibrobacter succinogenes* subsp. *succinogenes* S85 |
| 219556226 | NZ_ABQH01000061.1: <3 . . . 1196 | 1017 | ZP_03535302.1 | 1378 | *Mycobacterium tuberculosis* T17 |
| 228471665 | complement (NZ_ACLQ01000003.1: 154599 . . . 155657) | 1018 | ZP_04056438.1 | 1379 | *Capnocytophaga gingivalis* ATCC 33624 |
| 256370675 | NC_013123.1: 116952 . . . 117950 | 1019 | YP_003108500.1 | 1380 | *Candidatus Sulcia muelleri* SMDSEM |
| 6685772 | X89084.1: 1009 . . . 199 | 1020 | P77844 | 1381 | *Corynebacterium glutamicum* |
| 227876041 | NZ_ACKW01000045.1: 33898 . . . 34887 | 1021 | ZP_03994160.1 | 1382 | *Mobiluncus mulieris* ATCC 35243 |
| 227492324 | NZ_ACCQ01000004.1: 214416 . . . 215417 | 1022 | ZP_03922640.1 | 1383 | *Mobiluncus curtisii* ATCC 43063 |
| 225027017 | NZ_ACEP01000064.1: 10650 . . . 11609 | 1023 | ZP_03716209.1 | 1384 | *Eubacterium halli* DSM 3353 |
| 225028951 | complement (NZ_ACEP01000172.1: 22364 . . . 23416) | 1024 | ZP_03718143.1 | 1385 | *Eubacterium hallii* DSM 3353 |
| 257438679 | complement (NZ_ACOP02000029.1: 99 . . . 1124) | 1025 | ZP_05614434.1 | 1386 | *Faecalibacterium prausnitzii* A2-165 |
| 154496156 | complement (NZ_AAXG02000004.1: 103391 . . . 104380) | 1026 | ZP_02034852.1 | 1387 | *Bacteroides capillosus* ATCC 29799 |
| 225376322 | NZ_ACFY01000086.1: 6940 . . . 7992 | 1027 | ZP_03753543.1 | 1388 | *Roseburia inulinivorans* DSM 16841 |
| 257414121 | complement (NZ_ABYJ02000202.1: 41125 . . . 42165) | 1028 | ZP_04745275.2 | 1389 | *Roseburia intestinalis* L1-82 |
| 238923816 | NC_012781.1: 1324280 . . . 1325263 | 1029 | YP_002937332.1 | 1390 | *Eubacterium rectale* ATCC 33656 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 160893459 | NZ_AAYW02000007.1: 63870 . . . 64919 | 1030 | ZP_02074244.1 | 1391 | Clostridium sp. L2-50 |
| 229829305 | complement (NZ_ACIP02000002.1: 495313 . . . 496299) | 1031 | ZP_04455374.1 | 1392 | Shuttleworthia satelles DSM 14600 |
| 218282181 | complement (NZ_ABYT01000061.1: 45 . . . 1016) | 1032 | ZP_03488480.1 | 1393 | Eubacterium biforme DSM 3989 |
| 160916120 | complement (NZ_ABAW02000025.1: 71684 . . . 72694) | 1033 | ZP_02078327.1 | 1394 | Eubacterium dolichum DSM 3991 |
| 160915347 | NZ_ABAW02000020.1: 14646 . . . 15638 | 1034 | ZP_02077559.1 | 1395 | Eubacterium dolichum DSM 3991 |
| 212697404 | NZ_ABXA01000047.1: 41715 . . . 42701 | 1035 | ZP_03305532.1 | 1396 | Anaerococcus hydrogenalis DSM 7454 |
| 256545936 | complement (NZ_ACXU01000022.1: 22101 . . . 23087) | 1036 | ZP_05473291.1 | 1397 | Anaerococcus vaginalis ATCC 51170 |
| 227501001 | NZ_ACGC01000115.1: 23122 . . . 24108 | 1037 | ZP_03931050.1 | 1398 | Anaerococcus tetradius ATCC 35098 |
| 257067207 | complement (NC_013171.1: 1868769 . . . 1869752) | 1038 | YP_003153463.1 | 1399 | Anaerococcus prevotii DSM 20548 |
| 227485732 | complement (NZ_ABYO01000196.1: 43814 . . . 44833) | 1039 | ZP_03916048.1 | 1400 | Anaerococcus lactolyticus ATCC 51172 |
| 19746077 | NC_003485.1: 903788 . . . 904783 | 1040 | NP_607213.1 | 1401 | Streptococcus pyogenes MGAS8232 |
| 13622266 | AE004092.1: 923921 . . . 924916 | 1041 | AAK34003.1 | 1402 | Streptococcus pyogenes M1 GAS |
| 222153008 | NC_012004.1: 834034 . . . 835026 | 1042 | YP_002562185.1 | 1403 | Streptococcus uberis 0140J |
| 225868503 | NC_012470.1: 1034662 . . . 1035663 | 1043 | YP_002744451.1 | 1404 | Streptococcus equi subsp. Zooepidemicus |
| 254997415 | AP010655.1: 1031526 . . . 1032521 | 1044 | BAH88016.1 | 1405 | Streptococcus mutans NN2025 |
| 171779341 | NZ_ABJK02000020.1: 38474 . . . 39472 | 1045 | ZP_02920305.1 | 1406 | Streptococcus infantarius subsp. infantarius ATCC BAA-102 |
| 76787123 | complement (NC_007432.1: 1155758 . . . 1156750) | 1046 | YP_329798.1 | 1407 | Streptococcus agalactiae A909 |
| 228477151 | complement (NZ_ACLO01000062.1: 54543 . . . 55526) | 1047 | ZP_04061789.1 | 1408 | Streptococcus salivarius SK126 |
| 55821439 | complement (NC_006448.1: 1286014 . . . 1286997) | 1048 | YP_139881.1 | 1409 | Streptococcus thermophilus LMG 18311 |
| 237650772 | NZ_ABZC01000093.1: 10653 . . . 11627 | 1049 | ZP_04525024.1 | 1410 | Streptococcus pneumoniae CCRI 1974 |
| 262282806 | complement (NZ_GG7049411.1: 11119 . . . 12096) | 1050 | ZP_06060573.1 | 1411 | Streptococcus sp. 2_1_36FAA |
| 146318711 | complement (NC_009442.1: 1032399 . . . 1033379) | 1051 | YP_001198423.1 | 1412 | Streptococcus suis 05ZYH33 |
| 42518809 | NC_005362.1: 788505 . . . 789482 | 1052 | NP_964739.1 | 1413 | Lactobacillus johnsonii NCC 533 |
| 58337025 | NC_006814.3: 698578 . . . 699567 | 1053 | YP_193610.1 | 1414 | Lactobacillus acidophilus NCFM |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 227893214 | NZ_ACGU01000037.1: 27358 . . . 28347 | 1054 | ZP_04011019.1 | 1415 | *Lactobacillus ultunensis* DSM 16047 |
| 227877224 | NZ_ACKR01000025.1: 14947 . . . 15936 | 1055 | ZP_03995297.1 | 1416 | *Lactobacillus crispatus* JV-V01 |
| 260102516 | NZ_ACLM01000112.1: 6924 . . . 7913 | 1056 | ZP_05752753.1 | 1417 | *Lactobacillus helveticus* DSM 20075 |
| 227525975 | NZ_ACGQ01000041.1: 59881 . . . 60858 | 1057 | ZP_03956024.1 | 1418 | *Lactobacillus jensenii* JV-V16 |
| 228854857 | complement (NZ_ACOY01000013.1: 251390 . . . 252367) | 1058 | ZP_04645187.1 | 1419 | *Lactobacillus jensenii* 269-3 |
| 104773739 | NC_008054.1: 547017 . . . 548006 | 1059 | YP_618719.1 | 1420 | *Lactobacillus delbrueckii* subsp. *bulgaricus* ATCC 11842 |
| 259501464 | NZ_ACLN01000013.1: 15438 . . . 16418 | 1060 | ZP_05744366.1 | 1421 | *Lactobacillus iners* DSM 13335 |
| 16080818 | complement (NC_000964.3: 3865355 . . . 3866326) | 1061 | NP_391646.1 | 1422 | *Bacillus subtilis* subsp. *subtilis* str. 168 |
| 154687884 | complement (NC_009725.1: 3590964 . . . 3591935) | 1062 | YP_001423045.1 | 1423 | *Bacillus amyloliquefaciens* FZB42 |
| 52082282 | complement (NC_006270.3: 3821313 . . . 3822284) | 1063 | YP_081073.1 | 1424 | *Bacillus licheniformis* ATCC 14580 |
| 194016487 | complement (NZ_ABRX01000004.1: 144981 . . . 145952) | 1064 | ZP_03055101.1 | 1425 | *Bacillus pumilus* ATCC 7061 |
| 212640578 | complement (NC_011567.1: 2748264 . . . 2749247) | 1065 | YP_002317098.1 | 1426 | *Anoxybacillus flavithermus* WK1 |
| 239828646 | complement (NC_012793.1: 3393094 . . . 3394068) | 1066 | YP_002951270.1 | 1427 | *Geobacillus* sp. WCH70 |
| 138896990 | complement (NC_009328.1: 3468960 . . . 3469934) | 1067 | YP_001127443.1 | 1428 | *Geobacillus thermodenitrificans* NG80-2 |
| 56421950 | complement (NC_006510.1: 3456185 . . . 3457165) | 1068 | YP_149268.1 | 1429 | *Geobacillus kaustophilus* HTA426 |
| 149182788 | NZ_ABCF01000043.1: 11583 . . . 12554 | 1069 | ZP_01861251.1 | 1430 | *Bacillus* sp. SG-1 |
| 205375387 | NZ_ABFU01000065.2: 12128 . . . 13099 | 1070 | ZP_03228176.1 | 1431 | *Bacillus coahuilensis* m4-4 |
| 89101108 | complement (NZ_AAOX01000058.1: 10738 . . . 11715) | 1071 | ZP_01173945.1 | 1432 | *Bacillus* sp. NRRL B-14911 |
| 23100477 | complement (NC_004193.1: 3134492 . . . 3135466) | 1072 | NP_693944.1 | 1433 | *Oceanobacillus iheyensis* HTE831 |
| 229187615 | complement (NZ_ACLU01000117.1: 31676 . . . 32647) | 1073 | ZP_04314753.1 | 1434 | *Bacillus cereus* BGSC 6E1 |
| 46908338 | complement (NC_002973.6: 2171357 . . . 2172334) | 1074 | YP_014727.1 | 1435 | *Listeria monocytogenes* str. 4b F2365 |
| 229555968 | NZ_ACCR01000020.1: 18426 . . . 19403 | 1075 | ZP_04443757.1 | 1436 | *Listeria grayi* DSM 20601 |
| 15616385 | complement (NC_002570.2: 3947889 . . . 3948881) | 1076 | NP_244690.1 | 1437 | *Bacillus halodurans* C-125 |
| 56965668 | complement (NC_006582.1: 4069370 . . . 4070365) | 1077 | YP_177402.1 | 1438 | *Bacillus clausii* KSM-K16 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 229917170 | complement (NC_012673.1: 1410227 ... 1411216) | 1078 | YP_002885816.1 | 1439 | *Exiguobacterium* sp. AT1b |
| 172056261 | NC_010556.1: 233988 ... 234974 | 1079 | YP_001812721.1 | 1440 | *Exiguobacterium sibiricum* 255-15 |
| 163762281 | NZ_ABHZ01000002.1: 94480 ... 95457 | 1080 | ZP_02169346.1 | 1441 | *Bacillus selenitireducens* MLS10 |
| 242372812 | NZ_ACJB01000048.1: 8122 ... 9111 | 1081 | ZP_04818386.1 | 1442 | *Staphylococcus epidermidis* M23864: W1 |
| 223042925 | complement (NZ_ACFR01000002.1: 330954 ... 331943) | 1082 | ZP_03612973.1 | 1443 | *Staphylococcus capitis* SK14 |
| 239636796 | complement (NZ_ACPZ01000027.1: 569915 ... 570904) | 1083 | ZP_04677798.1 | 1444 | *Staphylococcus warneri* L37603 |
| 27467277 | NC_004461.1: 356818 ... 357807 | 1084 | NP_763914.1 | 1445 | *Staphylococcus epidermidis* ATCC 12228 |
| 258422775 | NZ_ACKI01000006.1: 980 ... 1966 | 1085 | ZP_05685678.1 | 1446 | *Staphylococcus aureus* A9635 |
| 70727403 | complement (NC_007168.1: 2403280 ... 2404269) | 1086 | YP_254319.1 | 1447 | *Staphylococcus haemolyticus* JCSC1435 |
| 228475091 | NZ_ACLP01000011.1: 16037 ... 17026 | 1087 | ZP_04059818.1 | 1448 | *Staphylococcus hominis* SK119 |
| 150011041 | EF456699.1: 1 ... 987 | 1088 | ABR57177.1 | 1449 | *Staphylococcus xylosus* |
| 73663433 | complement (NC_007356.1: 2190871 ... 2191857) | 1089 | YP_302214.1 | 1450 | *Staphylococcus saprophyticus* subsp. *saprophyticus* ATCC 15305 |
| 224475734 | NC_012121.1: 250258 ... 251247 | 1090 | YP_002633340.1 | 1451 | *Staphylococcus carnosus* subsp. *carnosus* TM300 |
| 222152076 | complement (NC_011999.1: 1968130 ... 1969119) | 1091 | YP_002561236.1 | 1452 | *Macrococcus caseolyticus* JCSC5402 |
| 227514417 | NZ_ACGI01000058.1: 71225 ... 72199 | 1092 | ZP_03944466.1 | 1453 | *Lactobacillus fermentum* ATCC 14931 |
| 256848058 | complement (NZ_GG698804.1: 125094 ... 126059) | 1093 | ZP_05553502.1 | 1454 | *Lactobacillus coleohominis* 101-4-CHN |
| 227529580 | NZ_ACGV01000117.1: 1634 ... 2608 | 1094 | ZP_03959629.1 | 1455 | *Lactobacillus vaginalis* ATCC 49540 |
| 148543634 | NC_009513.1: 451991 ... 452965 | 1095 | YP_001271004.1 | 1456 | *Lactobacillus reuteri* DSM 20016 |
| 259502766 | NZ_ACLL01000024.1: 18101 ... 19072 | 1096 | ZP_05745668.1 | 1457 | *Lactobacillus antri* DSM 16041 |
| 116618560 | complement (NC_008531.1: 1461235 ... 1462215) | 1097 | YP_818931.1 | 1458 | *Leuconostoc mesenteroides* subsp. *mesenteroides* ATCC 8293 |
| 170016912 | NC_010471.1: 577967 ... 578959 | 1098 | YP_001727831.1 | 1459 | *Leuconostoc citreum* KM20 |
| 241894748 | complement (NZ_ACKU01000002.1: 15496 ... 16476) | 1099 | ZP_04782044.1 | 1460 | *Weissella paramesenteroides* ATCC 33313 |
| 118587037 | NZ_AAUV01000054.1: 44038 ... 45132 | 1100 | ZP_01544468.1 | 1461 | *Oenococcus oeni* ATCC BAA-1163 |

TABLE 12a-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 259046893 | complement (NZ_ACKZ01000012.:1 86436 . . . 87425) | 1101 | ZP_05737294.1 | 1462 | *Granulicatella adiacens* ATCC 49175 |
| 260584167 | complement (NZ_GG703805.1: 786281 . . . 787264) | 1102 | ZP_05851915.1 | 1463 | *Granulicatella elegans* ATCC 700633 |
| 163789527 | complement (NZ_ABHH01000002.1: 8081 . . . 9061) | 1103 | ZP_02183965.1 | 1464 | *Carnobacterium* sp. AT7 |
| 257870102 | NZ_GG670288.1: 145742 . . . 146725 | 1104 | ZP_05649755.1 | 1465 | *Enterococcus gallinarum* EG2 |
| 227517869 | NZ_ACGL01000051.1: 2376 . . . 3401 | 1105 | ZP_03947918.1 | 1466 | *Enterococcus faecalis* TX0104 |
| 227552175 | complement (NZ_ACHL01000118.1: 1216 . . . 2232) | 1106 | ZP_03982224.1 | 1467 | *Enterococcus faecium* TX1330 |
| 81428954 | complement (NC_007576.1: 1313600 . . . 1314586) | 1107 | YP_395954.1 | 1468 | *Lactobacillus sakei* subsp. *sakei* 23K |
| 229823693 | NZ_ACIL02000007.1: 6499 . . . 7482 | 1108 | ZP_04449762.1 | 1469 | *Catonella morbi* ATCC 51271 |
| 125623617 | NC_009004.1: 752099 . . . 753079 | 1109 | YP_001032100.1 | 1470 | *Lactococcus lactis* subsp. *cremoris* MG1363 |
| 116494500 | NC_008526.1: 981403 . . . 982380 | 1110 | YP_806234.1 | 1471 | *Lactobacillus casei* ATCC 334 |
| 28377658 | NC_004567.1: 748192 . . . 749169 | 1111 | NP_784550.1 | 1472 | *Lactobacillus plantarum* WCFS1 |
| 116333321 | NC_008497.1: 702374 . . . 703348 | 1112 | YP_794848.1 | 1473 | *Lactobacillus brevis* ATCC 367 |
| 227524782 | complement (NZ_ACGP01000192.1: 2135 . . . 3112) | 1113 | ZP_03954831.1 | 1474 | *Lactobacillus hilgardii* ATCC 8290 |
| 11862872 | AB035800.1: 1006 . . . 1992 | 1114 | BAB19267.1 | 1475 | *Lactobacillus sanfranciscensis* |
| 227528239 | NZ_ACGS01000093.1: 64718 . . . 65695 | 1115 | ZP_03958288.1 | 1476 | *Lactobacillus ruminis* ATCC 25644 |
| 90962126 | complement (NC_007929.1: 1183945 . . . 1184922) | 1116 | YP_536042.1 | 1477 | *Lactobacillus salivarius* UCC118 |
| 259504733 | NZ_ACLK01000016.1: 55937 . . . 56917 | 1117 | ZP_05747635.1 | 1478 | *Erysipelothrix rhusiopathiae* ATCC 19414 |
| 116492140 | NC_008525.1: 385259 . . . 386230 | 1118 | YP_803875.1 | 1479 | *Pediococcus pentosaceus* ATCC 25745 |
| 160946581 | NZ_ABEE02000016.1: 72101 . . . 73072 | 1119 | ZP_02093784.1 | 1480 | *Parvimonas micra* ATCC 33270 |
| 169825312 | complement (NC_010376.1: 1782855 . . . 1783826) | 1120 | YP_001692923.1 | 1481 | *Finegoldia magna* ATCC 29328 |
| 229542439 | NZ_AAWV02000001.1: 1452854 . . . 1453825 | 1121 | ZP_04431499.1 | 1482 | *Bacillus coagulans* 36D1 |
| 241888505 | NZ_ACDZ02000004.1: 11622 . . . 12602 | 1122 | ZP_04775813.1 | 1483 | *Gemella haemolysans* ATCC 10379 |

In addition, 201 phosphate acetyltransferase sequences that are characterized by two domains (DRTGG and PTA_PTB) are provided in Table 12b. MSA and phylogenetic analysis were performed as described above. Percent identity with respect to experimentally verified (or human curated) sequences is equal to or larger than 40, except for 4 sequences derived from plant organisms. Furthermore, hmmer search of the 201 sequences against the profile HMM of subfamily 2 (Table 14), clearly indicates that all Group 2 sequences belong to the PTA subfamily (least significant Evalue is 4.1e-93).

TABLE 12b

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 152964825 | complement (NC_009664.2: 1430885 . . . 1432984) | 1484 | YP_001360609.1 | 1685 | Kineococcus radiotolerans SRS30216 |
| 88800302 | complement (NZ_AAOE01000024.1: 59450 . . . 61609) | 1485 | ZP_01115869.1 | 1686 | Reinekea blandensis MED297 |
| 254786809 | complement (NC_012997.1: 3139764 . . . 3141917) | 1486 | YP_003074238.1 | 1687 | Teredinibacter turnerae T7901 |
| 120554060 | complement (NC_008740.1: 1283732 . . . 1285885) | 1487 | YP_958411.1 | 1688 | Marinobacter aquaeolei VT8 |
| 83647145 | NC_007645.1: 4579211 . . . 4581358 | 1488 | YP_435580.1 | 1689 | Hahella chejuensis KCTC 2396 |
| 146308660 | NC_009439.1: 4021959 . . . 4024052 | 1489 | YP_001189125.1 | 1690 | Pseudomonas mendocina ymp |
| 116048757 | NC_008463.1: 4740071 . . . 4742185 | 1490 | YP_792443.1 | 1691 | Pseudomonas aeruginosa UCBPP-PA14 |
| 28868382 | complement (NC_004578.1: 1283902 . . . 1285992) | 1491 | NP_791001.1 | 1692 | Pseudomonas syringae pv. tomato str. DC3000 |
| 70728320 | complement (NC_004129.6: 1081214 . . . 1083313) | 1492 | YP_258069.1 | 1693 | Pseudomonas fluorescens Pf-5 |
| 104780139 | complement (NC_008027.1: 952666 . . . 954756) | 1493 | YP_606637.1 | 1694 | Pseudomonas entomophila L48 |
| 226945506 | complement (NC_012560.1: 3530138 . . . 3532276) | 1494 | YP_002800579.1 | 1695 | Azotobacter vinelandii DJ |
| 146281510 | complement (NC_009434.1: 1238536 . . . 1240632) | 1495 | YP_001171663.1 | 1696 | Pseudomonas stutzeri A1501 |
| 30248315 | complement (NC_004757.1: 326321 . . . 328408) | 1496 | NP_840385.1 | 1697 | Nitrosomonas europaea ATCC 19718 |
| 226946148 | NC_012560.1: 4145609 . . . 4147684 | 1497 | YP_002801221.1 | 1698 | Azotobacter vinelandii DJ |
| 226357371 | NC_012526.1: 2779899 . . . 2782016 | 1498 | YP_002787111.1 | 1699 | Deinococcus deserti VCD115 |
| 94984159 | complement (NC_008025.1: 46701 . . . 48812) | 1499 | YP_603523.1 | 1700 | Deinococcus geothermalis DSM 11300 |
| 15805114 | complement (NC_001263.1: 69707 . . . 71875) | 1500 | NP_293799.1 | 1701 | Deinococcus radiodurans R1 |
| 89899079 | complement (NC_007908.1: 264127 . . . 266178) | 1501 | YP_521550.1 | 1702 | Rhodoferax ferrireducens T118 |
| 90422592 | NC_007925.1: 1181422 . . . 1183572 | 1502 | YP_530962.1 | 1703 | Rhodopseudomonas palustris BisB18 |
| 90423512 | NC_007925.1: 2183340 . . . 2185475 | 1503 | YP_531882.1 | 1704 | Rhodopseudomonas palustris BisB18 |
| 115525859 | NC_008435.1: 4320999 . . . 4323140 | 1504 | YP_782770.1 | 1705 | Rhodopseudomonas palustris BisA53 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 167574473 | complement (NZ_ABBG01000507.1: 7891 ... 9969) | 1505 | ZP_02367347.1 | 1706 | Burkholderia oklahomensis C6786 |
| 83594327 | complement (NC_007643.1: 3449832 ... 3451943) | 1506 | YP_428079.1 | 1707 | Rhodospirillum rubrum ATCC 11170 |
| 90422165 | NC_007925.1: 696325 ... 698388 | 1507 | YP_530535.1 | 1708 | Rhodopseudomonas palustris BisB18 |
| 34496985 | complement (NC_005085.1: 1636285 ... 1638366) | 1508 | NP_901200.1 | 1709 | Chromobacterium violaceum ATCC 12472 |
| 224825239 | complement (NZ_ACIS01000004.1: 398128 ... 400215) | 1509 | ZP_03698345.1 | 1710 | Lutiella nitroferrum 2002 |
| 148652157 | complement (NC_009524.1: 415573 ... 417720) | 1510 | YP_001279250.1 | 1711 | Psychrobacter sp. PRwf-1 |
| 93005047 | complement (NC_007969.1: 257926 ... 260082) | 1511 | YP_579484.1 | 1712 | Psychrobacter cryohalolentis K5 |
| 257453691 | NZ_ACYI01000010.1: 16653 ... 18797 | 1512 | ZP_05618978.1 | 1713 | Enhydrobacter aerosaccus SK60 |
| 255321153 | NZ_ACVR01000080.1: 44385 ... 46529 | 1513 | ZP_05362319.1 | 1714 | Acinetobacter radioresistens SK82 |
| 50083778 | complement (NC_005966.1: 527524 ... 529686) | 1514 | YP_045288.1 | 1715 | Acinetobacter sp. ADP1 |
| 260549093 | NZ_GG704496.1: 86045 ... 88189 | 1515 | ZP_05823314.1 | 1716 | Acinetobacter sp. RUH2624 |
| 226953952 | complement (NZ_ABYN01000201.1: 23157 ... 25289) | 1516 | ZP_03824416.1 | 1717 | Acinetobacter sp. ATCC 27244 |
| 153005955 | NC_009675.1: 3624676 ... 3626811 | 1517 | YP_001380280.1 | 1718 | Anaeromyxobacter sp. Fw109-5 |
| 86159318 | complement (NC_007760.1: 3267950 ... 3270094) | 1518 | YP_466103.1 | 1719 | Anaeromyxobacter dehalogenans 2CP-C |
| 52425053 | complement (NC_006300.1: 977458 ... 979596) | 1519 | YP_088190.1 | 1720 | Mannheimia succiniciproducens MBEL55E |
| 152979320 | NC_009655.1: 1823344 ... 1825485 | 1520 | YP_001344949.1 | 1721 | Actinobacillus succinogenes 130Z |
| 251792685 | NC_012913.1: 968721 ... 970856 | 1521 | YP_003007411.1 | 1722 | Aggregatibacter aphrophilus NJ8700 |
| 145633066 | NZ_AAZF01000004.1: 73469 ... 75604 | 1522 | ZP_01788798.1 | 1723 | Haemophilus influenzae 3655 |
| 113460945 | complement (NC_008309.1: 873911 ... 876049) | 1523 | YP_719012.1 | 1724 | Haemophilus somnus 129PT |
| 15602570 | NC_002663.1: 821181 ... 823319 | 1524 | NP_245642.1 | 1725 | Pasteurella multocida subsp. multocida str. Pm70 |
| 260913970 | complement (NZ_ACZR01000013.1: 172766 ... 174904) | 1525 | ZP_05920444.1 | 1726 | Pasteurella dagmatis ATCC 43325 |
| 53729159 | complement (NZ_AACK01000004.1: 12180 ... 14318) | 1526 | ZP_00133992.2 | 1727 | Actinobacillus pleuropneumoniae serovar 1 str. 4074 |
| 240949203 | NZ_ACQL01000097.1: 15931 ... 18069 | 1527 | ZP_04753547.1 | 1728 | Actinobacillus minor NM305 |
| 33152520 | NC_002940.2: 1192390 ... 1194528 | 1528 | NP_873873.1 | 1729 | Haemophilus ducreyi 35000HP |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 254362832 | NZ_DS264681.1: 4949 . . . 7084 | 1529 | ZP_04978908.1 | 1730 | *Mannheimia haemolytica* PHL213 |
| 219870647 | NC_011852.1: 435431 . . . 437566 | 1530 | YP_002475022.1 | 1731 | *Haemophilus parasuis* SH0165 |
| 258637834 | NZ_ACYJ01000022.1: 41620 . . . 43764 | 1531 | ZP_05730581.1 | 1732 | *Pantoea* sp. At-9b |
| 188533336 | complement (NC_010694.1: 1324250 . . . 1326379) | 1532 | YP_001907133.1 | 1733 | *Erwinia tasmaniensis* Et1/99 |
| 85059585 | NC_007712.1: 2759501 . . . 2761645 | 1533 | YP_455287.1 | 1734 | *Sodalis glossinidius* str. 'morsitans' |
| 258631105 | complement (NZ_ACYK01000004.1: 104546 . . . 106687) | 1534 | ZP_05723922.1 | 1735 | *Dickeya dadantii* Ech586 |
| 261820783 | complement (NC_013421.1: 1606509 . . . 1608647) | 1535 | YP_003258889.1 | 1736 | *Pectobacterium wasabiae* WPP163 |
| 242239978 | NC_012880.1: 3004583 . . . 3006724 | 1536 | YP_002988159.1 | 1737 | *Dickeya dadantii* Ech703 |
| 22125515 | complement (NC_004088.1: 1788905 . . . 1791058) | 1537 | NP_668938.1 | 1738 | *Yersinia pestis* KIM 10 |
| 157371554 | NC_009832.1: 3673293 . . . 3675482 | 1538 | YP_001479543.1 | 1739 | *Serratia proteamaculans* 568 |
| 238920583 | NC_012779.1: 2589897 . . . 2592035 | 1539 | YP_002934098.1 | 1740 | *Edwardsiella ictaluri* 93-146 |
| 197285630 | NC_010554.1: 1898593 . . . 1900737 | 1540 | YP_002151502.1 | 1741 | *Proteus mirabilis* HI4320 |
| 37526984 | NC_005126.1: 3612456 . . . 3614597 | 1541 | NP_930328.1 | 1742 | *Photorhabdus luminescens* subsp. *laumondii* TTO1 |
| 238895817 | NC_012731.1: 3763302 . . . 3765449 | 1542 | YP_002920553.1 | 1743 | *Klebsiella pneumoniae* NTUH-K2044 |
| 146312483 | NC_009436.1: 3080629 . . . 3082770 | 1543 | YP_001177557.1 | 1744 | *Enterobacter* sp. 638 |
| 260598715 | NC_013282.1: 3057676 . . . 3059814 | 1544 | YP_003211286.1 | 1745 | *Cronobacter turicensis* |
| 601935 | D21123.1: 77 . . . 2218 | 1545 | BAA04663.1 | 1746 | *Escherichia coli* |
| 238898722 | complement (NC_012751.1: 1494526 . . . 1496655) | 1546 | YP_002924403.1 | 1747 | *Candidatus Hamiltonella defensa* 5AT (*Acyrthosiphon pisum*) |
| 227114079 | NZ_ABVX01000029.1: 23117 . . . 25261 | 1547 | ZP_03827735.1 | 1748 | *Pectobacterium carotovorum* subsp. *brasiliensis* PBR1692 |
| 89072717 | complement (NZ_AAOU01000004.1: 98074 . . . 100221) | 1548 | ZP_01159282.1 | 1749 | *Photobacterium* sp. SKA34 |
| 54309953 | NC_006370.1: 3245262 . . . 3247418 | 1549 | YP_130973.1 | 1750 | *Photobacterium profundum* SS9 |
| 262274670 | NZ_ADAQ01000011.1: 496361 . . . 498520 | 1550 | ZP_06052481.1 | 1751 | *Grimontia hollisae* CIP 101886 |
| 260768101 | complement (NZ_ACZP01000013.1: 239301 . . . 241427) | 1551 | ZP_05877035.1 | 1752 | *Vibrio furnissii* CIP 102972 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 260773044 | NZ_ACZO01000006.1: 1066216 . . . 1068360 | 1552 | ZP_05881960.1 | 1753 | Vibrio metschnikovii CIP 69.14 |
| 163802859 | complement (NZ_ABGR01000013.1: 61871 . . . 64036) | 1553 | ZP_02196748.1 | 1754 | Vibrio sp. AND4 |
| 37680318 | NC_005139.1: 2144915 . . . 2147059 | 1554 | NP_934927.1 | 1755 | Vibrio vulnificus YJ016 |
| 149188151 | complement (NZ_ABCH01000004.1: 163878 . . . 166022) | 1555 | ZP_01866446.1 | 1756 | Vibrio shilonii AK1 |
| 218708991 | complement (NC_011753.1: 1031606 . . . 1033810) | 1556 | YP_002416612.1 | 1757 | Vibrio splendidus LGP32 |
| 209695557 | NC_011312.1: 2262635 . . . 2264806 | 1557 | YP_002263486.1 | 1758 | Aliivibrio salmonicida LFI1238 |
| 229525709 | complement (NZ_ACHV01000001.1: 2574339 . . . 2576483) | 1558 | ZP_04415114.1 | 1759 | Vibrio cholerae bv. albensis VL426 |
| 145300284 | NC_009348.1: 3681431 . . . 3683584 | 1559 | YP_001143125.1 | 1760 | Aeromonas salmonicida subsp. salmonicida A449 |
| 237807651 | complement (NC_012691.1: 958413 . . . 960569) | 1560 | YP_002892091.1 | 1761 | Tolumonas auensis DSM 9187 |
| 90407162 | complement (NZ_AAPG01000006.1: 41954 . . . 44116) | 1561 | ZP_01215350.1 | 1762 | Psychromonas sp. CNPT3 |
| 119946918 | NC_008709.1: 4084304 . . . 4086466 | 1562 | YP_944598.1 | 1763 | Psychromonas ingrahamii 37 |
| 157374843 | complement (NC_009831.1: 2041698 . . . 2043839) | 1563 | YP_001473443.1 | 1764 | Shewanella sediminis HAW-EB3 |
| 170727231 | NC_010506.1: 3531467 . . . 3533608 | 1564 | YP_001761257.1 | 1765 | Shewanella woodyi ATCC 51908 |
| 127513322 | NC_009092.1: 2807561 . . . 2809699 | 1565 | YP_001094519.1 | 1766 | Shewanella loihica PV-4 |
| 167624517 | NC_010334.1: 3149368 . . . 3151515 | 1566 | YP_001674811.1 | 1767 | Shewanella halifaxensis HAW-EB4 |
| 117919999 | complement (NC_008577.1: 1806421 . . . 180857 | 1567 | YP_869191.1 | 1768 | Shewanella sp. ANA-3 |
| 119774631 | complement (NC_008700.1: 1807689 . . . 1809827) | 1568 | YP_927371.1 | 1769 | Shewanella amazonensis SB2B |
| 114563647 | NC_008345.1: 2956515 . . . 2958662 | 1569 | YP_751160.1 | 1770 | Shewanella frigidimarina NCIMB 400 |
| 91793762 | NC_007954.1: 2868611 . . . 2870791 | 1570 | YP_563413.1 | 1771 | Shewanella denitrificans OS217 |
| 157376672 | NC_009831.1: 4313346 . . . 4315484 | 1571 | YP_001475272.1 | 1772 | Shewanella sediminis HAW-EB3 |
| 167624655 | complement (NC_010334.1: 3320048 . . . 3322198) | 1572 | YP_001674949.1 | 1773 | Shewanella halifaxensis HAW-EB4 |
| 239996136 | complement (NZ_ABQB01000564.1: 6079 . . . 8301) | 1573 | ZP_04716660.1 | 1774 | Alteromonas macleodii ATCC 27126 |
| 109898905 | NC_008228.1: 3144369 . . . 3146513 | 1574 | YP_662160.1 | 1775 | Pseudoalteromonas atlantica T6c |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 119469286 | NZ_AAVS01000006.1: 30053 ... 32206 | 1575 | ZP_01612225.1 | 1776 | *Alteromonadales bacterium* TW-7 |
| 88860001 | complement (NZ_AAOH01000005.1: 230650 ... 232797) | 1576 | ZP_01134640.1 | 1777 | *Pseudoalteromonas tunicata* D2 |
| 71282469 | NC_003910.7: 3309465 ... 3311585 | 1577 | YP_269873.1 | 1778 | *Colwellia psychrerythraea* 34H |
| 152996332 | NC_009654.1: 2608121 ... 2610220 | 1578 | YP_001341167.1 | 1779 | *Marinomonas* sp. MWYL1 |
| 87121463 | NZ_AANE01000011.1: 112021 ... 114096 | 1579 | ZP_01077352.1 | 1780 | *Marinomonas* sp. MED121 |
| 146328905 | NC_009446.1: 489780 ... 491837 | 1580 | YP_001209362.1 | 1781 | *Dichelobacter nodosus* VCS1703A |
| 258544959 | NZ_ACKY01000059.1: 4448 ... 6562 | 1581 | ZP_05705193.1 | 1782 | *Cardiobacterium hominis* ATCC 15826 |
| 262104765 | complement (DS028152.1: 677306 ... 679621) | 1582 | EEY62817.1 | 1783 | *Phytophthora infestans* T30-4 |
| 262104764 | complement (DS028152.1: 674496 ... 676781) | 1583 | EEY62816.1 | 1784 | *Phytophthora infestans* T30-4 |
| 159472743 | XM_001694452.1: 258 ... 2636 | 1584 | XP_001694504.1 | 1785 | *Chlamydomonas reinhardtii* |
| 168000833 | XM_001753068.1: 1 ... 2367 | 1585 | XP_001753120.1 | 1786 | *Physcomitrella patens* subsp. *Patens* |
| 172038009 | complement (NC_010546.1: 3214848 ... 3216944) | 1586 | YP_001804510.1 | 1787 | *Cyanothece* sp. ATCC 51142 |
| 126658068 | NZ_AAXW01000014.1: 79066 ... 81162 | 1587 | ZP_01729220.1 | 1788 | *Cyanothece* sp. CCY0110 |
| 257060449 | NC_013161.1: 2659296 ... 2661419 | 1588 | YP_003138337.1 | 1789 | *Cyanothece* sp. PCC 8802 |
| 218441705 | complement (NC_011729.1: 5341705 ... 5343810) | 1589 | YP_002380034.1 | 1790 | *Cyanothece* sp. PCC 7424 |
| 166368837 | NC_010296.1: 5646854 ... 5648950 | 1590 | YP_001661110.1 | 1791 | *Microcystis aeruginosa* NIES-843 |
| 220909840 | NC_011884.1: 4551169 ... 4553265 | 1591 | YP_002485151.1 | 1792 | *Cyanothece* sp. PCC 7425 |
| 16330299 | NC_000911.1: 1250442 ... 1252535 | 1592 | NP_441027.1 | 1793 | *Synechocystis* sp. PCC 6803 |
| 86142732 | NZ_AANC01000005.1: 209172 ... 211268 | 1593 | ZP_01061171.1 | 1794 | *Leeuwenhoekiella blandensis* MED217 |
| 146301271 | complement (NC_009441.1: 4208789 ... 4210882) | 1594 | YP_001195862.1 | 1795 | *Flavobacterium johnsoniae* UW101 |
| 260061847 | NC_013222.1: 1408358 ... 1410454 | 1595 | YP_003194927.1 | 1796 | *Robiginitalea biformata* HTCC2501 |
| 88713711 | complement (NZ_AAOC01000008.1: 22821 ... 24917) | 1596 | ZP_01107792.1 | 1797 | *Flavobacteriales bacterium* HTCC2170 |
| 86133149 | complement (NZ_CH902588.1: 146636 ... 148729) | 1597 | ZP_01051731.1 | 1798 | *Polaribacter* sp. MED152 |
| 88803680 | NZ_AAOG01000005.1: 54861 ... 56951 | 1598 | ZP_01119204.1 | 1799 | *Polaribacter irgensii* 23-P |
| 213962668 | NZ_ABZV01000006.1: 103363 ... 105438 | 1599 | ZP_03390929.1 | 1800 | *Capnocytophaga sputigena* ATCC 33612 |
| 256820698 | complement (NC_013162.1: 2243972 ... 2246047) | 1600 | YP_003141977.1 | 1801 | *Capnocytophaga ochracea* DSM 7271 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 46581432 | NC_002937.3: 3152216 . . . 3154330 | 1601 | YP_012240.1 | 1802 | *Desulfovibrio vulgaris* str. Hildenborough |
| 218886955 | NC_011769.1: 2286534 . . . 2288648 | 1602 | YP_002436276.1 | 1803 | *Desulfovibrio vulgaris* str. 'Miyazaki F' |
| 78358281 | NC_007519.1: 3235663 . . . 3237822 | 1603 | YP_389730.1 | 1804 | *Desulfovibrio desulfuricans* subsp. *desulfuricans* str. G20 |
| 242280036 | complement (NC_012881.1: 2812652 . . . 2814769) | 1604 | YP_002992165.1 | 1805 | *Desulfovibrio salexigens* DSM 2638 |
| 258405159 | complement (NC_013223.1: 1218708 . . . 1220816) | 1605 | YP_003197901.1 | 1806 | *Desulfohalobium retbaense* DSM 5692 |
| 256828849 | NC_013173.1: 1143375 . . . 1145477 | 1606 | YP_003157577.1 | 1807 | *Desulfomicrobium baculatum* DSM 4028 |
| 225198782 | complement (NZ_ACJN01000010.1: 60728 . . . 62824) | 1607 | ZP_03737911.1 | 1808 | *Desulfonatronospira thiodismutans* ASO3-1 |
| 242278203 | NC_012881.1: 802309 . . . 804414 | 1608 | YP_002990332.1 | 1809 | *Desulfovibrio salexigens* DSM 2638 |
| 212704109 | complement (NZ_ABXU01000065.1: 34368 . . . 36470) | 1609 | ZP_03312237.1 | 1810 | *Desulfovibrio piger* ATCC 29098 |
| 220903578 | complement (NC_011883.1: 357004 . . . 359112) | 1610 | YP_002478890.1 | 1811 | *Desulfovibrio desulfuricans* subsp. *desulfuricans* str. ATCC 27774 |
| 51244410 | NC_006138.1: 608983 . . . 611115 | 1611 | YP_064294.1 | 1812 | *Desulfotalea psychrophila* LSv54 |
| 94986723 | NC_008011.1: 347892 . . . 350012 | 1612 | YP_594656.1 | 1813 | *Lawsonia intracellularis* PHE/MN1-00 |
| 119488858 | complement (NZ_AAVU01000021.1: 33384 . . . 35414) | 1613 | ZP_01621820.1 | 1814 | *Lyngbya* sp. PCC 8106 |
| 209524350 | NZ_ABYK01000010.1: 35808 . . . 37916 | 1614 | ZP_03272899.1 | 1815 | *Arthrospira maxima* CS-328 |
| 116748909 | NC_008554.1: 1826816 . . . 1828915 | 1615 | YP_845596.1 | 1816 | *Syntrophobacter fumaroxidans* MPOB |
| 241776655 | NZ_ACQQ01000008.1: 86078 . . . 88198 | 1616 | ZP_04773932.1 | 1817 | *Allochromatium vinosum* DSM 180 |
| 32476008 | NC_005027.1: 5198833 . . . 5200932 | 1617 | NP_869002.1 | 1818 | *Rhodopirellula baltica* SH 1 |
| 78776256 | NC_007575.1: 60204 . . . 62282 | 1618 | YP_392571.1 | 1819 | *Sulfurimonas denitrificans* DSM 1251 |
| 254458291 | complement (NZ_DS995288.1: 173480 . . . 175561) | 1619 | ZP_05071717.1 | 1820 | *Campylobacterales bacterium* GD 1 |
| 229532518 | NZ_ABUV01000006.1: 73569 . . . 75677 | 1620 | ZP_04421899.1 | 1821 | *Sulfurospirillum deleyianum* DSM 6946 |
| 152993574 | NC_009663.1: 2069625 . . . 2071724 | 1621 | YP_001359295.1 | 1822 | *Sulfurovum* sp. NBC37-1 |
| 120401715 | NC_008726.1: 740616 . . . 742694 | 1622 | YP_951544.1 | 1823 | *Mycobacterium vanbaalenii* PYR-1 |
| 145220810 | complement (NC_009338.1: 189392 . . . 191515) | 1623 | YP_001131488.1 | 1824 | *Mycobacterium gilvum* PYR-GCK |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 108797517 | NC_008146.1: 594117 ... 596231 | 1624 | YP_637714.1 | 1825 | *Mycobacterium* sp. MCS |
| 118473540 | NC_008596.1: 867578 ... 869656 | 1625 | YP_885188.1 | 1826 | *Mycobacterium smegmatis* str. MC2 155 |
| 169631304 | complement (NC_010397.1: 4294451 ... 4296532) | 1626 | YP_001704953.1 | 1827 | *Mycobacterium abscessus* |
| 240168870 | NZ_ACBV01000011.1: 33884 ... 35974 | 1627 | ZP_04747529.1 | 1828 | *Mycobacterium kansasii* ATCC 12478 |
| 183980733 | NC_010612.1: 853987 ... 856071 | 1628 | YP_001849024.1 | 1829 | *Mycobacterium marinum* M |
| 15607549 | NC_000962.2: 491786 ... 493858 | 1629 | NP_214922.1 | 1830 | *Mycobacterium tuberculosis* H37Rv |
| 41409983 | NC_002944.2: 4345845 ... 4347932 | 1630 | NP_962819.1 | 1831 | *Mycobacterium avium* subsp. *paratuberculosis* K-10 |
| 254818871 | complement (NZ_ABIN01000026.1: 2280 ... 4439) | 1631 | ZP_05223872.1 | 1832 | *Mycobacterium intracellulare* ATCC 13950 |
| 226304961 | NC_012490.1: 1605870 ... 1607948 | 1632 | YP_002764919.1 | 1833 | *Rhodococcus erythropolis* PR4 |
| 111019190 | complement (NC_008268.1: 2308925 ... 2311045) | 1633 | YP_702162.1 | 1834 | *Rhodococcus jostii* RHA1 |
| 54027320 | complement (NC_006361.1: 5652808 ... 5654895) | 1634 | YP_121562.1 | 1835 | *Nocardia farcinica* IFM 10152 |
| 227978095 | NZ_ABVA01000001.1: 785441 ... 787570 | 1635 | ZP_04025361.1 | 1836 | *Tsukamurella paurometabola* DSM 20162 |
| 262204223 | complement (NC_013441.1: 4704088 ... 4706208) | 1636 | YP_003275431.1 | 1837 | *Gordonia bronchialis* DSM 43247 |
| 256831883 | complement (NC_013174.1: 683848 ... 685947) | 1637 | YP_003160610.1 | 1838 | *Jonesia denitrificans* DSM 20603 |
| 260517199 | complement (NZ_ABUN01000002.1: 90744 ... 92939) | 1638 | ZP_05816650.1 | 1839 | *Sanguibacter keddieii* DSM 10542 |
| 229243856 | complement (NZ_ABTJ01000131.1: 4381 ... 6468) | 1639 | ZP_04368027.1 | 1840 | *Cellulomonas flavigena* DSM 20109 |
| 229821528 | NC_012669.1: 3401218 ... 3403323 | 1640 | YP_002883054.1 | 1841 | *Beutenbergia cavernae* DSM 12333 |
| 227428424 | complement (NZ_ABVC01000008.1: 150308 ... 152407) | 1641 | ZP_03911481.1 | 1842 | *Xylanimonas cellulosilytica* DSM 15894 |
| 119717178 | complement (NC_008699.1: 3139954 ... 3142044) | 1642 | YP_924143.1 | 1843 | *Nocardioides* sp. JS614 |
| 227381337 | complement (NZ_ABUC01000011.1: 233655 ... 235784) | 1643 | ZP_03864789.1 | 1844 | *Kribbella flavida* DSM 17836 |
| 88856399 | NZ_AAOB01000010.1: 2970 ... 5138 | 1644 | ZP_01131057.1 | 1845 | marine actinobacterium PHSC20C1 |
| 170780609 | NC_010407.1: 179995 ... 182112 | 1645 | YP_001708941.1 | 1846 | *Clavibacter michiganensis* subsp. *Sepedonicus* |
| 50954174 | NC_006087.1: 335128 ... 337257 | 1646 | YP_061462.1 | 1847 | *Leifsonia xyli* subsp. *xyli* str. CTCB07 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 114331961 | complement (NC_008344.1: 2107910 . . . 2110039) | 1647 | YP_748183.1 | 1848 | *Nitrosomonas eutropha* C91 |
| 256395328 | complement (NC_013131.1: 7130890 . . . 7133034) | 1648 | YP_003116892.1 | 1849 | *Catenulispora acidiphila* DSM 44928 |
| 258650827 | NC_013235.1: 639398 . . . 641491 | 1649 | YP_003199983.1 | 1850 | *Nakamurella multipartita* DSM 44233 |
| 257068066 | complement (NC_013172.1: 995592 . . . 997667) | 1650 | YP_003154321.1 | 1851 | *Brachybacterium faecium* DSM 4810 |
| 227497260 | complement (NZ_ACFH01000109.1: 3054 . . . 5108) | 1651 | ZP_03927492.1 | 1852 | *Actinomyces urogenitalis* DSM 15434 |
| 256824971 | NC_013169.1: 1149994 . . . 1152081 | 1652 | YP_003148931.1 | 1853 | *Kytococcus sedentarius* DSM 20547 |
| 260455562 | NZ_ACZH01000022.1: 9845 . . . 11917 | 1653 | ZP_05803950.1 | 1854 | *Streptomyces flavogriseus* ATCC 33331 |
| 182435904 | NC_010572.1: 2506931 . . . 2509012 | 1654 | YP_001823623.1 | 1855 | *Streptomyces griseus* subsp. *griseus* NBRC 13350 |
| 254387454 | NZ_DS570624.1: 26512 . . . 28596 | 1655 | ZP_05002693.1 | 1856 | *Streptomyces clavuligerus* ATCC 27064 |
| 254400535 | NZ_DS570905.1: 178100 . . . 180199 | 1656 | ZP_05015493.1 | 1857 | *Streptomyces sviceus* ATCC 29083 |
| 256813645 | NZ_ACFA01000303.1: 9482 . . . 11584 | 1657 | ZP_05538660.1 | 1858 | *Streptomyces griseoflavus* Tu4000 |
| 239928836 | NZ_ABYA01000185.1: 2180 . . . 4282 | 1658 | ZP_04685789.1 | 1859 | *Streptomyces ghanaensis* ATCC 14672 |
| 256804684 | complement (NZ_ACEZ01000169.1: 8822 . . . 10924) | 1659 | ZP_05534308.1 | 1860 | *Streptomyces viridochromogenes* DSM 40736 |
| 256785123 | NZ_ACEY01000098.1: 97187 . . . 99280 | 1660 | ZP_05523554.1 | 1861 | *Streptomyces lividans* TK24 |
| 29829365 | NC_003155.4: 3467325 . . . 3469415 | 1661 | NP_823999.1 | 1862 | *Streptomyces avermitilis* MA-4680 |
| 260646824 | FN554889.1: 3224239 . . . 3226344 | 1662 | CBG69921.1 | 1863 | *Streptomyces scabiei* 87.22 |
| 239982381 | complement (NZ_ABYC01000362.1: 40088 . . . 42163) | 1663 | ZP_04704905.1 | 1864 | *Streptomyces albus* J1074 |
| 254382385 | complement (NZ_DS570390.1: 111950 . . . 114034) | 1664 | ZP_04997745.1 | 1865 | *Streptomyces* sp. Mg1 |
| 256769973 | complement (NZ_ACEW01000403.1: 16454 . . . 18541) | 1665 | ZP_05509147.1 | 1866 | *Streptomyces* sp. C |
| 256776255 | NZ_ACEX01000277.1: 2545 . . . 4641 | 1666 | ZP_05514718.1 | 1867 | *Streptomyces hygroscopicus* ATCC 53653 |
| 254378850 | NZ_DS570550.1: 40417 . . . 42507 | 1667 | ZP_04994290.1 | 1868 | *Streptomyces* sp. SPB74 |
| 229854086 | complement (NZ_ABUU01000066.1: 39364 . . . 41415) | 1668 | ZP_04474082.1 | 1869 | *Streptosporangium roseum* DSM 43021 |
| 145596204 | NC_009380.1: 4234932 . . . 4237007 | 1669 | YP_001160501.1 | 1870 | *Salinispora tropica* CNB-440 |
| 159039600 | NC_009953.1: 4631907 . . . 4633976 | 1670 | YP_001538853.1 | 1871 | *Salinispora arenicola* CNS-205 |

TABLE 12b-continued

SEQ ID NOs of phosphotransacetylase target gene coding regions and proteins

| GI Number | GENBANK Nucleotide Sequence Accession Information | Nucleic Acid SEQ ID NO: | GENBANK Amino Acid Sequence Accession No. | Amino Acid SEQ ID NO: | Source Organism |
|---|---|---|---|---|---|
| 238060866 | NZ_GG657738.1: 2330097 . . . 2332163 | 1671 | ZP_04605575.1 | 1872 | *Micromonospora* sp. ATCC 39149 |
| 116671783 | complement (NC_008541.1: 3648900 . . . 3651011) | 1672 | YP_832716.1 | 1873 | *Arthrobacter* sp. FB24 |
| 148807608 | complement (EF6018801: 72 . . . 2150) | 1673 | ABR13603.1 | 1874 | *Arthrobacter oxydans* |
| 239916738 | complement (NC_012803.1: 190981 . . . 193056) | 1674 | YP_002956296.1 | 1875 | *Micrococcus luteus* NCTC 2665 |
| 255326162 | NZ_ACVO01000004.1: 127571 . . . 129661 | 1675 | ZP_05367249.1 | 1876 | *Rothia mucilaginosa* ATCC 25296 |
| 184199797 | complement (NC_010617.1: 164688 . . . 166781) | 1676 | YP_001854004.1 | 1877 | *Kocuria rhizophila* DC2201 |
| 254368446 | NZ_DS264133.1: 69966 . . . 72062 | 1677 | ZP_04984463.1 | 1878 | *Francisella tularensis* subsp. *holarctica* FSC022 |
| 167626922 | complement (NC_010336.1: 741506 . . . 743602) | 1678 | YP_001677422.1 | 1879 | *Francisella philomiragia* subsp. *philomiragia* ATCC 25017 |
| 94676965 | NC_007984.1: 392877 . . . 395012 | 1679 | YP_588827.1 | 1880 | *Baumannia cicadellinicola* str. Hc (*Homalodisca coagulata*) |
| P57273 | BA000003.2: 189582 . . . 191708 | 1680 | NP_240007.1 | 1881 | *Buchnera aphidicola* str. APS (*Acyrthosiphon pisum*) |
| 254444018 | NZ_DS990592.1: 1298899 . . . 1201010 | 1681 | ZP_05057494.1 | 1882 | *Verrucomicrobiae bacterium* DG1235 |
| 171914782 | NZ_ABIZ01000001.1: 6593044 . . . 6595128 | 1682 | ZP_02930252.1 | 1883 | *Verrucomicrobium spinosum* DSM 4136 |
| 114777389 | NZ_AATS01000006.1: 50467 . . . 52602 | 1683 | ZP_01452386.1 | 1884 | *Mariprofundus ferrooxydans* PV-1 |
| 94500866 | NZ_AAQH01000011.1: 33324 . . . 35456 | 1684 | ZP_01307392.1 | 1885 | *Bermanella marisrubri* |

In other embodiments, a polynucleotide, gene and/or polypeptide encoding phosphotransacetylase can have at least about 70% to about 75%, about 80% to about 85%, about 85% to about 90%, about 90% to about 95%, about 96%, about 97%, about 98%, or about 99% sequence identity to any one of the sequences of Tables 10 or 12a or 12b, wherein the polynucleotide, gene and/or polypeptide encodes a polypeptide having phosphotransacetylase activity.

In embodiments, a polynucleotide, gene and/or polypeptide encoding phosphotransacetylase corresponds to the Enzyme Commission Number EC 2.3.1.8.

In other embodiments, the phosphotransacetylase polynucleotide, gene and/or polypeptide sequences described herein or those recited in the art can be used to identify phosphotransacetylase sequences or phosphotransacetylase homologs in other cells, as described above for PDC.

Methods for gene expression in recombinant host cells, including, but not limited to, yeast cells are known in the art (see, for example, *Methods in Enzymology*, Volume 194, Guide to Yeast Genetics and Molecular and Cell Biology (Part A, 2004, Christine Guthrie and Gerald R. Fink (Eds.), Elsevier Academic Press, San Diego, Calif.). In embodiments, the coding region for the phosphoketolase and/or phosphotransacetylase genes to be expressed can be codon optimized for the target host cell, as well known to one skilled in the art. Expression of genes in recombinant host cells, including but not limited to yeast cells, can require a promoter operably linked to a coding region of interest, and a transcriptional terminator. A number of promoters can be used in constructing expression cassettes for genes, including, but not limited to, the following constitutive promoters suitable for use in yeast: FBA1, TDH3 (GPD), ADH1, and GPM1; and the following inducible promoters suitable for use in yeast: GAL1, GAL10 and CUP1. Other yeast promoters include hybrid promoters UAS(PGK1)-FBA1p (SEQ ID NO: 1893), UAS(PGK1)-ENO2p (SEQ ID NO: 1894), UAS(FBA1)-PDC1p (SEQ ID NO: 1895), UAS(PGK1)-PDC1p (SEQ ID NO: 1896), and UAS(PGK)-OLE1p (SEQ ID NO: 1897). Suitable transcriptional terminators that can be used in a chimeric gene construct for expression include, but are not limited to, FBA1t, TDH3t, GPM1t, ERG10t, GAL1t, CYC1t, and ADH1t.

Recombinant polynucleotides are typically cloned for expression using the coding sequence as part of a chimeric gene used for transformation, which includes a promoter operably linked to the coding sequence as well as a ribosome binding site and a termination control region. The coding region may be from the host cell for transformation and combined with regulatory sequences that are not native to the natural gene encoding phosphoketolase and/or phosphotransacetylase. Alternatively, the coding region may be from another host cell.

Vectors useful for the transformation of a variety of host cells are common and described in the literature. Typically the vector contains a selectable marker and sequences allowing autonomous replication or chromosomal integration in the desired host. In addition, suitable vectors can comprise a promoter region which harbors transcriptional initiation controls and a transcriptional termination control region, between which a coding region DNA fragment may be inserted, to provide expression of the inserted coding region. Both control regions can be derived from genes homologous to the transformed host cell, although it is to be understood that such control regions can also be derived from genes that are not native to the specific species chosen as a production host.

In embodiments, suitable promoters, transcriptional terminators, and phosphoketolase and/or phosphotransacetylase coding regions can be cloned into E. coli-yeast shuttle vectors, and transformed into yeast cells. Such vectors allow strain propagation in both E. coli and yeast strains, and can contain a selectable marker and sequences allowing autonomous replication or chromosomal integration in the desired host. Typically used plasmids in yeast include, but are not limited to, shuttle vectors pRS423, pRS424, pRS425, and pRS426 (American Type Culture Collection, Rockville, Md.), which contain an E. coli replication origin (e.g., pMB1), a yeast 2-micron origin of replication, and a marker for nutritional selection. The selection markers for these four vectors are HIS3 (vector pRS423), TRP1 (vector pRS424), LEU2 (vector pRS425) and URA3 (vector pRS426).

In embodiments, construction of expression vectors with a chimeric gene encoding the described phosphoketolases and/or phosphotransacetylases can be performed by the gap repair recombination method in yeast. In embodiments, a yeast vector DNA is digested (e.g., in its multiple cloning site) to create a "gap" in its sequence. A number of insert DNAs of interest are generated that contain an approximately 21 bp sequence at both the 5' and the 3' ends that sequentially overlap with each other, and with the 5' and 3' terminus of the vector DNA. For example, to construct a yeast expression vector for "Gene X," a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an E. coli strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. In embodiments, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding region X-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

The presence of phosphoketolase and phosphotransacetylase activity in the recombinant host cells disclosed herein can be confirmed using routine methods known in the art. In a non-limiting example, and as described in the Examples herein, transformants can be screened by PCR using primers for the phosphoketolase and phosphotransacetylase genes. In embodiments, and as described in the Examples herein, transformants can be screened by PCR with primers N1039 and N1040 (SEQ ID NOs: 639 and 640) to confirm integration of the xpk1 gene, and primers N1041 and N1042 (SEQ ID NOs: 641 and 642) can be used to confirm integration of the eutD gene. In another non-limiting example, and as described in the Examples herein, transformants can be screened for integration of phosphoketolase constructs and/or phosphotransacetylase constructs at the Δpdc1::ilvD(Sm) locus by the loss of ilvD(Sm) in the host cells.

In another non-limiting example, and as described in the examples herein, phosphoketolase activity can be assayed by expressing phosphoketolase identifiable by the methods disclosed herein in a recombinant host cell disclosed herein that lacks endogenous phosphoketolase activity. If phosphoketolase activity is present, such cells exhibit a reduced or eliminated requirement for exogenous two-carbon substrate supplementation for growth in culture.

In another non-limiting example, and as described in the examples herein, phosphoketolase and phosphotransacetylase activity can be assayed by expressing phosphoketolase and phosphotransacetylase activity identifiable by the methods disclosed herein in a recombinant host cell disclosed herein that lacks endogenous phosphoketolase and phosphotransacetylase activity. If phosphoketolase activity and phosphoketolase activity are present, such cells exhibit a reduced or eliminated requirement for exogenous two-carbon substrate supplementation for growth in culture.

In another non-limiting example, phosphoketolase and/or phosphotransacetylase activity can be confirmed by more indirect methods, such as by assaying for a downstream product in a pathway requiring phosphoketolase activity. For example, a polypeptide having phosphoketolase activity can catalyze the conversion of xylulose-5-phosphate into glyceraldehyde-3-phosphate and acetyl-phosphate and/or the conversion of fructose-6-phosphate into erythrose-4-phosphate and acetyl-phosphate. Also, a polypeptide having phosphotransacetylase activity can catalyze the conversion of acetyl-phosphate into acetyl-CoA.

Suitable Pathway Carbon Substrates and Exogenous Two-Carbon Substrate Supplementation PDC-KO cells fail to grow in glucose-containing media (e.g., 2% glucose), but PDC-KO cells carrying a functional butanediol biosynthetic pathway have been shown to grow on glucose supplemented with exogenous two-carbon substrates such as ethanol (see for example, US Patent Application Publication No. 20090305363, herein incorporated by reference). In embodiments, the host cells disclosed herein can be grown in fermentation media which contains a suitable pathway carbon substrate and two-substrate supplement, including combinations of suitable pathway carbon substrates with C2-substrate supplement. Non-limiting examples of suitable pathway carbon substrates include, but are not limited to, monosaccharides such as fructose, oligosaccharides such as lactose maltose, galactose, or sucrose, polysaccharides such as starch or cellulose or mixtures thereof and unpurified mixtures from renewable feedstocks such as cheese whey permeate, cornsteep liquor, sugar beet molasses, and barley malt, including any combinations thereof. In other embodiments, the suitable pathway carbon substrates can include lactate, glycerol, or combinations thereof.

In embodiments, a suitable carbon substrate can be a one-carbon substrate such as carbon dioxide, or methanol for which metabolic conversion into key biochemical intermediates has been demonstrated, or combinations thereof. In other embodiments related to methylotrophic organisms, the carbon substrate can be carbon containing compounds such as methylamine, glucosamine and a variety of amino acids for metabolic activity. In a non-limiting example, methylotrophic yeasts are known to utilize the carbon from methylamine to form trehalose or glycerol (Bellion et al., *Microb. Growth C1 Compd.*, [Int. Symp.], 7th (1993), 415-32, Editor(s): Murrell, J. Collin; Kelly, Don P. Publisher: Intercept, Andover, UK). In another non-limiting example, various species of *Candida* can metabolize alanine (Sulter et al., *Arch. Microbiol.* 153:485-489 (1990)). Hence it is contemplated that the source of carbon utilized in the present invention can encompass a wide variety of carbon containing substrates and will only be limited by the choice of organism.

In other embodiments, the suitable pathway carbon substrate can be glucose, fructose, and sucrose, or mixtures of these with five-carbon (C5) sugars such as xylose and/or arabinose for yeasts cells modified to use C5 sugars. In embodiments, sucrose can be derived from renewable sugar sources such as sugar cane, sugar beets, cassava, sweet sorghum, and mixtures thereof. In other embodiment, glucose and dextrose can derived from renewable grain sources through saccharification of starch based feedstocks including grains such as corn, wheat, rye, barley, oats, and mixtures thereof. In embodiments, the pathway carbon substrates can be derived from renewable cellulosic or lignocellulosic biomass through processes of pretreatment and saccharification, as described, for example, in U.S. Patent Application Publication No. US 20070031918 A1, which is herein incorporated by reference.

As used herein, "biomass" refers to any cellulosic or lignocellulosic material and includes, but is not limited to, materials comprising cellulose, and optionally further comprising hemicellulose, lignin, starch, oligosaccharides and/or monosaccharides. In embodiments, biomass can also comprise additional components, such as protein and/or lipid. In other embodiments, biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Other non-limiting examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

The recombinant host cells described herein can be cultured using standard laboratory techniques known in the art (see, e.g., *Methods in Yeast Genetics,* 2005, Cold Spring Harbor Laboratory Press, Cold Spring Harbor, N.Y., pp. 201-202). In embodiments related to media supplemented with exogenous two-carbon substrates, and as described in the Examples, recombinant host cells can be grown in synthetic complete medium supplemented with one or more exogenous two-carbon substrates as described herein at a concentration of about 0.01%, about 0.05%, about 0.1%, about 0.5%, about 1.0%, about 1.5%, about 1.5% or about 2% (v/v) of the media. In embodiments, the recombinant host cells can be grown in synthetic complete culture without uracil or histidine, supplemented with 0.5% (v/v) ethanol. In embodiments related to growth in media that is not supplemented with exogenous two-carbon substrates, the recombinant host cells described herein can be first grown in culture medium comprising an exogenous two-carbon substrate and then diluted (e.g., starting OD=0.1, 20 ml medium in a 125 ml vented flask) into media that is not supplemented with exogenous two-carbon substrate.

The growth of the recombinant host cells described herein can be measured by methods known in the art (see, e.g., *Methods in Yeast Genetics,* 2005, Cold Spring Harbor Laboratory Press, Cold Spring Harbor, N.Y., pp. 201-202). In a non-limiting example, the growth of the recombinant host cells described herein can be determined by measuring the optical density (OD) of cell cultures over time. For example, the OD at 600 nm for a yeast culture is proportional to yeast cell number. In another non-limiting example, the growth of the recombinant host cells described herein can be determined by counting viable cells in a sample of the culture over time.

Applicants have provided cells that have a reduced or eliminated requirement for two-carbon substrate supplementation for growth. In embodiments, such cells comprise (i) a deletion, mutation, and/or substitution in an endogenous gene encoding a polypeptide that converts pyruvate to acetaldehyde, acetyl-phosphate or acetyl-CoA that results in a requirement for exogenous two-carbon substrate supplementation for optimal growth; (ii) a heterologous polynucleotide encoding a polypeptide having phosphoketolase activity; and optionally (iii) a heterologous polynucleotide encoding a polypeptide having phosphotransacetylase activity. In embodiments, such cells comprise (i) a modification in an endogenous polypeptide having PDC activity which results in reduced or eliminated PDC activity; (ii) a heterologous polynucleotide encoding a polypeptide having phosphoketolase activity; and optionally (iii) a heterologous polynucleotide encoding a polypeptide having phosphotransacetylase activity. As such, Applicants have also provided methods of improving the growth of a recombinant host cell comprising at least one modification in an endogenous polypeptide that converts pyruvate to acetaldehyde, acetyl-phosphate or acetyl-CoA that results in a requirement for exogenous two-carbon substrate supplementation for optimal growth comprising transforming the host cell with a heterologous polynucleotide encoding a polypeptide having phosphoketolase activity. Applicants have also provided methods of improving the growth of a recombinant host cell comprising at least one modification in an endogenous polypeptide having pyruvate decarboxylase activity (e.g., having at least one deletion, mutation or substitution in an endogenous gene encoding a polypeptide having PDC activity that results in reduced or eliminated PDC activity) comprising transforming the host cell with a heterologous polynucleotide encoding a polypeptide having phosphoketolase activity. In other embodiments, the method further comprises transforming a recombinant host cell described herein with a heterologous polynucleotide encoding a polypeptide having phosphotransacetylase activity.

Applicants have also provided methods of reducing or eliminating the requirement for an exogenous two-carbon substrate for the growth of a recombinant host cell comprising at least one modification in an endogenous activity that converts pyruvate to acetaldehyde, acetyl-phosphate or acetyl-CoA that results in a requirement for exogenous two-carbon substrate supplementation for optimal growth comprising transforming the host cell with a heterologous polynucleotide encoding a polypeptide having phosphoketolase activity comprising transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

Applicants have also provided methods of reducing the requirement for an exogenous two-carbon substrate for the growth of a recombinant host cell comprising at least one modification in an endogenous polypeptide having PDC activity (e.g., having at least one deletion, mutation or substitution in an endogenous gene encoding a polypeptide having pyruvate decarboxylase activity) comprising transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In addition, Applicants have provided methods of eliminating the requirement for an exogenous two-carbon substrate for the growth of a recombinant host cell comprising at least one modification in an endogenous polypeptide having PDC activity (e.g., having at least one deletion, mutation or substitution in an endogenous gene encoding a polypeptide having PDC activity that results in reduced or eliminated PDC activity) comprising transforming the recombinant host cell with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In embodiments, a reduced requirement for exogenous two-carbon substrate supplementation can be a growth rate of the recombinant host cells described herein in media that is not supplemented with an exogenous two-carbon substrate that is the same or substantially equivalent to the growth rate of a recombinant host cell comprising a modification in an endogenous activity that converts pyruvate to acetaldehyde, acetyl-phosphate or acetyl-CoA grown in media that is supplemented with an exogenous two-carbon substrate. In embodiments, such a growth rate can be at least about 70%, at least about 75%, at least about 80%, at least about 85%, at least about 90%, at least about 95%, at least about 96%, at least about 97%, at least about 98%, or at least about 99% of the growth rate of a recombinant host cell comprising a modification in an endogenous activity that converts pyruvate to acetaldehyde, acetyl-phosphate or acetyl-CoA grown in media that is supplemented with an exogenous two-carbon substrate.

In embodiments, a reduced requirement for exogenous two-carbon substrate supplementation can be a growth rate of the recombinant host cells described herein in media that is not supplemented with an exogenous two-carbon substrate that is the same or substantially equivalent to the growth rate of a recombinant host cell comprising a modification in an endogenous PDC activity grown in media that is supplemented with an exogenous two-carbon substrate. In embodiments, such a growth rate can be at least about 70%, at least about 75%, at least about 80%, at least about 85%, at least about 90%, at least about 95%, at least about 96%, at least about 97%, at least about 98%, or at least about 99% of the growth rate of a recombinant host cell comprising a modification in an endogenous PDC activity grown in media that is supplemented with an exogenous two-carbon substrate.

In other embodiments, the recombinant host cells described herein have a growth rate in media that is not supplemented with an exogenous two-carbon substrate that is greater than the growth rate of a recombinant host cell comprising a modification in an endogenous activity that converts pyruvate to acetaldehyde, acetyl-phosphate or acetyl-CoA in media that is not supplemented with an exogenous two-carbon substrate.

In other embodiments, the recombinant host cells described herein have a growth rate in media that is not supplemented with an exogenous two-carbon substrate that is greater than the growth rate of a recombinant host cell comprising a modification in an endogenous PDC activity in media that is not supplemented with an exogenous two-carbon substrate.

In other embodiments, the recombinant host cells described herein can have an increased glucose consumption compared to a recombinant host cell comprising a modification in an endogenous polypeptide that converts pyruvate to acetaldehyde, acetyl-phosphate or acetyl-CoA.

In other embodiments, the recombinant host cells described herein can have an increased glucose consumption compared to a recombinant host cell comprising a modification in an endogenous polypeptide having PDC activity (e.g., at least one deletion, mutation, and/or substitution in an endogenous gene encoding a polypeptide having PDC activity that reduces or eliminates PDC activity).

Glucose consumption of the recombinant host cells described herein can be measured by methods known in the art (see, e.g., *Methods in Yeast Genetics,* 2005, Cold Spring Harbor Laboratory Press, Cold Spring Harbor, N.Y., pp. 201-202). In a non-limiting example, glucose consumption can be measured by quantitating the amount of glucose in culture media by HPLC or with a YSI Biochemistry Analyzer (YSI, Inc., Yellow Springs, Ohio).

In other embodiments, methods of producing a recombinant host cell are provided comprising transforming a recombinant host cell comprising a modification in an endogenous polynucleotide, gene or polypeptide encoding pyruvate decarboxylase (e.g., at least one deletion, mutation, and/or substitution in an endogenous gene encoding a polypeptide having pyruvate decarboxylase activity) with a heterologous polynucleotide encoding a polypeptide having phosphoketolase activity. In other embodiments, the method further comprises transforming the recombinant host cell with a heterologous polynucleotide encoding a polypeptide having phosphotransacetylase activity.

In other embodiments, methods for the conversion of xylulose 5-phosphate or fructose 6-phosphate into acetyl-phosphate are provided comprising (i) providing a recombinant host cell as described herein, or combinations thereof; and (ii) growing the recombinant host cell under conditions wherein xylulose 5-phosphate or fructose-6-phosphate is converted into acetyl-phosphate. In other embodiments, methods for the conversion of xylulose 5-phosphate or fructose-6-phosphate into acetyl-CoA are provided comprising (i) providing a recombinant host cell as described herein, or combinations thereof; and (ii) growing the recombinant host cell under conditions where xylulose 5-phosphate or fructose-6-phosphate is converted into acetyl-CoA.

In other embodiments, methods for the conversion of acetyl-phosphate to acetyl-CoA are provided comprising (i) providing a recombinant host cell as described herein, or combinations thereof; and (ii) growing the recombinant host cell under conditions where acetyl-phosphate is converted into acetyl-CoA. In other embodiments, methods for increasing the specific activity of a heterologous polypeptide having phosphoketolase activity in a recombinant host cell are provided comprising (i) providing a recombinant host cell as described herein, or combinations thereof; and (ii) growing the recombinant host cell under conditions wherein the heterologous polypeptide having phosphoketolase activity is expressed in functional form having a specific activity greater than the same recombinant host cell lacking the heterologous polypeptide having phosphoketolase activity.

In other embodiments, methods for increasing the specific activity of a heterologous polypeptide having phosphotransacetylase activity in a recombinant host cell are provided comprising (i) providing a recombinant host cell described herein, or combinations thereof; and (ii) growing the recombinant host cell under conditions whereby the heterologous polypeptide having phosphotransacetylase activity is expressed in functional form having a specific activity greater than the same recombinant host cell lacking a heterologous polypeptide having phosphotransacetylase activity.

In still other embodiments, methods for increasing the activity of the phosphoketolase pathway in a recombinant host cell are provided comprising (i) providing a recombinant host cell as described herein, or combinations thereof; and (ii) growing the host cell under conditions whereby the activity of the phosphoketolase pathway in the host cell is increased.

Threonine aldolase (E.C. number 4.1.2.5) catalyzes cleavage of threonine to produce glycine and acetaldehyde. Plasmid-based overexpression of a gene encoding this enzyme in *S. cerevisiae* PDC-KO strains was shown to eliminate the requirement for exogenous C2 supplementation (van Maris et al, Appl Environ Microbiol. 2003 April; 69(4):2094-9). In embodiments, recombinant host cells comprise (i) a deletion, mutation, and/or substitution in an endogenous gene encoding a polypeptide that converts pyruvate to acetaldehyde, acetyl-phosphate or acetyl-CoA that results in a requirement for exogenous two-carbon substrate supplementation for optimal growth; and (ii) a heterologous polynucleotide encoding a polypeptide having threonine aldolase activity.

Engineered Biosynthetic Pathways Using Pyruvate

In embodiments, the recombinant host cells described herein can be engineered to have a biosynthetic pathway for production of a product from pyruvate. A product from such a pyruvate-utilizing biosynthetic pathway includes, but is not limited to, 2,3-butanediol, isobutanol, 2-butanol, 2-butanone, valine, leucine, alanine, lactic acid, malic acid, fumaric acid, succinic acid and isoamyl alcohol. The features of any pyruvate-utilizing biosynthetic pathway may be engineered in the recombinant host cells described herein in any order. Any product made using a biosynthetic pathway that has pyruvate as the initial substrate can be produced with greater effectiveness in a recombinant host cell disclosed herein having a modification in an endogenous polypeptide that converts pyruvate to acetaldehyde, acetyl-phosphate or acetyl-CoA (such as pyruvate decarboxylase, pyruvate formate lyase, pyruvate dehydrogenase, pyruvate oxidase, or pyruvate:ferredoxin oxidoreductase) and having heterologous phosphoketolase and/or phosphotransacetylase activity, compared to a recombinant host cell having a modification in an endogenous polypeptide that converts pyruvate to acetaldehyde, acetyl-phosphate or acetyl-CoA (such as pyruvate decarboxylase, pyruvate formate lyase, pyruvate dehydrogenase, pyruvate oxidase, or pyruvate:ferredoxin oxidoreductase). Any product made using a biosynthetic pathway that has pyruvate as the initial substrate can be produced with greater effectiveness in a recombinant host cell disclosed herein having a modification in an endogenous polypeptide having PDC activity that reduces or eliminates PDC activity and having heterologous phosphoketolase and/or phosphotransacetylase activity, compared to a recombinant host cell having a modification in an endogenous polypeptide having PDC activity that reduces or eliminates PDC activity.

The biosynthetic pathway of the recombinant host cells described herein can be any pathway that utilizes pyruvate and produces a desired product. The pathway genes may include endogenous genes and/or heterologous genes. Typically at least one gene in the biosynthetic pathway is a heterologous gene. Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Genes and polypeptides that can be used for substrate to product conversions described herein as well as methods of identifying such genes and polypeptides, are described herein and/or in the art, for example, for isobutanol, in the Examples and in U.S. Pat. No. 7,851,188. Ketol-acid reductoisomerase (KARI) enzymes are described in U.S. Patent Appl. Pub. Nos. 20080261230 A1, 20090163376 A1, 20100197519 A1, and PCT Appl. Pub. No. WO/2011/041415. Examples of KARIs disclosed therein are those from *Lactococcus lactis, Vibrio cholera, Pseudomonas aeruginosa* PAO1, and *Pseudomonas fluorescens* PF5 mutants. KARIs include *Anaerostipes caccae* KARI variants "K9G9" and "K9D3" (SEQ ID NOs: 1911 and 1910, respectively). US Appl. Pub. No. 20100081154 A1, and U.S. Pat. No. 7,851,188 describe dihydroxyacid dehydratases (DHADs), including a DHAD from *Streptococcus mutans*. U.S. Patent Appl. Publ. No. 20090269823 A1 describes SadB, an alcohol dehydrogenase (ADH) from *Achromobacter xylosoxidans*. Alcohol dehydrogenases also include horse liver ADH and *Beijerinckia indica* ADH (protein SEQ ID NO: 1923).

An example of a biosynthetic pathway for producing 2,3-butanediol can be engineered in the recombinant host cells described herein, as described in U.S. Patent Application No. 20090305363, which is herein incorporated by reference. The 2,3-butanediol pathway is a portion of the 2-butanol biosynthetic pathway that is disclosed in U.S. Patent Application Publication No. US 20070292927 A1, which is herein incorporated by reference. Such pathway steps include, but are not limited to, conversion of pyruvate to acetolactate by acetolactate synthase, conversion of acetolactate to acetoin by acetolactate decarboxylase, and conversion of acetoin to 2,3-butanediol by butanediol dehydrogenase. The skilled person will appreciate that polypeptides having the activity of such pathway steps can be isolated from a variety of sources can be used in the recombinant host cells described herein.

In addition, examples of biosynthetic pathways for production of 2-butanone or 2-butanol that can be engineered in the recombinant host cells described herein are disclosed in U.S. Patent Application Publication Nos. US 20070292927 A1 and US 20070259410 A1, which are herein incorporated by reference. The pathway in U.S. Patent Application Publication No. US 20070292927 A1 is the same as described for butanediol production with the addition of the following steps:

2,3-butanediol to 2-butanone as catalyzed for example by diol dehydratase or glycerol dehydratase; and
2-butanone to 2-butanol as catalyzed for example by butanol dehydrogenase.

Described in U.S. Patent Application Publication No. US 20090155870 A1, which is herein incorporated by reference, is the construction of chimeric genes and genetic engineering of yeast for 2-butanol production using the U.S. Patent Application Publication No. US 20070292927 A1 disclosed biosynthetic pathway. Further description for gene construction and expression related to these pathways can be found, for example, in International Publication No. WO 2009046370 (e.g., butanediol dehydratases); and U.S. Patent Application Publication No. US 20090269823 A1 (e.g., butanol dehydrogenase) and U.S. Patent Application Publication No. US 20070259410 A1 which are herein incorporated by reference. The skilled person will appreciate that polypeptides having the activity of such pathway steps can be isolated from a variety of sources can be used in the recombinant host cells described herein.

Biosynthetic pathways for the production of isobutanol that may be used include those described in U.S. Pat. No. 7,851,188 and PCT Publication WO 2007050671, incorporated herein by reference. One isobutanol biosynthetic pathway comprises the following substrate to product conversions:

pyruvate to acetolactate, which may be catalyzed, for example, by acetolactate synthase;
acetolactate to 2,3-dihydroxyisovalerate, which may be catalyzed, for example, by acetohydroxy acid reductoisomerase;
2,3-dihydroxyisovalerate to α-ketoisovalerate, which may be catalyzed, for example, by acetohydroxy acid dehydratase;
α-ketoisovalerate to isobutyraldehyde, which may be catalyzed, for example, by a branched-chain keto acid decarboxylase; and
isobutyraldehyde to isobutanol, which may be catalyzed, for example, by a branched-chain alcohol dehydrogenase.

In some embodiments, the isobutanol biosynthetic pathway comprises at least one gene, at least two genes, at least three genes, or at least four genes that is/are heterologous to the yeast cell. In embodiments, each substrate to product conversion of an isobutanol biosynthetic pathway in a recombinant host cell is catalyzed by a heterologous polypeptide. In embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH as a cofactor.

An example of a biosynthetic pathway for production of valine that can be engineered in the recombinant host cells described herein includes the steps of acetolactate conversion to 2,3-dihydroxy-isovalerate by acetohydroxyacid reductoisomerase (ILV5), conversion of 2,3-dihydroxy-isovalerate to 2-keto-isovalerate by dihydroxy-acid dehydratase (ILV3), and conversion of 2-keto-isovalerate to valine by branched-chain amino acid transaminase (BAT2) and branched-chain amino acid aminotransferase (BAT1). Biosynthesis of leucine includes the same steps to 2-keto-isovalerate, followed by conversion of 2-keto-isovalerate to alpha-isopropylmalate by alpha-isopropylmalate synthase (LEU9, LEU4), conversion of alpha-isopropylmalate to beta-isopropylmalate by isopropylmalate isomerase (LEU1), conversion of beta-isopropylmalate to alpha-ketoisocaproate by beta-IPM dehydrogenase (LEU2), and finally conversion of alpha-ketoisocaproate to leucine by branched-chain amino acid transaminase (BAT2) and branched-chain amino acid aminotransferase (BAT1). It is desired for production of valine or leucine to overexpress at least one of the enzymes in these described pathways.

An example of a biosynthetic pathway for production of isoamyl alcohol that can be engineered in the recombinant host cells described herein includes the steps of leucine conversion to alpha-ketoisocaproate by branched-chain amino acid transaminase (BAT2) and branched-chain amino acid aminotransferase (BAT1), conversion of alpha-ketoisocaproate to 3-methylbutanal by ketoisocaproate decarboxylase (THI3) or decarboxylase ARO10, and finally conversion of 3-methylbutanal to isoamyl alcohol by an alcohol dehydrogenase such as ADH1 or SFA1. Production of isoamyl alcohol benefits from increased production of leucine or the alpha-ketoisocaproate intermediate by overexpression of one or more enzymes in biosynthetic pathways for these chemicals. In addition, one or both enzymes for the final two steps can be overexpressed.

An example of a biosynthetic pathway for production of lactic acid that can be engineered in the recombinant host cells described herein includes pyruvate conversion to lactic acid by lactate dehydrogenase. Engineering yeast for lactic acid production using lactate dehydrogenase, known as EC 1.1.1.27, is well known in the art such as in Ishida et al. (*Appl. Environ. Microbiol.* 71:1964-70 (2005)).

An example of a biosynthetic pathway for production of alanine that can be engineered in the recombinant host cells described herein includes pyruvate conversion to alanine by aminotransferase.

An example of a biosynthetic pathway for production of malate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a malate transporter can be expressed.

An example of a biosynthetic pathway for production of fumarate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a fumarase and a fumarate transporter can be expressed. Favorable production conditions and engineering of fungi for fumarate production is well known in the art, described e.g. by Goldberg et al. (*Journal of Chemical Technology and Biotechnology* 81:1601-1611 (2006)).

An example of a biosynthetic pathway for production of succinate that can be engineered in the recombinant host cells described herein includes pyruvate conversion to oxaloacetate by pyruvate carboxylase, and conversion of oxaloacetate to malate by malate dehydrogenase as described in Zelle et al. (*Applied and Environmental Microbiology* 74:2766-77 (2008)). In addition, a fumarase, a succinate dehydrogenase and a succinate transporter can be expressed.

The skilled person will appreciate that polypeptides having activities of the above-mentioned biosynthetic pathways can be isolated from a variety of sources can be used in the recombinant host cells described herein.

It will be appreciated that host cells comprising a butanol biosynthetic pathway such as an isobutanol biosynthetic pathway as provided herein may further comprise one or more additional modifications. U.S. Appl. Pub. No. 20090305363 (incorporated by reference) discloses increased conversion of pyruvate to acetolactate by engineering yeast for expression of a cytosol-localized acetolactate synthase and substantial elimination of pyruvate decarboxylase activity. Modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Appl. Pub. No. 20090305363 (incorporated herein by reference), modifications to a host cell that provide for increased carbon flux through an Entner-Doudoroff Pathway or reducing equivalents balance as described in U.S. Patent Appl. Pub. No. 20100120105 (incorporated herein by reference). Other modifications include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In embodiments, the polypeptide having acetolactate reductase activity is YMR226C (SEQ ID NO: 1912) of *Saccharomyces cerevisiae* or a homolog thereof. Additional modifications include a deletion, mutation, and/or substitution in an endogenous polynucleotide encoding a polypeptide having aldehyde dehydrogenase and/or aldehyde oxidase activity. In embodiments, the polypeptide having aldehyde dehydrogenase activity is ALD6 (SEQ ID NO: 1909) from *Saccharomyces cerevisiae* or a homolog thereof. A genetic modification which has the effect of reducing glucose repression wherein the yeast production host cell is pdc- is described in U.S. Appl. Publication No. 20110124060, incorporated herein by reference.

Recombinant host cells may further comprise (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe-S cluster biosynthesis; and/or (ii) at least one heterologous polynucleotide encoding a polypeptide affecting Fe-S cluster biosynthesis. In embodiments, the polypeptide affecting Fe-S cluster biosynthesis is encoded by AFT1 (nucleic acid SEQ ID NO: 1913, amino acid SEQ ID NO: 1914), AFT2 (SEQ ID NOs: 1915 and 1916), FRA2 (SEQ ID NOs: 1917 and 1918), GRX3 (SEQ ID NOs: 1919 and 1920), or CCC1 (SEQ ID NOs: 1921 and 1922). In embodiments, the polypeptide affecting Fe-S cluster biosynthesis is constitutive mutant AFT1 L99A, AFT1 L102A, AFT1 C291F, or AFT1 C293F.

Fermentation Media

The recombinant host cells disclosed herein can be grown in fermentation media for production of a product utilizing pyruvate. For maximal production of some products, such as 2,3-butanediol, isobutanol, 2-butanone, or 2-butanol, the recombinant host cells disclosed herein used as production hosts preferably have enhanced tolerance to the produced chemical, and have a high rate of carbohydrate utilization. These characteristics can be conferred by mutagenesis and selection, genetic engineering, or can be natural.

Fermentation media for production of the products disclosed herein may contain glucose. Additional carbon substrates for product production pathways can include but are not limited to those described above. It is contemplated that the source of carbon utilized can encompass a wide variety of carbon containing substrates and will only be limited by the choice of organism.

In addition to an appropriate carbon source, fermentation media can contain suitable minerals, salts, cofactors, buffers and other components, known to those skilled in the art, suitable for the growth of the cultures and promotion of the enzymatic pathway necessary for production of the desired product.

Culture Conditions

Typically cells are grown at a temperature in the range of about 20° C. to about 37° C. in an appropriate medium. Suitable growth media for the recombinant host cells described herein are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5 to pH 6.5 is preferred as the initial condition.

Fermentations can be performed under aerobic or anaerobic conditions, where anaerobic or microaerobic conditions are preferred.

The amount of product in the fermentation medium can be determined using a number of methods known in the art, for example, high performance liquid chromatography (HPLC) or gas chromatography (GC).

Industrial Batch and Continuous Fermentations

A batch method of fermentation can be used with the recombinant host cells described herein. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system can also be used with the recombinant host cells described herein. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although a batch mode can be performed, it is also contemplated that continuous fermentation methods could also be performed with the recombinant host cells described herein. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation.

Methods of modulating nutrients and growth factors for continuous fermentation processes as well as techniques for maximizing the rate of product formation are well known in the art of industrial microbiology and a variety of methods are detailed by Brock, supra.

It is contemplated that the present invention can be practiced using either batch, fed-batch or continuous processes and that any known mode of fermentation would be suitable. Additionally, it is contemplated that cells can be immobilized on a substrate as whole cell catalysts and subjected to fermentation conditions for production.

Product Isolation from Fermentation Medium

Products can be isolated from the fermentation medium by methods known to one skilled in the art. For example, bioproduced isobutanol may be isolated from the fermentation medium using methods known in the art for ABE fermentations (see, e.g., Durre, Appl. Microbiol. Biotechnol. 49:639-648 (1998), Groot et al., Process. Biochem. 27:61-75 (1992), and references therein). For example, solids may be removed from the fermentation medium by centrifugation, filtration, decantation, or the like. Then, the isobutanol may be isolated from the fermentation medium using methods such as distillation, azeotropic distillation, liquid-liquid extraction, adsorption, gas stripping, membrane evaporation, pervaporation or vacuum flash fermentation (see e.g., U.S. Pub. No. 20090171129 A1, and International Pub. No. WO2010/151832 A1, both incorporated herein by reference in their entirety).

Because butanol forms a low boiling point, azeotropic mixture with water, distillation can be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, Conceptual Design of Distillation Systems, McGraw Hill, New York, 2001).

The butanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The butanol can also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the butanol from the solvent.

Distillation in combination with adsorption can also be used to isolate isobutanol from the fermentation medium. In this method, the fermentation broth containing the isobutanol is distilled to near the azeotropic composition and then the remaining water is removed by use of an adsorbent, such as molecular sieves (Aden et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., J. Membr. Sci. 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. No. 20090305370, the disclosure of which is hereby incorporated in its entirety. U.S. Patent Appl. Pub. No. 20090305370 describes methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, the alcohol can be esterified by contacting the alcohol in a fermentation medium with an organic acid (e.g., fatty acids) and a catalyst (e.g. enzyme such as a lipase) capable of esterifying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

EXAMPLES

The meaning of abbreviations used is as follows: "min" means minute(s), "h" means hour(s), "sec" means second(s), "µl" means microliter(s), "ml" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "rpm" means revolutions per minute, "w/v" means weight/volume, "v/v" means volume/volume, "OD" means optical density, "bp" means base pair(s), and "PCR" means polymerase chain reaction.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987. Phusion® HF Master Mix (NEB Cat. No. F-531) and HotStarTaq® Master Mix (Qiagen Cat. No. 203443) were used for PCR in gene cloning and clone screening, respectively.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Wash., D C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

HPLC

Analysis for fermentation by-product composition is well known to those skilled in the art. For example, one high performance liquid chromatography (HPLC) method utilizes a Shodex SH-1011 column with a Shodex SH-G guard column (both available from Waters Corporation, Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol retention time is 47.6 minutes. For butanediol, meso-butanediol eluted at 26.0 min and 2R,3R-butanediol eluted at 27.7 min.

Example 1

Construction of Phosphoketolase/Phosphotransacetylase Expression Cassette

The xpk1 and eutD genes (GenBank GI numbers 28379168 (SEQ ID NO: 172) and 28377658 (SEQ ID NO: 1111), respectively) were obtained from *Lactobacillus plantarum* (ATCC No. BAA-793) via polymerase chain reaction (PCR) using primers N1039 and N1040 (for xpk1) and N1041 and N1042 (for eutD). The primer sequences of N1039, N1040, N1041 and N1042 correspond to SEQ ID Nos. 639-642, respectively.

The xpk1 and eutD genes were fused to a DNA fragment containing opposing yeast terminator sequences (CYC and ADH terminators, obtained from PacI digestion of pRS423::CUP1-alsS+FBA-budA, described in U.S. Patent Application Publication No. 20090155870, herein incorporated by reference) by overlap PCR method (Yu et al., *Fungal Genet. Biol.* 41: 973-981; 2003). The resulting PCR product was cloned into an *E. coli*-yeast shuttle vector using gap repair methodology (Ma et al., *Genetics* 58:201-216; 1981). The shuttle vector was based on pRS426 (ATCC No. 77107) and contained both GPD (also known as TDH3) and ADH1 promoters. The resulting vector contained xpk1 under control of the GPD promoter and eutD under control of the ADH1 promoter in opposing orientation. The sequence of the resulting vector (pRS426::GPD-xpk1+ADH1-eutD) is provided as SEQ ID No: 643 (see FIG. 5 for a map of this vector).

Example 2

Construction of Phosphoketolase/Phosphotransacetylase Integration Vector

An expression cassette of the pRS426::GPD-xpk1+ADH1-eutD vector (GPD-xpk1+ADH1-eutD) was prepared by digestion with EcoRI and SacI restriction enzymes. The resulting cassette was ligated into the yeast integration vector pUC19-URA3-MCS which was also prepared by digestion with EcoRI and SacI restriction enzymes.

Vector pUC19-URA3MCS is pUC19-based and contains the sequence of the URA3 gene from *Saccharomyces cerevisiae* situated within a multiple cloning site (MCS). pUC19 (American Type Culture Collection, Manassas, Va.; ATCC#37254) contains the pMB1 replicon and a gene coding for beta-lactamase for replication and selection in *Escherichia coli*. In addition to the coding sequence for URA3, the sequences from upstream and downstream of this gene are included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccharomyces cerevisiae* CEN.PK 113-7D (CBS 8340; Centraalbureau voor Schimmelcultures (CBS) Fungal Biodiversity Centre, Netherlands) genomic DNA was amplified with primers oBP438 (SEQ ID NO: 644), containing BamHI, AscI, PmeI, and FseI restriction sites, and oBP439 (SEQ ID NO: 645), containing XbaI, PacI, and NotI restriction sites. Genomic DNA was prepared using a Gentra Puregene Yeast/Bact kit (Qiagen). The PCR product and pUC19 were ligated with T4 DNA ligase after digestion with BamHI and XbaI to create vector pUC19-URA3MCS. The vector was confirmed by PCR and sequencing with primers oBP264 (SEQ ID NO:646) and oBP265 (SEQ ID NO:647).

The ligation reaction was transformed into *E. coli* Stbl3 cells, according to the manufacturer's instructions (Invitrogen, Carlsbad, Calif., Cat. No. C7373). Transformants were screened by polymerase chain reaction (PCR) to detect the eutD gene using the primers N1041 and N1042 (SEQ ID NOs: 641 and 642, respectively). Positive clones for eutD gene expression detected by PCR were further confirmed for eutD gene incorporation by digestion of the vector with SacII restriction enzyme.

Two confirmed clones were selected and an integration targeting sequence was added to the clones as follows. PCR was used to amplify regions of the genome of *S. cerevisiae* strain BY4700 (ATCC No. 200866) both 5' and 3' of the PDC1 gene using the following primers: N1049 and N1050 (5') and N1047 and N1048 (3') (SEQ ID NOs: 648-651, respectively). Primer N1049 enables the 3' end of the 161-bp PDC1 3' sequence to be fused to the 5' end of the 237 bp PDC1 5' sequence via PCR. This pdc1 3'-5'-fusion fragment (368 bp in length) was cloned into the pCRII-Blunt TOPO vector according to the manufacturer's instructions (Invitrogen, Carlsbad, Calif., Cat. No. K2800).

Transformants were screened by PCR to detect the pdc1 3'-5'-fusion fragment using primers N1047 and N1050. The pdc1 3'-5'-fusion fragment was isolated from positive clones and released from the vector by digestion with EcoRI enzyme, and ligated into a pUC19-URA3::GPD-xpk1+ADH-eutD vector that had been linearized by digestion with EcoRI restriction enzyme to generate the "phosphoketolase pathway" vector. Additionally, the pdc1 3'-5'-fusion fragment was ligated with pUC19-URA3-MCS digested with EcoRI restriction enzyme to generate the control vector. Both ligation reactions were transformed into *E. coli* Stbl3 cells according to the manufacturer's instructions (Invitrogen, Carlsbad, Calif., Cat. No. C7373). The resulting transformants were screened by PCR to detect the pdc1 3'-5'-fusion fragment using primers N1047 and N1050. Positive clones containing the pdc1 3'-5'-fusion fragment were identified and the vectors were digested with either NcoI restriction enzyme (control vector) or BsgI restriction enzyme (phosphoketolase pathway vector) to confirm cloning orientation. One control clone (=pUC19-URA3::pdc1) and one phosphoketolase pathway clone (=pUC19-URA3::pdc1::GPD-xpk1+ADH1-eutD; SEQ ID NO: 1898) were selected for integration.

Example 3

Construction of Pyruvate Decarboxylase Knockout (PDC-KO) Yeast Strain Containing Phosphoketolase and Phosphotransacetylase Genes The control and phosphoketolase pathway vectors described in Example 2 were linearized with AflII restriction enzyme and transformed into strain BP913 (CEN.PK113-7D Δura3::loxP Δhis3 Δpdc6 Δpdc1::ilvD(Sm) Δpdc5::sadB) to form control and phosphoketolase pathway strains. Strain BP913 is further described in Example 10.

Transformed cells were plated on synthetic complete medium without uracil containing ethanol as the sole carbon source (1% vol/vol) and screened by PCR using primers N238 and oBP264 (SEQ ID Nos. 652 and 646, respectively to confirm integration at the pdc1 locus. Integration at the Δpdc1::ilvD(Sm) locus resulted in the loss of ilvD(Sm).

Example 4

Figure 2:
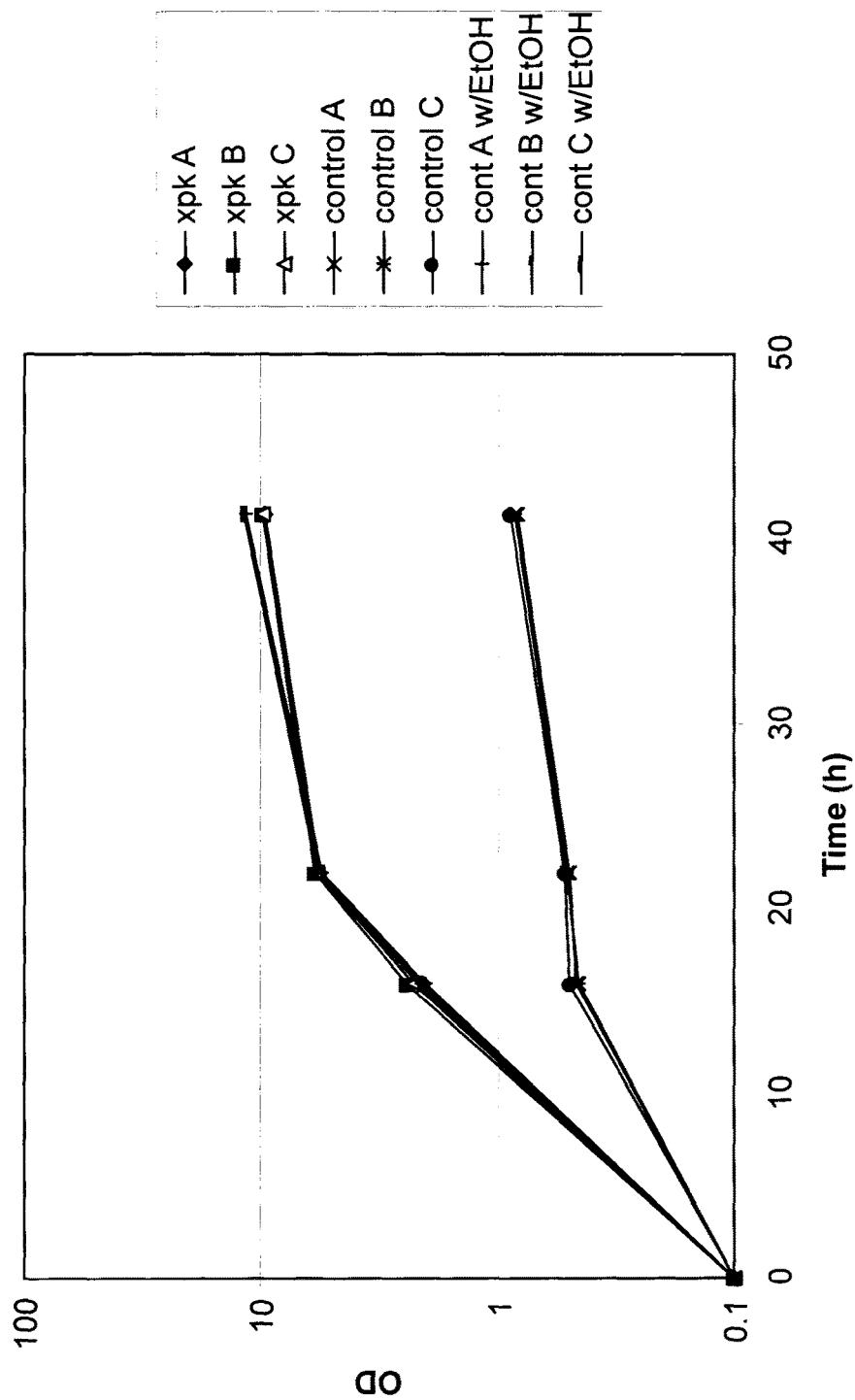
FIG. 2 depicts the growth of PDC-KO yeast strains expressing phosphoketolase and phosphotransacetylase without exogenous carbon substrate supplementation.

Introduction of Phosphoketolase and Phosphotransacetylase Allows Growth of PDC-KO Cells without Exogenous Two-Carbon Substrate Supplementation Pyruvate decarboxylase knockout (PDC-KO) yeast strains are unable to grow in media containing 2% glucose as the sole carbon source, but can grow in 2% glucose supplemented with ethanol as shown with a strain transformed with one or more plasmids encoding members of the butanediol pathway (described in U.S. Patent Application Publication No. 20090305363, herein incorporated by reference). To test whether the introduction of the phosphoketolase and phosphotransacetylase genes could support growth of PDC-KO cells, PDC-KO yeast were transformed with the phosphoketolase and phosphotransacetylase gene (as described in Example 3) and with the vector pRS423::CUP1-alsS+FBA-budA (described in U.S. Patent Application Publication No. 20090155870, herein incorporated by reference) encoding members of the butanediol pathway. After cultivation in media containing 2% glucose (synthetic complete minus his and ura) supplemented with 0.05% v/v ethanol, cultures were diluted into the same media lacking ethanol (starting OD=0.1, 20 ml medium in a 125 ml vented flask). For comparison, a control PDC-KO strain without introduction of the phosphoketolase and phosphotransacetylase genes was also diluted into medium supplemented with ethanol (0.05% vol/vol). The optical density at 600 nm was measured during growth (results shown in FIG. 2 and Table 13).

TABLE 13

| Strain | Condition | | | |
|---|---|---|---|---|
| | 0 h OD | 16 h OD | 22 h OD | 41.3 h OD |
| xpk A | 0.1 | 2.07 | 5.63 | 9.64 |
| xpk B | 0.1 | 2.44 | 5.93 | 9.78 |
| xpkC | 0.1 | 2.26 | 5.83 | 9.96 |
| control A | 0.1 | 0.47 | 0.5 | 0.822 |
| control B | 0.1 | 0.45 | 0.51 | 0.849 |
| control C | 0.1 | 0.5 | 0.52 | 0.879 |
| cont A w/EtOH | 0.1 | 2.01 | 5.49 | 11.44 |
| cont B w/EtOH | 0.1 | 2.16 | 5.7 | 11.5 |
| cont C w/EtOH | 0.1 | 2.12 | 5.76 | 11.76 |

The growth of PDC-KO yeast transformed with phosphoketolase and phosphotransacetylase in media that was not supplemented with ethanol (xpkA-xpkC, representing n=3 results) was indistinguishable from the growth of PDC-KO yeast strains grown in media containing 2% glucose that was supplemented with ethanol (cont A-cont C w/EtOH, representing n=3 results). The average growth rate of the phosphoketolase- and phosphotransacetylase-transformed strains under these conditions was 0.19 $h^{-1}$. A growth rate of 0.23 $h^{-1}$ for the phosphoketolase- and phosphotransacetylase-transformed strains was observed upon culturing under the same conditions with higher aeration (data not shown). PDC-KO yeast strains grown in media containing 2% glucose that was not supplemented with ethanol showed some growth in the first 16 hours, but then grew at a rate of only 0.01 $h^{-1}$ (control A-control C, representing n=3 results).

Example 5

Construction of Pyruvate Decarboxylase Knockout (PDC-KO) Yeast Strains Containing Either Phosphoketolase or Phosphotransacetylase Genes The integration vector described above (pUC19-URA3::pdc1::GPD-xpk1+ADH1-eutD) was modified to eliminate either the xpk1 phosphoketolase gene or the eutD phosphotransacetylase gene. Specifically, to remove eutD, the integration vector was digested with the ClaI and SpeI restriction enzymes to remove a 0.6 kb region from the eutD coding sequence, forming the vector pUC19-URA3::pdc1::GPD-xpk1. To remove xpk1, the integration vector was digested with the SpeI and KpnI restriction enzymes to remove the 3.4 kb region from SpeI to KpnI, forming the vector pUC19-URA3::pdc1::ADH-eutD. The resulting vectors, were linearized with digestion with the AflII restriction enzyme and transformed into BP913/pRS423::CUP1-alsS+FBA-budA cells (described in Example 3). Transformed cells were screened by PCR to confirm integration at the pdc1 locus and cultured, as described above.

Example 6

Introduction of Phosphoketolase Allows Growth of PDC-KO Cells without Exogenous Two-Carbon Substrate Supplementation To test whether the introduction of either the phosphoketolase or phosphotransacetylase genes could support the growth of PDC-KO cells, PDC-KO yeast were transformed with either the phosphoketolase or phosphotransacetylase genes (as described in Example 5) and with the vector pRS423::CUP1-alsS+FBA-budA encoding members of the butanediol pathway (as described in Example 4). After cultivation in media containing 2% glucose (synthetic complete minus his and ura) supplemented with 0.05% v/v ethanol, cultures were diluted into the same media lacking ethanol (starting OD=0.1, 20 ml medium in a 125 ml vented flask). For comparison, a PDC-KO strain without introduction of the phosphoketolase or phosphotransacetylase genes were grown under the same conditions. The optical density at 600 nm was measured during growth (results shown in FIG. 3 and Table 15).

TABLE 15

| Strain | 0 h OD | 24 h OD |
|---|---|---|
| xpk1 + eutD | 0.1 | 7.48 |
| none (control) | 0.1 | 0.575 |
| eutD only | 0.1 | 0.338 |
| eutD only | 0.1 | 0.28 |
| xpk1 only | 0.1 | 6.74 |
| xpk1 only | 0.1 | 7.26 |

Figure 3:
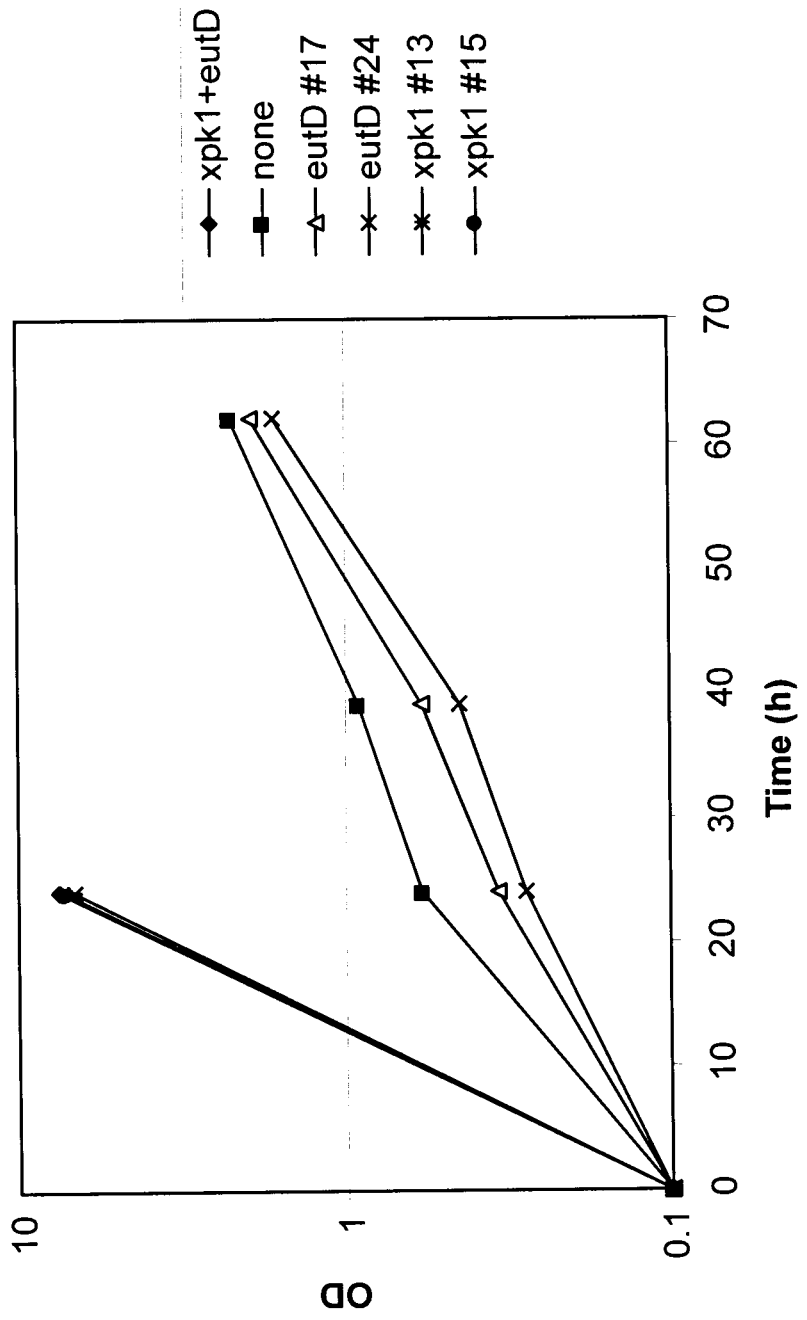
FIG. 3 depicts the growth of PDC-KO yeast strains expressing phosphoketolase and/or phosphotransacetylase in without exogenous carbon substrate supplementation.

The growth of PDC-KO yeast transformed with phosphoketolase in media that was not supplemented with exogenous carbon substrate (xpk1, FIG. 3) was indistinguishable from the growth of PDC-KO yeast transformed with phosphoketolase and phosphotransacetylase grown in media containing 2% glucose that was supplemented with ethanol (xpk1+eutD, FIG. 3). The growth of PDC-KO yeast transformed with phosphotransacetylase (eutD, FIG. 3) was not significantly improved compared to PDC-KO yeast strains in media that was not supplemented with exogenous two-carbon substrate (none, FIG. 3).

Example 7

Introduction of Phosphoketolase to PDC-KO Cells Increases Glucose Consumption and Butanediol Yield To test the effects of introduction of phosphoketolase into PDC-KO cells on glucose consumption and butanediol yield, PDC-KO yeast were transformed with either (1) phosphoketolase and phosphotransacetylase (as described in Example 4) and the vector pRS423::CUP1-alsS+FBA-budA encoding members of the butanediol (BDO) pathway (as described in Example 4) ("Xpk" in Table 16 below); or with (2) the vector pRS423::CUP1-alsS+FBA-budA encoding members of the butanediol pathway ("Control" in Table 6 below).

After cultivation in medium containing 2% glucose (synthetic complete minus histidine and uracil) supplemented with 0.05% ethanol, Xpk and Control cultures were diluted into medium without ethanol (starting OD=0.1, 20 ml medium in a 125 ml vented flask). Glucose consumption and butanediol yield of Xpk and Control cultures were measured by HPLC analysis of culture media for amount of glucose and butanediol as shown in the Table below.

TABLE 16

Introduction of Phosphoketolase Increases Glucose Consumption and Butanediol Yield of PDC-KO Cells.

| Strains | Glucose consumed (mM) | Butanediol Molar Yield |
|---|---|---|
| Xpk (n = 3) | 73.9 ± 2.4 | 0.475 ± 0.001 |
| Control (n = 3) | 48.3 ± 0.6 | 0.359 ± 0.003 |

The glucose consumption of Xpk cells (n=3) was nearly twice the amount of glucose consumption of control strains (n=3). In addition, the butanediol molar yield of Xpk cells was increased compared to the butanediol molar yield of Control cells.

Example 8

Construction of an Additional Phosphoketolase Pathway Integration Vector

A phosphoketolase/phosphotransacetylase integration vector similar to the one described in Example 2 was constructed. In this case the xpk1 and eutD gene constructs were cloned so that they would be integrated immediately downstream of the Δpdc1::ilvD(Sm) locus of BP913. To do this, the intergenic region between ilvD(Sm) and TRX1 was amplified from BP913 genomic DNA using primers N1110 and N1111 (SEQ ID Nos. 653 and 654). This was cloned into pUC19-URA3-MCS at the PmeI site, as follows. The ilvD-TRX1 PCR product was phosphorylated with polynucleotide kinase (NEB Cat. No. M0201), the vector was prepared by digesting with PmeI and treating with calf intestinal phosphatase, the two fragments were ligated overnight and cloned into E. coli Stbl3 cells. Clones were screened by PCR (using N1110 and N1111 primers) and then digested with BsgI to determine the orientation of the ilvD-TRX1 insertion. One clone from each orientation (pUC19-URA3::ilvD-TRX1 A and B) was carried over to the next step: addition of the xpk1/eutD expression cassette. The xpk1/eutD expression cassette from pRS426::GPD-xpk1+ADH1-eutD was obtained by digestion with BglII and EcoRV. The 5' overhanging DNA was filled in using Klenow Fragment. pUC19-URA3::ilvD-TRX1 was linearized with AflII and the 5' overhanging DNA was filled in using Klenow fragment. This vector was then ligated with the prepared xpk1/eutD cassette. Ligation reactions were transformed into E. coli Stbl3 cells. Clones were screened using primers for eutD (N1041 and N1042) and then digested with BamHI to determine orientation of the xpk1/eutD cassette relative to the ilvD-TRX1 DNA sequence.

The URA3 marker gene was then replaced with a geneticin resistance marker as follows. A chimeric geneticin resistance gene was constructed that contained the Kluyveromyces lactis TEF1 promoter and terminator (TEF1p-kan-TEF1t gene, provided as SEQ ID No. 655). This gene was maintained in a pUC19 vector (cloned at the SmaI site). The kan gene was isolated from pUC19 by first digesting with KpnI, removal of 3' overhanging DNA using Klenow Fragment (NEB, Cat. No. M212), digesting with HincII and then gel purifying the 1.8 kb gene fragment (Zymoclean™ Gel DNA Recovery Kit, Cat. No. D4001, Zymo Research, Orange, Calif.). The URA3 marker was removed from pUC19-URA3::ilvD::GPD-xpk1+ADH1-eutD::TRX1 (paragraph above) using NsiI and NaeI (the 3' overhanging DNA from NsiI digestion was removed with Klenow fragment). The vector and kan gene were ligated overnight and transformed into E. coli Stbl3 cells. Clones were screened by PCR using primers BK468 and either N1090 or N1113 (SEQ ID Nos. 656, 657, and 658, respectively)—positive PCR results indicate presence and orientation of kan gene. Clones in both orientations were digested with PmeI and transformed into BP913 with selection on yeast extract-peptone medium supplied with 1% (v/v) ethanol as carbon source and 200 µg/ml geneticin (G418). A single transformant was obtained, as confirmed by PCR (primers N886 and oBP264 for the 5' end N1090 and oBP512 for the 3' end, SEQ ID Nos. 659, 646, 657, and 660, respectively). FIG. 6 depicts the locus after integration of the plasmid.

Example 9

Construction of an Isobutanol-Producing Strain Carrying the Phosphoketolase Pathway The strain described in Example 8 was transformed with 2 plasmids containing genes for an isobutanol pathway pYZ090 and pYZ067 (SEQ ID NOs: 1892 and 1891).

pYZ090 was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI.

pYZ067 was constructed to contain the following chimeric genes: 1) the coding region of the ilvD gene from *S. mutans* UA159 with a C-terminal Lumio tag (nt 2260-3972) expressed from the yeast FBA1 promoter (nt 1661-2250) followed by the FBA1 terminator (nt 40005-4317) for expression of dihydroxy acid dehydratase, 2) the coding region for horse liver ADH (nt 4680-5807) expressed from the yeast GPM1 promoter (nt 5819-6575) followed by the ADH1 terminator (nt 4356-4671) for expression of alcohol dehydrogenase, and 3) the coding region of the kivD gene from *Lactococcus lactis* (nt 7175-8821) expressed from the yeast TDH3 promoter (nt 8830-9493) followed by the TDH3 terminator (nt 6582-7161) for expression of ketoisovalerate decarboxylase.

Transformants were obtained on synthetic complete medium lacking uracil and histidine with 1% (v/v) ethanol as carbon source and 100 µg/ml geneticin. Control strains (BP913) were also transformed with the same plasmids and plated without geneticin. A number of transformants were then patched to the same medium containing 2% glucose as carbon source and supplemented with 0.05% (v/v) ethanol. After 36 hours, patches were used to inoculate liquid medium (same composition as the plates). After 48 hours, ODs for both phosphoketolase pathway and control strains were similar (ca. 4-5 OD) and all were subcultured into medium lacking ethanol (i.e. no exogenous two-carbon substrate source). The phosphoketolase cultures grew without ethanol supplementation, similar to ethanol supplemented control strains. Results are shown in FIG. 7A (and Table 17A). These were subcultured again to confirm growth rates, and results are shown in FIG. 7B (and Table 17B). Phosphoketolase strains appeared to have a decreased lag phase compared to controls, but the exponential growth rates were not statistically different (average rate of 0.16 h$^{-1}$).

TABLE 17A

| | Condition | |
|---|---|---|
| Strain | 0 h OD | 18.3 h OD |
| xpk ISO 1 | 0.1 | 2.3 |
| xpk ISO 2 | 0.1 | 2.2 |
| xpk ISO 3 | 0.1 | 2.2 |
| ISO (no EtOH) 1 | 0.1 | 0.48 |
| ISO (no EtOH) 2 | 0.1 | 0.41 |
| ISO (no EtOH) 3 | 0.1 | 0.47 |
| ISO (+EtOH) 1 | 0.1 | 2.5 |
| ISO (+EtOH) 2 | 0.1 | 2.6 |
| ISO (+EtOH) 3 | 0.1 | 2.4 |

TABLE 17B

| | Condition | | | | |
|---|---|---|---|---|---|
| Strain | 0 h OD | 6.5 h OD | 23 h OD | 27 h OD | 48 h OD |
| xpk ISO 1 | 0.1 | 0.18 | 2.91 | 4 | 4.4 |
| xpk ISO 2 | 0.1 | 0.14 | 1.54 | 2.88 | 4.6 |
| xpk ISO 3 | 0.1 | 0.16 | 2.15 | 3.54 | 4.3 |
| ISO (+EtOH) 1 | 0.1 | 0.14 | 2.21 | 3.46 | 4.4 |
| ISO (+EtOH) 2 | 0.1 | 0.11 | 1.13 | 2.18 | 4.2 |
| ISO (+EtOH) 3 | 0.1 | 0.1 | 0.84 | 1.6 | 4.4 |

Example 10

Construction of *Saccharomyces cerevisiae* Strain BP913

The purpose of this example is to describe the construction of *Saccharomyces cerevisiae* strain BP913. The strain was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, and PDC6.

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion.

In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-loxP cassette was PCR-amplified from pLA54 template DNA (SEQ ID NO: 661). pLA54 contains the *K. lactis* TEF1 promoter and kanMX marker, and is flanked by loxP sites to allow recombination with Cre recombinase and removal of the marker. PCR was done using Phusion DNA polymerase and primers BK505 and BK506 (SEQ ID NOs: 662 and 663). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/ml) at 30 C. Transformants were screened to verify correct integration by PCR using primers LA468 and LA492 (SEQ ID NOs:664 and 665) and designated CEN.PK 113-7D Δura3::kanMX. HIS3 Deletion The four fragments for the PCR cassette for the scarless HIS3 deletion were amplified using Phusion High Fidelity PCR Master Mix (New England BioLabs) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 666) and primer oBP453 (SEQ ID NO: 667), containing a 5' tail with homology to the 5' end of HIS3 Fragment B. HIS3 Fragment B was amplified with primer oBP454 (SEQ ID NO: 668), containing a 5' tail with homology to the 3' end of HIS3 Fragment A, and primer oBP455 (SEQ ID NO: 669), containing a 5' tail with homology to the 5' end of HIS3 Fragment U. HIS3 Fragment U was amplified with primer oBP456 (SEQ ID NO: 670), containing a 5' tail with homology to the 3' end of HIS3 Fragment B, and primer oBP457 (SEQ ID NO: 671), containing a 5' tail with homology to the 5' end of HIS3 Fragment C. HIS3 Fragment C was amplified with primer oBP458 (SEQ ID NO: 672), containing a 5' tail with homology to the 3' end of HIS3 Fragment U, and primer oBP459 (SEQ ID NO: 673). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 666) and oBP455 (SEQ ID NO: 669). HIS3 Fragment UC was created by overlapping PCR by mixing HIS3 Fragment U and HIS3 Fragment C and amplifying with primers oBP456 (SEQ ID NO: 670) and oBP459 (SEQ ID NO: 673). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 666) and oBP459 (SEQ ID NO: 673). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II kit (Zymo Research, Orange, Calif.). Transformation mixtures were plated on synthetic complete media lacking uracil supplemented with 2% glucose at 30 C. Transformants with a his3 knockout were screened for by PCR with primers oBP460 (SEQ ID NO: 674) and oBP461 (SEQ ID NO: 671) using genomic DNA prepared with a Gentra Puregene Yeast/Bact kit (Qiagen). A correct transformant was selected as strain CEN.PK 113-7D Δura3::kanMX Δhis3::URA3. KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 715) using a Frozen-EZ Yeast Transformation II kit (Zymo Research, Orange, Calif.) and plating on synthetic complete medium lacking histidine and uracil supplemented with 2% glucose at 30 C. Transformants were grown in YP supplemented with 1% galactose at 30 C for ~6 hours to induce the Cre recombinase and KanMX marker excision and plated onto YPD (2% glucose) plates at 30 C for recovery. An isolate was grown overnight in YPD and plated on synthetic complete medium containing 5-fluoro-orotic acid (0.1%) at 30 C to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 676) and oBP451 (SEQ ID NO: 677) for Δura3 and primers oBP460 (SEQ ID NO: 674) and oBP461 (SEQ ID NO: 675) for Δhis3 using genomic DNA prepared with a Gentra Puregene Yeast/Bact kit (Qiagen, Valencia, Calif.).

PDC6 Deletion

The four fragments for the PCR cassette for the scarless PDC6 deletion were amplified using Phusion High Fidelity PCR Master Mix (New England BioLabs, Ipswich, Mass.) and CEN.PK 113-7D genomic DNA as template, prepared with a Gentra Puregene Yeast/Bact kit (Qiagen). PDC6 Fragment A was amplified with primer oBP440 (SEQ ID NO: 670) and primer oBP441 (SEQ ID NO: 679), containing a 5' tail with homology to the 5' end of PDC6 Fragment B. PDC6 Fragment B was amplified with primer oBP442 (SEQ ID NO: 680), containing a 5' tail with homology to the 3' end of PDC6 Fragment A, and primer oBP443 (SEQ ID NO: 681), containing a 5' tail with homology to the 5' end of PDC6 Fragment U. PDC6 Fragment U was amplified with primer oBP444 (SEQ ID NO: 682), containing a 5' tail with homology to the 3' end of PDC6 Fragment B, and primer oBP445 (SEQ ID NO: 683), containing a 5' tail with homology to the 5' end of PDC6 Fragment C. PDC6 Fragment C was amplified with primer oBP446 (SEQ ID NO: 684), containing a 5' tail with homology to the 3' end of PDC6 Fragment U, and primer oBP447 (SEQ ID NO: 685). PCR products were purified with a PCR Purification kit (Qiagen). PDC6 Fragment AB was created by overlapping PCR by mixing PDC6 Fragment A and PDC6 Fragment B and amplifying with primers oBP440 (SEQ ID NO: 678) and oBP443 (SEQ ID NO: 681). PDC6 Fragment UC was created by overlapping PCR by mixing PDC6 Fragment U and PDC6 Fragment C and amplifying with primers oBP444 (SEQ ID NO: 682) and oBP447 (SEQ ID NO: 685). The resulting PCR products were purified on an agarose gel followed by a Gel Extraction kit (Qiagen). The PDC6 ABUC cassette was created by overlapping PCR by mixing PDC6 Fragment AB and PDC6 Fragment UC and amplifying with primers oBP440 (SEQ ID NO: 678) and oBP447 (SEQ ID NO: 685). The PCR product was purified with a PCR Purification kit (Qiagen).

Competent cells of CEN.PK 113-7D Δura3::loxP Δhis3 were made and transformed with the PDC6 ABUC PCR cassette using a Frozen-EZ Yeast Transformation II kit (Zymo Research). Transformation mixtures were plated on synthetic complete media lacking uracil supplemented with 2% glucose at 30 C. Transformants with a pdc6 knockout were screened for by PCR with primers oBP448 (SEQ ID NO: 686) and oBP449 (SEQ ID NO: 687) using genomic DNA prepared with a Gentra Puregene Yeast/Bact kit (Qiagen). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30 C to select for isolates that lost the URA3 marker. The deletion and marker removal were confirmed by PCR and sequencing with primers oBP448 (SEQ ID NO: 686) and oBP449 (SEQ ID NO: 687) using genomic DNA prepared with a Gentra Puregene Yeast/Bact kit (Qiagen). The absence of the PDC6 gene from the isolate was demonstrated by a negative PCR result using primers specific for the coding sequence of PDC6, oBP554 (SEQ ID NO: 688) and oBP555 (SEQ ID NO: 689). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC #700610 (SEQ ID NO: 1886). The A fragment followed by the ilvD coding region from *Streptococcus mutans* for the PCR cassette for the PDC1 deletion-ilvDSm integration was amplified using Phusion High Fidelity PCR Master Mix (New England BioLabs) and NYLA83 genomic DNA as template (construction of strain NYLA83 is described in U.S. Application Pub. No. 20110124060 A1, incorporated herein by reference), prepared with a Gentra Puregene Yeast/Bact kit (Qiagen). PDC1 Fragment A-ilvDSm was amplified with primer oBP513 (SEQ ID NO: 690) and primer oBP515 (SEQ ID NO: 691), containing a 5' tail with homology to the 5' end of PDC1 Fragment B. The B, U, and C fragments for the PCR cassette for the PDC1 deletion-ilvDSm integration were amplified using Phusion High Fidelity PCR Master Mix (New England BioLabs) and CEN.PK 113-7D genomic DNA as template, prepared with a Gentra Puregene Yeast/Bact kit (Qiagen). PDC1 Fragment B was amplified with primer oBP516 (SEQ ID NO: 692), containing a 5' tail with homology to the 3' end of PDC1 Fragment A-ilvDSm, and primer oBP517 (SEQ ID NO: 693), containing a 5' tail with homology to the 5' end of PDC1 Fragment U. PDC1 Fragment U was amplified with primer oBP518 (SEQ ID NO: 694), containing a 5' tail with homology to the 3' end of PDC1 Fragment B, and primer oBP519 (SEQ ID NO: 695), containing a 5' tail with homology to the 5' end of PDC1 Fragment C. PDC1 Fragment C was amplified with primer oBP520 (SEQ ID NO: 696), containing a 5' tail with homology to the 3' end of PDC1 Fragment U, and primer oBP521 (SEQ ID NO: 697). PCR products were purified with a PCR Purification kit (Qiagen). PDC1 Fragment A-ilvDSm-B was created by overlapping PCR by mixing PDC1 Fragment A-ilvDSm and PDC1 Fragment B and amplifying with primers oBP513 (SEQ ID NO: 690) and oBP517 (SEQ ID NO: 693). PDC1 Fragment UC was created by overlapping PCR by mixing PDC1 Fragment U and PDC1 Fragment C and amplifying with primers oBP518 (SEQ ID NO: 694) and oBP521 (SEQ ID NO: 697). The resulting PCR products were purified on an agarose gel followed by a Gel Extraction kit (Qiagen). The PDC1 A-ilvDSm-BUC cassette was created by overlapping PCR by mixing PDC1 Fragment A-ilvDSm-B and PDC1 Fragment UC and amplifying with primers oBP513 (SEQ ID NO: 690) and oBP521 (SEQ ID NO: 697). The PCR product was purified with a PCR Purification kit (Qiagen).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II kit (Zymo Research). Transformation mixtures were plated on synthetic complete media lacking uracil supplemented with 2% glucose at 30 C. Transformants with a pdc1 knockout ilvDSm integration were screened for by PCR with primers oBP511 (SEQ ID NO: 698) and oBP512 (SEQ ID NO: 699) using genomic DNA prepared with a Gentra Puregene Yeast/Bact kit (Qiagen). The absence of the PDC1 gene from the isolate was demonstrated by a negative PCR result using primers specific for the coding sequence of PDC1, oBP550 (SEQ ID NO: 700) and oBP551 (SEQ ID NO: 701). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30 C to select for isolates that lost the URA3 marker. The deletion of PDC1, integration of ilvDSm, and marker removal were confirmed by PCR and sequencing with primers oBP511 (SEQ ID NO: 698) and oBP512 (SEQ ID NO: 699) using genomic DNA prepared with a Gentra Puregene Yeast/Bact kit (Qiagen). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS (described in Example 2). The coding sequence of sadB (SEQ ID NO: 718) and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 716) as template with primer oBP530 (SEQ ID NO: 702), containing an AscI restriction site, and primer oBP531 (SEQ ID NO: 703), containing a 5' tail with homology to the 5' end of PDC5 Fragment B. PDC5 Fragment B was amplified from CEN.PK 113-7D genomic DNA with primer oBP532 (SEQ ID NO: 704), containing a 5' tail with homology to the 3' end of sadB, and primer oBP533 (SEQ ID NO: 705), containing a PmeI restriction site. PCR products were purified with a PCR Purification kit (Qiagen). sadB-PDC5 Fragment B was created by overlapping PCR by mixing the sadB and PDC5 Fragment B PCR products and amplifying with primers oBP530 (SEQ ID NO: 702) and oBP533 (SEQ ID NO: 705). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 706) and oBP546 (SEQ ID NO: 707), containing a 5' tail with homology to the 5' end of PDC5 Fragment C. PDC5 Fragment C was amplified from CEN.PK 113-7D genomic DNA with primer oBP547 (SEQ ID NO: 708), containing a 5' tail with homology to the 3' end of PDC5 sadB-Fragment B-Fragment U, and primer oBP539 (SEQ ID NO: 709). PCR products were purified with a PCR Purification kit (Qiagen). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 706) and oBP539 (SEQ ID NO: 709). The resulting PCR product was purified on an agarose gel followed by a Gel Extraction kit (Qiagen). The PDC5 A-sadB-BUC cassette was created by amplifying PDC5 sadB-Fragment B-Fragment U-Fragment C with primers oBP542 (SEQ ID NO: 710) containing a 5' tail with homology to the 50 nucleotides immediately upstream of the native PDC5 coding sequence, and oBP539 (SEQ ID NO: 709). The PCR product was purified with a PCR Purification kit (Qiagen).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II kit (Zymo Research). Transformation mixtures were plated on synthetic complete media lacking uracil supplemented with 1% ethanol (no glucose) at 30 C. Transformants with a pdc5 knockout sadB integration were screened for by PCR with primers oBP540 (SEQ ID NO: 711) and oBP541 (SEQ ID NO: 712) using genomic DNA prepared with a Gentra Puregene Yeast/Bact kit (Qiagen). The absence of the PDC5 gene from the isolate was demonstrated by a negative PCR result using primers specific for the coding sequence of PDC5, oBP552 (SEQ ID NO: 713) and oBP553 (SEQ ID NO: 714). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30 C to select for isolates that lost the URA3 marker. The deletion of PDC5, integration of sadB, and marker removal were confirmed by PCR with primers oBP540 (SEQ ID NO: 711) and oBP541 (SEQ ID NO: 712) using genomic DNA prepared with a Gentra Puregene Yeast/Bact kit (Qiagen). The correct isolate was selected as strain CEN.PK 113-7D Δura3::loxP Δhis3 Δpdc6 Δpdc1::ilvDSm Δpdc5::sadB and designated as BP913.

Example 11

Construction of Strain NYLA83

This example describes insertion-inactivation of endogenous PDC1 and PDC6 genes of *S. cerevisiae*. PDC1, PDC5, and PDC6 genes encode the three major isozymes of pyruvate decarboxylase. The resulting strain was used as described in Example 10.

Construction of pRS425::GPM-sadB

A DNA fragment encoding a butanol dehydrogenase (SEQ ID NO: 717) from *Achromobacter xylosoxidans* (disclosed in US Patent Application Publication No. US20090269823) was cloned. The coding region of this gene called sadB for secondary alcohol dehydrogenase (SEQ ID NO: 718) was amplified using standard conditions from *A. xylosoxidans* genomic DNA, prepared using a Gentra Puregene kit (Gentra Systems, Inc., Minneapolis, Minn.; catalog number D-5500A) following the recommended protocol for gram negative organisms using forward and reverse primers N473 and N469 (SEQ ID NOs:725 and 726), respectively. The PCR product was TOPO-Blunt cloned into pCR4 BLUNT (Invitrogen) to produce pCR4Blunt::sadB, which was transformed into *E. coli* Mach-I cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs:727 and 728). The PCR product was then cloned using "gap repair" methodology in *Saccharomyces cerevisiae* (Ma et al. ibid) as follows. The yeast-*E. coli* shuttle vector pRS425::GPM::kivD::ADH which contains the GPM1 promoter (SEQ ID NO:721), kivD coding region from *Lactococcus lactis* (SEQ D NO:719), and ADH1 terminator (SEQ ID NO:722) (described in U.S. Pat. No. 7,851,188, Example 17) was digested with BbvCI and PacI restriction enzymes to release the kivD coding region. Approximately 1 μg of the remaining vector fragment was transformed into *S. cerevisiae* strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs:729 and 730).

Construction of pdc6:: $P_{GPM1}$-sadB Integration Cassette and PDC6 Deletion:

A pdc6::$P_{GPM1}$-sadB-ADH1t-URA3r integration cassette was made by joining the GPM-sadB-ADHt segment (SEQ ID NO:723) from pRS425::GPM-sadB (SEQ ID NO: 720) to the URA3r gene from pUC19-URA3r. pUC19-URA3r (SEQ ID NO:724) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) Gene 77:61-68) using as template pRS425::GPM-sadB and pUC19-URA3r plasmid DNAs, with Phusion DNA polymerase (New England Biolabs Inc., Beverly, Mass.; catalog no. F-540S) and primers 114117-11A through 114117-11D (SEQ ID NOs:731, 732, 733 and 734), and 114117-13A and 114117-13B (SEQ ID NOs:735 and 736).

The outer primers for the SOE PCR (114117-13A and 114117-13B) contained 5' and 3'~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 112590-34G and 112590-34H (SEQ ID NOs:737 and 738), and 112590-34F and 112590-49E (SEQ ID NOs: 739 and 740) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::$P_{GPM1}$-sadB-ADH1t.

Construction of pdc1::P$_{PDC1}$-ilvD Integration Cassette and PDC1 Deletion:

A pdc1::P$_{PDC1}$-ilvD-FBA1t-URA3r integration cassette was made by joining the ilvD-FBA1t segment (SEQ ID NO:741) from pLH468 (SEQ ID NO: 1888) to the URA3r gene from pUC19-URA3r by SOE PCR (as described by Horton et al. (1989) Gene 77:61-68) using as template pLH468 and pUC19-URA3r plasmid DNAs, with Phusion DNA polymerase (New England Biolabs Inc., Beverly, Mass.; catalog no. F-540S) and primers 114117-27A through 114117-27D (SEQ ID NOs:742, 743, 744 and 745).

The outer primers for the SOE PCR (114117-27A and 114117-27D) contained 5' and 3'~50 bp regions homologous to regions downstream of the PDC1 promoter and downstream of the PDC1 coding sequence. The completed cassette PCR fragment was transformed into BY4700 pdc6:: P$_{GPM1}$-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs 746 and 747), and primers 112590-49E and 112590-30F (SEQ ID NOs 740 and 748) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6.: P$_{GPM1}$-sadB-ADHt pdc1:: _P$_{PDC1}$-ilvD-FBA1t.

HIS3 Deletion

To delete the endogenous HIS3 coding region, a his3:: URA3r2 cassette was PCR-amplified from URA3r2 template DNA (SEQ ID NO: 749). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs:750 and 751) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: P$_{GPM1}$-sadB-ADH1t pdc1:: P$_{PDC1}$-ilvD-FBA1t Δhis3.

Construction of Pdc5::kanMX Integration Cassette and PDC5 Deletion:

A pdc5::kanMX4 cassette was PCR-amplified from strain YLR134W chromosomal DNA (ATCC No. 4034091) using Phusion DNA polymerase and primers PDC5::KanMXF and PDC5::KanMXR (SEQ ID NOs:752 and 753) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 µg/ml) at 30° C. Transformants were screened by PCR to verify correct integration at the PDC locus with replacement of the PDC5 coding region using primers PDC5kofor and N175 (SEQ ID NOs: 754 and 755). The identified correct transformants have the genotype: BY4700 pdc6:: P$_{GPM1}$-sadB-ADH1t pdc1:: P$_{PDC1}$-ilvD-FBA1t Δhis3 pdc5::kanMX4. The strain was named NYLA74.

Deletion of HXK2 (Hexokinase II):

A hxk2::URA3r cassette was PCR-amplified from URA3r2 template (described above) using Phusion DNA polymerase and primers 384 and 385 (SEQ ID NOs:756 and 757) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs:758 and 759). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs:760 and 761). The resulting identified strain named NYLA83 has the genotype: BY4700 pdc6.: P$_{GPM1}$-sadB-ADH1t pdc1:: P$_{PDC1}$-ilvD-FBA1t Δhis3 Δhxk2.

Example 12

Construction of *Saccharomyces cerevisiae* Strain PNY2257

Strain PNY2242 was constructed in several steps from BP913 (described above). First, the native GPD2 gene on Chromosome XV was deleted. The coding region was deleted using CRE-lox mediated marker removal (methodology described above), so the resulting locus contains one loxP site. The sequence of the modified locus is provided as SEQ ID NO: 1899 (Upstream region=nt 1-500; loxP site=nt 531-564; Downstream region=nt 616-1115). Second, the native FRA2 gene on Chromosome VII was deleted. Elimination of FRA2 was a scarless deletion of only the coding region. The sequence of the modified locus is provided as SEQ ID NO: 1900 (Upstream region=nt 1-501; Downstream region=nt 526-1025). Next, the ADH1 gene on Chromosome XV was deleted along with insertion of a chimeric gene comprised of the UAS(PGK1)-FBA1 promoter and the kivD coding region. The native ADH1 terminator was used to complete the gene. The sequence of the modified locus is provided as SEQ ID No. 1901 (Upstream region=nt 1-500; UAS(PGK1)FBA promoter=nt 509-1233; kivD coding region=nt 1242-2888; Downstream region (includes terminator)=nt 2889-3388). Next, a chimeric gene comprised of the FBA1 promoter, the alsS coding region and the CYC1 terminator was integrated into Chromosome XII, upstream of the TRX1 gene. The sequence of the modified locus is provided as SEQ ID No. 1902 (Upstream region=nt 1-154; FBA1 promoter=nt 155-802; alsS CDS=nt 810-2525; CYC1 terminator=nt 2534-2788; Downstream region=nt 2790-3015). Next, two copies of a gene encoding horse liver alcohol dehydrogenase were integrated into Chromosomes VII and XVI. On Chromosome VII, a chimeric gene comprised of the PDC1 promoter, the hADH coding region and the ADH1 terminator were placed into the fra2Δ locus (the original deletion of FRA2 is described above). The sequence of the modified locus is provided as SEQ ID No. 1903 (Upstream region=nt 1-300; PDC1 promoter=nt 309-1178; hADH coding region=nt 1179-2306; ADH1 terminator=nt 2315-2630; Downstream region=nt 2639-2900). On Chromosome XVI, a chimeric gene comprised of the PDC5 promoter, the hADH coding region and the ADH1 terminator were integrated in the region formerly occupied by the long term repeat element YPRCdelta15. The sequence of the modified locus is provided as SEQ ID No. 1904 (Upstream region=nt 1-150; PDC5 promoter=nt 159-696; hADH coding region=nt 697-1824; ADH1 terminator=nt 1833-2148; Downstream region=nt 2157-2656). Then the native genes YMR226c and ALD6 were deleted. Elimination of YMR226c was a scarless deletion of only the coding region. The sequence of the modified locus is provided as SEQ ID No. 1905 (Upstream region=nt 1-250; Downstream region=nt 251-451). The ALD6 coding region plus 700 bp of upstream sequence were deleted using CRE-lox mediated marker removal, so the resulting locus contains one loxP site. The sequence of the modified locus is provided as SEQ ID No. 1906 (Upstream region=nt 1-500; loxP site=nt 551-584; Downstream region=nt 678-1128). The geneticin-selectable phosphoketolase expression vector described in Example 8 was transformed into the strain and confirmed as described above (the locus is depicted in FIG. 6). Finally, plasmids were introduced into the strain for expression of KARI (pLH702, plasmid SEQ ID. No. 1907) and DHAD (pYZ067DkivDDhADH, SEQ ID. No. 1908), resulting in the strain named PNY2257. A control strain containing all of the elements above except for the phosphoketolase pathway construct is called PNY2242.

Growth rates were assessed as described in previous examples. Over a 24 hour period, PNY2257 displayed growth rates without ethanol or other two-carbon supplement similar to those growth rates observed for PNY2242 with supplementation.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10006058B2). An electronic copy of the "Sequence Listing" will also be available from the USPTO upon request and payment of the fee set forth in 37 CFR 1.19(b)(3).

What is claimed is:

1. A method for the production of isobutanol comprising growing a recombinant host cell comprising:
   (i) at least one genetic modification in an endogenous gene encoding a polypeptide having pyruvate decarboxylase activity, wherein the at least one genetic modification reduces or eliminates pyruvate decarboxylase activity;
   (ii) a heterologous polynucleotide encoding a polypeptide having phosphoketolase activity, wherein the heterologous polynucleotide encoding a polypeptide having phosphoketolase activity is xpk1 from *Lactobacillus plantarum*, xpkA from *Lactobacillus pentosus* MD363, or 6-phosphate phosphoketolase from *B. lactis*;
   (iii) at least one genetic modification in an endogenous gene encoding a polypeptide having glycerol-3-phosphate dehydrogenase activity, wherein the at least one genetic modification reduces or eliminates glycerol-3-phosphate dehydrogenase activity; and
   (iv) an isobutanol biosynthetic pathway comprising the substrate to product conversions:
      (a) pyruvate to acetolactate,
      (b) acetolactate to 2,3-dihydroxyisovalerate,
      (c) 2,3-dihydroxyisovalerate to 2-ketoisovalerate,
      (d) 2-ketoisovalerate to isobutyraldehyde,
      (e) isobutyraldehyde to isobutanol;
under conditions wherein isobutanol is produced and optionally recovering isobutanol.

2. The method of claim 1, wherein the isobutanol is recovered by distillation, azeotropic distillation, liquid-liquid extraction, adsorption, gas stripping, membrane evaporation, pervaporation, vacuum flash, or combinations thereof.

3. The method of claim 1, wherein the isobutanol is recovered by contacting the fermentation broth with an extractant.

4. The method of claim 3, wherein the extractant is $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, or mixtures thereof.

5. The recombinant host cell of claim 1, wherein the polypeptide having phosphoketolase activity comprises at least 85% identity to SEQ ID NO: 481.

6. The recombinant host cell of claim 1, wherein the recombinant host cell is *Saccharomyces cerevisiae*.

* * * * *